US012799083B2

(12) United States Patent
Bauer et al.

(10) Patent No.: US 12,799,083 B2
(45) Date of Patent: Nov. 17, 2026

(54) 2,5- OR 2,6-DISUBSTITUTED HYDROQUINONE DERIVATIVES WITH AT LEAST ONE CARBOXY, SULFO OR AMIDO GROUP USEFUL AS MEDICAMENTS

(71) Applicant: OM PHARMA SA, Meyrin (CH)

(72) Inventors: Jacques Bauer, St-Prex (CH); Olivier Martin, Saint Hilaire Saint Mesmin (FR)

(73) Assignee: OM PHARMA SA, Meyrin (CH)

(*) Notice: Subject to any disclaimer, the term of this patent is extended or adjusted under 35 U.S.C. 154(b) by 533 days.

(21) Appl. No.: 17/909,589

(22) PCT Filed: Mar. 8, 2021

(86) PCT No.: PCT/EP2021/055791
§ 371 (c)(1),
(2) Date: Sep. 6, 2022

(87) PCT Pub. No.: WO2021/180655
PCT Pub. Date: Sep. 16, 2021

(65) Prior Publication Data

US 2023/0150951 A1 May 18, 2023

(30) Foreign Application Priority Data

Mar. 11, 2020 (EP) .................................... 20162558

(51) Int. Cl.

| | |
|---|---|
| ***C07D 251/20*** | (2006.01) |
| ***A61P 3/00*** | (2006.01) |
| ***A61P 35/00*** | (2006.01) |
| ***A61P 37/00*** | (2006.01) |
| ***C07C 229/38*** | (2006.01) |
| ***C07C 233/47*** | (2006.01) |
| ***C07C 233/51*** | (2006.01) |
| ***C07C 233/81*** | (2006.01) |
| ***C07C 235/64*** | (2006.01) |
| ***C07C 275/42*** | (2006.01) |
| ***C07C 309/51*** | (2006.01) |
| ***C07C 317/46*** | (2006.01) |
| ***C07C 323/56*** | (2006.01) |
| ***C07D 213/79*** | (2006.01) |
| ***C07D 235/18*** | (2006.01) |
| ***C07D 257/04*** | (2006.01) |

(52) U.S. Cl.
CPC .......... *C07D 251/20* (2013.01); *C07C 229/38* (2013.01); *C07C 233/51* (2013.01); *C07C 235/64* (2013.01); *C07C 275/42* (2013.01); *C07C 309/51* (2013.01); *C07C 317/46* (2013.01); *C07D 235/18* (2013.01)

(58) Field of Classification Search
None
See application file for complete search history.

(56) References Cited

U.S. PATENT DOCUMENTS

| | | | |
|---|---|---|---|
| 4,208,328 | A | 6/1980 | Lavallee et al. |
| 9,556,111 | B2 | 1/2017 | Tasken et al. |
| 2006/0135773 | A1 | 6/2006 | Semple et al. |
| 2008/0139632 | A1 | 6/2008 | Almstead et al. |
| 2013/0121919 | A1 | 5/2013 | Feng et al. |
| 2013/0172333 | A1 | 7/2013 | Jain et al. |
| 2016/0269696 | A1 | 9/2016 | Clabau et al. |

FOREIGN PATENT DOCUMENTS

| | | | |
|---|---|---|---|
| CL | 2022001986 | A1 | 5/2023 |
| CN | 115279730 | A | 11/2022 |
| EP | 4118069 | A1 | 5/2024 |
| JP | 2023-517693 | A | 4/2023 |

(Continued)

OTHER PUBLICATIONS

RN2604445-65-8, registry database compound, 2021.*
Ad-Prevention, 2026, https://www.alz.org/alzheimers-dementia/research-and-progress/prevention.*
Jang et al., International Journal of Molecular Sciences, 2021, 22, 2719, pp. 1-16.*
Ryan et al., 2025, https://biospective.com/resources/tnf-alpha-neurodegenerative-disease.*
Luo et al., 2025, Frontiers in Immunology, 34 pages.*
International Search Report dated Apr. 26, 2021, for OM Pharma SA, International Application No. PCT/EP2021/055791, filed Mar. 8, 2021. (Exhibit 3).

(Continued)

*Primary Examiner* — Sun Jae Yoo
(74) *Attorney, Agent, or Firm* — WCF IP

(57) ABSTRACT

The present invention provides novel hydroquinone derivatives of formula (I), processes of preparation, as well as pharmaceutical compositions and methods of treating and/or preventing e.g. autoimmune, immunological, rheumatology, vascular disorders, ophthalmologic disorders, fibrotic disorders, metabolic and gastrointestinal disorders, neuroinflammatory and neurodegenerative diseases, neoplasms and cancer associated disorders, hormone related diseases and immunological disorders resulting from viral and bacterial infectious diseases and complications thereof. wherein $R_1$ is $COOR_4$, $(CH_2)nCOOR_4$, $SO_3H$, $(CH_2)nSO_3H$ or CONH—$R_{10}$; one of $R_2$ and $R_3$ is H and the other is $R_5$.

(I)

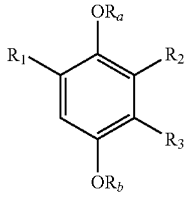

19 Claims, 19 Drawing Sheets

(56) References Cited

FOREIGN PATENT DOCUMENTS

| | | | |
|---|---|---|---|
| WO | 2009126551 | A2 | 10/2009 |
| WO | 2010142766 | A2 | 12/2010 |

OTHER PUBLICATIONS

Written Opinion of the International Searching Authority dated Apr. 26, 2021, for OM Pharma SA, International Application No. PCT/EP2021/055791, filed Mar. 8, 2021. (Exhibit 4).

Extended European Search Report dated Aug. 24, 2020, for OM Pharma SA, European Application No. 20162558.9, filed Mar. 11, 2020. (Exhibit 5).

Stefani et al. Synthesis of Proton-Transfer Fluorescent Dyes: 2,5-Bis(2'-Benzazolyl)Hydroquinones and Related Compounds. Dyes and Pigments, vol. 20, No. 2, pp. 97-107 (1992). (Exhibit 6).

Itami et al. Chiral Benzoquinones as a New Class of Ligands for Asymmetric Catalysis: Synthesis and Application to the Palladium(II)-Catalyzed 1,4-Dialkoxylation of 1,3-Dienes. Journal of Organic Chemistry, vol. 63, No. 19, pp. 6466-6471 (1998). (Exhibit 7).

Communication under Rule 71(3) EPC dated May 17, 2024, for OM Pharma SA, European Patent Application No. 21709062.0-1102, filed Mar. 8, 2021.

Decision to Grant a European Patent Pursuant to Article 97(1) EPC dated Sep. 26, 2024, for OM Pharma SA, European Patent Application No. 21709062.0-1102, filed Mar. 8, 2021.

Japanese Office Action dated Aug. 13, 2024, for OM Pharma SA, "New hydroquinone derivative", Japanese Patent Application No. 2022-554951, filed Mar. 8, 2021.

Chinese Office Action dated Dec 22, 2023, for OM Pharma SA, "2,5- OR 2,6-Disubstituted Hydroquinone Derivatives With At Least One Carboxy, Sulfo or Amido Group Useful as Medicaments", Chinese Patent Application No. 202180019787.4, filed Mar. 8, 2021.

Chinese Search Report dated Dec 21, 2023, for OM Pharma SA, "2,5- OR 2,6-Disubstituted Hydroquinone Derivatives With At Least One Carboxy, Sulfo or Amido Group Useful as Medicaments", Chinese Patent Application No. 202180019787.4, filed Mar. 8, 2021.

Chinese Office Action dated Aug. 24, 2024, for OM Pharma SA, "2,5- OR 2,6-Disubstituted Hydroquinone Derivatives With At Least One Carboxy, Sulfo or Amido Group Useful as Medicaments", Chinese Patent Application No. 202180019787.4, filed Mar. 8, 2021.

Chilean Office Action dated Jan. 10, 2024, for OM Pharma SA, "Substituted Hydroquinone Derived Compounds; Pharmaceutical Composition, and Use in the Treatment or Prevention of Autoimmune, Immunological, Vascular, Fibrotic, Ophthalmological, Metabolic, Gastrointestinal Disorders, Cancer or Neuroinflammatory and Neuroegenerative Diseases", Chilean Patent Application No. 202201986, filed Jul. 21, 2022.

Chilean Search Report dated Jan. 10, 2024, for OM Pharma SA, "Substituted Hydroquinone Derived Compounds; Pharmaceutical Composition, and Use in the Treatment or Prevention of Autoimmune, Immunological, Vascular, Fibrotic, Ophthalmological, Metabolic, Gastrointestinal Disorders, Cancer or Neuroinflammatory and Neuroegenerative Diseases", Chilean Patent Application No. 202201986, filed Jul. 21, 2022.

Chilean Office Action dated Aug. 19, 2024, for OM Pharma SA, "Substituted Hydroquinone Derived Compounds; Pharmaceutical Composition, and Use in the Treatment or Prevention of Autoimmune, Immunological, Vascular, Fibrotic, Ophthalmological, Metabolic, Gastrointestinal Disorders, Cancer or Neuroinflammatory and Neuroegenerative Diseases", Application No. 202201986, filed Jul. 21, 2022.

Chilean Search Report dated Aug. 19, 2024, for OM Pharma SA, "Substituted Hydroquinone Derived Compounds; Pharmaceutical Composition, and Use in the Treatment or Prevention of Autoimmune, Immunological, Vascular, Fibrotic, Ophthalmological, Metabolic, Gastrointestinal Disorders, Cancer or Neuroinflammatory and Neuroegenerative Diseases", Application No. 202201986, filed Jul. 21, 2022.

* cited by examiner

Figure 3 A

| Cytokines / Diseases | IL-1b | IL-2 | IL-3 | IL-4 | IL-5 | IL-6 | IL-7 | IL-8 | IL-9 | IL-10 | IL-12p70 | IL-13 | IL-14 | IL-15 | IL-17A | IL-17F | IL-18 | IL-21 | IL-22 | IL-23 | IL-33 | IFNγ | IFNb | TNFα | TGFbeta | TNFbeta | MCP-1 | MMPs |
|---|---|---|---|---|---|---|---|---|---|---|---|---|---|---|---|---|---|---|---|---|---|---|---|---|---|---|---|---|
| ALL/AML | | | x | | | | | x | | | | | | | | | | | | | | | | | | | | |
| Allergic Asthma | x | | x | x | x | x | | | x | | | x | | x | x | | x | | | | | | x | x | | | | |
| Allergic Rhinitis | | | | x | | | | | | x | | | | | | | x | | | | | | | x | x | | | |
| Alzheimer | x | | | | | | | | | | | | | | | | x | | | | | | | | x | | | |
| Ankylosing spondylitis | | | | | | | | | | | | | | | x | | | | | | | | | x | | | | x |
| Atherosclerosis | | | | | | | | | | | | | | | | | | | | | | | | | | | | |
| Atopic Dermatitis | | | | | x | | x | | | x | | | | | x | | x | | | | | x | | x | | | | |
| Bacterial infections | x | | | | | | | | | | | | | | | | | | | | | | | | | | | |
| Behcet disease | | | | | | | | | | | | | | | | | | x | | | | | | | | | | |
| Cancer | x | | x | | | | | | | x | x | | | | | | | x | x | | | x | | x | | | | |
| Cardiovascular pathologies | | | | | | | | | | | | | | | | | | | | | | | | | x | | | |
| CLL | | | | x | | | | | | | | | | | | | | | | | | | | | | | | |
| COPD | x | | | | x | | | x | | | | | | | | | | | | | | | | | | | | |
| Crohn’s disease | | | | | | | | | | | | | | | | x | x | | | x | x | | | x | | | | |
| Cystic fibrosis | | | | | | | | x | | | | | | | | | | | | | | | | | | | | |
| Diabetes | | | | x | | | x | | | x | | | | x | | | x | | | | | x | | | | | | |
| Eosinophilic GI | | | | | x | | | | | | | | | | | | | | | | | | | | | | | |
| Experimental Autoimmune Encephalomyelitis | | | | | | | | | | | | | | | | | | | | | | x | | | | | | |
| Fibrosis | | | | | | x | | | | | | x | | | | | | | | | | | | | x | | | |
| Food Allergy | | | | | | | | | x | | | | | | | | | | | | | | | | | | | |
| GHVD | | | | | | | | | | | | | | | | | | | | | | | | | | | | |
| Giant cell arthritis | | | | | | x | | | | | | | | | | | | | | | | | | x | | | | |
| Gout | x | | | | | x | | x | | | | | | | | | | | | | | | | | | | x | |
| Grave's disease | x | | | | | | | | | | | | | | | | | | | | | | | | | | | |

Figure 3 B

| Diseases \ Cytokines | IL-1b | IL-2 | IL-3 | IL-4 | IL-5 | IL-6 | IL-7 | IL-8 | IL-9 | IL-10 | IL-12p70 | IL-13 | IL-14 | IL-15 | IL-17A | IL-17F | IL-18 | IL-21 | IL-22 | IL-23 | IL-33 | IFNγ | IFNb | TNFα | TGFbeta | TNFbeta | MCP-1 | MMPs |
|---|---|---|---|---|---|---|---|---|---|---|---|---|---|---|---|---|---|---|---|---|---|---|---|---|---|---|---|---|
| Helminth infections | | | | | | | | | x | | | | | | | | | | | | | | | | | | | |
| Inflammatory Bowel Disease | x | | | | | | x | | | x | x | | | x | x | x | | | x | | | | | x | | | | |
| JID juvenile idiopathic arthritis AID, autoinflammatory disease including Still's disease | x | | | | | x | | | | | | | | | | | | | | | | | | x | | | | |
| Lymphoma | | | | | | | | | | | | | x | | | | | | | | | | | | | | | |
| Multiple sclerosis | x | | | | | | x | | | | | | | x | | | x | | | | | | x | | | | | |
| Myocardial infection | x | | | | | | | | | | | | | | | | | | | | | | | | | | | |
| Osteoarthritis | x | | | | | | | x | | | | | | | | | | | | | | | | | | | | x |
| Pancreatitis | | | | | | x | | x | | | | | | | x | | | | | | | | | | x | | | |
| Parasites infections | | | | x | | | | | | | | | | | | | | | | | x | | | | | | | |
| Psoriasis | x | | | | | x | | x | | | x | | | x | x | | x | | x | x | | | | x | | | | |
| Psoriatic arthritis | | | | | | | | | | | | | | | | | | | | | | | | x | | | | |
| Rheumatoid arthritis | x | | | | | x | x | x | | x | | | | x | x | | x | x | | | x | x | x | x | | | | |
| Sjogren syndrom | | | | | | | | | | | | | x | | | | | | | | | | | | | | | |
| Systematic Lupus Ery. | | | | | | x | | | | x | | | x | x | | | | x | | | | | x | x | | | | |
| Systemic Sclerosis | | | | | | | | | | | | | | | | | | | | | | | | x | | | | |
| T cell mediated autoimmune diseases | | x | | | | | | | | | | | | | | | | | | | | | | | | | | |
| Ulcerative colitis | | | | | | | | | x | | | | | | | | | | | x | | | | x | | | | |
| Vascular diseases | | | | | | | | | | | | | | | | | | | | | x | | | x | | | | |
| Viral infections | x | | | | | | | | | | | | | | | | | | | | | | x | | | | | |

Figure 4A

Products from KI-I and KI-6

| ArCOOH | R-$NH_2$ | Coupling conditions | Yield | Deprotection Conditions-A | Yield | Deprotection Conditions-B | Yield | Purification procedure | Final Product (amount, yield [1]) | Comments |
|---|---|---|---|---|---|---|---|---|---|---|
| **KI-1** (12.95 g) | 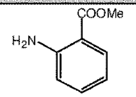 | TCFH (1.2 eq)<br>NMI (5 eq)<br>MeCN | 86% | LiOH (4 eq.)<br>THF-$H_2O$<br>Time = 36 h,<br>T° = 23 °C | 89% | $H_2$, Pd/C<br>DCM/EtOH<br>Time = 48 h,<br>T° = 23 °C | 84% | Trituration with MeCN | **Ia-001a**<br>(13.4 g, 36%) | |
| **KI-1** (53 g) | 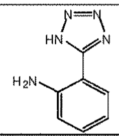 | TCFH (1.2 eq)<br>NMI (5 eq)<br>MeCN | 86% | LiOH (4 eq.)<br>THF-$H_2O$<br>Time = 26 h,<br>T° = 23 °C | Quant. | $H_2$, Pd/C<br>THF/EtOH<br>Time = 18 h,<br>T° = 23 °C | 82% | Trituration with MeCN and $Et_2O$ | **Ia-001aTz**<br>(30 g, 40%) | |
| **KI-1** (1 g) | 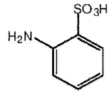 | 1) $SOCl_2$ (27 eq), DMF (drops)<br>2) DIPEA (2.2 eq), DMF | 43% | LiOH (5 eq.)<br>THF-$H_2O$<br>Time = 18 h,<br>T° = 23 °C | 86% | $H_2$, Pd/C<br>EtOAc<br>Time = 18 h,<br>T° = 23 °C | 80% | Normal work up | **Ia-001c**<br>(95 mg, 17%) | |
| **KI-1** (203 mg) | 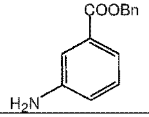 | 1) $SOCl_2$ (49 eq)<br>DCM, 50 °C, 4h<br>2) DIPEA (1.1 eq)<br>DCM | 62% | $H_2$, Pd/C<br>DCM/EtOH<br>Time = 1.5h,<br>T° = 23 °C | 57% | NaOH aq (22 eq)<br>2h, then<br>HCl 1N<br>T° = 23 °C | 60% | Filtration after addition of acid and trituration of solid in MeOH | **Ia-002a**<br>(34 mg, 60%) | |
| **KI-1** (1 g) | 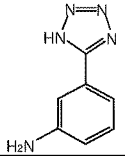 | HATU (1.5 eq)<br>DIPEA (5 eq)<br>DMF | 64% | LiOH (6 eq.)<br>THF-$H_2O$<br>Time = 18 h,<br>T° = 23 °C | 90% | $H_2$, Pd/C<br>EtOAc/EtOH<br>Time = 18 h,<br>T° = 23 °C | 91% | Trituration with MeCN and MTBE | **Ia-002aTz**<br>(285 mg, 30%) | |
| **KI-1** (190 mg) AX050 + LG043 | 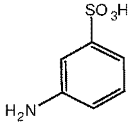 | 1) $SOCl_2$ (50 eq)<br>DCM, 50 °C<br>2) NaOH aq. 0.5 M (1.1 eq), $Na_2CO_3$ (0.6 eq), TBAB (0.1 eq), THF, rt, 5 d. | 95% ($Na^+$ salt) | $H_2$, Pd/C<br>$H_2O$/EtOH<br>Time = 2.5h<br>T° = 23 °C | 88% | NaOH aq (18 eq)<br>2h15, then<br>HCl 1N<br>T° = 23 °C | 50% | Filtration after addition of acid; lyophilisation of filtrate affords product | **Ia-002c** | |
| **KI-1Bn** (76 mg) | 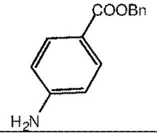 | 1) $SOCl_2$ (50 eq)<br>DCM, 50 °C, 3h<br>2) DIPEA (1.1 eq)<br>DCM | 82% | $H_2$, $Pd(OH)_2$<br>DCM/EtOH<br>Time = 4 h,<br>T° = 23 °C | 95% | | | Final product has low solubility in EtOH<br>Purif. Chromatogr. AcOEt/AcOH 95:5 | **Ia-003a**<br>(11 mg, 95%) | Single deprotection step as both precursors are benzyl esters<br>NMR ok |

Figure 4B

| | | | | | | | | | |
|---|---|---|---|---|---|---|---|---|---|
| **KI-1**<br>(1 g) | 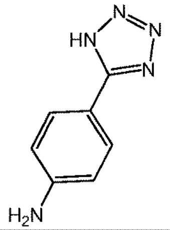 | HATU (1.5 eq)<br>DIPEA (5 eq)<br>DMF | 96% | LiOH (6 eq.)<br>THF-$H_2O$<br>Time = 21 h,<br>T° = 23 °C | 37% | $H_2$, Pd/C<br>EtOAc/EtOH<br>Time = 18 h,<br>T° = 23 °C | 37% | Trituration with MeCN and MTBE | **Ia-003aTz**<br>(0.022 g, 7%) |
| **KI-1**<br>(118 mg)<br>(LG 038) | 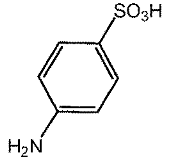 | 1) $SOCl_2$ (58 eq)<br>DCM, 50°C<br>2) NaOH aq. 0.5 M (1.1 eq), $Na_2CO_3$ (0.5 eq), TBAB (0.12 eq), THF, rt. | 69% | $H_2$, Pd/C<br>$H_2O$/EtOH<br>Time = 5.5h<br>T° = 23 °C | 88% | NaOH aq. 0.9 M, 2h, then HCl 37% (3.5 mL) | 82% | Evaporation of solvents and elimination of salts by selective solubilisation in EtOH | **Ia-003c**<br>(45 mg, 82%) |
| **KI-1**<br>(1 g) | 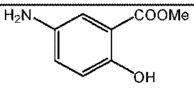 | 1) $SOCl_2$ (27 eq), DMF (drops)<br>2) DIPEA (1.1 eq), DCM, DMF | 24% | LiOH (6 eq.)<br>THF/DMSO-$H_2O$<br>Time = 5 days,<br>T° = 75 °C | 86% | $H_2$, Pd/C<br>DMF/EtOH<br>Time = 24 h,<br>T° = 23 °C | 76% | Trituration with MeCN and $Et_2O$ | **Ia-004a**<br>(0.145 g, 9%) |
| **KI-1**<br>(1 g) | 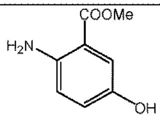 | 1) $SOCl_2$ (27 eq), DMF (drops)<br>2) DIPEA (1.1 eq), DCM, DMF | 33% | LiOH (6 eq.)<br>THF-$H_2O$<br>Time = 18 h,<br>T° = 23 °C | 94% | $H_2$, Pd/C<br>EtOAc<br>Time = 2 h,<br>T° = 23 °C | 84% | Normal work up | **Ia-006a**<br>(0.155 g, 15%) |
| **KI-1**<br>(1 g) | 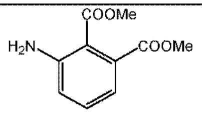 | 1) $SOCl_2$ (27 eq), DMF (drops)<br>2) DIPEA (1.1 eq), DCM. | 75% | LiOH (7 eq.)<br>THF-$H_2O$<br>Time = 18 h,<br>T° = 23 °C | 95% | $H_2$, Pd/C<br>EtOAc/EtOH<br>Time = 4 h,<br>T° = 23 °C | 66% | Normal work up | **Ia-011a**<br>(0.46 g, 27%) |
| **KI-1**<br>(1 g) | 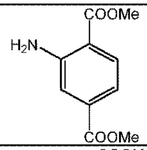 | 1) $SOCl_2$ (27 eq), DMF (drops)<br>2) DIPEA (1 eq), DCM | 57% | LiOH (6 eq.)<br>THF-$H_2O$<br>Time = 20 h,<br>T° = 23 °C | Quant | $H_2$, Pd/C<br>DCM/EtOH<br>Time = 1 h,<br>T° = 23 °C | 88% | Normal work up | **Ia-012a**<br>(0.414 g, 28%) |
| **KI-1**<br>(1.125 g) | 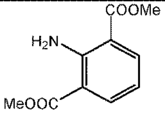 | 1) $SOCl_2$ (27 eq), DMF (drops)<br>2) DIPEA (1.1 eq), DCM | 75% | LiOH (30 eq.)<br>THF-$H_2O$<br>Time = 36 h,<br>T° = 23 °C | Quant | $H_2$, Pd/C<br>DCM/EtOH<br>Time = 18 h,<br>T° = 23 °C | 98% | Normal work up | **Ia-013a**<br>(0.644 g, 42%) |
| **KI-1**<br>(2.11 g) | 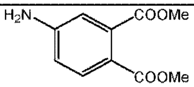 | 1) $SOCl_2$ (27 eq), DMF (drops)<br>2) DIPEA (1.1 eq), DCM | 41% | LiOH (6 eq.)<br>THF-$H_2O$<br>Time = 18 h,<br>T° = 23 °C | Quant | $H_2$, Pd/C<br>DCM/EtOH<br>Time = 18 h,<br>T° = 23 °C | 94% | Normal work up | **Ia-014a**<br>(0.156 g, 22%) |

Figure 4C

| | | | | | | | | | | |
|---|---|---|---|---|---|---|---|---|---|---|
| KI-1 (1.12 g) | 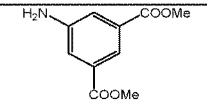 | 1) $SOCl_2$ (50 eq) DCM, 50°C, 4h 2) DIPEA (1.2 eq) DCM – 12h, rt col. chromatogr. PE/AcOEt | | $H_2$, Pd/C DCM/EtOH Time = 18 h, T° = 23 °C | 98% | NaOH aq (65 eq) 2h, rt, then HCl 37% at 0°C, Filtration, drying, wash with aq. HCl, EtOH | 84% | Trituration in $H_2O$, drying | **Ia-015a** (380 mg, 84%) | Product partially soluble in EtOH, avoid EtOH for washings |
| **KI-1** (0.5 g) | 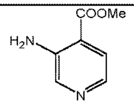 | TCFH (1.2 eq) NMI (5 eq) MeCN | 58% | LiOH (8 eq.) THF-$H_2O$ Time = 42 h, T° = 23 °C | Quant | $H_2$, Pd/C THF/EtOH Time = 18 h, T° = 23 °C | 41% | Trituration with MeCN | **Ia-023a** (0.054 g, 13%) | |
| **KI-1Bn** (84% + 16% diester) | 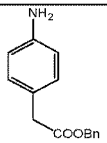 | 1) $SOCl_2$ (25 eq) DCM, 50°C, 4h 2) DIPEA (1.2 eq), DCM – 18h, rt col. chromatogr. PE/DCM 1:1 → DCM | 86% | $H_2$, Pd/C DCM/EtOH Time = 2 h, T° = 23 °C | 99% | | | Trituration with THF | **Ia-032a** (107 mg, 99%) | Single deprotection step as both precursors are benzyl esters |
| **KI-1** (1 g) | 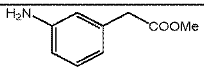 | 1) $SOCl_2$ (27 eq), DMF (drops) 2) DIPEA (1.1 eq), DCM | 73% | $H_2$, Pd/C EtOAc Time = 18 h, T° = 23 °C | 97% | LiOH (8 eq.) THF-$H_2O$ Time = 42 h, T° = 23 °C | 83% | Normal work up | **Ia-033a** (0.147 g, 46%) | |
| **KI-1** (1 g) | 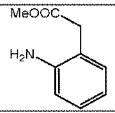 | 1) $SOCl_2$ (27 eq), DMF (drops) 2) DIPEA (1.1 eq), DMF | 39% | LiOH (6 eq.) THF-$H_2O$ Time = 18 h, T° = 23 °C | 85% | $H_2$, Pd/C DCM/EtOH Time = 20 h, T° = 23 °C | 31% | Prep HPLC | **Ia-034a** (0.07 g, 6%) | |
| **KI-1** (1 g) | 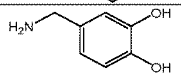 | HOBt (1.5 eq) EDC (1.5 eq) TEA (3.2 eq) DMF | 57% | LiOH (6 eq.) THF-$H_2O$ Time = 18 h, T° = 23 °C | 96% | $H_2$, Pd/C DCM/EtOH Time = 2 h, T° = 23 °C | 92% | Normal work up | **Ia-035a** (0.314 g, 22%) | Benzylation step before hydrolysis: BnBr (2 eq), $K_2CO_3$ (2 eq), DMF. Time = 24 h T° = 23 °C, Y= 79% |
| **KI-1** (1 g) | 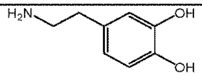 | 1) $SOCl_2$ (26 eq) 2) DIPEA (2.2 eq) DCM | 70% | -- | -- | cHCl (10 mL) AcOH (10 mL) | 31% | Prep HPLC | **Ia-035a-2** (0.081 g, 12%) | |
| **KI-1** (1 g) | 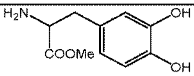 | 1) $SOCl_2$ (28 eq) 2) DIPEA (2.2 eq) DCM | 12% | LiOH (4 eq.) THF-$H_2O$ Time = 18 h, T° = 23 °C | 92% | $H_2$, Pd/C EtOH/EtOAc Time = 20 h, T° = 23 °C | 34% | Prep HPLC | **Ia-035a-3** (0.05 g, 1%) | Benzylation step before hydrolysis: BnBr (4 eq), $K_2CO_3$ (4 eq), DMF. Time = 18 h T° = 23 °C, Y= 99% |
| **KI-1** (0.5 g) | 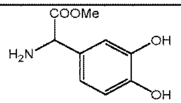 | 1) $SOCl_2$ (25 eq) 2) DIPEA (2.2 eq) DMF | 39% | LiOH (8 eq.) THF-$H_2O$ Time = 18 h, T° = 23 °C | 96% | $H_2$, Pd/C DCM/AcOH Time = 20 h, T° = 23 °C | 24% | Prep HPLC | **Ia-036a** (0.036 g, 2%) | Benzylation step before hydrolysis: BnBr (5 eq), $K_2CO_3$ (8 eq), DMF. Time = 18 h T° = 23 °C, Y= 51% Decomposed after prep purification (80% pure) |

Figure 4D

| | | | | | | | | | | |
|---|---|---|---|---|---|---|---|---|---|---|
| **KI-1** (1 g) | 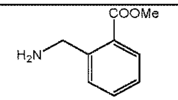 | 1) $SOCl_2$ (27 eq) 2) DIPEA (2.2 eq) DCM | 81% | _ | _ | cHCl (15 mL) AcOH (15 mL) Time = 6 h, T° = 80 °C | 44% | Prep HPLC | **Ia-053a** (106 mg, 20%) | |
| **KI-1** (1 g)? | 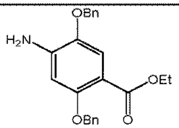 | TCFH (1.2 eq) NMI (5 eq) Aniline (1.1 eq) MeCN | 92% | LiOH (27 eq.) $THF-H_2O$ DMSO Time = 120 h, T° = 25 °C | 93% | $H_2$, Pd/C THF/EtOH Time = 18 h, T° = r.t. | 80% | Trituration with MeCN and *n*-pentane | **Ia-056a** (322 mg, 39%) | |
| **KI-1** (35.5 g, 2 eq) | 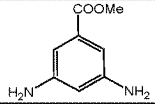 | HATU (3 eq) DiPEA (6 eq) DMF | 87% | LiOH (6 eq.) $THF-DMSO-H_2O$ Time = 48 h, T° = 23 °C | 98% | $H_2$, Pd/C DCM/EtOH Time = 18 h, T° = 23 °C | 98% | Trituration with MeCN | **Ib-010a** (19.3 g, 47%) | |
| **KI-6** (500 mg) | 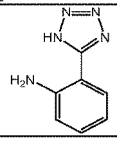 | TCFH (2.4 eq) NMI (6 eq) MeCN | 74% | -- | -- | $H_2$, Pd/C DCM/EtOH Time = 18 h, T° = 23 °C | 41% | Trituration with EtOH and $Et_2O$ | **Ic-001aTz2** (0.191 g, 17%) | |
| **KI-6** (20.3 g) | 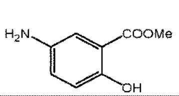 | 1) $SOCl_2$ (40 eq) 2) DIPEA (2.2 eq) DCM | 85% | LiOH (6 eq.) $DMSO-H_2O$ Time = 18 h, T° = 100 °C | 71% | $H_2$, Pd/C DMF Time = 1 h, T° = 23 °C | quant | Trituration with MeCN | **Ic-007a** (25.7 g, 34%) | |
| **KI-6** (1 g) | 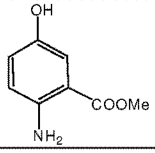 | 1) $SOCl_2$ (23 eq) 2) DIPEA (2.2 eq) DCM/DMF | 64% | NaOH (20 eq.) $H_2O$ Time = 6 h, T° = 23 °C | 88% | $H_2$, Pd/C DMF Time = 4 h, T° = 23 °C | 24% | Trituration with acetone | **Ic-009a** (41 mg, 8%) | |
| **KI-1** (70 g) | R =<br>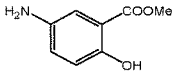<br>R′=<br>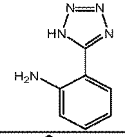 | TCFH (1.2 eq) NMI (5 eq) MeCN | 77% | LiOH (6 eq.) $THF-H_2O$ Time = 96 h, T° = 23 °C | 98% | $H_2$, Pd/C THF/EtOH Time = 36 h, T° = 23 °C | 80% | Trituration with $Et_2O$ | **Ic-001aTz/004a** (40.8 g, 34%) | The conditions for first coupling (R′) and hydrolysis have been mentioned in Entry 2 |
| **KI-1** (0.5 g) | 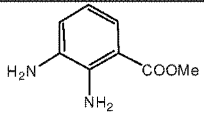 | 1) $SOCl_2$ (28 eq) 2) DIPEA (2.2 eq) DMF | 78% | LiOH (7 eq.) $THF-H_2O$ Time = 72 h, T° = 23 °C | 60% | $H_2$, Pd/C DCM/EtOH Time = 24 h, T° = 23 °C | 15% | Prep HPLC | **Id-030a** (10 mg, 4%) | Cyclization step: $MeSO_3H$ (3.3 eq), MeOH. Time = 17 h, T° = 70 °C |

Figure 5A

Products from KI-2 and KI-7

| ArCOOH | R-NH2 | Coupling conditions | Yield | Deprotection Conditions A | Yield | Deprotection Conditions B | Yield | Purification procedure | Final Product (amount, yield) | Comments |
|---|---|---|---|---|---|---|---|---|---|---|
| **KI-2** | 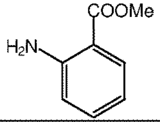 | 1) $SOCl_2$ (32 eq), DMF (drops)<br>2) DIPEA (1.1 eq), DCM | 72% | _ | _ | cHCl (10 mL) AcOH (10 mL) Time = 18 h, T° = 80 °C | 64% | Trituration with DCM and MeOH | **IIa-001a** (142 mg, 46%) | |
| **KI-2** | 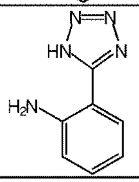 | TCFH (1.2 eq) NMI (5 eq) MeCN | 71% | LiOH (6 eq.) THF-$H_2O$ Time = 48 h, T° = r.t. | 77% | $H_2$, Pd/C THF/EtOH Time = 18 h, T° = r.t. | 53% | Trituration with MeCN, DCM and $Et_2O$ | **IIa-001aTz** (125 mg, 29%) | |
| **KI-2** | 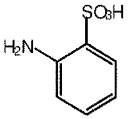 | 1) $SOCl_2$ (70 eq), DMF (drops)<br>2) DIPEA (2.2 eq), DMF | 70% | LiOH (4 eq.) THF-$H_2O$ Time = 72 h, T° = r.t. | 15% | $H_2$, Pd/C EtOH Time = 18 h, T° = r.t. | 54% | Trituration with MeCN | **IIa-001c** (20 mg, 4%) | |
| **KI-2Ac2** 675 mg | 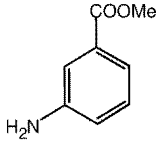 | 1. $SOCl_2$, DCM, reflux, 5h, conc.<br>2. DCM, amine (1 eq), Ipr$NEt_2$ (1,1 eq), 12h, rt. Extract. column chromatogr | 15% | EtOH, NaOH 1M, 0°C then 2h, rt. Acidification, conc. | 55% | Not needed | | | **IIa-002a** | Compound made from the diacetate of 2,5-dihydroxyisophtalic acid methyl ester |
| **KI-2Ac2** 500 mg | 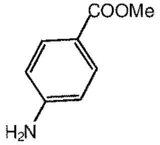 | 1. $SOCl_2$, DCM, reflux, 5h, conc.<br>2. DCM, amine (1.1 eq), ipr$NEt_2$ (1,1 eq 12h rt; extraction, column chromat | 16% | EtOH, NaOH 1M, 0°C then 2h, rt. Acidification, conc. | 69% | Not needed | | | **IIa-003a** | Compound made from the diacetate of 2,5-dihydroxyisophtalic acid methyl ester |
| **KI-2Ac2** | 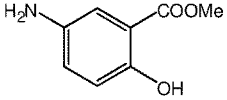 | 1) $SOCl_2$ (30 eq), DMF (drops)<br>2) DIPEA (1.1 eq), DCM | 75% | _ | _ | cHCl (10 mL) AcOH (10 mL) Time = 18 h, T° = 80 °C | 61% | Normal workup | **IIa-004a** (136 mg, 45%) | Compound from KI 2Ac2 |
| **KI-2** | 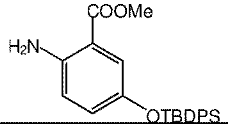 | 1) $SOCl_2$ (26 eq), DMF (drops)<br>2) Pyridine (1.2 eq), DCM | 72% | LiOH (6 eq.) THF-$H_2O$ Time = 24 h, T° = r.t. | 95% | $H_2$, Pd/C EtOH/EtOAc Time = 24 h, T° = r.t. | 71% | Normal workup | **IIa-006a** (209 mg, 51%) | The starting aniline was protected with a *tert*-Butyldiphenyl silyl group |

Figure 5B

| | | | | | | | | | | |
|---|---|---|---|---|---|---|---|---|---|---|
| **KI-2Ac$_2$** | 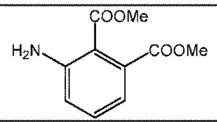 | 1) $SOCl_2$ (32 eq), DMF (drops) 2) DIPEA (2.2 eq), DCM | 70% | _ | _ | NaOH aq (60 eq) 6.5h, then HCl 1N T° = r.t. | 32% | Aqueous work-up then Prep HPLC | **IIa-011a** (130 mg, 22%) | Compound from KI-2Ac$_2$ |
| **KI-2Ac$_2$** | 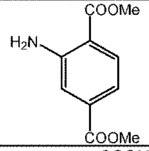 | 1) $SOCl_2$ (40 eq), DMF (drops) 2) DIPEA (1.1 eq), DCM | 33% | _ | _ | cHCl (10 mL) AcOH (10 mL) Time = 18 h, T° = 80 °C | 29% | Prep HPLC | **IIa-012a** (58 mg, 9%) | Compound from KI-2Ac$_2$ |
| **KI-2Ac$_2$** | 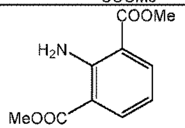 | 1) $SOCl_2$ (32 eq), DMF (drops) 2) DIPEA (1.1 eq), DCM | 34% | LiOH (12 eq.) THF-$H_2O$ Time = 96 h, T° = r.t. | 74% | $H_2$, Pd/C EtOH/EtOAc Time = 24 h, T° = r.t. | 95% | Normal work-up | **IIa-013a** (58 mg, 23%) | The amide coupling was performed from the KI-2Ac$_2$, followed by quantitative methanolysis and subsequent re-protection with benzyl protecting groups. |
| **KI-2** | 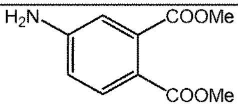 | 1) $SOCl_2$ (61 eq), DMF (drops) 2) DIPEA (1.1 eq), DCM | 59% | LiOH (6 eq.) THF-$H_2O$ Time = 48 h, T° = r.t. | 93% | $H_2$, Pd/C EtOH/EtOAc Time = 18 h, T° = r.t. | 77% | Trituration with MeCN | **IIa-014a** (170 mg, 42%) | |
| **KI-2Ac$_2$** 675 mg | 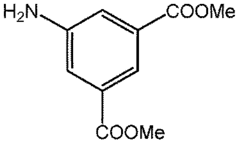 | 1. $SOCl_2$, (25 eq.), DCM, reflux, 5h, conc. 2. DCM, amine (1.0 eq), Ipr$NEt_2$ (1,1 eq) 12h rt; extraction, column chromatogr | 12% | EtOH, NaOH 1M, 0°C then 2h, rt. Aciditication, conc. | 77% | Not needed | | | **IIa-015a** | Compound made from the diacetate of 2,5-dihydroxyiso-phtalic acid methyl ester |
| **KI-2Ac$_2$** | 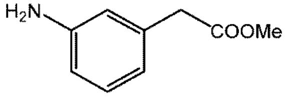 | 1) $SOCl_2$ (32 eq), DMF (drops) 2) DIPEA (1.1 eq), DCM | 55% | _ | _ | cHCl (9 mL) AcOH (9 mL) Time = 24 h, T° = 100 °C | 34% | Prep HPLC | **IIa-033a** (91 mg, 34%) | |
| **KI-2** | 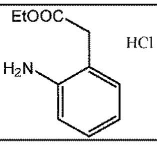 | 1) $SOCl_2$ (25 eq), DMF (drops) 2) DIPEA (2.2 eq), DMF | 35% | LiOH (8 eq.) THF-$H_2O$ Time = 6 h, T° = r.t. | 97% | $H_2$, Pd/C DCM/EtOAc Time = 24 h, T° = r.t. | 26% | Trituration with MeCN | **IIa-034a** (37 mg, 8%) | |

Figure 5C

| | | | | | | | | | | |
|---|---|---|---|---|---|---|---|---|---|---|
| **KI-2** | 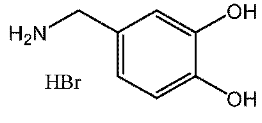 | 1) $SOCl_2$ (25 eq),<br>DMF (drops)<br>2) DIPEA (2.2 eq),<br>DMF<br>3)cHCl (5 mL) | 97% | LiOH (4 eq.)<br>THF-$H_2O$<br>Time = 24 h,<br>T° = r.t. | 56% | $H_2$, Pd/C<br>DCM/EtOH<br>Time = 24 h,<br>T° = r.t. | 59% | Prep HPLC | **IIa-035a**<br>(90 mg, 13%) | The amide coupling was performed from the KI-2Ac$_2$, followed by de-acetylation with cHCl in the work-up then subsequent protection with 4 benzyl protecting groups (43% yield) prior to LiOH hydrolysis. |
| **KI-2Ac$_2$** | 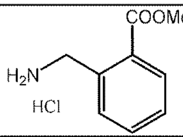 | 1) $SOCl_2$ (40 eq),<br>DMF (drops)<br>2) DIPEA (2.2 eq),<br>DMF | 78% | – | – | cHCl (19 mL)<br>AcOH (19 mL)<br>Time = 17 h,<br>T° = 80 °C | 24% | Prep HPLC | **IIa-053a**<br>(104 mg, 24%) | From KI-2Ac$_2$ |
| **KI-2Ac$_2$** | 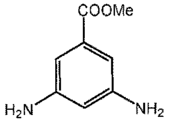 | 1) $SOCl_2$ (40 eq),<br>DMF (drops)<br>2) DIPEA (1.1 eq),<br>Aniline (0.5 eq.),<br>DCM | 22% | LiOH (8 eq.)<br>THF-$H_2O$<br>Time = 24 h,<br>T° = r.t | 34% | $H_2$, Pd/C<br>THF/EtOH<br>Time = 24 h,<br>T° = r.t. | 17% | Prep HPLC | **IIb-010a**<br>(8 mg, 5%) | The amide coupling was performed from the KI-2Ac$_2$, followed by methanolysis of the protecting acetyl (98% yield) and subsequent protection with 4 benzyl protecting groups (40% yield) prior to LiOH hydrolysis. |
| **KI-7** | 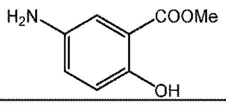 | TCFH (2.4 eq)<br>NMI (10 eq)<br>Aniline (2.4 eq)<br>MeCN | Quant. | LiOH (6 eq.)<br>THF-$H_2O$<br>Time = 24 h,<br>T° = 80 °C | 70% | $H_2$, Pd/C<br>THF<br>Time = 24 h,<br>T° = r.t. | 88% | Trituration with MeCN and $Et_2O$ | **IIc-007a**<br>(5.7 g, 61%) | |
| **KI-7** | 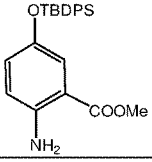 | 1) $SOCl_2$ (50 eq),<br>DMF (drops)<br>2) Pyridine (2.2 eq),<br>Aniline (2.2 eq.),<br>DCM | 76% | LiOH (6 eq.)<br>THF-$H_2O$<br>Time = 24 h,<br>T° = r.t. | 95% | $H_2$, Pd/C<br>EtOAc/EtOH<br>Time = 24 h,<br>T° = r.t. | 3% | Purified twice by Prep | **IIc-009a**<br>(11 mg, %) | The starting aniline was protected with a *tert*-Butyldiphenylsily (TBDPS) group. |

Figure 6

| Products from **KI-8** and **KI-9** | | | | | | | | | |
|---|---|---|---|---|---|---|---|---|---|
| **ArCOOH** | **R-$NH_2$** | **Coupling conditions** | **Yield** | **Deprotection Conditions-A** | **Yield** | **Deprotection Conditions-B** | **Yield** | **Purification procedure** | **Final Product (amount, yield)** |
| **KI-8** | 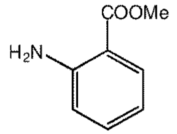 | 1) $(COCl)_2$ (6 eq), DMF (drops), DCM<br>2) DIPEA (1.1 eq), Aniline (1.1 eq), DCM | 75% | LiOH (6 eq.)<br>THF-$H_2O$<br>Time = 24 h,<br>T° = r.t. | 80% | $H_2$, Pd/C<br>DCM/EtOAc<br>Time = 24 h,<br>T° = r.t. | 51% | Trituration with MeCN | **IIIa-001a** |
| **KI-8** | 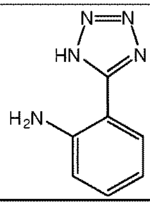 | TCFH (1.2 eq)<br>NMI (5 eq)<br>Aniline (1.2 eq)<br>MeCN | 75% | LiOH (6 eq.)<br>THF-$H_2O$<br>Time = 18 h,<br>T° = 70 °C | 93% | $H_2$, Pd/C<br>DCM/EtOH<br>Time = 18 h,<br>T° = r.t. | 43% | Trituration with MeCN | **IIIa-001aTz**<br>(27 mg, 29%) |
| **KI-8** | 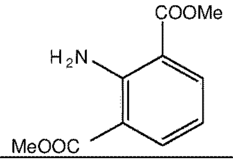 | TCFH (1.2 eq)<br>NMI (5 eq)<br>Aniline (1.2 eq)<br>MeCN | 29% | LiOH (16 eq.)<br>THF-$H_2O$<br>Time = 48 h,<br>T° = r.t. | Quant. | $H_2$, Pd/C<br>DCM/EtOH<br>Time = 18 h,<br>T° = r.t. | Quant. | Trituration with $Et_2O$ | **IIIa-013a**<br>(50 mg, 29%) |
| **KI-8** | 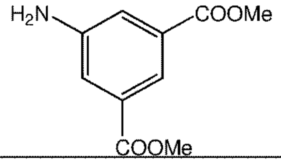 | TCFH (1.2 eq)<br>NMI (5 eq)<br>Aniline (1.2 eq)<br>MeCN | 71% | LiOH (8 eq.)<br>THF-$H_2O$<br>Time = 18 h,<br>T° = r.t. | 90% | $H_2$, Pd/C<br>DCM/EtOH<br>Time = 18 h,<br>T° = r.t. | 26% | Prep HPLC | **IIIa-015a**<br>(26 mg, 16%) |
| **KI-8** | 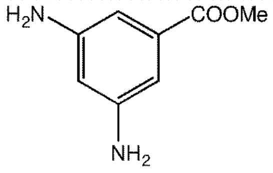 | TCFH (1.2 eq)<br>NMI (3 eq)<br>Aniline (0.5 eq)<br>MeCN | 75% | LiOH (6 eq.)<br>THF-$H_2O$,<br>DMSO<br>Time = 72 h,<br>T° = 55 °C | 85% | $H_2$, Pd/C<br>THF/EtOH<br>Time = 18 h,<br>T° = r.t. | 57% | The residue was dissolved into water, filtered and the water was removed in a freeze-drier | **IIIb-010a**<br>(755 mg, 57%) |

Figure 7

Products from KI-8 and KI-9

| SUBSTRATE | Deprotection ConditionsA | Yield | Deprotection ConditionsB | Yield | Purification procedure | Final Product (amount, yield) | Comments |
|---|---|---|---|---|---|---|---|
| **Deprotection Procedures** | | | | | | | |
| 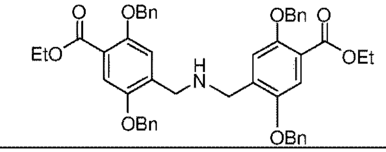 | LiOH (6 eq.)<br>THF-$H_2O$<br>Time = 72 h,<br>T° = 70 °C | Quant. | $H_2$, Pd/C<br>DCM/EtOH<br>Time = 18 h,<br>T° = r.t. | 50% | Trituration with MeCN | **IIIc-056a**<br>(44 mg, 50%) | The product may possibly be the HCl salt (HCl/Dioxane test didn't revealed protons shifts) |
| 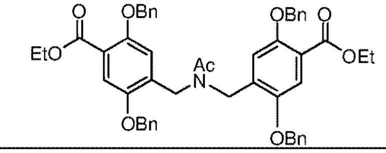 | LiOH (15 eq.)<br>THF-$H_2O$<br>Time = 96 h,<br>T° = 40 °C | Quant. | $H_2$, Pd/C<br>DCM/EtOH<br>Time = 48 h,<br>T° = r.t. | 67% | Trituration with $Et_2O$ | **IIIc-057a** | |
| 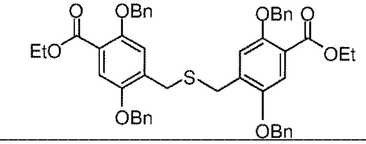 | Same conditions | | Same conditions | | | **IIIc-058a** | |
| 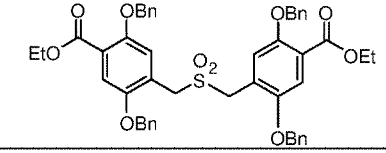 | Same conditions | | Same conditions | | | **IIIc-059a** | |
| 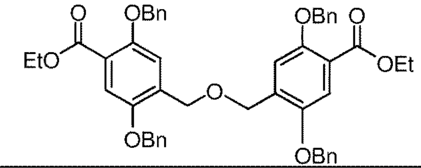 | LiOH (6 eq.)<br>THF-$H_2O$<br>Time = 24 h,<br>T° = 70 °C | Quant. | $H_2$, Pd/C<br>DCM<br>Time = 18 h,<br>T° = r.t. | 55% | Prep HPLC | **IIIc-060a**<br>(39 mg, 55%) | |
| 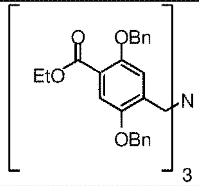 | LiOH (18 eq.)<br>THF-$H_2O$<br>Time = 96 h,<br>T° = 80 °C | 87% | $H_2$, Pd/C<br>THF/EtOH<br>Time = 18 h,<br>T° = r.t. | 73% | Trituration with water/acetone | **IIIc-061a**<br>(9.1 g, | Large scale synthesis |

Figure 8

| ArCOOH | R-$NH_2$ | Coupling conditions | Yield | Deprotection Conditions-A | Yield | Deprotection Conditions-B | Yield | Purification procedure | Final Product (amount, yield) |
|---|---|---|---|---|---|---|---|---|---|
| 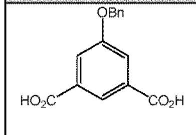 | 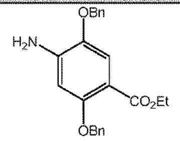 Aniline A | TCFH (4.2 eq)<br>NMI (9 eq)<br>MeCN | 58% | LiOH (8 eq.)<br>DMSO-$H_2O$<br>Time = 18 h,<br>T° = 100 °C | 42% | $H_2$, Pd/C<br>THF/EtOH<br>Time = 18 h,<br>T° = 23 °C | 88% | Trituration with MeCN and $Et_2O$ | **V-001a**<br>(110 mg, 21%) |
| 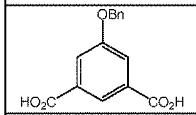 | 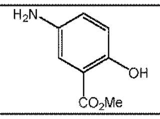 | TCFH (2.2 eq)<br>NMI (6 eq)<br>MeCN | 76% | LiOH (10 eq.)<br>THF-$H_2O$<br>Time = 48 h,<br>T° = r.t. | 77% | $H_2$, Pd/C<br>THF/EtOH<br>Time = 48 h,<br>T° = r.t. | 90% | Trituration with $Et_2O$ | **V-002a**<br>(513 mg, 52%) |
| **Deprotection Procedures** | | | | | | | | | |
| | 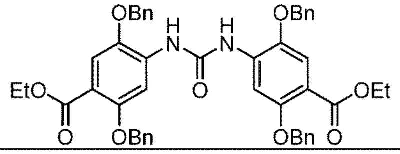 | | | LiOH (20 eq.)<br>THF-$H_2O$<br>Time = 168 h,<br>T° = from r.t to 80 °C | 76% | $H_2$, Pd/C<br>THF/EtOH<br>Time = 72 h,<br>T° = r.t. | 67% | Trituration with $Et_2O$ | **V-003a**<br>(48 mg, 50%) |

2,5- OR 2,6-DISUBSTITUTED HYDROQUINONE DERIVATIVES WITH AT LEAST ONE CARBOXY, SULFO OR AMIDO GROUP USEFUL AS MEDICAMENTS

FIELD OF THE INVENTION

This invention relates generally to novel hydroquinone derivatives, their preparation and to methods of treating disorders by administration of such compounds to a warm-blooded animal in need thereof. The present invention also relates to compounds that are useful in the prevention and/or treatment of autoimmune, immunological, rheumatology, vascular disorders, ophthalmologic disorders, fibrotic disorders, metabolic and gastro-intestinal disorders, neuroinflammatory and neurodegenerative diseases, neoplasms and cancer associated disorders, hormone related diseases and immunological disorders resulting from viral and bacterial infectious diseases, and complications thereof.

BACKGROUND OF THE INVENTION

Some hydroquinone-based derivatives like for example, 2,5-dihydroxybenzenesulfonic acid derivatives and specifically calcium dobesilate, ethamsylate and persilate are known in the art as active agents for the treatment of male sexual dysfunction and other vascular disorders of endothelial origin, both alone and in combination with other agents. For example, U.S. Pat. No. 6,147,112 describes a method for the use of 2,5-dihydroxybenzenesulfonic acid derivatives, preferably calcium dobesilate, ethamsylate and persilate. Calcium dobesilate or hydroquinone calcium sulfonate, with the chemical name 2,5-dihydroxybenzenesulfonic acid calcium salt, is being sold as Dexium (Delalande) and Doxium (Carrion), and a process for its preparation is described in U.S. Pat. No. 3,509,207.

There are many drugs that contain phenol or catechol groups which suffer from premature metabolism at the hydroxy group during absorption after oral administration. Previous efforts to protect the hydroxy groups have been generally unsuccessful as the protecting groups employed are either too labile (O═COR or O═CR) or too stable ($CH_3$). It is thus an object of the present invention to provide novel derivatives of hydroquinones, their pharmaceutically acceptable salts and formulations. These novel hydroquinones derivatives have particularly potent anti-fibrotic, anti-inflammatory and anti-angiogenic properties.

International publication WO2018160618A1 discloses certain substituted hydroquinones, 1,4-quinones, catechols, 1,2-quinones, anthraquinones, and anthrahydroquinones for use as redox mediators in emerging technologies, such as in mediated fuel cells or organic-mediator flow batteries.

Richter et al, in Synthesis, 1976, 1976(3), 192-194 disclose Bis-N-arylcarbamates and 2,5-Dihydroxy-3,6-bis[N-arylcarboxamido]-1,4-benzoquinones and their preparation from 2,5-Dihydroxy-1,4-benzoquinone and Aryl Isocyanates.

Japanese publication JP 51026839A discloses Benzanilides I (R═H, OH) as possessing antitubercular, analgesic, anti-inflammatory, and uric acid-excreting activities:

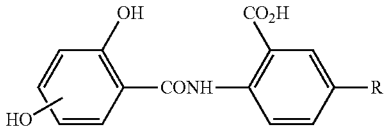

Benzanilides I

US granted patent U.S. Pat. No. 3,973,038 also discloses benzoylaniline compounds having general formula:

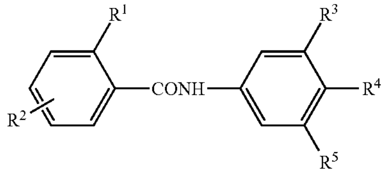

wherein ($R_1$═OH, acyloxy; $R_2$═H, OH, lower alkyl, halo, acyloxy; $R_3$═Cl, Br, lower alkyl; $R_4$═OH, $NH_2$, lower alkoxy, acyloxy; $R_5$═H, halo, CO2H, lower alkyl, acyloxy) having in vivo enzyme inhibition properties, in particular, histamine deacetylase and xanthine oxidase None of the prior art documents however disclose the novel class of hydroquinone derivative compounds of the present invention, which are particularly useful for the prevention and/or treatment of a variety of diseases including autoimmune, immunological, rheumatology, vascular disorders, ophthalmologic disorders, fibrotic disorders, metabolic and gastro-intestinal disorders, neuroinflammatory and neurodegenerative diseases, neoplasms and cancer associated disorders, hormone related diseases and immunological disorders resulting from viral and bacterial infectious diseases, and complications thereof.

The invention also relates to the treatment, prevention, and reduction of metabolic disorders, such as diabetes and obesity. As the levels of blood glucose rise postprandially, insulin is secreted and stimulates cells of the peripheral tissues (skeletal muscles and fat) to actively take up glucose from the blood as a source of energy. Loss of glucose homeostasis as a result of faulty insulin secretion or action typically results in metabolic disorders such as diabetes, which may be co-triggered or further exacerbated by obesity. Because these conditions are often fatal, strategies to restore adequate glucose clearance from the bloodstream are required. Metabolic disorders, particularly glucose and lipid regulatory disorders, are becoming increasingly prevalent as the populations in industrialized nations age and sedentary lifestyles become more common. Such disorders are frequently interrelated and are often predictors or results of each other.

For example, diabetes is caused by a combination of insulin resistance and defective secretion of insulin by pancreatic-D cells. Individuals with insulin resistance often have abdominal obesity, dyslipidemia, hypertension, glucose intolerance and a prothrombitic state (Metabolic syndrome). Correspondingly, obese individuals as a whole are at higher risk for acquiring insulin resistance. The breakdown of a metabolic pathway thus can trigger myriad disorders such as hyperlipidemia, obesity, diabetes, insulin resistance, glucose intolerance, hyperglycemia, metabolic syndrome and hypertension which may in turn trigger further metabolic dysfunction resulting in systemic issues and putting individuals at risk for additional complications and premature morbidity. Glucose and lipid levels are regulated in part by the liver which plays a role in synthesizing, storing, secreting, transforming, and breaking down glucose, proteins and lipids. Disease or traumatic injury can greatly reduce the liver's ability to carry out these normal activities. Thus, most of the clinical manifestations of liver dysfunction stem from cell damage and impairment of the normal liver capacities. Liver dysfunction can result from genetic conditions, inflammatory disorders, toxins such as drugs and alcohol, immunological disorders, vascular disorders or metabolic conditions. Regardless of the cause, liver damage can have a systemic effect on the function of metabolic processes and the regulation of blood glucose and serum lipid levels, exacerbating chronic disease states and leading to increased risks for further disease and morbidity. Both elevated and reduced levels of blood glucose trigger hormonal responses designed to restore glucose homeostasis. Low blood glucose triggers the release of glucagon from pancreatic a-cells. High blood glucose triggers the release of insulin from pancreatic b-cells. ACTH and growth hormones released from the pituitary, act to increase blood glucose by inhibiting uptake by extrahepatic tissues. Glucocorticoids also act to increase blood glucose levels by inhibiting glucose uptake. Cortisol, the major glucocorticoid released from the adrenal cortex, is secreted in response to the increase in circulating ACTH. The adrenal medullary hormone, epinephrine, stimulates production of glucose by activating glycogenolysis in response to stressful stimuli. etabolic disorders that effect glucose and lipid metabolism such as hyperlipidemia, obesity, diabetes, insulin resistance, hyperglycemia, glucose intolerance, metabolic syndrome and hypertension have long term health consequences leading to chronic conditions including cardiovascular disease and premature morbidity. Such metabolic and cardiovascular disorders may be interrelated, aggravating, or triggering each other and generating feedback mechanisms that are difficult to interrupt. Current pharmaceutical treatments for metabolic and cardiovascular disorders include combinations of lipid-lowering drugs, hypoglycemic drugs, antihypertensive agents, diet, and exercise. However, complicated therapeutic regimens can cause polypharmacy problems of increased side effects, drug-drug interactions, failure of adherence, and increased medication errors. There is therefore a compelling, unmet need in the art to identify new compounds, formulations, and methods to safely and effectively treat metabolic and cardiovascular disorders and conditions associated with metabolic disorders. Examples of metabolic conditions include, but are not limited to, pain, wound healing, fever, neuroinflammatory and neurodegenerative conditions, inflammation, heat production, homeothermy, breakdown of triglycerides, glycolysis, Krebs cycle, fermentation, photosynthesis, metabolic rate, biotic and abiotic stress, secretions, oxidative stress, stress, neoplastic growth, skin condition, cardiovascular conditions, neuroinflammatory and neurodegenerative conditions, mental and behavioural disorders. Such processes or conditions can occur in a cell, group of cells, or an entire organism.

Recent progress in molecular medicine has led to certain improvements in diagnostics and treatment of neoplastic diseases. Despite this partial success, these pathologies remain a considerable challenge. For certain types of cancers, the current therapy in some cases fails for several reasons. On the one hand, it is inherent resistance of tumour cells, their ability of constant mutation and therapy evasion, on the other hand it is also the heterogeneity of the tumour environment. It was shown that tumours of the same type highly differ for individual subjects from the viewpoint of their genomic profile which indicates the necessity of the so-called "personal" therapy. Even a bigger problem is the heterogeneity of mutations in the same tumour, as it has been recently shown for renal tumours, and this situation can be expected for other types of tumours as well. For this reason, it is necessary to search for new approaches and for an invariable intervention point(s) common for all or most malignant cells in the tumour and which preferably affects essential functions in cancer cells. It seems that such an intervention point could be at the metabolic level say for example mitochondria, i.e., organelles which are fundamental for the generation of energy necessary for all physiological as well as pathophysiological processes in cells. Although tumour cells use, from a major part, the so-called aerobic glycolysis for energy generation, mitochondrial respiration (i.e., consumption of oxygen linked to ATP formation) is inherent to most (if not all) types of tumours. Hence there is an unmet and compelling need in the art to identify new compounds, formulations, and methods to treat such neoplastic disorders safely and effectively.

SUMMARY OF THE INVENTION

The present invention provides novel hydroquinone derivatives, novel process of preparation, and novel key intermediates. The present invention also relates to pharmaceutical compositions comprising therapeutically effective amount of such hydroquinone derivatives and pharmaceutically acceptable excipient.

The invention further provides a method of treating and/or preventing angiogenic (vascular), inflammatory and/or fibrotic pathobiology, as they have anti-fibrotic, anti-inflammatory and anti-angiogenic effects. The present invention thus finally provides a method of treating and/or preventing a disease or disorder including immunological/rheumatology/vascular disorders, ophthalmologic disorders, fibrotic disorders, metabolic & gastro-intestinal disorders, neoplasms and cancer associated disorders comprising administering a subject in a need a therapeutically effective dose of the compounds and/or pharmaceutical compositions of the present invention as described above. In particular, the present invention provides a method of treating and/or preventing a disease or disorder autoimmune, immunological, rheumatology, vascular disorders, ophthalmologic disorders, fibrotic disorders, metabolic and gastro-intestinal disorders, neuroinflammatory and neurodegenerative diseases, neoplasms and cancer associated disorders, hormone related diseases and immunological disorders resulting from viral and bacterial infectious diseases and complications thereof.

Arrows indicate extravasation location. Scale bars, 30 μm. (B) Quantification of vascular leakage by assessing the number of extravasations per field (0.44 mm2). The effect of Ia-007a eye drops was significant by reducing the vascular leakage to the same level that occur in the non-diabetic control group. *$p<0.01$ in comparison with the other groups.

Figure 2:
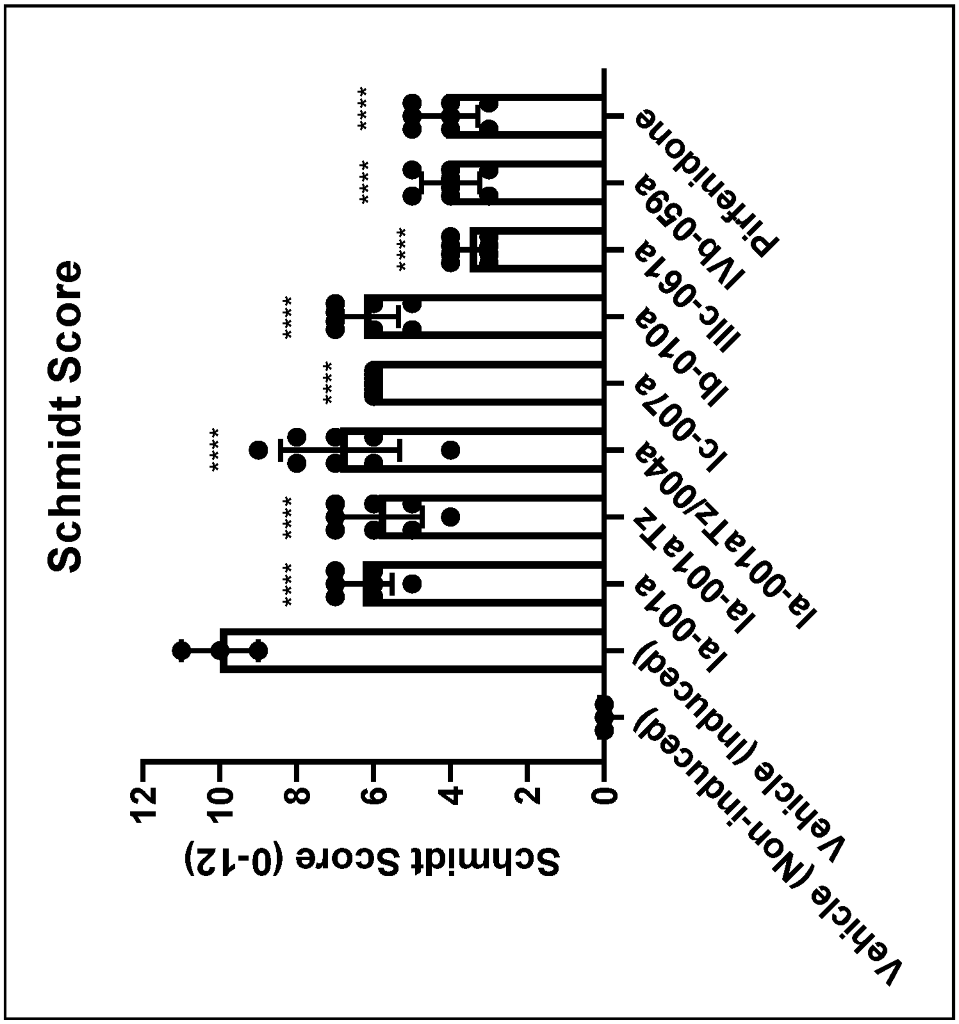

FIG. 2: (A) Schmidt score is the evaluation of the efficacy of the compounds based on the four histopathology assessment criteria which describe pancreatic injury based on the following scores (number in parenthesis) for the four parameters. (a) Edema Interstitial oedema with scores (0) None (1) Interlobular (2) Lobule involved (3) Isolated island like acinar cells. (b) Inflammatory infiltration=leukocytes infiltration with scores (0) None, (1)<20%, (2) 20%-50%, (3)>50%. (c) Parenchymal necrosis=Acinar cell necrosis with scores (0) None, (1)<5%, (2) 5%-20%, (3)>20%. (d) Haemorrhage with scores (0) None, (1) 1-2 points, (2) 3-5 points, (3)>5 points. Schmidt highest score=10 is caerulein induced+vehicle treatment and lowest score=0 is non-induced animals. Schmidt score is the total of a+b+c+d scores and * * * * means statistically significant difference with caerulein induced group as shown in FIG. 2. All products show improved Schmidts score compared to caerulein control animals.

Figure 3C:
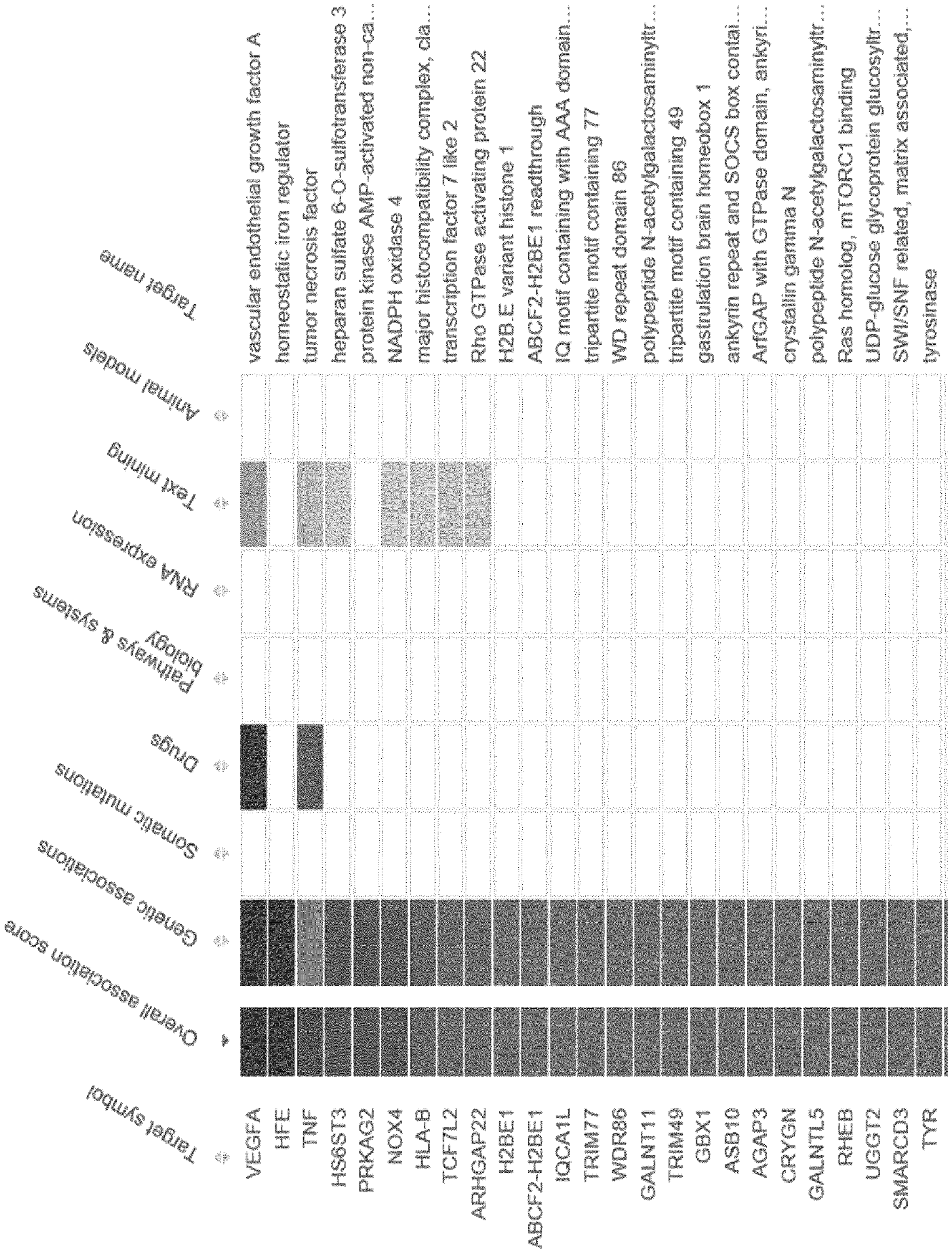
Figure 3D:
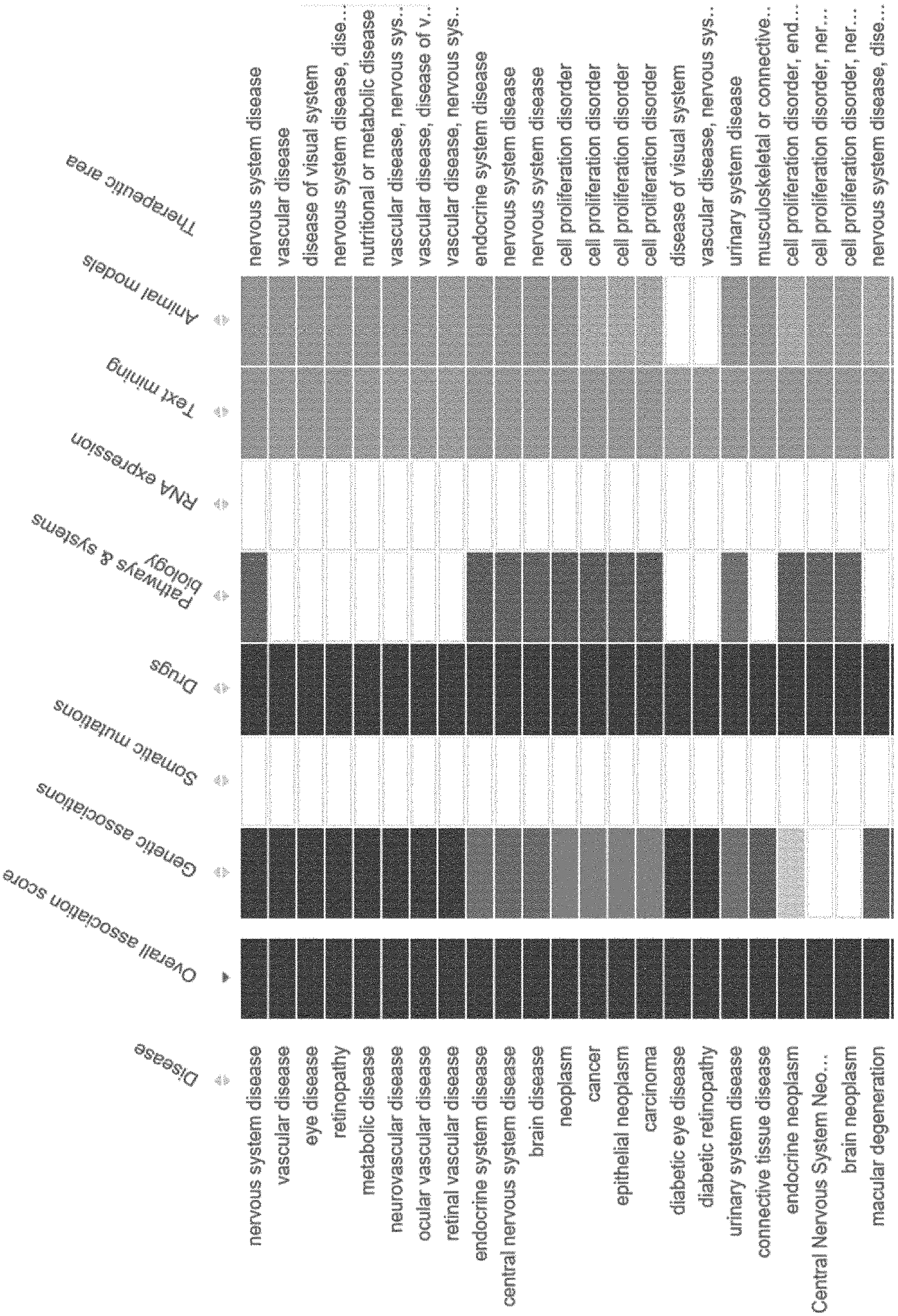

FIGS. 3A-D: FIGS. 3A-B represent a disease list with main cytokines involved in selected diseases (Akdis M. et al, J Allergy Clin Immunol 2016; 138:984-1010) and FIG. 3C represents part of the search results with cytokines and genes ranked by scores and likely to be involved in the selected disease given as an example "diabetic retinopathy" after search in https://www.targetvalidation.org/. In FIG. 3D, search was performed using VEGFA as the cytokine to find a list of diseases where VEGFA is mentioned. Only part of the diseases where VEGFA is involved are represented in FIG. 3D. ref: Open Targets Platform: new developments and updates two years on. Denise Carvalho et al (Nucleic Acids Research, Volume 47, Issue D1, 8 Jan. 2019, D1056-D1065, https://doi.org/10.1093/nar/gky1133).

FIGS. 4 (A-D): represent a table listing the conditions and yields of compounds of type Ia-Id as described in Examples 1.1 to 1.4. Overall yield calculated from starting material 2,5-dihydroxyterephthalic acid.

FIG. 5 (A-C): represent a table listing the conditions and yields of compounds of type IIa-IIc as described in Examples 1.5 to 1.7.

FIG. 6: represent a table listing the conditions and yields of compounds of type IIIa and IIIb as described in Examples 1.8 and 1.9.

FIG. 7: represent a table listing the conditions and yields of compounds of type IIIc as described in Example 1.10.

FIG. 8: is a table listing deprotection procedures as described in Example 1.12 relative to compounds type V.

Figure 9:
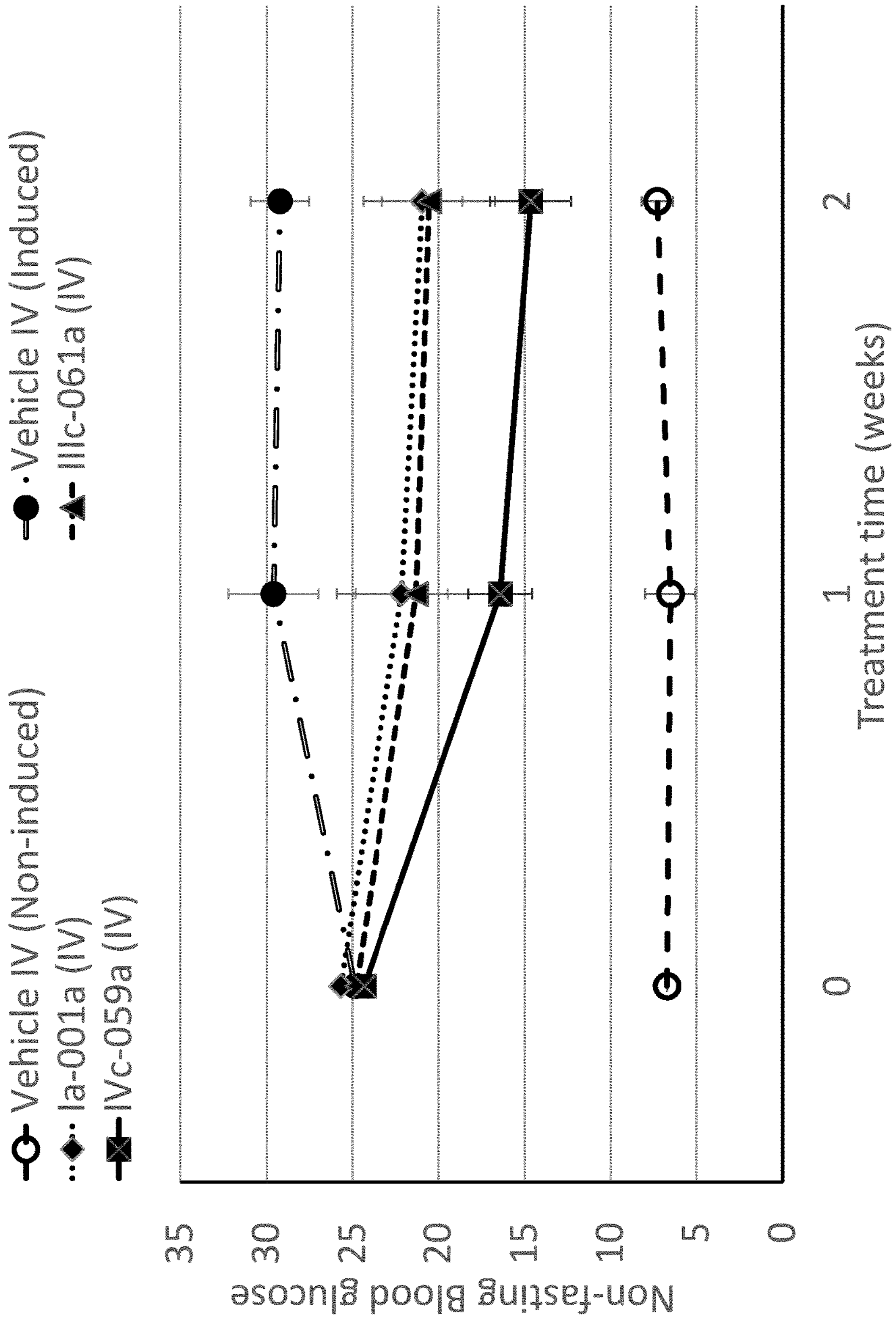

FIG. 9: shows non-fasting blood glucose levels (average±stdev of all animals) in the STZ-induced diabetes model in all animals of each group sampled after at day 0 before dosing, and after 7 and 14 days daily dosing by intravenous or per os routes.

Figure 10:
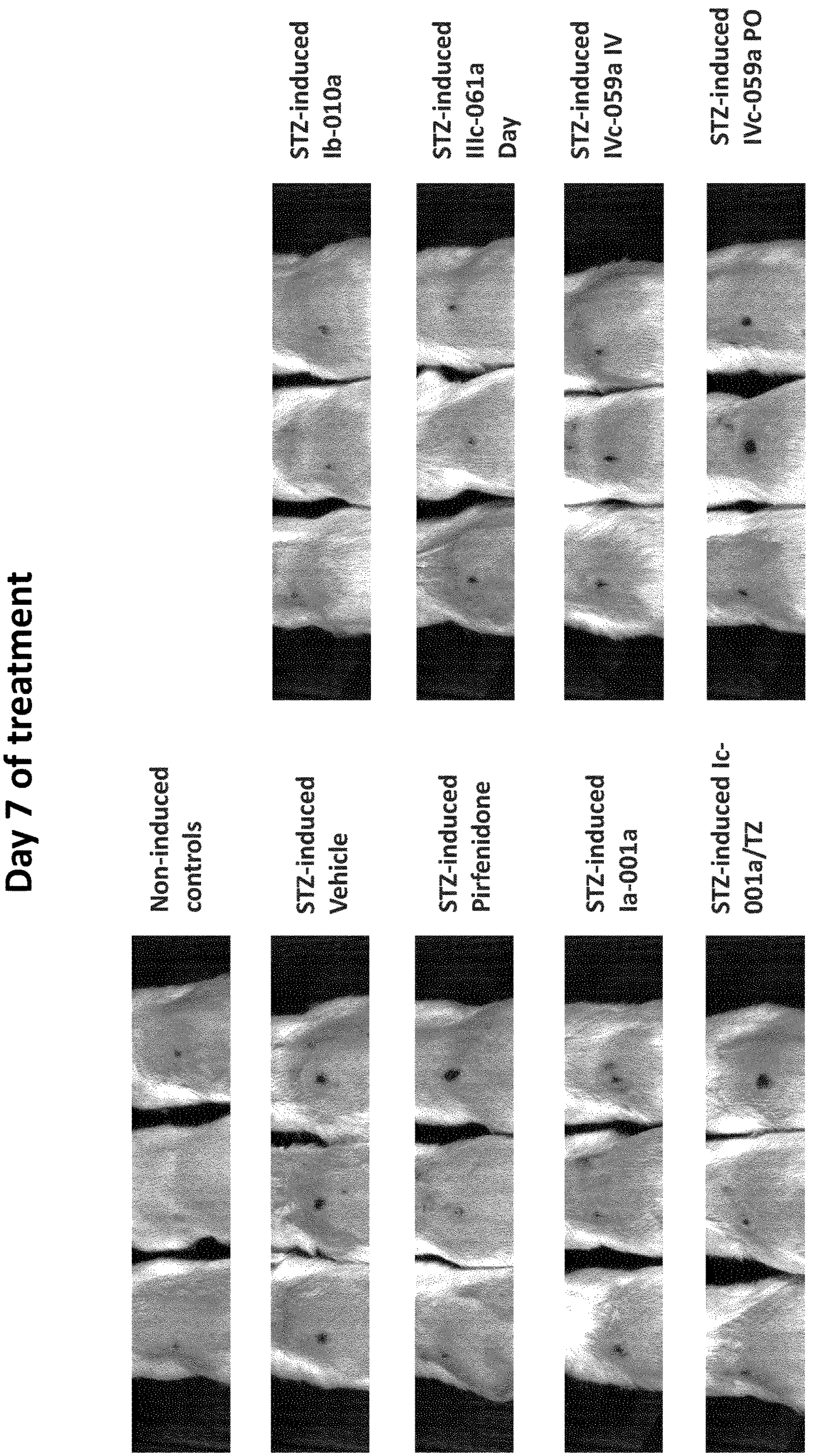

FIG. 10: shows accelerating wound healing in the STZ-induced diabetes model in 3 animals per group sampled after 7 days dosing daily by intravenous or per os routes.

Figure 11:
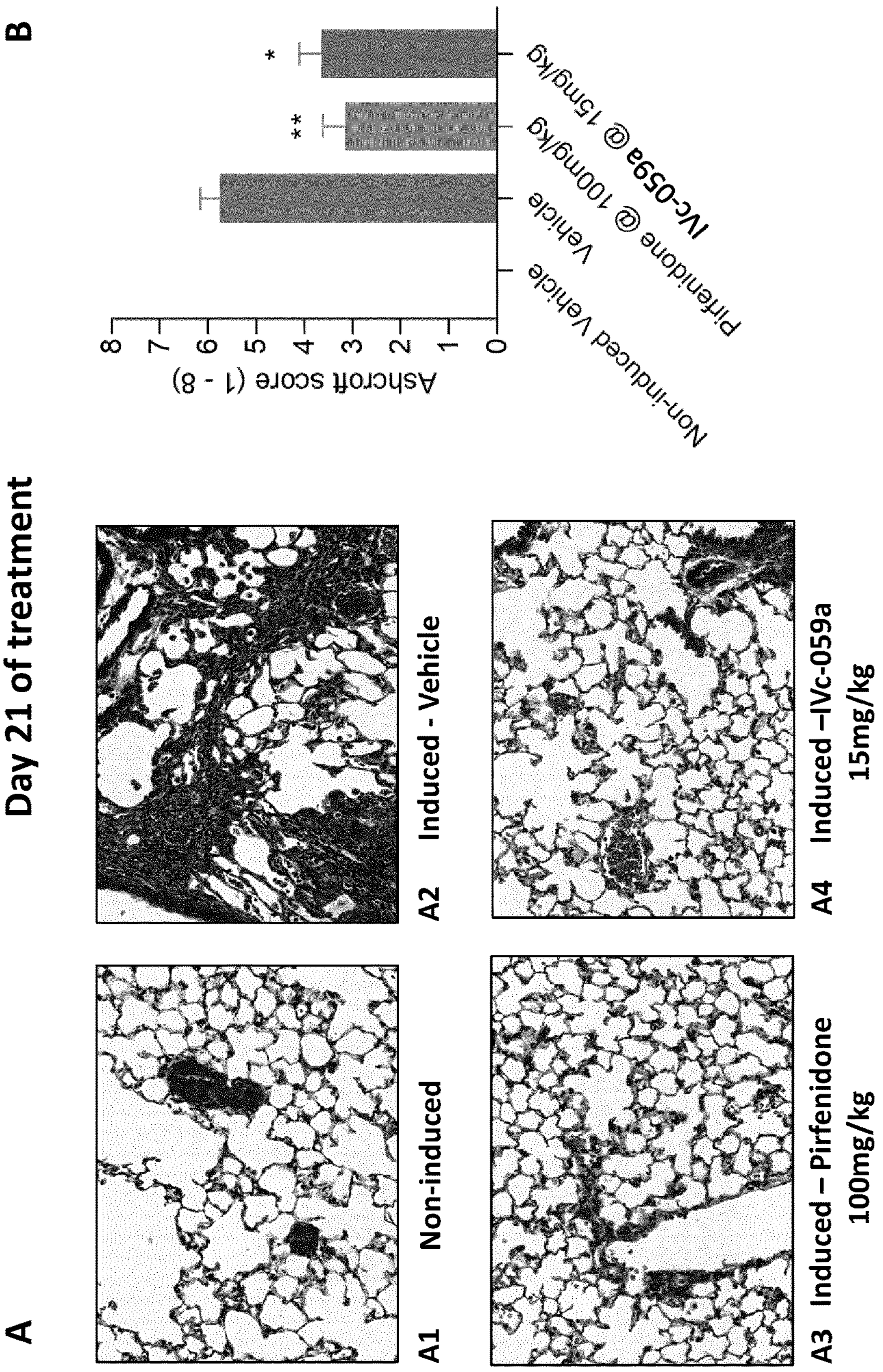

FIG. 11: FIG. 11A shows representative images of lung fibrosis at day 21 of treatment; (A1) non-induced (healthy); A2, Bleomycine induced with vehicle treatment; A3, Bleomycine induced with pirfenidone 100 mg/kg treatment; A4, Bleomycine induced with IVc-059a treatment. FIG. 11B shows the Ashcroft score of healthy, bleomycine induced non-treated versus pirfenidone versus IVc-059a.

DETAILED DESCRIPTION OF THE INVENTION

Disclosed herein are novel compounds useful for the treatment of subjects suffering from a disease, disorder, or dysfunction. Examples of such diseases, disorders, or dysfunctions include without limitation autoimmune, metabolic, inflammatory, degenerative and neoplastic disorders, in particular inflammatory pathologies, angiogenic diseases and/or fibrotic disorders such as diabetic retinopathy, diabetic nephropathy, ankylosing spondylitis, chronic pancreatitis, liver fibrosis, kidney fibrosis, as well as metabolic diseases caused by pancreas dysfunctions.

Hereinafter, unless otherwise specified, the collection of diseases, disorders, or dysfunctions that may be treated utilizing the novel compounds disclosed herein are collectively termed "medical conditions." The term "subject," as used herein, comprises any and all organisms and includes the term "patient." A subject to be treated according to the methods described herein may be one who has been diagnosed by a medical practitioner as suffering from a medical condition. Diagnosis may be performed by any suitable means. One skilled in the art will understand that a subject to be treated according to the present disclosure may have been subjected to standard tests to diagnose the medical conditions. As known to the ordinarily skilled artisan, the clinical features of medical conditions of the type disclosed herein vary according to the pathomechanisms.

Herein "treating" refers to utilizing the disclosed compounds for therapeutic purposes. Therapeutic treatment may be administered, for example, to a subject suffering from the medical condition in order to improve or stabilize the subject's condition. Thus, in the claims and embodiments described herein, treating refers to a subject undergoing for therapeutic purposes, the methodologies disclosed herein.

Prodrugs as used herein refers to any broad pro-drug strategy. For example, prodrug strategies were formally recognized by Adrian Albert in 1958 (Albert, A. Chemical aspects of selective toxicity. Nature, 1958, 182, 421-422) but started in the early part of the previous century, as exemplified by methenamine, phenacetin and prontosil. Prodrugs generally are molecules with little or no pharmacological activity but have a built-in structural lability, whether by chance or by design, that permits bioconversion in vivo into the active drug. The conversion can occur through a chemical or enzymatic process or a combination of the two. Active molecules are often associated with undesirable physicochemical properties that create considerable challenges for their delivery to the appropriate biological target. Prodrugs can improve metabolic instability which is typically attributed to hepatic metabolism. Similarly, unwanted intestinal metabolism of drugs can be overcomed by selective prodrug strategies. This instability can greatly reduce the total amount of a drug that reaches the systemic circulation and its target. Prodrugs can be used to protect active drugs from this first-pass effect by masking a metabolically labile but pharmacologically essential functional group, such as a phenol, to avoid rapid metabolism.

Prodrugs obtained via structural modifications of the drug are designed to influence the inherent physicochemical properties of a molecule to enable its delivery. These developments are not always integrated into the design of new molecules at the discovery phase. Often the analogue optimization, is the preferred path forward. Implementing an early prodrug strategy may result in more rapid clinical development and, ultimately, commercialization of a drug product.

Many prodrug strategies can be applied to influence the lipophilicity of a parent drug. Lipophilicity of drugs has been improved by masking its polar and ionized functionalities by short-chain hydrocarbon promoieties. Hydrophilic hydroxyl, carboxyl, phosphate or amine and other negatively or positively charged groups have been successfully converted to more lipophilic alkyl or aryl esters or N-acyl derivatives, which are rapidly hydrolysed back to the parent drugs in the body by ubiquitous esterases or peptidases.

The present invention thus provides a compound of Formula (I):

Formula (I)

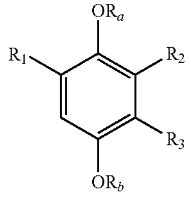

wherein:

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$, $R_2$ and $R_3$ are H or $R_5$, with the proviso that when one of $R_2$ and $R_3$ is $R_5$, the other is H and when one of $R_2$ and $R_3$ is H, the other is $R_5$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_5$=$R_6$, $R_7$ or $R_8$;

$R_6$=CONH—$R_9$, $CONHCOR_9$, $CONH(CH_2)_n$—$R_9$, or $CONHCH(COOR_4)(CH_2)_kR_9$, heteroaryl-$R_9$ wherein k=0-4;

$R_7$=benzoheteroaryl substituted with at least one or more groups selected from: $COOR_4$, $(CH_2)_nCOOR_4$, $SO_3H$, $(CH_2)_nSO_3H$, $OR_4$, azoles [5-membered N-containing heterocycles], or fluorine;

$R_8$=$(CH_2)_mX(CH_2)_pR_9$;

X=O, S, $SO_2$, NH, NAc, or $N(CH_2)_qR_9$;

$R_9$=aryl or heteroaryl substituted with at least one or more groups selected from $COOR_4$, $(CH_2)_nCOOR_4$, $(CH_2)_nSO_3H$, $OR_4$, $SO_3H$, azoles [5-membered N-containing heterocycles], fluorine, C=O, NHCO—$R_{10}$;

$R_{10}$=aryl, or heteroaryl, substituted with at least one or more groups selected from $COOR_4$, $(CH_2)_nCOOR_4$, $(CH_2)_nSO_3H$, $OR_4$, $SO_3H$, azoles [5-membered N-containing heterocycles], fluorine; wherein the aryl of $R_9$ and $R_{10}$ is an aromatic group containing from 6 to 14 carbon atoms, selected among phenyl, naphthyl, biphenyl group; and the heteroaryl $R_9$ and $R_{10}$ is an aromatic group containing 1 to 14 carbon atoms and one or more nitrogen; and n, m, p and q are independently 1-4.

The present invention further provides a compound of formula (I):

(I)

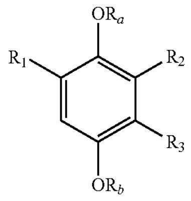

wherein:

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$, $R_2$ and $R_3$ are H or $R_5$, with the proviso that when one of $R_2$ and $R_3$ is $R_5$, the other is H and when one of $R_2$ and $R_3$ is H, the other is $R_5$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_5$=$R_6$, or $R_7$, $R_6$=CONH—$R_9$, $CONHCOR_9$, $CONH(CH_2)_n$—$R_9$, or $CONHCH(COOR_4)(CH_2)_kR_9$; wherein k=0-4;

$R_7$=benzoheteroaryl substituted with at least one or more groups selected from: $COOR_4$, $(CH_2)_nCOOR_4$, $SO_3H$, $(CH_2)_nSO_3H$, $OR_4$, azoles [5-membered N-containing heterocycles], or fluorine;

$R_9$=aryl, heteroaryl, substituted with at least one or more groups selected from $COOR_4$, $(CH_2)_nCOOR_4$, $(CH_2)_nSO_3H$, $OR_4$, $SO_3H$, azoles [5-membered N-containing heterocycles], fluorine, C=O, or NHCO—$R_{10}$;

$R_{10}$=aryl, heteroaryl, substituted with at least one or more groups selected from $COOR_4$, $(CH_2)_nCOOR_4$, $(CH_2)_nSO_3H$, $OR_4$, $SO_3H$, azoles [5-membered N-containing heterocycles], or fluorine; wherein the aryl of $R_9$ and $R_{10}$ is an aromatic group containing from 6 to 14 carbon atoms, selected among phenyl, naphthyl, biphenyl; and the heteroaryl of $R_9$ and $R_{10}$ is an aromatic group containing 1 to 14 carbon atoms and one or more nitrogen; and n, is independently 1-4.

The present invention also provides a compound of formula (I):

(I)

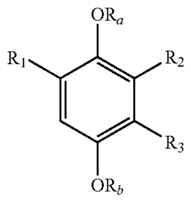

wherein:

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$;

$R_2$ and $R_3$ are H or $R_5$, with the proviso that when one of $R_2$ and $R_3$ is $R_5$, the other is H and when one of $R_2$ and $R_3$ is H, the other is $R_5$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_5$=$R_8$ $R_5$=$(CH_2)_mX(CH_2)_pR_9$;

X=O, S, $SO_2$, NH, NAc, or $N(CH_2)_qR_9$;

$R_9$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], fluorine, C=O, or NHCO—$R_{10}$;

$R_{10}$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], fluorine; wherein the aryl of $R_9$ an $R_{10}$ is an aromatic group containing from 6 to 14 carbon atoms, selected among phenyl, naphthyl, biphenyl group; wherein the heteroaryl $R_9$ an $R_{10}$ is an aromatic group containing 1 to 14 carbon atoms and one or more nitrogen; and n, m, p and q are independently 1-4.

The expression "alkyl" refers to a saturated, straight-chain or branched hydrocarbon group that contains from 1 to 20 carbon atoms, preferably from 1 to 12 carbon atoms, especially from 1 to 6 (e.g., 1, 2, 3 or 4) carbon atoms, for example a methyl, ethyl, propyl, iso-propyl, n-butyl, isobutyl, sec-butyl or tert-butyl. Furthermore, the term alkyl refers to groups in which one or more hydrogen atoms have been replaced by a halogen atom (preferably F or Cl) such as, for example, a 2,2,2-trichloroethyl or a trifluoromethyl group.

The expression "acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_4$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl.

The expression "aryl" refers to an aromatic group that contains one or more rings containing from 6 to 14 ring carbon atoms, preferably from 6 to 10 (especially 6) ring carbon atoms.

The expression "aralkyl" or "aryl$C_{1-4}$alkyl" refers to groups containing both aryl and also alkyl, alkenyl, alkynyl and/or cycloalkyl groups in accordance with the above definitions, but are not limited to benzyl, 2-phenylethyl, 3-phenylpropyl, and 2-naphth-2-ylethyl. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression "heteroaryl" refers to an aromatic group that contains one or more rings containing from 5 to 14 ring atoms, preferably from 5 to 10 (especially 5 or 6 or 9 or 10) ring atoms, and contains one or more (preferably 1, 2, 3 or 4) oxygen, nitrogen, phosphorus or sulfur ring atoms (preferably O, S or N).

Examples are pyridyl (e.g., 4-pyridyl), imidazolyl (e.g., 2-imidazolyl), phenylpyrrolyl (e.g., 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3-bifuryl, pyrazolyl (e.g. 3-pyrazolyl) and isoquinolinyl groups.

The expression "benzoheteroaryl" or "benzoheteroaromatic" refers to bicyclic rings comprising a phenyl ring fused to a monocyclic heteroaromatic ring. Examples of benzoheteroaryl include benzisoxazolyl, benzoxazolyl, benzisothiazolyl, benzothiazolyl, benzimidazolyl, benzofuryl, benzothienyl (including S-oxide and dioxide), quinolyl, isoquinolyl, indazolyl, indolyl, and the like.

The term "azole" refers to a five membered heteroaryl group having a nitrogen ring atom and between 0 and 3 additional ring heteroatoms selected from N, O or S. Imidazole, oxazole, thiazole and tetrazole are representative azole groups.

The expression "cycloalkyl" refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. Specific examples of cycloalkyl groups are a cyclopropyl, cyclobutyl, cyclopentyl, group.

The expression "optionnally substituted" refers to groups in which at least one, or optionally two, three or more hydrogen atoms may have been replaced by fluorine, chlorine, bromine, iodine atoms, or by OH, =O, SH, =S, $NH_2$, =NOH, $N_3$ or $NO_2$ groups. This expression refers furthermore to groups that may be substituted by at least one, two, three or more unsubstituted $C_1$-$C_{10}$ alkyl, $C_2$-$C_{10}$ alkenyl, $C_2$-$C_{10}$ alkynyl, heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{15}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more unsubstituted $C_1$-$C_6$alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl, or $C_2$-$C_{11}$ heteroaralkyl groups.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

Preferably, the present invention provides a hydroquinone derivative compound of formula (I), wherein:

(A)

$R_a$, $R_b$=H, $C_{1-4}$acyl, aryl$C_{1-4}$alkyl, $C_6$-$C_{10}$arylCO, $HOOC(CH_2)_nCO$, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl, $R_1$=$COOR_4$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=CONH—$R_9$;

or (B)

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl, $R_1$=$COOR_4$, $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=CONH—$R_9$.

In a first embodiment, the present invention thus includes compounds in accordance with Table 1:

TABLE 1

| Compound No. | Compound chemical names | Ra | Rb | R4 | R9 |
|---|---|---|---|---|---|
| A. | 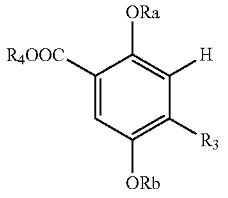 R3 = R5 = CONHR9 | | | | |
| Ia-001a | 4-(2-carboxyphenylaminocarbonyl)-2,5-dihydroxybenzoic acid | H | H | H | 2-carboxyphenyl |
| Ia-001a-Tz | 4-(2-(1H-tetrazol-5-yl)phenyl-aminocarbonyl)-2,5-dihydroxybenzoic acid | H | H | H | 2-(1H-tetrazol-5-yl)phenyl |
| Ia-001c | 2,5-dihydroxy-4-(2-sulfophenylaminocarbonyl)benzoic acid | H | H | H | 2-sulfophenyl |
| Ia-002a | 4-(3-carboxyphenylaminocarbonyl)-2,5-dihydroxybenzoic acid | H | H | H | 3-carboxyphenyl |
| Ia-002a-Tz | 4-(3-(1H-tetrazol-5-yl)phenyl-aminocarbonyl)-2,5-dihydroxybenzoic acid | H | H | H | 3-(1H-tetrazol-5-yl)phenyl |
| Ia-002c | 2,5-dihydroxy-4-(3-sulfophenylaminocarbonyl)benzoic acid | H | H | H | 3-sulfophenyl |
| Ia-003a | 4-(4-carboxyphenyl-aminocarbonyl)-2,5-dihydroxybenzoic acid | H | H | H | 4-carboxyphenyl |
| Ia-003a-Tz | 4-(4-(1H-tetrazol-5-yl)phenyl-aminocarbonyl)-2,5-dihydroxybenzoic acid | H | H | H | 4-(1H-tetrazol-5-yl)phenyl |
| Ia-003c | 2,5-dihydroxy-4-(4-sulfophenylaminocarbonyl)benzoic acid | H | H | H | 4-sulfophenyl |
| Ia-004a | 4-(3-carboxy-4-hydroxyphenylaminocarbonyl)-2,5-dihydroxybenzoic acid | H | H | H | 3-carboxy-4-hydroxyphenyl |
| Ia-005a | 4-(4-carboxy-3-hydroxyphenylaminocarbonyl)-2,5-dihydroxybenzoic acid | H | H | H | 4-carboxy-3-hydroxyphenyl |
| Ia-056a | 4-(4-carboxy-2,5-dihydroxyphenylaminocarbonyl)-2,5-dihydroxybenzoic acid | H | H | H | 4-carboxy-2,5-dihydroxyphenyl |
| Ia-006a | 4-(2-carboxy-4-hydroxyphenylaminocarbonyl)-2,5-dihydroxybenzoic acid | H | H | H | 2-carboxy-4-hydroxyphenyl |
| Ib-010a | 3,5-bis(2,5-dihydroxy-4-carboxybenzoylamino)benzoic acid | H | H | H | 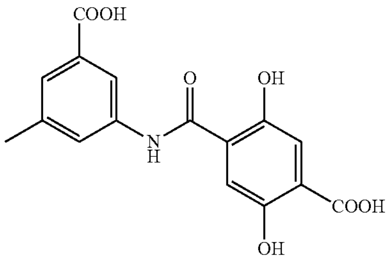 |
| Ia-011a | 3-(4-carboxy-2,5-dihydroxybenzamido)phthalic acid; | H | H | H | 2,3-dicarboxyphenyl |
| Ia-012a | 2-(4-carboxy-2,5-dihydroxybenzamido)terephthalic acid | H | H | H | 2,5-dicarboxyphenyl |
| Ia-013a | Compound 36: 2-(4-carboxy-2,5-dihydroxybenzamido)isophthalic acid | H | H | H | 2,6-dicarboxyphenyl |
| Ia-014a | Compound 38: 4-(4-carboxy-2,5-dihydroxybenzamido)phthalic acid | H | H | H | 3.4-dicarboxyphenyl |
| Ia-015a | 5-(4-carboxy-2,5-dihydroxybenzamido)isophthalic acid | H | H | H | 3.5-dicarboxyphenyl |
| Ia-016a | 2-(4-carboxy-2,5-dihydroxybenzamido)nicotinic acid | H | H | H | 3-carboxypyridin-2-yl |

TABLE 1-continued

| Compound No. | Compound chemical names | Ra | Rb | R4 | R9 |
|---|---|---|---|---|---|
| Ia-017a | 2-(4-carboxy-2,5-dihydroxybenzamido)isonicotinic acid | H | H | H | 4-carboxypyridin-2-yl |
| Ia-018a | 6-(4-carboxy-2,5-dihydroxybenzamido)nicotinic acid | H | H | H | 5-carboxypyridin-2-yl |
| Ia-019a | 6-(4-carboxy-2,5-dihydroxybenzamido)picolinic acid | H | H | H | 6-carboxypyridin-2-yl |
| Ia-020a | 2-(4-carboxy-2,5-dihydroxybenzamido)-5-fluoronicotinic acid | H | H | H | 3-carboxy-5-fluoropyridin-2-yl |
| Ia-021a | 6-(4-carboxy-2,5-dihydroxybenzamido)pyridine-2,5-dicarboxylic acid | H | H | H | 3,6-dicarboxypyridin-2-yl |
| Ia-022a | 2-(4-carboxy-2,5-dihydroxybenzamido)pyridine-3,5-dicarboxylic acid | H | H | H | 3,5-dicarboxypyridin-2-yl |
| Ia-023a | 3-(4-carboxy-2,5-dihydroxybenzamido)isonicotinic acid | H | H | H | 4-carboxypyridin-3-yl |
| Ia-024a | 5-(4-carboxy-2,5-dihydroxybenzamido)nicotinic acid | H | H | H | 5-carboxypyridin-3-yl |
| Ia-025a | 5-(4-carboxy-2,5-dihydroxybenzamido)picolinic acid | H | H | H | 6-carboxypyridin-3-yl |
| Ia-026a | 3-(4-carboxy-2,5-dihydroxybenzamido)picolinic acid | H | H | H | 2-carboxypyridin-3-yl |
| Ia-027a | 5-(4-carboxy-2,5-dihydroxybenzamido)-2-fluoroisonicotinic acid | H | H | H | 4-carboxy-6-fluoropyridin-3-yl |
| Ia-028a | 4-(4-carboxy-2,5-dihydroxybenzamido)nicotinic acid | H | H | H | 3-carboxypyridin-4-yl |
| Ia-029a | 4-(4-carboxy-2,5-dihydroxybenzamido)picolinic acid | H | H | H | 2-carboxypyridin-3-yl |
| Ia-032a | 4-(4-(carboxymethyl)phenylaminocarbonyl)-2,5-dihydroxybenzoic acid | H | H | H | 4-(carboxymethyl)phenyl |
| Ia-033a | 4-(3-(carboxymethyl)phenylaminocarbonyl)-2,5-dihydroxybenzoic acid | H | H | H | 3-(carboxymethyl)phenyl |
| Ia-033a-Hyp | 2,5-dihydroxy-4-(3-(1-hydroxy-1H-pyrazol-4-yl)phenylaminocarbonyl)benzoic acid | H | H | H | 3-(1-hydroxy-1H-pyrazol-4-yl) phenyl |
| Ia-034a | 4-(2-(carboxymethyl)phenylaminocarbonyl)-2,5-dihydroxybenzoic acid | H | H | H | 2-(carboxymethyl)phenyl |
| Ia-001a-E2-A2 | ethyl 4-(2-(ethoxycarbonyl)phenylaminocarbonyl)-2,5-diacetoxybenzoate | Ac | Ac | Et | 2-(ethoxycarbonyl)phenyl |
| Ia-001a-E2 | ethyl 4-(2-(ethoxycarbonyl)phenylaminocarbonyl)-2,5-dihydroxybenzoate | H | H | Et | 2-(ethoxycarbonyl)phenyl |
| Ia-001a-Tz-E1-A2 | ethyl 4-(2-(1H-tetrazol-5-yl)phenylaminocarbonyl)-2,5-diacetoxybenzoate | Ac | Ac | Et | 2-(1H-tetrazol-5-yl)phenyl |
| Ia-001a-Tz-E1 | ethyl 4-(2-(1H-tetrazol-5-yl)phenylaminocarbonyl)-2,5-dihydroxybenzoate | H | H | Et | 2-(1H-tetrazol-5-yl)phenyl |
| Ia-004a-E2 | ethyl 2,5-dihydroxy-4-(4-hydroxy-3-(methoxycarbonyl)phenylaminocarbonyl)benzoate | H | H | Et | 4-hydroxy-3-(methoxycarbonyl)phenyl |
| Ib-010a-E3-A4 | ethyl 3,5-bis(2,5-diacetoxy-4-ethoxycarbonylbenzoylamino)benzoate | Ac | Ac | Et | 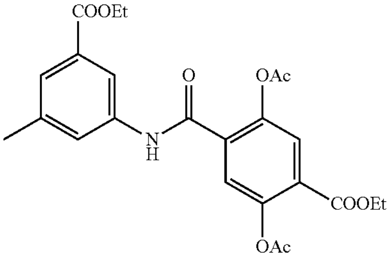 |
| Ib-010a-E3 | ethyl 3,5-bis(2,5-dihydroxy-4-ethoxycarbonylbenzoylamino)benzoate | H | H | Et | 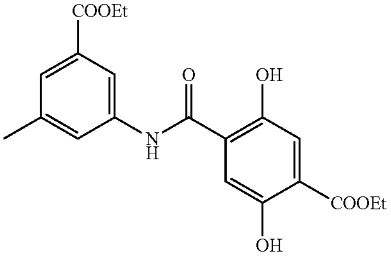 |
| Ia-023a-E2 | ethyl 3-(4-(ethoxycarbonyl)-2,5-dihydroxybenzamido)isonicotinate | H | H | Et | 4-ethoxycarbonylpyridin-3-yl |
| Ia-056a-E2 | Compound 390: Ethyl 4-(4-ethoxycarbonyl-2,5-dihydroxyphenylaminocarbonyl)-2,5-dihydroxybenzoate | H | H | Et | 4-ethoxycarbonyl-2,5-dihydroxyphenyl |

TABLE 1-continued

| Compound No. | Compound chemical names | Ra | Rb | R4 | R9 |
|---|---|---|---|---|---|
| B. | 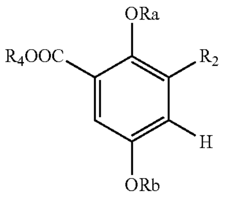 R2 = R5 = CONHR9 | | | | |
| IIa-001a | 3-(2-carboxyphenylaminocarbonyl)-2,5-dihydroxybenzoic acid | H | H | H | 2-carboxyphenyl |
| IIa-001a-Tz | 3-(2-(1H-tetrazol-5-yl)phenylaminocarbonyl)-2,5-dihydroxybenzoic acid | H | H | H | 2-(1H-tetrazol-5-yl)phenyl |
| IIa-001c | 2,5-dihydroxy-3-(2-sulfophenylaminocarbonyl)benzoic acid | H | H | H | 2-sulfophenyl |
| IIa-002a | 3-(3-carboxyphenylaminocarbonyl)-2,5-dihydroxybenzoic acid | H | H | H | 3-carboxyphenyl |
| IIa-002a-Tz | 3-(3-(1H-tetrazol-5-yl)phenylaminocarbonyl)-2,5-dihydroxybenzoic acid | H | H | H | 3-(1H-tetrazol-5-yl)phenyl |
| IIa-002c | 2,5-dihydroxy-3-(3-sulfophenylaminocarbonyl)benzoic acid | H | H | H | 3-sulfophenyl |
| IIa-003a | 3-(4-carboxyphenylaminocarbonyl)-2,5-dihydroxybenzoic acid | H | H | H | 4-carboxyphenyl |
| IIa-003a-Tz | 3-(4-(1H-tetrazol-5-yl)phenylaminocarbonyl)-2,5-dihydroxybenzoic acid | H | H | H | 4-(1H-tetrazol-5-yl)phenyl |
| IIa-003c | 2,5-dihydroxy-3-(4-sulfophenylaminocarbonyl)benzoic acid | H | H | H | 4-sulfophenyl |
| IIa-004a | 3-(3-carboxy-4-hydroxyphenylaminocarbonyl)-2,5-dihydroxybenzoic acid | H | H | H | 3-carboxy-4-hydroxyphenyl |
| IIa-005a | 3-(4-carboxy-3-hydroxyphenylaminocarbonyl)-2,5-dihydroxybenzoic acid | H | H | H | 4-carboxy-3-hydroxyphenyl |
| IIa-006a | 3-(2-carboxy-4-hydroxyphenylaminocarbonyl)-2,5-dihydroxybenzoic acid | H | H | H | 2-carboxy-4-hydroxyphenyl |
| IIb-010a | 3,5-Bis(2,5-dihydroxy-3-carboxybenzoylamino)benzoic acid | H | H | H | 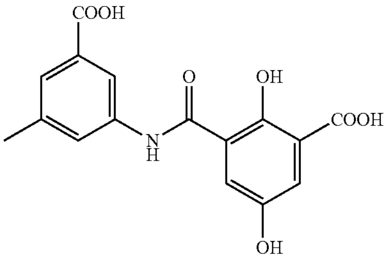 |
| IIa-011a | 3-(3-carboxy-2,5-dihydroxybenzamido)phthalic acid | H | H | H | 2,3-dicarboxyphenyl |
| IIa-012a | 2-(3-carboxy-2,5-dihydroxybenzamido)terephthalic acid | H | H | H | 2,5-dicarboxyphenyl |
| IIa-013a | 2-(3-carboxy-2,5-dihydroxybenzamido)isophthalic acid | H | H | H | 2,6-dicarboxyphenyl |
| IIa-014a | 4-(3-carboxy-2,5-dihydroxybenzamido)phthalic acid | H | H | H | 3,4-dicarboxyphenyl |
| IIa-015a | 5-(3-carboxy-2,5-dihydroxybenzamido)isophthalic acid | H | H | H | 3,5-dicarboxylic acid |
| IIa-016a | 2-(3-carboxy-2,5-dihydroxybenzamido)nicotinic acid | H | H | H | 3-carboxypyridin-2-yl |
| IIa-017a | 2-(3-carboxy-2,5-dihydroxybenzamido)isonicotinic acid | H | H | H | 4-carboxypyridin-2-yl |
| IIa-018a | 6-(3-carboxy-2,5-dihydroxybenzamido)nicotinic acid | H | H | H | 5-carboxypyridin-2-yl |
| IIa-019a | 6-(3-carboxy-2,5-dihydroxybenzamido)picolinic acid | H | H | H | 6-carboxypyridin-2-yl |
| IIa-020a | 2-(3-carboxy-2,5-dihydroxybenzamido)-5-fluoronicotinic acid | H | H | H | 3-carboxy-5-fluoropyridin-2-yl |
| IIa-021a | 6-(3-carboxy-2,5-dihydroxybenzamido)pyridine-2,5-dicarboxylic acid | H | H | H | 3,6-dicarboxypyridin-2-yl |
| IIa-022a | 2-(3-carboxy-2,5-dihydroxybenzamido)pyridine-3,5-dicarboxylic acid | H | H | H | 3,5-dicarboxypyridin-2-yl |
| IIa-023a | 3-(3-carboxy-2,5-dihydroxybenzamido)isonicotinic acid | H | H | H | 4-carboxypyridin-3-yl |

TABLE 1-continued

| Compound No. | Compound chemical names | Ra | Rb | R4 | R9 |
|---|---|---|---|---|---|
| IIa-024a | 5-(3-carboxy-2,5-dihydroxybenzamido)nicotinic acid | H | H | H | 5-carboxypy ridin-3-yl |
| IIa-025a | 5-(3-carboxy-2,5-dihydroxybenzamido)picolinic acid | H | H | H | 6-carboxypyridin-3-yl |
| IIa-026a | 3-(3-carboxy-2,5-dihydroxybenzamido)picolinic acid | H | H | H | 2-carboxypyridin-3-yl |
| IIa-027a | 5-(3-carboxy-2,5-dihydroxybenzamido)-2-fluoroisonicotinic acid | H | H | H | 4-carboxy-6-fluoropyridin-3-yl |
| IIa-028a | 4-(3-carboxy-2,5-dihydroxybenzamido)nicotinic acid | H | H | H | 3-carboxypyridin-4-yl |
| IIa-029a | Compound 172: 4-(3-carboxy-2,5-dihydroxybenzamido)picolinic acid; | H | H | H | 2-carboxypyridin-3-yl |
| IIa-032a | 3-(4-(carboxymethyl)phenylaminocarbonyl)-2,5-dihydroxybenzoic acid | H | H | H | 4-(carboxymethyl)phenyl |
| IIa-033a | 3-(3-(carboxymethyl)phenylaminocarbonyl)-2,5-dihydroxybenzoic acid | H | H | H | 3-(carboxymethyl)phenyl |
| IIa-033a-Hyp | 2,5-dihydroxy-3-(3-(1-hydroxy-1H-pyrazol-4-yl)phenylaminocarbonyl)benzoic acid | H | H | H | 3-(1-hydroxy-1H-pyrazol-4-yl)phenyl |
| IIa-034a | 3-(2-(carboxymethyl)phenylaminocarbonyl)-2,5-dihydroxybenzoic acid | H | H | H | 2-(carboxymethyl)phenyl |
| IIa-001aTz-E1 | ethyl 3-(2-(1H-tetrazol-5-yl)phenylaminocarbonyl)-2,5-dihydroxybenzoate | H | H | Et | 2-(1H-tetrazol-5-yl)phenyl |
| IIa-034a-E2 | ethyl 3-(2-(ethoxycarbonylmethyl)phenylaminocarbonyl)-2,5-dihydroxybenzoate | H | H | Et | 2-(2-ethoxycarbonylmethyl)phenyl |

Preferably, the present invention provides a compound of formula (I), wherein:

(A)

$R_a$, $R_b$=H;

$R_1$=$SO_3H$, $R_2$=H; $R_3$=$R_5$, and $R_5$=$R_6$=CONH—$R_9$;

or (B)

$R_a$, $R_b$=H;

$R_1$=$SO_3H$, $R_3$=H; $R_2$=$R_5$; and $R_5$=$R_6$=CONH—$R_0$.

In a second embodiment, the present invention includes compounds in accordance with Table 2:

TABLE 2

| Compound No. | Compound chemical names | Ra | Rb | R9 |
|---|---|---|---|---|
| A. | 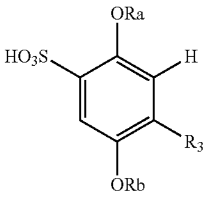 R3 = R5 = CONHR9 | | | |
| Ia-001b | 2-(2,5-dihydroxy-4-sulfobenzamido)benzoic acid | H | H | 2-carboxyphenyl |
| Ia-001d | 2,5-dihydroxy-4-(2-sulfophenylaminocarbonyl)benzenesulfonic acid | H | H | 2-sulfophenyl |
| Ia-002b | 3-(2,5-dihydroxy-4-sulfobenzamido)benzoic acid | H | H | 3-carboxyphenyl |
| Ia-002d | 2,5-dihydroxy-4-(3-sulfophenylaminocarbonyl)benzenesulfonic acid | H | H | 3-sulfophenyl |
| Ia-003b | 4-(2,5-dihydroxy-4-sulfobenzamido)benzoic acid | H | H | 4-carboxyphenyl |
| Ia-003d | 2,5-dihydroxy-4-(4-sulfophenylaminocarbonyl)benzenesulfonic acid | H | H | 4-sulfophenyl |
| Ia-004b | 5-(2,5-dihydroxy-4-sulfobenzamido)-2-hydroxybenzoic acid | H | H | 3-carboxy-4-hydroxyphenyl |
| Ia-005b | 4-(2,5-dihydroxy-4-sulfobenzamido)-2-hydroxybenzoic acid | H | H | 4-carboxy-3-hydroxyphenyl |
| Ia-006b | 2-(2,5-dihydroxy-4-sulfobenzamido)-5-hydroxybenzoic acid | H | H | 2-carboxy-4-hydroxyphenyl |

TABLE 2-continued

| Compound No. | Compound chemical names | Ra | Rb | R9 |
|---|---|---|---|---|
| Ib-010b | 3,5-bis(2,5-dihydroxy-4-sulfobenzamido)benzoic acid | H | H | 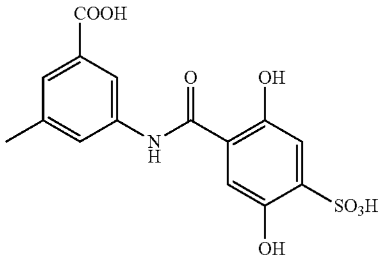 |
| Ia-011b | 3-(2,5-dihydroxy-4-sulfobenzamido)phthalic acid | H | H | 2,3-dicarboxyphenyl |
| Ia-012b | 2-(2,5-dihydroxy-4-sulfobenzamido)terephthalic acid | H | H | 2,5-dicarboxyphenyl |
| Ia-013b | 2-(2,5-dihydroxy-4-sulfobenzamido)isophthalic acid | H | H | 2,6-dicarboxyphenyl |
| Ia-014b | 4-(2,5-dihydroxy-4-sulfobenzamido)phthalic acid | H | H | 3,4-dicarboxyphenyl |
| Ia-015b | 5-(2,5-dihydroxy-4-sulfobenzamido)isophthalic acid | H | H | 3,5-dicarboxyphenyl |
| Ia-016b | 2-(2,5-dihydroxy-4-sulfobenzamido)nicotinic acid | H | H | 3-carboxypyridin-2-yl |
| Ia-017b | 2-(2,5-dihydroxy-4-sulfobenzamido)isonicotinic acid | H | H | 4-carboxypyridin-2-yl |
| Ia-018b | 6-(2,5-dihydroxy-4-sulfobenzamido)nicotinic acid | H | H | 5-carboxypyridin-2-yl |
| Ia-019b | 6-(2,5-dihydroxy-4-sulfobenzamido)picolinic acid | H | H | 6-carboxypyridin-2-yl |
| Ia-020b | 2-(2,5-dihydroxy-4-sulfobenzamido)-5-fluoronicotinic acid | H | H | 3-carboxy-5-fluoropyridin-2-yl |
| Ia-021b | 6-(2,5-dihydroxy-4-sulfobenzamido)pyridine-2,5-dicarboxylic acid | H | H | 3,6-dicarboxypyridin-2-yl |
| Ia-022b | 2-(2,5-dihydroxy-4-sulfobenzamido)pyridine-3,5-dicarboxylic acid | H | H | 3,5-dicarboxypyridin-2-yl |
| Ia-023b | 3-(2,5-dihydroxy-4-sulfobenzamido)isonicotinic acid | H | H | 4-carboxypyridin-3-yl |
| Ia-024b | 5-(2,5-dihydroxy-4-sulfobenzamido)nicotinic acid | H | H | 5-carboxypyridin-3-yl |
| Ia-025b | 5-(2,5-dihydroxy-4-sulfobenzamido)picolinic acid | H | H | 6-carboxypyridin-3-yl |
| Ia-026a | 3-(2,5-dihydroxy-4-sulfobenzamido)picolinic acid | H | H | 2-carboxypyridin-3-yl |
| Ia-027b | 5-(2,5-dihydroxy-4-sulfobenzamido)-2-fluoroisonicotinic acid | H | H | 4-carboxy-6-fluoropyridin-3-yl |
| Ia-028b | 4-(2,5-dihydroxy-4-sulfobenzamido)nicotinic acid | H | H | 3-carboxypyridin-4-yl |
| Ia-029b | 4-(2,5-dihydroxy-4-sulfobenzamido)picolinic acid | H | H | 2-carboxypyridin-3-yl |
| Ia-032b | (4-(2,5-dihydroxy-4-sulfobenzamido)phenyl)acetic acid | H | H | 4-(carboxymethyl)phenyl |
| Ia-033b | (3-(2,5-dihydroxy-4-sulfobenzamido)phenyl)acetic acid | H | H | 3-(carboxymethyl)phenyl |
| Ia-034b | (2-(2,5-dihydroxy-4-sulfobenzamido)phenyl)acetic acid | H | H | 2-(carboxymethyl)phenyl |

B.

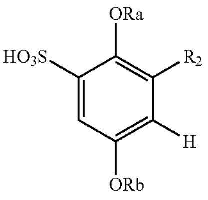

R2 = R5 = CONHR9

| | | | | |
|---|---|---|---|---|
| IIa-001b | 2-(2,5-dihydroxy-3-sulfobenzamido)benzoic acid | H | H | 2-carboxyphenyl |
| IIa-001d | 2,5-dihydroxy-3-(2-sulfophenylaminocarbonyl)benzenesulfonic acid | H | H | 2-sulfophenyl |
| IIa-002b | 3-(2,5-dihydroxy-3-sulfobenzamido)benzoic acid | H | H | 3-carboxyphenyl |
| IIa-002d | 2,5-dihydroxy-3-(3-sulfophenylaminocarbonyl)benzenesulfonic acid | H | H | 3-sulfophenyl |
| IIa-003b | 4-(2,5-dihydroxy-3-sulfobenzamido)benzoic acid | H | H | 4-carboxyphenyl |
| IIa-003d | 2,5-dihydroxy-3-(4-sulfophenylaminocarbonyl)benzenesulfonic acid | H | H | 4-sulfophenyl |

TABLE 2-continued

| Compound No. | Compound chemical names | Ra | Rb | R9 |
|---|---|---|---|---|
| IIa-004b | 5-(2,5-dihydroxy-3-sulfobenzamido)-2-hydroxybenzoic acid | H | H | 3-carboxy-4-hydroxyphenyl |
| IIa-005b | 4-(2,5-dihydroxy-3-sulfobenzamido)-2-hydroxybenzoic acid; | H | H | 4-carboxy-3-hydroxyphenyl |
| IIa-006b | 2-(2,5-dihydroxy-3-sulfobenzamido)-5-hydroxybenzoic acid | H | H | 2-carboxy-4-hydroxyphenyl |
| IIb-010b | 3-(2,5-dihydroxy-3-sulfobenzamido)-5-(2,5-dihydroxy-4-sulfobenzamido)benzoic acid | H | H | 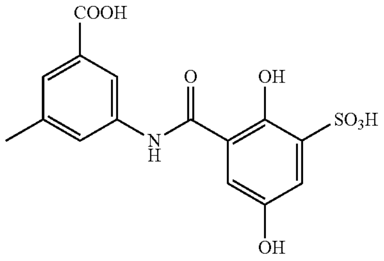 |
| IIa-011b | 3-(2,5-dihydroxy-3-sulfobenzamido)phthalic acid; | H | H | 2,3-dicarboxyphenyl |
| IIa-012b | 2-(2,5-dihydroxy-3-sulfobenzamido)terephthalic acid | H | H | 2,5-dicarboxyphenyl |
| IIa-013b | 2-(2,5-dihydroxy-3-sulfobenzamido)isophthalic acid | H | H | 2,6-dicarboxyphenyl |
| IIa-014b | 4-(2,5-dihydroxy-3-sulfobenzamido)phthalic acid | H | H | 3,4-dicarboxyphenyl |
| IIa-015b | 5-(2,5-dihydroxy-3-sulfobenzamido)isophthalic acid | H | H | 3,5-dicarboxyphenyl |
| IIa-016b | 2-(2,5-dihydroxy-3-sulfobenzamido)nicotinic acid | H | H | 3-carboxypyridin-2-yl |
| IIa-017b | 2-(2,5-dihydroxy-3-sulfobenzamido)isonicotinic acid | H | H | 4-carboxypyridin-2-yl |
| IIa-018b | 6-(2,5-dihydroxy-3-sulfobenzamido)nicotinic acid | H | H | 5-carboxypyridin-2-yl |
| IIa-019b | 6-(2,5-dihydroxy-3-sulfobenzamido)picolinic acid | H | H | 6-carboxypyridin-2-yl |
| IIa-020b | 2-(2,5-dihydroxy-3-sulfobenzamido)-5-fluoronicotinic acid | H | H | 3-carboxy-5-fluoropyridin-2-yl |
| IIa-021b | 6-(2,5-dihydroxy-3-sulfobenzamido)pyridine-2,5-dicarboxylic acid; | H | H | 3,6-dicarboxypyridin-2-yl |
| IIa-022b | 2-(2,5-dihydroxy-3-sulfobenzamido)pyridine-3,5-dicarboxylic acid | H | H | 3,5-dicarboxypyridin-2-yl |
| IIa-023b | 3-(2,5-dihydroxy-3-sulfobenzamido)isonicotinic acid | H | H | 4-carboxypyridin-3-yl |
| IIa-024b | 5-(2,5-dihydroxy-3-sulfobenzamido)nicotinic acid | H | H | 5-carboxypyridin-3-yl |
| IIa-025b | 5-(2,5-dihydroxy-3-sulfobenzamido)picolinic acid | H | H | 6-carboxypyridin-3-yl |
| IIa-026b | 3-(2,5-dihydroxy-3-sulfobenzamido)picolinic acid | H | H | 2-carboxypyridin-3-yl |
| IIa-027b | 5-(2,5-dihydroxy-3-sulfobenzamido)-2-fluoroisonicotinic acid | H | H | 4-carboxy-6-fluoropyridin-3-yl |
| IIa-028b | 4-(2,5-dihydroxy-3-sulfobenzamido)nicotinic acid | H | H | 3-carboxypyridin-4-yl |
| IIa-029b | Compound 173: 4-(2,5-dihydroxy-3-sulfobenzamido)picolinic acid | H | H | 2-carboxypyridin-3-yl |
| IIa-032b | (4-(2,5-dihydroxy-3-sulfobenzamido)phenyl)acetic acid | H | H | 4-(carboxymethyl)phenyl |
| IIa-033b | (3-(2,5-dihydroxy-3-sulfobenzamido)phenyl)acetic acid | H | H | 3-(carboxymethyl)phenyl |
| IIa-034b | (2-(2,5-dihydroxy-3-sulfobenzamido)phenyl)acetic acid | H | H | 2-(carboxymethyl)phenyl |

Preferably, the present invention provides a hydroquinone derivative compound of formula (I), wherein:

(A)

$R_a$, $R_b$=H;

$R_1$=$(CH_2)_nCOOR_4$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=CONH—$R_9$;

Or (B)

$R_a$, $R_b$=H;

$R_1$=$(CH_2)_nCOOR_4$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=CONH—$R_9$.

In a third embodiment, the present invention includes compounds in accordance with Table 3:

TABLE 3

| Compound No. | Compound chemical names | R1 | Ra | Rb | R9 |
|---|---|---|---|---|---|
| A. | | 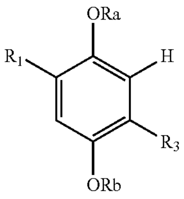 | | | |
| | | R3 = R5 = R6 = CONH-R9 | | | |
| IIIa-001a | 2-(4-(carboxymethyl)-2,5-dihydroxybenzamido)benzoic acid | CH2COOH | H | H | 2-carboxyphenyl |
| IIIa-001a-Tz | (2-(1H-tetrazol-5-yl)phenylaminocarbonyl)-2,5-dihydroxyphenyl)acetic acid | CH2COOH | H | H | 2-(1H-tetrazol-5-yl)phenyl |
| IIIa-001c | (2,5-dihydroxy-4-(2-sulfophenylaminocarbonyl)phenyl)acetic acid | CH2COOH | H | H | 2-sulfophenyl |
| IIIa-002a | 3-(4-(carboxymethyl)-2,5-dihydroxybenzamido)benzoic acid; | CH2COOH | H | H | 3-carboxyphenyl |
| IIIa-002c | (2,5-dihydroxy-4-(3-sulfophenylaminocarbonyl)phenyl)acetic acid; | CH2COOH | H | H | 3-sulfophenyl |
| IIIa-003a | 4-(4-(carboxymethyl)-2,5-dihydroxybenzamido)benzoic acid; | CH2COOH | H | H | 4-carboxyphenyl |
| IIIa-003c | 2-(2,5-dihydroxy-4-(4-sulfophenylaminocarbonyl)phenyl)acetic acid; | CH2COOH | H | H | 4-sulfophenyl |
| IIIa-004a | Compound 216: 5-(4-(carboxymethyl)-2,5-dihydroxybenzamido)-2-hydroxybenzoic acid | CH2COOH | H | H | 3-carboxy-4-hydroxyphenyl |
| IIIa-005a | 4-(4-(carboxymethyl)-2,5-dihydroxybenzamido)-2-hydroxybenzoic acid | CH2COOH | H | H | 4-carboxy-3-hydroxyphenyl |
| IIIa-006a | 2-(4-(carboxymethyl)-2,5-dihydroxybenzamido)-5-hydroxybenzoic acid | CH2COOH | H | H | 2-carboxy-4-hydroxyphenyl |
| IIIb-010a | 3,5-Bis(2,5-dihydroxy-4-carboxymethylbenzoylamino)benzoic acid | CH2COOH | H | H | 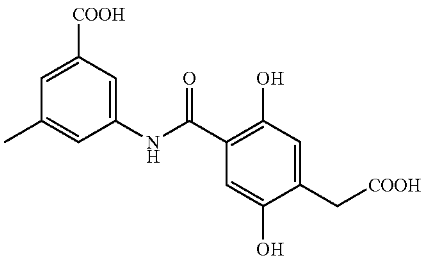 |
| IIIa-011a | 3-(4-(carboxymethyl)-2,5-dihydroxybenzamido)phthalic acid | CH2COOH | H | H | 2,3-dicarboxyphenyl |
| IIIa-012a | 2-(4-(carboxymethyl)-2,5-dihydroxybenzamido)terephthalic acid | CH2COOH | H | H | 2,5-dicarboxyphenyl |
| IIIa-013a | 2-(4-(carboxymethyl)-2,5-dihydroxybenzamido)isophthalic acid | CH2COOH | H | H | 2,6-dicarboxyphenyl |
| IIIa-014a | 4-(4-(carboxymethyl)-2,5-dihydroxybenzamido)phthalic acid | CH2COOH | H | H | 3.4-dicarboxyphenyl |
| IIIa-015a | 5-(4-(carboxymethyl)-2,5-dihydroxybenzamido)isophthalic acid | CH2COOH | H | H | 3.5-dicarboxyphenyl |
| IIIa-016a | 2-(4-(carboxymethyl)-2,5-dihydroxybenzamido)nicotinic acid | CH2COOH | H | H | 3-carboxypyridin-2-yl |
| IIIa-017a | 2-(4-(carboxymethyl)-2,5-dihydroxybenzamido)isonicotinic acid | CH2COOH | H | H | 4-carboxypyridin-2-yl |
| IIIa-018a | 6-(4-(carboxymethyl)-2,5-dihydroxybenzamido)nicotinic acid | CH2COOH | H | H | 5-carboxypyridin-2-yl |
| IIIa-019a | 6-(4-(carboxymethyl)-2,5-dihydroxybenzamido)picolinic acid | CH2COOH | H | H | 6-carboxypyridin-2-yl |
| IIIa-020a | 2-(4-(carboxymethyl)-2,5-dihydroxybenzamido)-5-fluoronicotinic acid | CH2COOH | H | H | 3-carboxy-5-fluoropyridin-2-yl |
| IIIa-021a | 6-(4-(carboxymethyl)-2,5-dihydroxybenzamido)pyridine-2,5-dicarboxylic acid | CH2COOH | H | H | 3,6-dicarboxypyridin-2-yl |

TABLE 3-continued

| Compound No. | Compound chemical names | R1 | Ra | Rb | R9 |
|---|---|---|---|---|---|
| IIIa-022a | 2-(4-(carboxymethyl)-2,5-dihydroxybenzamido)pyridine-3,5-dicarboxylic acid | CH2COOH | H | H | 3,5-dicarboxypyridin-2-yl |
| IIIa-023a | 3-(4-(carboxymethyl)-2,5-dihydroxybenzamido)isonicotinic acid; | CH2COOH | H | H | 4-carboxypyridin-3-yl |
| IIIa-024a | 5-(4-(carboxymethyl)-2,5-dihydroxybenzamido)nicotinic acid | CH2COOH | H | H | 5-carboxypy ridin-3-yl |
| IIIa-025a | 5-(4-(carboxymethyl)-2,5-dihydroxybenzamido)picolinic acid | CH2COOH | H | H | 6-carboxypyridin-3-yl |
| IIIa-026a | 3-(4-(carboxymethyl)-2,5-dihydroxybenzamido)picolinic acid | CH2COOH | H | H | 2-carboxypyridin-3-yl |
| IIIa-027a | 5-(4-(carboxymethyl)-2,5-dihydroxybenzamido)-2-fluoroisonicotinic acid | CH2COOH | H | H | 4-carboxy-6-fluoropyridin-3-yl |
| IIIa-028a | 4-(4-(carboxymethyl)-2,5-dihydroxybenzamido)nicotinic acid; | CH2COOH | H | H | 3-carboxypyridin-4-yl |
| IIIa-029a | 4-(4-(carboxymethyl)-2,5-dihydroxybenzamido)picolinic acid; | CH2COOH | H | H | 2-carboxypyridin-3-yl |
| IIIa-032a | (4-(4-(carboxymethyl)-2,5-dihydroxybenzamido)phenyl)acetic acid | CH2COOH | H | H | 4-(carboxymethyl)phenyl |
| IIIa-033a | (3-(4-(carboxymethyl)-2,5-dihydroxybenzamido)phenyl)acetic acid | CH2COOH | H | H | 3-(carboxymethyl)phenyl |
| IIIa-034a | (2-(4-(carboxymethyl)-2,5-dihydroxybenzamido)phenyl)acetic acid | CH2COOH | H | H | 2-(carboxymethyl)phenyl |
| IIIa-001a-E2 | methyl 2-(4-(ethoxycarbonylmethyl)-2,5-dihydroxybenzamido)benzoate | CH2COOEt | H | H | 2-(methoxycarbonyl)phenyl |
| IIIa-001aTz-E1 | Compound 383: ethyl (4-(2-(1H-tetrazol-5-yl)phenylaminocarbonyl)-2,5-dihydroxyphenyl)acetate; | CH2COOEt | H | H | 2-(1H-tetrazol-5-yl)phenyl |
| IIIa-015a-E3 | diethyl 5-(4-(ethoxycarbonylmethyl)-2,5-dihydroxybenzamido)isophthalate | CH2COOEt | H | H | 3,5-diethoxycarbonylphenyl |
| IIIb-010a-E3 | methyl 3,5-bis(4-(ethoxycarbonylmethyl)-2,5-dihydroxybenzamido)benzoate | CH2COOEt | H | H | 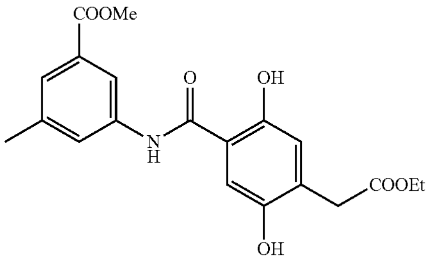 |
| B. | 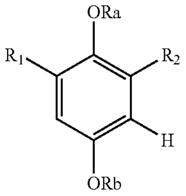 R2 = R5 = R6 = CONHR9 | | | | |
| IVa-001a | 2-(3-(carboxymethyl)-2,5-dihydroxybenzamido)benzoic acid | CH2COOH | H | H | 2-carboxyphenyl |
| IVa-001c | (2,5-dihydroxy-3-(2-sulfophenylaminocarbonyl)phenyl)acetic acid | CH2COOH | H | H | 2-sulfophenyl |
| IVa-002a | 3-(3-(carboxymethyl)-2,5-dihydroxybenzamido)benzoic acid | CH2COOH | H | H | 3-carboxyphenyl |
| IVa-002c | (2,5-dihydroxy-3-(3-sulfophenylaminocarbonyl)phenyl)acetic acid | CH2COOH | H | H | 3-sulfophenyl |
| IVa-003a | 4-(3-(carboxymethyl)-2,5-dihydroxybenzamido)benzoic acid | CH2COOH | H | H | 4-carboxyphenyl |
| IVa-003c | (2,5-dihydroxy-3-(4-sulfophenylaminocarbonyl)phenyl)acetic acid | CH2COOH | H | H | 4-sulfophenyl |
| IVa-004a | 5-(3-(carboxymethyl)-2,5-dihydroxybenzamido)-2-hydroxybenzoic acid | CH2COOH | H | H | 3-carboxy-4-hydroxyphenyl |

TABLE 3-continued

| Compound No. | Compound chemical names | R1 | Ra | Rb | R9 |
|---|---|---|---|---|---|
| IVa-005a | 4-(3-(carboxymethyl)-2,5-dihydroxybenzamido)-2-hydroxybenzoic acid | CH2COOH | H | H | 4-carboxy-3-hydroxyphenyl |
| IVa-006a | Compound 295: 2-(3-(carboxymethyl)-2,5-dihydroxybenzamido)-5-hydroxybenzoic acid; | CH2COOH | H | H | 2-carboxy-4-hydroxyphenyl |
| IVb-010a | 3,5-Bis(2,5-dihydroxy-3-carboxymethylbenzoylamino)benzoic acid | CH2COOH | H | H | 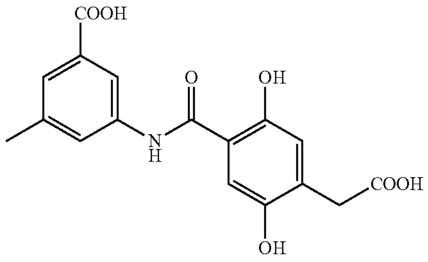 |
| IVa-011a | 3-(3-(carboxymethyl)-2,5-dihydroxybenzamido)phthalic acid | CH2COOH | H | H | 2,3-dicarboxyphenyl |
| IVa-012a | 2-(3-(carboxymethyl)-2,5-dihydroxybenzamido)terephthalic acid | CH2COOH | H | H | 2,5-dicarboxyphenyl |
| IVa-013a | 2-(3-(carboxymethyl)-2,5-dihydroxybenzamido)isophthalic acid | CH2COOH | H | H | 2,6-dicarboxyphenyl |
| IVa-014a | 4-(3-(carboxymethyl)-2,5-dihydroxybenzamido)phthalic acid | CH2COOH | H | H | 3.4-dicarboxyphenyl |
| IVa-015a | 5-(3-(carboxymethyl)-2,5-dihydroxybenzamido)isophthalic acid | CH2COOH | H | H | 3,5-dicarboxyphenyl |
| IVa-016a | 2-(3-(carboxymethyl)-2,5-dihydroxybenzamido)nicotinic acid | CH2COOH | H | H | 3-carboxypyridin-2-yl |
| IVa-017a | 2-(3-(carboxymethyl)-2,5-dihydroxybenzamido)isonicotinic acid | CH2COOH | H | H | 4-carboxypyridin-2-yl |
| IVa-018a | 6-(3-(carboxymethyl)-2,5-dihydroxybenzamido)nicotinic acid | CH2COOH | H | H | 5-carboxypyridin-2-yl |
| IVa-019a | 6-(3-(carboxymethyl)-2,5-dihydroxybenzamido)picolinic acid | CH2COOH | H | H | 6-carboxypyridin-2-yl |
| IVa-020a | 2-(3-(carboxymethyl)-2,5-dihydroxybenzamido)-5-fluoronicotinic acid | CH2COOH | H | H | 3-carboxy-5-fluoropyridin-2-yl |
| IVa-021a | 6-(3-(carboxymethyl)-2,5-dihydroxybenzamido)pyridine-2,5-dicarboxylic acid | CH2COOH | H | H | 3,6-dicarboxypyridin-2-yl |
| IVa-022a | 2-(3-(carboxymethyl)-2,5-dihydroxybenzamido)pyridine-3,5-dicarboxylic acid | CH2COOH | H | H | 3,5-dicarboxypyridin-2-yl |
| IVa-023a | 3-(3-(carboxymethyl)-2,5-dihydroxybenzamido)isonicotinic acid | CH2COOH | H | H | 4-carboxypyridin-3-yl |
| IVa-024a | 5-(3-(carboxymethyl)-2,5-dihydroxybenzamido)nicotinic acid | CH2COOH | H | H | 5-carboxypyridin-3-yl |
| IVa-025a | 5-(3-(carboxymethyl)-2,5-dihydroxybenzamido)picolinic acid | CH2COOH | H | H | 6-carboxypyridin-3-yl |
| IVa-026a | 3-(3-(carboxymethyl)-2,5-dihydroxybenzamido)picolinic acid | CH2COOH | H | H | 2-carboxypyridin-3-yl |
| IVa-027a | 5-(3-(carboxymethyl)-2,5-dihydroxybenzamido)-2-fluoroisonicotinic acid | CH2COOH | H | H | 4-carboxy-6-fluoropyridin-3-yl |
| IVa-028a | 4-(3-(carboxymethyl)-2,5-dihydroxybenzamido)nicotinic acid | CH2COOH | H | H | 3-carboxypyridin-4-yl |
| IVa-029a | 4-(3-(carboxymethyl)-2,5-dihydroxybenzamido)picolinic acid | CH2COOH | H | H | 2-carboxypyridin-3-yl |
| IVa-032a | (4-(3-(carboxymethyl)-2,5-dihydroxybenzamido)phenyl)acetic acid | CH2COOH | H | H | 4-(carboxymethyl)phenyl |
| IVa-033a | (3-(3-(carboxymethyl)-2,5-dihydroxybenzamido)phenyl)acetic acid | CH2COOH | H | H | 3-(carboxymethyl)phenyl |
| IVa-034a | (2-(3-(carboxymethyl)-2,5-dihydroxybenzamido)phenyl)acetic acid | CH2COOH | H | H | 2-(carboxymethyl)phenyl |

Preferably, the present invention provides a hydroquinone derivative compound of formula (I), wherein:

(A)

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=CONH—$R_{10}$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino- $C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=CONH—$R_9$,

Or (B)

$R_a$, $R_b$=H, $C_{1-4}$acyl, aryl$C_{1-4}$alkyl, $C_6$-$C_{10}$arylCO, $HOOC(CH_2)_nCO$, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=CONH—$R_{10}$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=CONH—$R_9$.

In a fourth embodiment, the present invention includes compounds in accordance with Table 4:

TABLE 4

| Compound No. | Compound chemical names | Ra | Rb | R10 | R9 |
|---|---|---|---|---|---|
| A. | 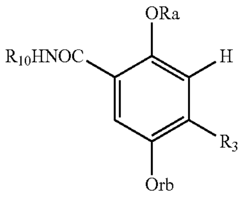<br>R3 = R5 = R6 = CONH-$R_9$ | | | | |
| Ic-001a-Tz/1-004a | 5-(4-(2-(1H-tetrazol-5-yl)phenylaminocarbonyl)-2,5-dihydroxybenzamido)-2-hydroxy benzoic acid | H | H | 3-carboxy-4-hydroxyphenyl | 2-(1H-tetrazol-5-yl)phenyl |
| Ic-001a-Tz(2) | $N_1$,$N_4$-bis(2-(1H-tetrazol-5-yl)phenyl)-2,5-dihydroxyterephthalamide | H | H | 2-(1H-tetrazol-5-yl)phenyl | 2-(1H-tetrazol-5-yl)phenyl |
| Ic-007a | 5-(4-(3-carboxy-4-hydroxyphenylaminocarbonyl)-2,5-dihydroxybenzamido)-2-hydroxy benzoic acid; | H | H | 3-carboxy-4-hydroxyphenyl | 3-carboxy-4-hydroxyphenyl |
| Ic-007b | 5-(2,5-dihydroxy-4-(4-hydroxy-3-sulfophenylaminocarbonyl)benzamido)-2-hydroxy benzenesulphonic acid | H | H | 4-hydroxy-3-sulfonylphenyl | 4-hydroxy-3-sulfonylphenyl |
| Ic-008a | 4-(4-(4-carboxy-3-hydroxyphenylaminocarbonyl)-2,5-dihydroxybenzamido)-2-hydroxy benzoic acid | H | H | 4-carboxy-3-hydroxyphenyl | 4-carboxy-3-hydroxyphenyl |
| Ic-008b | 4-(2,5-dihydroxy-4-(3-hydroxy-4-sulfophenylaminocarbonyl)benzamido)-2-hydroxy benzenesulphonic acid | H | H | 3-hydroxy-4-sulfonylphenyl | 3-hydroxy-4-sulfonylphenyl |
| Ic-009a | 2-(2,5-dihydroxy-4-(4-hydroxy-2-carboxyphenylaminocarbonyl) benzamido)-5-hydroxy benzoic acid | H | H | 2-carboxy-4-hydroxyphenyl | 2-carboxy-4-hydroxyphenyl |
| Ic-009b | 2-(2,5-dihydroxy-4-(4-hydroxy-2-sulfophenylaminocarbonyl) benzamido)-5-hydroxy benzene sulphonic acid | H | H | 4-hydroxy-2-sulfophenyl | 4-hydroxy-2-sulfophenyl |
| Ib-001a-Tz/1-004a-E1 | methyl 5-(4-(2-(1H-tetrazol-5-yl)phenylaminocarbonyl)-2,5-dihydroxybenzamido)-2-hydroxybenzoate; | H | H | 4-hydroxy-3-(methoxycarbonyl) phenyl- | 2-(1H-tetrazol-5-yl)phenyl |
| Ic-007a-E2-A4 | methyl 5-(2,5-diacetoxy-4-(4-acetoxy-3-(methoxycarbonyl)phenylaminocarbonyl) benzamido)-2-acetoxybenzoate; | Ac | Ac | 4-acetoxy-3-(methoxycarbonyl) phenyl | 4-acetoxy-3-(methoxycarbonyl)phenyl |
| Ic-007a-E2 | methyl 5-(2,5-dihydroxy-4-(4-hydroxy-3-(methoxycarbonyl)phenylaminocarbonyl) benzamido)-2-hydroxybenzoate; | H | H | 4-hydroxy-3-(methoxycarbonyl) phenyl | 4-hydroxy-3-(methoxycarbonyl)phenyl |

TABLE 4-continued

| Compound No. | Compound chemical names | Ra | Rb | R10 | R9 |
|---|---|---|---|---|---|
| Ic-007a-pive2 | 1-(2,2-dimethylpropanoyloxy)ethyl 5-[[4-[[3-[1-(2,2-dimethylpropanoyloxy)ethoxycarbonyl]-4-hydroxy-phenyl]carbamoyl]-2,5-dihydroxy-benzoyl]amino]-2-hydroxybenzoate | H | H | 3-[1-(2,2-dimethylpropanoyloxy) ethoxycarbonyl]-4-hydroxyphenyl | 3-[1-(2,2-dimethylpropanoyloxy) ethoxycarbonyl]-4-hydroxy-phenyl |
| Ic-009a-E2 | : methyl 2-(2,5-dihydroxy-4-(4-hydroxy-2-(methoxycarbonyl)phenylaminocarbonyl) benzamido)-5-hydroxybenzoate | H | H | 4-hydroxy-2-(methoxycarbonyl) phenyl | 4-hydroxy-2-(methoxycarbonyl)phenyl |
| B. | 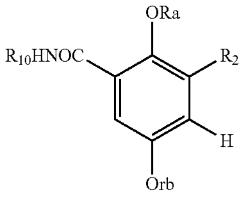 R2 = R5 = R6 = CONH-R9 | | | | |
| IIc-007a | 5-(3-(3-carboxy-4-hydroxyphenylaminocarbonyl)-2,5-dihydroxybenzamido)-2-hydroxy benzoic acid | H | H | 3-carboxy-4-hydroxyphenyl | 3-carboxy-4-hydroxyphenyl |
| IIc-007b | 5-(2,5-dihydroxy-3-(4-hydroxy-3-sulfophenylaminocarbonyl)benzamido)-2-hydroxy benzenesulphonic acid | H | H | 4-hydroxy-3-sulfophenyl | 4-hydroxy-3-sulfophenyl |
| IIc-008a | 4-(3-(3-hydroxy-4-carboxyphenylaminocarbonyl)-2,5-dihydroxybenzamido)-2-hydroxy benzoic acid | H | H | 3-hydroxy-4-carboxyphenyl | 3-hydroxy-4-carboxyphenyl |
| IIc-008b | 4-(2,5-dihydroxy-3-(3-hydroxy-4-sulfophenylaminocarbonyl)benzamido)-2-hydroxy benzenesulphonic acid | H | H | 3-hydroxy-4-sulfophenyl | 3-hydroxy-4-sulfophenyl |
| IIc-009a | 2-(3-(2-carboxy-4-hydroxyphenylaminocarbonyl)-2,5-dihydroxybenzamido)-5-hydroxyl benzoic acid | H | H | 2-carboxy-4-hydroxyphenyl | 2-carboxy-4-hydroxyphenyl |
| IIc-009b | 2-(2,5-dihydroxy-3-(4-hydroxy-2-sulfophenylaminocarbonyl)benzamido)-5-hydroxy benzenesulphonic acid | H | H | 4-hydroxy-2-sulfophenyl | 4-hydroxy-2-sulfophenyl |

Preferably, the present invention provides a hydroquinone derivative compounds of formula (I), wherein:

(A)

$R_a$, $R_b$=H;

$R_1$=$COOR_4$; $(CH_2)_nCOOR_4$; $R_4$=H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=$CONHCOR_9$;

Or (B)

$R_a$, $R_b$=H;

$R_1$=$COOR_4$; $(CH_2)_nCOOR_4$; $R_4$=H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_{2-6}$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=$CONHCOR_9$.

In a fifth embodiment, the present invention includes compounds in accordance with Table 5:

TABLE 5

| Compound No. | Compound chemical names | R1 | R9 |
|---|---|---|---|
| A. | 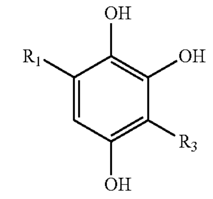 R3 = R5 = R6 = $CONHCOR_9$ | | |
| Ia-040a | N-(1,3,4,5-tetrahydroxycyclohexylcarbonyl)4-carboxy-2,5-dihydroxybenzamide | COOH | 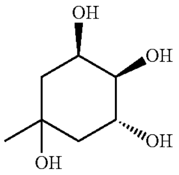 |
| Ia-041a | N-(4-carboxy-2,5-dihydroxybenzoyl)4-carboxy-2,5-dihydroxy-benzamide | COOH | 2,5-dihydroxy-4-carboxyphenyl |
| Ia-042a | N-(3-carboxy-2,5-dihydroxybenzoyl)4-carboxy-2,5-dihydroxy-benzamide | COOH | 2,5-dihydroxy-3-carboxyphenyl |
| Ia-043a | N-(3,4-dihydroxybenzoyl)4-carboxy-2,5-dihydroxybenzamide | COOH | 3,4-dihydroxyphenyl |
| Ia-044a | N-(3,5-dihydroxybenzoyl)4-carboxy-2,5-dihydroxybenzamide | COOH | 3,5-dihydroxyphenyl |
| IIIa-040a | N-(1,3,4,5-tetrahydroxycyclohexylcarbonyl)3-carboxy-2,5-dihydroxybenzamide | CH2COOH | 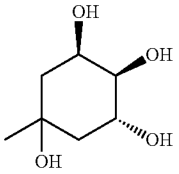 |
| IIIa-041a | N-(4-carboxy-2,5-dihydroxybenzoyl)3-carboxy-2,5-dihydroxy-benzamide | CH2COOH | 2,5-dihydroxy-4-carboxyphenyl |
| IIIa-042a | N-(3-carboxy-2,5-dihydroxybenzoyl)3-carboxy-2,5-dihydroxy-benzamide | CH2COOH | 2,5-dihydroxy-3-carboxyphenyl |
| IIIa-043a | N-(3,4-dihydroxybenzoyl)3-carboxy-2,5-dihydroxybenzamide | CH2COOH | 3,4-dihydroxyphenyl |
| IIIa-044a | N-(3,5-dihydroxybenzoyl)3-carboxy-2,5-dihydroxybenzamide | CH2COOH | 3,5-dihydroxyphenyl |
| B. | 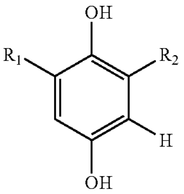 R2 = R5 = R6 = CONHCOR9 | | |
| IIa-040a | N-(1,3,4,5-tetrahydroxycyclohexylcarbonyl)4-carboxymethyl-2,5-dihydroxybenzamide | COOH | 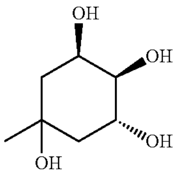 |
| IIa-041a | N-(4-carboxy-2,5-dihydroxybenzoyl)4-carboxymethyl-2,5-dihydroxy-benzamide | COOH | 2,5-dihydroxy-4-carboxyphenyl |
| IIa-042a | N-(3-carboxy-2,5-dihydroxybenzoyl)4-carboxymethyl-2,5-dihydroxy-benzamide | COOH | 2,5-dihydroxy-3-carboxyphenyl |
| IIa-043a | N-(3,4-dihydroxybenzoyl)4-carboxymethyl-2,5-dihydroxybenzamide | COOH | 3,4-dihydroxyphenyl |
| IIa-044a | N-(3,5-dihydroxybenzoyl)4-carboxymethyl-2,5-dihydroxybenzamide | COOH | 3,5-dihydroxyphenyl |

TABLE 5-continued

| Compound No. | Compound chemical names | R1 | R9 |
|---|---|---|---|
| IVa-040a | N-(1,3,4,5-tetrahydroxycyclohexylcarbonyl)3-carboxymethyl-2,5-dihydroxybenzamide | CH2COOH | 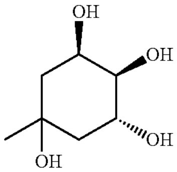 |
| IVa-041a | N-(4-carboxy-2,5-dihydroxybenzoyl)3-carboxymethy 1-2,5-dihydroxy-benzamide | CH2COOH | 2,5-dihydroxy-4-carboxyphenyl |
| IVa-042a | N-(3-carboxy-2,5-dihydroxybenzoyl)3-carboxymethy 1-2,5-dihydroxy-benzamide | CH2COOH | 2,5-dihydroxy-3-carboxyphenyl |
| IVa-043a | N-(3,4-dihydroxybenzoyl)3-carboxymethyl-2,5-dihydroxybenzamide | CH2COOH | 3,4-dihydroxyphenyl |
| IVa-044a | N-(3,5-dihydroxybenzoyl)3-carboxymethyl-2,5-dihydroxybenzamide | CH2COOH | 3,5-dihydroxyphenyl |

Preferably, the present invention provides a hydroquinone derivative compound of formula (I), wherein (A)

$R_a$, $R_b$=H;

$R_1$=$COOR_4$; $(CH_2)_nCOOR_4$; $R_4$=H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=$CONH(CH_2)_n$—$R_9$;

Or (B)

$R_a$, $R_b$=H;

$R_1$=$COOR_4$; $(CH_2)_nCOOR_4$; $R_4$=H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=$CONH(CH_2)_n$—$R_9$.

In a sixth embodiment, the present invention includes compounds in accordance with Table 6:

TABLE 6

| No. | Compound chemical names | R1 | n | R9 |
|---|---|---|---|---|
| A. | 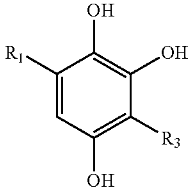 R3 = R5 = R6 = $CONH(CH_2)_n$—$R_9$ | | | |
| Ia-035a | 4-(3,4-dihydroxyphenylmethylaminocarbonyl)-2,5-dihydroxybenzoic acid; | COOH | 1 | 3,4-dihydroxyphenyl |
| Ia-035a-2 | 4-(2-(3,4-dihydroxyphenyl)ethylaminocarbonyl)-2,5-dihydroxybenzoic acid; | COOH | 2 | 3,4-dihydroxyphenyl |
| Ia-037a | 4-(3,5-dihydroxyphenylmethylaminocarbonyl)-2,5-dihydroxybenzoic acid; | COOH | 1 | 3,5 -dihydroxyphenyl |
| Ia-038a | 4-((4,5-dihydroxy-3-oxocyclohex-1-enyl)methylaminocarbonyl)-2,5-dihydroxybenzoic acid; | COOH | 1 | 4,5-dihydroxy-3-oxocyclohex-1-enyl) |
| Ia-039a | 2,5-dihydroxy-4-((3,4,5-trihydroxycyclohexyl)methylaminocarbonyl)benzoic acid | COOH | 1 | 3,4,5-trihydroxycyclohexyl) |
| Ia-053a | 4-(2-carboxyphenylmethylaminocarbonyl)-2,5-dihydroxybenzoic acid | COOH | 1 | 2-carboxyphenyl |
| Ia-054a | 4-(3-carboxyphenylmethylaminocarbonyl)-2,5-dihydroxybenzoic acid | COOH | 1 | 3-carboxyphenyl |
| Ia-055a | 4-(4-carboxyphenylmethylaminocarbonyl)2,5-dihydroxybenzoic acid | COOH | 1 | 4-carboxyphenyl |
| IIIa-035a | 3-(3,4-dihydroxyphenylmethylaminocarbonyl)-2,5-dihydroxybenzoic acid | CH2COOH | 1 | 3,4-dihydroxyphenyl |
| IIIa-037a | 3-(2-(3,4-dihydroxyphenyl)ethylaminocarbonyl)-2,5-dihydroxybenzoic acid | CH2COOH | 1 | 3,5-dihydroxyphenyl |

TABLE 6-continued

| No. | Compound chemical names | R1 | n | R9 |
|---|---|---|---|---|
| IIIa-038a | 3-(3,5-dihydroxyphenylmethylaminocarbonyl)-2,5-dihydroxybenzoic acid | CH2COOH | 1 | 4-((4,5-dihydroxy-3-oxocyclohex-1-enyl) |
| IIIa-039a | 3-((4,5-dihydroxy-3-oxocyclohex-1-enyl)methylaminocarbonyl)-2,5-dihydroxybenzoic acid | CH2COOH | 1 | 3,4,5-trihydroxycyclohexyl) |
| IIIa-053a | 2,5-dihydroxy-3-((3,4,5-trihydroxycyclohexyl)methylaminocarbonyl)benzoic acid | CH2COOH | 1 | 2-carboxyphenyl |
| IIIa-054a | 3-(2-carboxyphenylmethylaminocarbonyl)-2,5-dihydroxybenzoic acid | CH2COOH | 1 | 3-carboxyphenyl |
| IIIa-055a | 3-(3-carboxyphenylmethylaminocarbonyl)-2,5-dihydroxybenzoic acid | CH2COOH | 1 | 4-carboxyphenyl |
| B. | 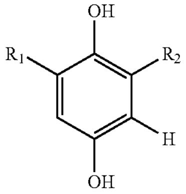 R2 = R5 = R6 = CONH(CH2)n—R9 | | | |
| II-035a | 3-(4-carboxyphenylmethylaminocarbonyl)-2,5-dihydroxybenzoic acid | COOH | 1 | 3,4-dihydroxyphenyl |
| IIa-035a-2 | (4-(3,4-dihydroxyphenylmethylaminocarbonyl)-2,5-dihydroxyphenyl)acetic acid | COOH | 2 | 3,4-dihydroxyphenyl |
| IIa-037a | (4-(3,5-dihydroxyphenylmethylaminocarbonyl)-2,5-dihydroxyphenyl)acetic acid | COOH | 1 | 3,5 -dihydroxyphenyl |
| IIa-038a | (4-((4,5-dihydroxy-3-oxocyclohex-1-enyl)methylaminocarbonyl)-2,5-dihydroxyphenyl)acetic acid | COOH | 1 | 4,5-dihydroxy-3-oxocyclohex-1-enyl) |
| IIa-039a | Compound 191: (2,5-dihydroxy-4-((3,4,5-trihydroxycyclohexyl)methylaminocarbonyl)phenyl)acetic acid | COOH | 1 | 3,4,5-trihydroxycyclohexyl |
| IIa-053a | (4-(2-carboxyphenylmethylaminocarbonyl)-2,5-dihydroxyphenyl)acetic acid | COOH | 1 | 2-carboxyphenyl |
| IIa-054a | (4-(3-carboxyphenylmethylaminocarbonyl)-2,5-dihydroxyphenyl)acetic acid | COOH | 1 | 3-carboxyphenyl |
| IIa-055a | (4-(4-carboxyphenylmethylaminocarbonyl)-2,5-dihydroxyphenyl)acetic acid | COOH | 1 | 4-carboxyphenyl |
| IVa-035a | (3-(3,4-dihydroxyphenylmethylaminocarbonyl)-2,5-dihydroxyphenyl)acetic acid | CH2COOH | 1 | 3,4-dihydroxyphenyl |
| IVa-037a | (3-(3,5-dihydroxyphenylmethylaminocarbonyl)-2,5-dihydroxyphenyl)acetic acid | CH2COOH | 1 | 3,5-dihydroxyphenyl |
| IVa-038a | (3-((4,5-dihydroxy-3-oxocyclohex-1-enyl)methylaminocarbonyl)-2,5-dihydroxyphenyl)acetic acid | CH2COOH | 1 | 4,5-dihydroxy-3-oxocyclohex-1-enyl) |
| IVa-039a | (2,5-dihydroxy-3-((3,4,5-trihydroxycyclohexyl)metiiylcarbonylamino)phenyl)acetic acid | CH2COOH | 1 | 3,4,5-trihydroxycyclohexyl |
| IVa-053a | (3-(2-carboxyphenylmetiiylaminocarbonyl)-2,5-dihydroxyphenyl)acetic acid | CH2COOH | 1 | 2-carboxyphenyl |
| IVa-054a | (3-(3-carboxyphenylmethylaminocarbonyl)-2,5-dihydroxyphenyl)acetic acid | CH2COOH | 1 | 3-carboxyphenyl |
| IVa-055a | (3-(4-carboxyphenylmetiiylaminocarbonyl)-2,5-dihydroxyphenyl)acetic acid | CH2COOH | 1 | 4-carboxyphenyl |

Preferably, the present invention provides a hydroquinone derivative compound of formula (I), wherein:

$R_a$, $R_b$=H;

$R_2$=$SO_3H$;

$R_2$=H; $R_3$=$R_5$; and $R_5$=$R_6$=CONH($CH_2$)=$R_9$.

According to a seventh embodiment, the present invention includes compounds in accordance with Table 7 below:

TABLE 7

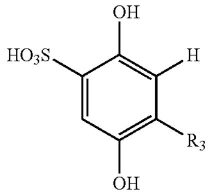

$R3 = R5 = CONH(CH_2)_n—R_9$

| Compound No. | Compound chemical names | n | R9 |
|---|---|---|---|
| Ia-053b | 2-((2,5-dihydroxy-4-sulfobenzamido)methyl)benzoic acid | 1 | 2-carboxyphenyl |
| Ia-054b | 3-((2,5-dihydroxy-4-sulfobenzamido)methyl)benzoic acid | 1 | 3-carboxyphenyl |
| Ia-055b | 4-((2,5-dihydroxy-4-sulfobenzamido)methyl)benzoic acid | 1 | 4-carboxyphenyl |

Preferably, the present invention relates to a hydroquinone derivative compound of formula (I) wherein:

(A)

$R_a$, $R_b$═H;

$R_1$═$COOR_4$; $(CH_2)_nCOOR_4$; $R_4$═H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$═H; $R_3$═$R_5$; and $R_5$═$R_6$═$CONHCH(COOR_4)(CH_2)_k$—$R_9$;

Or (B)

$R_a$, $R_b$═H;

$R_1$═$COOR_4$; $(CH_2)_nCOOR_4$; $R_4$═H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$═H; $R_2$═$R_5$; and $R_5$═$R_6$═$CONHCH(COOR_4)(CH_2)_k$—$R_9$.

According to an eighth embodiment, the present invention includes compounds in accordance with Table 8 below:

TABLE 8

| Compound No. | Compound chemical names | RI | R4 | k | R9 |
|---|---|---|---|---|---|
| A. | 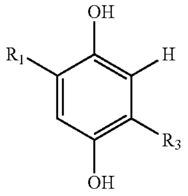 $R_3 = R_5 = R_6 = CONHCH(COOR_4)(CH_2)_kR_9$ | | | | |
| Ia-035a-3 | 4-(1-carboxy-2-(3,4-dihydroxyphenyl)ethylaminocarbonyl)-2,5-dihydroxybenzoic acid | COOH | H | 1 | 3,4-dihydroxyphenyl |
| Ia-036a | 4-(carboxy(3,4-dihydroxyphenyl)methylaminocarbonyl)-2,5-dihydroxybenzoic acid | COOH | H | 0 | 3,4-dihydroxyphenyl |
| IIIa-036a | 3-(1-carboxy-2-(3,4-dihydroxyphenyl)ethylaminocarbonyl)-2,5-dihydroxybenzoic acid | $CH_2COOH$ | H | 0 | 3,4-dihydroxyphenyl |

TABLE 8-continued

| Compound No. | Compound chemical names | RI | R4 | k | R9 |
|---|---|---|---|---|---|
| B. | 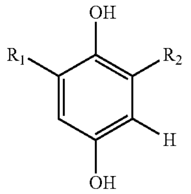 $R_2 = R_5 = R_6 = CONHCH(COOR_4)(CH_2)_kR_9$ | | | | |
| IIa-035a-3 | 3-(carboxy(3,4-dihydroxyphenyl)methylaminocarbonyl)-2,5-dihydroxybenzoic acid | COOH | H | 1 | 3,4-dihydroxyphenyl |
| IIa-036a | (4-(carboxy(3,4-dihydroxyphenyl)methylaminocarbonyl)-2,5-dihydroxyphenyl)acetic acid | COOH | H | 0 | 3,4-dihydroxyphenyl |
| IVa-036a | (3-(carboxy(3,4-dihydroxyphenyl)methylaminocarbonyl)-2,5-dihydroxyphenyl)acetic acid | $CH_2COOH$ | H | 0 | 3,4-dihydroxyphenyl |

In a specific embodiment, the present invention provides a hydroquinone derivative compounds of formula (I), wherein (A)

$R_a$, $R_b$=H;

$R_1$=$COOR_4$; $(CH_2)_nCOOR_4$; $SO_3H$, $(CH_2)_nSO_3H$, or CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=heteroaryl-$R_9$,

Or (B)

$R_a$, $R_b$=H;

$R_1$=$COOR_4$; $(CH_2)_nCOOR_4$; $SO_3H$, $(CH_2)_nSO_3H$, or CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=heteroaryl-$R_9$

According to a ninth embodiment, the present invention includes compounds in accordance with Table 9:

TABLE 9

| Compound No. | Compound chemical names | R1 | Heteroaryl-R9 |
|---|---|---|---|
| A. | 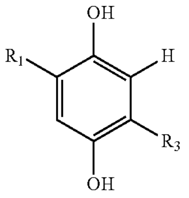 R3 = R5 = R6 = heteroaryl-R9 | | |
| Ia-045a | 4,6-Bis(4-carboxy-2,5-dihydroxyphenyl)-1,3,5-triazin-2-one | COOH | 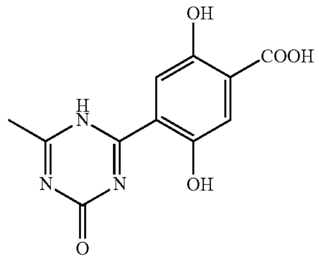 [SMILES: Cc1nc(=O)nc(-c2cc(O)c(C(=O)O)cc2O)[nH]1] |

TABLE 9-continued

| Compound No. | Compound chemical names | R1 | Heteroaryl-R9 |
| --- | --- | --- | --- |
| Ia-046a | 4-(4-carboxy-2,5-dihydroxyphenyl)-6-(3-carboxy-2,5-dihydroxyphenyl)-1,3,5-triazin-2-one | COOH | 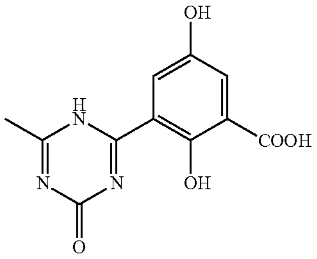 [SMILES: Cc1nc(=O)nc(-c2cc(O)cc(C(=O)O)c2O)[nH]1] |
| Ia-047a | 4-(4-carboxy-2,5-dihydroxyphenyl)-6-(3,4-dihydroxyphenyl)-1,3,5-triazin-2-one | COOH | 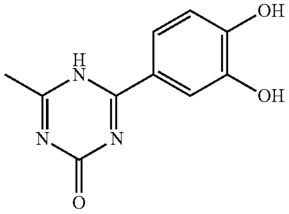 [SMILES: Cc1nc(=O)nc(-c2ccc(O)c(O)c2)[nH]1] |
| Ia-048a | 4-(4-carboxy-2,5-dihydroxyphenyl)-6-(3,5-dihydroxyphenyl)-1,3,5-triazin-2-one | COOH | 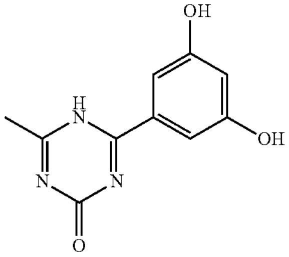 [SMILES: Cc1nc(=O)nc(-c2cc(O)cc(O)c2)[nH]1] |
| Ia-049a | 4,6-Bis(4-carboxy-2,5-dihydroxyphenyl)-1,3,5-triazine | COOH | 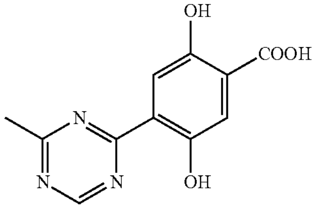 [SMILES: Cc1ncnc(-c2cc(O)c(C(=O)O)cc2O)n1] |
| Ia-050a | 2-(4-Carboxy-2,5-dihydroxyphenyl)-4-(3-carboxy-2,5-dihydroxyphenyl)-1,3,5-triazine | COOH | 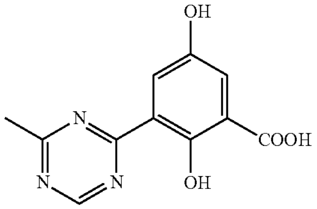 [SMILES: Cc1ncnc(-c2cc(O)cc(C(=O)O)c2O)n1] |
| Ia-051a | 2-(4-Carboxy-2,5-dihydroxyphenyl)-4-(3,4-dihydroxyphenyl)-1,3,5-triazine | COOH | 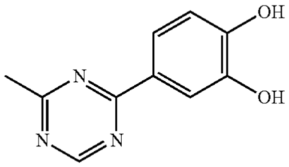 |
| Ia-052a | 2-(4-Carboxy-2,5-dihydroxyphenyl)-4-(3,5-dihydroxyphenyl)-1,3,5-triazine | COOH | 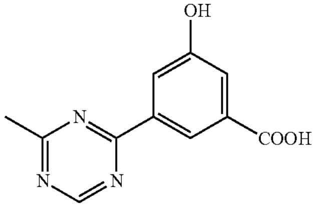 [SMILES: Cc1ncnc(-c2cc(O)cc(C(=O)O)c2)n1] |

TABLE 9-continued

| Compound No. | Compound chemical names | R1 | Heteroaryl-R9 |
|---|---|---|---|
| IIa-046a | 4,6-Bis(3-carboxy-2,5-dihydroxyphenyl)-1,3,5-triazin-2-one | COOH | 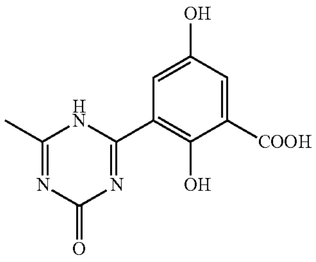 [SMILES: Cc1nc(=O)nc(-c2cc(O)cc(C(=O)O)c2O)[nH]1] |
| IIa-050a | 4-(3-Carboxy-2,5-dihydroxyphenyl)-6-(4-carboxy-2,5-dihydroxyphenyl)-1,3,5-triazin-2-one | COOH | 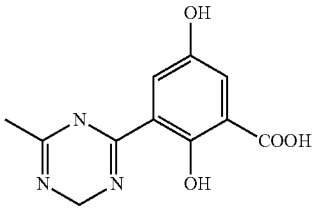 [SMILES: CC1=NCN=C(c2cc(O)cc(C(=O)O)c2O)N1] |
| IIIa-045a | 4-(3-Carboxy-2,5-dihydroxyphenyl)-6-(3,4-dihydroxyphenyl)-1,3,5-triazin-2-one | CH2COOH | 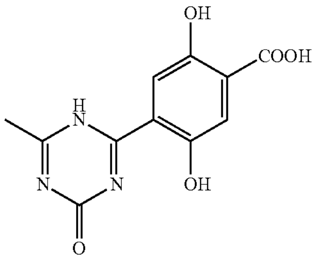 [SMILES: Cc1nc(=O)nc(-c2cc(O)c(C(=O)O)cc2O)[nH]1] |
| IIIa-046a | 4-(3-Carboxy-2,5-dihydroxyphenyl)-6-(3,5-dihydroxyphenyl)-1,3,5-triazin-2-one | CH2COOH | 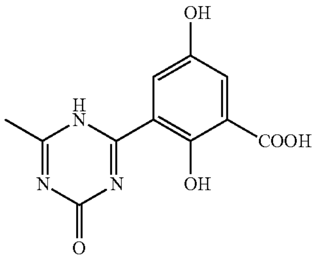 [SMILES: Cc1nc(=O)nc(-c2cc(O)cc(C(=O)O)c2O)[nH]1] |
| IIIa-047a | 4,6-Bis(3-carboxy-2,5-dihydroxyphenyl)-1,3,5-triazine | CH2COOH | 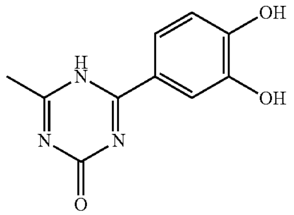 [SMILES: Cc1nc(=O)nc(-c2ccc(O)c(O)c2)[nH]1] |
| IIIa-048a | 2-(3-Carboxy-2,5-dihydroxyphenyl)-4-(4-carboxy-2,5-dihydroxyphenyl)-1,3,5-triazine | CH2COOH | 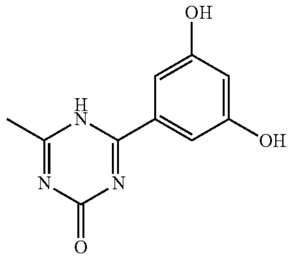 [SMILES: Cc1nc(=O)nc(-c2cc(O)cc(O)c2)[nH]1] |

TABLE 9-continued

| Compound No. | Compound chemical names | R1 | Heteroaryl-R9 |
|---|---|---|---|
| IIIa-049a | 2-(3-Carboxy-2,5-dihydroxyphenyl)-4-(3,4-dihydroxyphenyl)-1,3,5-triazine | CH2COOH | 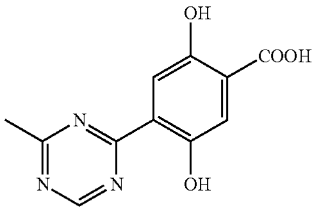 [SMILES: Cc1ncnc(-c2cc(O)c(C(=O)O)cc2O)n1] |
| IIIa-050a | 2-(3-Carboxy-2,5-dihydroxyphenyl)-4-(3,5-dihydroxyphenyl)-1,3,5-triazine | CH2COOH | 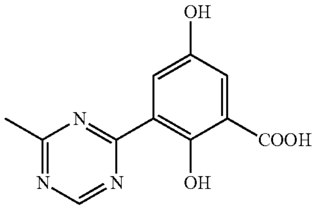 [SMILES: Cc1ncnc(-c2cc(O)cc(C(=O)O)c2O)n1] |
| IIIa-051a | 2-(3-Carboxymethyl-2,5-dihydroxyphenyl)-4-(3,4-dihydroxyphenyl)-1,3,5-triazine | CH2COOH | 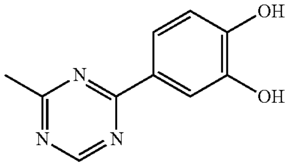 |
| IIIa-052a | 2-(3-Carboxymethyl-2,5-dihydroxyphenyl)-4-(3,5-dihydroxyphenyl)-1,3,5-triazine | CH2COOH | 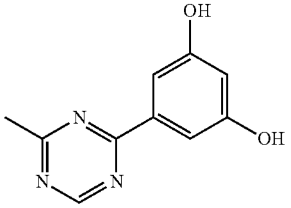 |

B.

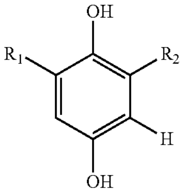

R2 = R5 = R6 = heteroaryl-R9

| | | | |
|---|---|---|---|
| IIa-045a | 4-(4-Carboxymethyl-2,5-dihydroxyphenyl)-6-(3,4-dihydroxyphenyl)-1,3,5-triazin-2-one | COOH | 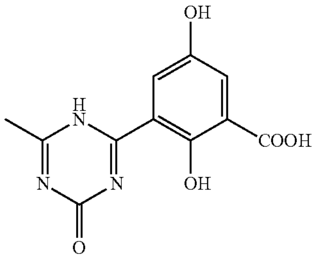 [SMILES: Cc1nc(=O)nc(-c2cc(O)cc(C(=O)O)c2O)[nH]1] |
| IIa-047a | 4-(4-Carboxymethyl-2,5-dihydroxyphenyl)-6-(3,5-dihydroxyphenyl)-1,3,5-triazin-2-one | COOH | 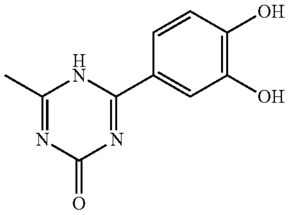 [SMILES: Cc1nc(=O)nc(-c2ccc(O)c(O)c2)[nH]1] |

TABLE 9-continued

| Compound No. | Compound chemical names | R1 | Heteroaryl-R9 |
| --- | --- | --- | --- |
| IIa-048a | 2-(4-Carboxy-2,5-dihydroxyphenyl)-4-(4-carboxymethyl-2,5 -dihydro xyphenyl)-1,3,5 -triazine | COOH | 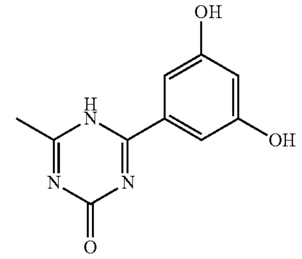 [SMILES: Cc1nc(=O)nc(-c2cc(O)cc(O)c2)[nH]1] |
| IIa-049a | 2-(3-Carboxy-2,5-dihydroxyphenyl)-4-(4-carboxymethyl-2,5 -dihydroxyphenyl)-1,3,5-triazine | COOH | 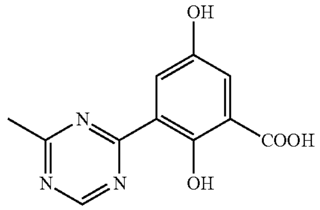 [SMILES: Cc1ncnc(-c2cc(O)cc(C(=O)O)c2O)n1] |
| IIa-051a | 2-(4-Carboxymethyl-2,5-dihydroxyphenyl)-4-(3,4-dihydroxyphenyl)-1,3,5-triazine | COOH | 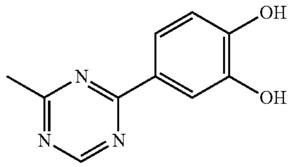 |
| IIa-052a | 2-(4-Carboxymethyl-2,5-dihydroxyphenyl)-4-(3,5-dihydroxyphenyl)-1,3,5-triazine | COOH | 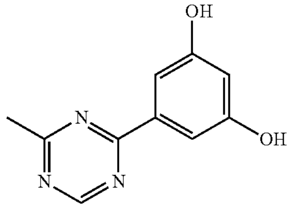 |
| IVa-045a | 4-(4-Carboxy-2,5-dihydroxyphenyl)-6-(3-carboxymethyl-2,5-dihydroxyphenyl)-1,3,5-triazin-2-one | CH2COOH | 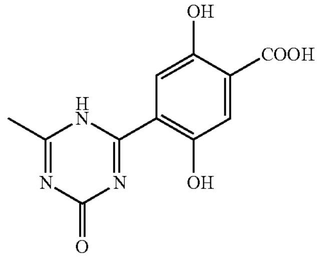 [SMILES: Cc1nc(=O)nc(-c2cc(O)c(C(=O)O)cc2O)[nH]1] |
| IVa-046a | 4-(3-Carboxy-2,5-dihydroxyphenyl)-6-(3-carboxymethyl-2,5 -dihydroxyphenyl)-1,3,5-triazin-2-one | CH2COOH | 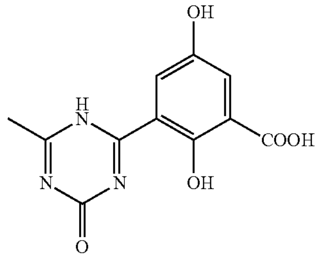 [SMILES: Cc1nc(=O)nc(-c2cc(O)cc(C(=O)O)c2O)[nH]1] |

TABLE 9-continued

| Compound No. | Compound chemical names | R1 | Heteroaryl-R9 |
|---|---|---|---|
| IVa-047a | 4-(3-Carboxymethyl-2,5-dihydroxyphenyl)-6-(3,4-dihydroxyphenyl)-1,3,5-triazin-2-one | CH2COOH | 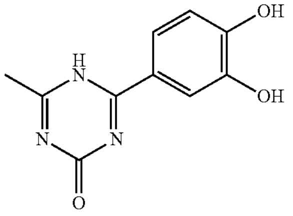 [SMILES: Cc1nc(=O)nc(-c2ccc(O)c(O)c2)[nH]1] |
| IVa-048a | 4-(3-Carboxymethyl-2,5-dihydroxyphenyl)-6-(3,5-dihydroxyphenyl)-1,3,5-triazin-2-one | CH2COOH | 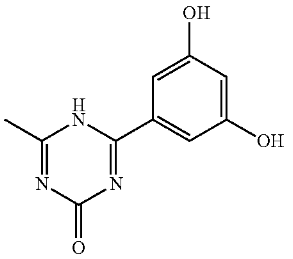 [SMILES: Cc1nc(=O)nc(-c2cc(O)cc(O)c2)[nH]1] |
| IVa-049a | 2-(4-Carboxy-2,5-dihydroxyphenyl)-4-(3-carboxymethyl-2,5-dihydroxyphenyl)-1,3,5 -triazine | CH2COOH | 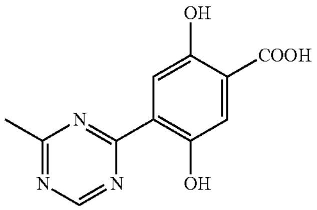 [SMILES: Cc1ncnc(-c2cc(O)c(C(=O)O)cc2O)n1] |
| IVa-050a | 2-(3-Carboxy-2,5-dihydroxyphenyl)-4-(3-carboxymethyl-2,5 -dihydroxyphenyl)-1,3,5-triazine | CH2COOH | 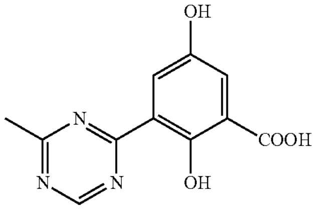 [SMILES: Cc1ncnc(-c2cc(O)cc(C(=O)O)c2O)n1] |
| IVa-051a | 2-(3-Carboxymethyl-2,5-dihydroxyphenyl)-4-(3,4-dihydroxyphenyl)-1,3,5-triazine | CH2COOH | 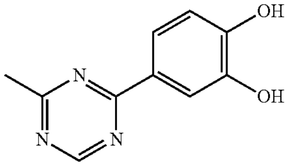 |
| IVa-052a | 2-(3-Carboxymethyl-2,5-dihydroxyphenyl)-4-(3,5-dihydroxyphenyl)-1,3,5-triazine | CH2COOH | 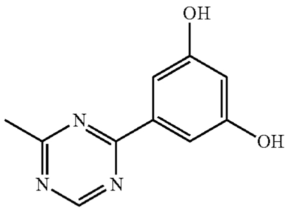 |

Preferably, the present invention provides a hydroquinone derivative compound of formula (I), wherein:

(A)

$R_a$, $R_b$=H;

$R_1$=$COOR_4$; $(CH_2)_nCOOR_4$; $SO_3H$, $(CH_2)_nSO_3H$, CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_7$=benzoheteroaryl substituted with at least one or more groups selected from: $COOR_4$, $(CH_2)_nCOOR_4$, $SO_3H$, $(CH_2)_nSO_3H$, $OR_4$, azoles [5-membered N-containing heterocycles], or fluorine;

Or (B)

$R_a$, $R_b$=H;

$R_1$=$COOR_4$; $(CH_2)_nCOOR_4$; $SO_3H$, $(CH_2)_nSO_3H$, or CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_7$=benzoheteroaryl substituted with at least one or more groups selected from: $COOR_4$, $(CH_2)_nCOOR_4$, $SO_3H$, $(CH_2)_nSO_3H$, $OR_4$, azoles [5-membered N-containing heterocycles], or fluorine.

According to a tenth embodiment, the present invention includes compounds in accordance with Table 10:

TABLE 10

| Compound No. | Compound chemical names | R1 | R3 |
|---|---|---|---|
| A. | | 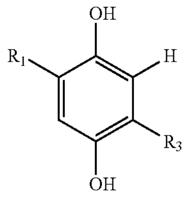<br>R3 = R5 = R7 | |
| Id-030a | 2-(4-Carboxy-2,5-dihydroxyphenyl)-1H-benzo[d]imidazole-4-carboxylic acid | COOH | 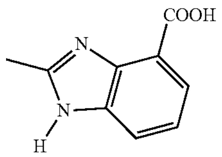 |
| Id-030a-E2 | Methyl 2-(4-ethoxycarbonyl-2,5-dihydroxyphenyl)-1H-benzo[d]imidazole-4-carboxylate | COOEt | 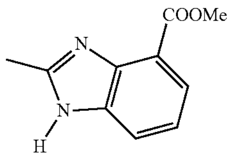 |
| Id-030b | 2-(2,5-Dihydroxy-4-sulfophenyl)-1H-benzo[d]imidazole-4-carboxylic acid | SO3H | 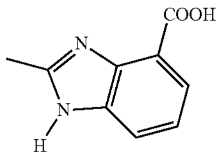 |
| Id-031a | 2-(4-Carboxy-2,5-dihydroxyphenyl)-1H-benzo[d]imidazole-5-carboxylic acid | COOH | 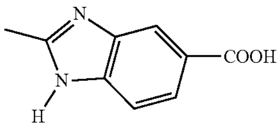 |
| Id-031b | 2-(2,5-Dihydroxy-4-sulfophenyl)-1H-benzo[d]imidazole-5-carboxylic acid | SO3H | 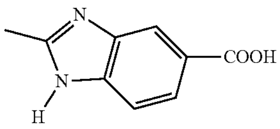 |
| IIId-030a | 2-(3-Carboxy-2,5-dihydroxyphenyl)-1H-benzo[d]imidazole-4-carboxylic acid | CH2COOH | 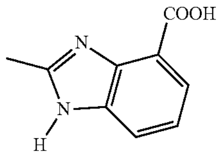 |

TABLE 10-continued

| Compound No. | Compound chemical names | R1 | R3 |
|---|---|---|---|
| IIId-031a | 2-(2,5-Dihydroxy-3-sulfophenyl)-1H-benzo[d]imidazole-4-carboxylic acid | CH2COOH | 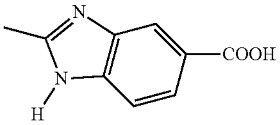 |
| B. | 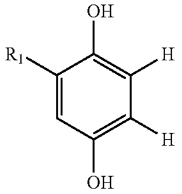 R2 = R5 = R7 | | |
| IId-030a | 2-(3-Carboxy-2,5-dihydroxyphenyl)-1H-benzo[d]imidazole-5-carboxylic acid | COOH | 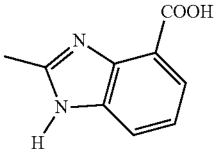 |
| IId-030b | 2-(2,5-Dihydroxy-3-sulfophenyl)-1H-benzo[d]imidazole-5-carboxylic acid | SO3H | 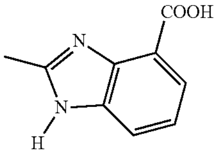 |
| IId-031a | 2-(4-(Carboxymethyl)-2,5-dihydroxyphenyl)-1H-benzo[d]imidazole-4-carboxylic acid | COOH | 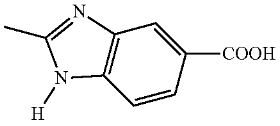 |
| IId-030a | 2-(4-(Carboxymethyl)-2,5-dihydroxyphenyl)-1H-benzo[d]imidazole-5-carboxylic acid | SO3H | 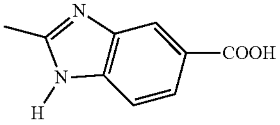 |
| IVd-030a | 2-(3-(Carboxymethyl)-2,5-dihydroxyphenyl)-1H-benzo[d]imidazole-4-carboxylic acid | CH2COOH | 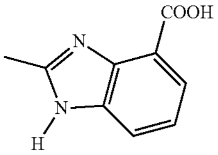 |
| IVd-031a | 2-(3-(Carboxymethyl)-2,5-dihydroxyphenyl)-1H-benzo[d]imidazole-5-carboxylic acid | CH2COOH | 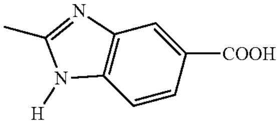 |

Preferably, the present invention provides a hydroquinone derivative compound of formula (I), wherein:

(A)

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$; $(CH_2)_nCOOR_4$; $SO_3H$, $(CH_2)_nSO_3H$, or CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_8$=$(CH_2)_mX(CH_2)_pR_9$;

wherein X=O, S, $SO_2$, NH, NAc, or $N(CH_2)_qR_9$;

Or (B)

$R_a$, $R_b$=H, $C_{1-4}$acyl, aryl$C_{1-4}$alkyl, $C_6$-$C_{10}$arylCO, HOOC($CH_2$)$_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$; ($CH_2$)$_n$$COOR_4$; $SO_3H$, ($CH_2$)$_n$$SO_3H$, or CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_8$=($CH_2$)$_m$X($CH_2$)$_p$$R_9$;

wherein X=O, S, $SO_2$, NH, NAc, or N($CH_2$)$R_9$.

According to an eleventh embodiment, the present invention includes compounds in accordance with Table 11:

TABLE 11

| No. | Compound chemical names | R1 | Ra | Rb | m | X | p | R9 |
|---|---|---|---|---|---|---|---|---|
| A. | 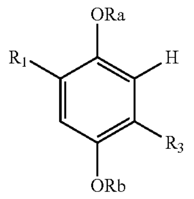 R3 = $(CH_2)_mX(CH_2)_pR_9$ | | | | | | | |
| IIIc-056a | Bis(4-carboxy-2,5-dihydroxyphenylmethyl)amine | COOH | H | H | 1 | NH | 1 | 4-carboxy-2,5-dihydroxyphenyl |
| IIIc-056b | 4-((2,5-Dihydroxy-4-sulfophenylmethylamino)methyl)-2,5-dihydroxybenzoic acid | SO3H | H | H | 1 | NH | 1 | 4-carboxy-2,5-dihydroxyphenyl |
| IIIc-056c | Compound 267: 4-((2,5-Dihydroxy-3-sulfophenylmethylamino)methyl)-2,5-dihydroxybenzoic acid | COOH | H | H | 1 | NH | 1 | 2,5-dihydroxy-3-sulfophenyl |
| IIIc-056d | Bis(2,5-dihydroxy-4-sulfophenylmethyl)amine | SO3H | H | H | 1 | NH | 1 | 2,5-dihydroxy-4-sulfophenyl |
| IIIc-057a | N,N-Bis(4-carboxy-2,5-dihydroxyphenylmethyl)acetamide | COOH | H | H | 1 | NH(COCH3) | 1 | 4-carboxy-2,5-dihydroxyphenyl |
| IIIc-057b | N-(2,5-dihydroxy-4-sulfophenylmethyl) N-(4-carboxy-2,5-dihydroxyphenylmethyl) acetamide | SO3H | H | H | 1 | NH(COCH3) | 1 | 4-carboxy-2,5-dihydroxyphenyl |
| IIIc-057c | N-(2,5-dihydroxy-3-sulfophenylmethyl) N-(4-carboxy-2,5-dihydroxyphenylmethyl) acetamide | COOH | H | H | 1 | NH(COCH3) | 1 | 2,5-dihydroxy-3-sulfophenyl |
| IIIc-057d | N,N-Bis(2,5-dihydroxy-4-sulfophenylmethyl)acetamide | SO3H | H | H | 1 | NH(COCH3) | 1 | 2,5-dihydroxy-4-sulfophenyl |
| IIIc-058a | 4-((2,5-Dihydroxy-4-carboxyphenyl)methylthiomethyl)-2,5-dihydroxybenzoic acid | COOH | H | H | 1 | S | 1 | 4-carboxy-2,5-dihydroxyphenyl |
| IIIc-058b | 4-((2,5-Dihydroxy-4-sulfophenyl)methylthiomethyl)-2,5 -dihydroxybenzoic acid | SO3H | H | H | 1 | s | 1 | 4-carboxy-2,5-dihydroxyphenyl |
| IIIc-058c | 4-((2,5-Dihydroxy-3-sulfophenyl)methylthiomethyl)-2,5 -dihydroxybenzoic acid | COOH | H | H | 1 | s | 1 | 2,5-dihydroxy-3-sulfophenyl |
| IIIc-058d | 4-((2,5-Dihydroxy-4-sulfophenyl)methylthiomethyl)-2,5 -dihydroxybenzenesulfonic acid; | SO3H | H | H | 1 | s | 1 | 2,5-dihydroxy-4-sulfophenyl |
| IIIc-059a | 4-((2,5-Dihydroxy-4-carboxyphenyl)methylsulfonylmethyl)-2,5-dihydroxybenzoic acid; | COOH | H | H | 1 | SO2 | 1 | 4-carboxy-2,5-dihydroxyphenyl |
| IIIc-059b | 4-((2,5-Dihydroxy-4-sulfophenyl)methylsulfonylmethyl)-2,5-dihydroxybenzoic acid; | SO3H | H | H | 1 | SO2 | 1 | 4-carboxy-2,5-dihydroxyphenyl |
| IIIc-059c | 4-((2,5-Dihydroxy-3-sulfophenyl)methylsulfonylmethyl)-2,5-dihydroxybenzoic acid | COOH | H | H | 1 | SO2 | 1 | 2,5-dihydroxy-3-sulfophenyl |
| IIIc-059d | 4-((2,5-Dihydroxy-4-sulfophenyl)methylsulfonylmethyl)-2,5-dihydroxybenzenesulfonic acid | SO3H | H | H | 1 | SO2 | 1 | 2,5-dihydroxy-4-sulfophenyl |
| IIIc-060a | 4-((2,5-Dihydroxy-4-carboxyphenyl)methoxymethyl)-2,5-dihydroxybenzoic acid | COOH | H | H | 1 | O | 1 | 4-carboxy-2,5-dihydroxyphenyl |
| IIIc-060b | 4-((2,5-dihydroxy-4-sulfophenyl)methoxymethyl)-2,5-dihydroxybenzoic acid; | SO3H | H | H | 1 | O | 1 | 4-carboxy-2,5-dihydroxyphenyl |

TABLE 11-continued

| No. | Compound chemical names | R1 | Ra | Rb | m | X | p | R9 |
|---|---|---|---|---|---|---|---|---|
| IIIc-060c | 4-((2,5-dihydroxy-3-sulfophenyl)methoxymethyl)-2,5-dihydroxybenzoic acid | COOH | H | H | 1 | O | 1 | 2,5-dihydroxy-3-sulfophenyl |
| IIIc-060d | 4-((2,5-Dihydroxy-4-sulfophenyl)methoxymethyl)-2,5-dihydroxybenzenesulfonic acid | SO3H | H | H | 1 | O | 1 | 2,5-dihydroxy-4-sulfophenyl |
| IIIc-061a | Tris(4-carboxy-2,5-dihydroxyphenylmethyl)amine | COOH | H | H | 1 | N(CH2)qR9 q = 1: R9 = 4-carboxy-2,5-dihydroxyphenyl | 1 | 4-carboxy-2,5-dihydroxyphenyl |
| IIIc-061a-E3 | Tris (4-ethoxycarbonyl-2,5-dihydroxyphenylmethyl)amine | COOEt | H | H | | (CH2)qR9 q = 1: R9 = 4-ethoxycarboxy-2,5-dihydrocyphenyl | 1 | 4-ethoxycarbonyl-2,5-dihydroxyphenyl |

B.

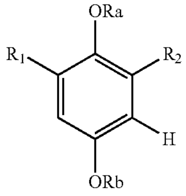

$R2 = (CH_2)_mX(CH_2)_pR_9$

| No. | Compound chemical names | R1 | Ra | Rb | m | X | p | R9 |
|---|---|---|---|---|---|---|---|---|
| IVc-056a | Bis(3-carboxy-2,5-dihydroxyphenylmethyl)amine | COOH | H | H | 1 | NH | 1 | 3-carboxy-2.5-dihydroxyphenyl |
| IVc-056b | 3-((2,5-Dihydroxy-3-sulfophenylmethylamino)methyl)-2,5-dihydroxybenzoic acid | SO3H | H | H | 1 | NH | 1 | 3-carboxy-2,5-dihydroxyphenyl |
| IVc-056c | 3-((2,5-Dihydroxy-4-sulfophenylmethylamino)methyl)-2,5-dihydroxybenzoic acid | COOH | H | H | 1 | NH | 1 | 2,5-dihydroxy-3-sulfophenyl |
| IVc-056d | Bis(2,5-dihydroxy-3-sulfophenylmethyl)amine | SO3H | H | H | 1 | NH | 1 | 2,5-dihydroxy-4-sulfophenyl |
| IVc-057a | N,N-Bis(3-carboxy-2,5-dihydroxyphenylmethyl)acetamide | COOH | H | H | 1 | NH(COCH3) | 1 | 3-carboxy-2,5-dihydroxyphenyl |
| IVc-057b | N-(2,5-dihydroxy-3-sulfophenylmethyl)N-(3-carboxy-2,5-dihydroxyphenylmethyl) acetamide | SO3H | H | H | 1 | NH(COCH3) | 1 | 3-carboxy-2,5-dihydroxyphenyl |
| IVc-057c | N-(2,5-dihydroxy-4-sulfophenylmethyl)N-(3-carboxy-2,5-dihydroxyphenylmethyl) acetamide | COOH | H | H | 1 | NH(COCH3) | 1 | 2,5-dihydroxy-3-sulfophenyl |
| IVc-057d | N,N-Bis(2,5-dihydroxy-3-sulfophenylmethyl)acetamide | SO3H | H | H | 1 | NH(COCH3) | 1 | 2,5-dihydroxy-4-sulfophenyl |
| IVc-058a | 3-((2,5-Dihydroxy-3-carboxyphenyl)methylthiomethyl)-2,5-dihydroxybenzoic acid | COOH | H | H | 1 | S | 1 | 3-carboxy-2,5-dihydroxyphenyl |
| IVc-058b | 3-((2,5-Dihydroxy-3-sulfophenyl)methylthiomethyl)-2,5-dihydroxybenzoic acid | SO3H | H | H | 1 | S | 1 | 3-carboxy-2,5-dihydroxyphenyl |
| IVc-058c | 3-((2,5-Dihydroxy-4-sulfophenyl)methyithiomethyl)-2,5-dihydroxybenzoic acid | COOH | H | H | 1 | s | 1 | 2,5-dihydroxy-3-sulfophenyl |
| IVc-058d | 3-((2,5-Dihydroxy-3-sulfophenyl)methylthiomethyl)-2,5-dihydroxybenzenesulfonic acid | SO3H | H | H | 1 | S | 1 | 2,5-dihydroxy-4-sulfophenyl |
| IVc-059a | 3-((2,5-Dihydroxy-3-carboxyphenyl)methylsulfonylmethyl)-2,5-dihydroxybenzoic acid | COOH | H | H | 1 | SO2 | 1 | 3-carboxy-2,5-dihydroxyphenyl |
| IVc-059b | 3-((2,5-Dihydroxy-3-sulfophenyl)methylsulfonylmethyl)-2,5-dihydroxybenzoic acid | SO3H | H | H | 1 | SO2 | 1 | 3-carboxy-2,5-dihydroxyphenyl |
| IVc-059c | 3-((2,5-Dihydroxy-4-sulfophenyl)methylsulfonylmethyl)-2,5-dihydroxybenzoic acid | COOH | H | H | 1 | SO2 | 1 | 2,5-dihydroxy-3-sulfophenyl |
| IVc-059d | 3-((2,5-Dihydroxy-3-sulfophenyl)methylsulfonylmethyl)-2,5-dihydroxybenzenesulfonic acid | SO3H | H | H | 1 | SO2 | 1 | 2,5-dihydroxy-4-sulfophenyl |
| IVc-060a | 3-((2,5-Dihydroxy-3-carboxyphenyl)methoxymethyl)-2,5-dihydroxybenzoic acid | COOH | H | H | 1 | O | 1 | 3-carboxy-2,5-dihydroxyphenyl |

TABLE 11-continued

| No. | Compound chemical names | R1 | Ra | Rb | m | X | p | R9 |
|---|---|---|---|---|---|---|---|---|
| IVc-060b | 3-((2,5-dihydroxy-3-sulfophenyl)methoxymethyl)-2,5-dihydroxybenzoic acid | SO3H | H | H | 1 | O | 1 | 3-carboxy-2,5-dihydroxyphenyl |
| IVc-060c | 3-((2,5-dihydroxy-4-sulfophenyl)methoxymethyl)-2,5-dihydroxybenzoic acid | COOH | H | H | 1 | O | 1 | 2,5-dihydroxy-3-sulfophenyl |
| IVc-060d | 3-((2,5-Dihydroxy-3-sulfophenyl)methoxymethyl)-2,5-dihydroxybenzenesulfonic acid | SO3H | H | H | 1 | O | 1 | 2,5-dihydroxy-4-sulfophenyl |
| IVc-061a | Tris (3-carboxy-2,5-dihydroxyphenylmethyl)amine | COOH | H | H | 1 | $N(CH_2)qR_9$ q = 1: $R_9$ = 3-carboxy-2,5-dihydroxyphenyl | 1 | 3-carboxy-2,5-dihydroxyphenyl |
| IVc-059a-E2-A4 | Methyl 3-((2,5-diacetoxy-3-methoxycarbonylphenyl)methylsulfonyl-methyl)-2,5-diacetoxybenzoate | COOMe | Ac | Ac | 1 | SO2 | 1 | 2,5-diacetoxy-3-(methoxycarbonyl)phenyl |
| IVc-059a-E2 | Methyl 3-((2,5-dihydroxy-3-methoxycarbonylphenyl)methylsulfonyl-methyl)-2,5-hydroxybenzoate | COOMe | H | H | 1 | SO2 | 1 | 2,5-dihydroxy-3-(methoxycarbonyl)phenyl |
| IVc-059a-mpe2 | 2-Morpholinoethyl 3-((2,5-dihydroxy-3-(2-morpholinoethoxycarbonyl)phenyl)methyl-sulfonylmethyl)-2,5-hydroxybenzoate | COOR R = 2-morpholinoethyl | H | H | 1 | SO2 | 1 | 2,5-dihydroxy-3-(2-morpholinoethoxycarbonyl) phenyl |
| IVc-061a-E3 | Tris (3-carboxy-2,5-dihydroxyphenylmethyl)amine | COOEt | H | H | 1 | $N(CH_2)qR_9$ q = 1: $R_9$ = 3-ethoxycarbonyl-2,5-dihydroxyphenyl | 1 | 3-ethoxycarbonyl-2,5-dihydroxyphenyl |

According to yet another embodiment, the present invention includes compounds in accordance with Table 12:

TABLE 12

| Compound No. | Compound chemical names | Structures |
|---|---|---|
| V-001a | 4-(3-(2,5-dihydroxy-4-carboxyphenylcarbamoyl)-5-hydroxybenzamido)-2,5-dihydroxy benzoic acid | 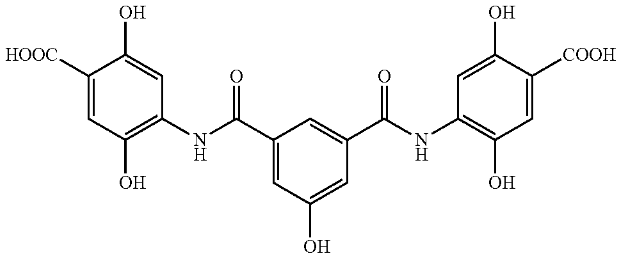 [SMILES: O=C(Nc1cc(O)c(C(=O)O)cc1O)c1cc(O)cc(C(=O)Nc2cc(O)c(C(=O)O)cc2O)c1] |
| V-001a diethyl ester | 4-(3-(4-(ethoxycarbonyl)-2,5-dihydroxyphenylcarbamoyl)-5-hydroxybenzamido)-2,5-dihydroxybenzoic acid ethyl ester | 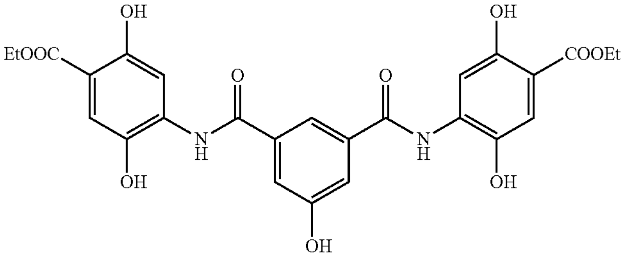 [SMILES: CCOC(=O)c1cc(O)c(NC(=O)c2cc(O)cc(C(=O)Nc3cc(O)c(C(=O)OCC)cc3O)c2)cc1O] |

TABLE 12-continued

| Compound No. | Compound chemical names | Structures |
|---|---|---|
| V-002a | 2-hydroxy-5-(3-hydroxy-5-(4-hydroxy-3-carboxyphenylcarbamoyl)benzamido)benzoic acid | 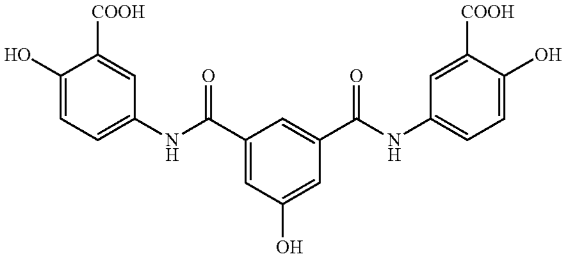 |
| V-002a diethyl ester | 5-(3-(3-(ethoxy carbonyl)-4-hydroxyphenylcarbamoyl)-5-hydroxybenzamido)-2-hydroxy benzoic acid ethyl ester | 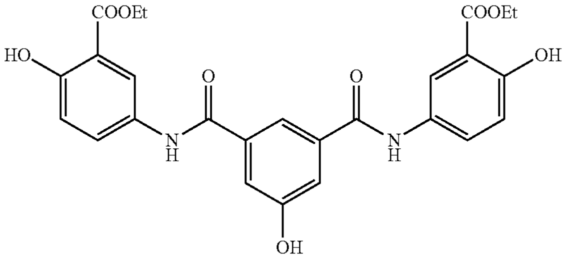 [SMILES: O=C(Nc1ccc(O)c(C(=O)O)c1)c1cc(O)cc(C(=O)Nc2ccc(O)c(C(=O)O)c2)c1] |
| V-003a | 4,4'-carbonylbis(azanediyl)bis(2,5-dihydroxybenzoic acid) | 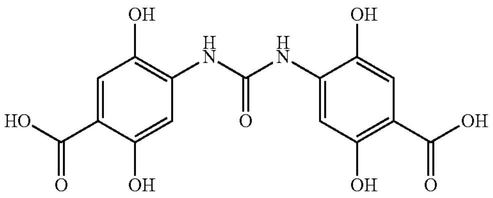 [SMILES: O=C(Nc1cc(O)c(C(=O)O)cc1O)Nc1cc(O)c(C(=O)O)cc1O] |
| V-003a diethyl ester | Diethyl 4,4'-carbonylbis(azanediyl)bis(2,5-dihydroxybenzoate) | 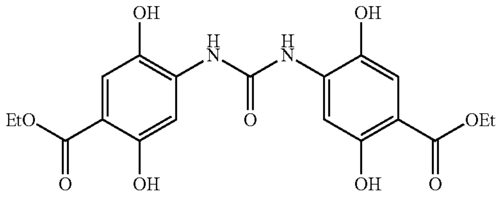 [SMILES: CCOC(=O)c1cc(O)c(NC(=O)Nc2cc(O)c(C(=O)OCC)cc2O)cc1O] |

The present invention also relates to a process for the preparation of the hydroquinone derivative compound of formula (I), which comprises:

Step (a): Coupling of hydroquinone-derived carboxylic acid, protected at the phenolic functions, with an aniline carrying diverse functional groups, by way of the corresponding acyl chloride or using an amide coupling agent such as TCFH in the presence of NMI;

Step (b): Deprotection of the ester functions typically by a saponification reaction; and Step (c): Deprotection of the phenolic functions typically by catalytic hydrogenation.

Or, alternatively,

Step (d): Reduction of the hydroquinone-derived carboxylic acid, protected at the phenolic functions, to produce a benzylic alcohol (e) Activation of the benzylic alcohol function and substitution with a benzylic nucleophile (alcohol, thiol, primary or secondary amine) carrying diverse functional groups;

(f) Deprotection of the ester functions typically by a saponification reaction; and (g) Deprotection of the phenolic functions typically by catalytic hydrogenation.

The process is schematically represented below:

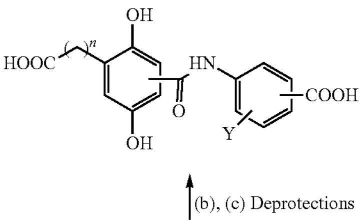

-continued

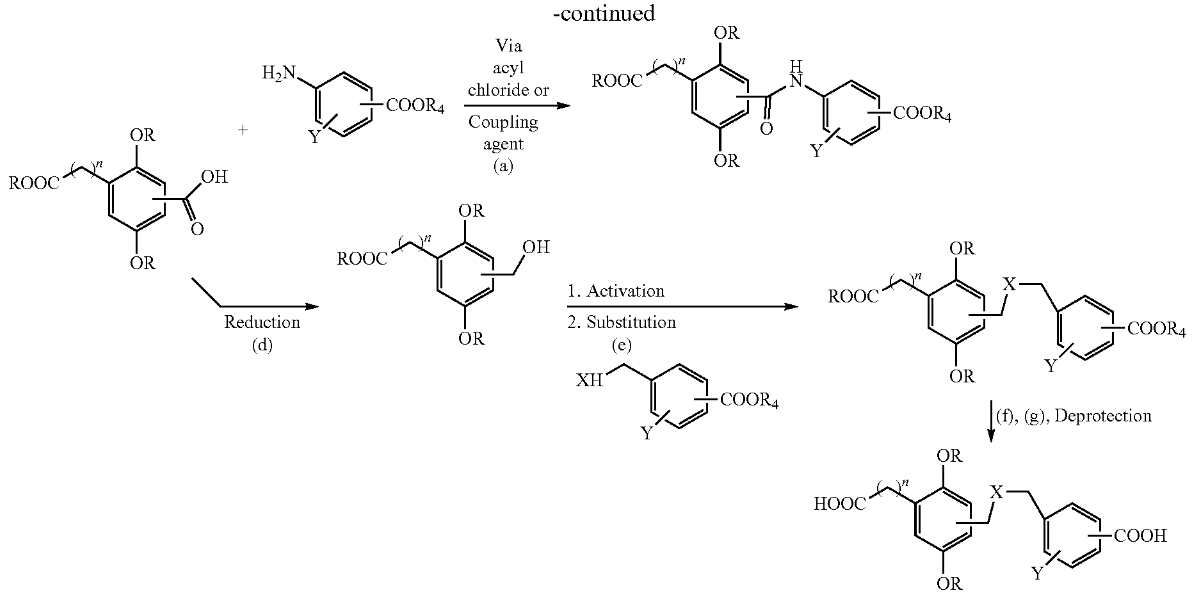

The hydroquinone derivative compounds of the present invention may be present as optically active forms (stereoisomers), E/Z isomers, enantiomers, racemates, diastereoisomers thereof, and hydrates and solvates thereof. Solvates of the compounds are due to the mutual attraction between the molecules of the compound and the inert solvent used. Solvates e.g. monohydrate, dihydrates or alcoholates.

The hydroquinone derivatives of the present invention may also be present as pharmaceutically acceptable salts, wherein the parent hydroquinone derivatives are modified by preparing acidic or basic salts thereof.

Examples of pharmaceutically acceptable salts include, among others, mineral or organic acid salts of basic residues, such as amines; and alkaline or organic salts of acidic residues, such as carboxylic acids and the like. Pharmaceutically acceptable salts may include conventional non-toxic salts or quaternary ammonium salts which are suitable for all routes of administration of the compounds, for example, from non-toxic organic or inorganic acids. For example, said conventional non-toxic salts include those derived from inorganic acids, such as hydrochloric, hydrobromic, sulfuric, sulfamic, phosphoric, nitric and the like; and salts prepared from organic acids such as acetic, propionic, succinic, glycolic, stearic, lactic, malic, tartaric, citric, ascorbic, pamoic, maleic, hydroxyleleic, phenylacetic, glutamic, benzoic, salicylic, sulfanyl, 2-acetoxy-benzoic, fumaric, toluenesulfonic, methanesulfonic, ethanedisulfonic, oxalic, isethionic, trifluoroacetic and the like.

Pharmaceutically acceptable salts are described for cations and anions "Pharmaceutical salts: A summary on doses of salt formers from the Orange Book. Saal C, European Journal of Pharmaceutical Sciences, 2013, 49, 614-623. By way of examples of cations, we may cite aluminum, arginine, benzathine, calcium, chloroprocaine, choline, diethanolamine, diethylamine, ethanolamine, ethylenediamine, lysine, magnesium, histidine, lithium, meglumine, potassium, procaine, sodium, triethylamine, zinc. by way of examples of anions, we may cite acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, tosylate. Alternatively, zwiterions may be used as salts such as free amino-acids arginine or lysine as cationic counterions and glutamate or aspartate as anionic counterions.

Short peptides (2 to 20 amino acids) as repeated units of Arginine or Lysine and their combinations with other neutral amino acids. These cationic cell penetrating peptides (CPP) may be used as enhancers for the penetration of drug into cells.

Pharmaceutically acceptable salts of the compounds useful in the present invention may be for example synthesized from the parent compound containing a basic or acidic moiety by conventional chemical procedures. Generally, said salts can be prepared by reacting the free acid or the basic forms of these compounds with a stoichiometric amount of the appropriate base or acid in water or in an organic solvent, or in a mixture of the two; In general, non-aqueous media such as ether, ethyl acetate, ethanol, isopropanol, or acetonitrile are preferred. In Remington's Pharmaceutical Sciences, 17th ed., Mack Publishing Company, Easton, PA, 1985, p. 1418, whose disclosure is incorporated herein by reference, lists of suitable salts are presented.

Suitable dosages according to the invention and as described herein in the various embodiments may vary depending upon the condition, age and species of the subject, and can be readily determined by those skilled in the art. The total daily dosages employed in both veterinary and human medicine will suitably be in the range 0.01-2000 mg/kg body weight, preferably from 0.1-1000 mg/kg body weight, preferably from 1-100 mg/kg and these may be administered as single or divided doses, and in addition, the upper limit can also be exceeded when this is found to be indicated. Such dosage may be adjusted to the individual requirements in each case including the specific compounds being administered, the route of administration, the condition being treated, as well as the patient being treated. However, the compounds can also be administered as depot preparations (implants, slow-release formulations, etc.) weekly, monthly or at even longer intervals. In such cases the dosage may be much higher than the daily one and may be adapted to the administration form, the body weight, and the concrete indication. The appropriate dosage can be determined by conducting conventional model tests, preferably animal models. In general, in the case of oral or parenteral administration to adult humans weighing approximately 70 kg, a daily dosage of about 10 mg to about 10.000 mg, preferably from about 200 mg to about 1000 mg, should be appropriate, although the upper limit may be exceeded when indicated. It is to be understood that the above therapeutically effective dosages need not be the result of a single administration and are usually the result of the administration of a plurality of unit doses. Those unit doses can in turn comprise portions of a daily or weekly dosage, and thus, the therapeutically effective dose is determined over the period of treatment (contacting). For example, for oral administration, the daily dose can be about 0.04 to about 1.0 mg/kg of body weight, more preferably about 0.04 to about 0.20 mg/kg/day, more preferably still at about 0.05 to about 0.15 mg/kg/day, and most preferably about 0.1 mg/kg body weight. In general, the amount of active substance administered can vary over a relatively wide range to achieve, and preferably maintain, the desired plasma concentration. Unit dosage forms of the active ingredient can contain about 0.1 milligrams to about 15 milligrams thereof. A preferred unit dosage form contains about 0.1 to about 1 milligram of agent and can be administered 2 to 5 times per day. However, it should be noted that other alternative routes like continuous infusion at a rate designed to maintain the above-described plasma concentration is also contemplated. Duration of a particular treatment can also vary, depending on severity of the disease, whether the treatment is intended for an acute manifestation or for prophylactic purposes, and like considerations. Typical administration lasts for a time period of about 5 to about 14 days, with a 7-day time course being usual. Courses (cycles) of administration can also be repeated at monthly intervals, or parenteral unit dosages can be delivered at weekly intervals. Oral unit dosages can be administered at intervals of one to several days to provide the determined therapeutically effective dose. The appropriate dosage of the compounds of the invention will depend on the type of disease to be treated, on the severity and course of the disease, on whether the agent is administered for preventive or therapeutic purposes, of the patient's medical history, and of the response to the compounds, and of the criteria of the responsible physician. The determination of the appropriate dose or route of administration is clearly within the capabilities of a current physician. Animal experiments provide a reliable guide for the determination of effective doses for human therapy. The inter-species scaling of effective doses can be carried out following the principles established by Mordenti, J. and Chappell, W. "The use of interspecies scaling in toxicokinetics", in Toxicokinetics and New Drug Development, editors Yacobi et al., Pergamon Press, New York, 1989, pp. 42-96.

The present invention further provides a pharmaceutical composition comprising (i) a therapeutically effective amount of the hydroquinone derivative compound of formula (I) or a pharmaceutically acceptable salt, or a prodrug, or stereoisomer thereof, and (ii) a pharmaceutically acceptable excipient or excipients.

The pharmaceutical excipients according to the present invention may be selected from the group consisting of conventional excipients, such as but no limited to solubilizers, binders, fillers, disintegrants, lubricants, pH modifiers, permeation enhancers, release modifiers, preservatives, coating agents, carriers, taste masking agents and combinations thereof.

The pharmaceutical composition of the compounds of the present invention with one or more pharmaceutical components, may be formulated with said excipients as liquid medicines, solid or semi-solid medicines, and/or gaseous medicines.

When they are present in solid formulations, these may include without any limitations, granules, pellets, tablets, capsules, powders, films, lozenges, crushable tablets, dissolvable tablets, disintegrating tablets, dispersible tablets, film coated tablets, and controlled, sustained, extended, or modified release formats of any of the above-mentioned solid formats. Such formulations may also be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems.

The compositions may be prepared using any one or more of techniques such as direct blending, dry granulation, wet granulation, homogenization, milling, micronization, extrusion and spheronization. Compositions may be presented as uncoated, film coated, sugar coated, powder coated, enteric coated, and modified release coated. When they are present in liquid formulations, these may include without any limitations, any liquid forms such as solutions, suspensions, nanosuspensions, dispersions, colloids, emulsions, lotions, creams, ointments, tinctures, and freeze-dried compositions. When they are present in gaseous formulations these may include without any limitations, milled powder or blend, micronized powder, or blend, nanosuspensions, aerosols, sprays, droplets, mists, nebulised solutions, or suspensions, and/or atomized vapors.

Pharmaceutical compositions according to the present invention may further comprise any additives such as vehicles, binding agents, perfumes, flavoring agents, sweeteners, colorants, antiseptics, antioxidants, stabilizing agents, and surfactants, if desired.

Pharmaceutical compositions and compounds according to the present invention may be formulated for administration via enteral routes, such as oral routes; parenteral routes via injections such as intravenous, subcutaneous, intraocular, intramuscular, or intraperitoneal injections; topical routes, such as ocular routes, mucosal and transmucosal routes, including sublingual/buccal routes; as well as as pulmonary, nasal, intranasal, intrabronchial, intrapulmonary routes. Ocular routes of administration include topical ocular administration, intraocular, intravitreal, or retrobulbar administration.

Preferred formulations of the compounds according to the present invention comprise liquid oral formulations, ocular formulations, and intravenous and intraperitoneal formulations.

Liquid oral formulations are solution and suspension formats for oral drug administration are common, convenient, and deemed safe. They can be used to deliver relatively large quantities of drug and are frequently used for the paediatric population and for those who experience difficulties in swallowing tablets or capsules. Introduction via the gastrointestinal tract provides fast dissolution and drug absorption, however tolerability and interaction with other materials in the tract must be considered. Properties of the active pharmaceutical ingredient (API) can lend themselves to be formulated in simple aqueous based oral solutions however when API are poorly soluble, formulations need to be designed around the molecule to enhance solubility and bioavailability. Introduction of surfactant, solvents, buffers, and oils increase solubility and reduce precipitation and/or degradation on interaction with gastric fluids. Where suspensions are required, particle size is often reduced and controlled to enhance drug solubility, permeation and ultimately drug absorption. As formulation development progresses, preservatives and flavours are introduced to enable patient conformity and shelf-life appropriateness.

Ocular formulations are ophthalmic formulations are delivered directly to the eye and are frequently liquids in solution or suspension formats. Administration to the eye avoids metabolism by the gastrointestinal tract and can be used for drugs which are poorly absorbed when given orally. Eye drops are sterile and isotonic with a nominal pH of 4-8 to avoid eye irritation. Excipients including solubilizing agents, chelating agents, polymers, surfactants, permeation enhancers and cyclodextrins are added to the formulation to improve stability, modify viscosity, or increase solubility, permeability, and bioavailability of poorly soluble drugs.

Intravenous formulations allow rapid absorption after parenteral drug delivery of the entire dose reaching the patients system for an immediate response. This mode of introduction avoids metabolism by the gastrointestinal tract and can be used for drugs which are poorly absorbed when given orally. Injections are typically sterile, isotonic water-based solutions and are designed to not induce pain on administration. For poorly soluble drugs, formulations are modified with organic co-solvents, surfactants, and buffers to increase solubility with nano-suspension formulations also being acceptable. For those molecules which are unstable in solution, formulations can be lyophilised for dilution at the point of use.

The present invention also provides kits, comprising a composition comprising a therapeutically effective dose of one or more compounds of the present invention or the formulations thereof as well as a delivery device for administration of the said composition or formulation and further comprising a package insert incorporating manual instructions for usage.

To prepare the present pharmaceutical compositions, the active ingredient according to the invention may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. Compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, polyethylene glycol, water, ethanol, and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers, and adjuvants, see Remington's Pharmaceutical Sciences, edited by E. W. Martin (Mack Publishing Company, 18th ed., 1990).

The compositions also can include stabilizers and preservatives. Examples of pharmaceutically acceptable solvents that may be used in the present composition may be found in reference books such as the Handbook of Pharmaceutical Excipients (Ninth Edition, Pharmaceutical Press, London and American Pharmacists Association, Washington, 2020), Aulton's Pharmaceutics, The Design and Manufacture of Medicines. (Fifth edition, Editors: Kevin Taylor and Michael Aulton, Elsevier, 2017)," Ullmann's Encyclopedia of Industrial Chemistry, 6th Ed." (various editors, 1989-1998, Marcel Dekker) and in "Pharmaceutical Dosage Forms and Drug Delivery Systems" (ANSEL et al., 1994 et 2011, WILLIAMS & WILKINS). Non-limiting examples of pharmaceutically-acceptable solvents that may be used in the present composition include, but are not limited to, propylene glycol (also known as 1,2-dihydroxypropane, 2-hydroxypropanol, methyl ethylene glycol, methyl glycol or propane-1,2-diol), ethanol, methanol, propanol, isopropanol, butanol, glycerol, polyethylene glycol (PEG), glycol, Cremophor EL or any forms of polyethoxylated castor oil, dipropylene glycol, dimethyl isosorbide, propylene carbonate, N-methylpyrrolidone, glycofurol, tetraethyleneglycol, propylene glycol fatty acid esters, and mixtures thereof.

The compounds according to the invention have demonstrated anti-fibrotic, anti-inflammatory, and antiangiogenic effects. Several diseases listed herein after involving not only one but two or even the three targets. Disease Categories showing pre-dominant angiogenic (vascular), inflammatory and/or fibrotic pathobiology.

In some embodiments the present invention is directed to pro-drugs of the compounds according to the present invention. Benefits of such prodrugs are obtained by methods known to a person of skill in art, for example by adding the appropriate cleavable functional groups that would generate for example, a better aqueous solubility for parenteral delivery or for oral delivery.

Pro-drugs for molecules of the invention exhibiting very polar and charged properties is especially preferred as these functional groups may positively influence the passive permeability across biological membranes. The main obstacles for polar and charged drugs is their poor membrane permeability which often leads to low and variable oral absorption and to low oral bioavailability. Furthermore, oral absorption of polar and charged drugs is often associated with substantial interspecies variability. Poorly permeable drugs also have low exposure levels in specific target organs even after topical administration. Improving membrane permeability has been one of the most fruitful areas of prodrug research to date. Different prodrug strategies have been developed for the drugs according to the invention to overcome topical route barriers onto the eye, oral mucosa barriers, transporter effects or other topical uses.

Prodrug strategies were formally recognized by Adrian Albert in 1958 (Albert, A. Chemical aspects of selective toxicity. Nature, 1958, 182, 421-422) but started in the early part of the previous century, as exemplified by methenamine, phenacetin and prontosil. Prodrugs are molecules with little or no pharmacological activity but have a built-in structural lability, whether by chance or by design, that permits bioconversion in vivo into the active drug. The conversion can occur through a chemical or enzymatic process or a combination of the two. Active molecules are often associated with undesirable physicochemical properties that create considerable challenges for their delivery to the appropriate biological target.

Prodrugs obtained via structural modifications of the drug are designed to influence the inherent physicochemical properties of a molecule to enable its delivery. These developments are not always integrated into the design of new molecules at the discovery phase. Often the analogue optimization, is the preferred path forward. Implementing an early prodrug strategy may result in more rapid clinical development and, ultimately, commercialization of a drug product.

Prodrug strategies for the most common functional groups on parent drugs are described in Rautio J, 2018 (Jarkko Rautio et al, Nature Reviews Drug Discovery, 2018, 17, 559-587). This review describes the expanding role of prodrugs in contemporary drug design and development and the prodrug strategies for the most common functional groups on parent drugs.

Benefits of prodrugs are obtained by adding the appropriate cleavable functional groups that would generate for example, a better aqueous solubility for parenteral delivery or for oral delivery. On the other hand, for very polar and charged molecules, these functional groups may positively influence the passive permeability across biological membranes. The main obstacles for polar and charged drugs is their poor membrane permeability which often leads to low and variable oral absorption and to low oral bioavailability.

Furthermore, oral absorption of polar and charged drugs is often associated with substantial interspecies variability. Poorly permeable drugs also have low exposure levels in specific target organs even after topical administration. Improving membrane permeability has been one of the most fruitful areas of prodrug research to date. Many prodrug strategies can be applied to influence the lipophilicity of a parent drug. Lipophilicity of drugs has been improved by masking its polar and ionized functionalities by short-chain hydrocarbon promoieties. Hydrophilic hydroxyl, carboxyl, phosphate or amine and other negatively or positively charged groups have been successfully converted to more lipophilic alkyl or aryl esters or N-acyl derivatives, which are rapidly hydrolysed back to the parent drugs in the body by ubiquitous esterases or peptidases.

The majority of lipophilic prodrugs have been developed to improve membrane permeability and oral absorption. The same prodrug strategy can be applied to improve topical administration of parent drugs that are absorbed through the skin or eye. During topical administration on the eye, the prodrug readily penetrates the cornea after instillation where it is hydrolysed predominately by ocular carboxylesterase.

Prodrugs can also exploit carrier-mediated transport. These transporters are membrane proteins that play an important role in controlling the intake and efflux of crucial polar endogenous nutrients. Their specificity is not limited to endogenous substrates, and drugs that bear a close structural resemblance to endogenous substrates, can also be carried across cell membranes by transporters. Carrier-mediated transport is particularly important for polar and charged drugs, as they have negligible passive diffusion across biological membranes. Prodrugs that can take advantage of carrier-mediated transport mechanisms offer intriguing targets in drug design. Similarly, prodrugs can bring improved metabolic stability.

Prodrugs can improve metabolic instability which is typically attributed to hepatic metabolism. Similarly, unwanted intestinal metabolism of drugs can be overcomed by selective prodrug strategies. This instability can greatly reduce the total amount of a drug that reaches the systemic circulation and its target. Prodrugs can be used to protect active drugs from this first-pass effect by masking a metabolically labile but pharmacologically essential functional group, such as a phenol, to avoid rapid metabolism.

To solve the problem of insufficient plasma levels and prolong the duration of action, drugs are usually controlled by formulations, such as suspensions and polymeric matrices, which control drug release and avoid peak effects and prolong their actions. Prodrugs can be used to achieve controlled release of an active drug by modifying its aqueous solubility and dissolution properties in a way that affects the release rate of the active drug, the rate of absorption or its tissue distribution.

Prodrugs have been especially useful in the development of several subcutaneous or intramuscular sustained-release depot injections, which maintain therapeutic plasma levels of a parent drug for weeks to months. These prodrugs are typically fatty acid esters, such as decanoates, palmitates, enanthates, cypionates or valerates, that are formulated in an oil-based vehicle, which results in the slow release of the prodrug and, hence, modulates the disposition of the parent drug. The high lipophilicity of these prodrugs also results in binding to blood and tissue proteins, which slows enzymatic conversion and consequently results in the slow appearance of an active drug in the systemic circulation.

Better targeting and lower side effects is often achieved with prodrugs targeting cleaved in an acidic environment of a tumor tissue, in endosomes or lysosomes with an acid labile prodrug. A similar approach is also achieved using site-specific enzymes and the prodrug is predominately cleaved in the desired organ or tissue where the enzyme is at the highest concentration. For charged drugs, the intracellular cleavage leads to high cellular concentration of the negatively or positively charged drug which stay confined in the target cell.

Different prodrug strategies have been developed for the drugs according to the invention to overcome topical route barriers onto the eye, oral mucosa barriers, transporter effects or other topical uses.

Drugs according to the invention are bearing charged polar groups. The problem to solve depends on the route of administration and the need for a long or short duration of drug action. Examples of prodrugs that are cleaved by mouse as well as human tissue and blood esterases have been synthesized successfully.

The compounds of the invention carry carboxylic functions and phenol groups. A wide diversity of prodrugs derived from these functions can be considered: for example, carboxylic acids have been converted most frequently into esters: simple alkyl esters (methyl, ethyl, isopropyl and longer chains), functionalized alkyl esters such as morpholinoalkyl esters, pyrrolidinoalkyl esters, N-methylpiperazino-alkyl esters, also aryl esters such as guaiacol derived esters; mixed acetal esters such as acyloxymethyl (or 1-ethyl) or alkoxycarbonyloxymethyl (or 1-ethyl) esters and (oxodioxolyl)methyl esters are also efficient prodrug functions for carboxylic acids. A diversity of esters and functionalized ethers have been used as prodrugs based on phenols: simple aliphatic esters, aromatic esters, hemiesters of dicarboxylic acids, amino acid esters, carbamate esters, phosphate monoesters, phosphonooxymethyl ethers, acyloxymethyl (or 1-ethyl) ethers, alkoxycarbonyloxymethyl (or 1-ethyl) ethers, aminoacyloxymethyl ethers, and the like.

Therefore, the present invention provides a method of treating and/or preventing a disease or disorder autoimmune, immunological, rheumatology, vascular disorders, ophthalmologic disorders, fibrotic disorders, metabolic and gastrointestinal disorders, neuroinflammatory and neurodegenerative diseases, neoplasms and cancer associated disorders, hormone related diseases and immunological disorders resulting from viral and bacterial infectious diseases and complications thereof, comprising administering a subject in a need a therapeutically effective dose of the compounds and/or pharmaceutical compositions of the present invention as described above.

Pharmaceutical compositions and methods according to the present invention are particularly suitable for a subject which is a human or non-human animal subject.

Compounds according to the invention may target diseases basis on their individual cytokine profiles as described in BIODATA provided for several compounds (See FIGS. 3A-D). The following web site Open Targets Platform (URL: https://www.targetvalidation.org/, Denise Carvalho et al, Nucleic Acids Research, Volume 47, Issue D1, 8 Jan. 2019, D1056-D1065, https://doi.org/10.1093/nar/gky1133) gives a complete picture based on current bibliographic information and can be searched by disease or cytokine.

Two typical examples: (a) disease specific search for diabetic retinopathy leads to the following cytokines described with a high correlation with the disease (FIG. 3C). The three top cytokines are as an example for diabetic retinopathy search indicate VEGFA score=1 (vascular endothelial growth factor A), HFE score=1 (homeostatic iron regulator) and TNF score=0.86 (tumor necrosis factor) and (b) searching for VEGFA: leads to nervous system disease, vascular disease, eye disease, retinopathy and several other diseases shown in FIG. 3D.

To illustrate the potency of compounds on small group of inflammatory cytokines, the effects of the compounds were assessed on human whole blood (Example 3.6) and their IC50 values on inhibition of LPS induced inflammation (Table 13, in μM).

TABLE 13

| Compound | GM-CSF | IFNγ | IL-1b | IL-2 | IL-4 | IL-5 | IL-6 | IL-9 | IL-10 | IL-12p70 |
|---|---|---|---|---|---|---|---|---|---|---|
| Ia-001a | 100 | 30.5 | 34.4 | 94.3 | 100 | 100 | 1.24 | 5.63 | 100 | 1.5 |
| Ia-001a-Tz | 100 | 100 | 100 | 7.99 | 100 | 100 | 0.75 | 8.63 | 26.1 | 32.4 |
| Ia-001a-Tz/004a | 3.4 | 0.61 | 100 | 4.91 | 100 | 100 | 3.04 | 8.48 | 19.5 | 12.2 |
| Ic-001a-Tz2 | 100 | 1.38 | 100 | 9.45 | 100 | 100 | 0.52 | 9.13 | 100 | 29.1 |
| Ia-001c | 100 | 0.44 | 100 | 12.8 | 100 | 100 | 0.95 | 46.9 | 1.9 | 0.44 |
| Ia-003a-Tz | 100 | 2.95 | 100 | 43 | 100 | 100 | 1.41 | 3.62 | 6.94 | 1.26 |
| Ic-007a | 100 | 1.44 | 100 | 100 | 100 | 100 | 0.09 | 27.1 | 12.5 | 0.49 |
| Ib-010a | 100 | 2.22 | 33.3 | 2.74 | 100 | 100 | 1.02 | 11.58 | 100 | 0.27 |
| Ib-010a-E3 | 100 | 2.79 | 100 | 36.2 | 100 | 100 | 0.24 | 26.8 | 100 | 0.84 |
| Ia-015a | 2.76 | 100 | 100 | 7.08 | 100 | 100 | 0.77 | 1.47 | 5.27 | 0.12 |
| IIc-007a | 26 | 0.11 | 100 | 12.8 | 100 | 100 | 0.05 | 2.14 | 17.9 | 3.37 |
| IIc-009a | 100 | 0.54 | 100 | 19.6 | 100 | 100 | 0.27 | 18.9 | 11.31 | 100 |
| IIa-053a | 100 | 1.04 | 100 | 1.67 | 100 | 100 | 2.2 | 1.41 | 100 | 0.27 |
| IIIa-001aTz | 100 | 18.9 | 100 | 100 | 100 | 100 | 1.98 | 3.01 | 7.78 | 0.48 |
| IIIa-013a | 27.8 | 0.15 | 100 | 57.1 | 100 | 100 | 3.55 | 11.9 | 37.3 | 0.5 |
| IIIc-057a | 100 | 0.9 | 16.2 | 24.2 | 100 | 100 | 0.19 | 11.1 | 100 | 0.73 |
| IIIc-061a | 31.2 | 2.48 | 100 | 100 | 100 | 100 | 0.18 | 8.85 | 17.9 | 37.2 |
| IVc-058a | 100 | 10.6 | 27.5 | 3.82 | 100 | 100 | 0.21 | 31.1 | 16.4 | 4.23 |
| IVc-059a | 100 | 4.34 | 38.6 | 21.2 | 100 | 100 | 0.11 | 0.4 | 1.31 | 42 |
| IVc-059a-E2-A4 | 1.83 | 3.5 | 14.1 | 10.4 | 100 | 100 | 0.99 | 2.9 | 16.8 | 51.4 |

| Compound | IL-13 | IL-17A | IL-17F | IL-18 | IL-21 | IL-33 | TGFbeta | TNFa | β |
|---|---|---|---|---|---|---|---|---|---|
| Ia-001a | 26.4 | 0.1 | 14.7 | 100 | 100 | 19.3 | 100 | 0.02 | 13.20 |
| Ia-001a-Tz | 32.1 | 0.11 | 46.5 | 100 | 100 | 23.6 | 100 | 0.63 | 53.00 |
| Ia-001a-Tz/004a | 1.5 | 0.02 | 2.4 | 46.6 | 0.3 | 1.67 | 100 | 0.002 | 3.02 |
| Ic-001a-Tz2 | 0.12 | 0.31 | 0.15 | 33.9 | 32 | 0.23 | 100 | 0.1 | 0.41 |
| Ia-001c | 86.1 | 0.09 | 89.7 | 100 | 100 | 100 | 100 | 0.05 | 29.70 |
| Ia-003a-Tz | 89.6 | 0.07 | 83.9 | 100 | 1.49 | 72.2 | 100 | 0.18 | 55.00 |
| Ic-007a | 30.1 | 0.04 | 22.9 | 100 | 1.9 | 18.4 | 100 | 0.27 | 6.52 |
| Ib-010a | 100 | 0.42 | 100 | 100 | 67.8 | 31.3 | 100 | 0.31 | 49.30 |
| Ib-010a-E3 | 33 | 0.52 | 34.2 | 100 | 100 | 20 | 100 | 0.98 | 38.20 |
| Ia-015a | 0.15 | 0.05 | 0.15 | 100 | 57.2 | 0.24 | 100 | 0.17 | 0.30 |
| IIc-007a | 0.25 | 0.01 | 0.26 | 100 | 9.41 | 0.18 | 100 | 0.03 | 0.29 |
| IIc-009a | 0.13 | 0.001 | 0.13 | 2.95 | 8.01 | 0.29 | 100 | 0.11 | 6.94 |
| IIa-053a | 29.9 | 100 | 28.8 | 100 | 100 | 12.1 | 100 | 0.02 | 91.50 |
| IIIa-001aTz | 0.15 | 0.17 | 0.16 | 27.7 | 3 | 0.14 | 100 | 0.31 | 0.23 |
| IIIa-013a | 0.37 | 0.15 | 0.41 | 100 | 1.63 | 1.11 | 100 | 0.51 | 0.89 |
| IIIc-057a | 4.73 | 1.32 | 5.06 | 100 | 1.56 | 2.93 | 100 | 0.15 | 1.58 |
| IIIc-061a | 0.31 | 0.04 | 0.32 | 32.4 | 6.38 | 0.31 | 100 | 0.03 | 0.81 |
| IVc-058a | 55.9 | 0.1 | 86.8 | 100 | 3.2 | 33.9 | 100 | 0.18 | 59.30 |
| IVc-059a | 100 | 0.16 | 100 | 100 | 1.87 | 27.5 | 100 | 0.16 | 0.33 |
| IVc-059a-E2-A4 | 18.7 | 0.02 | 25.8 | 100 | 100 | 23.2 | 100 | 0.3 | 19.40 |

Immunological/rheumatology/vascular disorders may include for example peritonitis, Kawasaki disease (KD), Takayasu arteritis (TA), microscopic polyangiitis (MP), giant cell arteritis (GCA), antiphospholipid syndrome (APS), Behcet's Disease (BD), granulomatosis with polyangiitis (GPA) or Wegener's granulomatosis (WG), eosinophilic granulomatosis with polyangiitis, Churg-Strauss syndrome (EGPA), and rosacea (RO).

Rheumatology's disorders in particular affect joints tendons, ligaments and bones with pain, loss of motions, and inflammation. These include many types of arthritis such as osteoarthritis (OA), rheumatoid arthritis (RA), lupus, spondyloarthropathies: ankylosing spondylitis (AS) and psoriatic arthritis (PsA), Sjogren's syndrome, Gout, scleroderma, Infectious arthritis, juvenile idiopathic arthritis, polymyalgia rheumatica.

Peritonitis is an inflammation of the peritoneum usually due to a bacterial or fungal infection. There are two types of peritonitis. First type is spontaneous peritonitis which may develop as a complication of liver disease, such as cirrhosis, or of kidney disease. Secondary peritonitis may result from abdomen perforation, or as a complication of other medical conditions. Left untreated, peritonitis can lead to severe, potentially life-threatening infection.

Kawasaki Disease causes inflammation in the walls of medium-sized arteries throughout the body. It primarily affects children. The inflammation tends to affect the coronary arteries, which supply blood to the heart muscle. Kawasaki disease is sometimes called mucocutaneous lymph node syndrome because it also affects lymph nodes that swell during an infection, skin, and the mucous membranes inside the mouth, nose and throat.

Takayasu Arteritis is a rare type of vasculitis, a group of disorders that cause blood vessel inflammation.

In Takayasu's arteritis, the inflammation damages the aorta and its main branches. The disease can lead to narrowed or blocked arteries, or to aneurysm. Takayasu's arteritis can also lead to arm or chest pain, high blood pressure, and eventually heart failure or stroke. Medications are needed to control the inflammation in the arteries and prevent complications.

Granulomatosis with polyangiitis is an uncommon disorder that causes inflammation of the blood vessels in the nose, sinuses, throat, lungs and kidneys. Formerly called Wegener's granulomatosis, this condition is one of a group of blood vessel disorders called vasculitis. It slows blood flow to some organs. The affected tissues can develop areas of inflammation called granulomas, which can affect how these organs work. Without treatment, the condition can be fatal.

Giant cell arteritis is an inflammation of the lining of the arteries. Most often, it affects the arteries in the head, especially in the temples. For this reason, giant cell arteritis is sometimes called temporal arteritis. Giant cell arteritis frequently causes headaches, scalp tenderness, jaw pain and vision problems. Untreated, it can lead to blindness.

Antiphospholipid syndrome occurs when the immune system mistakenly creates antibodies that make blood much more likely to clot. This can cause dangerous blood clots in the legs, kidneys, lungs and brain. In pregnant women, antiphospholipid syndrome also can result in miscarriage and stillbirth. There is no cure for antiphospholipid syndrome. Only medications available can reduce risk of blood clots. Behcet's disease, also called Behcet's syndrome, is a rare disorder that causes blood vessel inflammation. The disease can lead to numerous signs and symptoms that can seem unrelated at first. They can include mouth sores, eye inflammation, skin rashes and lesions, and genital sores. Current treatment may help reducing the symptoms of Behcet's disease and to prevent serious complications, such as blindness.

Churg-Strauss syndrome is a disorder marked by blood vessel inflammation. This inflammation can restrict blood flow to organs and tissues, sometimes permanently damaging them. This condition is also known as eosinophilic granulomatosis with polyangiitis (EGPA). Asthma is the most common sign of Churg-Strauss syndrome. The disorder can also cause other problems, such as hay fever, rash, gastrointestinal bleeding, and pain and numbness in hands and feet. Churg-Strauss syndrome has no cure.

Current medications include steroids and other powerful immunosuppressant drugs to help to control symptoms.

Rosacea is a common skin condition that causes redness and visible blood vessels in the face. It may also produce small, red, pus-filled bumps. These signs and symptoms may flare up for weeks to months and then go away for a while. Rosacea can be mistaken for acne, other skin problems or natural ruddiness.

There is no cure for rosacea, but treatment can control and reduce the signs and symptoms. Osteoarthritis is the most common form of arthritis, affecting millions of people worldwide. It occurs when the protective cartilage wears down over time. Although osteoarthritis can damage any joint, the disorder most commonly affects joints in hands, knees, hips and spine. Osteoarthritis symptoms can usually be managed, although the damage to joints cannot be reversed.

Lupus is an autoimmune disease. It causes the immune system to produce proteins called autoantibodies that attack own tissues and organs, including the kidneys. Lupus nephritis is a frequent complication in people who have systemic lupus erythematosus (commonly known as lupus). Lupus nephritis occurs when lupus autoantibodies affect structures of the kidneys. This causes kidney inflammation and may lead to blood in the urine, protein in the urine, high blood pressure, impaired kidney function or even kidney failure.

Scleroderma is a group of rare diseases that involve the hardening and tightening of the skin and connective tissues. There are many different types of scleroderma. In some people, scleroderma affects only the skin. But in many people, scleroderma also harms structures beyond the skin, such as blood vessels, internal organs and the digestive tract (systemic scleroderma). there is no cure for scleroderma. Sjogren's syndrome is a disorder of the immune system identified by its two most common symptoms: dry eyes and a dry mouth. The condition often accompanies other immune system disorders, such as rheumatoid arthritis and lupus. In Sjogren's syndrome, the mucous membranes and moisture-secreting glands of the eyes and mouth are usually affected first—resulting in decreased tears and saliva.

Infectious or septic arthritis is a painful infection in a joint that can come from germs that travel through the bloodstream from another part of the body. Septic arthritis can also occur when a penetrating injury, such as an animal bite or trauma, delivers germs directly into the joint. People who have artificial joints are also at risk of septic arthritis. Knees are most commonly affected, but septic arthritis also can affect hips, shoulders and other joints. The infection can quickly and severely damage the cartilage and bone within the joint, so prompt treatment is crucial.

Juvenile idiopathic arthritis, formerly known as juvenile rheumatoid arthritis, is the most common type of arthritis in children under the age of 16. Juvenile idiopathic arthritis can cause persistent joint pain, swelling and stiffness. Some children may experience symptoms for only a few months, while others have symptoms for many years. Some types of juvenile idiopathic arthritis can cause serious complications, such as growth problems, joint damage, and eye inflammation.

Polymyalgia rheumatica is an inflammatory disorder that causes muscle pain and stiffness, especially in the shoulders and hips. Signs and symptoms of polymyalgia rheumatica usually begin quickly and are worse in the morning. Most people who develop polymyalgia rheumatica are older than 65. This condition is related to another inflammatory condition called giant cell arteritis.

Ophthalmologic disorders may include for example and without any limitations, age macular degeneration (AMD or ARMD, dry and wet forms), pterygium (PTE), diabetic retinopathy (DR), diabetic macular edema (DME), Stargardt disease (SD), proliferative vitreoretinopathy (PVR), dry eye syndrome (DYS), endophthalmitis, central serous chorioretinopathy (CSC), retinitis pigmentosa (RP), glaucoma and glaucoma associated complications, and uveitis (UVE).

Wet macular degeneration is a chronic eye disorder that causes blurred vision or a blind spot in the visual field. It is generally caused by abnormal blood vessels that leak fluid or blood into the macula. The macula is in the part of the retina responsible for central vision. Wet macular degeneration is one of two types of age-related macular degeneration. The wet type always begins as the dry type. Dry macular degeneration is more common and less severe. It also causes blurred or reduced central vision, due to thinning of the macula. Dry macular degeneration may first develop in one or both eyes and then affect both eyes. Vision loss is typically central but is retained in the peripheral vision. Diabetic retinopathy is a diabetes complication that affects eyes. It is caused by damage to the blood vessels of the retina. At first, diabetic retinopathy may cause no symptoms or only mild vision problems.

Eventually, it can cause blindness. The condition can develop in anyone who has type 1 or type 2 diabetes. DME is a serious eye complication which occurs when microaneurysms protrude from the vessel walls, leaking or oozing fluid and blood into the retina, thereby causing edema in the macula.

Stargadt disease is an eye disease that causes vision loss in children and young adults. It is an inherited disease and thus is passed on to children from their parents. Stargardt disease is a form of macular degeneration and is often called juvenile macular degeneration.

PVR is a disease that develops as a complication of rhegmatogenous retinal detachment. PVR occurs in about 8-10% of patients undergoing primary retinal detachment surgery and prevents the successful surgical repair of rhegmatogenous retinal detachment. PVR can be treated with surgery to reattach the detached retina but the visual outcome of the surgery is very poor.

Dry eye disease is a common condition that occurs when tears are not able to provide adequate lubrication of the eyes. Tears can be inadequate and unstable for many reasons. For example, dry eyes may occur if you do not produce enough tears or if you produce poor-quality tears. This tear instability leads to inflammation and damage of the eye's surface.

Endophthalmitis is an inflammation of the inside of the eye which may occur after eye injection or surgery. Signs are typically: blurred vision or other changes in vision, eye pain, redness of the eye, sensitivity of the eye to light, or tearing.

Retinitis pigmentosa (RP) is a group of rare, genetic disorders that involve a breakdown and loss of cells in the retina, which is the light sensitive tissue that lines the back of the eye. Common symptoms include difficulty seeing at night and a loss of side (peripheral) vision.

Glaucoma is a group of eye conditions that damage the optic nerve, the health of which is vital for good vision. This damage is often caused by an abnormally high eye pressure. Glaucoma is one of the leading causes of blindness for people over the age of 60. It can occur at any age but is more common in older adults. Many forms of glaucoma have no warning signs. The effect is so gradual with no change in vision until the condition is at an advanced stage.

Uveitis is a form of eye inflammation. It affects the middle layer of tissue in the eye wall or uvea. Uveitis warning signs often come on suddenly and get worse quickly. They include eye redness, pain, and blurred vision. Possible causes of uveitis are infection, injury, or an autoimmune or inflammatory disease.

Uveitis can be serious, leading to permanent vision loss.

Compounds and pharmaceutical compositions according to the present invention may also be used in a method of treating and/or preventing retinal neurodegenerative disease selected from the group consisting of diabetic retinopathy, age-related macular degeneration, glaucoma, and retinitis pigmentosa. Retinal neurodegenerative diseases refer to retinal conditions characterized by progressive neuronal loss.

Diabetic retinopathy, age-related macular degeneration, glaucoma, and retinitis pigmentosa are considered retinal diseases in which neurodegeneration plays an essential role.

According to this preferred embodiment, the compounds according to the present invention may be combined with other active agents to enhance the therapeutic efficacy of the condition to be treated and particularly with dipeptidyl peptidase-4 inhibitor (DPPIV) or a pharmaceutically acceptable salt thereof, for use in the topical eye treatment and/or prevention of a retinal neurodegenerative disease. The DPPIV inhibitor may be selected from the group consisting of sitagliptin, saxagliptin, vildagliptin, linagliptin, anagliptin, teneligliptin, alogliptin, trelagliptin, gemigliptin, omarigliptin, its pharmaceutically acceptable salts, and mixtures thereof.

Compounds according to the present invention may be also advantageously combined with anti-VEGF treatment in order to reduce the number of intraocular anti-VEGF antibody injections needed by the patients. Administration to the patients having retinal neurodegenerative diseases, such as for example diabetic retinopathy, age related macular degeneration slows the progression of these diseases and reduces the anti-VEGF pharmacotherapy that patients need.

Fibrotic disorders may include for example and without any limitations, cystic fibrosis, retroperitoneal fibrosis, idiopathic pulmonary fibrosis, combined pulmonary fibrosis & emphysema (CPFE), eosinophilic angiocentric fibrosis, intestinal fibrosis, ovarian fibrosis, nephrotenic systemic fibrosis, oral submucous fibrosis (OSMF) and liver fibrosis.

Cystic fibrosis (CF) is an inherited disorder that causes severe damage to the lungs, digestive system, and other organs in the body. It affects the cells that produce mucus, sweat and digestive juices. Instead of acting as lubricants, the secretions plug up tubes, ducts, and passageways, especially in the lungs and pancreas.

Pulmonary fibrosis is a lung disease that occurs when lung tissue becomes damaged and scarred. This thickened, stiff tissue makes it more difficult for the lungs to work properly. The scarring associated with pulmonary fibrosis can be caused by a multitude of factors. The lung damage caused by pulmonary fibrosis cannot be repaired, but medications and therapies can sometimes help ease symptoms and improve quality of life.

Emphysema is a lung condition that causes shortness of breath. The alveoli are damaged, and over time, the inner walls of the alveoli weaken and rupture, creating larger air spaces instead of many small ones.

This reduces the surface area of the lungs and, in turn, the amount of oxygen that reaches the bloodstream. Damaged alveoli do not work properly, leading to old air being trapped, and leaving no room for fresh, oxygen-rich air to enter.

Metabolic & gastro-intestinal disorders may include for example and without any limitations, diabetes induced complications: diabetic nephropathy (DN), diabetic retinopathy (DR), diabetic cardiomyopathy (DCDM), or diabetic foot ulcer (DFU). Hepatic diseases may include Nonalcoholic fatty liver disease (NAFLD), non alcoholic steatic hepatosis (NASH), primary biliary cholangitis (PBC), hepatic fibrosis or cirrhosis (HF), inflammatory bowel disease (IBD): ulcerative colitis, Crohn's disease, intestinal fibrosis. In addition to diabetic nephropathy, other kidney diseases may include polycystic kidney disease (PKD), chronic kidney disease (CKD), nephrogenic systemic fibrosis (NSF), and pancreatitis (acute and chronic).

Diabetic nephropathy is a serious kidney-related complication of type 1 diabetes and type 2 diabetes. It is also called diabetic kidney disease. About 25% of people with diabetes eventually develop kidney disease. Diabetic nephropathy affects kidneys' ability to do their usual work of removing waste products and extra fluid from the body. Over many years, the condition slowly damages kidneys' delicate filtering system, and may progress to kidney failure, also called end-stage kidney disease. Kidney failure is a life-threatening condition.

Nonalcoholic fatty liver disease (NAFLD) is an umbrella term for a range of liver conditions affecting people who drink little to no alcohol. As the name implies, the main characteristic of NAFLD is too much fat stored in liver cells. The most common form of chronic liver disease. Some individuals with NAFLD can develop nonalcoholic steatohepatitis (NASH), an aggressive form of fatty liver disease, which is marked by liver inflammation and may progress to advanced scarring (cirrhosis) and liver failure. This damage is similar to the damage caused by heavy alcohol use.

Primary biliary cholangitis is a chronic autoimmune disease in which the bile ducts in the liver are slowly destroyed. When the bile ducts are damaged, bile can back up in the liver and sometimes lead to irreversible cirrhosis. A combination of genetic and environmental factors triggers the disease.

IBD describes disorders that involve chronic inflammation of the digestive tract. Types of IBD include ulcerative colitis which involves ulcers along the superficial lining of the colon and rectum, as well as Crohn's disease which is characterized by inflammation of the lining of the digestive tract, which often can involve the deeper layers of the digestive tract. Both ulcerative colitis and Crohn's disease usually are characterized by diarrhea, rectal bleeding, abdominal pain, fatigue, weight loss, and sometimes lead to life-threatening complications.

Neoplasms and cancer associated disorders may include for example and without any limitations, pancreatic cancer: mostly fibrotic, renal cell carcinoma, radiation induced fibrosis, primary myelofibrosis, desmoplasia, fibrosarcoma, hepatocellular carcinoma, retinoblastoma, intra-ocular lymphoma, and melanoma (desmoplastic, conjunctival, uveal).

The invention also relates to the treatment, prevention, and reduction of viral infections via binding to virus proteins heparan sulfate binding sites. The compounds according to the invention interact with the heparan sulfate binding region of Growth factors (FGF, VEGF and other growth factors) and Growth factor receptors (FGFR, VEGFR and others). Many viruses are known to interact with mammalian cells using their affinity to heparan sulfate moieties bound to cell membranes. Viruses bearing on their surface proteins heparan sulfate (HS) binding domains use this HS affinity as one of the main entrance doors to approach and infect cells and bind to heparan sulfate attached to the cells. When attached to HS viruses are able to infect cells using various invading mechanisms specific to each virus. The strong interaction of the compounds according to the invention with the heparan binding domain of proteins and specifically viral proteins is preventing viral infection of blood cells, endothelial cells lining blood vessels and organs as well as surface epithelial cells present in the mouth, nasal mucosa, and lungs and also in the gastrointestinal tract. Several virus species are known with high affinity to heparan sulphates such as but not limited to respiratory syncytial virus, human metapneumovirus, influenza (H1N1 and the like), human rhinovirus (HRV), rhinosyncitial virus (RV), chikungunya virus, coronavirus such as CoV, SARS-CoV, MERS-Cov, COVID-19 (SARS-CoV-2 and their variants). HS is a necessary co-factor for SARS-CoV-2 infection. HS interacts with the receptor-binding domain of the SARS-CoV-2 spike glycoprotein, adjacent to ACE2, shifting the spike structure to an open conformation to facilitate ACE2 binding. Viral and bacterial infectious diseases may also include septic shock, inflammation in the eye such as endophthalmitis due to surgery or infection.

EXAMPLES

Example 1: Synthesis of the Compounds and Intermediates

Example 1.1: Molecules of Type Ia: Monoamides, 25 Examples

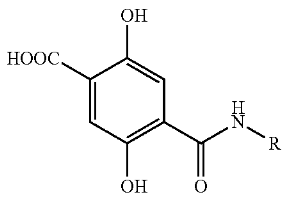

Synthesis of Precursors

Scheme 1. Synthetic Intermediates KI-1 and KI-6

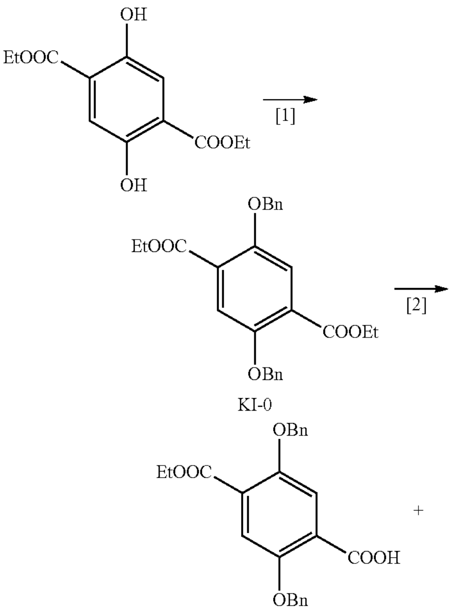

KI-0

KI-1

-continued

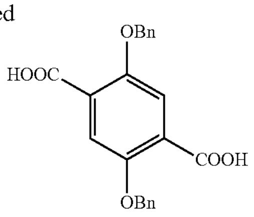

KI-6

Procedures:

Synthesis of KI-1 an KI-6 (Steps [1],[2])

Diethyl 2,5-bis(benzyloxy)terephthalate (KI-0) (Step [1]). Potassium carbonate-325 mesh (326.1 g, 2.4 mol) was added portion wise to a stirred solution of diethyl 2,5-dihydroxy-terephthalate (200.0 g, 0.79 mol) in DMF (800.0 mL) at ambient temperature over 15 min. Benzyl bromide (280.0 mL, 2.4 mol) was then added to the reaction flask in a dropwise manner over 30 min, and the resulting mixture was heated at 100 °C for 2 h, resulting in the formation of a thick cream-coloured precipitate. The reaction mixture was cooled down to ambient temperature and treated with a solution of saturated aqueous ammonium chloride (2 L). The resulting suspension was stirred for 30 min, then filtered. The solid material was washed with a solution of saturated aqueous ammonium chloride (2×200 mL). The solid was then suspended in ethanol (400 mL), filtered and dried in the vacuum oven to give the desired product as a white solid (341.0 g, 0.785 mol, 99.8%)

UPLC-MS (acidic method, 2 min): rt=1.36 min, no ionization observed, peak area >95%

$^1$H NMR (400 MHz, DMSO-$d_6$) δ 7.51-7.44 (m, 6H), 7.44-7.36 (m, 4H), 7.36-7.28 (m, 2H), 5.17 (s, 4H), 4.29 (q, J=7.1 Hz, 4H), 1.26 (t, J=7.1 Hz, 6H).

2,5-Bis(benzyloxy)-4-(ethoxycarbonyl)benzoic acid (KI-1) and 2,5-bis(benzyloxy)terephthalic acid (KI-6) (step [2])

A solution of potassium hydroxide (14.2 g, 0.25 mol) in water (200.0 mL) was rapidly added to a solution of diethyl 2,5-bis(benzyloxy)terephthalate (100 g, 0.23 mol) in 1,4-dioxane (1 L), and the resulting mixture was stirred overnight at ambient temperature. The solvent was removed in vacuo, resulting in the formation of a white slurry. The crude was suspended in EtOH (500 mL) and filtered and the collected solid was dried in vacuum oven to afford pure diethyl 2,5-bis(benzyloxy)terephthalate (23.0 g, 0.053 mol, 23%)

UPLC-MS (acidic method, 2 min): rt=1.36 min, no ionization observed, peak area 98% The ethanolic filtrate was concentrated to give an oil. Ethyl acetate (500 mL) was added to form a precipitate which was filtered and washed with ethyl acetate (200 mL) to afford 2,5-bis(benzyloxy) terephthalic acid (KI-6) as white solid (18.9 g, 0.042 mol, 18%).

UPLC-MS (acidic method, 2 min): rt=1.22 min, m/z 377.1 [M−H]$^-$, peak area 95%

$^1$H NMR (400 MHz, DMSO-$d_6$) δ 7.52-7.45 (m, 4H), 7.41-7.33 (m, 4H), 7.33-7.26 (m, 4H), 5.13 (s, 4H).

The filtrate was washed with a saturated solution of aqueous sodium carbonate (200 mL), aqueous 1 M hydrochloric acid (500 mL) and brine (500 mL), then dried ($Na_2SO_4$), filtered and concentrated to dryness to give 2,5-bis(benzyloxy)-4-(ethoxycarbonyl)benzoic acid (KI-1) as a white solid (53 g, 0.130 mol, 57.0%).

UPLC-MS (acidic method, 2 min): rt=1.22 min, m/z 405.3 [M−H]$^-$, peak area 96%

$^1$H NMR (400 MHz, DMSO-$d_6$) δ 7.52-7.27 (m, 13H), 5.17 (s, 4H), 4.28 (q, J=7.1 Hz, 2H), 1.26 (t, J=7.1 Hz, 3H).

Large Scale Protocole for the Synthesis of KI-1

A 10 L jacketed vessel was charged with diethyl 2,5-bis (benzyloxy)terephthalate (500.00 g, 1.15 mol), 1,4-dioxane (2.5 L), potassium hydroxide (71.00 g, 1.26 mol) and water (500 mL). The reaction mixture was stirred overnight at room temperature. LCMS Analysis showed the reaction had gone half-way to completion, showing also the by-product (di-acid) and starting material (di-ester) in the ratio of (diester:mono-acid:diacid=28:58:14). (diacid: 4.44 rt, monoacid: 5.08 rt, diester: 5.68 rt). At this stage solvent was removed in vacuo. The crude product was taken into a 2:1 mixture of ethanol:water (3 L), in a 10 L jacketed vessel, stirred overnight and filtered in order to give: Solid: (diester: mono-acid:diacid=86:12:2, 110.00 g, colourless solid) Filtrates: (diester:mono-acid:diacid 3:63:34)

The filtrates were concentrated in vacuo in order to afford an oil. This oil was taken up in ethyl acetate (2.5 L), stirred overnight in a 10 L jacketed vessel and filtered in order to give a white solid (150.00 g).

Solid: (diester:mono-acid:diacid=trace: 40:60).

The filtrates were collected, washed with a saturated aqueous solution of sodium bicarbonate (100 mL), 1N hydrochloric acid solution (200 mL) and brine (200 mL), dried over anhydrous sodium sulfate and filtered. The solvent was removed under reduced pressure to afford the desired product, 2,5-bis(benzyloxy)-4-(ethoxycarbonyl)benzoic acid (KI-1), as a white solid, which was dried in the vacuum oven at 50 °C for 48 h (225.00 g, 49% yield) (yields vary between 49-65%).

Scheme 2: Synthetic Intermediate KI-1Bn

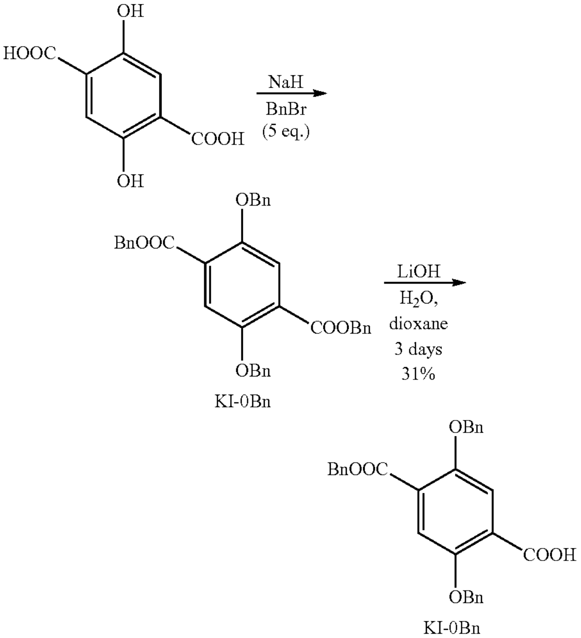

KI-0Bn

KI-0Bn
contains 16% KI-0Bn

Procedure:

Synthesis of KI-1Bn:

2,5-Bis(benzyloxy)-4-(benzyloxycarbonyl)benzoic acid (KI-1Bn). To a solution of 2,5-dihydroxytere-phthalic acid (1.97 g, 10 mmol) in DMF (20 mL) at 0 °C was added sodium hydride (2.0 g, 50 mmol) under stirring, then benzyl bromide (5.95 mL, 50 mmol, 5 eq) dropwise over 5 min, and the resulting mixture kept at room temp. for 2 h. The mixture was then heated at 60 °C for 18 h. The reaction mixture was cooled down to ambient temperature and treated cautiously with MeOH (5 mL). The mixture was concentrated under reduced pressure, and the residual material co-evaporated with heptane (3×). The residue was taken in DCM (30 mL), the organic phase washed with 1M HCl (25 mL), the separated aqueous layer was extracted with DCM (3×30 mL) and the combined organic phases dried (MgSO4) and concentrated. The crude solid was recrystallized from EtOH (~30 mL) to afford pure KI-0Bn (2.286 g, 41%). A sample of KI-0Bn (282 mg, 0.5 mmol) was added to a mixture of 1,4-dioxane (10 mL) and lithium hydroxide hydrate (22 mg, 0.52 mmol), and the mixture was heated to 80 °C for 3 d. The mixture was cooled down to room temp., taken in AcOEt (30 mL) and the solution washed with 1M HCl (2 mL). The organic phase was dried and concentrated, and the residue submitted to column chromatography to afford monoester KI-1Bn contaminated by about 16% of diester KI-0Bn.

KI-0Bn: $^1$H NMR (400 MHz, $CDCl_3$): δ 7.51 (s, 2H), 7.36-7.30 (m, 20H), 5.34 (s, 4H), 5.11 (s, 4H).

KI-1Bn: $^1$H NMR (250 MHz, $CDCl_3$): δ 7.86 (s, 1H), 7.61 (s, 1H), 7.41-7.30 (m, 20H), 5.36 (s, 2H), 5.26 (s, 2H), 5.16 (s, 2H).

Synthesis of Monoamides h. Excess thionyl chloride was removed in vacuo and the residue was co-distilled with toluene (3×20 mL) to afford the acyl chloride. A solution of the acyl chloride in DCM (10 mL) was rapidly added to a solution of amine (dimethyl 2-aminoisophthalate, 210 mg, 3.1 mmol) and N,N-diisopropylethylamine (0.53 mL, 3.045 mmol) in DCM (10 mL) at ambient temperature and the reaction was stirred for 18 h. The reaction was diluted with DCM (70 mL) and was washed with a 1 M aqueous hydrochloric acid (100 mL), water (100 mL), dried ($Na_2SO_4$), filtered and concentrated to give the crude product, which was purified by silica gel chromatography eluting with a gradient of ethyl acetate (0 to 25%) in iso-hexane to the desired product as a white solid (1.24 g, 2.075 mmol, 75%).

UPLC-MS (acidic method, 2 min): rt=1.37 min; m/z=598.2 $[M+H]^+$, peak area >95%

$^1$H NMR (400 MHz, DMSO-$d_6$) δ 11.60 (s, 1H), 8.02 (d, J=7.8 Hz, 2H), 7.69 (s, 1H), 7.59-7.23 (m, 12H), 5.49 (s, 2H), 5.19 (s, 2H), 4.28 (q, J=7.1 Hz, 2H), 3.71 (s, 6H), 1.26 (t, J=7.1 Hz, 3H).

General Procedure B for Amide Coupling [3B1]

Coupling using a condensation agent, from KI-1 or KI-6

Model Reaction (Ia-001a)

Methyl 2-(2,5-bis(benzyloxy)-4-(ethoxycarbonyl)benzoylamino)benzoate. 1-Methylimidazole (13.0 mL, 163 mmol) was added to a mixture of 2,5-bis(benzyloxy)-4-(ethoxycarbonyl)benzoic acid (KI-1, 12.95 g, 32 mmol) and methyl anthranilate (5.729 g, 38 mmol, 1.190 eq) in MeCN Scheme 3. Synthesis of Monoamides Ia

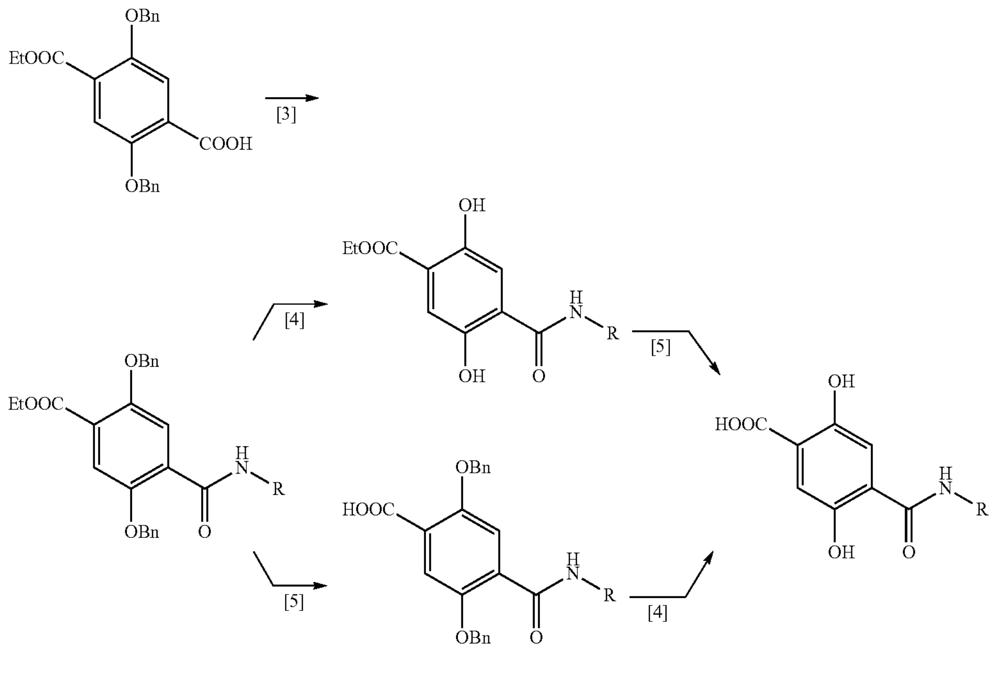

General Procedure A for Amide Coupling [3A]

Coupling via acyl chloride, from KI-1 or KI-6

Model Reaction (Ia-013a)

Dimethyl 2-(2,5-bis(benzyloxy)-4-(ethoxycarbonyl)benzoylamino)isophthalate. 2,5-Bis(benzyloxy)-4-(ethoxycarbonyl)benzoic acid (KI-1, 1.1 g, 2.8 mmol) was dissolved in thionyl chloride (6 mL), and the resulting mixture was stirred for 5 min. A few drops of DMF were added, and the resulting mixture was stirred at ambient temperature for 18

(150 mL) at ambient temperature. Chloro-N,N,N',N'-tetramethylformamidinium hexafluorophosphate (TCFH) (10.728 g, 0.038 mol) was added portionwise over 30 min, and the resulting mixture was stirred overnight at ambient temperature. The reaction mixture was treated with 1 M aqueous hydrochloric acid (700 mL). The resulting suspension was stirred for 10 min, then filtered. The solid material was washed with water (2×200 mL). The solid was then suspended in ethanol (200 mL), filtered, washed with ether (100 mL) and dried in the vacuum oven to give the desired product as a white solid (14.7 g, 27 mmol, 86%)

UPLC-MS (acidic method, 2 min): rt=1.43 min; m/z=540.2 $[M+H]^+$, peak area >99%

$^1$H NMR (400 MHz, DMSO-$d_6$) δ 11.87 (s, 1H), 8.65 (d, J=8.4 Hz, 1H), 7.98 (dd, J=8.0, 1.7 Hz, 1H), 7.81-7.61 (m, 2H), 7.59-7.12 (m, 12H), 5.41 (s, 2H), 5.20 (s, 2H), 4.28 (q, J=7.1 Hz, 2H), 3.74 (s, 3H), 1.27 (t, J=7.1 Hz, 3H).

General Deprotection Procedures [4], [5]

Saponification

Model Reaction (Ia-013a)

2-(2,5-Bis(benzyloxy)-4-carboxybenzoylamino)isophthalic acid. The solution of lithium hydroxide (42 mg, 1 mmol) in water (4 mL) was added to the solution of dimethyl 2-(2,5-bis(benzyloxy)-4-(ethoxycarbonyl)benzoylamino) isophthalate (100 mg, 0.167 mmol) in THF (6 mL) and the resulting mixture was stirred at ambient temperature for 18 h. Additional LiOH (6 eq) in water (4 mL) was added to the reaction mixture which was stirred for an additional 23 h. After completion, water (50 mL) was added to the reaction and the mixture was washed with ethyl acetate (50 mL). The aqueous layer was acidified with a 1 M aqueous hydrochloric acid to pH=2 and extracted with ethyl acetate (2×50 mL). The organic layers were collected, dried ($Na_2SO_4$), filtered and concentrated to give the title compound as a white solid (82 mg, 0.151 mmol, 91%).

UPLC-MS (acidic method, 2 min): rt=1.02 min; m/z=542.1 $[M+H]^+$, peak area >95%

$^1$H NMR (400 MHz, DMSO-$d_6$) δ 13.18 (s, 2H), 11.74 (s, 1H), 8.00 (d, J=7.8 Hz, 2H), 7.71 (s, 1H), 7.58-7.43 (m, 5H), 7.40-7.24 (m, 7H), 5.47 (s, 2H), 5.14 (s, 2H).

Debenzylation

Model Reaction (Ia-013a)

2-(2,5-Dihydroxy-4-carboxybenzoylamino)isophthalic acid (Ia-013a). Pd/C (94 mg, 10%) was added to a solution of 2-(2,5-bis(benzyloxy)-4-carboxybenzoylamino)isophthalic acid (0.94 g, 1.74 mmol) in a 10:30 mixture of EtOH and DCM. The mixture was placed under hydrogen at atmospheric pressure at ambient temperature and stirred for 18 h. After completion, the mixture was filtered through Celite, which was washed with DCM and MeOH. The filtrate and washings were combined and concentrated under reduced pressure to afford the desired product Ia-013a as a yellow solid (644 mg, 1.69 mmol, 98%).

UPLC-MS (acidic method, 4 min): rt=0.91 min; m/z=362.0 $[M+H]^+$, peak area >98%

$^1$H NMR (DMSO-$d_6$) δ: 13.11 (s, 2H), 11.70 (s, 1H), 11.13 (s, 1H), 7.97 (d, J=7.8 Hz, 2H), 7.47 (s, 1H), 7.41 (s, 1H), 7.38 (t, J=7.7 Hz, 1H)

Scheme 4a. Synthesis of Monoamides Ia from KI-1Bn

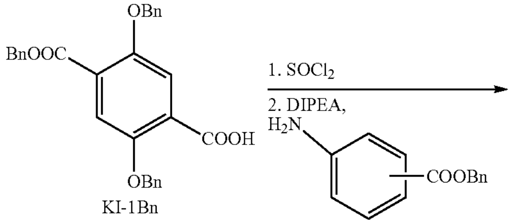

KI-1Bn

-continued

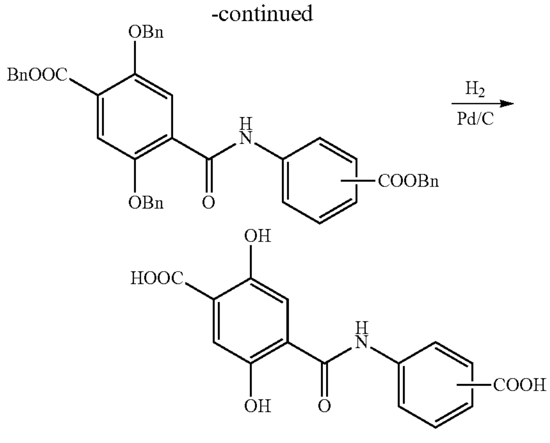

General procedure from KI-1Bn

Coupling Via Acyl Chloride

Model Reaction: synthesis of Ia-032a

Benzyl 4-(2,5-bis(benzyloxy)-4-(benzyloxycarbonyl) benzoylamino)phenylacetate. To a solution of KI-1Bn (233 mg, 84% purity) in DCM (10 mL) was added $SOCl_2$ (1.8 mL, 60 eq) and the mixture was heated at 50 °C for 3 h. The solvents were evaporated and the residue co-evaporated with toluene (3×10 mL), to give the crude acyl chloride (237 mg, 99%). This material was dissolved in DCM (3 mL), and diisopropylethylamine (0.08 mL, 1.15 eq) was added, followed by a solution of benzyl 4-aminophenylacetate (92 mg, 0.95 eq) in DCM (3 mL). Final reaction volume was 10 mL. The reaction mixture was stirred at room temp. for 18 h. The mixture was diluted with DCM (15 mL), washed with sat aqueous ammonium chloride (12 mL). The separated aqueous phase was extracted with DCM (2×2 mL), the organic phases were combined, dried (MgSO4), and concentrated. The crude product was submitted to column chromatography (Pet. Et./DCM 1:1 then gradient to 100% DCM) to give a first fraction of pure KI-0Bn, and second fraction containing the pure desired product (237 mg, 86%, corrected for the purity of KI-1Bn).

$^1$H NMR (400 MHz, $CDCl_3$): δ 10.10 (s, 1H), 8.08 (s, 1H), 7.65 (s, 1H), 7.53-7.30 (m, 20H), 7.22-7.13 (br AB, 4H), 5.39, 5.22, 5.21, 5.12 (4s, 4×2H), 3.61 (s, 2H). 4-(4-(Carboxymethyl)phenylaminocarbonyl)-2,5-dihydroxybenzoic acid (Ia-032a). To a solution of precursor prepared above (225 mg, 0.33 mmol) in DCM (20 mL) was added 5% Pd on charcoal (72 mg), followed by EtOH (20 mL). The flask was flushed with Ar (3×) then filled with hydrogen (atmospheric pressure) and the mixture stirred for 2 h at room temperature. The catalyst was removed by filtration over a millipore filter, the filtrate was evaporated, and the residue dried to afford the product Ia-032a as a light yellow solid (107 mg, 99%).

$^1$H NMR (250 MHz, DMSO-$d_6$): δ 12.28 (br, 1H), 10.92 (s, 1H), 10.44 (s, 1H), 7.65 (br d, 2H), 7.41 (s, 1H), 7.38 (s, 1H), 7.25 (br d, 2H), 3.55 (s, 2H).

For Examples:

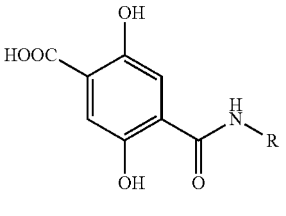

-continued

R =

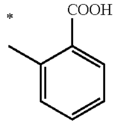

Ia-001a

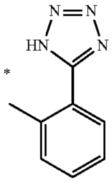

Ia-001aTz

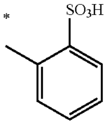

Ia-001c

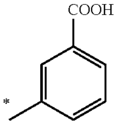

Ia-002a

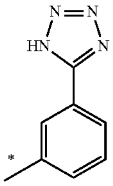

Ia-002aTz

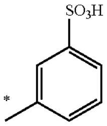

Ia-002c

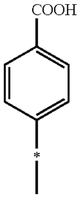

Ia-003a

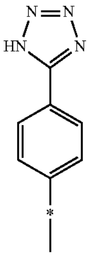

Ia-003aTz

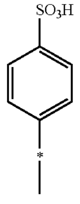

Ia-003c

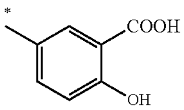

Ia-004a

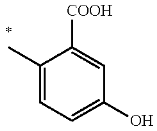

Ia-006a

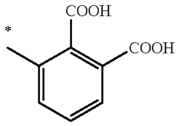

Ia-011a

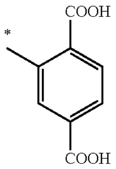

Ia-012a

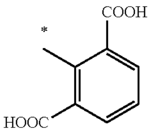

Ia-013a

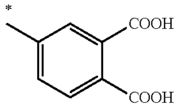

Ia-014a

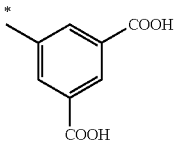

Ia-015a

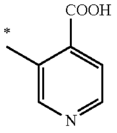

Ia-023a

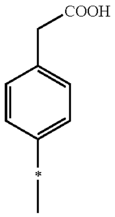

Ia-032

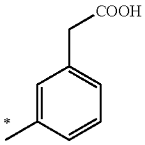

Ia-033a

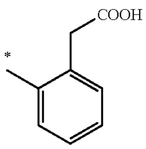

Ia-034a

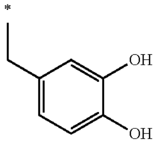

Ia-035a

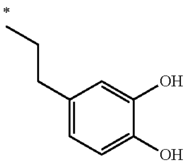

Ia-035a-2

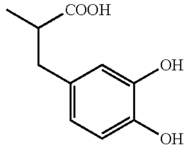

Ia-035a-3

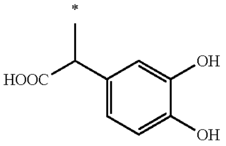

Ia-036a

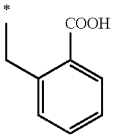

Ia-053a

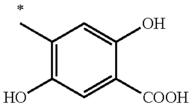

Ia-056a

For conditions and yields: See FIGS. 4A-D

1) 4-(2-Carboxyphenylaminocarbonyl)-2,5-dihydroxybenzoic acid, compound Ia-001a UPLC-MS (acidic method, 2 min): r.t=0.95 mins, m/z=316 $[M-H]^-$, peak area >97%

$^1$H NMR (400 MHz, DMSO-$d_6$) δ 12.22 (s, 1H), 10.85 (s, 1H), 8.65 (d, J=8.4 Hz, 1H), 8.01 (dd, J=8.0, 1.7 Hz, 1H), 7.71-7.56 (m, 1H), 7.41 (d, J=6.9 Hz, 2H), 7.22 (t, J=7.6 Hz, 1H).

HRMS: $[M+H]^+$, calc. for $C_{15}H_{12}NO_7$: 318.06083, found: 318.06080.

Biodata: Ia-001a: FGF-1 IC50 [μM]=41; FGF-2 IC50 [μM]=39; VEGF-A1 IC50 [μM]=7.3; VEGFR-Phosphorylation inhibition IC50 [μM]=2.25; PMN ROS [inhibition at 0.3 μM [%]=48; PMN ROS inhibition IC50 [μM]=0.355; Neutrophil adhesion inhibition [%]=44.3; Whole Blood: GM-CSF IC50 [μM]=>100; IFNγ IC50 [μM]=30.5; IL-1β IC50 [μM]=34.4; IL-2 IC50 [μM]=94.3; IL-4 IC50 [μM] =>100; IL-5 IC50 [μM]=>100; IL-6 IC50 [μM]=1.24; IL-9 IC50 [μM]=5.63; IL-10 IC50 [μM]=>100; IL-12p70 IC50 [μM]=1.5; IL-13 IC50 [μM]=26.4; IL-17A IC50 [μM]=0.1; IL-17F IC50 [μM]=14.7; IL-18 IC50 [μM]=>100; IL-21 IC50 [μM]=>100; IL-33 IC50 [μM]=19.3; TGFβ IC50 [μM]=>100; TNF α IC50 [μM]=0.02; TNFβ IC50 [μM]=13.2

Diethyl Ester:

UPLC-MS (acidic method, 2 min): r.t=1.39 mins, m/z=372.2 $[M-H]^-$, peak area >98%

$^1$H NMR (400 MHz, DMSO-$d_6$) δ 11.96 (s, 1H), 11.05 (s, 1H), 9.87 (s, 1H), 8.57 (dd, J=8.5, 1.2 Hz, 1H), 7.99 (dd, J=7.9, 1.7 Hz, 1H), 7.65 (ddd, J=8.7, 7.3, 1.7 Hz, 1H), 7.49 (s, 1H), 7.40 (s, 1H), 7.25 (td, J=7.6, 1.2 Hz, 1H), 4.35 (m, 4H), 1.33 (m, 6H).

HRMS: $[M+H]^+$, calc. for $C_{19}H_{20}NO_7$: 374.12342, found: 374.12354

Biodata: Ia-001a-E2: FGF-1 IC50 [μM]=9.2; FGF-2 IC50 [μM]=200; VEGF-A1 IC50 [μM]=123; VEGFR-Phosphorylation inhibition IC50 [μM]=1.25; PMN ROS [inhibition at 0.3 μM [%]=51.47; PMN ROS inhibition IC50 [μM]=2.58; Neutrophil adhesion inhibition [%]=50.5

2) 4-(2-(1H-Tetrazol-5-yl)phenylaminocarbonyl)-2,5-dihydroxybenzoic acid, compound Ia-001aTz UPLC-MS (acidic method, 4 min): rt=1.17 min; m/z=342.0 $[M+H]^+$, peak area >96%

$^1$H NMR (400 MHz, DMSO-$d_6$) δ 11.60 (s, 1H), 10.90 (s, 2H), 8.47 (d, J=8.4 Hz, 1H), 7.93 (d, J=7.9 Hz, 1H), 7.61 (t, J=7.9 Hz, 1H), 7.50-7.32 (m, 3H).

HRMS: $[M+H]^+$, calc. for $C_{15}H_{12}N_5O_5$: 342.08329, found: 342.08318

Biodata: Ia-001a-Tz: FGF-1 IC50 [μM]=6.2; FGF-2 IC50 [μM]=20; VEGF-A1 IC50 [μM]=17; VEGFR-Phosphorylation inhibition IC50 [μM]=0.23; PMN ROS [inhibition at 0.3 μM [%]=54.33; PMN ROS inhibition IC50 [μM]=1.54; Neutrophil adhesion inhibition [%]=69.75; Whole Blood: GM-CSF IC50 [μM]=>100; IFNγ IC50 [μM]=>100; IL-1β IC50 [μM]=>100; IL-2 IC50 [μM]=7.99; IL-4 IC50 [μM] =>100; IL-5 IC50 [μM]=>100; IL-6 IC50 [μM]=0.75; IL-9 IC50 [μM]=8.63; IL-10 IC50 [μM]=26.1; IL-12p70 IC50 [μM]=32.4; IL-13 IC50 [μM]=32.1; IL-17A IC50 [μM] =0.11; IL-17F IC50 [μM]=46.5; IL-18 IC50 [μM]=>100; IL-21 IC50 [μM]=>100; IL-33 IC50 [μM]=23.6; TGFβ IC50 [μM]=>100; TNF α IC50 [μM]=0.63; TNF β IC50 [μM]=53

Ethyl Ester:

UPLC-MS (acidic method, 2 min): r.t=1.08 mins, m/z=370.1 $[M+H]^+$, peak area >97%

$^1$H NMR (400 MHz, DMSO-$d_6$) δ 11.48 (s, 1H), 9.88 (s, 1H), 8.46 (d, J=8.4 Hz, 1H), 7.89 (dd, J=7.8, 1.6 Hz, 1H), 7.62 (ddd, J=8.6, 7.4, 1.6 Hz, 1H), 7.47 (s, 1H), 7.42-7.34 (m, 2H), 4.37 (q, J=7.1 Hz, 2H), 1.34 (t, J=7.1 Hz, 3H).

HRMS: [M+H]$^+$, calc. for $C_{17}H_{16}N_5O_5$: 370.11460, found: 370.11458

Biodata: Ia-001a-Tz-E1: FGF-1 IC50 [μM]=200; FGF-2 IC50 [μM]=200; VEGF-A1 IC50 [μM]=200; VEGFR-Phosphorylation inhibition IC50 [μM]=3.8; PMN ROS [inhibition at 0.3 μM [%]=75.97; PMN ROS inhibition IC50 [μM]=N.D.; Neutrophil adhesion inhibition [%]=98.88

Ethyl Ester Diacetate:

UPLC-MS (acidic method, 4 min): r.t=1.57 mins, m/z=454.1 [M+H]$^+$, peak area >97%

$^1$H NMR (400 MHz, DMSO-$d_6$) δ 11.23 (s, 1H), 8.23 (d, J=8.6 Hz, 1H), 7.96 (dd, J=7.9, 1.7 Hz, 1H), 7.84 (s, 1H), 7.73 (s, 1H), 7.64 (t, J=7.5 Hz, 1H), 7.43 (td, J=7.6, 1.2 Hz, 1H), 4.32 (q, J=7.1 Hz, 2H), 2.34 (s, 3H), 2.18 (s, 3H), 1.32 (t, J=7.1 Hz, 3H).

HRMS: [M+H]$^+$, calc. for $C_{21}H_{20}N_5O_7$: 454.13572, found: 454.13542

Biodata: Ia-001a-Tz-E1-A2: FGF-1 IC50 [μM]=60; FGF-2 IC50 [μM]=200; VEGF-A1 IC50 [μM]=200; VEGFR-Phosphorylation inhibition IC50 [μM]=ND; PMN ROS [inhibition at 0.3 μM [%]=49.85; PMN ROS inhibition IC50 [μM]=N.D.; Neutrophil adhesion inhibition [%]=98.2

3) 2,5-dihydroxy-4-(2-sulfophenylaminocarbonyl) Benzoic Acid, Compound Ia-001c UPLC-MS (acidic method, 2 min): rt=0.73 min; m/z=352.0 [M−H]$^-$, peak area >99%

$^1$H NMR (400 MHz, DMSO-$d_6$) δ 11.54 (s, 1H), 10.99 (s, 1H), 8.34 (d, J=8.2 Hz, 1H), 7.74 (dd, J=7.7, 1.7 Hz, 1H), 7.42-7.28 (m, 3H), 7.12 (td, J=7.5, 1.2 Hz, 1H).

HRMS: [M+H]$^+$, calc. for $C_{14}H_{12}NO_8S$: 354.02781, found: 354.02754.

Biodata: Ia-001c: FGF-1 IC50 [μM]=21; FGF-2 IC50 [μM]=13; VEGF-A1 IC50 [μM]=100; VEGFR-Phosphorylation inhibition IC50 [μM]=3.31; PMN ROS [inhibition at 0.3 μM [%]=40.36; PMN ROS inhibition IC50 [μM]=2.4; Neutrophil adhesion inhibition [%]=31.33; Whole Blood: GM-CSF IC50 [μM]=>100; IFNγ IC50 [μM]=0.44; IL-1β IC50 [μM]=>100; IL-2 IC50 [μM]=12.8; IL-4 IC50 [μM]=>100; IL-5 IC50 [μM]=>100; IL-6 IC50 [μM]=0.95; IL-9 IC50 [μM]=46.9; IL-10 IC50 [μM]=1.9; IL-12p70 IC50 [μM]=0.44; IL-13 IC50 [μM]=86.1; IL-17A IC50 [μM]=0.09; IL-17F IC50 [μM]=89.7; IL-18 IC50 [μM]=>100; IL-21 IC50 [μM]=>100; IL-33 IC50 [μM]=>100; TGFβ IC50 [μM]=>100; TNF c IC50 [μM]=0.05; TNF β IC50 [μM]=29.7

4) 4-(3-Carboxyphenylaminocarbonyl)-2,5-dihydroxybenzoic acid, compound Ia-002a $^1$H-NMR (250 MHZ, DMSO-$d_6$) δ ~13 (v br, 1H), 10.82 (br s, 1H), 10.60 (br s, 1H), 8.38 (s, 1H). 7.92 (d, 1H), 7.71 (d, 1H), 7.49 (t, 1H), 7.39 (s, 2H)

Biodata: 1a-002a: FGF-1 IC50 [μM]=20; FGF-2 IC50 [μM]=59; VEGF-A1 IC50 [μM]=71; VEGFR-Phosphorylation inhibition IC50 [μM]=5.7; PMN ROS [inhibition at 0.3 μM [%]=42.1; PMN ROS inhibition IC50 [μM]=0.312; Neutrophil adhesion inhibition [%]=27.92

5) 4-(3-(1H-Tetrazol-5-yl)phenylaminocarbonyl)-2,5-dihydroxybenzoic acid, compound Ia-002aTz UPLC-MS (acidic method, 4 min): rt=1.13 min; m/z=342.0 [M+H]$^+$, peak area >99%

$^1$H NMR (400 MHz, DMSO-$d_6$) δ 10.81 (s, 1H), 10.67 (s, 1H), 8.54 (s, 1H), 7.91-7.84 (m, 1H), 7.79 (dt, J=7.8, 1.4 Hz, 1H), 7.60 (t, J=7.9 Hz, 1H), 7.41 (d, J=2.2 Hz, 2H).

HRMS: [M+H]$^+$, calc. for $C_{15}H_{12}N_5O_5$: 342.08329, found: 342.08317

Biodata: Ia-002a-Tz: FGF-1 IC50 [μM]=10; FGF-2 IC50 [μM]=53; VEGF-A1 IC50 [μM]=57; VEGFR-Phosphorylation inhibition IC50 [μM]=100; PMN ROS [inhibition at 0.3 μM [%]=66.61; PMN ROS inhibition IC50 [μM]=1.86; Neutrophil adhesion inhibition [%]=38.5

6) 2,5-Dihydroxy-4-(3-sulfophenylaminocarbonyl) benzoic acid, compound Ia-002c $^1$H-NMR (250 MHZ, DMSO-$d_6$) δ 11.04 (s, 1H), 10.53 (s, 1H), 7.96 (s, 1H), 7.69 (d, 1H), 7.43 (s, 2H) and 7.40-7.28 (m, 2H)

Biodata: Ia-002c: FGF-1 IC50 [μM]=14; FGF-2 IC50 [μM]=150; VEGF-A1 IC50 [μM]=150; VEGFR-Phosphorylation inhibition IC50 [μM]=100; PMN ROS [inhibition at 0.3 μM [%]=38.9; PMN ROS inhibition IC50 [μM]=0.405; Neutrophil adhesion inhibition [%]=1.87

7) 4-(4-Carboxyphenylaminocarbonyl)-2,5-dihydroxybenzoic acid, compound Ia-003a $^1$H-NMR (250 MHz, DMSO-$d_6$) δ 12.8 (br, 1H), 10.73 (s, 1H), 10.68 (s, 1H), 7.94 (d of AB, 2H), 7.84 (d of AB, 2H), 7.39 (s, 1H), 7.34 (s, 1H) HRMS (AX033)

Biodata: Ia-003a: FGF-1 IC50 [μM]=12; FGF-2 IC50 [μM]=34; VEGF-A1 IC50 [μM]=150; VEGFR-Phosphorylation inhibition IC50 [μM]=ND; PMN ROS [inhibition at 0.3 μM [%]=44.4; PMN ROS inhibition IC50 [μM]=0.414; Neutrophil adhesion inhibition [%]=39.1

8) 4-(4-(1H-Tetrazol-5-yl)phenylaminocarbonyl)-2,5-dihydroxybenzoic acid, compound Ia-003aTz UPLC-MS (acidic method, 2 min): rt=0.79 min; m/z=342.0 [M+H]$^+$, peak area >97%

$^1$H NMR (400 MHz, DMSO-$d_6$) δ 10.77 (s, 1H), 10.70 (s, 1H), 8.04 (d, J=8.7 Hz, 2H), 7.96 (d, J=8.5 Hz, 2H), 7.41 (s, 1H), 7.37 (s, 1H).

HRMS: [M+H]$^+$, calc. for $C_{15}H_{12}N_5O_5$: 342.08329, found: 342.08326

Biodata: Ia-003a-Tz: FGF-1 IC50 [μM]=6.7; FGF-2 IC50 [μM]=45; VEGF-A1 IC50 [μM]=13; VEGFR-Phosphorylation inhibition IC50 [μM]=6.4; PMN ROS [inhibition at 0.3 μM [%]=62.21; PMN ROS inhibition IC50 [μM]=2.49; Neutrophil adhesion inhibition [%]=30.33; Whole Blood: GM-CSF IC50 [μM]=>100; IFNγ IC50 [μM]=2.95; IL-1β IC50 [μM]=>100; IL-2 IC50 [μM]=43; IL-4 IC50 [μM]=>100; IL-5 IC50 [μM]=>100; IL-6 IC50 [μM]=1.41; IL-9 IC50 [μM]=3.62; IL-10 IC50 [μM]=6.94; IL-12p70 IC50 [μM]=1.26; IL-13 IC50 [μM]=89.6; IL-17A IC50 [μM]=0.07; IL-17F IC50 [μM]=83.9; IL-18 IC50 [μM]=>100; IL-21 IC50 [μM]=1.49; IL-33 IC50 [μM]=72.2; TGFβ IC50 [μM]=>100; TNF c IC50 [μM]=0.18; TNF β IC50 [μM]=55.

9) 2,5-Dihydroxy-4-(4-sulfophenylaminocarbonyl) benzoic acid, compound Ia-003c $^1$H-NMR (400 MHz, DMSO-$d_6$) δ 10.90 (s, 1H), 10.51 (s, 1H), 7.66 (d of AB, 2H), 7.58 (d of AB, 2H), 7.40 (s, 1H), 7.39 (S, 1H)

Biodata: Ia-003c: FGF-1 IC50 [μM]=35; FGF-2 IC50 [μM]=150; VEGF-A1 IC50 [μM]=150; VEGFR-Phosphorylation inhibition IC50 [μM]=0.4; PMN ROS [inhibition at 0.3 μM [%]=N.D.; PMN ROS inhibition IC50 [μM]–; Neutrophil adhesion inhibition [%]=N.D.

10) 4-(3-Carboxy-4-hydroxyphenylaminocarbonyl)-2,5-dihydroxybenzoic acid, compound Ia-004a UPLC-MS (acidic method, 6.5 min): rt=1.40 min; m/z=332.0 $[M-H]^-$, peak area >96%

$^1$H NMR (400 MHz, DMSO-$d_6$) δ 10.94 (s, 1H), 10.37 (s, 1H), 8.20 (d, J=2.7 Hz, 1H), 7.74 (dd, J=8.9, 2.8 Hz, 1H), 7.39 (s, 1H), 7.34 (s, 1H), 6.93 (d, J=8.9 Hz, 1H).

HRMS: $[M+H]^+$, calc. for $C_{15}H_{12}NO_8$: 334.05574, found: 334.05572

Biodata: Ia-004a: FGF-1 IC50 [μM]=32; FGF-2 IC50 [μM]=15; VEGF-A1 IC50 [μM]=28; VEGFR-Phosphorylation inhibition IC50 [μM]=7.7; PMN ROS [inhibition at 0.3 μM [%]=64.61; PMN ROS inhibition IC50 [μM]=0; Neutrophil adhesion inhibition [%]=28.38 Ethyl Methyl ester:

UPLC-MS (acidic method, 2 min): r.t=1.16 mins, m/z=376.1 $[M+H]^+$, peak area >95%

$^1$H NMR (400 MHz, DMSO-$d_6$) δ 10.90 (s, 1H), 10.50 (s, 1H), 10.36 (s, 1H), 9.91 (s, 1H), 8.26 (d, J=2.7 Hz, 1H), 7.76 (dd, J=8.9, 2.8 Hz, 1H), 7.43 (s, 1H), 7.36 (s, 1H), 7.01 (d, J=8.9 Hz, 1H), 4.37 (q, J=7.1 Hz, 2H), 3.91 (s, 3H), 1.34 (t, J=7.1 Hz, 3H).

HRMS: $[M+H]^+$, calc. for $C_{18}H_{18}NO_8$: 376.10269, found: 376.10259

Biodata: Ia-004a-E2: FGF-1 IC50 [μM]=35; FGF-2 IC50 [μM]=36; VEGF-A1 IC50 [μM]=200; VEGFR-Phosphorylation inhibition IC50 [μM]=6.1; PMN ROS [inhibition at 0.3 μM [%]=85.34; PMN ROS inhibition IC50 [μM]=N.D.; Neutrophil adhesion inhibition [%]=97.65

11) 4-(2-Carboxy-4-hydroxyphenylaminocarbonyl)-2,5-dihydroxybenzoic acid, compound Ia-006a UPLC-MS (acidic method, 2 min): rt=0.81 min; m/z=334.0 $[M+H]^+$, peak area >96%

$^1$H NMR (400 MHz, DMSO-$d_6$) δ 13.33 (s, 1H), 11.86 (s, 1H), 10.90 (s, 1H), 9.66 (s, 1H), 8.39 (d, J=9.0 Hz, 1H), 7.40 (d, J=6.8 Hz, 2H), 7.03 (dd, J=9.0, 3.0 Hz, 1H).

HRMS: $[M+H]^+$, calc. for $C_{15}H_{12}NO_8$: 334.05574, found: 334.05562.

Biodata: Ia-006a: FGF-1 IC50 [μM]=89; FGF-2 IC50 [μM]=224; VEGF-A1 IC50 [μM]=100; VEGFR-Phosphorylation inhibition IC50 [μM]=11.8; PMN ROS [inhibition at 0.3 μM [%]=60.56; PMN ROS inhibition IC50 [μM]=1.2; Neutrophil adhesion inhibition [%]=25.33

12) 3-(4-Carboxy-2,5-dihydroxybenzamido)phthalic acid, compound Ia-011a

UPLC-MS (acidic method, 2 min): rt=0.69 min; m/z=360.1 $[M-H]^-$, peak area >89%

$^1$H NMR (400 MHz, DMSO-$d_6$) δ 13.46 (s, 2H), 11.37 (s, 1H), 10.97 (s, 1H), 8.33 (dd, J=8.2, 1.3 Hz, 1H), 7.63 (dd, J=7.7, 1.3 Hz, 1H), 7.57 (t, J=7.9 Hz, 1H), 7.52 (s, 1H), 7.44 (s, 1H).

HRMS: $[M+H]^+$, calc. for $C_{16}H_{12}NO_9$: 362.05065, found: 362.05036

Biodata: Ia-011a: FGF-1 IC50 [μM]=35; FGF-2 IC50 [μM]=110; VEGF-A1 IC50 [μM]=200; VEGFR-Phosphorylation inhibition IC50 [μM]=100; PMN ROS [inhibition at 0.3 μM [%]=57.71; PMN ROS inhibition IC50 [μM]=N.D.; Neutrophil adhesion inhibition [%]=42.32

13) 2-(4-Carboxy-2,5-dihydroxybenzamido)terephthalic acid, compound Ia-012a

UPLC-MS (acidic method, 4 min): rt=1.12 min; m/z=362.1 $[M+H]^+$, peak area >96%

$^1$H NMR (400 MHz, DMSO-$d_6$) δ 13.41 (brs, 2H), 12.29 (s, 1H), 10.94 (s, 1H), 9.26 (d, J=1.7 Hz, 1H), 8.09 (d, J=8.2 Hz, 1H), 7.73 (dd, J=8.2, 1.7 Hz, 1H), 7.42 (s, 2H).

HRMS: $[M+H]^+$, calc. for $C_{16}H_{12}NO_9$: 362.05065, found: 362.05046.

Biodata: Ia-012a: FGF-1 IC50 [μM]=38; FGF-2 IC50 [μM]=36; VEGF-A1 IC50 [μM]=30; VEGFR-Phosphorylation inhibition IC50 [μM]=100; PMN ROS [inhibition at 0.3 μM [%]=59.52; PMN ROS inhibition IC50 [μM]=1.85; Neutrophil adhesion inhibition [%]=28.5

14) 2-(4-Carboxy-2,5-dihydroxybenzamido)isophthalic acid, compound Ia-013a

UPLC-MS (acidic method, 4 min): rt=0.91 min; m/z=362.0 $[M+H]^+$, peak area >98%

$^1$H NMR (400 MHz, DMSO-$d_6$) δ 13.11 (s, 2H), 11.70 (s, 1H), 11.13 (s, 1H), 7.97 (d, J=7.8 Hz, 2H), 7.47 (s, 1H), 7.41 (s, 1H), 7.38 (t, J=7.7 Hz, 1H) HRMS: $[M+H]^+$, calc. for $C_{16}H_{12}NO_9$: 362.05065, found: 362.05041

Biodata: Ia-013a: FGF-1 IC50 [μM]=29; FGF-2 IC50 [μM]=18; VEGF-A1 IC50 [μM]=17; VEGFR-Phosphorylation inhibition IC50 [μM]=100; PMN ROS [inhibition at 0.3 μM [%]=38.52; PMN ROS inhibition IC50 [μM]=2.38; Neutrophil adhesion inhibition [%]=27.67 15) 4-(4-Carboxy-2,5-dihydroxybenzamido)phthalic acid, compound Ia-014a:

UPLC-MS (acidic method, 4 min): rt=0.98 min; m/z=362.1 $[M+H]^+$, peak area >94%

$^1$H NMR (400 MHz, DMSO-$d_6$) δ 10.76 (s, 1H), 10.70 (s, 1H), 8.14 (s, 1H), 7.94-7.84 (m, 2H), 7.38 (s, 1H), 7.30 (s, 1H).

HRMS: $[M+H]^+$, calc. for $C_{16}H_{12}NO_9$: 362.05065, found: 362.05047

Biodata: Ia-014a: FGF-1 IC50 [μM]=20; FGF-2 IC50 [μM]=20; VEGF-A1 IC50 [μM]=88; VEGFR-Phosphorylation inhibition IC50 [μM]=100; PMN ROS [inhibition at 0.3 μM [%]=61.3; PMN ROS inhibition IC50 [μM]=1; Neutrophil adhesion inhibition [%]=9.667

16) 5-(4-Carboxy-2,5-dihydroxybenzamido)isophthalic acid, compound Ia-015a $^1$H NMR (250 MHz, DMSO-$d_6$) δ 10.74 (s, 1H), 8.56 (narrow d, 2H), 8.22 (narrow t, 1H), 7.41 (s, 1H) and 7.37 (s, 1H)

Biodata: Ia-015a: FGF-1 IC50 [μM]=20; FGF-2 IC50 [μM]=9.3; VEGF-A1 IC50 [μM]=19; VEGFR-Phosphorylation inhibition IC50 [μM]=0.15; PMN ROS [inhibition at 0.3 μM [%]=43.8; PMN ROS inhibition IC50 [μM]=0.387; Neutrophil adhesion inhibition [%]=17.38; Whole Blood: GM-CSF IC50 [μM]=2.76; IFNγ IC50 [μM]=>100; IL-1β IC50 [μM]=>100; IL-2 IC50 [μM]=7.08; IL-4 IC50 [μM]=>100; IL-5 IC50 [μM]=>100; IL-6 IC50 [μM]=0.77; IL-9 IC50 [μM]=1.47; IL-10 IC50 [μM]=5.27; IL-12p70 IC50 [μM]=0.12; IL-13 IC50 [μM]=0.15; IL-17A IC50

[μM]= 0.05; IL-17F IC50 [μM]=0.15; IL-18 IC50 [μM]=>100; IL-21 IC50 [μM]=57.2; IL-33 IC50 [μM]=0.24; TGFβ IC50 [μM]=>100; TNF c IC50 [μM]=0.17; TNF β IC50 [μM]=0.3.

17) 3-(4-carboxy-2,5-dihydroxybenzamido)isonicotinic acid, compound Ia-023a

UPLC-MS (acidic method, 4 min): rt=0.63 min; m/z=319.1 $[M+H]^+$, peak area >93%

$^1$H NMR (400 MHz, DMSO-$d_6$) δ 12.17 (s, 1H), 11.03 (s, 1H), 9.78 (s, 1H), 8.46 (d, J=5.0 Hz, 1H), 7.82 (d, J=5.0 Hz, 1H), 7.45 (s, 1H), 7.43 (s, 1H).

HRMS: $[M+H]^+$, calc. for $C_{14}H_{11}N_2O_7$: 319.05608, found: 319.05610

Biodata: Ia-023a: FGF-1 IC50 [μM]=N.D.; FGF-2 IC50 [μM]=63; VEGF-A1 IC50 [μM]=143; VEGFR-Phosphorylation inhibition IC50 [μM]=100; PMN ROS [inhibition at 0.3 μM [%]=61.95; PMN ROS inhibition IC50 [μM]=0; Neutrophil adhesion inhibition [%]=13.37

Diethyl Ester:

UPLC-MS (acidic method, 4 min): r.t=1.87 mins, m/z=375.1 $[M+H]^+$, peak area >98%

$^1$H NMR (400 MHz, DMSO-d6) δ 11.79 (s, 1H), 11.23 (s, 1H), 9.87 (s, 1H), 9.68 (s, 1H), 8.50 (d, J=5.0 Hz, 1H), 7.81 (dd, J=5.1, 0.7 Hz, 1H), 7.53 (s, 1H), 7.41 (s, 1H), 4.46-4.27 (m, 4H), 1.41-1.25 (m, 6H).

HRMS: $[M+H]^+$, calc. for $C_{18}H_{19}N_2O_7$: 375.11867, found: 375.11867

Biodata: Ia-023a-E2: FGF-1 IC50 [μM]=N.D.; FGF-2 IC50 [μM]=76; VEGF-A1 IC50 [μM]=141; VEGFR-Phosphorylation inhibition IC50 [μM]=6.6; PMN ROS [inhibition at 0.3 μM [%]=69.47; PMN ROS inhibition IC50 [μM]=0; Neutrophil adhesion inhibition [%]=34

18) 4-(4-(carboxymethyl)phenylaminocarbonyl)-2,5-dihydroxybenzoic acid, compound Ia-032a $^1$H NMR (250 MHz, DMSO-d6): δ 12.28 (br, 1H), 10.92 (s, 1H), 10.44 (s, 1H), 7.65 (br d, 2H), 7.41 (s, 1H), 7.38 (s, 1H), 7.25 (br d, 2H), 3.55 (s, 2H).

Biodata: Ia-032a: FGF-1 IC50 [μM]=N.D.; FGF-2 IC50 [μM]=91; VEGF-A1 IC50 [μM]=N.D.; VEGFR-Phosphorylation inhibition IC50 [μM]=100; PMN ROS [inhibition at 0.3 μM [%]=N.D.; PMN ROS inhibition IC50 [μM]–; Neutrophil adhesion inhibition [%]=N.D.

19) 4-(3-(Carboxymethyl)phenylaminocarbonyl)-2,5-dihydroxybenzoic acid, compound Ia-033a UPLC-MS (acidic method, 6.5 min): rt=1.71 min; m/z=332.1 $[M+H]^+$, peak area >99%

$^1$H NMR (400 MHz, DMSO-$d_6$) δ 10.89 (s, 1H), 10.46 (s, 1H), 7.65 (s, 1H), 7.59 (d, J=8.1 Hz, 1H), 7.40 (s, 1H), 7.38 (s, 1H), 7.03 (d, J=7.6 Hz, 1H), 3.57 (s, 2H).

HRMS: $[M+H]^+$, calc. for $C_{16}H_{14}NO_7$: 332.07647, found: 332.07644

Biodata: Ia-033a: FGF-1 IC50 [μM]=60; FGF-2 IC50 [μM]=165; VEGF-A1 IC50 [μM]=281; VEGFR-Phosphorylation inhibition IC50 [μM]=100; PMN ROS [inhibition at 0.3 μM [%]=57.73; PMN ROS inhibition IC50 [μM]=1.32; Neutrophil adhesion inhibition [%]=38

20) 4-(2-(Carboxymethyl)phenylaminocarbonyl)-2,5-dihydroxybenzoic acid, compound Ia-034a UPLC-MS (acidic method, 2 min): rt=0.82 min; m/z=332.1 $[M+H]^+$, peak area >98%

$^1$H NMR (400 MHz, DMSO-$d_6$) δ 7.78 (d, J=8.1 Hz, 1H), 7.31 (d, J=3.0 Hz, 2H), 7.28 (d, J=7.6 Hz, 2H), 7.15 (t, J=7.4 Hz, 1H), 3.63 (s, 2H).

HRMS: $[M+H]^+$, calc. for $C_{16}H_{14}NO_7$: 332.07648, found: 332.07641

Biodata: Ia-034a: FGF-1 IC50 [μM]=79; FGF-2 IC50 [μM]=14; VEGF-A1 IC50 [μM]=102; VEGFR-Phosphorylation inhibition IC50 [μM]=100; PMN ROS [inhibition at 0.3 μM [%]=49.07; PMN ROS inhibition IC50 [μM]=2.28; Neutrophil adhesion inhibition [%]=15

21) 4-(3,4-Dihydroxyphenylmethylaminocarbonyl)-2,5-dihydroxybenzoic acid, compound Ia-035a UPLC-MS (acidic method, 2 min): rt=1.02 min; m/z=320.1 $[M+H]^+$, peak area >91%

$^1$H NMR (400 MHz, DMSO-$d_6$) δ 11.56 (s, 1H), 9.21 (t, J=5.9 Hz, 1H), 8.91 (s, 1H), 8.79 (s, 1H), 7.46 (s, 1H), 7.28 (s, 1H), 6.72 (d, J=2.1 Hz, 1H), 6.67 (d, J=8.0 Hz, 1H), 6.57 (dd, J=8.0, 2.1 Hz, 1H), 4.32 (d, J=5.8 Hz, 2H).

HRMS: $[M+H]^+$, calc. for $C_{15}H_{14}NO_7$: 320.07648, found: 320.07650

Biodata: Ia-035a: FGF-1 IC50 [μM]=20; FGF-2 IC50 [μM]=71; VEGF-A1 IC50 [μM]=200; VEGFR-Phosphorylation inhibition IC50 [μM]=36; PMN ROS [inhibition at 0.3 μM [%]=75.13; PMN ROS inhibition IC50 [μM]=0.41; Neutrophil adhesion inhibition [%]=27

22) 4-(2-(3,4-Dihydroxyphenyl)ethylaminocarbonyl)-2,5-dihydroxybenzoic acid, compound Ia-035a-2

UPLC-MS (acidic method, 2 min): rt=0.77 min; m/z=332.0 $[M-H]^-$, peak area >99%

$^1$H NMR (400 MHz, DMSO-$d_6$) δ 11.50 (s, 1H), 8.85 (t, J=5.6 Hz, 1H), 8.76 (s, 1H), 8.66 (s, 1H), 7.41 (s, 1H), 7.28 (s, 1H), 6.67-6.60 (m, 2H), 6.48 (dd, J=8.0, 2.1 Hz, 1H), 3.44 (q, J=6.8 Hz, 2H), 2.67 (dd, J=8.6, 6.0 Hz, 2H). δ 11.56 (s, 1H), 9.21 (t, J=5.9 Hz, 1H), 8.91 (s, 1H), 8.79 (s, 1H), 7.46 (s, 1H), 7.28 (s, 1H), 6.72 (d, J=2.1 Hz, 1H), 6.67 (d, J=8.0 Hz, 1H), 6.57 (dd, J=8.0, 2.1 Hz, 1H), 4.32 (d, J=5.8 Hz, 2H).

HRMS: $[M+H]^+$, calc. for $C_{16}H_{16}NO_7$: 334.09213, found: 334.09242

Biodata: Ia-035a-2: FGF-1 IC50 [μM]=10; FGF-2 IC50 [μM]=65; VEGF-A1 IC50 [μM]=109; VEGFR-Phosphorylation inhibition IC50 [μM]=10; PMN ROS [inhibition at 0.3 μM [%]=58.81; PMN ROS inhibition IC50 [μM]=1.1; Neutrophil adhesion inhibition [%]=21.5

23) 4-(1-Carboxy-2-(3,4-dihydroxyphenyl)ethylaminocarbonyl)-2,5-dihydroxybenzoic acid, compound Ia-035a-3

UPLC-MS (acidic method, 2 min): rt=0.70 min; m/z=376.0 $[M-H]^-$, peak area >99%

$^1$H NMR (400 MHz, DMSO-$d_6$) δ 12.90 (s, 1H), 11.11 (s, 1H), 8.98 (d, J=7.4 Hz, 1H), 8.73 (d, J=13.1 Hz, 2H), 7.45 (s, 1H), 7.31 (s, 1H), 6.61 (dd, J=5.1, 2.9 Hz, 2H), 6.47 (dd, J=8.1, 2.1 Hz, 1H), 3.01 (dd, J=13.9, 4.9 Hz, 1H), 2.96-2.84 (m, 1H).

HRMS: $[M+H]^+$, calc. for $C_{17}H_{16}NO_9$: 378.08196, found: 378.08195

Biodata: Ia-035a-3: FGF-1 IC50 [μM]=34; FGF-2 IC50 [μM]=207; VEGF-A1 IC50 [μM]=198; VEGFR-Phosphorylation inhibition IC50 [μM]=10; PMN ROS [inhibition at 0.3 μM [%]=79.62; PMN ROS inhibition IC50 [μM]=0.66; Neutrophil adhesion inhibition [%]=22

24) 4-(Carboxy(3,4-dihydroxyphenyl)methylaminocarbonyl)-2,5-dihydroxybenzoic acid, compound Ia-036a UPLC-MS (acidic method, 2 min): rt=0.62 min; m/z=362.1 $[M-H]^-$, peak area >92%

$^1$H NMR (400 MHz, DMSO-$d_6$) δ 11.00 (s, 1H), 9.32 (d, J=6.7 Hz, 1H), 9.05 (s, 1H), 8.97 (s, 1H), 7.40 (s, 1H), 7.34 (s, 1H), 6.81 (d, J=2.1 Hz, 1H), 6.75-6.64 (m, 2H), 5.29 (d, J=6.6 Hz, 1H).

HRMS: $[M+H]^+$, calc. for $C_{16}H_{14}NO_9$: 364.06630, found: 364.06615

Biodata: Ia-036a: FGF-1 IC50 [μM]=N.D.; FGF-2 IC50 [μM]=37; VEGF-A1 IC50 [μM]=123; VEGFR-Phosphorylation inhibition IC50 [μM]=1.6; PMN ROS [inhibition at 0.3 μM [%]=87.17; PMN ROS inhibition IC50 [μM]=N.D.; Neutrophil adhesion inhibition [%]=30.77

25) 4-(2-Carboxyphenylmethylaminocarbonyl)-2,5-dihydroxybenzoic acid, compound Ia-053a UPLC-MS (acidic method, 4 min): rt=1.08 min; m/z=332.0 $[M+H]^+$, peak area >97%

$^1$H NMR (400 MHz, DMSO-$d_6$) δ 13.09 (s, 1H), 11.19 (s, 1H), 9.34-9.27 (m, 1H), 7.91 (dd, J=7.8, 1.4 Hz, 1H), 7.55 (dd, J=7.5, 1.5 Hz, 1H), 7.46 (d, J=7.9 Hz, 2H), 7.39 (td, J=7.5, 1.4 Hz, 1H), 7.32 (s, 1H), 4.82 (d, J=5.9 Hz, 2H).

HRMS: $[M+H]^+$, calc. for $C_{16}H_{14}NO_7$: 332.07648, found: 332.07622

Biodata: Ia-053a: FGF-1 IC50 [μM]=150; FGF-2 IC50 [μM]=124; VEGF-A1 IC50 [μM]=210; VEGFR-Phosphorylation inhibition IC50 [μM]=100; PMN ROS [inhibition at 0.3 μM [%]=52.92; PMN ROS inhibition IC50 [μM]=2.5; Neutrophil adhesion inhibition [%]=18.67

Scheme 4b. Synthesis of ethyl 4-amino-2,5-dibenzyloxybenzoate (aniline A)

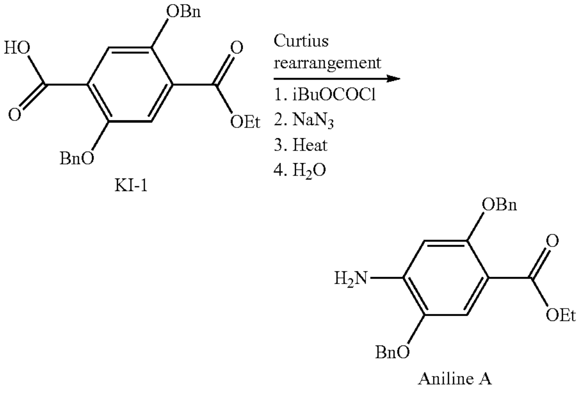

KI-1
Aniline A

Protocole: Synthesis of Aniline A

Ethyl 4-amino-2,5-dibenzyloxybenzoate (Aniline A). To a cooled solution (ice bath) of 2,5-bis(benzyloxy)-4-(ethoxycarbonyl)benzoic acid (KI-1) (2.0 g, 4.9 mmol) and $Et_3N$ (1.6 mL, 11.3 mmol) in THF (25 mL) under inert atmosphere ($N_2$), was slowly added DPPA (1.1 mL, 5.2 mmol). The mixture was slowly warmed up to r.t and stirred at this temperature for 3 h. Then water (8 mL) was added and the reaction mixture was heated to 70 °C for 2 h. The reaction mixture was poured into a saturated solution of sodium hydrogencarbonate (250 mL) and stirred for 5 min before being extracted with EtOAc (3×100 mL). The combined organic layers were dried over sodium sulphate, filtered, and concentrated under reduced pressure to give a colourless oil. The residue was purified by flash column chromatography (iso-Hexane/EtOAc 1:0 then gradient to 30% EtOAc) to yield the title compound Aniline A (1.0 g, 53%) as an off-white solid.

UPLC-MS (acidic method, 2 min): rt=1.26 min; m/z=378.2 $[M+H]^+$, peak area 94%

$^1$H NMR (400 MHz, DMSO-$d_6$) δ 7.54-7.46 (m, 4H), 7.44-7.36 (m, 4H), 7.35-7.25 (m, 3H), 6.46 (s, 1H), 5.65 (s, $NH_2$), 5.06 (s, 2H), 5.02 (s, 2H), 4.16 (q, J=7.1 Hz, 2H), 1.22 (t, J=7.1 Hz, 3H).

26) 4-(4-Carboxy-2,5-dihydroxyphenylaminocarbonyl)-2,5-dihydroxybenzoic acid, compound Ia-056a UPLC-MS (acidic method, 4 min): rt=0.90 min; m/z=348.0 $[M-H]^-$, peak area 97% 1H NMR (400 MHz, DMSO-d6) δ 11.28 (brs, 1H), 11.26 (s, 1H), 9.97 (s, 1H), 8.09 (s, 1H), 7.48 (s, 1H), 7.42 (s, 1H), 7.26 (s, 1H).

Diethyl Ester:

UPLC-MS (acidic method, 4 min): rt=1.86 min; m/z=404.2 $[M-H]^-$, peak area 92%

$^1$H NMR (400 MHz, DMSO-$d_6$) δ 11.48 (brs, 1H), 11.32 (brs, 1H), 10.28 (s, 1H), 10.07 (brs, 1H), 9.88 (s, 1H), 8.12 (s, 1H), 7.58 (s, 1H), 7.39 (s, 1H), 7.28 (s, 1H), 4.46-4.27 (m, 4H), 1.46-1.12 (m, 6H).

Example 1.2—Molecules of Type Ib: Diamides from Diamines, 1 Example

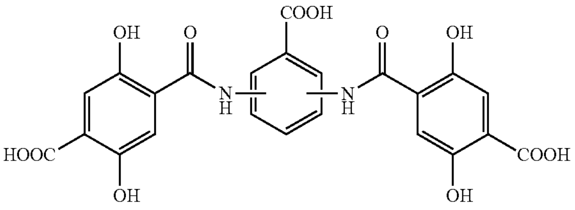

Scheme 5. Synthesis of Diamides of type Ib

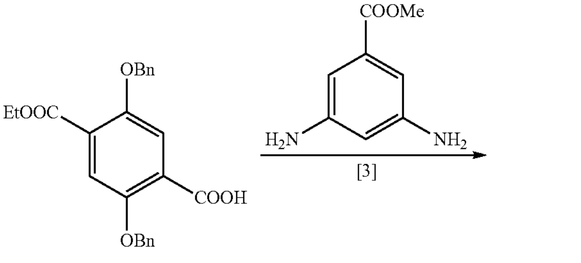

2

-continued

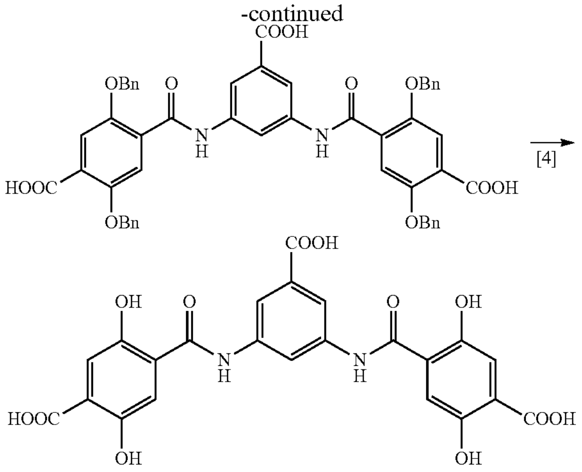

Synthetic Procedures: See General Procedures, Steps [3], [4], [5]

Example

Ib-010a

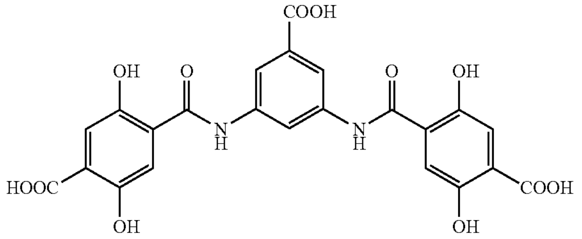

For conditions and yields: See FIGS. 4A-D 27) 3,5-Bis(2,5-dihydroxy-4-carboxybenzoylamino) benzoic acid, compound Ib-010a UPLC-MS (acidic method, 4 min): rt=0.98 min; m/z=511.0 [M−H]$^-$, peak area >93%

$^1$H NMR (400 MHz, DMSO-d$_6$) δ 10.81 (s, 2H), 10.65 (s, 2H), 8.38 (d, J=2.0 Hz, 1H), 8.12 (d, J=2.0 Hz, 2H), 7.39 (d, J=2.3 Hz, 4H).

HRMS: [M+H]$^+$, calc. for $C_{23}H_{17}N_2O_{12}$: 513.07760, found: 513.07736, Biodata: Ib-010a: FGF-1 IC50 [μM]=14; FGF-2 IC50 [μM]=3.8; VEGF-A1 IC50 [μM]=15; VEGFR-Phosphorylation inhibition IC50 [μM]=1.6; PMN ROS [inhibition at 0.3 μM [%]=71.84; PMN ROS inhibition IC50 [μM]=1.06; Neutrophil adhesion inhibition [%]=1.5; Whole Blood: GM-CSF IC50 [μM]=>100; IFNγ IC50 [μM]=2.22; IL-1β IC50 [μM]=33.3; IL-2 IC50 [μM]=2.74; IL-4 IC50 [μM]=>100; IL-5 IC50 [μM]=>100; IL-6 IC50 [μM]=1.02; IL-9 IC50 [μM]=11.58; IL-10 IC50 [μM]=>100; IL-12p70 IC50 [μM]=0.27; IL-13 IC50 [μM]=>100; IL-17A IC50 [μM]=0.42; IL-17F IC50 [μM]=>100; IL-18 IC50 [μM]=>100; IL-21 IC50 [μM]=67.8; IL-33 IC50 [μM]=31.3; TGFβ IC50 [μM]=>100; TNF α IC50 [μM]=0.31; TNF β IC50 [μM]=49.3 Triethyl ester:

UPLC-MS (acidic method, 2 min): r.t=1.29 mins, m/z=597.1 [M+H]$^+$, peak area >96%

$^1$H NMR (400 MHz, DMSO-d$_6$) δ 10.80 (s, 2H), 10.68 (s, 2H), 9.95 (s, 2H), 8.40 (t, J=2.0 Hz, 1H), 8.15 (d, J=2.0 Hz, 2H), 7.42 (s, 2H), 7.39 (s, 2H), 4.42-4.33 (m, 6H), 1.38-1.33 (m, 9H).

HRMS: [M+H]$^+$, calc. for $C_{29}H_{29}N_2O_{12}$: 597.17150, found: 597.17131

Biodata: Ib-010a-E3: FGF-1 IC50 [μM]=26; FGF-2 IC50 [μM]=226; VEGF-A1 IC50 [μM]=200; VEGFR-Phosphorylation inhibition IC50 [μM]=0.09; PMN ROS [inhibition at 0.3 μM [%]=36.41; PMN ROS inhibition IC50 [μM]=6.52; Neutrophil adhesion inhibition [%]=79.5; Whole Blood: GM-CSF IC50 [μM]=>100; IFNγ IC50 [μM]=2.79; IL-1β IC50 [μM]=>100; IL-2 IC50 [μM]=36.2; IL-4 IC50 [μM]=>100; IL-5 IC50 [μM]=>100; IL-6 IC50 [μM]=0.24; IL-9 IC50 [μM]=26.8; IL-10 IC50 [μM]=>100; IL-12p70 IC50 [μM]=0.84; IL-13 IC50 [μM]=33; IL-17A IC50 [μM]=0.52; IL-17F IC50 [μM]=34.2; IL-18 IC50 [μM]=>100; IL-21 IC50 [μM]=>100; IL-33 IC50 [μM]=20; TGFβ IC50 [μM]=>100; TNF α IC50 [μM]=0.98; TNF β IC50 [μM]=38.2.

Triethyl Ester Tetraacetate:

UPLC-MS (acidic method, 2 min): r.t=1.19 mins, m/z=782.1 [M+NH$_4$]$^+$, peak area 91%

$^1$H NMR (400 MHz, DMSO-d$_6$) δ 10.84 (s, 2H), 8.40 (m, 1H), 8.08 (d, J=2.0 Hz, 2H), 7.80 (s, 2H), 7.63 (s, 2H), 4.45-4.22 (m, 6H), 2.32 (s, 6H), 2.23 (s, 6H), 1.38-1.27 (m, 9H).

Biodata: Ib-010a-E3-A4: FGF-1 IC50 [μM]=200; FGF-2 IC50 [μM]=200; VEGF-A1 IC50 [μM]=200; VEGFR-Phosphorylation inhibition IC50 [μM]=0.54; PMN ROS [inhibition at 0.3 μM [%]=54.86; PMN ROS inhibition IC50 [μM]=1.49; Neutrophil adhesion inhibition [%]=96

Example 1.3.—Molecules of Type Ic: Diamides from Diacids, 4 Examples

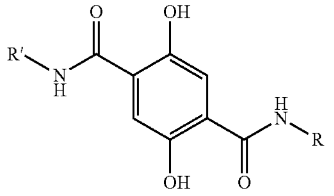

Scheme 6. Synthesis of Amides of type Ic with R= R'

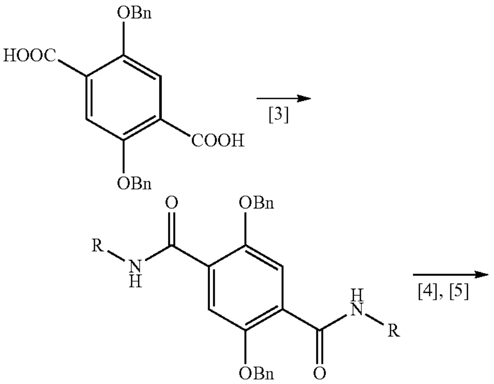

-continued

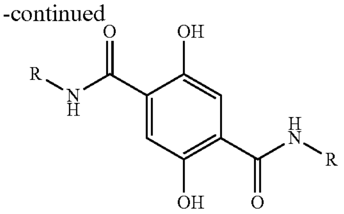

Procedures: see general procedures from KI-6 [3], [4], [5]

EXAMPLES

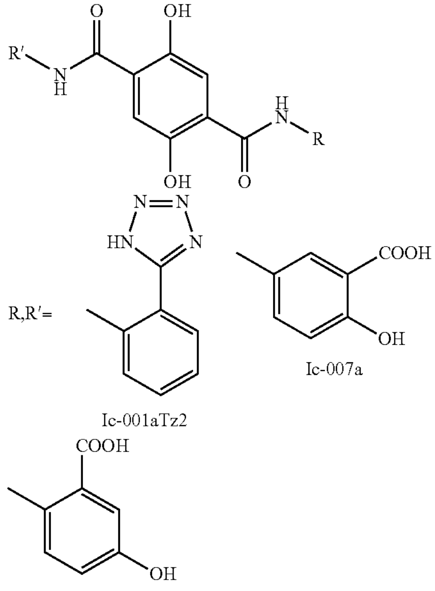

Ic-001aTz2

Ic-007a

Ic-009a

For conditions and yields: See FIGS. 4A-D

28) $N_1$,$N_4$-Bis(2-(1H-tetrazol-5-yl)phenyl)-2,5-dihydroxyterephthalamide, compound Ic-001aTz2

UPLC-MS (acidic method, 2 min): rt=0.97 min; m/z=485.1 $[M+H]^+$, peak area >97%

$^1$H NMR (400 MHz, DMSO-$d_6$) δ 11.53 (s, 1H), 10.98 (s, 1H), 8.49 (dd, J=8.4, 1.2 Hz, 1H), 7.90 (dd, J=7.8, 1.6 Hz, 1H), 7.62 (ddd, J=8.7, 7.4, 1.6 Hz, 1H), 7.58 (s, 1H), 7.37 (td, J=7.6, 1.2 Hz, 1H).

HRMS: $[M+H]^+$, calc. for $C_{22}H_{17}N_{10}O_4$: 485.14287, found: 485.17274

Biodata: Ic-001aTz2: FGF-1 IC50 [μM]=200; FGF-2 IC50 [μM]=70; VEGF-A1 IC50 [μM]=45; VEGFR-Phosphorylation inhibition IC50 [μM]=2.2; PMN ROS [inhibition at 0.3 μM [%]=60.64; PMN ROS inhibition IC50 [μM]=N.D.; Neutrophil adhesion inhibition [%]=97.15; Whole Blood: GM-CSF IC50 [μM]=>100; IFNγ IC50 [μM]= 1.38; IL-1β IC50 [μM]=>100; IL-2 IC50 [μM]=9.45; IL-4 IC50 [μM]=>100; IL-5 IC50 [μM]=>100; IL-6 IC50 [μM]= 0.52; IL-9 IC50 [μM]=9.13; IL-10 IC50 [μM]=>100; IL-12p70 IC50 [μM]=29.1; IL-13 IC50 [μM]=0.12; IL-17A IC50 [μM]=0.31; IL-17F IC50 [μM]=0.15; IL-18 IC50 [μM]= 33.9; IL-21 IC50 [μM]=32; IL-33 IC50 [μM]=0.23; TGFβ IC50 [μM]=>100; TNF α IC50 [μM]=0.1; TNF β IC50 [μM]=0.41.

29) 5-(4-(3-Carboxy-4-hydroxyphenylaminocarbonyl)-2,5-dihydroxybenzamido)-2-hydroxybenzoic acid, compound Ic-007a UPLC-MS (acidic method, 2 min): rt=0.80 min; m/z=469.1 $[M+H]^+$, peak area >91%

$^1$H NMR (400 MHz, DMSO-$d_6$) δ 8.08 (s, 2H), 7.65 (s, 2H), 7.59 (s, 2H), 7.30-6.89 (m, 5H), 6.79 (d, J=8.8 Hz, 2H).

$^{13}$C NMR (100 MHz, DMSO-d6) δ 172.1, 165.2, 158.3, 150.1, 130.2, 129.2 (CH), 122.8, 122.6 (CH), 117.7 (CH), 117.3 (CH), 113.3.

HRMS: $[M+H]^+$, calc. for $C_{22}H_{17}N_2O_{10}$: 469.08777, found: 469.08739

Biodata: Ic-007a: FGF-1 IC50 [μM]=13; FGF-2 IC50 [μM]=5.4; VEGF-A1 IC50 [μM]=3.2; VEGFR-Phosphorylation inhibition IC50 [μM]=0.09; PMN ROS [inhibition at 0.3 μM [%]=57.99; PMN ROS inhibition IC50 [μM]=2.7; Neutrophil adhesion inhibition [%]=57.5; Whole Blood: GM-CSF IC50 [μM]=>100; IFNγ IC50 [μM]=1.44; IL-1β IC50 [μM]=>100; IL-2 IC50 [μM]=>100; IL-4 IC50 [μM]=>100; IL-5 IC50 [μM]=>100; IL-6 IC50 [μM]=0.09; IL-9 IC50 [μM]=27.1; IL-10 IC50 [μM]=12.5; IL-12p70 IC50 [μM]=0.49; IL-13 IC50 [μM]=30.1; IL-17A IC50 [μM]=0.04; IL-17F IC50 [μM]=22.9; IL-18 IC50 [μM]=>100; IL-21 IC50 [μM]=1.9; IL-33 IC50 [μM]=18.4; TGFβ IC50 [μM]=>100; TNF α IC50 [μM]=0.27; TNF β IC50 [μM]=6.52

Dimethyl Ester:

UPLC-MS (acidic method, 2 min): r.t=1.13 mins, m/z=497.0 $[M+H]^+$, peak area >95%

$^1$H NMR (400 MHz, DMSO-d6) δ 11.08 (s, 2H), 10.48 (s, 2H), 10.38 (s, 2H), 8.27 (d, J=2.8 Hz, 2H), 7.89-7.74 (m, 2H), 7.56 (s, 2H), 7.03 (d, J=8.9 Hz, 2H), 3.93 (s, 6H).

HRMS: $[M+H]^+$, calc. for $C_{24}H_{21}N_2O_{10}$: 497.11907, found: 497.11874.

Biodata: Ic-007a-E2: FGF-1 IC50 [μM]=23; FGF-2 IC50 [μM]=49; VEGF-A1 IC50 [μM]=200; VEGFR-Phosphorylation inhibition IC50 [μM]=0.25; PMN ROS [inhibition at 0.3 μM [%]=21.33; PMN ROS inhibition IC50 [μM]=7.9; Neutrophil adhesion inhibition [%]=2

Alternative, Large-Scale Synthesis of Ic-007a a) 5-(4-(3-Methoxycarbonyl-4-hydroxyphenylaminocarbonyl)-2,5-dibenzyloxybenzamido)-2-hydroxybenzoic acid methyl ester A 5 L flange flask was charged with 2,5-bis(benzyloxy) terephthalic acid (KI-6, 141.00 g, 0.373 mol), benzyltriethylammonium chloride (850 mg, 3.73 mmol, 0.01 eq) and chloroform (2.5 L). Then it was fitted with a nitrogen inlet, thermometer, pressure-equalizing dropping funnel, outlet to blank Dreschel bottle and sodium hydroxide bubbler. The stirred solution was warmed to 55 °C, and thionyl chloride (59 mL, 0.802 mol, 2.15 eq) was added dropwise over a period of 40 min. The solution was held at 55 °C for 6 h, then allowed to cool to room temperature overnight. An aliquot was sonicated in ethanol for 5 min., then analysed by LCMS analysis, which showed only diethylester. The mixture was transferred to two round bottom flasks and the volatiles were removed in vacuo; the acid chloride was azeotroped with toluene (800 mL in each flask). A 10 L jacketed vessel was charged with methyl 5-amino-2-hydroxybenzoate (137.00 g, 0.819 mol, 2.2 eq), and dichloromethane (2.5 L, 18 vol); the solution was cooled to 15 °C. The acid chloride was taken up in dichloromethane (2.5 L, 18 vol) and added to the stirred reaction. The reaction immediately forms large amounts of solid and stirring becomes difficult; also the reaction exotherms to 30 °C. However, on protracted stirring the mixture becomes a pink/purple fine suspension. The mixture was stirred at 25 °C over 72 h. The suspension was filtered, washed with dichloromethane (2 L, 14 vol) and the resulting solid dried in a vacuum oven to give 240.00 g of product (94% yield).

b) 5-(4-(3-Carboxy-4-hydroxyphenylaminocarbonyl)-2,5-dihydroxybenzamido)-2-hydroxy benzoic acid, Ic-007a Saponification: A 5 L 3-neck round bottom flask was charged with freshly ground 5-(4-(3-methoxycarbonyl-4-hydroxyphenylaminocarbonyl)-2,5-dibenzyloxybenzamido)-2-hydroxy-benzoic acid methyl ester (150.00 g, 0.22 mol) and isopropanol (1.5 L, 10 vol). The mixture was warmed up to 50 °C and tetrabutylammonium hydroxide (444 mL, 0.67 mol, 3 eq) and water (1.1 L, 7 vol) were added. After 1 h some solids remained, so a further 60 mL of tetrabutylammonium hydroxide solution was added together with water (120 mL), the mixture stirred at 50 °C for 6 h, then allowed to cool to room temperature overnight. Additional tetrabutylammonium hydroxide (80 mL) was added and the mixture was further stirred at 60 °C for 1 h until no solid remained.

Hydrogenolysis: The reaction was degassed (3 cycles with $N_2$), then the catalyst (30.00 g, 10% Pd on C) was added as a slurry in water (100 mL). The reaction was further degassed (3 cycles with $N_2$, 2 with $H_2$) and placed under $H_2$ (balloon pressure) at 50 °C overnight. The reaction was recharged with hydrogen and held at 50 °C for a further 4 h after which time LCMS analysis showed complete reaction. The reaction mixture was degassed (3 cycles with $N_2$), filtered through a pad of celite and washed with warm water/isopropanol (1 L, 1:1, 60 °C.). The volume was reduced to ~1.2 L in vacuo. The mixture was transferred to a 5 L flange flask with water (~3 L). The flask was fitted with an overhead stirrer (large anchor-type) and acidified with hydrochloric acid (35%). During the addition a heavy precipitate formed. The mixture was heated at 55 °C for 6 h, then allowed to cool to room temperature over 72 h. The mixture was filtered and the solid slurried in 1M aq HCl (3 L) and heated to 50 °C for 3 h, before allowing to cool to r.t. overnight. The mixture was filtered, washed with 1M aq HCl (2 L), water (1.5 L) and acetone (1 L). The solid was dried in the vacuum oven to give 100.00 g of product still contaminated by ~5 mol % of tetrabutylammonium salt (NMR). This solid was stirred in 1M aq hydrochloric acid (3 L) at 70 °C for 8 h, then allowed to cool to r.t. overnight. The solid was filtered, washed with water and dried in the vacuum oven. The amount of tetrabutylammonium was reduced to ~0.62 mol %. (85.90 g, 82% yield) (brown powder).

30) 2-(2,5-Dihydroxy-4-(4-hydroxy-2-carboxyphenylaminocarbonyl)benzamido)-5-hydroxybenzoic acid, compound Ic-009a UPLC-MS (acidic method, 2 min): rt=0.85 min; m/z=469.0 $[M+H]^+$, peak area >98%

$^1H$ NMR (400 MHz, DMSO-$d_6$) δ 13.31 (s, 2H), 11.93 (s, 2H), 10.85 (s, 2H), 9.64 (s, 2H), 8.41 (d, J=9.0 Hz, 2H), 7.55 (s, 2H), 7.39 (d, J=3.0 Hz, 2H), 7.03 (dd, J=9.0, 3.0 Hz, 2H).

HRMS: calc. for $C_{22}H_{17}N_2O_{10}$: 469.08777, found: 469.08755

Biodata: Ic-009a: FGF-1 IC50 [μM]=32; FGF-2 IC50 [μM]=202; VEGF-A1 IC50 [μM]=208; VEGFR-Phosphorylation inhibition IC50 [μM]=ND; PMN ROS [inhibition at 0.3 μM [%]=72.85; PMN ROS inhibition IC50 [μM]=N.D.; Neutrophil adhesion inhibition [%]=72.21 Dimethyl ester:

UPLC-MS (acidic method, 2 min): r.t=1.03 mins, m/z=497.1 $[M+H]^+$, peak area >92%

$^1H$ NMR (400 MHz, DMSO-d6) δ 11.69 (s, 2H), 11.01 (s, 2H), 9.75 (s, 2H), 8.36 (d, J=9.0 Hz, 2H), 7.62 (s, 2H), 7.37 (d, J=3.0 Hz, 2H), 7.07 (dd, J=9.0, 3.0 Hz, 2H), 3.87 (s, 6H).

HRMS: calc. for $C_{24}H_{21}N_2O_{10}$: 497.11907, found: 497.11913

Biodata: Ic-009a-E2: FGF-1 IC50 [μM]=23; FGF-2 IC50 [μM]=30; VEGF-A1 IC50 [μM]=200; VEGFR-Phosphorylation inhibition IC50 [μM]=0.02; PMN ROS [inhibition at 0.3 μM [%]=24.12; PMN ROS inhibition IC50 [μM]=N.D.; Neutrophil adhesion inhibition [%]=41.05

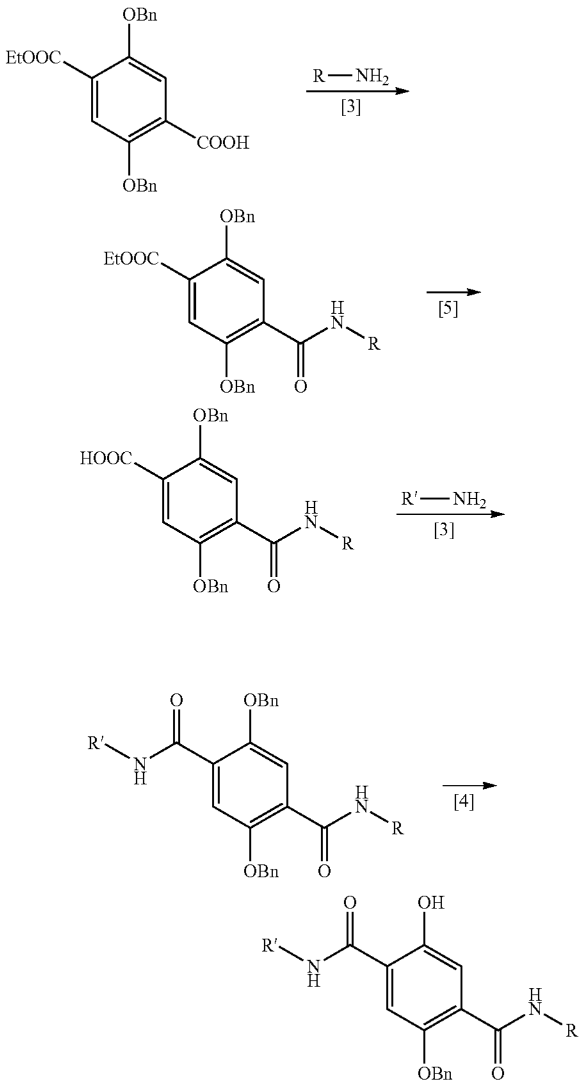

Synthetic Procedures: See general procedure from KI-1.

Example

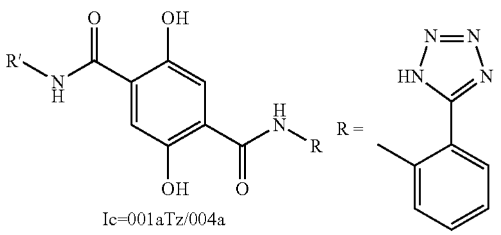

Ic=001aTz/004a

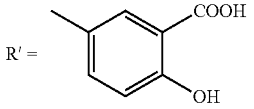

For conditions and yields: See FIGS. 4A-D 31) 5-(4-(2-(1H-Tetrazol-5-yl)phenylaminocarbonyl)-2,5-dihydroxybenzamido)-2-hydroxybenzoic acid, compound Ic-001aTz/004a UPLC-MS (acidic method, 4 min): rt=1.40 min; m/z=477.2 $[M-H]^-$, peak area >99%

$^1H$ NMR (400 MHz, DMSO-$d_6$) δ 10.92 (s, 1H), 10.42 (s, 1H), 8.47 (dd, J=8.4, 1.2 Hz, 1H), 8.25 (d, J=2.7 Hz, 1H), 7.98-7.88 (m, 1H), 7.76 (dd, J=8.9, 2.8 Hz, 1H), 7.63-7.56 (m, 2H), 7.51 (s, 1H), 7.37 (td, J=7.6, 1.2 Hz, 1H), 6.97 (d, J=8.9 Hz, 1H).

HRMS: $[M+H]^+$, calc. for $C_{22}H_{17}N_6O_7$: 477.11532, found: 477.11475

Biodata: Ic-001a-Tz/004a: FGF-1 IC50 [μM]=19; FGF-2 IC50 [μM]=87; VEGF-A1 IC50 [μM]=25; VEGFR-Phosphorylation inhibition IC50 [μM]=2.6; PMN ROS [inhibition at 0.3 μM [%]=82.83; PMN ROS inhibition IC50 [μM]=N.D.; Neutrophil adhesion inhibition [%]=96.99; Whole Blood: GM-CSF IC50 [μM]=3.4; IFNγ IC50 [μM]=0.61; IL-1β IC50 [μM]=>100; IL-2 IC50 [μM]=4.91; IL-4 IC50 [μM]=>100; IL-5 IC50 [μM]=>100; IL-6 IC50 [μM]=3.04; IL-9 IC50 [μM]=8.48; IL-10 IC50 [μM]=19.5; IL-12p70 IC50 [μM]=12.2; IL-13 IC50 [μM]=1.5; IL-17A IC50 [μM]=0.02; IL-17F IC50 [μM]=2.4; IL-18 IC50 [μM]=46.6; IL-21 IC50 [μM]=0.3; IL-33 IC50 [μM]=1.67; TGFβ IC50 [μM]=>100; TNF α IC50 [μM]=0.002; TNF β IC50 [μM]=3.02 Methyl ester:

UPLC-MS (acidic method, 2 min): r.t=1.06 mins, m/z=491.1 $[M+H]^+$, peak area >89%

$^1H$ NMR (400 MHz, DMSO-d6) δ 11.55 (s, 1H), 10.90 (s, 1H), 10.45 (s, 1H), 10.37 (s, 1H), 8.47 (dd, J=8.4, 1.2 Hz, 1H), 8.30 (d, J=2.7 Hz, 1H), 7.91 (dd, J=7.8, 1.6 Hz, 1H), 7.76 (dd, J=8.9, 2.7 Hz, 1H), 7.63 (ddd, J=8.7, 7.4, 1.6 Hz, 1H), 7.58 (s, 1H), 7.51 (s, 1H), 7.38 (td, J=7.6, 1.2 Hz, 1H), 7.02 (d, J=8.8 Hz, 1H), 3.93 (s, 4H).

HRMS: $[M+H]^+$, calc. for $C_{23}H_9N_6O_7$: 491.13097, found: 491.13071

Biodata: Ic-001a-Tz/004a-E1: FGF-1 IC50 [μM]=104; FGF-2 IC50 [μM]=200; VEGF-A1 IC50 [μM]=35; VEGFR-Phosphorylation inhibition IC50 [μM]=0.1; PMN ROS [inhibition at 0.3 μM [%]=73.97; PMN ROS inhibition IC50 [μM]=N.D.; Neutrophil adhesion inhibition [%]=97.56

Example 1.4. Molecules of Type Id: Benzimidazole-Linked, 1 Example

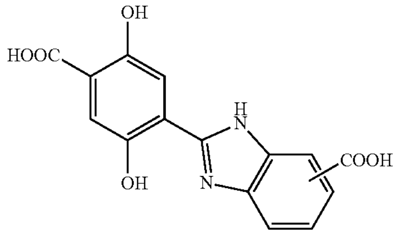

Scheme 8. Synthesis of compounds of type Id

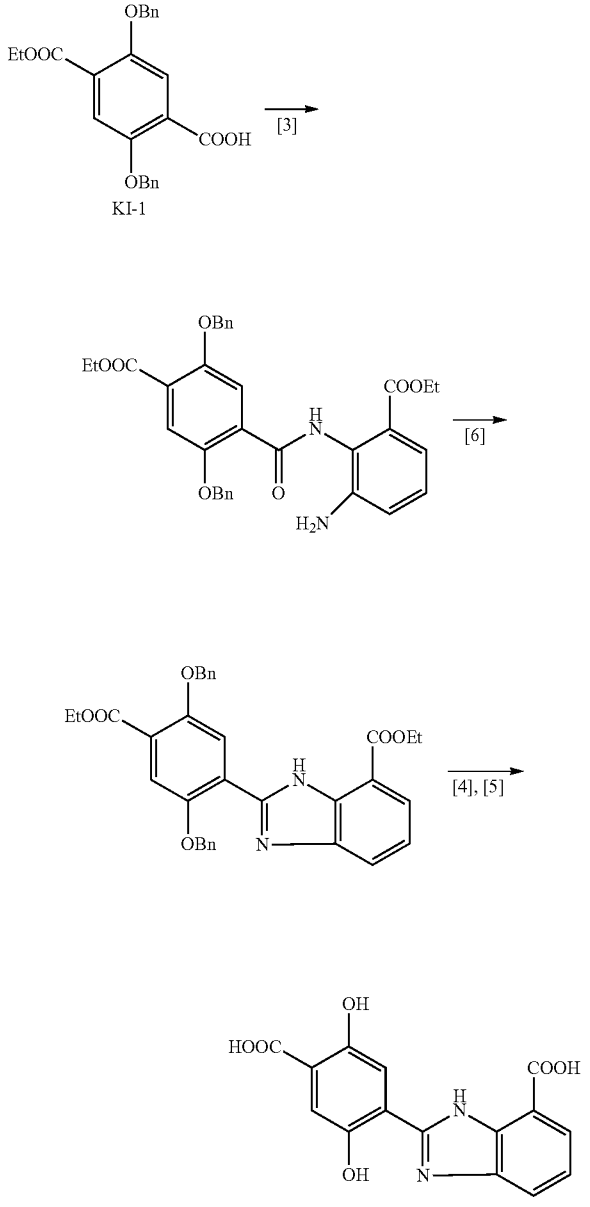

Cyclization step: see FIGS. 4A-D

Example 1d-030a

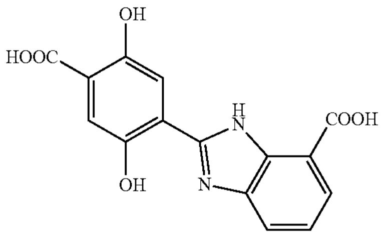

32) 2-(4-Carboxy-2,5-dihydroxyphenyl)-1H-benzo[d]imidazole-4-carboxylic acid, compound Id-030a UPLC-MS (acidic method, 4 min): rt=0.99 min; m/z=313.1 $[M-H]^-$, peak area >97%

$^1H$ NMR (400 MHz, DMSO-$d_6$) δ 8.10 (d, J=8.2 Hz, 1H), 8.05 (d, J=7.7 Hz, 1H), 7.80 (s, 1H), 7.68 (t, J=8.0 Hz, 1H), 7.62 (s, 1H) Biodata—unstable in DMSO Ethyl Methyl ester:

UPLC-MS (acidic method, 4 min): r.t=2.09 mins, m/z=357.1 $[M+H]^+$, peak area >89%

$^1H$ NMR (400 MHz, DMSO-$d_6$+$D_2O$ 10%) δ 7.97 (d, J=8.0 Hz, 1H), 7.90-7.83 (m, 2H), 7.44-7.36 (m, 2H), 4.35 (q, J=7.1 Hz, 2H), 3.94 (s, 3H), 1.33 (t, J=7.1 Hz, 3H).

HRMS: $[M+H]^+$, calc. for $C_{18}H_{17}N_2O_6$: 357.10811, found: 357.10827

Biodata: Id-030a-E2: FGF-1 IC50 [μM]=115; FGF-2 IC50 [μM]=200; VEGF-A1 IC50 [μM]=200; VEGFR-Phosphorylation inhibition IC50 [μM]=0.33; PMN ROS [inhibition at 0.3 μM [%]=0; PMN ROS inhibition IC50 [μM]=0; Neutrophil adhesion inhibition [%]=43

Example 1.5: Molecules of type IIa: Monoamides, 16 examples

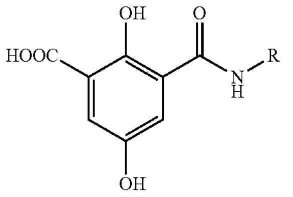

Synthesis of Precursors

Scheme 9a. Synthesis of Intermediates KI-2 and KI-7

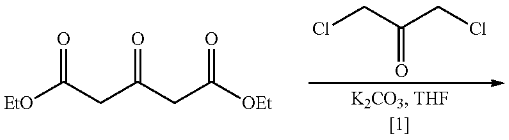

-continued

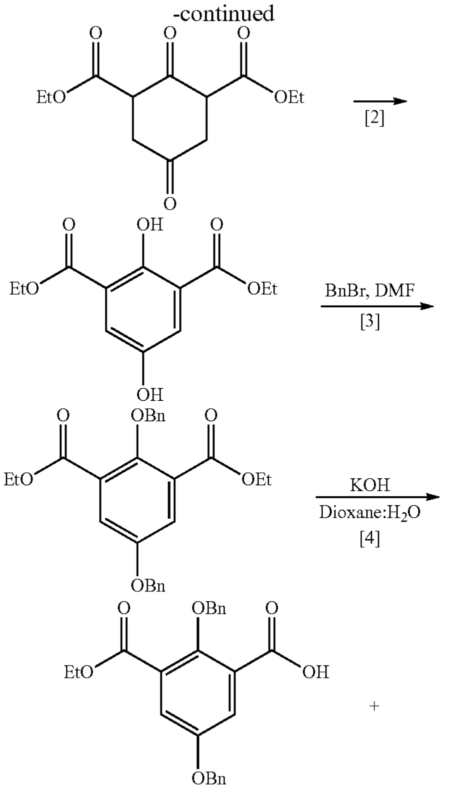

KI-2

+

KI-7

Procedures:

Synthesis of KI-2 an KI-7

2,6-Di(ethoxycarbonyl)cyclohexane-1,4-dione [Step 1][Ref: Rodriguez et al. Synth. Comm. 28 (1998) 2259-69]: 1,3-Dichloroacetone (12.5 g, 0.1 mol) in THF (500 mL) was added dropwise, over a period of 30 min, to a suspension of diethyl 1,3-acetonedicarboxylate (18 mL, 0.1 mol) and potassium carbonate-325 mesh (21.5 g, 0.15 mol) in THF (1 L) at reflux temperature. After 2 h, the reaction was complete and the mixture was cooled down to room temperature then filtered thought Celite©; the solid residue was washed with THF (200 mL), the solvent was then removed under reduced pressure. The crude product was purified by flash column chromatography (Hexanes/EtOAc 0 to 20%) to give the title compound (9.3 g, 37% yield).

UPLC-MS (acidic method, 2 min): rt=1.01 min; m/z=257.1 $[M+H]^-$, peak area >74%

$^1H$ NMR (400 MHz, DMSO-$d_6$) Complex mixture of enol and cis/trans isomers δ 12.10 (s), 4.23 (q, J=7.1 Hz), 4.11 (m), 3.85-3.77 (m), 3.70 (s), 3.10-2.89 (m), 2.89-2.80 (m), 2.62-2.58 (m), 1.25 (t, J=7.1 Hz), 1.22-1.15 (m, 9H).

Diethyl 2,5-dihydroxyisophthalate [Step 2]: [Protocole taken from Zhong et al.: Chem Eur. J. 25 (2019) 8177-8169]: To a stirred solution of 2,6-di(ethoxycarbonyl)-cyclohexane-1,4-dione (5.0 g, 20 mmol) in AcOH (17 mL) at room temperature was added NBS (3.5 g, 20 mmol) in portions over 30 min.

After 20 additional min, the reaction was quenched by the addition of water (100 ml). The desired product separated as a solid. After filtration and drying, the title compound was isolated as a white solid (4.6 g, 93% yield).

UPLC-MS (acidic method, 2 min): rt=1.00 min; m/z=253.1 $[M-H]^-$, peak area >90%

$^1$H NMR (400 MHz, DMSO-$d_6$) δ 10.85 (s, 1H), 9.57 (s, 1H), 7.39 (s, 2H), 4.32 (q, J=7.1 Hz, 4H), 1.31 (t, J=7.1 Hz, 6H).

Diethyl 2,5-bis(benzyloxy)isophthalate [Step 3]: To a suspension of diethyl 2,5-dihydroxyisophthalate (19.0 g, 75 mmol) and potassium carbonate-325 mesh (82.6 g, 598 mmol) in DMF (83 mL) was added dropwise benzyl bromide (43.0 mL, 362 mmol) over 10 min. The reaction mixture was heated at 100 °C during 2 h. After cooling down to room temperature the solvent was removed under reduced pressure. Water (500 mL) was then added to the residue. The mixture was extracted with EtOAc (3×250 mL), the gathered organic layers were washed with brine (300 mL), dried over $Na_2SO_4$, filtered then concentrated under reduced pressure. The crude material was purified by flash column chromatography (Hexanes/EtOAc 0 to 15%) to give the title compound (29.4 g, 90% yield).

UPLC-MS (acidic method, 2 min): rt=1.38 min; m/z=435.2 $[M+H]^+$, peak area >90%

$^1$H NMR (400 MHz, DMSO-d6) δ 7.50 (s, 2H), 7.49-7.45 (m, 2H), 7.44-7.37 (m, 5H), 7.37-7.29 (m, 3H), 5.17 (s, 2H), 4.95 (s, 2H), 4.26 (q, J=7.1 Hz, 4H), 1.22 (t, J=7.1 Hz, 6H).

2,5-bis(benzyloxy)-3-(ethoxycarbonyl)benzoic acid (KI-2) [Step 4]: A solution of potassium hydroxide (4.4 g, 79 mmol) in water (66 mL) was rapidly added to a solution of diethyl 2,5-bis(benzyloxy)isophthalate (31.3 g, 72 mmol) in 1,4-dioxane (430 mL). The reaction mixture was stirred at room temperature for 1.5 h. 1,4-Dioxane was removed under reduced pressure, an aqueous saturated solution of $Na_2CO_3$ (1 L) was then added, the aqueous layer was extracted with EtOAc (3×500 mL), dried over $Na_2SO_4$, filtered and the solvent was removed in vacuo. The residue was purified by filtration over a Silica Pad using Hexanes/EtOAc (1/1) then EtOAc (1% v/v AcOH) as eluent to yield two different fractions: The starting material: Diethyl 2,5-bis(benzyloxy) isophthalate (20.4 g, 65% yield).

UPLC-MS (acidic method, 2 min): rt=1.38 min; m/z=435.2 $[M+H]^+$, peak area >78%

$^1$H NMR (400 MHz, DMSO-d6) δ 7.50 (s, 2H), 7.49-7.45 (m, 2H), 7.44-7.37 (m, 5H), 7.37-7.29 (m, 3H), 5.17 (s, 2H), 4.95 (s, 2H), 4.26 (q, J=7.1 Hz, 4H), 1.22 (t, J=7.1 Hz, 6H).

The desired product, 2,5-bis(benzyloxy)-3-(ethoxycarbonyl)benzoic acid as a white fluffy solid, (KI-2) (3.5 g, 12% yield).

UPLC-MS (acidic method, 2 min): rt=1.22 min; m/z=405.1 $[M-H]^-$, peak area >90%

$^1$H NMR (400 MHz, DMSO-$d_6$) δ 13.30 (s, 1H), 7.48 (t, J=3.0 Hz, 2H), 7.46-7.42 (m, 5H), 7.39 (m, 3H), 7.37-7.31 (m, 2H), 5.17 (s, 2H), 4.96 (s, 2H), 4.25 (q, J=7.1 Hz, 2H), 1.22 (t, J=7.1 Hz, 3H).

The original saturated aqueous solution of $Na_2CO_3$ was then acidified to pH-7 using concentrated hydrochloric acid. Then extracted with EtOAc (2×500 mL), dried over sodium sulfate, filtered and concentrated under reduced pressure to give a mixture of KI-2 and KI-7 (3.0 g, 11% yield).

UPLC-MS (acidic method, 2 min): rt=1.00 min; m/z=377.1 $[M-H]^-$, peak area 25%, rt=1.22 min; m/z=405.1 $[M-H]^-$, peak area 56%

$^1$H NMR (400 MHz, DMSO-$d_6$) δ 13.23 (s, 2H), 7.52-7.29 (m, 12H), 5.17 (s, 2H), 4.97 (s, 2H).

Scheme 9b: Alternative Synthesis of KI-7

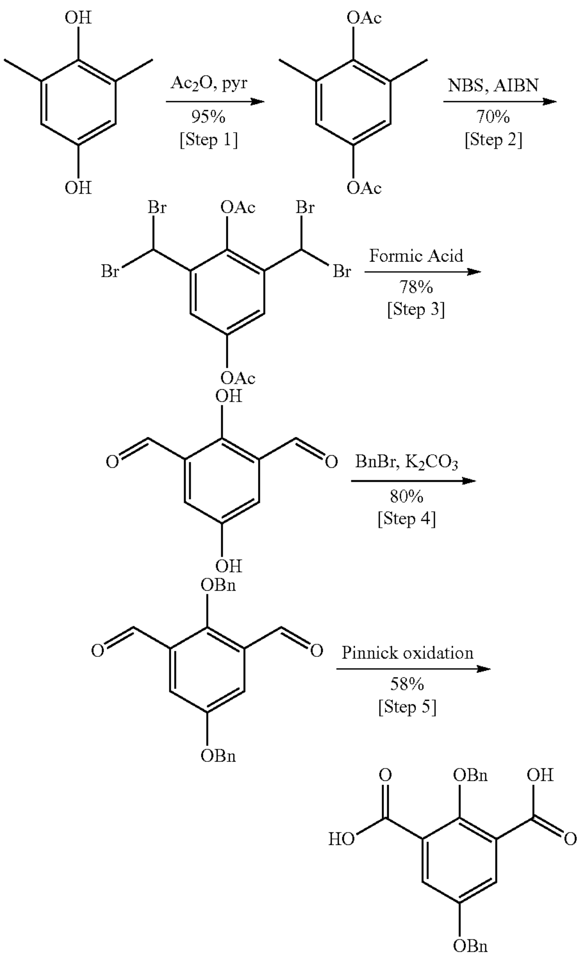

KI-7

2,6-Dimethyl-1,4-phenylene diacetate [Step 1]: To a stirred solution of 2,6-dimethylhydroquinone (5.0 g, 36 mmol) in pyridine (10 mL) was rapidly added acetic anhydride (10 mL). The solution was stirred at room temperature for 18 h. The solvent was then removed under reduced pressure and the residue was dissolved with EtOAc (250 mL) and subsequently washed with an aqueous solution of hydrochloric acid (1 M, 250 mL), a saturated aqueous solution of $NaHCO_3$ (250 mL) and water (250 mL), dried over $Na_2SO_4$, filtered and the solvent was removed in vacuo, to afford the title compound (7.4 g, 92%) as a white solid.

UPLC-MS (acidic method, 2 min): rt=1.07 min; m/z=240.2 $[M+NH_4]^+$, peak area >90%

$^1$H NMR (400 MHz, DMSO-$d_6$) δ 6.88 ($H_4$r, 2H), 2.37-2.30 (m, 3H), 2.27-2.21 (m, 3H), 2.12-2.02 (m, 6H).

2,6-Bis(dibromomethyl)-1,4-phenylene diacetate [Step 2]: To a stirred solution of 2,6-dimethyl-1,4-phenylene diacetate (6.34 g, 29 mmol) in 1,2-Dichloroethane (130 mL) was sequentially added 2,2'-Azobis(2-methylpropionitrile) (AIBN) (0.93 g, 6 mmol) and N-Bromosuccinimide (NBS) (25.39 g, 143 mmol). The solution was stirred under reflux for 24 h. Additional 2,2'-Azobis(2-methylpropionitrile) (AIBN) (0.93 g, 6 mmol) and N-Bromosuccinimide (NBS) (5.08 g, 28.6 mmol) were added and the reaction mixture was stirred under reflux for another 24 h. The reaction was cooled down to room temperature and the residual solid was removed by filtration and washed with DCM (250 mL). The filtrate was washed with an aqueous saturated solution of sodium hydrogen carbonate (250 mL), an aqueous solution of hydrochloric acid (1 M, 250 mL) and brine (250 mL). The organic layer was then dried with sodium sulfate, filtered and concentrated under reduced pressure to afford the title compound (9.38 g, 61%) as an orange oil.

UPLC-MS (acidic method, 2 min): rt=1.23 min; m/z=553.1 $[M+NH_4]^+$, peak area >88%

$^1H$ NMR (400 MHz, DMSO-$d_6$) δ 7.69 (s, 2H), 7.31 (s, 2H), 2.49 (s, 3H), 2.32 (s, 3H).

2,5-Dihydroxyisophthalaldehyde [Step 3]: To a stirred suspension of 2,6-bis(dibromomethyl)-1,4-phenylene diacetate (3.89 g, 7.23 mmol) in formic acid (50 mL) was added water (5 mL). The mixture was stirred under reflux for 18 h. The reaction mixture was then slowly poured into aqueous saturated sodium hydrogen carbonate (300 mL). The formed precipitate was then isolated by filtration to give the title compound (0.94 g, 78%) as a brown solid.

UPLC-MS (acidic method, 2 min): rt=0.74 min; m/z=165.0 $[M-H]^-$, peak area >98% 2,5-Bis(benzyloxy) isophthalaldehyde [Step 4]: Potassium carbonate-325 mesh (2.34 g, 17.0 mmol) was added to a stirred solution of 2,5-dihydroxyisophthalaldehyde (0.94 g, 5.7 mmol) in DMF (6 mL) at ambient temperature. Benzyl bromide (2.0 mL, 17.0 mmol) was then added to the reaction flask, and the resulting mixture was heated at 100 °C for 18 h. The reaction mixture was cooled down to ambient temperature and treated with a solution of saturated aqueous ammonium chloride (100 mL). The resulting suspension was stirred for 30 min, then filtered. The solid material was washed with a solution of saturated aqueous ammonium chloride (2×50 mL). The solid was then triturated with ethanol (5 mL), dried by suction to give the desired product as a brown solid (1.58 g, 68%)

UPLC-MS (acidic method, 2 min): rt=1.28 min, no ionization observed, peak area 78%

$^1H$ NMR (400 MHz, DMSO-$d_6$) δ 10.14 (s, 2H), 7.63 (s, 2H), 7.53-7.28 (m, 10H), 5.23 (s, 2H), 5.21 (s, 2H). 2,5-Bis (benzyloxy)isophthalic acid (KI-7) [Step 5]: 2,5-bis(benzyloxy)isophthalaldehyde (1.58 g, 4.5 mmol) was dissolved in a 2-methyl-2-butene solution in THF (2.0 M, 25 mL). A solution of sodium chlorite (5.1 g, 45.0 mmol) and potassium dihydrogen phosphate (4.6 g, 33.8 mmol) in water (25 mL) was then added and the reaction mixture was stirred at room temperature for 18 h. The reaction mixture was then poured into a saturated aqueous solution of $NaHCO_3$ (400 mL). The aqueous layer was washed with EtOAc (3×100 mL) followed by acidification with conc. hydrochloric acid (pH~1). The aqueous layer was then extracted with DCM (2×150 mL) and $Et_2O$ (2×200 mL), the gathered organic layer was dried with sodium sulfate, filtered and concentrated under reduced pressure. The residue was then triturated with n-pentane (3×50 mL) to give the title compound KI-7 as a white solid (0.98 g, 58%).

UPLC-MS (acidic method, 2 min): rt=1.03 min, m/z=379.1 $[M+H]^+$, peak area >96%

$^1H$ NMR (400 MHz, DMSO-$d_6$) δ 13.23 (s, 2H), 7.57-7.28 (m, 12H), 5.17 (s, 2H), 4.97 (s, 2H).

Scheme 9c: Synthesis of KI-$2Ac_2$

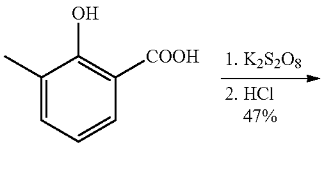

-continued

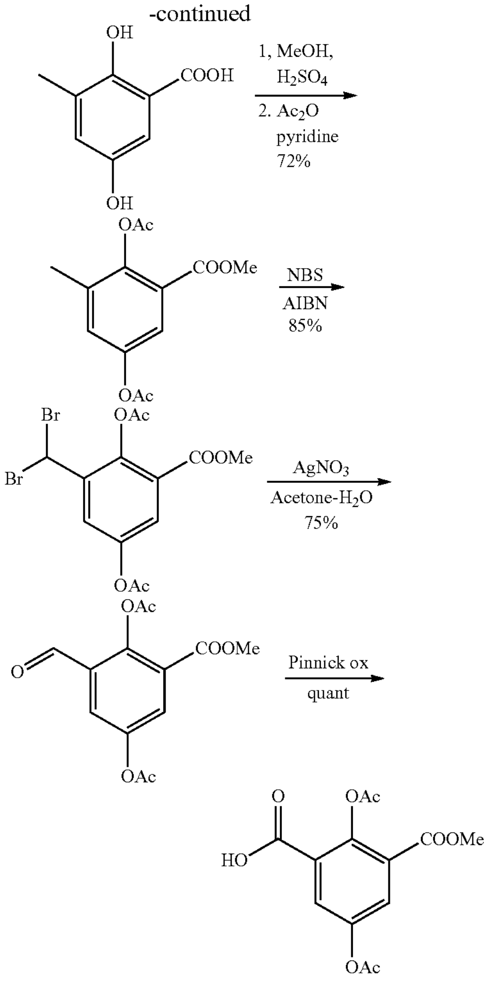

KI-$2Ac_2$

Methyl 2,5-diacetoxy-3-methylbenzoate. 3-Methylsalicylic acid was oxidized with persulfate as reported by Nudenberg et al (J Org. Chem. 1943, 8, 500-508). 3-Methylsalicylic acid (15.0 g, 98.6 mmol) was dissolved in a solution of sodium hydroxide (15.0 g, 375 mmol, 3.8 eq.) in water (37.5 mL). The light brown solution was cooled to 20 °C and treated, while stirring, with 7.75 mL portions of 40% sodium hydroxide and 33.8 mL portions of 10% potassium persulfate solutions, beginning with the hydroxide, at such a rate that a temperature of 30-35 °C was maintained and until ten portions of each were added. After the addition was completed, stirring was continued for 1 h, the mixture was allowed to stand at room temperature for 16-20 h, and conc HCl was then added until blue to Congo. Unreacted 3-methylsalicylic acid separated at this point as a solid and was removed by filtration. The filtrate was extracted with ether several times (5×50 mL) to recover the remainder of 3-methylsalicylic acid. The aqueous solution was then treated with conc HCl (100 mL) and then refluxed for 2 h to decompose the intermediate monosulfate. The warm solution was allowed to cool to r.t. and the almost black crystalline solid which precipitated was filtered, washed with water, and dried. Extraction of the aqueous filtrate with ether gave an additional batch of 2,5-dihydroxy-3-methylbenzoic acid as a brown solid (total: 7.71 g, 47%). Mp 212-214 °C; $^1H$ NMR (250 MHz, DMSO): δ 10.94 (br. s., 1H), 7.00 (dd, J=3.0 and 0.75, $1H_{ar}$), 6.86 (dd, J=3.0 and 0.75, $1H_{ar}$), 2.12 (s, 3H).

Esterification. Concentrated sulfuric acid (0.7 mL) was carefully added at 0 °C and under nitrogen to a solution of 2,5-dihydroxy-3-methylbenzoic acid (2.05 g, 12.2 mmol) in MeOH (7 mL). The reaction mixture was then stirred for 6 h at 100 °C. After cooling down to r.t., the solvent was removed under reduced pressure. The crude product obtained was dissolved in ethyl acetate (50 mL) and the solution washed with water (20 mL), 10% aq. $NaHCO_3$ (20 mL), 5% aq. HCl (20 mL), and brine (20 mL), and was then dried ($MgSO_4$). After filtering, the organic layer was concentrated in vacuo to give the residue which was purified by flash chromatography on silica gel (petroleum ether/ethyl acetate=9/1) to afford methyl 2,5-dihydroxy-3-methylbenzoate as a white solid (370 mg, 75%). Mp 101-103 °C; $^1H$ NMR (250 MHz, $CDCl_3$): δ 10.56 (d, J=0.50 Hz, 1H), 7.12 (dd, J=3.25 and 0.50 Hz, $1H_{ar}$), 6.90 (dt, J=3.00 and 0.50 Hz, $1H_{ar}$), 4.45 (s, 3H), 2.24 (s, 3H); HRMS ($ESI^+$): m/z calcd for $C_9H_{11}O_4[M+H]^+$: 183.0652; found 183.0651.

Acetylation. Excess acetic anhydride (10 mL) was added to a solution of methyl 2,5-dihydroxy-3-methyl-benzoate (4.43 g, 24.3 mmol) in pyridine (10 mL) under argon. After 12 h of stirring at r.t., pyridine and acetic anhydride were eliminated by co-evaporation with toluene (25 mL) under reduced pressure. The crude product was then dissolved in ethyl acetate (15 mL) and the solution washed successively with a 2% aq HCl (5 mL), saturated aq $NaHCO_3$ (5 mL) and brine (5 mL). The organic phase was dried ($MgSO_4$) and the solvent was evaporated under reduced pressure. The colorless oil obtained was purified by flash chromatography on silica gel (petroleum ether/ethyl acetate=8/2) to afford the acetylated title product (2,5-acetoxy-3-methyl-benzoate) as a white solid (6.25 g, 97%). Mp 69-71 °C; $^1H$ NMR (250 MHz, $CDCl_3$): δ 7.58 (dd, J=3.00 and 0.50 Hz, $1H_{ar}$), 7.18 (dd, J=3.00 and 0.75 Hz, $1H_{ar}$), 3.85 (s, 3H), 2.37 (s, 3H), 2.30 (s, 3H), 2.22 (s, 3H); HRMS ($ESI^+$): m/z calcd for $C_{13}H_{18}NO_6$ $[M+NH_4]^+$: 284.1129; found 284.1128.

Methyl 2,5-diacetoxy-3-dibromomethylbenzoate. A solution of methyl 2,5-diacetoxy-3-methyl-benzoate (2.15 g, 8.08 mmol), N-bromosuccinimide (2.87 mg, 16.2 mmol, 2.0 eq.) and azobisisobutyronitrile (AIBN, 27.0 mg, 0.162 mmol, 0.02 eq.) in carbon tetrachloride (45 mL) was refluxed for about 12 h until a white solid was floating on the surface. After cooling down, the mixture was filtered, and the filtrate was then concentrated under reduced pressure. The colorless oil obtained was purified by flash chromatography on silica gel (petroleum ether/ethyl acetate=9/1) to afford the dibrominated product as a white solid (3.29 g, 84%). Mp 117-119 °C; $^1H$ NMR (250 MHz, $CDCl_3$): δ 7.86 (d, J=2.75 Hz, $1H_{ar}$), 7.78 (d, J=2.75 Hz, $1H_{ar}$), 6.81 (s, 1H), 3.86 (s, 3H), 2.42 (s, 3H), 2.33 (s, 3H); HRMS ($ESI^+$): m/z calcd for $C_{13}H_{12}Br_2NaO_6$ $[M+Na]^+$: 444.8893; found 444.8896.

Methyl 2,5-diacetoxy-3-formylbenzoate. A solution of methyl 2,5-diacetoxy-3-dibromo-methylbenzoate (2.30 g, 5.42 mmol) and silver nitrate (2.29 g, 13.5 mmol, 2.5 eq.) in a mixture acetone—$H_2O$ (4.7:1, 40 mL) was stirred at r.t. and in the dark during 12 h. The mixture was then filtered, and the filtrate was extracted with ethyl acetate (2×20 mL). The combined organic phases were washed with brine (5 mL), dried ($MgSO_4$) and concentrated under reduced pressure. The colorless oil thus obtained was purified by flash chromatography on silica gel (petroleum ether/ethyl acetate=9/1) to afford the aldehyde as a yellow solid (1.14 g, 75%). Mp 102-104 °C; 1H NMR (250 MHz, CDC13): □ 10.17 (s, 1H), 8.00 (d, J=3.00 Hz, 1Har), 7.82 (d, J=3.00 Hz, 1Har), 3.90 (s, 3H), 2.44 (s, 3H), 2.34 (s, 3H).

2,5-Diacetoxyisophthalic acid monomethyl ester (KI-$2Ac_2$). A solution of sodium hydrogen phosphate (1.35 g, 9.81 mmol, 2.5 eq.) in water (3.5 mL) was added dropwise to a solution of methyl 2,5-diacetoxy-3-formylbenzoate (1.10 g, 3.93 mmol) in DMSO (14 mL). The mixture was then cooled to 0 °C and a solution of sodium chlorite (1.06 g, 9.34 mmol, 2.4 eq.) in water (3.5 mL) was slowly added. After 72 h of stirring at r.t., the mixture was quenched with aqueous saturated $NaHCO_3$ (10 mL) and extracted with ethyl acetate (2×30 mL). The aqueous phase was then acidified with 1M HCl to pH=1 and extracted ethyl acetate (2×30 mL). The combined organic phases were washed with brine (5 mL), dried ($MgSO_4$) and concentrated under reduced pressure. The orange oil obtained was used in the next step without any purification.

Synthesis of Monoamides

Scheme 10. Synthesis of Monoamides IIa

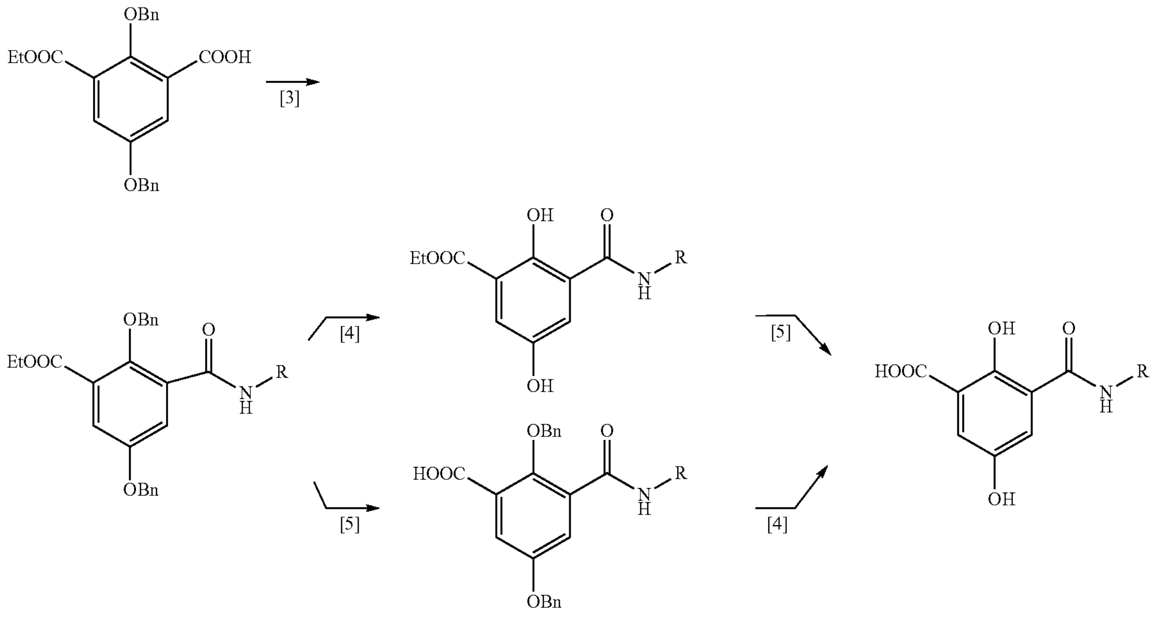

Protocols: Synthesis of Monoamides
Amide Coupling and Deprotection Procedures
See General Procedures from KI-1 and KI-6 steps [3], [4], [5], same procedures from KI-2, KI-2$Ac_2$ and KI-7
EXAMPLES
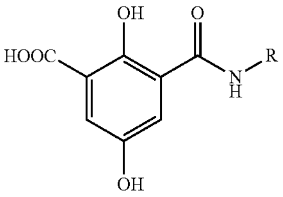
IIa-001a
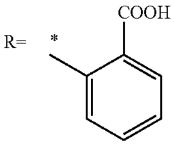
IIa-001aTz
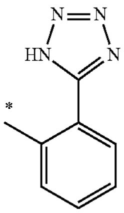
IIa-001c
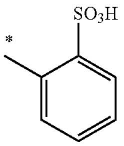
IIa-002a
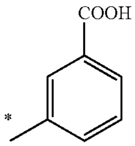
IIa-003a
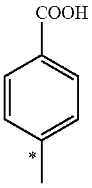
IIa-004a
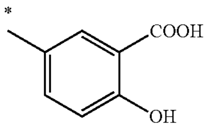
IIa-006a
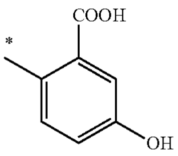
-continued
IIa-011a
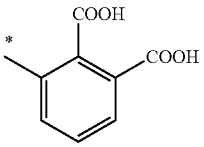
IIa-012a
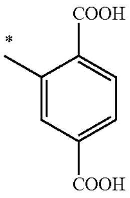
IIa-013a
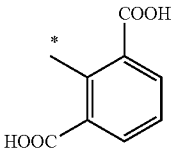
IIa-014a
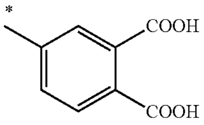
IIa-015a
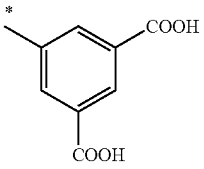
IIa-033a
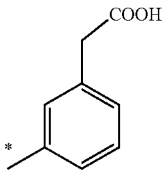
IIa-034a
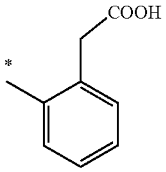
IIa-035a
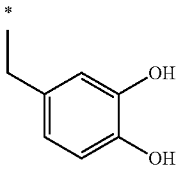
II-053a
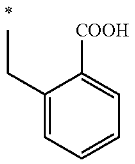

For conditions and yields: See Table 2 (FIGS. 5A-C)

33) 3-(2-Carboxyphenylaminocarbonyl)-2,5-dihydroxybenzoic acid, compound IIa-001a UPLC-MS (acidic method, 2 min): rt=0.86 min; m/z=318.0 $[M+H]^+$, peak area >92%

$^1$H NMR (400 MHz, DMSO-d6) δ 13.49 (s, 1H), 12.16 (s, 1H), 9.54 (s, 1H), 8.70 (dd, J=8.5, 1.2 Hz, 1H), 7.99 (dd, J=7.9, 1.7 Hz, 1H), 7.70-7.51 (m, 2H), 7.42 (d, J=3.3 Hz, 1H), 7.20 (td, J=7.6, 1.2 Hz, 1H).

HRMS: $[M+H]^+$, calc. for $C_{15}H_{12}NO_7$: 318.06083, found: 318.06082

Biodata: IIa-001a: FGF-1 IC50 [μM]=8.6; FGF-2 IC50 [μM]=11; VEGF-A1 IC50 [μM]=150; VEGFR-Phosphorylation inhibition IC50 [μM]=100; PMN ROS [inhibition at 0.3 μM [%]=30.5; PMN ROS inhibition IC50 [μM]=0.408; Neutrophil adhesion inhibition [%]=36.24

34) 3-(2-(1H-Tetrazol-5-yl)phenylaminocarbonyl)-2,5-dihydroxybenzoic acid, compound IIa-001aTz UPLC-MS (acidic method, 2 min): rt=0.71 min; m/z=342.1 $[M+H]^+$, peak area >99%

$^1$H NMR (400 MHz, DMSO-$d_6$) δ 11.40 (s, 1H), 9.49 (s, 1H), 8.51 (d, J=8.3 Hz, 1H), 7.87 (d, J=7.7 Hz, 1H), 7.72-7.51 (m, 2H), 7.51-7.26 (m, 2H) HRMS: $[M+H]^+$, calc. for $C_{15}H_{12}N_5O_5$: 342.08329, found: 342.08317

Biodata: IIa-001a-Tz: FGF-1 IC50 [μM]=N.D.; FGF-2 IC50 [μM]=9.8; VEGF-A1 IC50 [μM]=187; VEGFR-Phosphorylation inhibition IC50 [μM]=ND; PMN ROS [inhibition at 0.3 μM [%]=74.15; PMN ROS inhibition IC50 [μM]=N.D.; Neutrophil adhesion inhibition [%]=24.18 Ethyl ester UPLC-MS (acidic method, 4 min): rt=1.46 min; m/z=370.1 $[M+H]^+$, peak area >92%

$^1$H NMR (400 MHz, DMSO-$d_6$) δ 11.51 (s, 1H), 11.37 (s, 1H), 9.63 (s, 1H), 8.47 (d, J=8.3 Hz, 1H), 7.92 (dd, J=7.8, 1.6 Hz, 1H), 7.66-7.57 (m, 2H), 7.43 (d, J=3.2 Hz, 1H), 7.38 (td, J=7.6, 1.2 Hz, 1H), 4.40 (q, J=7.1 Hz, 2H), 1.36 (t, J=7.1 Hz, 3H),

HRMS: $[M+H]^+$, calc. for $C_{17}H_{16}N_5O_5$: 370.11460, found: 370.11444

Biodata: IIa-001aTz-E1: FGF-1 IC50 [μM]=200; FGF-2 IC50 [μM]=42; VEGF-A1 IC50 [μM]=200; VEGFR-Phosphorylation inhibition IC50 [μM]=100; PMN ROS [inhibition at 0.3 μM [%]=68.86; PMN ROS inhibition IC50 [μM]=N.D.; Neutrophil adhesion inhibition [%]=81.94

35) 2,5-Dihydroxy-3-(2-sulfophenylaminocarbonyl) benzoic acid, compound IIa-001c UPLC-MS (acidic method, 2 min): rt=0.63 min; m/z=354.0 $[M+H]^+$, peak area >80%

$^1$H NMR (400 MHz, DMSO-$d_6$) δ 11.18 (s, 1H), 9.48 (s, 1H), 8.34-8.27 (m, 1H), 7.72 (dd, J=7.7, 1.7 Hz, 1H), 7.52 (d, J=3.2 Hz, 1H), 7.41-7.31 (m, 2H), 7.08 (td, J=7.5, 1.2 Hz, 1H).

HRMS: $[M+H]^+$, calc. for $C_{14}H_{12}NO_8S$: 354.02781, found: 354.02781

Biodata: IIa-001c: FGF-1 IC50 [μM]=N.D.; FGF-2 IC50 [μM]=71; VEGF-A1 IC50 [μM]=283; VEGFR-Phosphorylation inhibition IC50 [μM]=ND; PMN ROS [inhibition at 0.3 μM [%]=72.62; PMN ROS inhibition IC50 [μM]=N.D.; Neutrophil adhesion inhibition [%]=43.53

36) 3-(3-Carboxyphenylaminocarbonyl)-2,5-dihydroxybenzoic acid, compound IIa-002a $^1$H NMR (250 MHz, $CD_3OD$): δ 8.37 (t, 1H), 7.93 (br d, 1H), 7.81 (br d, 1), 7.76 (d, 1H), 7.52 (d, 1H), 7.48 (t, 1H).

HRMS (ESI-): $[M-H]^-$, calc. for $C_{15}H_{10}NO_7$: 316.0461, found: 318.0463

Biodata: IIa-002a: FGF-1 IC50 [μM]=19; FGF-2 IC50 [μM]=131; VEGF-A1 IC50 [μM]=150; VEGFR-Phosphorylation inhibition IC50 [μM]=ND; PMN ROS [inhibition at 0.3 μM [%]=43.3; PMN ROS inhibition IC50 [μM]=0.299; Neutrophil adhesion inhibition [%]=17.39

37) 3-(4-Carboxyphenylaminocarbonyl)-2,5-dihydroxybenzoic acid)amide, compound IIa-003a $^1$H NMR (250 MHz, $CD_3OD$): □ 8.06 (BB' of AA'BB', 2H), 7.85 (AA' of AA'BB', 2H), 7.75 (d, 1H), 7.58 (d, 1H)

HRMS (ESI-): calcd for $C_{15}H_{10}NO_7$ $[M-H]^-$: 316.0461; found 316.0462

Biodata: IIa-003a: FGF-1 IC50 [μM]=22; FGF-2 IC50 [μM]=13; VEGF-A1 IC50 [μM]=150; VEGFR-Phosphorylation inhibition IC50 [μM]=2.5; PMN ROS [inhibition at 0.3 μM [%]=59.3; PMN ROS inhibition IC50 [μM]=N.D.; Neutrophil adhesion inhibition [%]=35.27

38) 3-(3-Carboxy-4-hydroxyphenylaminocarbonyl)-2,5-dihydroxybenzoic acid, compound IIa-004a UPLC-MS (acidic method, 2 min): rt=0.76 min; m/z=334.0 $[M+H]^+$, peak area >99%

$^1$H NMR (400 MHz, DMSO-$d_6$) δ 14.02 (brs, 1H), 11.07 (brs, 1H), 10.32 (s, 1H), 9.47 (brs, 1H), 8.27 (d, J=2.7 Hz, 1H), 7.76 (dd, J=8.9, 2.7 Hz, 1H), 7.42 (d, J=3.2 Hz, 1H), 7.36 (d, J=3.2 Hz, 1H), 6.96 (d, J=8.9 Hz, 1H).

HRMS: $[M+H]^+$, calc. for $C_{15}H_{12}NO_8$: 334.05574, found: 334.05571

Biodata: IIa-004a: FGF-1 IC50 [μM]=47; FGF-2 IC50 [μM]=33; VEGF-A1 IC50 [μM]=200; VEGFR-Phosphorylation inhibition IC50 [μM]=100; PMN ROS [inhibition at 0.3 μM [%]=63.5; PMN ROS inhibition IC50 [μM]=1.002; Neutrophil adhesion inhibition [%]=36

39) 3-(2-Carboxy-4-hydroxyphenylaminocarbonyl)-2,5-dihydroxybenzoic acid, compound IIa-006a UPLC-MS (acidic method, 2 min): rt=0.65 min; m/z=334.0 $[M+H]^+$, peak area >99%

$^1$H NMR (400 MHz, DMSO-$d_6$) δ 13.36 (s, 1H), 11.83 (s, 1H), 9.62 (s, 1H), 9.47 (s, 1H), 8.47 (d, J=9.1 Hz, 1H), 7.64 (d, J=3.3 Hz, 1H), 7.41 (d, J=3.2 Hz, 1H), 7.37 (d, J=3.0 Hz, 1H), 7.03 (dd, J=9.1, 3.0 Hz, 1H).

HRMS: $[M+H]^+$, calc. for $C_{15}H_{12}NO_8$: 334.05574, found: 334.05548

Biodata: IIa-006a: FGF-1 IC50 [μM]=N.D.; FGF-2 IC50 [μM]=43; VEGF-A1 IC50 [μM]=121; VEGFR-Phosphorylation inhibition IC50 [μM]=2.9; PMN ROS [inhibition at 0.3 μM [%]=84.29; PMN ROS inhibition IC50 [μM]=N.D.; Neutrophil adhesion inhibition [%]=20.29

40) 3-(3-Carboxy-2,5-dihydroxybenzamido)phthalic acid, compound IIa-011a

UPLC-MS (acidic method, 2 min): rt=0.72 min; m/z=360.1 $[M-H]^-$, peak area >77%

$^1$H NMR (400 MHz, DMSO-$d_6$) δ 10.83 (s, 1H), 9.55 (s, 1H), 8.43 (dd, J=7.9, 1.5 Hz, 1H), 7.73 (d, J=3.3 Hz, 1H), 7.63-7.53 (m, 2H), 7.46 (d, J=3.3 Hz, 1H),

HRMS: $[M+H]^+$, calc. for $C_{16}H_{12}NO_9$: 362.05066, found: 362.05045,

Biodata: IIa-011a: FGF-1 IC50 [μM]=141; FGF-2 IC50 [μM]=123; VEGF-A1 IC50 [μM]=200; VEGFR-Phosphorylation inhibition IC50 [μM]=100; PMN ROS [inhibition at 0.3 μM [%]=58.1; PMN ROS inhibition IC50 [μM]=1.18; Neutrophil adhesion inhibition [%]=26

41) 2-(3-Carboxy-2,5-dihydroxybenzamido)terephthalic acid, compound IIa-012a

UPLC-MS (acidic method, 2 min): rt=0.73 min; m/z=362.0 [M+H], peak area >97%

$^1$H NMR (DMSO-$d_6$) δ: 13.81 (s, 1H), 13.34 (s, 1H), 12.23 (s, 1H), 9.50 (s, 1H), 9.30 (d, J=1.6 Hz, 1H), 8.06 (d, J=8.2 Hz, 1H), 7.71 (dd, J=8.2, 1.7 Hz, 1H), 7.64 (d, J=3.3 Hz, 1H), 7.43 (d, J=3.3 Hz, 1H),

HRMS: $[M+H]^+$, calc. for $C_{16}H_{12}NO_9$: 362.05066, found: 362.05046,

Biodata: IIa-012a: FGF-1 IC50 [μM]=150; FGF-2 IC50 [μM]=150; VEGF-A1 IC50 [μM]=32; VEGFR-Phosphorylation inhibition IC50 [μM]=3.31; PMN ROS [inhibition at 0.3 μM [%]=44.8; PMN ROS inhibition IC50 [μM]=0.313; Neutrophil adhesion inhibition [%]=7.5

42) 2-(3-Carboxy-2,5-dihydroxybenzamido)isophthalic acid, compound IIa-013a

UPLC-MS (acidic method, 2 min): rt=1.68 min; m/z=362.0 $[M+H]^+$, peak area >96%

$^1$H NMR (400 MHz, DMSO-$d_6$) δ 13.12 (brs, 3H), 11.71 (s, 1H), 9.47 (s, 1H), 7.96 (s, 1H), 7.94 (s, 1H), 7.66 (d, J=3.3 Hz, 1H), 7.44 (d, J=3.3 Hz, 1H), 7.35 (t, J=7.8 Hz, 1H).

HRMS: $[M+H]^+$, calc. for $C_{16}H_{12}NO_9$: 362.05066, found: 362.05047

Biodata: IIa-013a: FGF-1 IC50 [μM]=137; FGF-2 IC50 [μM]=12; VEGF-A1 IC50 [μM]=34; VEGFR-Phosphorylation inhibition IC50 [μM]=100; PMN ROS [inhibition at 0.3 μM [%]=57.68; PMN ROS inhibition IC50 [μM]=2.54; Neutrophil adhesion inhibition [%]=15.75

43) 4-(3-Carboxy-2,5-dihydroxybenzamido)phthalic acid, compound IIa-014a

UPLC-MS (acidic method, 2 min): rt=0.63 min; m/z=362.1 $[M+H]^+$, peak area >88%

$^1$H NMR (400 MHz, DMSO-d6) δ 10.80 (s, 1H), 9.45 (s, 1H), 8.01 (d, J=2.2 Hz, 1H), 7.86 (dd, J=8.5, 2.2 Hz, 1H), 7.74 (d, J=8.5 Hz, 1H), 7.45-7.33 (m, 2H),

HRMS: $[M+H]^+$, calc. for $C_{16}H_{12}NO_9$: 362.05066, found: 362.05048

Biodata: IIa-014a: FGF-1 IC50 [μM]=40; FGF-2 IC50 [μM]=61; VEGF-A1 IC50 [μM]=91; VEGFR-Phosphorylation inhibition IC50 [μM]=17.6; PMN ROS [inhibition at 0.3 μM [%]=73.94; PMN ROS inhibition IC50 [μM]=N.D.; Neutrophil adhesion inhibition [%]=21.5

44) 5-(3-Carboxy-2,5-dihydroxybenzamido)isophthalic acid, compound IIa-015a $^1$H NMR (250 MHz, $CD_3OD$): δ 8.60 (d, J=1.5 Hz, 2H), 8.44 (t, J=1.5 Hz, 1H), 7.75 (d, J=3.2 Hz, 1H), 7.56 (d, J=3.2 Hz, 1)

HRMS ($ESI^+$): m z calcd for $C_{16}H_{12}NO_9$ $[M+H]^+$: 362.0507; found 362.0505 [LM-163]

Biodata: IIa-015a: FGF-1 IC50 [μM]=N.D.; FGF-2 IC50 [μM]=125; VEGF-A1 IC50 [μM]=N.D.; VEGFR-Phosphorylation inhibition IC50 [μM]=ND; PMN ROS [inhibition at 0.3 μM [%]=N.D.; PMN ROS inhibition IC50 [μM]=N.D.; Neutrophil adhesion inhibition [%]=N.D.

45) (3-(3-(Carboxymethyl)phenylaminocarbonyl)-2,5-dihydroxybenzoic acid, compound IIa-033a UPLC-MS (acidic method, 2 min): rt=0.78 min; m/z=330.1 $[M-H]^-$, peak area >98%

$^1$H NMR (400 MHz, DMSO-$d_6$) δ 10.40 (s, 1H), 9.45 (s, 1H), 7.66 (t, J=1.9 Hz, 1H), 7.63-7.57 (m, 1H), 7.45 (d, J=3.3 Hz, 1H), 7.38 (d, J=3.2 Hz, 1H), 7.29 (t, J=7.8 Hz, 1H), 7.05-6.95 (m, 1H), 3.56 (s, 2H).

HRMS: $[M+H]^+$, calc. for $C_{16}H_{14}NO_7$: 332.07648, found: 332.07644,

Biodata: IIa-033a: FGF-1 IC50 [μM]=35; FGF-2 IC50 [μM]=32; VEGF-A1 IC50 [μM]=200; VEGFR-Phosphorylation inhibition IC50 [μM]=4.9; PMN ROS [inhibition at 0.3 μM [%]=50.64; PMN ROS inhibition IC50 [μM]=0.914; Neutrophil adhesion inhibition [%]=11.75

46) 3-(2-(Carboxymethyl)phenylaminocarbonyl)-2,5-dihydroxybenzoic acid, compound IIa-034a UPLC-MS (acidic method, 2 min): rt=0.74 min; m/z=332.0 $[M+H]^+$, peak area >95%

$^1$H NMR (400 MHz, DMSO-$d_6$) δ 12.48 (s, 1H), 10.65 (s, 1H), 9.30 (s, 1H), 7.97 (d, J=8.3 Hz, 1H), 7.64 (d, J=3.2 Hz, 1H), 7.40 (d, J=3.3 Hz, 1H), 7.33-7.26 (m, 2H), 7.13 (td, J=7.5, 1.3 Hz, 1H), 3.70 (s, 2H).

HRMS: $[M+H]^+$, calc. for $C_{16}H_{14}NO_7$: 332.07648, found: 332.07653

Biodata: IIa-034a: FGF-1 IC50 [μM]=22; FGF-2 IC50 [μM]=5.7; VEGF-A1 IC50 [μM]=86; VEGFR-Phosphorylation inhibition IC50 [μM]=100; PMN ROS [inhibition at 0.3 μM [%]=69.2; PMN ROS inhibition IC50 [μM]=N.D.; Neutrophil adhesion inhibition [%]=26.58 Diethyl ester UPLC-MS (acidic method, 2 min): rt=1.12 min; m/z=388.1 $[M+H]^+$, peak area >99%

$^1$H NMR (400 MHz, DMSO-$d_6$) δ 11.81 (s, 1H), 9.58 (s, 1H), 7.77 (t, J=8.5 Hz, 1H), 7.65 (d, J=3.4 Hz, 1H), 7.42 (d, J=3.4 Hz, 1H), 7.36-7.31 (m, 2H), 7.20 (t, J=7.4 Hz, 1H), 4.39 (q, J=7.1 Hz, 2H), 4.05 (q, J=7.1 Hz, 2H), 3.77 (s, 2H), 1.36 (t, J=7.1 Hz, 3H), 1.13 (t, J=7.1 Hz, 3H).

HRMS: $[M+H]^+$, calc. for $C_{20}H_{22}NO_7$: 388.13907, found: 388.13887

Biodata: IIa-034a-E2: FGF-1 IC50 [μM]=N.D.; FGF-2 IC50 [μM]=164; VEGF-A1 IC50 [μM]=200; VEGFR-Phosphorylation inhibition IC50 [μM]=ND; PMN ROS [inhibition at 0.3 μM [%]=68.73; PMN ROS inhibition IC50 [μM]=N.D.; Neutrophil adhesion inhibition [%]=11.86

47) 3-(3,4-Dihydroxyphenylmethylaminocarbonyl)-2,5-dihydroxybenzoic acid, compound IIa-035a UPLC-MS (acidic method, 2 min): rt=0.69 min; m/z=318.0 $[M-H]^-$, peak area >99%

$^1$H NMR (400 MHz, DMSO-$d_6$) δ 9.38 (s, 1H), 8.84 (s, 1H), 8.75 (s, 1H), 7.55 (d, J=3.2 Hz, 1H), 7.34 (d, J=3.2 Hz, 1H), 6.74 (d, J=2.1 Hz, 1H), 6.67 (d, J=8.0 Hz, 1H), 6.58 (dd, J=8.1, 2.1 Hz, 1H), 4.34 (d, J=5.7 Hz, 2H).

HRMS: $[M+H]^+$, calc. for $C_{15}H_{14}NO_7$: 320.07647, found: 320.07625.

Biodata: IIa-035a: FGF-1 IC50 [μM]=16; FGF-2 IC50 [μM]=61; VEGF-A1 IC50 [μM]=45; VEGFR-Phosphorylation inhibition IC50 [μM]=0.52; PMN ROS [inhibition at 0.3 μM [%]=76.99; PMN ROS inhibition IC50 [μM]=1; Neutrophil adhesion inhibition [%]=36.67

48) 3-(2-Carboxyphenylmethylaminocarbonyl)-2,5-dihydroxybenzoic acid, compound IIa-053a UPLC-MS (acidic method, 4 min): rt=1.08 min; m/z=332.0 $[M+H]^+$, peak area >97%

$^1H$ NMR (DMSO-$d_6$) δ: 13.13 (brs, 1H), 12.73 (brs, 1H), 9.40 (s, 1H), 9.05 (s, 1H), 7.91 (dd, J=7.8, 1.4 Hz, 1H), 7.65-7.29 (m, 5H), 4.80 (d, J=6.1 Hz, 2H).

HRMS: $[M+H]^+$, calc. for $C_{16}H_{14}NO_7$: 332.07648, found: 332.07626

Biodata: IIa-053a: FGF-1 IC50 [μM]=84; FGF-2 IC50 [μM]=18; VEGF-A1 IC50 [μM]=37; VEGFR-Phosphorylation inhibition IC50 [μM]=0.27; PMN ROS [inhibition at 0.3 μM [%]=63.13; PMN ROS inhibition IC50 [μM]=0.62; Neutrophil adhesion inhibition [%]=20; Whole Blood: GM-CSF IC50 [μM]=>100; IFNγ IC50 [μM]=1.04; IL-1β IC50

[μM]=>100; IL-2 IC50 [μM]=1.67; IL-4 IC50 [μM]=>100; IL-5 IC50 [μM]=>100; IL-6 IC50 [μM]=2.2; IL-9 IC50 [μM]=1.41; IL-10 IC50 [μM]=>100; IL-12p70 IC50 [μM]=0.27; IL-13 IC50 [μM]=29.9; IL-17A IC50 [μM]=>100; IL-17F IC50 [μM]=28.8; IL-18 IC50 [μM]=>100; IL-21 IC50 [μM]=>100; IL-33 IC50 [μM]=12.1; TGFβ IC50 [μM]=>100; TNF c IC50 [μM]=0.02; TNF β IC50 [μM]=91.5.

Example 1.6. Molecules of type IIb: Diamides from diamines, 1 example

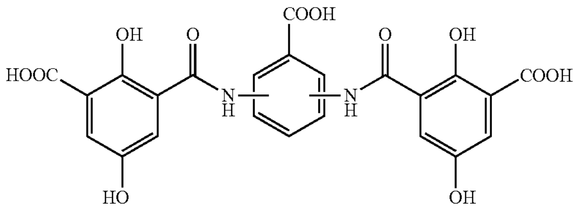

Scheme 11. Synthesis of Diamides of type IIb

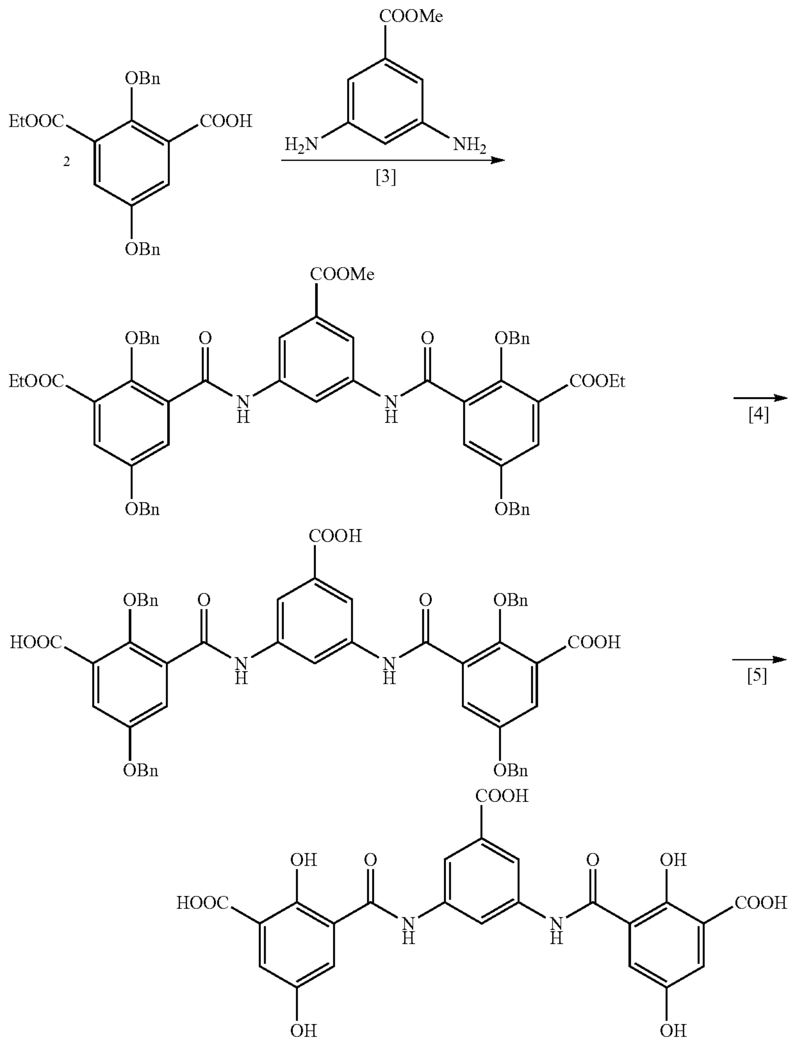

Procedure: see general procedure from KI-1 [3], [4], [5]

For example:

IIb-010a

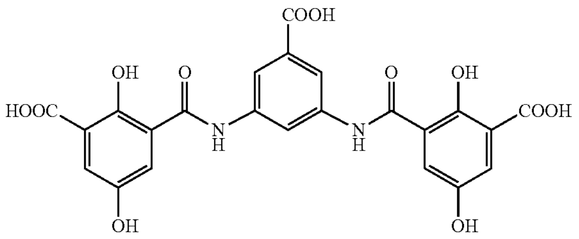

For conditions and yields: See Table 2 (FIGS. 5A-C)

49) 3,5-Bis(2,5-dihydroxy-3-carboxybenzoylamino)benzoic acid, compound IIb-010a:

UPLC-MS (acidic method, 4 min): rt=0.98 min; m/z=511.1 $[M-H]^-$, peak area >93%

$^1H$ NMR (400 MHz, DMSO-$d_6$) δ 10.81 (s, 2H), 10.65 (s, 2H), 8.38 (m, 1H), 8.12 (d, J=2.0 Hz, 2H), 7.39 (d, J=2.3 Hz, 4H).

HRMS: $[M+H]^+$, calc. for $C_{23}H_{17}N_2O_2$: 513.07760, found: 513.07774

Biodata: IIb-010a: FGF-1 IC50 [μM]=200; FGF-2 IC50 [μM]=102; VEGF-A1 IC50 [μM]=28; VEGFR-Phosphorylation inhibition IC50 [μM]=ND; PMN ROS [inhibition at 0.3 μM [%]=81.87; PMN ROS inhibition IC50 [μM]=N.D.; Neutrophil adhesion inhibition [%]=59.84

Example 1.7. Molecules of type IIc: Diamides from diacids, 2 examples

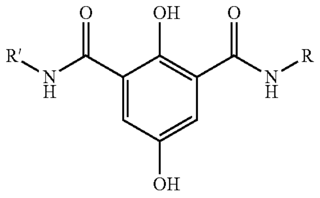

Scheme 12. Synthesis of Amides of type IIc with R═R'

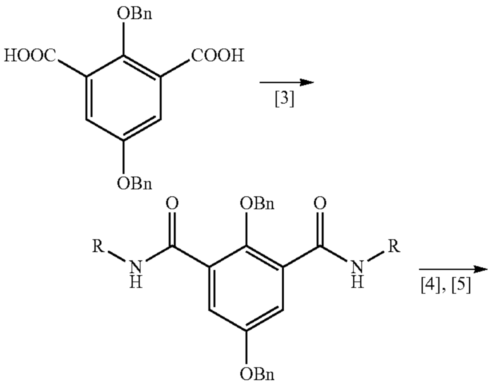

-continued

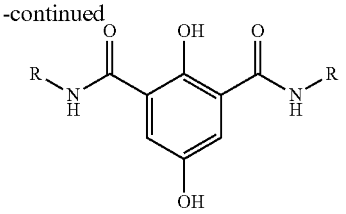

Procedure: see general procedure from KI-6 [3], [4], [5]

For examples

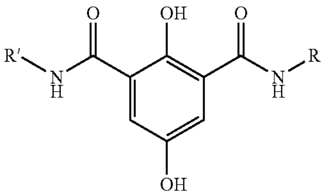

R, R' =

IIc-007a

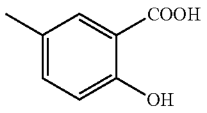

IIc-009a

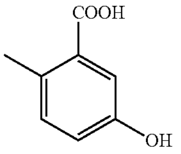

For conditions and yields: See Table 2 (FIGS. 5A-C)

50) 5-(3-(3-Carboxy-4-hydroxyphenylaminocarbonyl)-2,5-dihydroxybenzamido)-2-hydroxybenzoic acid, compound IIc-007a UPLC-MS (acidic method, 4 min): rt=1.20 min; m/z=469.1 $[M+H]^+$, peak area >91%

$^1H$ NMR (400 MHz, DMSO-d6) δ 10.41 (s, 2H), 9.51 (s, 1H), 8.22 (d, J=2.7 Hz, 2H), 7.79 (dd, J=9.0, 2.7 Hz, 2H), 7.58 (s, 2H), 6.98 (d, J=8.9 Hz, 2H), $^{13}C$ NMR (100 MHz, DMSO-$d_6$) δ 172.1, 166.1, 158.3, 152.0, 149.4, 130.2, 129.5 (CH), 122.8 (CH), 120.3, 119.8 (CH), 117.7 (CH). 113.0.

HRMS: $[M+H]^+$, calc. for $C_{22}H_{17}N_2O_{10}$: 469.08777, found: 469.08803

Biodata: IIc-007a: FGF-1 IC50 [μM]=11; FGF-2 IC50 [μM]=91; VEGF-A1 IC50 [μM]=8.2; VEGFR-Phosphorylation inhibition IC50 [μM]=0.44; PMN ROS [inhibition at 0.3 μM [%]=93.04; PMN ROS inhibition IC50 [μM]=N.D.; Neutrophil adhesion inhibition [%]=64.61; Whole Blood: GM-CSF IC50 [μM]=26; IFNγ IC50 [μM]=0.11; IL-1β IC50 [μM]=>100; IL-2 IC50 [μM]=12.8; IL-4 IC50 [μM]=>100; IL-5 IC50 [μM]=>100; IL-6 IC50 [μM]=0.05; IL-9 IC50 [μM]=2.14; IL-10 IC50 [μM]=17.9; IL-12p70 IC50 [μM]=3.37; IL-13 IC50 [μM]=0.25; IL-17A IC50 [μM]=0.01; IL-17F IC50 [μM]=0.26; IL-18 IC50 [μM]=>100; IL-21 IC50 [μM]=9.41; IL-33 IC50 [μM]=0.18; TGFβ IC50 [μM]= >100; TNF c IC50 [μM]=0.03; TNF β IC50 [μM]= 0.29

Alternative Large Scale Synthesis of IIc-007a 2,5-Dibenzyloxyisophthalic Acid (KI-7)

To a 5 L jacketed vessel was charged 2,5-dibenzyloxy-isophthalaldehyde (Scheme 9b)(300 g, 866 mmol), resorcinol (286 g, 2.60 mol), $KH_2PO_4$ (354 g, 2.60 mol), acetone (1.5 L) and water (516 ml). The slurry was stirred at 15-25 °C. A solution of 80% $NaClO_2$ (294 g, 2.60 mol) in water (1 L) was charged at 15-30 °C over 90 mins (exotherm). After the addition was complete, the reaction was stirred at 15-25 °C for 1 hr. A solution of 85% $H_3PO_4$ (85 ml, 1.24 mol) in water (1175 ml) [~1M] was charged over 10 mins at T<30 °C (exotherm) affording a precipitate. The batch was cooled to 0-5 °C and filtered. The solids were washed with water (3×1.2 L) and oven dried (50 °C) to afford 325.6 g diacid KI-7. HPLC: 98.9%; NMR >95%. Corrected yield (90.6%).

5-(3-(3-Methoxycarbonyl-4-hydroxyphenylaminocarbonyl)-2,5-dibenzyloxybenzamido)-2-hydroxybenzoic acid methyl ester. To a 2 L jacketed vessel was charged diacid KI-7 (80 g, 211 mmol), HBTU (2-(1H-benzotriazol-1-yl)-1,1,3,3-tetramethyluronium hexafluorophosphate) (176.8 g, 466 mmol) and THF (560 ml). The batch was stirred at 15-25 °C and N-methylimidazole (50.6 ml, 635 mmol) was charged. After 30 min, methyl 5-amino-2-hydroxybenzoate (77.8 g, 466 mmol) was charged and the reaction stirred at 25 °C overnight. Water (1.2 L) was charged and the batch stirred at 20 °C for 30 min. The batch was filtered, washed with water (2×480 ml) then MeCN (320 ml). The resulting solid (236 g) was charged back to the vessel along with MeCN (800 ml). The slurry was heated to 50 °C for 40 min then cooled to 20 °C. The batch was filtered and washed with MeCN (320 ml). NMR analysis of the solid (156 g) indicated no TMU, HOBt, NMI or HBTU. The material was dried at 50 °C overnight to afford 125 g diamide. HPLC: 98.2%. NMR: >97%. Yield: 88%.

5-(3-(3-Carboxy-4-hydroxyphenylaminocarbonyl)-2,5-dibenzyloxybenzamido)-2-hydroxybenzoic acid. To a 2 L jacketed vessel was charged the previous diamide (110 g, 163 mmol), THF (550 ml) and water (1100 ml). The batch was stirred at 15-25 °C and 85% KOH (32.2 g, 488 mmol) charged (minor exotherm). The solution was heated to 50 °C for 4 h then cooled to 20 °C and stirred out overnight. 6M aq. AcOH (550 ml, 3.3 mol) was then charged over 30 min at 15-25 °C. After the addition was complete, the batch was stirred for 30 mins and then filtered. The solids were washed with water (3×550 ml) then oven dried at 50 °C. This afforded 102 g free diacid. HPLC: 98.9% (0.3% monoamide, 0.19% mono-acid). NMR: >97%. Yield: 97%.

5-(3-(3-Carboxy-4-hydroxyphenylaminocarbonyl)-2,5-dihydroxybenzamido)-2-hydroxybenzoic acid IIc-007a. To a 2 L jacketed vessel under $N_2$ was charged 10% Pd/C (10 g, 50% wet, type 87 L) followed by the previous diacid (100 g, 154 mmol), AcOH (5 ml, 88 mmol) and THF (1200 ml). The batch was stirred then sparged with $H_2$ and heated to 40 °C for 2 hr. The batch was sparged with $N_2$ and then filtered (GF/F). The vessel was rinsed with THF (300 ml) and the rinse used to wash the catalyst on the filter. The filtrate was charged to the vessel and the volume adjusted to 2 L with THF (400 ml). The solution was warmed to 30 °C, SPM32 (10 g) charged, and the batch stirred at 30 °C overnight. The SPM32 was filtered off and washed with THF (200 ml). The solvent was removed in vacuo to afford a light yellow solid (110 g). NMR analysis indicated 28% THF. The material was slurried in EtOH (1 L) at 20 °C for 2 hr and then filtered off. The solids were washed with EtOH (400 ml) and oven dried at 60 °C overnight. NMR indicated 8.7% EtOH, no THF. The material was further dried at 80 °C for 4 nights to afford 66.5 g IIc-007a as an off-white solid in a 92% yield. HPLC: 99.5% (0.31% monoamide). NMR: 4.6% EtOH, no THF. Pd by ICP-OES: <2 ppm.

IIc-007a-THF solvate: Concentration of the THF filtrate gives a yellow solid, typically containing 25-30% THF by NMR, which could not be removed through drying, indicating a non-stoichiometric solvate. A small sample of the THF solvate (1.45 g) was heated to 50 °C in THF (10 ml) for 1 hr, cooled to RT and isolated, washing with 3 ml THF. This afforded 1.13 g IIc-007a-THF. NMR: 27% THF. HPLC: 99.6% (0.1% monoamide). The isolation of the THF solvate by filtration leads to an increase in purity and an effective purge of the major impurity (monoamide, IIa-004a) from 0.7% to 0.1%. Recovery yield: 78%. THF solvate solubility in THF calculated as –25 mg/ml at 20 °C.

Desolvation trials were performed on the material in acetone, EtOH and EtOAc. Each batch was heated for 1 hr at 50 °C in 20 vols of solvent, then isolated at RT and oven dried (60 °C.). Ethanol was chosen as the desolvation solvent due to the low level of EtOH incorporated in the product after drying and excellent purge of THF from the system. The desolvation step was performed on 12.1 g product (25% THF). To the material was charged EtOH (20 vols) and the batch was stirred at RT overnight. A sample was filtered off and this indicated successful desolvation at RT. Overall yield: 8.67 g. HPLC: 99.4%. NMR: >97% (0.8% EtOH). XRPD indicated a high degree of crystallinity of the isolated product. The product IIc-007a also forms a DMSO solvates (DMSO:product in 3:2 ratio).

51) 2-(3-(2-Carboxy-4-hydroxyphenylaminocarbonyl)-2,5-dihydroxybenzamido)-5-hydroxylbenzoic acid, compound IIc-009a UPLC-MS (acidic method, 2 min): rt=0.79 min; m/z=469.1 [M+H]$^+$, peak area >95%

$^1$H NMR (400 MHz, DMF-d7) δ 10.11 (s, 1H), 10.01 (s, 2H), 8.71 (d, J=9.0 Hz, 2H), 8.01 (s, 2H), 7.82 (d, J=3.0 Hz, 2H), 7.46 (d, J=8.9 Hz, 2H).

HRMS: [M+H]$^+$, calc. for $C_{22}H_{17}N_2O_{10}$: 469.08777, found: 469.08714

Biodata: IIc-009a: FGF-1 IC50 [μM]=30; FGF-2 IC50 [μM]=N.D.; VEGF-A1 IC50 [μM]=182; VEGFR-Phosphorylation inhibition IC50 [μM]=1.7; PMN ROS [inhibition at 0.3 μM [%]=75.31; PMN ROS inhibition IC50 [μM]=N.D.; Neutrophil adhesion inhibition [%]=53.15; Whole Blood: GM-CSF IC50 [μM]=>100; IFNγ IC50 [μM]=0.54; IL-1β IC50 [μM]=>100; IL-2 IC50 [μM]=19.6; IL-4 IC50 [μM]=>100; IL-5 IC50 [μM]=>100; IL-6 IC50 [μM]=0.27; IL-9 IC50 [μM]=18.9; IL-10 IC50 [μM]=11.31; IL-12p70 IC50 [μM]=>100; IL-13 IC50 [μM]=0.13; IL-17A IC50 [μM]=0.001; IL-17F IC50 [μM]=0.13; IL-18 IC50 [μM]=2.95; IL-21 IC50 [μM]=8.01; IL-33 IC50 [μM]=0.29; TGFβ IC50 [μM]=>100; TNF c IC50 [μM]=0.11; TNF β IC50 [μM]=6.94.

Example 1.8: Molecules of Type IIIa: Monoamides, 4 Examples

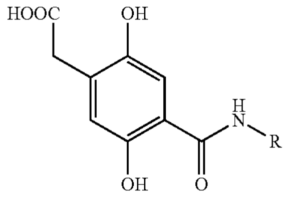

Synthesis of Precursors

Scheme 13. Synthetic Intermediates: KI-8 and KI-9 from KI-1

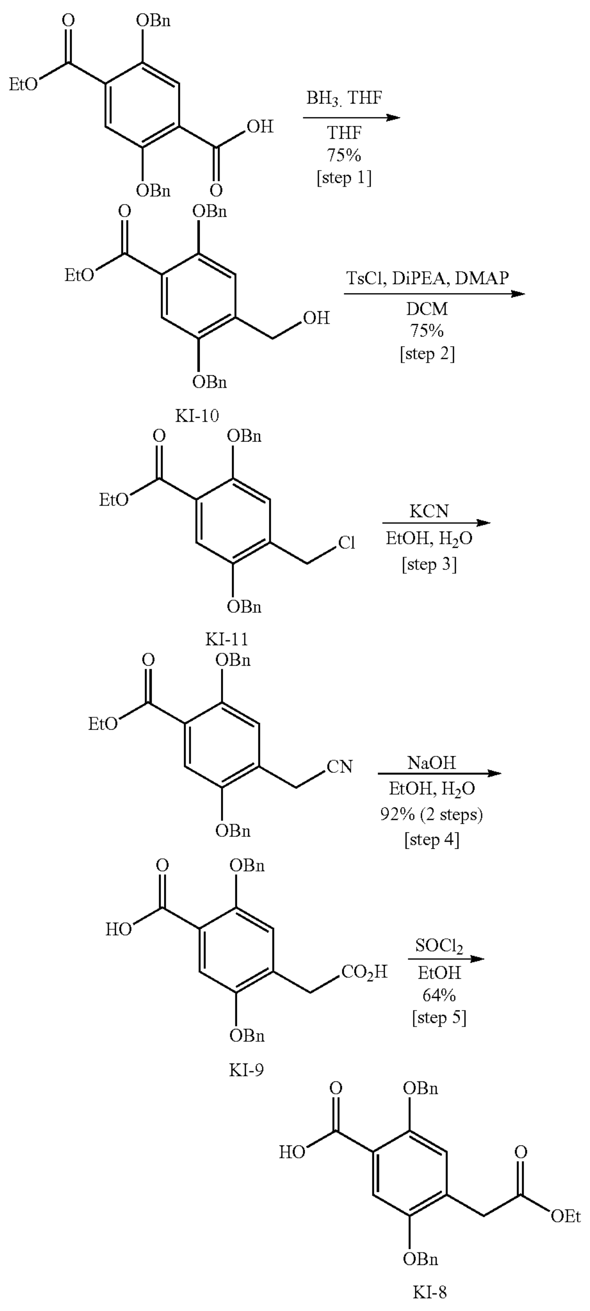

Synthetic Protocols

Intermediates KI-8 and KI-9 (by way of KI-10 and KI-11)

Ethyl 2,5-bis(benzyloxy)-4-(hydroxymethyl)benzoate (KI-10) [Step 1]: To a cooled solution at −20 °C of KI-1 (62.3 g, 153 mmol) in THF (700 mL) under positive flow of inert gas ($N_2$) was slowly added a pre-cooled solution of $BH_3$.THF (615.0 mL, 615 mmol) (at −10 °C). The addition was done in such a way that the internal temperature of the reaction never exceeded −15 °C. The reaction was slightly warmed, the internal temperature being not allowed to exceed −7 °C. The mixture was maintained at this temperature for 2.5 h. The reaction mixture was then poured into ice/water (8 L). The blurry white mixtures obtained were left to stir at room temp. for 2 h and the residual white suspension was filtered through a fritted funnel (Porosity 3). The white solid thus obtained was further dried into vacuum oven at 40 °C overnight, to afford ethyl 2,5-bis(benzyloxy)-4-(hydroxymethyl)benzoate (KI-10) (60.5 g, 97% yield) as a white solid.

UPLC-MS (acidic method, 2 min): rt=1.25 min; m/z=391.2 $[M-H]^-$, peak area >68%

$^1$H NMR (400 MHz, DMSO-$d_6$) δ 7.54-7.48 (m, 2H), 7.48-7.43 (m, 2H), 7.43-7.35 (m, 4H), 7.35-7.27 (m, 4H), 5.28 (t, J=5.4 Hz, 1H), 5.13 (s, 2H), 5.11 (s, 2H), 4.58 (d, J=5.4 Hz, 2H), 4.25 (q, J=7.1 Hz, 2H), 1.26 (t, J=7.1 Hz, 3H).

Alternatively intermediate KI-10 can be obtained from KI-1 by way of a mixed anhydride (treatment of KI-1 with isobutylchloroformate in THF in the presence of triethylamine) followed by reduction of the mixed anhydride with sodium borohydride in THF (yields 85-90%, 150 g-scale).

Ethyl 2,5-bis(benzyloxy)-4-(chloromethyl)benzoate (KI-11) [Step 2]: Tosyl chloride (17.0 g, 70 mmol) was added slowly to a cooled solution (ice bath) of KI-10 (25.0 g, 64 mmol), DIPEA (12.2 mL, 70 mmol) and DMAP (0.778 g, 6 mmol) in DCM (260 mL). The reaction mixture was stirred at 60 °C for 30 h, whereupon the reaction was judged complete. DCM (100 mL) was added and the organic layer was separated, washed with saturated aqueous sodium hydrogen carbonate (4×50 mL), water (2×50 mL) and brine (50 mL), dried over sodium sulphate and concentrated. The crude product was submitted to column chromatography (Hexanes/EtOAc 0-20%) to give ethyl 2,5-bis(benzyloxy)-4-(chloromethyl)benzoate (KI-11) (23.5 g, 75%).

UPLC-MS (acidic method, 2 min): rt=1.39 min; m/z=no ion, peak area >84%.

$^1$H NMR (400 MHz, DMSO-$d_6$) δ 7.54-7.44 (m, 4H), 7.43-7.36 (m, 6H), 7.36-7.28 (m, 2H), 5.18 (s, 2H), 5.13 (s, 2H), 4.76 (s, 2H), 4.26 (q, J=7.1 Hz, 2H), 1.25 (t, J=7.1 Hz, 3H).

Alternatively intermediate KI-11 can be obtained by treating KI-10 with thionyl chloride (1.14 equiv) in dichloromethane at −10 °C, then evaporation of the solvent and precipitation from heptane (yield 90%, 300 g-scale)

Ethyl 2,5-bis(benzyloxy)-4-(cyanomethyl)benzoate [Step 3]: A suspension of KI-11 (7.5 g, 18.2 mmol) in a mixture of EtOH (90 mL) and $H_2O$ (45 mL) was treated with potassium cyanide (1.8 g, 27.4 mmol). The reaction mixture was heated to 75 °C and stirred at this temperature for 16 h. The reaction mixture was diluted with water (500 mL) and extracted with EtOAc (2×200 mL), the combined organic phases were then washed with brine (200 mL), dried over sodium sulfate, filtered and concentrated in vacuo. The crude product was isolated as a mixture of ethyl 2,5-bis(benzyloxy)-4-(cyanomethyl)benzoate and 2,5-bis(benzyloxy)-4-(cyanomethyl)benzoic acid (7.1 g), the product was used in the next step without further purification.

UPLC-MS (acidic method, 2 min): rt=1.30 min; m/z=402.2 $[M+H]^+$, peak area >65% and rt=1.15 min; m/z=374.1 $[M+H]^+$, peak area >8%.

$^1$H NMR (400 MHz, DMSO-$d_6$) δ 7.56-7.27 (m, 12H), 5.19 (s, 2H), 5.14 (s, 2H), 4.26 (q, J=7.1 Hz, 2H), 3.95 (s, 2H), 1.25 (t, J=7.1 Hz, 3H).

2,5-Bis(benzyloxy)-4-(carboxymethyl)benzoic acid (KI-9) [Step 4]: To a suspension of ethyl 2,5-bis(benzyloxy)-4-(cyanomethyl)benzoate (7.1 g, 13.2 mmol) in EtOH (20 mL) was added a solution of sodium hydroxide (8.5 g, 212.5 mmol) in water (50 mL) and the reaction mixture was stirred under reflux for 18 h. The reaction mixture was diluted with water (100 mL) and the resulting solution was washed with EtOAc (2×100 mL), the thus obtained organic layer was extracted with water (100 mL) and all aqueous layers were gathered. Then the aqueous layer was acidified to pH~3 with a saturated aqueous solution of citric acid, the formed precipitate was filtered and dried under reduced pressure. The solid was further dried in the vac. oven at 40 °C overnight to give 2,5-bis(benzyloxy)-4-(carboxymethyl) benzoic acid (KI-9) (6.4 g, 92% yield) as a yellowish solid.

UPLC-MS (acidic method, 2 min): rt=1.07 min; m/z=393.2 $[M+H]^+$, peak area >74%.

$^1$H NMR (400 MHz, DMSO-d6) δ 12.46 (s, 2H), 7.55-7.27 (m, 11H), 7.19 (s, 1H), 5.11 (s, 2H), 5.09 (s, 2H), 3.61 (s, 2H).

2,5-Bis(benzyloxy)-4-(2-ethoxycarbonylmethyl)benzoic acid (KI-8) [Step 5]: KI-9 (5.5 g, 14.0 mmol) was suspended in EtOH (30 mL) and the suspension was treated with thionyl chloride (0.52 mL, 7.1 mmol) and the reaction mixture was stirred at room temperature for 24 h. Then, the reaction mixture was poured into a saturated solution of sodium bicarbonate (1 L), leading to a white suspension. The solid was isolated by filtration and further triturated with $Et_2O$ (2×20 mL). The solid was further dried in the vac. oven overnight to give 2,5-bis(benzyloxy)-4-(2-ethoxycarbonyl-methyl)benzoic acid (KI-8) (4.2 g, 64%) as a white solid.

UPLC-MS (acidic method, 2 min): rt=1.23 min; m/z=419.3 $[M-H]^-$, peak area >79%.

$^1$H NMR (400 MHz, DMSO-$d_6$) δ 12.68 (brs, 1H), 7.58-7.27 (m, 11H), 7.19 (s, 1H), 5.11 (s, 2H), 5.08 (s, 2H), 4.01 (q, J=7.1 Hz, 2H), 3.66 (s, 2H), 1.11 (t, J=7.1 Hz, 3H).

Synthesis of Monoamides

Synthetic Protocols

Amide Coupling and Deprotection Procedures:

See General Procedures from KI-1 and KI-6 steps [3], [4], [5]

EXAMPLES

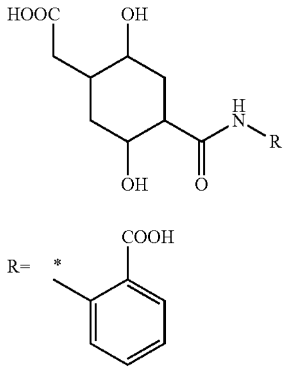

IIIa-001a

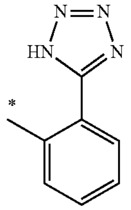

IIIa-001aTz

Scheme 14. Synthesis of Monoamides IIIa

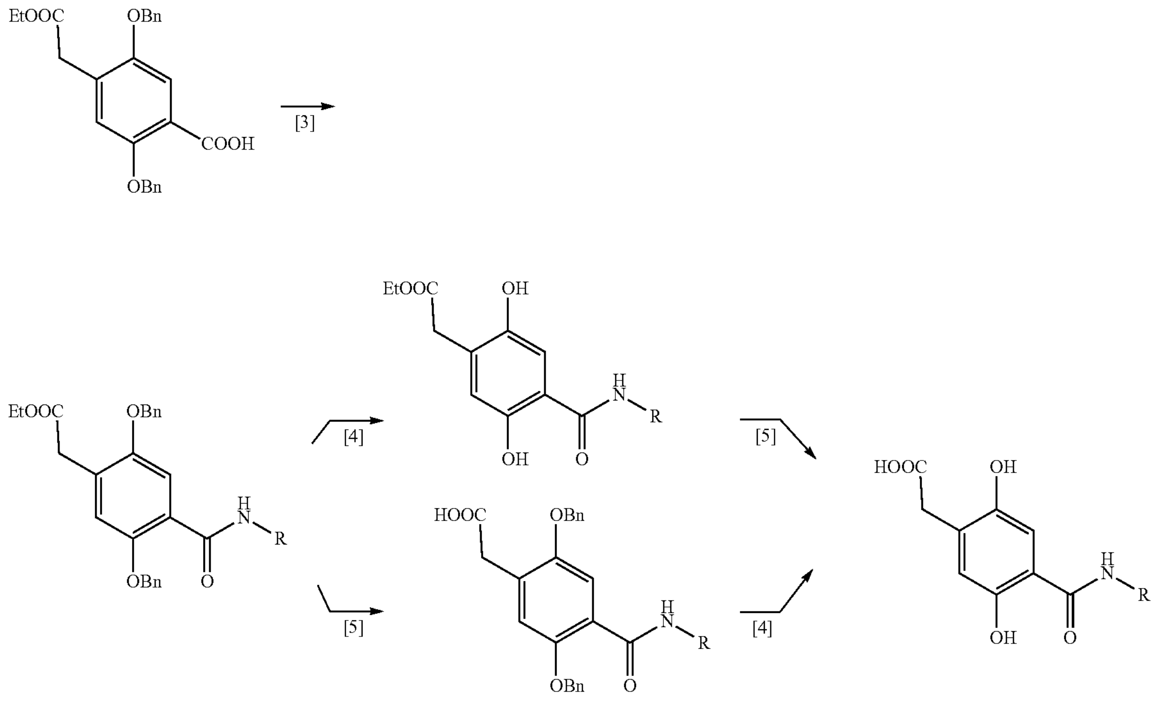

-continued

IIIa-013a

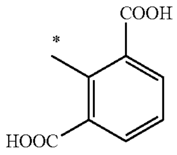

IIIa-015a

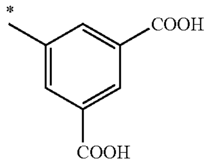

For conditions and yields: See Table 3 (FIG. 6)

52) 2-(4-(Carboxymethyl)-2,5-dihydroxybenzamido)benzoic acid, compound IIIa-001a UPLC-MS (acidic method, 2 min): rt=0.89 min; m/z=332.1 $[M+H]^+$, peak area >98%

$^1H$ NMR (400 MHz, DMSO-d6) δ 13.38 (s, 1H), 12.17 (s, 1H), 10.67 (s, 1H), 9.23 (s, 1H), 8.64 (dd, J=8.5, 1.2 Hz, 1H), 8.00 (dd, J=7.9, 1.7 Hz, 1H), 7.62 (ddd, J=8.7, 7.3, 1.7 Hz, 1H), 7.33 (s, 1H), 7.19 (td, J=7.6, 1.2 Hz, 1H), 6.80 (s, 1H), 3.49 (s, 2H).

HRMS: $[M+H]^+$, calc. for $C_{16}H_{14}NO_7$: 332.07648, found: 332.07666

Biodata: IIIa-001a: FGF-1 IC50 [μM]=62; FGF-2 IC50 [μM]=10; VEGF-A1 IC50 [μM]=32; VEGFR-Phosphorylation inhibition IC50 [μM]=ND; PMN ROS [inhibition at 0.3 μM [%]=74.79; PMN ROS inhibition IC50 [μM]=N.D.; Neutrophil adhesion inhibition [%]=30.4 Ethyl methyl ester UPLC-MS (acidic method, 2 min): rt=1.14 min; m/z=374.2 $[M+H]^+$, peak area >96%.

$^1H$ NMR (400 MHz, DMSO-d6) δ 11.91 (s, 1H), 10.78 (s, 1H), 9.25 (s, 1H), 8.60 (dd, J=8.5, 1.2 Hz, 1H), 7.97 (dd, J=8.0, 1.7 Hz, 1H), 7.64 (ddd, J=8.7, 7.3, 1.7 Hz, 1H), 7.38 (s, 1H), 7.26-7.18 (m, 1H), 6.81 (s, 1H), 4.08 (q, J=7.1 Hz, 2H), 3.88 (s, 3H), 3.56 (s, 2H), 1.19 (t, J=7.1 Hz, 3H).

HRMS: $[M+H]^+$, calc. for $C_{19}H_{20}NO_7$: 374.12342, found: 374.12333

Biodata: IIIa-001a-E2: FGF-1 IC50 [μM]=200; FGF-2 IC50 [μM]=33; VEGF-A1 IC50 [μM]=43; VEGFR-Phosphorylation inhibition IC50 [μM]=ND; PMN ROS [inhibition at 0.3 μM [%]=69.66; PMN ROS inhibition IC50 [μM]=N.D.; Neutrophil adhesion inhibition [%]=44.46 53) (2-(1H-Tetrazol-5-yl)phenylaminocarbonyl)-2,5-dihydroxyphenyl)acetic acid, compound IIIa-001aTz:

UPLC-MS (acidic method, 2 min): rt=0.87 min; m/z=356.1 [M+H], peak area >95%.

$^1H$ NMR (400 MHz, DMSO-$d_6$) δ 12.22 (s, 1H), 11.43 (s, 1H), 10.74 (s, 1H), 9.21 (s, 1H), 8.46 (dd, J=8.5, 1.2 Hz, 1H), 7.87 (d, J=8.1 Hz, 1H), 7.60 (td, J=8.6, 7.9, 1.6 Hz, 1H), 7.39-7.30 (m, 2H), 6.80 (s, 1H), 3.48 (s, 2H).

HRMS: $[M+H]^+$, calc. for $C_{16}H_{14}N_5O_5$: 356.09894, found: 356.09889

Biodata: IIIa-001aTz: FGF-1 IC50 [μM]=51; FGF-2 IC50 [μM]=14; VEGF-A1 IC50 [μM]=12; VEGFR-Phosphorylation inhibition IC50 [μM]=0.71; PMN ROS [inhibition at 0.3 μM [%]=69.35; PMN ROS inhibition IC50 [μM]=N.D.; Neutrophil adhesion inhibition [%]=39.74; Whole Blood: GM-CSF IC50 [μM]=>100; IFNγIC50 [μM]=18.9; IL-1β IC50 [μM]=>100; IL-2 IC50 [μM]=>100; IL-4 IC50 [μM]=>100; IL-5 IC50 [μM]=>100; IL-6 IC50 [μM]=1.98; IL-9 IC50 [μM]=3.01; IL-10 IC50 [μM]=7.78; IL-12p70 IC50 [μM]=0.48; IL-13 IC50 [μM]=0.15; IL-17A IC50 [μM]=0.17; IL-17F IC50 [μM]=0.16; IL-18 IC50 [μM]=27.7; IL-21 IC50 [μM]=3; IL-33 IC50 [μM]=0.14; TGFβ IC50 [μM]=>100; TNF α IC50 [μM]=0.31; TNF β IC50 [μM]=0.23.

Ethyl ester:

UPLC-MS (acidic method, 4 min): rt=1.56 min; m/z=384.2 $[M+H]^+$, peak area >95%.

$^1H$ NMR (400 MHz, DMSO-$d_6$) δ 11.34 (s, 1H), 10.73 (s, 1H), 9.25 (s, 1H), 8.45 (dd, J=8.5, 1.2 Hz, 1H), 7.85 (dd, J=7.8, 1.6 Hz, 1H), 7.61 (ddd, J=8.7, 7.4, 1.6 Hz, 1H), 7.39-7.30 (m, 2H), 6.80 (s, 1H), 4.08 (q, J=7.1 Hz, 2H), 3.56 (s, 2H), 1.19 (t, J=7.1 Hz, 3H).

HRMS: $[M+H]^+$, calc. for $C_{18}H_8N_5O_5$: 384.13024, found: 384.12999

Biodata: IIIa-001aTz-E1: FGF-1 IC50 [μM]=200; FGF-2 IC50 [μM]=200; VEGF-A1 IC50 [μM]=200; VEGFR-Phosphorylation inhibition IC50 [μM]=0.32; PMN ROS [inhibition at 0.3 μM [%]=70.03; PMN ROS inhibition IC50 [μM]=N.D.; Neutrophil adhesion inhibition [%]=91.76

54) 2-(4-(Carboxymethyl)-2,5-dihydroxybenzamido)isophthalic acid, compound IIIa-013a UPLC-MS (acidic method, 4 min): rt=0.82 min; m/z=376.0 $[M+H]^+$, peak area >89%.

$^1H$ NMR (400 MHz, DMSO-d6) δ 13.67-11.48 (m, 3H), 10.82 (s, 1H), 9.19 (s, 1H), 7.95 (d, J=7.8 Hz, 2H), 7.36 (s, 1H), 7.33 (t, J=7.8 Hz, 1H), 6.79 (s, 1H), 3.48 (s, 2H).

HRMS: $[M+H]^+$, calc. for $C_{17}H_{14}NO_9$: 376.06630, found: 376.06638

Biodata: IIIa-013a: FGF-1 IC50 [μM]=17; FGF-2 IC50 [μM]=31; VEGF-A1 IC50 [μM]=43; VEGFR-Phosphorylation inhibition IC50 [μM]=1.3; PMN ROS [inhibition at 0.3 μM [%]=76.55; PMN ROS inhibition IC50 [μM]=N.D.; Neutrophil adhesion inhibition [%]=30.667; Whole Blood: GM-CSF IC50 [μM]=27.8; IFNγ IC50 [μM]=0.15; IL-1β IC50 [μM]=>100; IL-2 IC50 [μM]=57.1; IL-4 IC50 [μM]=>100; IL-5 IC50 [μM]=>100; IL-6 IC50 [μM]=3.55; IL-9 IC50 [μM]=11.9; IL-10 IC50 [μM]=37.3; IL-12p70 IC50 [μM]=0.5; IL-13 IC50 [μM]=0.37; IL-17A IC50 [μM]=0.15; IL-17F IC50 [μM]=0.41; IL-18 IC50 [μM]=>100; IL-21 IC50 [μM]=1.63; IL-33 IC50 [μM]=1.11; TGFβ IC50 [μM]=>100; TNF α IC50 [μM]=0.51; TNF β IC50 [μM]=0.89.

55) 5-(4-(Carboxymethyl)-2,5-dihydroxybenzamido)isophthalic acid, compound IIIa-015a UPLC-MS (acidic method, 4 min): rt=0.93 min; m/z=376.0 $[M+H]^+$, peak area >96%.

$^1H$ NMR (400 MHz, DMSO-d6+10% D20) δ 8.34 (s, 2H), 8.18 (s, 1H), 7.38 (s, 1H), 6.71 (s, 1H), 3.39 (s, 2H).

HRMS: $[M+H]^+$, calc. for $C_{17}H_{14}NO_9$: 376.06630, found: 376.06665

Biodata: IIIa-015a: FGF-1 IC50 [μM]=16; FGF-2 IC50 [μM]=114; VEGF-A1 IC50 [μM]=202; VEGFR-Phosphorylation inhibition IC50 [μM]=0.89; PMN ROS [inhibition at 0.3 μM [%]=78.76; PMN ROS inhibition IC50 [μM]=N.D.; Neutrophil adhesion inhibition [%]=12.13 Ethyl dimethyl ester UPLC-MS (acidic method, 4 min): rt=1.69 min; m/z=432.1 $[M+H]^+$, peak area >97%.

$^1H$ NMR (400 MHz, DMSO-d6) δ 9.23 (s, 1H), 8.58 (s, 1H), 8.58 (s, 1H), 8.23-8.21 (m, 1H), 7.31 (s, 1H), 6.81 (s, 1H), 4.08 (q, J=7.0 Hz, 2H), 3.91 (s, 6H), 3.58 (s, 2H), 1.19 (t, J=7.1 Hz, 3H),

HRMS: $[M+H]^+$, calc. for $C_{21}H_{22}NO_9$: 432.12891, found: 432.02903

Biodata: IIIa-015a-E3: FGF-1 IC50 [μM]=N.D.; FGF-2 IC50 [μM]=191; VEGF-A1 IC50 [μM]=87; VEGFR-Phosphorylation inhibition IC50 [μM]=7.2; PMN ROS [inhibition at 0.3 μM [%]=91.37; PMN ROS inhibition IC50 [μM]=N.D.; Neutrophil adhesion inhibition [%]=61.22

Example 1.9. Molecules of Type IIIb: Diamides from Diamines, 1 Example

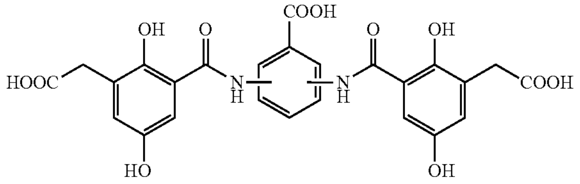

Scheme 15. Synthesis of Diamides of type IIIb

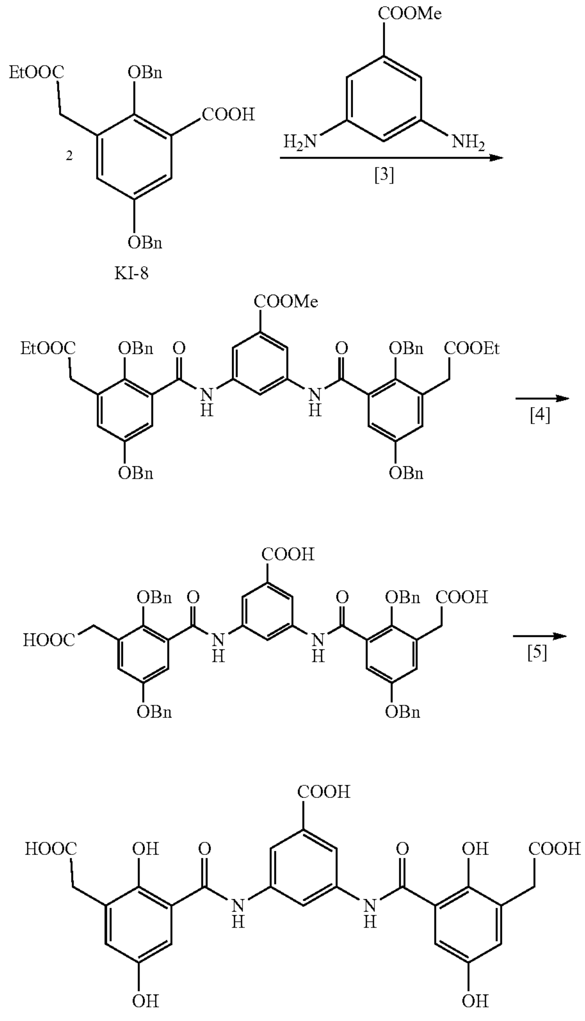

Procedure: see general procedure from KI-1 steps [3], [4], [5]

For example:

IIIb-010a

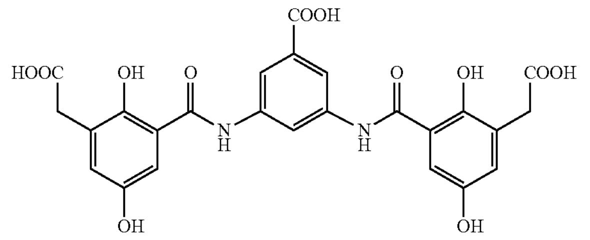

For conditions and yields: See Table 3 (FIG. 6)

56) 3,5-Bis(2,5-dihydroxy-4-carboxymethylbenzoylamino)benzoic acid, compound IIIb-010a UPLC-MS (acidic method, 4 min): rt=1.08 min; m/z=539.2.1 $[M-H]^-$, peak area 80%.

$^1H$ NMR (400 MHz, DMSO-$d_6$) δ 10.85 (brs, 2H), 10.57 (brs, 2H), 9.20 (s, 2H), 8.26 (m, 1H), 8.09 (d, J=2.0 Hz, 2H), 7.36 (s, 2H), 6.82 (s, 2H), 3.50 (s, 4H).

HRMS: $[M+H]^+$, calc. for $C_{23}H_{17}N_2O_{12}$: 513.07760, found: 513.07774 Triethyl ester UPLC-MS (acidic method, 4 min): rt=1.81 min; m/z=623.3 $[M-H]^-$, peak area 94%.

$^1H$ NMR (400 MHz, DMSO-$d_6$) δ 10.87 (s, 2H), 10.65 (s, 2H), 9.23 (s, 2H), 8.31-8.28 (m, 1H), 8.10 (d, J=2.0 Hz, 2H), 7.35 (s, 2H), 6.81 (s, 2H), 4.35 (q, J=7.1 Hz, 2H), 4.08 (q, J=7.1 Hz, 4H), 3.58 (s, 4H), 1.35 (t, J=7.1 Hz, 3H), 1.19 (t, J=7.1 Hz, 6H).

Biodata: IIIb-010a-E3: FGF-1 IC50 [μM]=200; FGF-2 IC50 [μM]=200; VEGF-A1 IC50 [μM]=200; VEGFR-Phosphorylation inhibition IC50 [μM]=0.65; PMN ROS [inhibition at 0.3 μM [%]=N.D.; PMN ROS inhibition IC50 [μM]=N.D.; Neutrophil adhesion inhibition [%]=0

Example 1.10: MOLECULES OF TYPE IIIc. Dimers, 6 examples

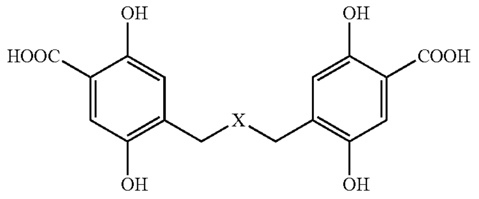

Synthetic Schemes and Procedures

Scheme 16: X=O

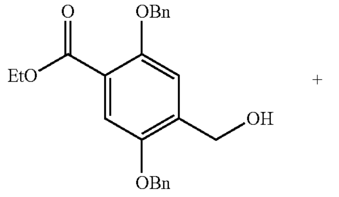

-continued

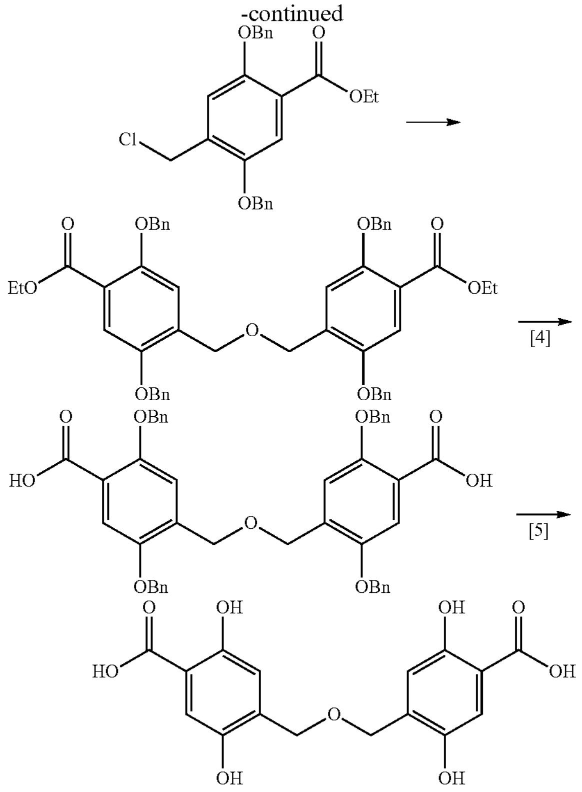

Synthetic Procedures

Formation of Ether Linkage from KI-10 and KI-11

Ethyl 2,5-dibenzyloxy-4-[(2,5-dibenzyloxy-4-ethoxycarbonyphenyl)methoxymethyl]benzoate [Step 1]: To a solution of KI-11 (340 mg, 0.83 mmol) and KI-10 (250 mg, 0.64 mmol) in DMF (6 mL), cooled down in an ice bath, was added portionwise sodium hydride (76 mg, 1.9 mmol). After 1 h, the reaction mixture was poured into a saturated aqueous solution of ammonium chloride (50 mL) and the material was extracted with EtOAc (3×30 mL), the organic phase was further washed with water (2×50 mL) and brine (50 mL), dried with sodium sulfate and concentrated under reduced pressure. The crude product was purified by flash column chromatography (Hexanes/EtOAc 0 to 20%) to give the title compound (161 mg, 33% yield) as a brown solid.

Deprotection Procedures:

See General procedures [4], [5]

For examples

IIIb-060a

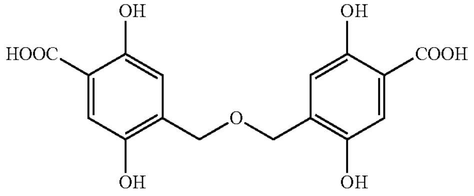

For conditions and yields: See Table 4 (deprotections) (FIG. 7) 57) 4-((2,5-Dihydroxy-4-carboxyphenyl)methoxymethyl)-2,5-dihydroxybenzoic acid, compound IIIc-060a:

UPLC-MS (acidic method, 4 min): rt=0.94 min; m/z=349.1 [M−H]$^-$, peak area >90%.

$^1$H NMR (400 MHz, DMSO-d6) δ 7.20 (s, 2H), 6.92 (s, 2H), 4.56 (s, 4H),

Biodata: IIIc-060a: FGF-1 IC50 [μM]=200; FGF-2 IC50 [μM]=51; VEGF-A1 IC50 [μM]=114; VEGFR-Phosphorylation inhibition IC50 [μM]=1.3; PMN ROS [inhibition at 0.3 μM [%]=86.84; PMN ROS inhibition IC50 [μM]=N.D.; Neutrophil adhesion inhibition [%]=41.38

Scheme 17: X = NH

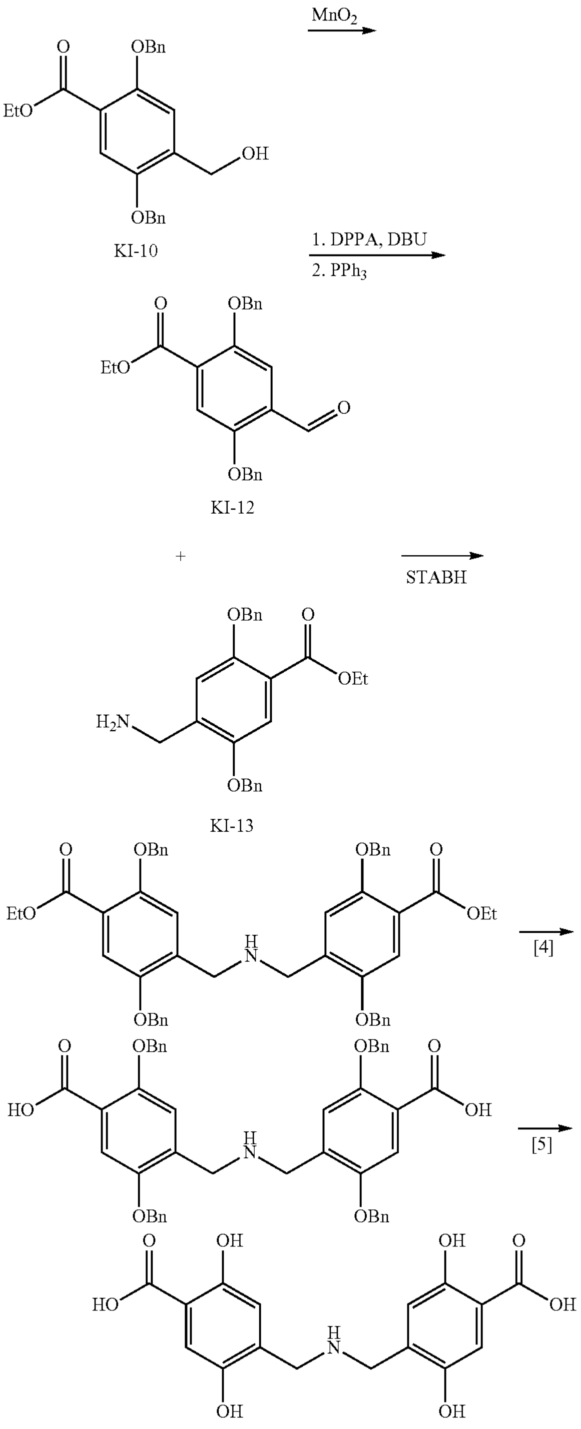

Synthetic Procedures

Formation of amine linkage from KI-12 and KI-13 via KI-10 and KI-11 Ethyl 2,5-Bis(benzyloxy)-4-formylbenzoate (KI-12): To a solution of KI-10 (3.4 g, 8.6 mmol) in dichloromethane (50 mL) was added manganese dioxide (4.5 g, 51.9 mmol). The resulting suspension was stirred under reflux for 4 h. The reaction was filtered through a pad of Celite® and the solid washed with dichloromethane (300 mL), the solvent was then removed under reduced pressure to give the title compound (3.2 g, 94% yield) as a yellowish solid.

UPLC-MS (acidic method, 2 min): rt=1.33 min; m/z=no ion, peak area >93%

$^1$H NMR (400 MHz, DMSO-$d_6$) δ 10.39 (s, 1H), 7.56 (s, 1H), 7.54-7.26 (m, 11H), 5.28 (s, 2H), 5.20 (s, 2H), 4.30 (q, J=7.1 Hz, 2H), 1.27 (t, J=7.1 Hz, 3H).

Ethyl 4-(azidomethyl)-2,5-bis(benzyloxy)benzoate: To a suspension of KI-10 (3.0 g, 7.6 mmol) and 1,8-Diazabicyclo [5.4.0]undec-7-ene (DBU) (1.5 mL. 9.9 mmol) in toluene (30 mL) was added diphenyl phosphoryl azide (DPPA) (2 mL, 9.1 mmol). The resulting mixture was stirred at room temperature for 18 h. An aqueous solution of 1M hydrogen chloride (200 mL) was added and the product was extracted with EtOAc (3×100 mL), the combined organic layers were washed with water (2×50 mL), dried over sodium sulfate and concentrated under reduced pressure. The residue was purified by flash column chromatography (Hexanes/EtOAc 0 to 20%) to yield the title compound (3.1 g, 98%) as a colourless oil that became a white solid over time.

UPLC-MS (acidic method, 2 min): rt=1.37 min; m/z=390.2, [M+H-$N_2$], peak area >93%

$^1$H NMR (400 MHz, DMSO-$d_6$) δ 7.53-7.46 (m, 4H), 7.44-7.26 (m, 8H), 5.16 (s, 2H), 5.14 (s, 2H), 4.48 (s, 2H), 4.26 (q, J=7.1 Hz, 2H), 1.25 (t, J=7.1 Hz, 3H).

Ethyl 4-(aminomethyl)-2,5-bis(benzyloxy)benzoate (KI-13): To a solution of ethyl 4-(azidomethyl)-2,5-bis(benzyloxy)benzoate (2.8 g, 6.7 mmol) in THF (60 mL) and water (6 mL) was added polymer-bound triphenylphosphine (4.7 g, ~3 mmol/g loading) and the resulting mixture was left to stir at room temperature for 18 h. The resin was removed by filtration and washed with water (100 mL) and EtOAc (2×100 mL). The phases were separated, and the aqueous layer was further extracted with EtOAc (100 mL), the gathered organic layers were washed with brine (200 mL), dried over sodium sulfate and concentrated to give the title compound (KI-13) (1.8 g, 70% yield) as a white solid.

UPLC-MS (basic method, 2 min): rt=1.20 min; m/z=392.2, [M+H]$^+$, peak area >93%

$^1$H NMR (400 MHz, DMSO-$d_6$) δ 7.60-7.22 (m, 12H), 5.14 (s, 2H), 5.10 (s, 2H), 4.24 (q, J=7.1 Hz, 2H), 3.75 (s, 2H), 1.25 (t, J=7.1 Hz, 3H).

Ethyl 2,5-dibenzyloxy-4-[(2,5-dibenzyloxy-4-ethoxycarbonylphenyl)methylaminomethyl] benzo-ate: KI-12 (500 mg, 1.3 mmol) and KI-13 (641 mg, 1.6 mmol) were dissolved in DCM (35 mL) followed by addition of activated molecular sieves (10 beads). The resulting mixture was stirred at room temperature for 5 h. Sodium triacetoxyborohydride (654 mg, 3.1 mmol) was then added and the resulting mixture was stirred at room temperature for 18 h. DCM (25 mL) was added, the reaction mixture was decanted into a separating funnel and washed with water (50 mL), dried with sodium sulfate and concentrated under reduced pressure. The residue was purified by flash column chromatography ((Hexanes/EtOAc 0 to 50%) to yield the titled compound (631 mg, 64% yield) as a colourless oil that became solid over time.

UPLC-MS (acidic method, 2 min): rt=1.37 min; m/z=766.3, [M+H]$^+$, peak area >92%

$^1$H NMR (400 MHz, DMSO-$d_6$) δ 7.47-7.42 (m, 4H), 7.38-7.25 (m, 20H), 5.08 (s, 4H), 5.04 (s, 4H), 4.25 (q, J=7.1 Hz, 4H), 3.76 (s, 4H), 1.25 (t, J=7.1 Hz, 6H).

Deprotection procedures: See General procedures [4], [5]

For conditions and yields: See FIG. 7.

For examples

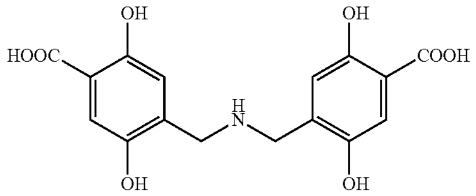

58) Bis(4-carboxy-2,5-dihydroxyphenylmethyl)amine, compound IIIc-056a

UPLC-MS (acidic method, 4 min): rt=0.57 min; m/z=350.0 [M+H]$^+$, peak area >96%.

$^1$H NMR (400 MHz, DMSO-d6) δ 9.97 (s, 2H), 9.08 (s, 2H), 7.31 (s, 2H), 7.02 (s, 2H), 4.11 (s, 4H).

HRMS: [M+H]$^+$, calc. for $C_{16}H_{16}NO_8$: 350.08704, found: 350.08706

Biodata: IIIc-056a: FGF-1 IC50 [μM]=200; FGF-2 IC50 [μM]=35; VEGF-A1 IC50 [μM]=200; VEGFR-Phosphorylation inhibition IC50 [μM]=ND; PMN ROS [inhibition at 0.3 μM [%]=90.07; PMN ROS inhibition IC50 [μM]=N.D.; Neutrophil adhesion inhibition [%]=35

Scheme 18: X = NAc

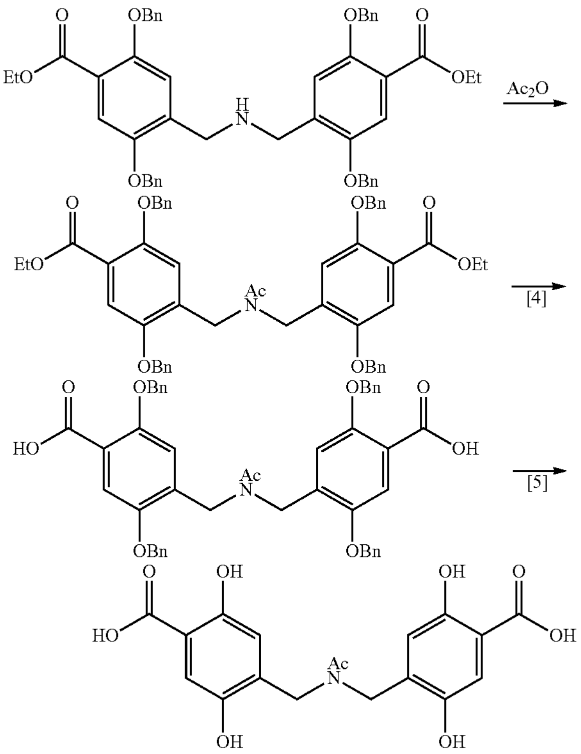

Synthetic Procedures

N,N-Bis-[2,5-dibenzyloxy-4-ethoxycarbonylphenylmethyl]acetamide: To a solution of N,N-bis-[2,5-dibenzyloxy-4-ethoxycarbonylphenylmethyl]amine (300 mg, 0.39 mmol) and pyridine (0.2 mL, 2.4 mmol) in DCM (6 mL), under an atmosphere of nitrogen, was added acetic anhydride (0.2 mL, 2.1 mmol). The reaction mixture was stirred at room temperature for 1 h and concentrated under reduced pressure. The residue was purified by flash column chromatography (Hexanes/EtOAc, 0 to 50%) to give the title compound (316 mg, 92% yield) as a colourless oil.

UPLC-MS (acidic method, 2 min): rt=1.44 min; m/z=808.2 $[M+H]^+$, peak area >95%.

$^1H$ NMR (400 MHz, DMSO-d6) δ 7.49-7.17 (m, 22H), 6.92 (s, 1H), 6.72 (s, 1H), 5.03 (s, 2H), 5.00 (s, 2H), 4.96 (s, 2H), 4.94 (s, 2H), 4.46 (s, 4H), 4.31-4.16 (m, 4H), 1.96 (s, 3H), 1.28-1.20 (m, 6H).

Deprotection Procedures:

See General procedures [4], [5]

For examples

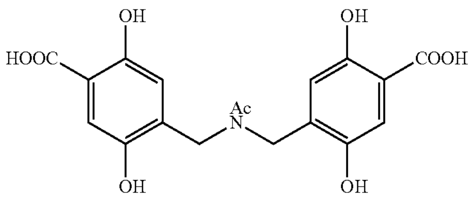

For conditions and yields: See FIG. 7 (deprotections)

59) N,N-Bis(4-carboxy-2,5-dihydroxyphenylmethyl) acetamide, compound IIIc-057a

UPLC-MS (acidic method, 4 min): rt=0.84 min; m/z=392.1 $[M+H]^+$, peak area >99%.

$^1H$ NMR (400 MHz, DMSO-d6) δ 9.50 (s, 1H), 9.34 (s, 1H), 7.22 (s, 1H), 7.17 (s, 1H), 6.63 (s, 1H), 6.53 (s, 1H), 4.48 (s, 2H), 4.39 (s, 2H), 2.11 (s, 3H).

HRMS: $[M+H]^+$, calc. for $C_{18}H_{18}NO_9$: 392.09761, found: 392.09766

Biodata: IIIc-057a: FGF-1 IC50 [μM]=87; FGF-2 IC50 [μM]=77; VEGF-A1 IC50 [μM]=38; VEGFR-Phosphorylation inhibition IC50 [μM]=0.2; PMN ROS [inhibition at 0.3 μM [%]=90.34; PMN ROS inhibition IC50 [μM]=N.D.; Neutrophil adhesion inhibition [%]=40.04; Whole Blood: GM-CSF IC50 [μM]=>100; IFNγ IC50 [μM]=0.9; IL-1β IC50 [μM]=16.2; IL-2 IC50 [μM]=24.2; IL-4 IC50 [μM]=>100; IL-5 IC50 [μM]=>100; IL-6 IC50 [μM]=0.19; IL-9 IC50 [μM]=11.1; IL-10 IC50 [μM]=>100; IL-12p70 IC50 [μM]=0.73; IL-13 IC50 [μM]=4.73; IL-17A IC50 [μM]=1.32; IL-17F IC50 [μM]=5.06; IL-18 IC50 [μM]=>100; IL-21 IC50 [μM]=1.56; IL-33 IC50 [μM]=2.93; TGFβ IC50 [μM]=>100; TNF c IC50 [μM]=0.15; TNF β IC50 [μM]=1.58.

Scheme 19: X = $NCH_2C_6H_3(OH)_2COOH$

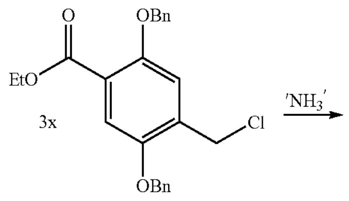

KI-11

-continued

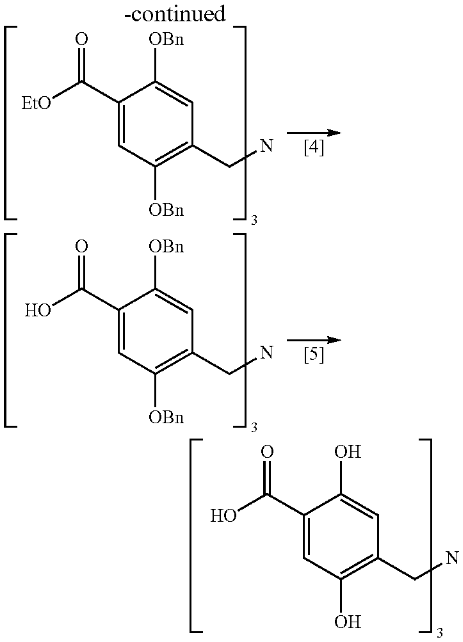

Synthetic Procedures

Formation of Tertiary Amine from KI-11 and $NH_3$

Tris(4-ethoxycarbony-2,5-dibenzyloxyphenylmethyl) amine: A sealed tube was charged with KI-11 (32.5 g, 79 mmol), sodium iodide (0.79 g, 5 mmol), a solution of ammonia in MeOH (7 N) (38 mL, 264 mmol) and EtOAc (80 mL). The tube was then sealed and the reaction mixture was heated at 60 °C for 24 h. After 24 h, the starting material (KI-11) was consumed and the reaction mixture contained the desired product but also monomeric and dimeric structures. Water (100 mL) was added and the resulting mixture was extracted with EtOAc (3×100 mL), the gathered organic layer was dried over $Na_2SO_4$, filtered and concentrated under reduced pressure. The residue obtained was dissolved in EtOAc (165 mL) and KI-11 (2.5 g, 6 mmol), sodium iodide (0.79 g, 5 mmol), DIPEA (10 mL, 58 mmol) were added and the resulting solution was heated at 60 °C. After 18 h, water (100 mL) was added and the resulting mixture was extracted with EtOAc (3×100 mL), the gathered organic layer was dried over $Na_2SO_4$, filtered and concentrated under reduced pressure. The residue was purified by recrystallisation using EtOH/EtOAc 95/5 (20 mL) as solvent to yield to the title compound (15.0 g, 50%) as white crystals.

UPLC-MS (basic method, 2 min): rt=1.71 min; m/z=1140.3 $[M+H]^+$, peak area >99%.

$^1H$ NMR (400 MHz, DMSO-$d_6$) δ 6.56-6.49 (m, 12H), 6.48-6.38 (m, 24H), 4.22 (s, 6H), 4.04 (s, 6H), 3.42 (q, J=7.1 Hz, 6H), 3.00 (s, 6H), 0.42 (t, J=7.1 Hz, 9H).

Alternatively, the product can be purified via silica gel flash column chromatography: scale, up to 270 g; Instrument: Combiflash Torrent; cartridge: RediSep Column, Silica 3 kg; loading type: Crude dissolved into 1 L of heptane:toluene (1:1). Elution with ethyl acetate/heptane. Detection: UV—240 nm Deprotection Procedures: See General Procedures [4], [5]

For Conditions and Yields: See FIG. 7 (Deprotections)

Alternative, Large Scale Deprotection Procedures:

Saponification. Tris(4-ethoxycarbony-2,5-dibenzyloxyphenylmethyl)amine (95.00 g, 0.083 mol), sodium hydroxide (40.00 g, 0.99 mol), water (570 mL) and tetrahydrofuran (1.9 L) were added to a 5 L round bottom flask. The reaction mixture was heated, using a temperature block, at 80 °C. (reflux temperature was 65 °C) for 48 h then stirred at room temperature for 24 h. The solvents were then removed in vacuo. The crude material was collected and further diluted with water (2.85 L). In another 10 L flask, a mixture of acetic acid (180 mL) and water (950 mL) was stirred at rt. The mixture of the crude product in water was added to the acetic acid mixture over a period of 30 min. while stirring with an overhead stirrer, and a cream solid precipitated. The reaction mixture was stirred for an additional 1 h and the solid was isolated upon filtration; the mother liquor pH was 4,2. The solid isolated was stirred with water (1425 mL) for 1 h then filtered. The mother liquor pH was 4,5. The solid recovered was stirred with more water (1425 mL) for 1 h then filtered; the mother liquor pH was 4.5. The above solid was stirred with acetone (950 mL) for 1 h and filtered. The cream colour solid was dried in the vacuum oven at 50 °C for 48 h prior to analysis (82.00 g, 93% yield) (yields vary between 90-95%).

Note: The pH is a critical parameter during the washings in order to keep the product in the free acid form and removing the excess acetic acid from the product.

Ideal pH: 4.2 to 4.5 (final sodium content vary between 2 ppm-20 ppm).

Hydrogenolysis and Isolation. Tris(4-carboxy-2,5-dibenzyloxyphenylmethyl)amine (58.00 g, 54.00 mmol, 1 eq) and tetrahydrofuran (1160 mL) were charged in a 2 L round bottom flask. The mixture was degassed with nitrogen, then flushed with hydrogen/vacuum cycle 4-5 times. Palladium on carbon (JM 10% 424 Pd/C, 70 g, 15% loading) was added to the reaction mixture and stirred at 25 °C for 5-6 h. The reaction was then degassed and the catalyst removed by filtration through a pad of celite, which was washed with tetrahydrofuran (3×1160 mL). Finally, the filtrates were concentrated under reduce pressure. The crude solid was collected, stirred with heptane (1160 mL) and filtered in order to give a grey solid, which was dried in the vacuum oven at 50 °C overnight (32.50 g, >100% yield on crude basis). The crude material collected was dissolved in ethanol (325 mL) and heated to 60 °C. (clear solution). Then, water was slowly added (325 mL) at 60 °C. (keeping the temperature at least at 50 °C during addition) over a period of 15-20 min. At this stage a hazy liquid was observed. The hazy reaction mixture was stirred at reflux temperature for 30 min.

After this time, the reaction mixture was allowed to cool to room temperature for another 30 min. The precipitated solid was isolated upon filtration and washed with a 1:1 mixture of ethanol:water (66 mL).

The solid was dried in the vacuum oven at 50 °C for at least 72 h prior to analysis, in order to afford the desired product IIIc-061a (22.00 g, 76% yield) (yield vary between 65-75%). LCMS: >95%, NMR: >95% purity.

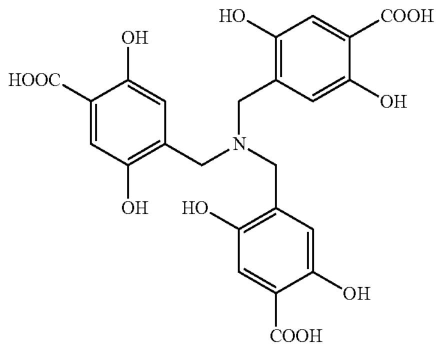 [SMILES: O=C(O)c1cc(O)c(CN(Cc2cc(O)c(C(=O)O)cc2O)Cc2cc(O)c(C(=O)O)cc2O)cc1O]

Tris(4-carboxy-2,5-dihydroxyphenylmethyl)amine, compound IIIc-061a:

UPLC-MS (acidic method, 4 min): rt=0.74 min; m/z=516.0 $[M+H]^+$, peak area >86%.

$^1$H NMR (400 MHz, DMSO-d6) δ 7.27 (s, 3H), 6.83 (s, 3H), 4.33 (s, 6H).

$^{13}$C NMR (100 MHz, DMSO-$d_6$) δ 172.0, 154.3, 148.3, 134, 117.8 (CH), 114.9 (CH), 112.4, 53.6 ($CH_2$).

HRMS: $[M+H]^+$, calc. for $C_{24}H_{22}NO_{12}$: 516.11365, found: 516.11389

Biodata: IIIc-061a: FGF-1 IC50 [μM]=9; FGF-2 IC50 [μM]=7.6; VEGF-A1 IC50 [μM]=21; VEGFR-Phosphorylation inhibition IC50 [μM]=4.3; PMN ROS [inhibition at 0.3 μM [%]=92.5; PMN ROS inhibition IC50 [μM]=N.D.; Neutrophil adhesion inhibition [%]=58.69; Whole Blood: GM-CSF IC50 [μM]=31.2; IFNγ IC50 [μM]=2.48; IL-1β IC50 [μM]=>100; IL-2 IC50 [μM]=>100; IL-4 IC50 [μM]=>100; IL-5 IC50 [μM]=>100; IL-6 IC50 [μM]=0.18; IL-9 IC50 [μM]=8.85; IL-10 IC50 [μM]=17.9; IL-12p70 IC50 [μM]=37.2; IL-13 IC50 [μM]=0.31; IL-17A IC50 [μM]=0.04; IL-17F IC50 [μM]=0.32; IL-18 IC50 [μM]=32.4; IL-21 IC50 [μM]=6.38; IL-33 IC50 [μM]=0.31; TGFβ IC50 [μM]=>100; TNF c IC50 [μM]=0.03; TNF β IC50 [μM]=0.81 Triethyl ester UPLC-MS (acidic method, 2 min): rt=1.05 min; m/z=600.2 $[M+H]^+$, peak area >82%.

$^1$H NMR (400 MHz, DMSO-d6) δ 10.02 (s, 3H), 9.54 (s, 3H), 7.17 (s, 3H), 7.00 (s, 3H), 4.33 (q, J=7.1 Hz, 6H), 3.59 (s, 6H), 1.31 (t, J=7.1 Hz, 9H).

HRMS: $[M+H]^+$, calc. for $C_{30}H_{34}NO_{12}$: 600.20755, found: 600.20790

Biodata: IIIc-061a-E3: FGF-1 IC50 [μM]=200; FGF-2 IC50 [μM]=200; VEGF-A1 IC50 [μM]=200; VEGFR-Phosphorylation inhibition IC50 [μM]=0.34; PMN ROS [inhibition at 0.3 μM [%]=N.D.; PMN ROS inhibition IC50 [μM]=N.D.; Neutrophil adhesion inhibition [%]=10.4

Scheme 20: X = S

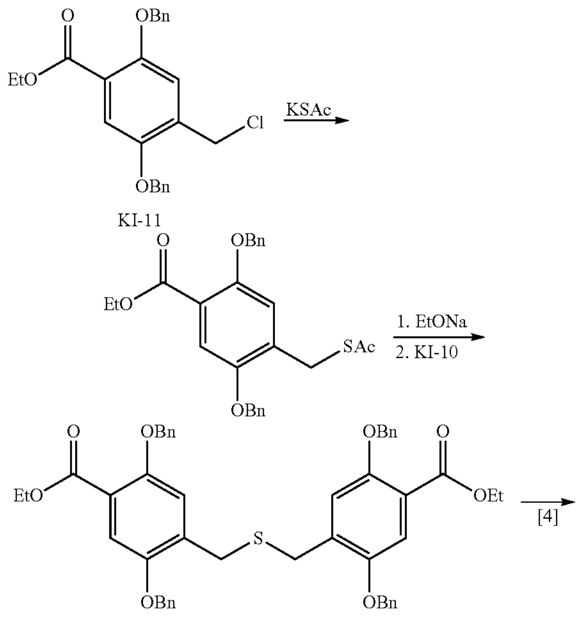

KI-11

-continued

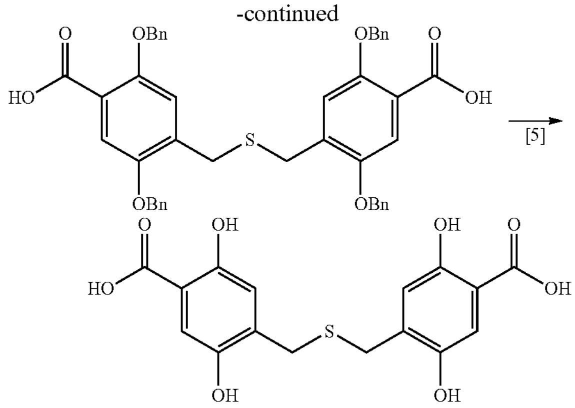

Synthetic Procedures

Formation of Thioether Linkage from KI-11

See Scheme 21. Same conditions to create the thioether linkage.

Deprotection procedures: see General procedures [4], [5]

For examples

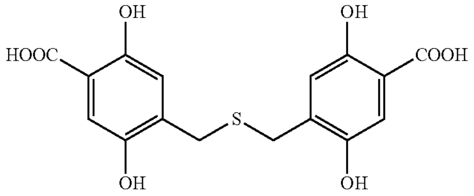 [SMILES: O=C(O)c1cc(O)c(CSCc2cc(O)c(C(=O)O)cc2O)cc1O]

For conditions and yields: See FIG. 7 (deprotections)

60) 4-((2,5-Dihydroxy-4-carboxyphenyl)methylthiomethyl)-2,5-dihydroxybenzoic acid, compound IIIc-058a UPLC-MS (acidic method, 2 min): rt=0.84 min; m/z=365.1 $[M-H]^-$, peak area >79%

$^1H$ NMR (400 MHz, Methanol-$d_4$) δ 7.25 (s, 2H), 6.83 (s, 2H), 3.69 (s, 4H).

HRMS: $[M+H]^+$, calc. for $C_{16}H_{15}O_8S$: 367.04822, found: 367.04768,

Biodata: IIIc-058a: FGF-1 IC50 [μM]=12; FGF-2 IC50 [μM]=12; VEGF-A1 IC50 [μM]=124; VEGFR-Phosphorylation inhibition IC50 [μM]=0.29; PMN ROS [inhibition at 0.3 μM [%]=61.22; PMN ROS inhibition IC50 [μM]=1.17; Neutrophil adhesion inhibition [%]=23

Scheme 21: X = $SO_2$

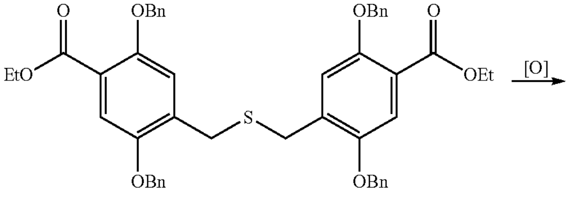

-continued

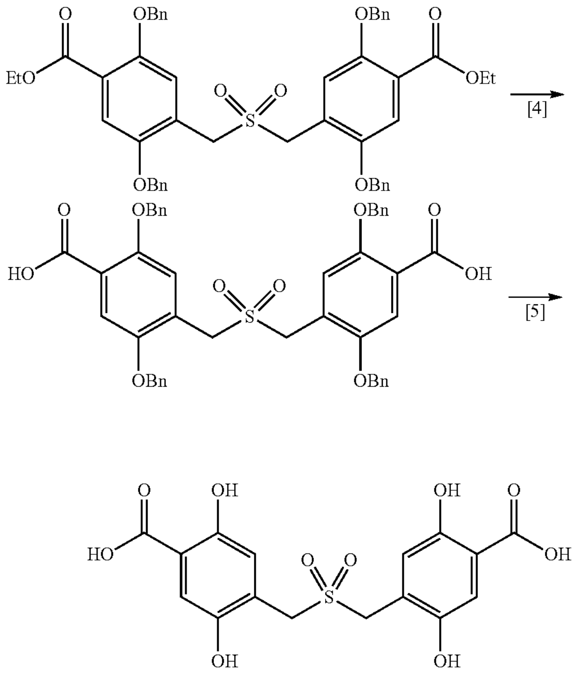

Synthetic Procedures

Oxidation of Thioether Linkage

See preparation of IVc-059a: same conditions of oxidation.

Deprotection procedures: see General procedures [4], [5]

For examples

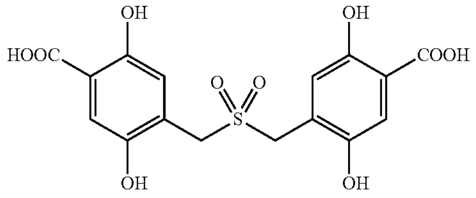 [SMILES: O=C(O)c1cc(O)c(CS(=O)(=O)Cc2cc(O)c(C(=O)O)cc2O)cc1O]

For conditions and yields: See FIG. 7 (deprotections)

61) 4-((2,5-Dihydroxy-4-carboxyphenyl)methylsulfonylmethyl)-2,5-dihydroxybenzoic acid, compound IIIc-059a UPLC-MS (acidic method, 2 min): rt=0.72 min; m/z=397.1 $[M-H]^-$, peak area >97%

$^1H$ NMR (400 MHz, DMSO-$d_6$) δ 13.94 (brs, 2H), 10.63 (brs, 2H), 9.71 (s, 2H), 7.27 (s, 2H), 6.91 (s, 2H), 4.44 (s, 4H).

HRMS: $[M+H]^+$, calc. for $C_{16}H_{15}O_{10}S$: 399.03804, found: 399.03768

Biodata: IIIc-059a: FGF-1 IC50 [μM]=47; FGF-2 IC50 [μM]=50; VEGF-A1 IC50 [μM]=200; VEGFR-Phosphorylation inhibition IC50 [μM]=3.61; PMN ROS [inhibition at 0.3 μM [%]=66.39; PMN ROS inhibition IC50 [μM]=1; Neutrophil adhesion inhibition [%]=14.67

Example 1.11: Compounds of Type IVc

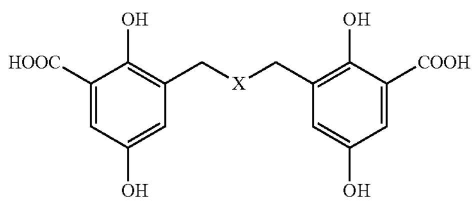

Scheme 22: X = S
Synthesis *via* dimethyl ether

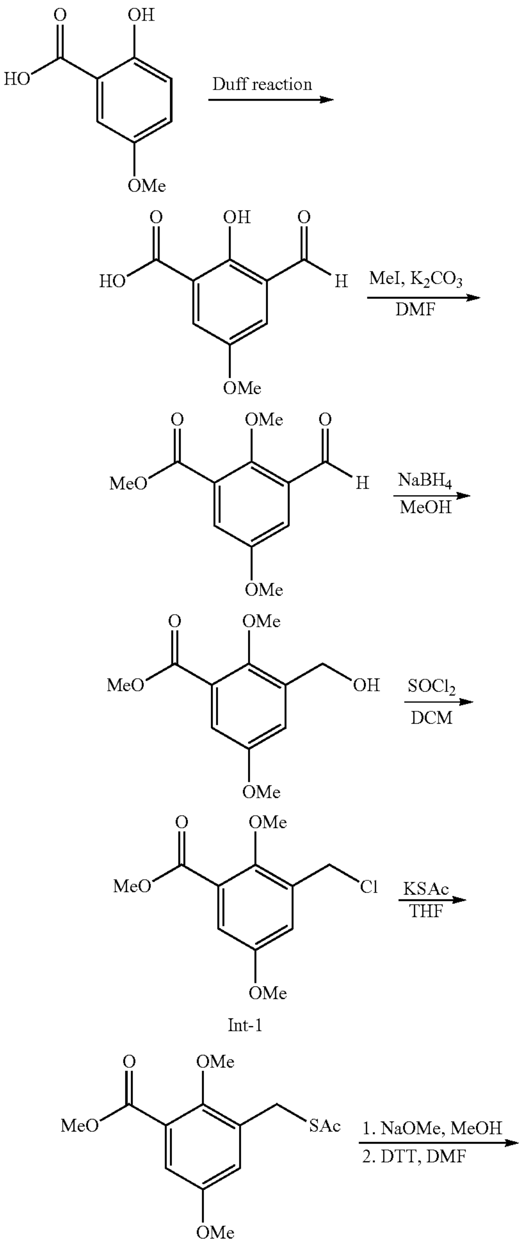

-continued

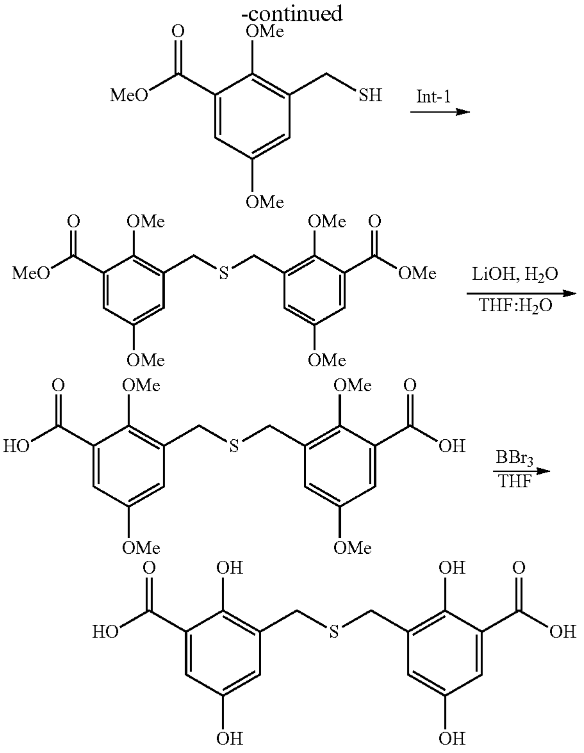

Synthetic Procedures

Synthesis from 5-O-methyl gentisic acid

3-Formyl-2-hydroxy-5-methoxybenzoic acid. Hexamethylenetetramine (40.019 g, 0.285 mol) was added to the mixture of 2-hydroxy-5-methoxybenzoic acid (24.0 g, 0.143 mol) in trifluoroacetic acid (190.0 mL). The reaction was refluxed for 18 h. After completion, the reaction was cooled down to ambient temperature and a solution of 2M hydrochloric acid (700 mL) was added to the mixture which was stirred at ambient temperature for 24 h. The precipitate was filtered, washed with water (500 mL) and dried in the vacuum oven to give 3-formyl-2-hydroxy-5-methoxybenzoic acid as a pale yellow solid (21.30 g, 0.11 mol, 77.0%)

UPLC-MS (acidic method, 2 min): rt=0.69 min; m/z=195.1 $[M-H]^-$, peak area >98%

$^1H$ NMR (400 MHz, DMSO-$d_6$) δ 10.36 (s, 1H), 7.62 (d, J=3.4 Hz, 1H), 7.44 (d, J=3.4 Hz, 1H), 3.78 (s, 3H).

Methyl 3-formyl-2,5-dimethoxybenzoate. Methyl iodide (6.7 mL, 0.107 mol) was added to a mixture of 3-formyl-2-hydroxy-5-methoxybenzoic acid (10.0 g, 0.05 mol) and potassium carbonate-325 mesh (28.18 g, 0.20 mol) in DMF (100.0 mL). The resulting mixture was stirred at ambient temperature for 18 h. The reaction was cooled down to ambient temperature and treated with cold water (400 mL) resulting in the formation of a precipitate. The resulting suspension was stirred for 10 min, then filtered and dried in the vacuum oven to give methyl 3-formyl-2,5-dimethoxybenzoate as a yellow solid (8.90 g, 0.04 mol, 78.0%).

UPLC-MS (acidic method, 2 min): rt=0.95 min; m/z=225.1 $[M+H]^+$, peak area >98%

$^1H$ NMR (400 MHz, DMSO-$d_6$) δ 10.27 (s, 1H), 7.55 (d, J 3.4 Hz, 1H), 7.41 (d, J 3.4 Hz, 1H), 3.88 (s, 3H), 3.87 (s, 3H), 3.83 (s, 3H).

Methyl 3-(hydroxymethyl)-2,5-dimethoxybenzoate. Sodium borohydride (16.198 g, 0.428 mol) was added slowly to a solution of methyl 3-formyl-2,5-dimethoxybenzoate (48.0 g, 0.214 mol) in MeOH (900 mL) at 0 °C and the resulting mixture was stirred at ambient temperature for 15 min. The solvent was removed in vacuo and the residue was dissolved in DCM (200 mL) then washed with water (200 mL). The organic layer was dried over $Na_2SO_4$, filtered, and concentrated to dryness to give methyl 3-(hydroxymethyl)-2,5-dimethoxybenzoate as white solid (45.6 g, 0.20 mol, 95.0%)

UPLC-MS (acidic method, 2 min): rt=0.84 min; no ionization, peak area >98%

$^1H$ NMR (400 MHz, DMSO-$d_6$) δ 7.20 (d, J 3.2 Hz, 1H), 7.08 (d, J 3.3 Hz, 1H), 5.24 (t, J 5.7 Hz, 1H), 4.54 (d, J 5.6 Hz, 2H), 3.83 (s, 3H), 3.76 (s, 3H), 3.68 (s, 3H).

Methyl 3-(chloromethyl)-2,5-dimethoxybenzoate. Thionyl chloride (17.2 mL, 0.235 mol) was added dropwise to a solution of methyl 3-(hydroxymethyl)-2,5-dimethoxybenzoate (45.60 g, 0.20 mol) over 30 min at ambient temperature. The resulting mixture was stirred for 18 h at ambient temperature. After completion, the reaction mixture was washed with a saturated solution of aqueous sodium carbonate (3×500 mL) and brine (500 mL). The organic layer was dried over $Na_2SO_4$, filtered and concentrated to dryness to give methyl 3-(chloromethyl)-2,5-dimethoxybenzoate as a brown solid (49.1 g, 0.18 mol, 90%)

UPLC-MS (acidic method, 2 min): rt=1.10 min; no ionization, peak area >92%

$^1H$ NMR (400 MHz, DMSO-$d_6$) δ 7.29 (d, J 3.2 Hz, 1H), 7.22 (d, J 3.3 Hz, 1H), 4.74 (s, 2H), 3.85 (s, 3H), 3.77 (s, 3H), 3.76 (s, 3H).

Methyl 3-(acetylthiomethyl)-2,5-dimethoxybenzoate. Potassium thioacetate (15.54 g, 0.136 mol) was added to the solution of methyl 3-(chloromethyl)-2,5-dimethoxybenzoate (22.20 g, 0.091 mol) in THF (500.0 mL) at ambient temperature. The reaction mixture was stirred a 75 °C for 18 h. After completion, the solvent was removed under reduced pressure to give a red oily residue which was treated with a saturated brine solution (500 mL), then extracted with diethyl ether (2×250 mL). The organic phases were combined, dried over $Na_2SO_4$, filtered and concentrated to dryness to yield methyl 3-(acetylthiomethyl)-2,5-dimethoxybenzoate as a brown solid (25.50 g, 0.09 mol, 99%).

UPLC-MS (acidic method, 2 min): rt=1.10 min; no ionization, peak area >92%

$^1H$ NMR (400 MHz, DMSO-$d_6$) δ 7.12 (d, J 3.3 Hz, 1H), 7.10 (d, J 3.2 Hz, 1H), 4.10 (s, 2H), 3.84 (s, 3H), 3.74 (s, 3H), 3.70 (s, 3H), 2.35 (s, 3H).

Methyl 3-(mercaptomethyl)-2,5-dimethoxybenzoate. To a solution of methyl 3-(acetylthiomethyl)-2,5-dimethoxybenzoate (25.5 g, 89.68 mmol) in dry methanol (800 mL) was added in a dropwise manner at 0 °C, a solution of sodium methanolate (5.81 g, 107.62 mmol) under a nitrogen atmosphere. The mixture was stirred at room temperature for 45 min before being quenched with Dowex X8($H^+$) ion-exchange resin and stirred for 15 min. After filtration, the solvent was evaporated under reduced pressure to give the crude product as a brown oil (which contained the desired product and the corresponding disulphide compound in a 2:1 ratio). The residue was dissolved in DMF (400.0 mL) and treated with dithiothreitol (DTT) (33.95 g, 0.26 mol) under a nitrogen atmosphere. The reaction mixture was stirred at 75 °C for 18 h. After completion of the disulphide to thiol conversion, the solvent was evaporated. The resulting residue was dissolved in DCM (1 L), washed with brine (7×500 mL), dried over $Na_2SO_4$, filtered and concentrated to dryness to yield homogeneous methyl 3-(mercaptomethyl)-2,5-dimethoxybenzoate as a brown oil (21.40 g, 88.32 mmol, 99%)

UPLC-MS (acidic method, 2 min): rt=1.05 min; m/z=243.1 $[M+H]^+$, peak area >95%

$^1H$ NMR (400 MHz, DMSO-$d_6$) δ 7.19 (d, J 3.2 Hz, 1H), 7.09 (d, J 3.3 Hz, 1H), 3.83 (s, 3H), 3.76 (s, 3H), 3.73 (s, 3H), 3.71 (d, J 8.0 Hz, 2H), 2.93 (t, J 8.0 Hz, 1H).

Dimethyl 3,3'-(thiobis(methylene))bis(2,5-dimethoxybenzoate). Triethylamine (19.0 mL, 136.61 mmol) was added to a solution of methyl 3-(mercaptomethyl)-2,5-dimethoxybenzoate (21.40 g, 88.32 mmol) and methyl 3-(chloromethyl)-2,5-dimethoxybenzoate (22.69 g, 92.74 mmol) under a nitrogen atmosphere. The reaction was stirred at ambient temperature for 18 h. After completion, the solvent was removed under vacuum to give a brown oil residue which was treated with water (1 L), then extracted with diethyl ether (3×500 mL). The organic phases were combined, washed with brine (5×250 mL), dried over $Na_2SO$, filtered and concentrated to dryness to yield the crude product as a brown oil, which was purified by silica gel chromatography: elution was made with a gradient of ethyl acetate (0 to 20%) in iso-hexane to yield dimethyl 3,3'-(thiobis(methylene))bis(2,5-dimethoxybenzoate) as a brown solid (29.9 g, 66.37 mmol, 76%)

UPLC-MS (acidic method, 2 min): rt=1.22 min; m/z=451.2 $[M+H]^+$, peak area >92%

$^1H$ NMR (400 MHz, DMSO-$d_6$) δ 7.12-7.08 (m, 4H), 3.83 (s, 6H), 3.76 (s, 4H), 3.73 (s, 6H), 3.67 (s, 6H). 3,3'-(thiobis(methylene))bis(2,5-dimethoxybenzoic acid). A solution of Lithium hydroxide monohydrate (1.0 g, 23.83 mmol) in water (30.0 mL) was added to the solution of dimethyl 3,3'-(thiobis(methylene))bis(2,5-dimethoxybenzoate) (2.0 g, 4.44 mmol) in THF (100.0 mL). The reaction was stirred at ambient temperature for 48 h. After completion, water (100 mL) was added to the reaction and the mixture was washed with ethyl acetate (100 mL). The aqueous layer was acidified with a 1 M aqueous hydrochloric acid to pH=2 and extracted with ethyl acetate (3×100 mL). The organic layers were collected, dried ($Na_2SO_4$), filtered and concentrated to give 3,3'-(thiobis(methylene))bis(2,5-dimethoxybenzoic acid) as a brown solid (1.91 g, 4.11 mmol, 93%)

UPLC-MS (acidic method, 2 min): rt=0.93 min; m/z=421.1 $[M-H]^-$, peak area >95%

$^1H$ NMR (400 MHz, DMSO-$d_6$) δ 12.96 (s, 2H), 7.10 (d, J 3.3 Hz, 2H), 7.08 (d, J 3.2 Hz, 2H), 3.76 (s, 4H), 3.73 (s, 6H), 3.69 (s, 6H). 3-[(2,5-Dihydroxy-3-carboxyphenyl) methylthiomethyl]-2,5-dihydroxybenzoic acid. To a solution of preceding thioether (5.0 g, 0.01 mol) in DCM (200.0 mL) was added slowly a 1M solution of tribromoborane in DCM (100.7 mL, 0.101 mol) at 0 °C and the reaction mixture was refluxed for 48 h.

After this time, the solid was filtered, washed with DCM (500 mL) and then suspended in a solution of 1M hydrochloric acid (50 mL). The resulting mixture was refluxed for 2 h. The resulting brown suspension was filtered and dried to give the crude product, which was purified by reverse phase column chromatography (25 g, MeCN:$H_2O$ 5% to 95% over 12 CV) to yield 2,5-dihydroxy-3-[(2,5-dihydroxy-3-carboxyphenyl)methylthiomethyl]benzoic acid as white solid (1.1 g, 0.003 mol, 26%).

UPLC-MS (acidic method, 2 min): rt=0.70 min; m/z=365.1 $[M-H]^-$, peak area >95%

$^1H$ NMR (400 MHz, DMSO-$d_6$) δ 13.86 (s, 2H), 11.09 (s, 2H), 9.14 (s, 2H), 7.08 (d, J=3.1 Hz, 2H), 7.02 (d, J=3.1 Hz, 2H), 3.65 (s, 4H).

Example 62) 3-((2,5-Dihydroxy-3-carboxyphenyl)methylthiomethyl)-2,5-dihydroxybenzoic acid, compound IVc-058a UPLC-MS (acidic method, 2 min): rt=0.70 min; m/z=365.1 $[M-H]^-$, peak area >95%

$^1H$ NMR (400 MHz, DMSO-$d_6$) δ 13.86 (s, 2H), 11.09 (s, 2H), 9.14 (s, 2H), 7.08 (d, J=3.1 Hz, 2H), 7.02 (d, J=3.1 Hz, 2H), 3.65 (s, 4H).

HRMS: $[M+H]^+$, calc. for $C_{16}H_{15}O_8S$: 367.04822, found: 367.04734

Biodata: IVc-058a: FGF-1 IC50 [μM]=36; FGF-2 IC50 [μM]=4.9; VEGF-A1 IC50 [μM]=83; VEGFR-Phosphorylation inhibition IC50 [μM]=0.53; PMN ROS [inhibition at 0.3 μM [%]=77.04; PMN ROS inhibition IC50 [μM]=0.29; Neutrophil adhesion inhibition [%]=43.5; Whole Blood: GM-CSF IC50 [μM]=>100; IFNγ IC50 [μM]=10.6; IL-1β IC50 [μM]=27.5; IL-2 IC50 [μM]=3.82; IL-4 IC50 [μM]=>100; IL-5 IC50 [μM]=>100; IL-6 IC50 [μM]=0.21; IL-9 IC50 [μM]=31.1; IL-10 IC50 [μM]=16.4; IL-12p70 IC50 [μM]=4.23; IL-13 IC50 [μM]=55.9; IL-17A IC50 [μM]=0.1; IL-17F IC50 [μM]=86.8; IL-18 IC50 [μM]=>100; IL-21 IC50 [μM]=3.2; IL-33 IC50 [μM]=33.9; TGFβ IC50 [μM]=>100; TNF α IC50 [μM]=0.18; TNF β IC50 [μM]=59.3.

Scheme 23: X = $SO_2$

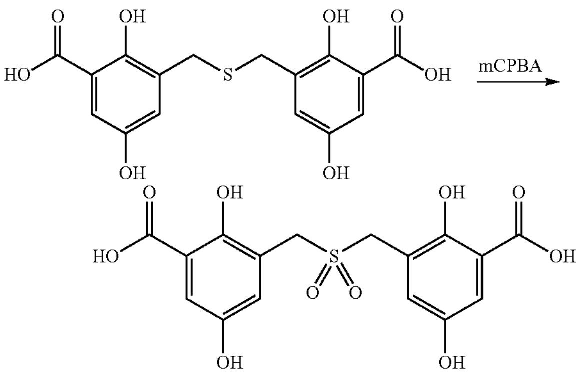

Synthesis from Compound IVc-058a 3-((2,5-Dihydroxy-3-carboxyphenyl)methylsulfonylmethyl)-2,5-dihydroxybenzoic acid. To a solution of thioether IVc-058a (4.25 g, 9.28 mmol) in DMF (20.0 mL) was added slowly a solution of 3-chlorobenzene-1-carboperoxy acid (mCPBA purity grade <77%, 5.80 g, 25.88 mmol) in DMF (20.0 mL). The reaction mixture was stirred for 18 h at ambient temperature. The crude product was submitted for HPLC purification (see general conditions) to give a white solid (3.20 g) which was triturated with 1M HCl (50 mL) to yield the desired product as white solid (2.55 g, 6.40 mmol, 56%)

UPLC-MS (acidic method, 4 min): rt=0.68 min; m/z=397.1 $[M-H]^-$, peak area >95%

63) 3-((2,5-Dihydroxy-3-carboxyphenyl)methylsulfonylmethyl)-2,5-dihydroxybenzoic acid, compound IVc-059a UPLC-MS (acidic method, 4 min): rt=0.68 min; m/z=397.1 $[M-H]^-$, peak area >95%

$^1H$ NMR (400 MHz, DMSO-$d_6$) δ 11.24 (s, 1H), 9.32 (s, 1H), 7.21 (d, J=3.1 Hz, 1H), 7.09 (d, J=3.1 Hz, 1H), 4.44 (s, 2H).

$^{13}C$ NMR (100 MHz, DMSO-$d_6$) δ 172.4, 153.4, 149.2, 117.4, 116.1 (CH), 113.3 (CH), 53.6 ($CH_2$).

HRMS: $[M+H]^+$, calc. for $C_{16}H_{15}O_{10}S$: 399.03804, found: 399.03775

Biodata: IVc-059a: FGF-1 IC50 [μM]=6.7; FGF-2 IC50 [μM]=2.7; VEGF-A1 IC50 [μM]=12; VEGFR-Phosphorylation inhibition IC50 [μM]=4.8; PMN ROS [inhibition at 0.3 μM [%]=74; PMN ROS inhibition IC50 [μM]=0.147; Neutrophil adhesion inhibition [%]=10; Whole Blood: GM-CSF IC50 [μM]=>100; IFNγ IC50 [μM]=4.34; IL-1β IC50 [μM]=38.6; IL-2 IC50 [μM]=21.2; IL-4 IC50 [μM]=>100; IL-5 IC50 [μM]=>100; IL-6 IC50 [μM]=0.11; IL-9 IC50 [μM]=0.4; IL-10 IC50 [μM]=1.31; IL-12p70 IC50 [μM]=42; IL-13 IC50 [μM]=>100; IL-17A IC50 [μM]=0.16; IL-17F IC50 [μM]=>100; IL-18 IC50 [μM]=>100; IL-21 IC50 [μM]=1.87; IL-33 IC50 [μM]=27.5; TGFβ IC50 [μM]=>100; TNF α IC50 [μM]=0.16; TNF β IC50 [μM]=0.33

Dimethyl Ester

UPLC-MS (acidic method, 2 min): rt=0.94 min; m/z=427.1 $[M+H]^+$, peak area >95%

$^1H$ NMR (400 MHz, DMSO-$d_6$) δ 10.28 (s, 2H), 9.43 (s, 2H), 7.21 (d, J=3.1 Hz, 2H), 7.13 (d, J=3.1 Hz, 2H), 4.47 (s, 4H), 3.91 (s, 6H).

HRMS: $[M+H]^+$, calc. for $C_{18}H_{19}O_{10}S$: 427.06934, found: 427.06942

Biodata: IVc-059a-E2: FGF-1 IC50 [μM]=78; FGF-2 IC50 [μM]=94; VEGF-A1 IC50 [μM]=200; VEGFR-Phosphorylation inhibition IC50 [μM]=2.7; PMN ROS [inhibition at 0.3 μM [%]=45.67; PMN ROS inhibition IC50 [μM]=2.64; Neutrophil adhesion inhibition [%]=50.5 Dimethyl ester tetraacetate UPLC-MS (acidic method, 2 min): rt=1.05 min; m/z=593.1 $[M-H]^-$, peak area >95%

$^1H$ NMR (400 MHz, DMSO-$d_6$) δ 7.75 (d, J=2.8 Hz, 2H), 7.53 (d, J=2.9 Hz, 2H), 4.65 (s, 4H), 3.81 (s, 6H), 2.31 (s, 6H), 2.23 (s, 6H).

HRMS: $[M+H]^+$, calc. for $C_{26}H_{27}O_{14}S$: 595.11160, found: 595.11149

Biodata: IVc-059a-E2-A4: FGF-1 IC50 [μM]=54; FGF-2 IC50 [μM]=200; VEGF-A1 IC50 [μM]=25; VEGFR-Phosphorylation inhibition IC50 [μM]=ND; PMN ROS [inhibition at 0.3 μM [%]=29.17; PMN ROS inhibition IC50 [μM]=4.13; Neutrophil adhesion inhibition [%]=87.5; Whole Blood: GM-CSF IC50 [μM]=1.83; IFNγ IC50 [μM]=3.5; IL-1β IC50 [μM]=14.1; IL-2 IC50 [μM]=10.4; IL-4 IC50 [μM]=>100; IL-5 IC50 [μM]=>100; IL-6 IC50 [μM]=0.99; IL-9 IC50 [μM]=2.9; IL-10 IC50 [μM]=16.8; IL-12p70 IC50 [μM]=51.4; IL-13 IC50 [μM]=18.7; IL-17A IC50 [μM]=0.02; IL-17F IC50 [μM]=25.8; IL-18 IC50 [μM]= >100; IL-21 IC50 [μM]=>100; IL-33 IC50 [μM]=23.2; TGFβ IC50 [μM]=>100; TNFα IC50 [μM]=0.3; TNF β IC50 [μM]=19.4

Alternative, Scalable Synthesis of IVc-059a

Scheme 24: synthesis of IVc-059a from 2, 5-dibenzyloxyphthalaldehyde

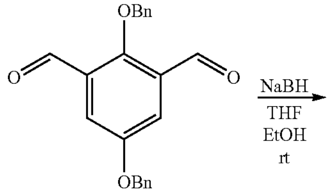

-continued

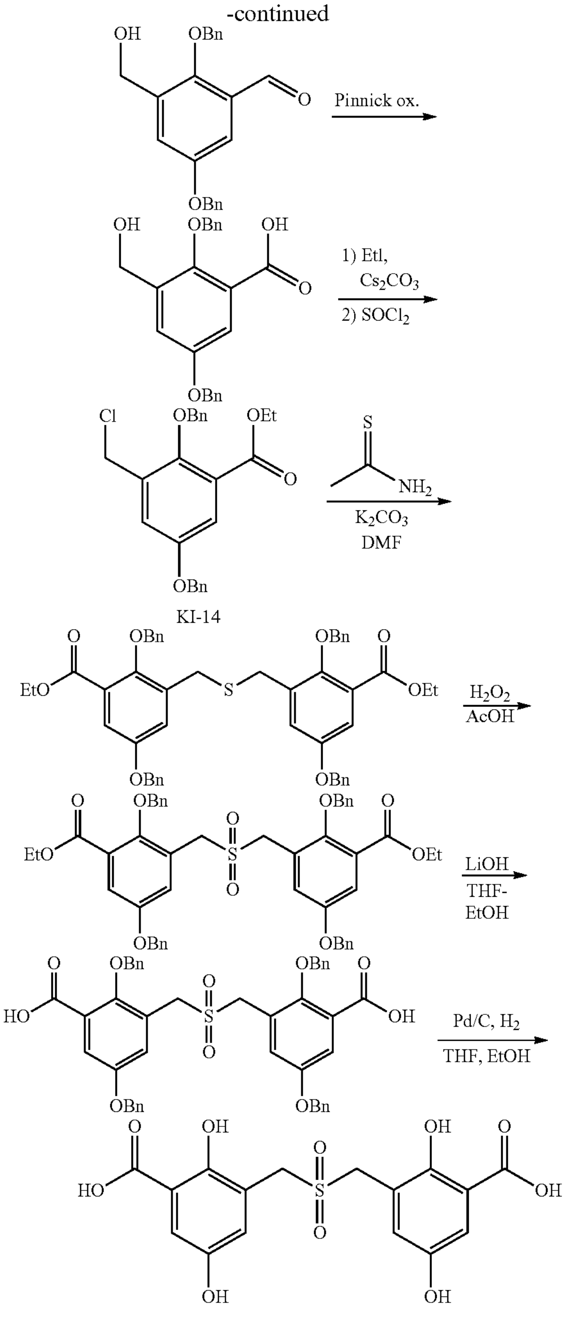

IVc-059a 2,5-Bis(benzyloxy)-3-(hydroxymethyl)benzaldehyde [Step 1]: 2,5-Bis(benzyloxy)-isophthalaldehyde (25.0 g, 72.1 mmol) (see Scheme 9b) was dissolved in THF (150 mL) and EtOH (15 mL) was added. The brown solution was kept under positive flow of nitrogen and stirred at r.t for 10 min then solid NaBH4 (695 mg, 18.37 mmol) was added portion-wise over 20 min, the internal temperature of the reaction was not allowed to exceed 25 °C. (water bath used). The reaction mixture was left to stir at r.t for 30 min then every 15 min additional $NaBH_4$ was added until complete conversion of the starting material (total: 107 mg, in two portions). The reaction mixture was then poured into water (1.2 L) and stirred for 20 min. The thus formed brown precipitate was isolated by filtration and the solid obtained was further dried in the vacuum oven at 40 °C until constant mass to afford the title compound (22.9 g, 76% corrected yield) as a brown oil. NMR profile showed 83% of desired product, 15% of over-reduced diol, 2% of starting material, the material was carried over to the next step without further purification.

UPLC-MS (acidic method, 2 min): r.t=1.19 min, 86%, m/z=347.2 [M−H]−

1H NMR (400 MHz, DMSO-d6) δ 10.11 (s, 1H), 7.52-7.28 (m, 11H), 7.19 (d, J=3.3 Hz, 1H), 5.34 (t, J=5.6 Hz, 1H), 5.15 (s, 2H), 4.99 (s, 2H), 4.60 (d, J=5.6 Hz, 2H).

2,5-Bis(benzyloxy)-3-(hydroxymethyl)benzoic acid [Step 2]: 2,5-Bis(benzyloxy)-3-(hydroxy-methyl)benzaldehyde (44.3 g, 103 mmol, 81% purity) and $KH_2PO_4$ (25.9 g, 190 mmol) were dissolved in acetone (440 mL) and water (130 mL). Resorcinol (21.0 g, 191 mmol) was added and the reaction mixture was stirred at r.t for 10 min. A solution of sodium chlorite (21.5 g, 191 mmol) in water (60 mL) was added slowly over 30 min, not allowing the internal temperature to go above 25 °C. The reaction mixture was stirred at r.t for 3 h and a 2 M aqueous solution of $H_3PO_4$ (95 mL) was added. The mixture was stirred for 20 min and cooled down to 6 °C with an ice bath before being filtered. The solid was further washed with water until the pH of the filtrate was ~6. The solid obtained was suspended in water (c.a. 300 mL) and a pre-cooled (5-10 °C) solution of NaOH (17 g, 412 mmol) in water (200 mL) was added. The suspension was stirred at r.t for 30 min before being filtered on a sinter funnel. The isolated solid was further washed with 1 M aqueous NaOH (2×50 mL) and water (50 mL). The alkaline liquor was then acidified using a 6N HCl aqueous solution pre-cooled (5-10 °C) until pH ~1. The resulting suspension was magnetically stirred for 20 min before being filtered, the solid obtained that was further dried in the vacuum oven at 40 °C until constant mass to yield the title compound as a light beige solid (34.8 g, 88%).

UPLC-MS (acidic method, 2 min): rt=1.06 min, 99%, m/z=363.2 $[M-H]^-$. 1H NMR (400 MHz, DMSO-d6) δ 13.02 (s, 1H), 7.51-7.31 (m, 10H), 7.28 (d, J=3.2 Hz, 1H), 7.22 (d, J=3.3 Hz, 1H), 5.21 (s, 1H), 5.12 (s, 2H), 4.88 (s, 2H), 4.53 (s, 2H).

Ethyl 2,5-bis(benzyloxy)-3-(hydroxymethyl)benzoate [Step 3]: 2,5-Bis(benzyloxy)-3-(hydroxy-methyl)benzoic acid (32.5 g, 89.3 mmol) and $Cs_2CO_3$ (32.3 g, 99.2 mmol) were suspended in DMF (200 mL) and ethyl iodide (9.0 mL, 112 mmol) was added to the reaction mixture. After stirring at r.t for 3 h the reaction mixture was poured into a saturated aqueous solution of NH4Cl (1 L) and solid NaCl (~30 g) was added. After stirring for 10 min, the material was extracted with EtOAc (2×500 mL). The gathered organic layer was washed with brine (2×500 mL), dried with sodium sulfate, filtered and concentrated under reduced pressure to give a brown oil residue (42.0 g, crude, 89.3 mmol). The crude material was carried over to the next step without further purification.

UPLC-MS (acidic method, 2 min): rt=1.24 min, 93%, m/z=weak ionisation. 1H NMR (400 MHz, DMSO-d6) δ 7.51-7.32 (m, 10H), 7.31 (d, J=3.3 Hz, 1H), 7.22 (d, J=3.3 Hz, 1H), 5.24 (t, J=5.6 Hz, 1H), 5.13 (s, 2H), 4.87 (s, 2H), 4.54 (d, J=5.6 Hz, 2H), 4.26 (q, J=7.1 Hz, 2H), 1.24 (t, J=7.1 Hz, 3H)

Ethyl 2,5-bis(benzyloxy)-3-(chloromethyl)benzoate (KI-14) [Step 4]: Ethyl 2,5-bis(benzyloxy)-3-(hydroxymethyl) benzoate (42 g crude material from previous step, 89.3 mmol) was dissolved in DCM (200 mL) under inert atmosphere ($N_2$), then $SOCl_2$ (9.8 mL, 133.9 mmol) was added at 0 °C. (ice bath) and the reaction mixture was allowed to warm up to r.t. After 2 h the volatiles were removed under reduced pressure followed by azeotrope distillation using toluene (3×100 mL) leading to a semi solid brown oil (38.0 g, crude, 89.3 mmol).

UPLC-MS (acidic method, 2 min): rt=1.40 min, 91%, m/z=weak ionisation. 1H NMR (400 MHz, DMSO-d6) δ 7.54-7.26 (m, 12H), 5.14 (s, 2H), 4.95 (s, 2H), 4.71 (s, 2H), 4.28 (q, J=7.1 Hz, 2H), 1.28-1.22 (t, J=7.1 Hz, 3H).

Bis(2,5-dibenzyloxy-3-ethoxycarbonylphenylmethyl)sulfide [Step 5]: To a solution of KI-14 (38.0 g, crude material, 89.3 mmol) in DMF (420 mL) was added thioacetamide (8.4 g, 111.8 mmol) followed by the addition of $K_2CO_3$— 325 Mesh (16.7 g, 120.8 mmol). The reaction was heated at 45 °C for 48 h. The reaction was cooled down to room temperature followed by addition of thioacetamide (2.5 g, 33.3 mmol) and $K_2CO_3$— 325 Mesh (5.0 g, 36.1 mmol) and further stirring at 45 °C for 18 h to complete the reaction. The reaction mixture was poured into water (4 L). The reaction mixture was stirred for 20 min before addition of EtOAc (2 L) followed by solid NaCl (~60 g). The phases were separated followed by additional extraction using EtOAc (1.5 L). The gathered organic layer was washed with Brine (1.5 L), dried over $Na_2SO_4$, filtered and concentrated under reduced pressure to give the crude title compound (39.8 g, 44.6 mmol) as a brown oil which was used in the following step without purification.

UPLCMS (acidic method, 2 min): rt=1.57 min, m/z=800.5 $[M+NH4]^+$, peak area 77%.

1H NMR (400 MHz, DMSO-d6) δ 7.46-7.17 (m, 24H), 5.05 (s, 4H), 4.83 (s, 4H), 4.23 (q, J=7.1 Hz, 4H), 3.73 (s, 4H), 1.20 (t, J=7.1 Hz, 6H).

Bis(2,5-dibenzyloxy-3-ethoxycarbonylphenylmethyl) sulfone [Step 6]: To a solution of Bis(2,5-dibenzyloxy-3-ethoxycarbonylphenylmethyl)sulfide (39.8 g crude, 44.6 mmol) in acetic acid (850 mL) was added slowly a 30% wt. solution of hydrogen peroxide (50 mL, 490 mmol). The reaction was stirred at r.t for 18 h. The reaction mixture was poured into ice/water (5 L) and stirred at room temperature for 30 min followed by addition of EtOAc (2 L) and solid NaCl (~40 g). After separation of the phases, the aqueous layer was extracted one more time with EtOAc (1 L). The gathered organic layer was washed with Brine (1.5 L), dried over $Na_2SO_4$, filtered and concentrated under reduced pressure to give a brown solid. The solid was suspended in MTBE (250 mL) and magnetically stirred for 30 min followed by filtration and further trituration with MTBE (150 mL) to yield the title compound (23.56 g, 28.9 mmol, 64% yield over 4 steps).

UPLC-MS (acidic method, 2 min): rt=1.48 min; m/z=832.5 $[M+NH4]^+$, peak area 96% 1H NMR (400 MHz, DMSO-d6) δ 7.50-7.24 (m, 24H), 5.08 (s, 4H), 4.85 (s, 4H), 4.50 (s, 4H), 4.26 (q, J=7.1 Hz, 4H), 1.25-1.17 (m, 6H).

Bis(2,5-dibenzyloxy-3-carboxyphenylmethyl)sulfone [Step 7]: A solution of lithium hydroxide (9.7 g, 233 mmol) in water (100 mL) was added to a solution of bis(2,5-dibenzyloxy-3-ethoxycarbonylphenylmethyl)sulfone (33.3 g, 38.8 mmol) in THF (350 mL) and the resulting mixture was stirred at reflux for 18 h. After this time, most of the THF was removed under reduced pressure leading to a white suspension. Upon addition of water (3 L) and aqueous solution of sodium hydroxide (1 M, 1 L) the mixture remains a suspension. The suspension was stirred at r.t for 18 h and the aqueous layer was acidified to pH~1 by addition of 6 M aqueous hydrochloric acid solution and the resultant solid was collected by filtration and washed with water, until the liquors were neutral, the thus obtained white solid was further dried in the vacuum oven at 40 °C until constant mass to give the title compound as a white solid (29.4 g, 38.7 mmol, 99%).

UPLC-MS (acidic method, 2 min): rt=1.39 min; m/z=757.1 $[M-H]^-$, peak area 100% 1H NMR (400 MHz, DMSO-d6) δ 13.23 (s, 2H), 7.47-7.25 (m, 24H), 5.08 (s, 4H), 4.88 (s, 4H), 4.48 (s, 4H).

Bis(2,5-dihydroxy-3-carboxyphenylmethyl)sulfone [Step 8], IVc-059a: To a suspension of bis(2,5-dibenzyloxy-3-carboxyphenylmethyl)sulfone (10.08 g, 13.28 mmol) in EtOH (140 mL) and THF (140 mL) was added palladium on charcoal (20% wt., 2 g) as a suspension in water (20 mL). After several vacuum/hydrogen cycles the mixture was maintained under an atmosphere of $H_2$ at 25 °C and stirred for 20 h. After completion, the mixture was filtered through Celite® using THF. The filtrate was concentrated under reduced pressure to give an off-white solid. The residue was then suspended in acetonitrile (100 mL) and heated to reflux under magnetic stirring, the mixture was then cooled down to −5 °C before being filtered and further washed cold acetonitrile. The product was further dried in the vacuum oven at 40 °C until constant mass to afford the desired product as a white solid (5.35 g, 12.78 mmol, 96%).

UPLC-MS (acidic method, 4 min): rt=0.67 min; m/z=397.1 $[M-H]^-$, peak area 100% NMR Data: see above.

Example 1.12—Molecules of type V: Reference compounds

Diamides Derived from 5-Hydroxyisophthalic Acid

2 Examples

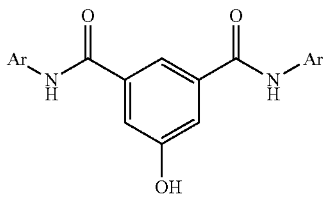

Synthetic Schemes and Procedures

Scheme 25: synthesis of V-001a

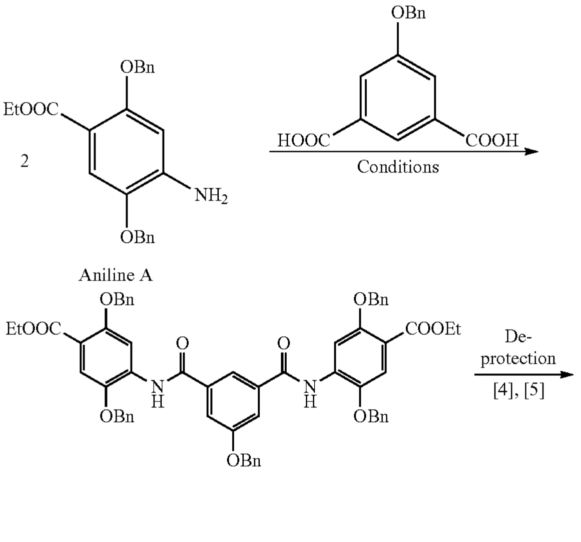

-continued

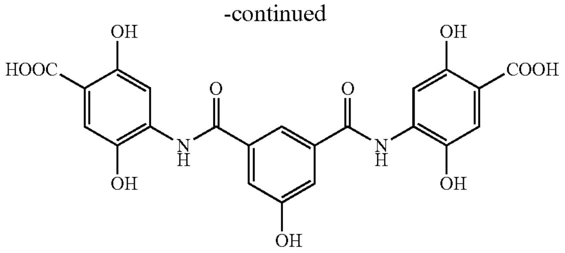

Formation of Amide Linkage

See General procedure B for Amide Coupling [3B1] using aniline A (2 moles) or methyl 5-aminosalicylate Deprotection procedures: See General procedures [4], [5]

For details see FIG. 8

For examples

V-001a

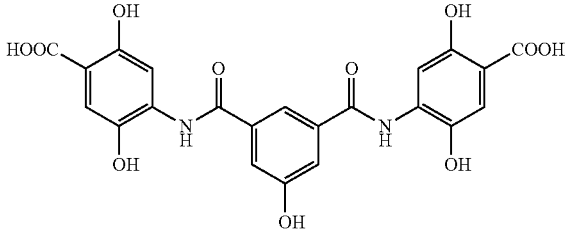

64) 5-Hydroxyisophthalic acid bis-N-(4-carboxy-2, 5-dihydroxyphenyl)amide (V-001a)

UPLC-MS (acidic method, 2 min): rt=0.72 min; m/z=483.0 $[M+H]^+$, peak area >95%

$^1$H NMR (400 MHz, DMSO-d6) δ 10.28 (s, 1H), 9.83 (s, 2H), 9.48 (s, 2H), 7.92 (s, 1H), 7.68 (s, 2H), 7.52 (d, J=1.5 Hz, 2H), 7.30 (s, 2H).

Diethyl Ester

UPLC-MS (acidic method, 2 min): rt=1.09 min; m/z=539.2 $[M-H]^-$, peak area 94%

$^1$H NMR (400 MHz, DMSO-d6) δ 10.23 (s, 2H), 9.92 (s, 2H), 9.49 (s, 2H), 7.91 (s, 1H), 7.73 (s, 2H), 7.51 (d, J=1.5 Hz, 2H), 7.32 (s, 2H), 4.35 (q, J=7.1 Hz, 4H), 1.34 (t, J=7.1 Hz, 6H).

V-002a

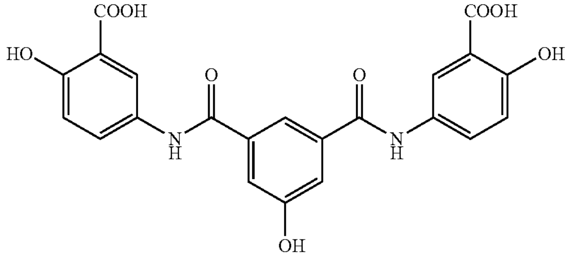

65) 5-Hydroxyisophthalic acid bis-N-(3-carboxy-4-hydroxyphenyl)amide (V-002a)

UPLC-MS (acidic method, 4 min): rt=1.00 min; m/z=451.1 $[M-H]^-$, peak area 97%

$^1$H NMR (400 MHz, DMSO-d6) δ 10.31 (s, 2H), 10.11 (s, 1H), 8.28 (d, J=2.7 Hz, 2H), 7.98 (m, 1H), 7.89 (dd, J=9.0, 2.7 Hz, 2H), 7.50 (d, J=1.5 Hz, 2H), 6.97 (d, J=9.0 Hz, 2H).

Urea-Linked Gentisic Acid Units 1 Example

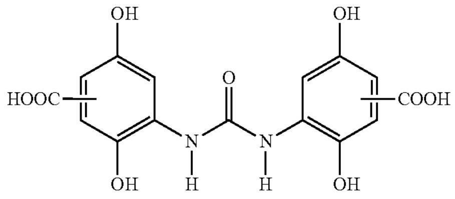

Synthetic Scheme and Procedures

Scheme 26: synthesis of V-003a

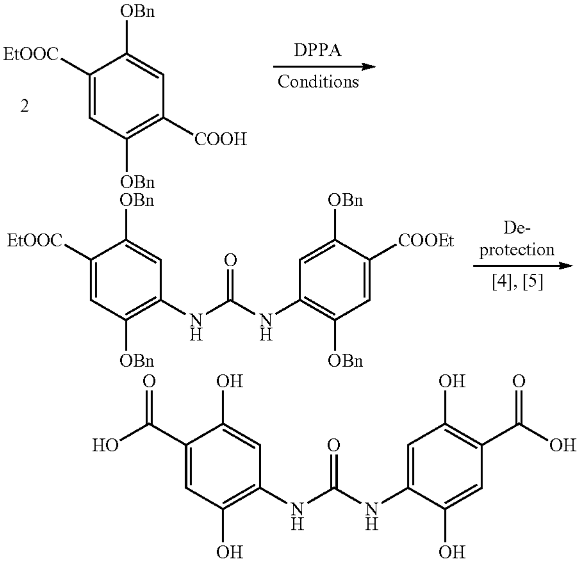

Formation of Urea Linkage

Procedure from KI-1:

N,N'-Bis(2,5-dibenzyloxy-4-ethoxycarbonylphenyl)urea. To a cooled solution (ice bath) of 2,5-bis(benzyloxy)-4-(ethoxycarbonyl)benzoic acid (KI-1) (2.0 g, 4.9 mmol) and $Et_3N$ (1.6 mL, 11.3 mmol) in THF (25 mL) under inert atmosphere ($N_2$), was slowly added DPPA (1.1 mL, 5.2 mmol). The mixture was slowly warmed up to r.t and stirred at this temperature for 3 h. Then tBuOH (8 mL) was added and the reaction mixture was stirred at r.t for 18 h. The reaction profile showed a majority of urea linkage product instead of the desired Boc-aniline. The mixture was poured into a saturated solution of sodium hydrogencarbonate (250 mL) and stirred for 5 min before being extracted with EtOAc (3×50 mL). The combined organic layers were dried over sodium sulfate, filtered, and concentrated under reduced pressure to give a colourless oil. The residue was purified by flash column chromatography (iso-Hexane/EtOAc 1:0 then gradient to 30% EtOAc) to yield the title compound (1.1 g, 56%) as an off-white solid.

UPLC-MS (basic method, 2 min): rt=1.50 min; m/z=781.2 $[M+H]^+$, peak area 85%

$^1$H NMR (400 MHz, DMSO-$d_6$) δ 9.49 (s, 2H), 8.18 (s, 2H), 7.58-7.45 (m, 8H), 7.43-7.35 (m, 8H), 7.35-7.28 (m, 6H), 5.27 (s, 4H), 5.11 (s, 4H), 4.22 (q, J=7.1 Hz, 4H), 1.24 (t, J=7.1 Hz, 6H).

Deprotection procedures: See General procedures [4], [5]
For details see FIG. 8
For example 66) N,N'-Bis(2,5-dihydroxy-4-carboxyphenyl)urea (V-003a)

V-003a

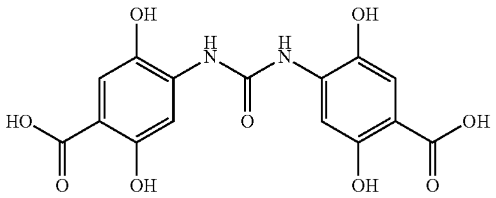

UPLC-MS (acidic method, 4 min): rt=0.90 min; m/z=363.1 $[M-H]^-$, peak area 93%

$^1$H NMR (400 MHz, DMSO-d6) δ 13.36 (s, 2H), 10.86 (s, 2H), 9.64 (s, 2H), 9.48 (s, 2H), 7.77 (s, 2H), 7.17 (s, 2H).

Diethyl Ester

UPLC-MS (acidic method, 4 min): rt=1.79 min; m/z=419.2 $[M-H]^-$, peak area 97%

$^1$H NMR (400 MHz, DMSO-d6) δ 10.26 (s, 2H), 9.74 (s, 2H), 9.53 (s, 2H), 7.81 (s, 2H), 7.20 (s, 2H), 4.32 (q, J=7.1 Hz, 4H), 1.33 (t, J=7.1 Hz, 6H).

Example 1.13: Formation of salts a) Solids.

General protocole: salts were obtained as solids by adding the appropriate number of equivalent of base to solutions or suspensions of the desired compounds in water, sonicating until full dissolution, adjusting if needed the pH to values between 7.0 and 7.4 by addition of aqueous HCl or excess base, then lyophilizing the solution. Alternatively certain salts could be obtained by dissolution in DMSO followed by precipitation with EtOH (IIc-007a). Solids were generated from the following bases: sodium hydroxide, diethylamine (DEA), lysine (Lys), meglumine (Meg), triethanolamine (TEA).

For examples: Sodium and diethylammonium (DEA) salts of Ic-007a, IIc-007a, IIIc-061a as solids were obtained according to the general protocole without adjusting the pH.

Approximate Solubilities in Water:

Ic-007a-DEA2: <10 mg/mL
Ic-007a-DEA3: >20 mg/mL
IIc-007a-DEA1: >10 mg/mL
IIc-007a-DEA2: >20 mg/mL
IIIc-061a-DEA3: >25 mg/mL

Stability of Free Acids and Salts as Solids:

The free acids Ic-007a, IIc-007a, IIIc-061a, and the following salts Ic-007a-DEA2, IIc-007a-DEA2, IIIc-061a-DEA3 were stable as solids for up to 56 d at temperatures of 4 °C, 20 °C and 40 °C; the salt Ic-007a-DEA3 was stable at the same temperatures for up to 36 d.

b) Solutions

General protocole: salts were obtained as solutions by adding the appropriate number of equivalent of base to solutions or suspensions of the desired compounds in water, sonicating until full dissolution, adjusting if needed the pH to values between 7.0 and 7.4 by addition of aqueous HCl or excess base. The following bases were investigated: ethylamine, triethylamine, ethylenediamine, diethanolamine, triethanolamine, choline, meglumine, lysine and arginine.

For examples:

Salts of Ic-007a:

Soluble salts were obtained with meglumine, lysine and diethanolamine after stirring the mixture for 2 d at 40 °C. A solid form of the Ic-007a-Lys2 salt was obtained from DMSO by precipitation with ethanol.

The salt was stable as a solution in water for at least 7 d at room temperature.

Salts of IIc-007a:

DEA1-salt: on small scale, the mono-diethylammonium salt was obtained by the general procedure without adjusting the pH. Solubility: 17.4 mg/mL vs 1.8 mg/mL for the parent diacid Large Scale Process and Characterization:

To IIc-007a (20 g, 42.7 mmol) was charged EtOH (200 ml). The reaction was stirred at RT to afford a slurry. DEA (4.4 ml, 42.7 mmol) was charged and the reaction heated at 50 °C for 2 h. The batch was cooled to RT and the solids filtered off. The filter cake was washed with EtOH (50 mL) and oven dried at 40 °C to afford 21.5 g mono-DEA salt as a yellow solid in a 98% yield. NMR: 1.6% EtOH, 1.04 eq DEA. HPLC: 99.6%.

The solid-state data for the mono-DEA salt of IIc-007a showed a clear crystalline pattern in the XRPD analysis. The TGA trace showed a loss of minor amount of EtOH<120 °C indicating that the EtOH may be dried off at 60-80 °C. One then observed the loss of the DEA (theory 13.5% wt for 1:1 salt) associated with the melt endotherm in the DSC (peak at 273.8 °C), followed by a melt of the free acid form.

DEA2-salt, pH adjusted: obtained by the general procedure with pH adjustment (0.51 additional equiv of $Et_2NH$ required to reach pH=7.25). The salt in solution exhibits clear degradation after 21 d at 40 °C, and extensive degradation after 24 h at 80 °C.

DEA2-salt, pH not adjusted: obtained by the general procedure without pH adjustment. pH of solution=5.87. The salt in solution exhibited no degradation after 21 d at 4 °C, 20 °C, and 40 °C.

Lys2-salt, pH not adjusted: obtained by the general procedure using 2 equiv of L-lysine. pH of solution=5.74.

NOTE: by analogy with the bis (N-methyl)amide of 2-hydroxyisophthalic acid (pKa of phenol=6.81), the 2-OH group of the isophthalic bis-amide core of IIc-007a is remarkably acidic and its ionization leads to degradation of the molecule. This effect is not observed for Ic-007a (expected pKa of the phenolic functions in the range of 9.8-10.0). Thus it is important not to adjust the pH of solutions of dicationic salts of IIc-007a.

Salts of IIIc-061a:

DEA3-salt, pH adjusted: obtained by the general procedure using 3 equiv of $Et_2NH$ with pH adjustment (0.8 additional equiv of HCl (0.5 M) required to reach final pH=7.22). The salt in solution exhibited no degradation after 21 d at 4 °C, 20 °C, and slight degradation at 40 °C after 33 d.

Meg3-salt, pH adjusted: obtained by the general procedure using 3 equiv of meglumine with pH adjustment to reach final pH=7.22 (HCl 0.5M). The salt in solution exhibited no degradation after 21 d at 4 °C, 20 °C, and 40 °C after 14 d.

Salts of IVc-059a,

DEA2-salt, pH adjusted: obtained by the general procedure with pH adjustment (0.32 additional equiv of $Et_2NH$ required to reach pH=7.3). The salt in solution exhibits stability after 26 d at 4 °C, 20 °C and 40 °C.

Example 1.14: Prodrugs

Prodrugs of Ic-007a 1) 2-Morpholinoethyl 5-[[2,5-dihydroxy-4-[[4-hydroxy-3-(2-morpholinoethoxycarbonyl) phenyl]carbamoyl]benzoyl]amino]-2-hydroxy-benzoate (Ic-007a-mpe2)

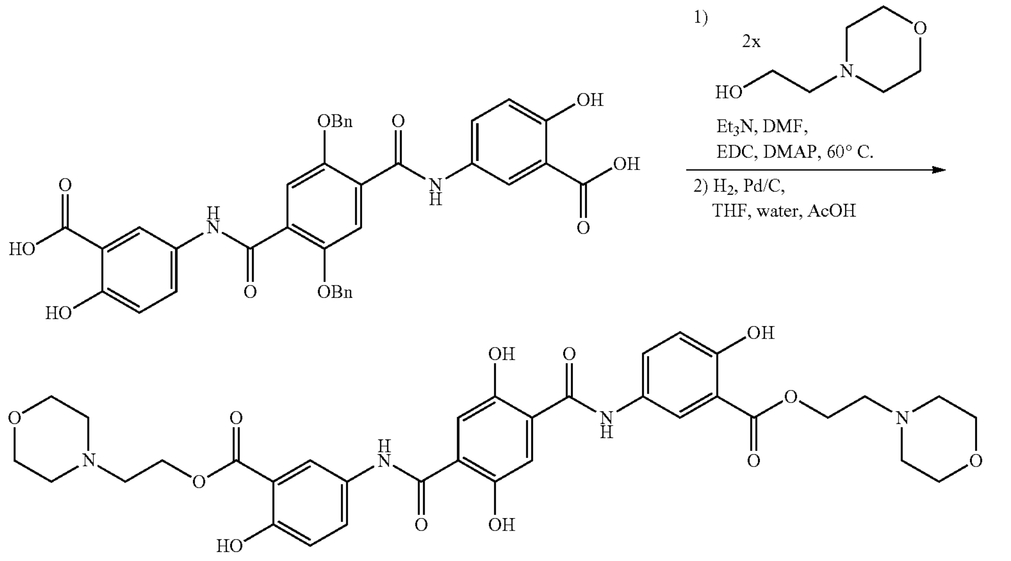

Esterification. A suspension of 5-[[2,5-dibenzyloxy-4-[(3-carboxy-4-hydroxyphenyl) carbamoyl]-benzoyl]amino]-2-hydroxy-benzoic acid (130 mg, 0.2 mmol) in N,N-dimethylformamide (4 ml) was stirred at room temperature. N,N-dimethylpyridin-4-amine (49 mg, 0.4 mmol) and a solution of 2-morpholinoethanol (53 mg, 0.4 mmol) in N,N-dimethylformamide (0.5 ml) was added. 1-Ethyl-3-(3-dimethylaminopropyl)carbodiimide hydrochloride (115 mg, 0.6 mmol) was added and the reaction mixture was heated in a microwave reactor at 60 °C for 1.5 hours. The reaction mixture was filtered, the filtrate was diluted with tetrahydrofuran and the solvent was evaporated. The residue purified by silica gel chromatography eluting with 0-40% methanol in dichloromethane to give the title product as a white solid (80 mg, 45%). LCMS (m/z) [M+H] 875.1.

Hydrogenolysis: A solution of the diester obtained above (80 mg, 0.092 mmol) in tetrahydrofuran (12 ml) and water (4 ml) was prepared and 10% palladium on carbon (50 mg, 10% paste) was added. The reaction mixture was stirred under a hydrogen atmosphere for 17 hours. The catalyst was removed by filtration and the solvent evaporated. The residue was purified by reverse phase preparative HPLC on a C18 column using a gradient of 10-97% (acetonitrile+0.1% formic acid):(water+0.1% formic acid). The residue was triturated with diethyl ether and dried under vacuum to yield the title product Ic-007a-mpe2 as a yellow solid (22 mg, 35%).

$^1$H NMR (d6-DMSO ppm) δ 11.16-11.00 (br s, 1H), 10.46 (s, 1H), 10.45-10.15 (br s, 1H), 8.25 (d, J=2.7 Hz, 1H), 7.77 (dd, J=9.0, 2.7 Hz, 1H), 7.53 (s, 1H), 7.01 (d, J=9.0 Hz, 1H), 4.46 (t, J=5.4 Hz, 2H), 3.62-3.56 (m, 4H), 2.77-2.69 (m, 2H), 2.56-2.50 (m, 4H, partly obscured by DMSO peak). LCMS (m/z) [M+H] 695.0.

2) 5-[[2,5-Dihydroxy-4-[[4-hydroxy-3-(2-morpholinoethoxycarbonyl)phenyl]carbamoyl]benzoyl] amino]-2-hydroxy-benzoic acid (Ic-007a-mpe1)

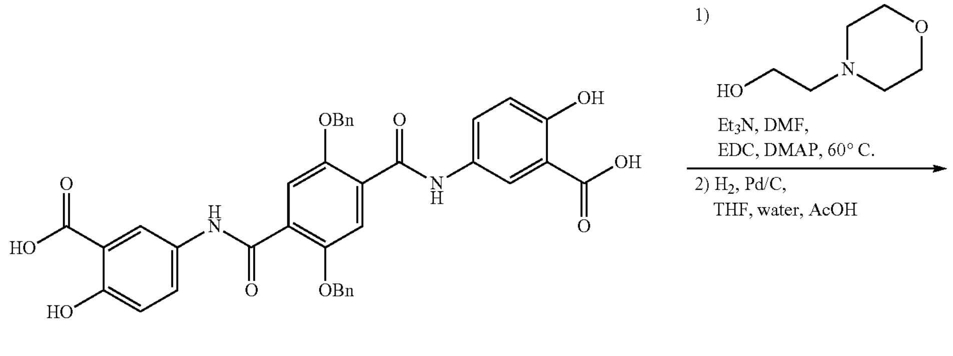

-continued

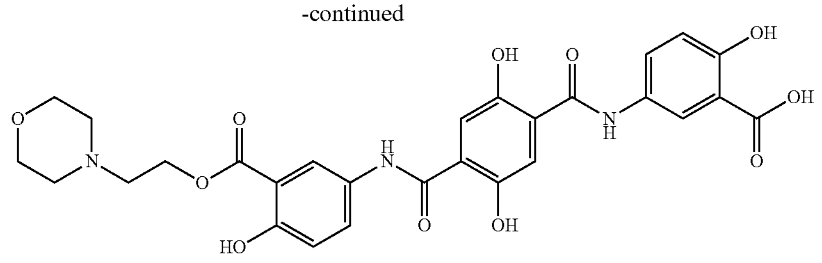

Esterification. A solution of 5-[[2,5-dibenzyloxy-4-[(3-carboxy-4-hydroxy-phenyl)-carbamoyl]benzoyl]amino]-2-hydroxy-benzoic acid (324 mg, 0.5 mmol) and triethylamine (101 mg, 0.15 ml, 1 mmol) in N,N-dimethylformamide (7 ml) was stirred at room temperature. A solution of 2-morpholinoethanol (66 mg, 0.5 mmol) in N,N-dimethylformamide (1 ml) and N,N-dimethylpyridin-4-amine (122 mg, 1 mmol) was added. 1-Ethyl-3-(3-dimethylaminopropyl)carbodiimide hydrochloride (115 mg, 0.6 mmol) was added and the reaction mixture was stirred at room temperature for 2 hours was then heated in a microwave at 60 °C for 4 hours. The reaction was repeated on a similar scale and the reaction mixtures combined. The solvent was evaporated and the residue was triturated with diethyl ether to give a mixture of the mono and diester (230 mg). LCMS (m/z) [M+H] 762.0 (mono ester).

Hydrogenolysis. The mixture of mono and diester (230 mg) obtained above was dissolved in acetic acid (10 ml), tetrahydrofuran (15 ml) and water (5 ml) and 10% palladium on carbon (150 mg, 10% paste) was added. The reaction mixture was stirred under a hydrogen atmosphere for 16 hours. The catalyst was removed by filtration and the solvent evaporated to give a yellow gum (140 mg). The residue was purified by reverse phase preparative HPLC on a C18 column using a gradient of 10-70% (acetonitrile+0.1% formic acid):(water+0.1% formic acid). The residue was triturated with diethyl ether and dried under vacuum to yield the title monoester Ic-007a-mpe1 as a yellow solid (11 mg).

$^1$H NMR (d6-DMSO ppm) δ 11.33-11.29 (br s, 1H), 11.13-10.08 (br s, 1H), 10.50-10.44 (br s, 2H), 10.36-10.30 (br s, 1H), 8.25 (d, J=2.4 Hz, 1H), 8.06-8.02 (m, 1H), 7.78 (dd, J=9.0, 2.4 Hz, 1H), 7.69-7.60 (m, 2H), 7.52 (s, 1H), 7.01 (d, J=9.0 Hz, 1H), 6.75 (d, J=8.7 Hz, 1H), 4.50-4.45 (m, 2H), 3.65-3.55 (m, 4H), 2.81-2.71 (m, 2H), 2.60-2.50 (m, 4H, partially obscured by DMSO peak). LCMS (m/z) [M+H] 582.0.

3) 1-(2,2-dimethylpropanoyloxy)ethyl 5-[[4-[[3-[1-(2,2-dimethylpropanoyloxy)ethoxycarbonyl]-4-hydroxy-phenyl]carbamoyl]-2,5-dihydroxy-benzoyl]amino]-2-hydroxy-benzoate (Ic-007a-pive2) And 4) 5-[[4-[[3-[1-(2,2-dimethylpropanoyloxy)ethoxycarbonyl]-4-hydroxy-phenyl]carbamoyl]-2,5-dihydroxy-benzoyl]amino]-2-hydroxy-benzoic acid (Ic-007a-pive1)

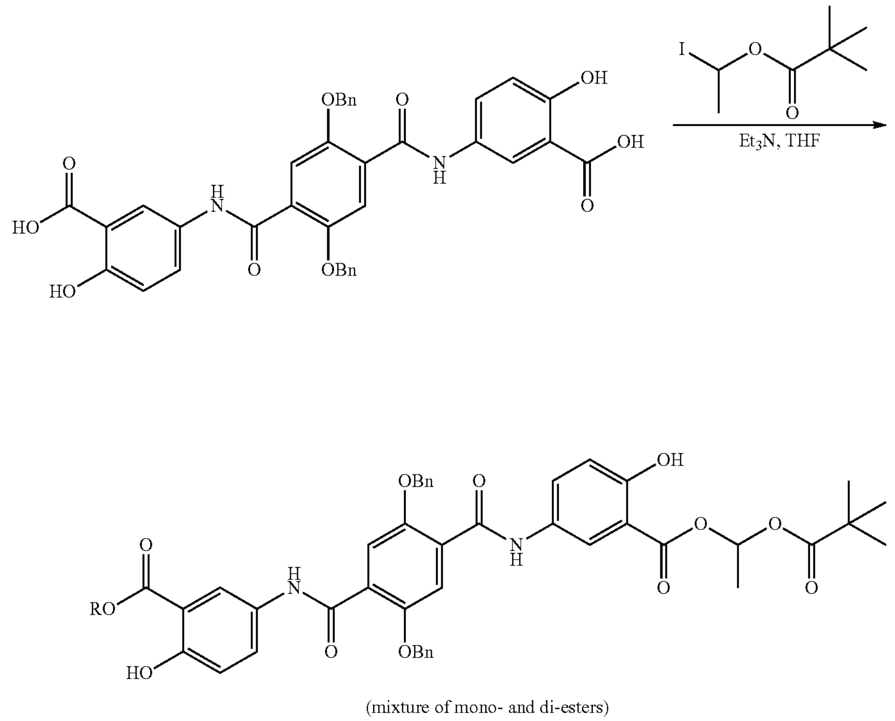

(mixture of mono- and di-esters)

Esterification. A solution of 5-[[2,5-dibenzyloxy-4-[(3-carboxy-4-hydroxy-phenyl)carbamoyl]benzoyl]amino]-2-hydroxy-benzoic acid (324 mg, 0.5 mmol) and triethylamine (152 mg, 0.21 mmol) in N,N-dimethylformamide (10 mL) was stirred at 0 °C and 1-iodoethyl 2,2-dimethylpropanoate (572 mg, 2 mmol) was added. The reaction mixture was allowed to warm to room temperature and stirred at room temperature for 24 hours. The dimethylformamide was evaporated and the residue was partitioned between dichloromethane and aqueous sodium metabisulfite. The organic phase was dried over anhydrous magnesium sulphate and evaporated to give a 1:1 mixture of the mono and diester (187 mg). The reaction was repeated and the 1:1 mixtures of esters combined. LCMS (m/z) [M+H] 777.0 (mono ester) and 905.1 (diester).

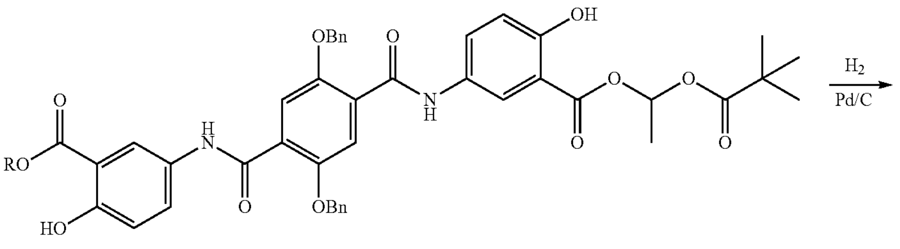

(mixture of mono- and di-esters)

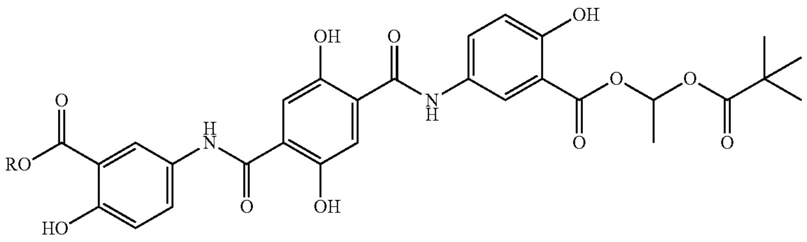

(mixture of mono- and di-esters)

Hydrogenolysis

The mixture of mono and diesters (320 mg) obtained above was dissolved in tetrahydrofuran (50 ml) and water (5 ml) and 10% palladium on carbon (300 mg, 10% paste) was added. The reaction mixture was stirred under a hydrogen atmosphere for 20 hours. The catalyst was removed by filtration and the solvent was evaporated. LCMS indicated only partial deprotection had been achieved. The residue was dissolved in tetrahydrofuran (36 ml) and water (6 ml) and 10% palladium on carbon (600 mg, 10% paste) was added. The reaction mixture was stirred under a hydrogen atmosphere for 22 hours. The catalyst was removed by filtration and the solvent was evaporated. The residue was purified by reverse phase preparative HPLC on a C18 column using a gradient of 40-97% (acetonitrile+0.1% formic acid):(water+0.1% formic acid). The residues were triturated with diethyl ether and dried under vacuum to yield the title products:

Diester (Ic-007a-pive2): yellow solid (60 mg). $^1$H NMR (d6-DMSO ppm) δ 11.05 (s, 1H), 10.46 (s, 1H), 10.18 (s, 1H), 8.18 (br s, 1H), 7.83-7.77 (m, 1H), 7.52 (s, 1H), 7.05-6.96 (m, 2H), 1.58 (d, J=5.5 Hz, 3H), 1.17 (s, 9H). LCMS (m/z) [M+H] 724.9.

Biodata: $T_{1/2}$ (mouse plasma): 62.2 min (ester cleaved; 65% remaining after 1 h); $T_{1/2}$ (human plasma): >180 min.

Monoester (Ic-007a-pive1): yellow solid (35 mg). $^1$H NMR (d6-DMSO ppm) δ 11.13 (s, 1H), 11.06 (s, 1H), 10.46 (s, 1H), 10.42 (s, 1H), 10.18 (s, 1H), 8.21-8.18 (m, 2H), 8.78-8.72 (m, 2H), 7.55 (s, 1H), 7.52 (s, 1H), 7.03-6.92 (m, 3H), 1.58 (d, J=5.5 Hz, 3H), 1.17 (s, 9H). LCMS (m/z) [M+H] 596.9

Biodata: $T_{1/2}$ (mouse plasma): 44.6 min (ester cleaved; 49% remaining after 1 h); $T_{1/2}$ (human plasma): >180 min.

Prodrugs of IIc-007a 1) 2,2-Dimethylpropanoyloxymethyl 5-[[3-[[3-(2,2-dimethylpropanoyloxymethoxycarbonyl)-4-hydroxy-phenyl]carbamoyl]-2,5-dihydroxy-benzoyl]amino]-2-hydroxy-benzoate (IIc-007a-pivm2)

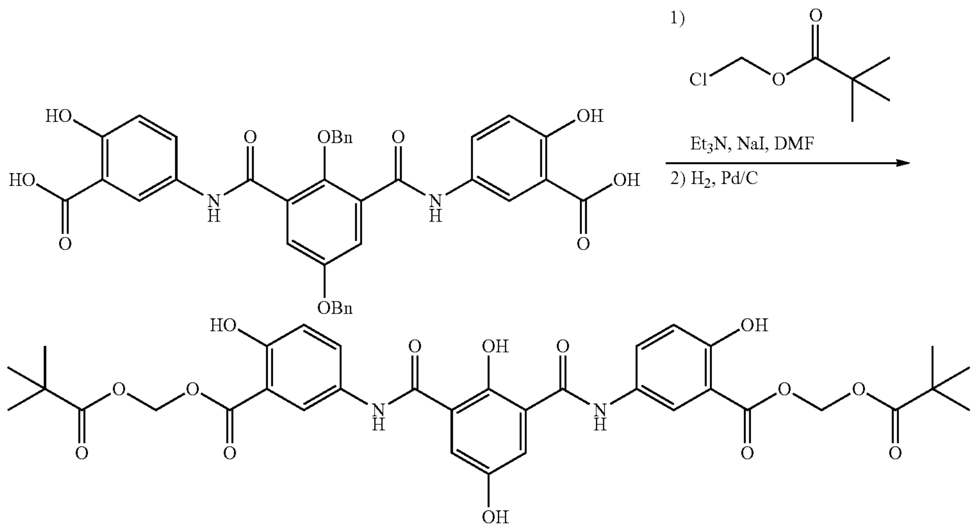

Esterification. A solution of 5-[[2,5-dibenzyloxy-3-[(3-carboxy-4-hydroxy-phenyl)carbamoyl]benzoyl]amino]-2-hydroxy-benzoic acid (280 mg, 0.432 mmol) in N,N-dimethyl formamide was prepared and chloromethyl 2,2-dimethylpropanoate (137 μL, 0.95 mmol) was added, followed by triethylamine (167 μL, 1.2 mmol)) and sodium iodide (143 mg, 0.95 mmol). The stirred solution was heated at 50 °C. for 18 hours. The solution was then cooled and partitioned between saturated ammonium chloride solution and ethyl acetate. The organic layer was dried over sodium sulfate, filtered and evaporated. The residue was purified by chromatography on a silica column using a gradient of 100% iso-hexane to 50% ethyl acetate, 50% iso-hexane to yield the diester as a colourless gum (192 mg, 51%). LCMS (m/z) [M+H] 876.9.

Hydrogenolysis: A solution of diester obtained above (192 mg, 0.219 mmol) in tetrahydrofuran (4.5 mL) was prepared and added to a stirred suspension of 10% palladium on carbon (40 mg, 0.04 mmol) in water (1.5 mL). The stirred reaction mixture was placed under a hydrogen atmosphere for 18 hours. The reaction was filtered to remove the catalyst and the solution was evaporated to give a cream solid (142 mg). The solid was purified by HPLC on a C18 column using a gradient of 60% acetonitrile, 40% water to 100% acetonitrile (0.1% formic acid) to give the title diester IIc-007a-pivm2 as a white solid (75 mg, 49%). $^{1}H$ NMR ($DMSO-D_6$ ppm) δ 13.03 (br s, 1H), 10.43 (br s, 2H), 10.16 (s, 2H), 9.52 (br s, 1H), 8.17 (d, J=2.7 Hz, 2H), 7.82 (dd, J=8.9 Hz, 2.7 Hz, 2H), 7.55 (s, 2H), 7.02 (d, J=8.9 Hz, 2H), 5.98 (s, 4H), 1.17 (s, 18H). LCMS (m/z) [M−H] 694.9.

2) 5-[[3-[[3-[1-(2,2-Dimethylpropanoyloxy)ethoxycarbonyl]-4-hydroxy-phenyl]carbamoyl]-2,5-dihydroxy-benzoyl]amino]-2-hydroxy-benzoic acid (IIc-007a-pivel)

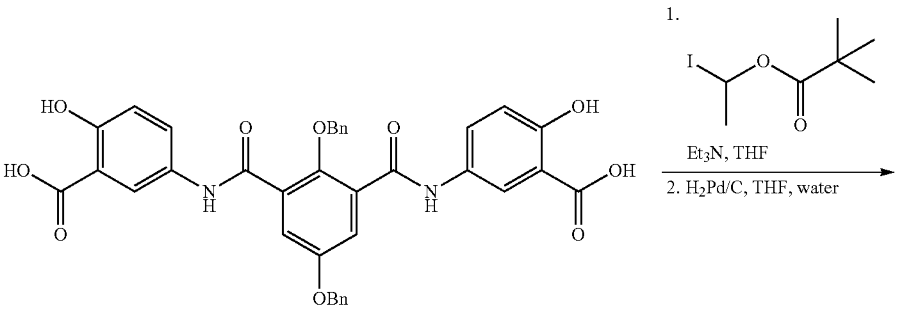

-continued

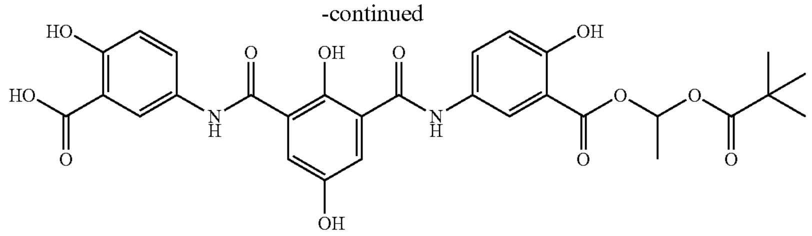

Esterification. A solution of 5-[[2,5-dibenzyloxy-3-[(3-carboxy-4-hydroxy-phenyl)carbamoyl]benzoyl]amino]-2-hydroxy-benzoic acid (324 mg, 0.5 mmol) and triethylamine (101 mg, 0.14 ml, 1.0 mmol) in N,N-dimethylformamide (10 ml) was stirred at 0 °C. 1-Iodoethyl 2,2-dimethylpropanoate (154 mg, 0.6 mmol) was added. The reaction mixture was stirred at room temperature for 21 hours. Additional triethylamine (0.14 ml, 1.0 mmol) and 1-iodoethyl 2,2-dimethylpropanoate (154 mg, 0.6 mmol) was added and the reaction mixture was stirred at r.t. for 1 hour. The solvent was evaporated. The residue was partitioned between dichloromethane and sodium metabisulfite solution. The organic extracts were combined, washed with brine and dried by passing the solution through a hydrophobic frit. The filtrate was evaporated to give a mixture of mono and diesters. The residue was purified by silica gel chromatography eluting with 5-100% ethyl acetate in iso-hexanes followed by 10% methanol in dichloromethane to give the mono ester as a yellow solid (121 mg). LCMS (m/z) [M+H] 777.

Hydrogenolysis. A solution of monoester obtained above (121 mg, 0.15 mmol) in tetrahydrofuran (16 ml) and water (4 ml) containing 10% palladium on carbon (250 mg, 10% paste) was stirred under a hydrogen atmosphere for 18 hours. The catalyst was removed by filtration and the solvent was evaporated. The residue was purified by reverse phase preparative HPLC using a gradient of 40-97% (acetonitrile+0.1% formic acid):(water+0.1% formic acid) to give the monoester IIc-007a-pivel as a yellow solid (34 mg). $^1$H NMR (DMSO-D6" ppm) δ 13.15 (br s, 1H), 10.47 (br s, 2H), 10.18 (s, 1H), 9.47 (br s, 1H), 8.21 (d, J=3 Hz 1H), 8.17 (d, J=3 Hz 1H), 7.82 (dd, J=9, 3 Hz 1H), 7.78 (dd, J=9, 3 Hz 1H), 7.59-7.55 (m, 2H), 7.03 (d, J=9 Hz 1H), 6.99 (q, J=5.4 Hz 1H), 7.96 (d, J=9 Hz 1H), 1.58 (d, J=5.4 Hz, 3H), 1.17 (s, 9H). LCMS (m/z) [M−H] 595.1.

Prodrugs of IVc-059a 1) 2,5-Dihydroxy-3-[[2,5-hydroxy-3-(2-morpholinoethoxycarbonyl)phenyl]methylsulfonyl-methyl]benzoic acid (IVc-059a-mpe1)

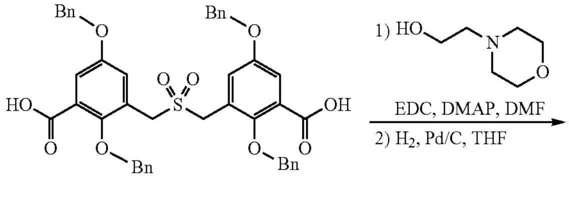

-continued

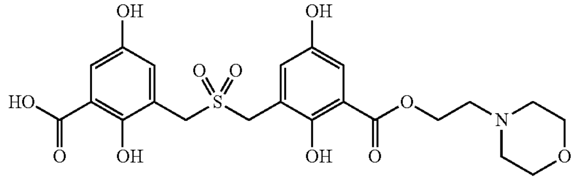

Esterification. A solution of 2,5-dibenzyloxy-3-[(2,5-dibenzyloxy-3-carboxyphenyl) methylsulfonyl-methyl]benzoic acid (300 mg, 0.40 mmol) and 2-morpholinoethanol (53 mg, 0.40 mmol) in N,N-dimethylformamide (93 mL) was prepared and 1-ethyl-3-(3-dimethylaminopropyl)carbodiimide (EDC, 93 mg, 0.48 mmol) and N,N-dimethylpyridin-4-amine (10 mg, 0.08 mmol) were added. The reaction mixture was stirred at room temperature for 18 hours. The resulting solution was evaporated to dryness and the residue was purified by HPLC on a C18 column using a gradient of 30% acetonitrile, 70% water to 100% acetonitrile (0.1% formic acid) to yield the morpholinoethyl ester as a colourless gum (111 mg, 32%). LCMS (m/z) [M+H] 872.1.

Hydrogenolysis. A solution of the above monoester (111 mg, 0.127 mmol) in tetrahydrofuran (3 mL) was added to a stirred suspension of 10% palladium on carbon (20 mg, 0.019 mmol) in water (1 mL). The stirred reaction mixture was placed under a hydrogen atmosphere for 18 hours. The reaction was filtered to remove the catalyst and the solution was evaporated to give a brown solid.

The solid was purified by HPLC on a C18 column using a gradient of 10% acetonitrile, 90% water to 60% acetonitrile, 40% water (0.1% formic acid) to give a white solid (20.5 mg). The solid was triturated with diethyl ether and dried under vacuum to yield the title product IVc-059a-mpel as a white solid (5 mg, 8%).

$^1$H NMR (DMSO-d6 ppm) δ 10.33 (br s, 1H), 9.30 (s, 1H) 8.92 (s, 1H), 7.08-7.15 (m, 3H), 6.91 (d, J=3.1 Hz, 1H), 4.40 (t, J=5.0 Hz, 2H), 4.36 (s, 2H), 3.65-3.72 (m, 4H), 3.05 (t, J=5.0 Hz, 2H), 2.78-2.87 (m, 4H). LCMS (m/z) [M+H] 511.9.

Biodata: stable up to 60 min in mouse plasma 2) 2,5-Dihydroxy-3-[[2,5-hydroxy-3-(2-morpholino-ethoxycarbonyl)phenyl]methylsulfonyl-methyl]benzoic acid 2-morpholinoethyl ester (IVc-059a-mpe2)

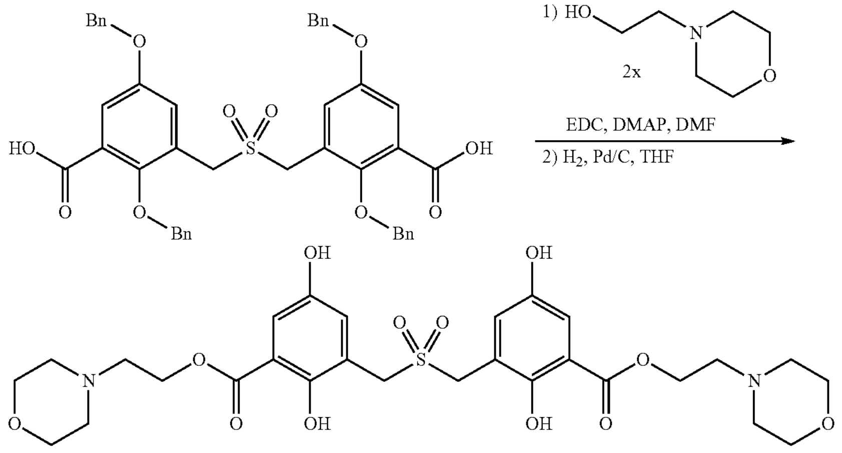

A solution of 2,5-dibenzyloxy-3-[(2,5-dibenzyloxy-3-carboxyphenyl)methylsulfonylmethyl]benzoic acid (69 mg, 0.091 mmol) and 2-morpholinoethanol (25 mg, 0.19 mmol) in N,N-dimethylformamide (1 mL) was prepared and 1-ethyl-3-(3-dimethylaminopropyl)carbodiimide (42 mg, 0.48 mmol) and N,N-dimethylpyridin-4-amine (5 mg, 0.04 mmol) were added. The reaction mixture was stirred at room temperature for 18 hours. The resulting solution was evaporated to dryness and the residue was purified by chromatography on a silica column using 10% methanol, 90% dichloromethane to yield the title product as a colourless gum (58 mg, 65%). LCMS (m/z) [M+H] 985.0.

A solution of the diester obtained above (58 mg, 0.059 mmol) in tetrahydrofuran (1.5 mL) was prepared and added to a stirred suspension of 10% palladium on carbon (5 mg, 0.005 mmol) in water (0.5 mL). The stirred reaction mixture was placed under a hydrogen atmosphere for 18 hours. The reaction was filtered to remove the catalyst and the solution was evaporated to give a brown solid. The solid was purified by HPLC on a C18 column using a gradient of 10% acetonitrile, 90% water to 60% acetonitrile, 40% water (0.1% formic acid) to give a white solid (13.7 mg).

The solid was triturated with diethyl ether and dried under vacuum to yield the title product IVc-059a-mpe2 as a white solid (9.1 mg, 25%).

$^1$H NMR ($CD_3OD$ ppm) δ 8.34 (br s, 2H), 7.32 (d, J=3.1 Hz, 2H), 7.16 (d, J=3.1 Hz, 2H), 4.52 (t, J=5.5 Hz, 4H), 4.45 (s, 4H), 3.68-3.73 (m, 8H), 2.83 (t, J=5.5 Hz, 4H), 2.58-2.65 (m, 8H). LCMS (m/z) [M+H]625.0.

Biodata: stable up to 60 min in mouse plasma; $T_{1/2}$ (human plasma): >180 min.

3) 3-[[3-[1-(2,2-Dimethylpropanoyloxy)ethoxycarbonyl]-2,5-dihydroxy-phenyl]methyl-sulfonyl-methyl]-2,5-dihydroxy-benzoic acid 1-(2,2-dimethylpropanoyloxy)ethyl ester (IVc-059a-pive2)

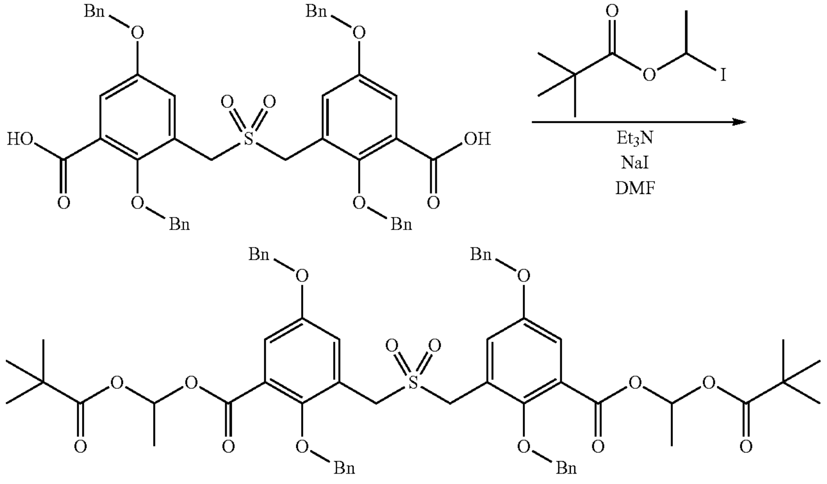

+

-continued

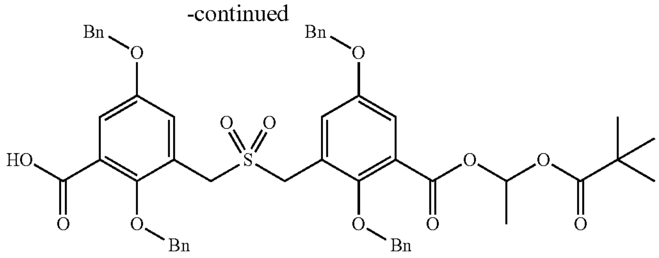

Esterifcation. A solution of 2,5-dibenzyloxy-3-[(2,5-dibenzyloxy-3-carboxy-phenyl)methyl-sulfonylmethyl]benzoic acid (200 mg, 0.263 mmol) in anhydrous N,N-dimethylformamide (5 mL) was prepared and triethylamine (88 μL, 0.63 mmol), sodium iodide (8 mg, 0.053 mmol) and crude 1-iodoethyl 2,2-dimethylpropanoate (ca. 4.2 mmol) were added. The reaction mixture was stirred at room temperature for 18 hours. The resulting solution was evaporated to a small volume and the residue was partitioned between dichloromethane and sodium thiosulfate solution. The organic layer was filtered through a hydrophobic frit and evaporated. The residue was purified by chromatography on a silica gel column eluting with a gradient of 100% iso-hexane to 50:50 ethyl acetate/iso-hexane to yield the di-ester as a colourless gum (110 mg, 41%). LCMS (m/z) [M+Na] 1037.0 The monoester was also isolated from the same column as a colourless gum (90 mg, 40%). LCMS (m/z) [M+Na] 909.6.

Hydrogenolysis:

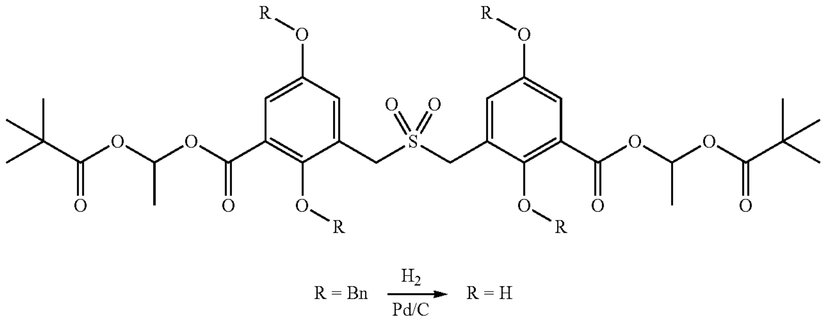

A solution of diester isolated above (110 mg, 0.108 mmol) in tetrahydrofuran (3 mL) was added to a stirred suspension of 10% palladium on carbon (20 mg, 0.02 mmol) in water (1 mL). The stirred reaction mixture was placed under a hydrogen atmosphere for 48 hours. The reaction mixture was filtered to remove the catalyst, the solution was evaporated and the residue was purified by chromatography on a silica column eluting with a gradient of 100% dichloromethane to 10% methanol, 90% dichloromethane to give the title product IVc-059a-pive2 as a cream solid (55 mg, 78%).

$^1H$ NMR ($CDCl_3$ ppm) δ 10.55 (s, 2H), 7.24-7.28 (m, 2H), 7.14-7.18 (m, 2H), 7.05 (q, J=5.4 Hz, 2H), 6.18 (br s, 2H), 4.30-4.50 (m, 4H), 1.60 (d, J=5.4 Hz, 6H), 1.21 (s, 18H). LCMS (m/z) [M−H] 653.9.

Biodata: hydrolyzed rapidly in mouse and human plasma 4) 3-[[3-[1-(2,2-Dimethylpropanoyloxy)ethoxycarbonyl]-2,5-dihydroxy-phenyl]methylsulfonylmethyl]-2,5-dihydroxy-benzoic acid (IVc-059a-pivel)

Hydrogenolysis:

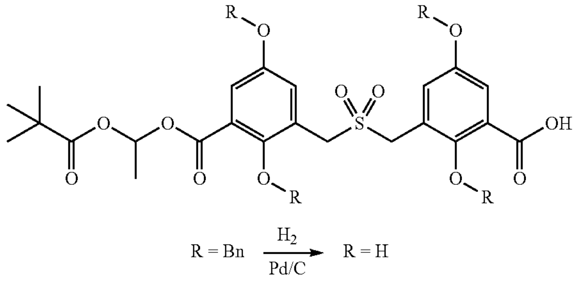

A solution of monoester isolated above (90 mg, 0.104 mmol) in tetrahydrofuran (3 mL) was added to a stirred suspension of 10% palladium on carbon (20 mg, 0.02 mmol) in water (1 mL). The stirred reaction mixture was placed under a hydrogen atmosphere for 48 hours. The reaction was filtered to remove the catalyst, the solution was evaporated and the residue was purified by chromatography on a silica column eluting with a gradient of 100% dichloromethane to 20% methanol, 80% dichloromethane to yield the title product IVc-059a-pivel as a cream solid (22.5 mg, 43%). 1H NMR ($CD_3OD$ ppm) δ 7.39 (d, J=3.1 Hz, 1H), 7.25 (d, J=3.1 Hz, 1H), 7.18 (d, J=3.1 Hz, 1H), 7.05 (q, J=5.4 Hz, 1H), 6.96 (d, J=3.1 Hz, 1H), 4.40-4.45 (m, 4H), 1.61 (d, J=5.4 Hz, 3H), 1.21 (s, 9H). LCMS (m/z) [M−H] 524.9.

Biodata: Hydrolyzed Rapidly in Mouse Plasma 5) 2,2-Dimethylpropanoyloxymethyl 2,5-dihydroxy-3-[[2,5-dihydroxy-3-(2,2-dimethyl-propanoyloxymethoxycarbonyl)phenyl]methylsulfonylmethyl] benzoate (IVc-059a-pivm2)

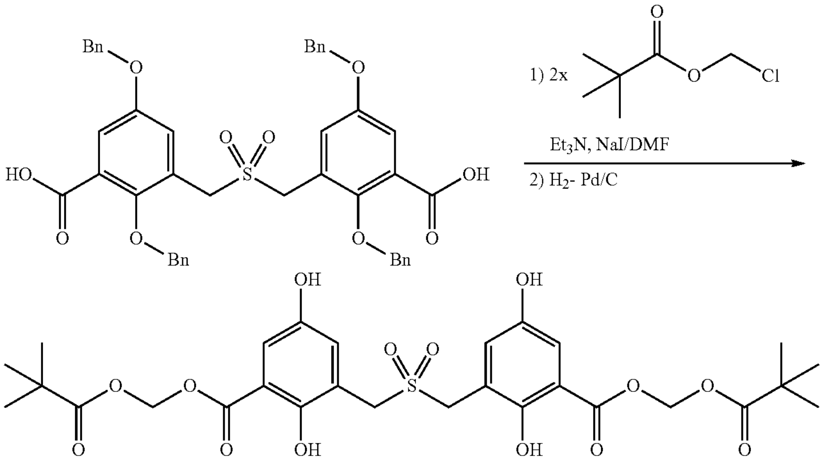

Esterification. A solution of 2,5-dibenzyloxy-3-[(2,5-dibenzyloxy-3-carboxy-phenyl) methylsulfonyl-methyl] benzoic acid (100 mg, 0.131 mmol) in anhydrous N,N-dimethylformamide (1 mL) was prepared and chloromethyl 2,2-dimethylpropanoate (91 μL, 0.631 mmol) was added followed by triethylamine (110 μL, 0.789 mmol) and sodium iodide (87 mg, 0.579 mmol). The reaction mixture was heated at 50 °C for 6.5 hours. The resulting solution was evaporated and the residue was partitioned between ethyl acetate and water. The organic layer was dried over sodium sulfate, filtered and evaporated. The residue was purified by chromatography on a silica gel column eluting with a gradient of 100% iso-hexane to 50% ethyl acetate, 50% iso-hexane to yield the diester product as a colourless gum (85 mg, 66%). LCMS (m/z) [M+Na] 1010.0.

Hydrogenolysis: A solution of diester obtained above (85 mg, 0.086 mmol) in tetrahydrofuran (3 mL) was added to a stirred suspension of 10% palladium on carbon (20 mg, 0.02 mmol) in water (1 mL). The stirred reaction mixture was placed under a hydrogen atmosphere for 18 hours. The reaction was filtered to remove the catalyst, the solution was evaporated and the residue was purified by chromatography on a silica gel column eluting with a gradient of 100% iso-hexane to 60% ethyl acetate, 40% iso-hexane to yield the diester IVc-059a-pivm2 as a white solid (31 mg, 57%).

$^1H$ NMR ($CDCl_3$ ppm) δ 7.29 (d, J=2.9 Hz, 2H), 7.19 (d, J=2.9 Hz, 2H), 5.97 (s, 4H), 4.42 (s, 4H), 1.22 (s, 18H). LCMS (m/z) [M−H] 624.8.

Biodata: hydrolyzed rapidly in mouse plasma, $T_{1/2}$=14.1 min; $T_{1/2}$ (human plasma): >180 min.

6) 2,5-Dihydroxy-3-[[2,5-dihydroxy-3-(2,2-dimethylpropanoyloxymethoxycarbonyl)phenyl]methylsulfonylmethyl]benzoic acid (IVc-059a-pivm1)

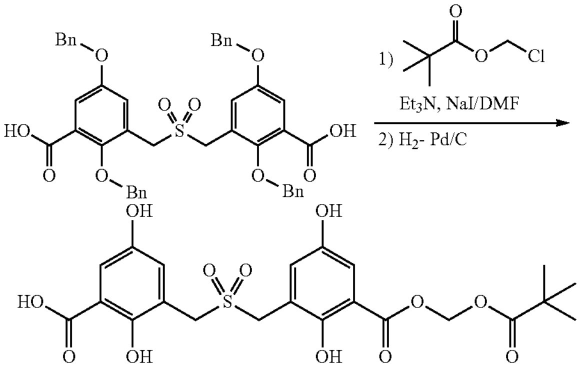

Esterification: A solution of 2,5-dibenzyloxy-3-[(2,5-dibenzyloxy-3-carboxyphenyl)methylsulfonyl methyl]benzoic acid (300 mg, 0.395 mmol) in anhydrous N,N-dimethylformamide (3 mL) was prepared and chloromethyl 2,2-dimethylpropanoate (57 μL, 0.395 mmol) was added followed by triethylamine (68 μL, 0.489 mmol) and sodium iodide (129 mg, 0.870 mmol). The reaction mixture was heated at 50 °C for 4 hours. The resulting solution was cooled, then evaporated. The residue was purified by chromatography on a silica column eluting with a gradient of 20% ethyl acetate, 80% iso-hexane to 80% ethyl acetate, 20% iso-hexane to yield the monoester product as a white solid (121 mg, 35%). LCMS (m/z) [M−H] 871.0.

Hydrogenolysis: A solution of monoester obtained above (121 mg, 0.138 mmol) in tetrahydrofuran (3 mL) was added to a stirred suspension of 10% palladium on carbon (20 mg, 0.02 mmol) in water (1 mL). The stirred reaction mixture was placed under a hydrogen atmosphere for 48 hours. The reaction was filtered to remove the catalyst, the solution was evaporated and the residue was purified by HPLC on a C18 column eluting with a gradient of 30% acetonitrile, 70% water to 100% acetonitrile (0.1% formic acid) to yield the monoester IVc-059a-pivm1 as a white solid (30 mg, 42%).

$^1H$ NMR ($CD_3OD$ ppm) δ 7.34 (d, J=3.0 Hz, 1H), 7.27 (d, J=3.1 Hz, 1H), 7.20 (d, J=3.1 Hz, 1H), 7.08 (d, J=3.0 Hz, 1H), 6.01 (s, 2H), 4.45 (s, 4H), 1.22 (s, 9H). LCMS (m/z) [M−H] 510.9.

Biodata: hydrolyzed rapidly in mouse plasma, $T_{1/2}$=6.7 min; $T_{1/2}$(human plasma): >180 min.

Example 2: General Experimental Methods

NMR Spectroscopy $^1H$ NMR spectra were recorded at 400 MHz on a Bruker Advance III NMR spectrometer. Samples were prepared in deuterated chloroform ($CDCl_3$) or dimethylsulphoxide (DMSO-$d_6$) and the raw data were processed using the Mnova NMR software. High-resolution mass spectra were recorded with a MaXis ESI qTOF ultrahigh-resolution mass spectrometer

UPLC-MS Analysis

UPLC-MS analysis was conducted on a Waters Acquity UPLC system consisting of an Acquity I-Class Sample Manager-FL, Acquity I-Class Binary Solvent Manager and Acquity I-Class UPLC Column Manager. UV detection was achieved using an Acquity I-Class UPLC PDA detector (scanning from 210-400 nm), whereas mass detection was achieved using an Acquity QDa detector (mass scanning from 100-1250 Da; positive and negative modes simultaneously). A Waters Acquity UPLC BEH C18 column (2.1×50 mm, 1.7 mm) was used to achieve the separation of the analytes.

Samples were prepared by dissolving (with or without sonication) into 1 mL of a 1:1 (v/v) mixture of MeCN in $H_2O$. The resulting solutions were filtered through a 0.45 m syringe filter before being submitted for analysis. All of the solvents (including formic acid and 36% ammonia solution) used were used as the HPLC grade.

Four different analytical methods were used for this work, the details of which are presented below. Acidic run (2 min): 0.1% v/v Formic acid in water [Eluent A]; 0.1% v/v Formic acid in MeCN [Eluent B]; Flow rate 0.8 mL/min; injection volume 2 L and 1.5 min equilibration time between samples.

TABLE 14

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Acidic run (4 min): 0.1% v/v formic acid in water [Eluent A]; 0.1% v/v formic acid in MeCN [Eluent B]; Flow rate 0.8 mL/min; injection volume 2 μL and 1.5 min equilibration time between samples.

TABLE 15

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Acidic run (6.5 min): 10 mM ammonium formate+0.1% v/v formic acid [Eluent A]; 0.1% v/v formic acid in MeCN [Eluent B]; Flow rate 0.6 mL/min; injection volume 2 μL.

TABLE 16

| Time (min) | Eluent A (%) | Eluent B (%) |
|---|---|---|
| 0.00 | 95 | 5 |
| 0.50 | 95 | 5 |
| 4.00 | 5 | 95 |
| 4.50 | 5 | 95 |
| 4.52 | 95 | 5 |
| 6.50 | 95 | 5 |

Basic run (2 min): 0.1% ammonia in water [Eluent A]; 0.1% ammonia in MeCN [Eluent B]; Flow rate 0.8 mL/min; injection volume 2 μL and 1.5 min equilibration time between samples.

TABLE 17

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic run (4 min): 0.1% ammonia in water [Eluent A]; 0.1% ammonia in MeCN [Eluent B]; Flow rate 0.8 mL/min; injection volume 2 µL and 1.5 min equilibration time between samples.

TABLE 18

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Basic run (6.5 min): 10 mM ammonium bicarbonate+ 0.1% v/v 35% ammonia solution [Eluent A]; 0.1% v/v formic acid in MeCN [Eluent B]; Flow rate 0.6 mL/min; injection volume 2 µL.

TABLE 19

| Time (min) | Eluent A (%) | Eluent B (%) |
|---|---|---|
| 0.00 | 95 | 5 |
| 0.50 | 95 | 5 |
| 4.00 | 5 | 95 |
| 4.50 | 5 | 95 |
| 4.52 | 95 | 5 |
| 6.50 | 95 | 5 |

Preparative HPLC Purification

Preparative HPLC was performed using Waters autopurification system with XBridge Prep C18 column (19×150 mm). The Waters system consisted of a Waters 2545 Binary Prep Pump, a Waters 2767 Sample Manager, a Waters SFO Column Organiser, a Waters 2998 DAD, a Waters 515 Make up Pump and an Acquity QDa mass spectrometer The purification system was controlled by MassLynx software (version 4.2) with Open Access Login module.

Mobile phases consisted of (A) 10 mM Ammonium Formate (+0.10% v/v formic acid) and (B) acetonitrile (+0.1% v/v formic acid).

Samples were prepared by dissolving in 10% v/v water in DMSO to give a concentration of ~150 mg/mL.

A volume of 320 mL of the prepared sample was loaded onto the column and purified using gradient elution at room temperature with a flow rate of 25 mL/min. There is a 1.5 minutes equilibration between injections.

TABLE 20

| Gradient: | |
|---|---|
| Time (min) | % (A) |
| 0.0 | 95 |
| 0.5 | 95 |
| 14.5 | 0 |
| 17.4 | 0 |
| 17.5 | 95 |
| 18.0 | 95 |

Example 3: In Vitro Screening Methods

Example 3.1: In Vitro HUVEC Cells FGF1, FGF2 and VEGF-A Inhibition Method

Aim of this in vitro method is to assess compounds effects on FGF-2, FGF-1, or VEGF-A induced sprouting of human umbilical vein endothelial cells (HUVEC) in the spheroid-based cellular angiogenesis assay. Before adding the growth factors to the cells, they were preincubated with the compound. Sunitinib was tested as a control (without preincubation).

Sunitinib control inhibited FGF-2, FGF-1 and VEGF-A induced HUVEC sprouting as expected. IC50 values determined for the tested compounds are expressed in microM [µM] and the values for the inhibition of FGF-1, FGF2 and VEGF-A induced growth (sprouting) are listed after each compound in the examples after chemical characterization.

Sprouting test was performed on the compounds dissolved in DMSO to reach 100-fold concentrated stock solutions and dissolved in culture media. Sunitinib as reference compound was provided by ProQinase GmbH. Growth factors were purchased from rhFGF-basic (FGF-2), Peprotech, New Jersey, USA, #100-18C, Lot #0415571; rhFGF-acidic (FGF-1), Peprotech, New Jersey, USA, #100-17A, Lot #031207; hVEGF-A165 (ProQinase GmbH, Freiburg, Germany; 05.02.2010) were used for stimulation of HUVEC cells growth.

Test system: Endothelial cells from human umbilical vein (HUVEC) from pooled donors were stored frozen with 70% medium, 20% FCS, 10% DMSO at about $1\times10^6$ cells/ampoule. HUVEC cells, primary human umbilical vein endothelial cells (PromoCell, Heidelberg, Germany), were used after passage 3 to 4. Morphology of the cells are adherent, cobblestone-like growing as monolayer and were cultured in endothelial cell growth and basal medium (ECGM/ECBM, PromoCell). The subculture was split 1:3; every 3-5 days, seed out at ca. $1\times10^4$ cells/$cm^2$ and incubated at 37 °C with 5% $CO_2$ with a doubling time 24-48 hours Dilution of test compounds: 100× concentrated solutions (concerning to the final assay concentrations) of each test compound were prepared with the appropriate solvent (in DMSO or in water). These 100×compound solutions were further diluted in endothelial cell growth and basal medium (ECBM) 1:7.5 to get a 13.33× concentrated solution. 75 µl of the 13.33×solution was subsequently mixed with 25 µl of 40× concentrated stimulus (solved in ECBM), resulting in a 10×concentrated stimulus/compound mixture. This mixture (100 µl) was incubated for 30 min at 37 °C and then added to 900 µl gel, containing the HUVEC spheroids (resulting in the final assay concentration).

Test method: the experiments were pursued in modification of the originally published protocol (Korff and Augustin: J Cell Sci 112: 3249-58, 1999). In brief, spheroids were prepared as described (Korff and Augustin: J Cell Biol 143: 1341-52, 1998) by pipetting 400 HUVEC in a hanging drop on plastic dishes to allow overnight spheroid aggregation. 50

HUVEC spheroids were then seeded in 0.9 ml of a collagen gel and pipetted into individual wells of a 24 well plate to allow polymerization. The test compounds were preincubated with the growth factors (FGF-1, FGF-2 or VEGF-A final concentration 25 ng/mL) in a 10-fold concentrated solution and subsequently, 100 μl of this solution was added on top of the polymerized gel. All compounds were diluted in solvent (DMSO or water) as 100×stocks first (which means 100×stocks of each final assay concentration were prepared in solvent). Subsequently, these stocks were further diluted in medium (resulting in the 13.33×stocks of each final assay concentration) with final concentrations tested: 100, 50, 25, 12.5, 6.25, 3.13 and $1.56\times10^{-6}$ M). Plates were incubated at 37 °C for 24 hours and fixed by adding 4% PFA (Roth, Karlsruhe, Germany).

Quantification of growth factor inhibition: sprouting intensity of HUVEC spheroids treated with the growth factor and the inhibitors were quantitated by an image analysis system determining the cumulative sprout length per spheroid (CSL). Pictures of single spheroids were taken using an inverted microscope and the digital imaging software NIS-Elements BR 3.0 (Nikon). Subsequently, the spheroid pictures were uploaded to the homepage of the company Wimasis for image analysis. The cumulative sprout length of each spheroid was determined using the imaging analysis tool WimSprout. The mean of the cumulative sprout length of 10 randomly selected spheroids was analyzed as an individual data point. For IC50 determination, raw data were converted into percent HUVEC sprouting relative to solvent control (containing the stimulus), which was set to 100% and basal control (without stimulation), which was set to 0%. IC50 values were determined using GraphPad Prism 5 software with constrain of bottom to 0 and top to 100 using a nonlinear regression curve fit with variable hill slope.

Results: The dose response relationship on growth factor induced sprouting of endothelial cells was assessed for all compounds. IC50 values were determined using standard parameters based on the signal of the solvent control as top constraint (100% HUVEC sprouting) and the signal of the basal control as bottom constraint (0%). The respective IC50 values for each compound on FGF1, FGF2 and VEGFA were summarized under each compound below their chemical characterization in paragraph BIODATA.

Example 3.2: In Vitro Neutrophil Adhesion Under Static Conditions, Method

Human neutrophils obtained from buffy coats of healthy donors were suspended at $3\times10^6$/ml in adhesion buffer (PBS containing 1 mM CaCl2)/MgCl2 and 10% FCS, pH 7.2). Neutrophils were preincubated for 30 min at 37 °C with 40 μM and 80 μM of the compounds.

Adhesion assays were performed on 18-well glass slides coated for 18 h at 4 °C with human fibrinogen (20 μg/well in endotoxin-free PBS); 20 μl of cell suspension were added to each well and stimulated for 1 min at 37 °C with 5 μl of fMLP 1 nM final concentration. After washing, adherent cells were fixed in glutaraldehyde 1.5% in PBS and counted by computer-assisted enumeration. Statistical analysis was performed by calculating mean and standard deviation (SD); significance was calculated by unpaired t-test. All statistical analyses were performed using GraphPad Prism 6 (GraphPad Software).

The respective inhibition of neutrophil adhesion expressed in [%] for each compound were summarized under each compound below their chemical characterization in paragraph BIODATA.

Example 3.3: In Vitro Testing on the Inhibition of Reactive Oxygen Species (ROS) Production in Human Neutrophils NADPH oxidase, located in the plasma membrane and in the membranes of specific granules, produces superoxide anions from which other ROS, such as hydrogen peroxide, singlet oxygen, hypochlorite, and active hydroxyl radicals. ROS are released into the surrounding medium or into a membrane-enclosed subcellular organelle. One quick and sensitive method for measuring the generation of these metabolites is chemiluminescence (CL). Isoluminol amplified CL technique, is very sensitive and widely used to study respiratory burst (mainly extracellular production of ROS) induced in neutrophils.

Human neutrophils were isolated from buffy coats which obtained from healthy donors. The isolated neutrophils ($3\times10^6$/ml) were suspended in Hanks' Balanced Salt Solution (HBSS) with Calcium and Magnesium. Neutrophils were pre-incubated with the compounds at different concentrations (0.1, 0.3, 1, 3 and 10 μM) for 30 min at 37 °C. The black 96-well cell culture plates were coated with human fibrinogen (0.25 mg/ml in PBS), and incubated overnight at 4 °C or 2 hr at 37 °C. Then the plates were washed with endotoxin-free PBS. The neutrophils were incubated (priming) with TNF-α (20 ng/ml) for 10 minutes at 37 °C. Thereupon the 75 μl of cell suspension and 75 μl (Isoluminol+HRP solution) were added to each well. The chemiluminescence was recorded (every 25 sec for 250 sec) after fMLP (1 μM) activation using a Multilabel Reader victor3 (Perkin Elmer, USA). Background values, defined as the mean chemiluminescent values of isoluminol diluted in HBSS, were subtracted from all readings (CPS, count per second). The assays were done in duplicate or triplicate.

The results obtained from isoluminol amplified CL assay revealed that compounds strongly reduced ROS level in a concentration-dependent manner in fMLP+TNF-α stimulated PMN.

The PMN ROS inhibition at 0.3 μM expressed in [%] and IC50 [μM] were summarized under each compound below their chemical characterization in paragraph BIODATA.

Example 3.4: In Vitro Human Neutrophil and Human Monocyte Inflammatory Cytokine Production, Method Neutrophils and monocytes were isolated from buffy coats of healthy donors, under endotoxin-free conditions. Briefly, buffy coats were stratified on Ficoll-Paque PLUS gradient, and then centrifuged at 400×g for 30 min at room temperature. Neutrophils were then collected and subjected to dextran sedimentation followed by hypotonic lysis to remove erythrocytes. Monocytes were instead isolated from PBMCs, after centrifugation over Percoll gradients. Human neutrophils and monocytes were suspended at 5×106/ml and 2.5×106/ml, respectively, in RPMI 1640 medium supplemented with 10% low endotoxin FBS (<0.5 EU/ml; from BioWhittaker-Lonza, Basel, Switzerland) and then plated in 24-well tissue culture plates at 37 °C, 5% CO2 atmosphere, in the presence or absence of different concentrations (20-40 μM) of the compounds. After 1 h of treatment with drugs, monocytes were stimulated with 0.1 μg/ml, whereas neutrophils with 1 μg/ml ultrapure LPS from *E. coli* 0111:B4 strain (InvivoGen). After 6 h of LPS stimulation, neutrophils and monocytes were collected and spun at 300×g for 5 min. Cell-free supernatants were immediately frozen at −80 °C.

Cytokine concentrations in cell-free supernatants were measured by commercially available ELISA kits, specific for human: CXCL8, IL-6, TNF-α (Mabtech, Sweden). Detection limits of these ELISAs were: 4 pg/ml for CXCL8, 10 pg/ml for IL-6 and 4 pg/ml for TNF-α.

Statistical analysis was performed by calculating mean and standard deviation (SD); significance was calculated by unpaired t-test. All statistical analyses were performed using GraphPad Prism 6 (GraphPad Software).

The cytokine values were expressed in ng/ml for each compound and summarized for each compound below their chemical characterization in paragraph BIODATA.

Example 3.5: In Vitro Inhibition by Compounds of the VEGF-165 Induced Phosphorylation of VEGF-Receptor on Primary Human Umbilical Vein Endothelial Cells (HUVEC), Method Cell culture: Primary human umbilical vein endothelial cells (HUVECs) were routinely cultured in 0.1% gelatin pre-coated flasks or dishes, up to passage 6. The effect of compounds alone at different concentrations (0, 1.25, 2.5, 5, 10 and 20 μM) on cellular viability was assessed by CCK-8 kit using a Tecan Microplate Reader (Genios). To measure the effect of compounds on VEGF-induced cell viability, HUVECs ($1\times10^4$ cells/well) were treated with VEGF (25 ng/ml) pre-mixed with various concentrations of compounds (0, 1.25, 2.5, 5, 10 and 20 μM) in culture medium without serum and growth factors (starvation medium) for 24 h and 48 h. Compounds in this concentration range did not affect cell viability.

Rabbit primary antibodies for VEGFR-2, p-Tyr1175 were acquired from Cell Signaling Technology (Leiden, The Netherlands). Phospho-VEGFR-2 (Tyr1175) Sandwich ELISA Kit was from Cell Signaling Technology.

HUVECs were pre-incubated with compounds at 0, 0.16, 0.31, 0.63, 1.25, 2.5, 5, 10 and 20 μM for 60 min with three subsequent washing steps with warm medium before stimulation with VEGF165 (25 ng/mL) for 2 min. Western blot analysis was performed using anti-phospho-VEGFR-2 antibody and total VEGFR-2 was used as a loading control after membrane stripping.

Inhibition of VEGFR-2-phosphorylation results are expressed as IC50 in microM [μM] versus VEGF-treated HUVECs control without inhibitory compound.

The respective IC50 expressed in [μM] values for each compound are summarized under each compound below their chemical characterization in paragraph BIODATA.

Example 3.6: In Vitro Cytokine Release Inhibition by Compounds Following LPS Induction on Human Whole Blood Aim of this in vitro method is to assess compounds effects on release of a panel of cytokines from whole blood following lipopolysaccharide (LPS) induced inflammatory reaction. Whole blood was incubated with compounds for 1 h prior to LPS induction. Cytokine levels in blood were measured using a multiplex FACS-based panel.

IC50 values determined for the tested compounds expressed in microM [μM] and the values for the inhibition of cytokines were listed for each compound.

Effect on cytokines release after LPS induction was performed on the compounds dissolved in DMSO or $H_2O$ to reach 10-fold concentrated stock solutions and dissolved in culture media.

Test system: Whole blood was removed from a single donor (into lithium heparin coated tubes; BD Vacutainer; 367886) and diluted 1:5 with RPMI 1640 (Thermo Fisher, 61870036). Within 30 minutes of sampling, blood was incubated with compounds for 1 h prior to LPS stimulation (O111:B4—Sigma L4391; 10 ng/ml final concentration). Stimulation continued under standard cell culture conditions (37 °C with 5% $CO_2$) overnight (18 h), after which plates were centrifuged and supernatant removed and frozen at −80 °C until used for analyses.

Dilution of test compounds: 10×concentrated solutions (concerning to the final assay concentrations) of each test compound were prepared with the appropriate solvent (in DMSO or in water). These 10× compound solutions (10 μl) were then added to 90 μl pre-diluted whole blood (whole blood: RPMI1640, 1:5) resulting in the final assay concentration.

Test method: Diluted whole blood (80 μl) was pre-incubated with compounds (10 μl) to give final assay concentrations of 100, 30, 10, 3, 1, 0.3 and $0.1\times10^{-6}$M. Blood was incubated at 37 °C with 5% $CO_2$ for 1 h. LPS was diluted in cell culture media to a concentration of 10 ng/ml; 10 μl was added to the whole blood to give a final concentration of 10 ng/ml. Plates were incubated at 37 °C for 18 h. Plates were centrifuged at 3,000 RPM for 5 minutes at 4 °C and supernatant removed and frozen at −80 °C until FACS analysis was carried out.

Cytokine release was measured using a custom multiplex system (ELISA Genie) according to manufacturers instructions. Prepared samples were run on an Attune NxT flow cytometer (Thermo Fisher).

Quantification of cytokine release inhibition: known concentration standards were run as part of the cytokine panel to allow quantification of each cytokine concentration in each sample. This was carried out using FCAP Array v3.0 software. For IC50 determination, raw data were converted into percent concentration relative to solvent control, which was set to 100%. IC50 values were determined using GraphPad Prism 8 software with constrain of bottom to 0 and top to 100 using a nonlinear regression curve fit with variable hill slope.

Results: The dose response relationship on cytokine release following LPS induction of inflammatory response in whole blood was assessed for all compounds. IC50 values were determined for each compound for a panel of cytokines (GM-CSF, IFN-gamma, IL-1beta, IL-2, IL-4, IL-5, IL-6, IL-8, IL-9, IL-10, IL-12p40, IL-13, IL-17A, IL-17F, IL-18, IL-21, IL-22, IL-33, TGF-beta, TNF-alpha, TNF-beta).

The respective cytokines IC50s expressed in [μM] values for each compound were summarized under each compound below their chemical characterization in paragraph BIODATA and also in Table 13.

Example 4: Compound Formulations

Example 4.1: Oral Formulations of Compound Ic-007a

Five formulations were developed and reviewed for suitability. These were both suspension and solutions whose details are given in the following Table.

TABLE 21

Formulation details for the suspension and solutions of compound Ic-007a.

| Component | Suspension A | Solution D | Solution A Amount (%) | Solution B | Solution C |
|---|---|---|---|---|---|
| API | 1% w/v (10 mg/mL) | 0.1% w/v (1 mg/mL) | 1% w/v (10 mg/mL) | 1% w/v (10 mg/mL) | 1% w/v (10 mg/mL) |
| DMSO | 5% v/v | 5% v/v | 5% v/v | 5% v/v | 5% v/v |
| PEG 400 | 10% v/v | 10% v/v | 10% v/v | 10% v/v | 10% v/v |
| Solutol HS15 | 10% w/v | 10% w/v | 10% w/v | 10% w/v | 10% w/v |
| Sodium Hydroxide 1M | n/a | n/a | To pH 6 | To pH 8 | To pH 9 |
| Water | to 100% | to 100% | to 100% | to 100% | to 100% |

Manufacture: Suspension A and Solution D:

Method example for 100 mL (scale as appropriate for final volume required). Solvent stock was prepared by measuring 5 mL DMSO into a clean vessel. Correct quantity of compound Ic-007a was weighed out and gradually added to the DMSO solution with mixing on a shaker, vortex or sonicator. The Solutol was melted in a water bath at 60 °C in a clean dry vessel. As solutol solidified at room temperature, the molten Solutol was kept in a water bath at 60 °C during formulation preparation. 10 g (10% w/v) of molten Solutol was added into a warmed suitable marked (to final volume 100 mL) container. 10 mL PEG 400 was added to the Solutol in the warmed 100 mL container. The DMSO drug stock solution was added into the Solutol and PEG400 mixture and the contents were instantly mixed, and 35 mL of deionised water was added and mixed in a 40 °C bath with intermittent vortexing to dissolve the large particles. The formulation was cooled to room temperature and made up to final 100 mL volume with deionised water.

Manufacture of Solutions A, B & C:

Method example for 100 mL (scale as appropriate for final volume required). Solvent stock was prepared by measuring 5 mL DMSO into a clean vessel. 1 g of compound Ic-007a was weighed out and gradually added to the DMSO solution with mixing on a shaker, vortex or sonicate if required). The Solutol was melted in a water bath at 60 °C in a clean dry vessel. As Solutol solidifies at room temperature, the molten Solutol was kept in a water bath at 60 °C during formulation preparation. 10 g (10% w/v) of molten Solutol was weighed into a warmed suitable marked (to final volume 100 mL) container. 10 mL PEG 400 was added to the Solutol in the warmed 100 mL container. The DMSO drug stock solution was added into the marked container of Solutol and PEG 400 mixture and instantly mixed to the contents. 35 mL of deionised water was added and mixed to the contents and placed in a 40 °C bath with intermittent vortexing to dissolve large particles. The formulation was cooled down to room temperature and further adjusted the pH of the formulation using 1M sodium hydroxide (NaOH) solution to pH 6, 7, 8 and 9. Initial formulations were made on a 1 mL scale and had a starting pH of 4.3. A volume of 3 μL NaOH 1M was added to achieve pH 6 (solution A), 22 μL for pH 8 (Solution B) and 43 μL for pH 9 (Solution C). These formulations were dosed immediately after manufacture.

The 10 mg/mL suspension formulation and the 1 mg/mL solution formulation were found to be physically stable over two weeks at ambient conditions.

Example 4.2: Oral Formulations of Compound Ia-001a-Tz

Compound Ia-001a-Tz was prepared as a 10 mg/mL oral solution in the formulations with the vehicle composition shown in the Table below.

The vehicle was a carrier or inert medium used as a solvent (or diluent) in which the medicinally active agent was formulated and or administered.

TABLE 22

Formulation details for oral formulation of compounds Ia-001aTz.

| Vehicle | Composition |
|---|---|
| A | 40% PEG400, 10% Transcutol, 10% Solutol HS15, 40% type 1 water |
| B | 40% PEG400, 10% Transcutol, 10% Solutol HS15, 40% aq solution comprising 0.5% HPMC 606 |
| C | 40% PEG400, 10% Transcutol, 10% Solutol HS15, 40% aq solution comprising 0.5% Kollidon VA 64 |
| D | 40% PEG400, 10% Transcutol, 10% Cremophor RH40, 40% type 1 water |
| E | 40% PEG400, 10% Transcutol, 10% Vitamin E TPGS, 40% type 1 water |
| F | 40% PEG400, 10% Transcutol, 5% Solutol HS15, 45% type 1 water |
| G | 40% PEG400, 10% Transcutol, 5% Solutol HS15, 45% aq solution comprising 1% Kollidon VA 64 |

Method of Manufacture

To prepare a 10 mg/g solution, 10 mg of the compound was weighed accurately into a vial and 1 ml of vehicle was added directly onto the API and vortexed to give a solution.

Preparation of Vehicles

Formulation A: 10 g of vehicle were prepared by weighing 4 g of PEG400 into a clean 20 mL glass vessel. 1 g Transcutol was added, and the components were mixed by stirring. To this, 1 g of Solutol HS15 was added, followed by 4 g of type 1 water. The mixture was left stirring for 1 h at room temperature to allow all the components to dissolve.

Formulation B: 10 g of vehicle were prepared by weighing 4 g of PEG400 into a clean 20 mL glass vessel. 1 g Transcutol was added, and the components were mixed by stirring. To this, 1 g of Solutol HS15 was added. The 0.5% HPMC 606 aqueous solution was prepared by weighing 50 mg of HPMC 606 into a clean glass vial. To this, 9.95 g of type 1 water was added. The components were stirred for 1 h at room temperature to ensure adequate mixing. 4 g of the aqueous solution comprising 0.5% HPMC 606 was then added to solution of PEG400, Transcutol and Solutol HS15.

The mixture was left stirring for 1 h at room temperature to allow all the components to dissolve.

Formulation C: 10 g of vehicle were prepared by weighing 4 g of PEG400 into a clean a 20 mL glass vessel. 1 g Transcutol was added, and the components were mixed by stirring. To this, 1 g of Solutol HS15 was added. The 0.5% Kollidon VA64 aqueous solution was prepared by weighing 50 mg of Kollidon VA64 into a clean glass vial. To this, 9.95 g of type 1 water was added. The components were stirred for 1 h at room temperature to ensure adequate mixing. 4 g of the aqueous solution comprising Kollidon VA64 was then added to solution of PEG400, Transcutol and Solutol HS15. The mixture was left stirring for 1 h at room temperature to allow all the components to dissolve. Formulation D: 10 g of vehicle were prepared by weighing 4 g of PEG400 into a clean 20 mL glass vessel. 1 g Transcutol was added, and the components were mixed by stirring. To this, 1 g of Cremophor RH40 was added, followed by 4 g of type 1 water. The mixture was left stirring for 1 h at room temperature to allow all the components to dissolve.

Formulation E: 10 g of vehicle were prepared by weighing 4 g of PEG400 into a clean 20 mL glass vessel. 1 g Transcutol was added, and the components were mixed by stirring. To this, 1 g of Vitamin E TPGS was added, followed by 4 g of type 1 water. The mixture was left stirring for 1 h at room temperature to allow all the components to dissolve.

Formulation F: 10 g of vehicle were prepared by weighing 4 g of PEG400 into a clean 20 mL glass vessel. 1 g Transcutol was added, and the components were mixed by stirring. To this, 0.5 g of Solutol HS15 was added, followed by 4.5 g of type 1 water. The mixture was left stirring for 1 h at room temperature to allow all the components to dissolve.

Formulation G: 10 g of vehicle were prepared by weighing 4 g of PEG400 into a clean 20 mL glass vessel. 1 g Transcutol was added, and the components were mixed by stirring. To this, 0.5 g of Solutol HS15 was added. The 1% Kollidon VA64 aqueous solution was prepared by weighing 100 mg of Kollidon VA64 into a clean glass vial. To this, 9.9 g of type 1 water was added. The components were stirred for 1 h at room temperature to ensure adequate mixing. 4.5 g of the aqueous solution comprising Kollidon VA64 was then added to solution of PEG400, Transcutol and Solutol HS15. The mixture was left stirring for 1 h at room temperature to allow all the components to dissolve.

Example 4.3. Oral formulations of compound IIc-007a, IVc-059a, IIIc-061a

Compounds IIc-007a, IVc-059a, IIIc-061a were prepared as oral formulations using the components detailed in the Table below.

TABLE 23

Oral Formulation details for oral formulation of compounds IIc-007a, IVc-059a, IIIc-061a

| Component | Amount (% w/w) | |
|---|---|---|
| | Formulation 1 | Formulation 2 |
| PEG 400 | 40.0 | 31.0 |
| Transcutol HP | 3.5 | 10.0 |
| Meglumine | 4.0 | 4.0 |
| Cremophor RH 40 | 12.5 | 15.0 |
| DMSO | 5.0 | 5.0 |
| 15% SLS aq. solution | 35.0 | 35.0 |

Preparation of Aqueous Solution of SLS 15% at 50 mL Scale:

7.5 g of SLS was accurately weighed in a 50 mL volumetric flask. Water was added to the 50 mL volume and stirred until complete solubilisation is achieved.

Preparation of Formulation Vehicles:

Formulation 1: 100 g of vehicle were prepared by weighing 40 g of PEG 400 (40.0%) into a plastic beaker. 3.5 g Transcutol (3.5%), 12.5 g Cremophor RH40 (12.5%), 4.0 g Meglumine (4.0%), 5 g DMSO (5.0%), and 35 g 15% SLS aq. solution (35.0%, final SLS 5.25%). The mixture was left stirring for 1 h at room temperature to allow all the components to dissolve.

Formulation 2: 100 g of vehicle were prepared by weighing 40 g of PEG 400 (40.0%) into a plastic beaker. 10.0 g Transcutol (10.0%), 15.0 g Cremophor RH40 (15.0%), 4.0 g Meglumine (4.0%), 5 g DMSO (5.0%), and 35 g 15% SLS aq. solution (35.0%, final SLS 5.25%). The mixture was left stirring for 1 h at room temperature to allow all the components to dissolve.

Vehicle was added directly to each compound prior to vortexing and sonicating for 10 minutes. If required, the pH of the formulation was adjusted with 1M sodium hydroxide or 1M hydrochloric acid to reach the pH range suitable for oral dosing. IIc-007a solutions were made at concentrations up to and including 70 mg/mL. IIIc-061a solutions were made at concentrations up to and including 40 mg/mL.

IVc-059a solutions were made at concentrations up to and including 150 mg/mL.

Example 4.4: Intravenous (IV) Formulations

Compounds Ia-001a, Ia-001a-Tz, Ia-001a-Tz/004a, Ic-007a, Ib-010a, IVc-059a, IIIc-061a were prepared as intravenous formulations.

The formulation details given in the following Table 24 were used for IV administration in the different preclinical in vivo models. Solutions of each compound were manufactured by adjusting the pH with sodium hydroxide solution until a solution was obtained.

TABLE 24

IV formulation composition

| Component | Amount (%) |
|---|---|
| API drug substance | 1% w/v |
| DMSO | 5% v/v |
| PEG 400 | 10% v/v |
| Solutol HS15 | 10% w/v |
| Sodium Hydroxide 1M | q.s. |
| Saline solution 0.9% | to 100 % |

Method of Manufacture:

Method example for 10 mL (scale as appropriate for final volume required). Solvent stock was prepared by measuring 0.5 mL DMSO into a clean vessel. 100 mg of each compound was weighed out and gradually added to the DMSO solution with mixing on a shaker, vortex or sonicate if required). Solutol was melted in a water bath at 60 °C in a clean dry vessel. As Solutol solidified at room temperature, the molten Solutol was kept in a water bath at 60 °C during formulation preparation. 1 g (10% w/v) of molten Solutol was weighed into a warmed suitable marked (to final volume 10 mL) container. 1 mL PEG 400 was added to the Solutol in the warmed 10 mL container. The DMSO drug stock solution was added into the marked container of Solutol and PEG 400 mixture and instantly mixed to the contents. An 0.9% saline solution* was added to achieve 85% of target volume and mixed the contents in a 40 °C bath with intermittent vortexing to dissolve large particles. The formulation was cooled down to room temperature, made up to final target volume (10 mL) with 0.9% saline solution* and pH of the formulation adjusted using 1M sodium hydroxide (NaOH) solution to pH 7.4. The formulations were filtered using a 0.2 μm filter into a sterile vial inside a Class II biological hood. Formulations were used for dosing in animals. * For some compounds, 0.9% saline solution was substituted for pH 7.4 PBS solution.

Example 4.5: Intravenous (IV) and Intraperitoneal (IP) Formulations

Compounds Ic-007a, IIc-007a, IVc-059a, IIIc-061a were prepared as formulations for intravenous and intraperitoneal administration. The formulations contained water and diethylamine in molar equivalents of each corresponding compound as detailed in Table 25. These formulations were used for IV and IP administrations in the different preclinical in vivo models.

Method of Manufacture:

Method example for 1 mL (scale as appropriate for final volume required). 10 mg of each compound was accurately weighed into a clean vial. The corresponding amount of diethylamine was added to the vial. Water was then added to make up to 1 mL volume. The contents were vortexed or sonicated to form a solution. Where needed, the pH of the solution was altered using 1M hydrochloric acid to bring this into a range suitable for IV or IP dosing.

TABLE 25

Diethylamine molar equivalents required for compounds in IV and IP formulations.

| Compound | Ic-007a | IIc-007a | IIIc-061a | IVc-059a |
|---|---|---|---|---|
| Molar equivalent of diethylamine required | 2.0 | 2.0 | 3.1 | 2.0 |
| Diethylamine required to make 1 mL of IV formulation | 44 μL | 44 μL | 62 μL | 51.9 μL |

Example 4.6: Ocular Formulations

Several compounds according to the present invention were submitted for formulation development into an ocular format. The compounds, their final concentration and form are given in the following Table 26.

TABLE 26

Ocular formulations

| Compounds | Concentration (% w/v) | Suspension/ solution |
|---|---|---|
| IVc-059a | 5 mg/mL (0.5) | Solution |
| Ia-001a-Tz/004a | 5 mg/mL (0.5) | Solution |
| Ia-001a-Tz | 10 mg/mL (1.0) | Solution |
| IIIc-061a | 10 mg/mL (1.0) | Solution |
| Ia-001a | 10 mg/mL (1.0) | Solution |
| Ic-007a | 5 mg/mL (0.5) | Suspension |
| Ib-010a | 10 mg/mL (1.0) | Suspension |

Composition: The formulation composition is detailed in the following Table 27. The concentration of the APIs and their resulting format varied.

TABLE 27

Ocular formulation composition.

| Component | Amount (%) |
|---|---|
| API drug substance | See Tables above |
| Kolliphor EL | 5% w/v |
| Povidone | 0.5% w/v |
| HPMC | 0.5% w/v |
| Polysorbate 80 | 0.1% v/v |
| pH 7.4 PBS buffer (adjustment of pH with NaOH 1M) | To volume |

Method of Manufacture:

For those compounds that created solutions, the following method of manufacture was followed: A total of 50 mg of Kolliphor EL was weight out into a clean dry vessel. The correct amount of compound was weighed out and gradually added to the Kolliphor EL whilst mixing on a magnetic stirrer. Heating to 30 °C helped to mix the drug into the Kolliphor preparation. In a separate container, an aqueous solution of HPMC at 0.5% w/v, povidone at 0.5% w/v and polysorbate 80 at 0.10% in pH 7.4 Phosphate-buffered saline (PBS) buffer was prepared. A volume of 600 μL of the aqueous solution was added to the Kolliphor EL and drug whilst mixing and was vortexed immediately. The pH was adjusted to 7.4 using 1 M NaOH in the formulation while mixing. Volume was adjusted to target volume using the aqueous solution. The formulation was filtered using a 0.2 μm filter into a sterile vial inside a Class II biological hood. Formulations are ready for dosing.

For the compounds that created suspensions, the following method of manufacture was followed: An amount of 50 mg of Kolliphor EL was weighed into a clean dry vessel. The correct amount of the different compounds was weighed and gradually added to the Kolliphor EL whilst mixing on a magnetic stirrer. Heating to 30 °C helped to mix the drug into the Kolliphor. In a separate container, an aqueous solution of HPMC at 0.5% w/v, povidone at 0.5% w/v and polysorbate 80 at 0.1% in pH 7.4 Phosphate-buffered saline (PBS) buffer was prepared. The aqueous solution was filtered using a 0.22 μm filter. A volume of 600 μL of the aqueous solution was added to the Kolliphor and drug whilst mixing, and then vortex immediately. The pH was adjusted to 7.4 using filtered 1 M NaOH with continuous mixing the formulation. Volume was adjusted to target volume using the aqueous solution. The formulations were sonicated prior to dosing to allow flocculates to break up and disperse.

Ocular formulation of compounds Ic-007a, IIc-007a

TABLE 28

Composition of ocular formulation with Ic-007a and IIc-007a.

| Components | 1 Amount (%) | 2 |
|---|---|---|
| Ic-007a | 0.5% w/v (5 mg/mL) | — |
| IIc-007a | — | 0.5% w/v (5 mg/mL) |
| Kolliphor EL | 5% w/v | 5% w/v |
| Povidone | 0.5% w/v | 0.5% w/v |
| HPMC | 0.5% w/v | 0.5% w/v |
| Polysorbate 80 | 0.1% v/v | 0.1% v/v |
| pH 7.4 PBS buffer (adjustment of pH with NaOH 0.5M) | To volume | To volume |

Method of Manufacture:

A total of 50 mg of Kolliphor EL was weight out into a clean dry vessel. The correct amount of compound was weighed out and gradually added to the Kolliphor EL whilst mixing on a magnetic stirrer. Heating to 30 °C helped to mix the drug into the Kolliphor preparation. In a separate container, an aqueous solution of HPMC at 0.5% w/v, povidone at 0.5% w/v and polysorbate 80 at 0.1% in pH 7.4 Phosphate-buffered saline (PBS) buffer was prepared. A volume of 600 μL of the aqueous solution was added to the Kolliphor EL and drug whilst mixing and was vortexed immediately. The pH was adjusted to 7.4 using 1 M NaOH in the formulation while mixing. Volume was adjusted to target volume using the aqueous solution. The formulation was filtered using a 0.2 μm filter into a sterile vial inside a Class II biological hood.

Solution of compound IIc-007a: A total of 50 mg of Kolliphor EL was weight out into a clean dry vessel. The correct amount of compound (target concentration 5 mg/mL) was weighed out and gradually added to the Kolliphor EL whilst mixing on a magnetic stirrer. Heating to 30 °C helped to mix the drug into the Kolliphor preparation. In a separate container, an aqueous solution of HPMC at 0.5% w/v, povidone at 0.5% w/v and polysorbate 80 at 0.1% in pH 7.4 Phosphate-buffered saline (PBS) buffer was prepared. A volume of 600 μL of the aqueous solution was added to the Kolliphor EL and drug whilst mixing and was vortexed immediately. The pH was adjusted to 7.4 using 0.5 M NaOH in the formulation while mixing. Volume was adjusted to target volume using the aqueous solution. The formulation was filtered using a 0.2 μm filter into a sterile vial inside a Class II biological hood. Formulations are ready for dosing. Prior to use, vortex compound IIc-007a solutions for 2 minutes and use within 10 minutes. *appearance of gel/colloidal structure may be observed but is re-dispersed after vortexing.

Suspension of compound Ic-007a: A total of 50 mg of Kolliphor EL was weight out into a clean dry vessel. The correct amount of compound (target concentration 5 mg/mL) was weighed out and gradually added to the Kolliphor EL whilst mixing on a magnetic stirrer. Heating to 30 °C helped to mix the drug into the Kolliphor preparation. In a separate container, an aqueous solution of HPMC at 0.5% w/v, povidone at 0.5% w/v and polysorbate 80 at 0.1% in pH 7.4 Phosphate-buffered saline (PBS) buffer was prepared.

The aqueous solution was filtered using a 0.22 μm filter. A volume of 600 μL of the aqueous solution was added to the Kolliphor EL and drug whilst mixing and was vortexed immediately. The pH was adjusted to 7.4 using 0.5 M NaOH in the formulation while mixing. Volume was adjusted to target volume using the aqueous solution.

Prior to use, suspension of compound Ic-007a was sonicated to break the flocculate/aggregates using the following protocol: a small petri dish/beaker was filled with water inside a sonicator. The vial was put inside the beaker/petri dish and sonicated for 10 minutes at 40 °C. After 10 minutes the vial was removed and vortexed for 2 minutes and sonicated again for 10 minutes. The process was repeated for total of 50 minutes.

Ocular formulations of IIc-007a

The composition of the vehicles and compound concentration are shown in the Table 29.

TABLE 29 compositions of formulations A, B and C

| Formulation | Composition | IIc-007a concentration |
|---|---|---|
| A | 0.4% w/w TRIS<br>0.5% w/w HPMC<br>0.5% w/w PVP K30<br>0.1% w/w tween 80 in $H_2O$ | 5 mg/g |
| B | 0.4% w/w TRIS<br>5% w/w cremophor EL in $H_2O$ | 5 mg/g |
| C | 5% w/w cremophor EL<br>1.2% w/w PVP K90<br>0.9% w/w TRIS in $H_2O$ | 10 mg/g |
| D | Diethylamine 0.3% w/v: in $H_2O$ | 10 mg/g |

To prepare a 10 mg/g solution, 10 mg of the compound was weighed accurately into a vial and 1 ml of vehicle was added directly onto the API and vortexed to give a solution.

To prepare a 5 mg/g solution, 5 mg of the compound was weighed accurately into a vial and 1 ml of vehicle was added directly onto the API and vortexed to give a solution.

Preparation of Vehicles

Formulation A: 50 g of vehicle were prepared by weighing 0.25 g of HPMC (0.5% w/w) inside a 100 mL duran glass bottle. 49.25 g of type 1 water were then added to the bottle followed by 0.200 g TRIS (0.4% w/w), 50 mg Tween 80 (0.1% w/w) and 0.25 g PVP K30 (0.5% w/w). The mixture was left stirring for 1 h at room temperature to allow all the components to dissolve.

Formulation B: 50 g of vehicle were prepared by weighing 2.5 g of cremophor EL (5% w/w) inside a 100 mL duran glass bottle. 47.3 g of type 1 water were then added to the bottle followed by 200 mg TRIS (0.4% w/w).

Formulation C: 50 g of vehicle were prepared by weighing 2.5 g of cremophor EL (5% w/w) inside a 100 mL duran glass bottle. 46.45 g of type 1 water were then added to the bottle followed by 450 mg TRIS (0.9% w/w) and 600 mg PVP K90 (1.2% w/w). The mixture was left stirring for 1 h at room temperature to allow all the components to dissolve.

Formulation D: Diethylamine 0.3% w/v: 9.9 g diethylamine vehicle was prepared by adding 9869 μL type 1 water in a 14 mL glass vial. 44.2 μL (31.3 mg) diethylamine were then added using a pipette to the vial. The solution was left 5 minutes stirring to ensure the homogeneity.

Ocular Formulations of IVc-059a

The composition of the vehicles and compound concentration are shown in Table 30.

TABLE 30 compositions of formulations A, B and C

| Formulation | Composition | IVc-059a concentration |
|---|---|---|
| A | 5% w/w cremophor EL<br>1.2% w/w PVP K90<br>0.9% w/w TRIS in $H_2O$ | 10 mg/g |
| B | Diethylamine 0.3% w/v: in $H_2O$<br>pH adjusted with diethylamine | 10 mg/g |
| C | 0.5% w/w HPMC,<br>0.5% w/w PVP K30,<br>0.1% w/w tween 80 in PBS<br>pH adjusted with NaOH | 10 mg/g |

To prepare a 10 mg/g solution, 10 mg of the compound was weighed accurately into a vial and 1 ml of vehicle was added directly onto the API and vortexed to give a solution.

Preparation of Vehicles

Formulation A: 50 g of vehicle were prepared by weighing 2.5 g of cremophor EL (5% w/w) inside a 100 mL duran glass bottle. 46.45 g of type 1 water were then added to the bottle followed by 450 mg TRIS (0.9% w/w) and 600 mg PVP K90 (1.2% w/w). The mixture was left stirring for 1 h at room temperature to allow all the components to dissolve.

Formulation B: Diethylamine 0.3% v/v: 9.9 g diethylamine vehicle was prepared by adding 9869 μL type 1 water in a 14 mL glass vial. 44.2 μL (31.3 mg) diethylamine were then added using a pipette to the vial. The solution was left 5 minutes stirring to ensure the homogeneity.

Formulation C: 50 g of vehicle were prepared by weighing 49.45 g of PBS (preparation method below) was weighed inside a 100 mL duran glass bottle. Successively, 250 mg HPMC (0.5% w/w), 250 mg PVP K30 (0.5% w/w), and 50 μL (liquid displacement pipette) of tween 80 (0.1% w/w) were added to the glass bottle. The mixture was left stirring for 1 h at room temperature to allow all the components to dissolve.

PBS preparation: 799.1 mg of NaCl, 21.6 mg KCl, 24.9 mg KH2PO4, 180.4 mg Na2HPO4.2H2O were accurately weighed and dissolved in 100 mL type 1 water. pH of the solution was 7.6.

Ocular Formulations of Ic-007a and IIc-007a

Compounds were formulated as solutions in the vehicles shown in Table 31.

TABLE 31 compositions of formulations A, B, C and D

| Component | Amount (% w/w) | | | |
|---|---|---|---|---|
| | Vehicle A | Vehicle B | Vehicle C | Vehicle D |
| Cremophor EL | 5.0 | 5.0 | 5.0 | 5.0 |
| PEG 400 | 0 | 0 | 0.4 | 0 |
| TRIS | 0.9 | 0.9 | 0.9 | 0.9 |
| Meglumine | 0 | 0 | 0 | 1.0 |
| Kollophor RH40 | 0 | 0.2 | 0.2 | 0.2 |
| Water | 94.1 | 93.9 | 93.5 | 92.9 |

Vehicle Preparation at 50 g Scale

Vehicle A: 50 g of vehicle were prepared by adding 0.45 g TRIS (0.9% w/w) and 2.5 g Cremphor EL (5.0% w/w) to 47.05 g of water (94.1% w/w). The mixture was left stirring for 1 h at room temperature to allow all the components to dissolve.

Vehicle B: 50 g of vehicle were prepared by adding 0.45 g TRIS (0.9% w/w), 2.5 g Cremphor EL (5.0% w/w) followed by 0.1 g Kolliphor RH40 (0.2% w/w) to 46.95 of water (93.9% w/w). The mixture was left stirring for 1 h at room temperature to allow all the components to dissolve.

Vehicle C: 50 g of vehicle were prepared by adding 0.45 g TRIS (0.9% w/w), 2.5 g Cremphor EL (5.0% w/w) followed by 0.1 g Kolliphor RH40 (0.2% w/w) and 0.2 g PEG400 to 46.75 of water (93.5% w/w). The mixture was left stirring for 1 h at room temperature to allow all the components to dissolve.

Vehicle D: 50 g of vehicle were prepared by adding 0.45 g TRIS (0.9% w/w), 0.5 g meglume (1.0% w/w), 2.5 g Cremphor EL (5.0% w/w) followed by 0.1 g Kolliphor RH40 (0.2% w/w) to 46.45 of water (92.9% w/w). The mixture was left stirring for 1 h at room temperature to allow all the components to dissolve.

Vehicle was added directly to the API to create the concentrations listed in the Table 32. The sample was vortexed and sonicated until a solution was obtained.

TABLE 32

Compound concentration in formulations using vehicle A, B, C and D

| | API concentration (mg/mL) | | | |
|---|---|---|---|---|
| | Vehicle A | Vehicle B | Vehicle C | Vehicle D |
| Ic-007a | 10 | 10 | 10 | 20 |
| IIc-007a | 10 | 10 | 10 | 20 |

To prepare a 10 mg/g solution, 10 mg of the compound was weighed accurately into a vial and 1 ml of vehicle was added directly onto the API and vortexed to give a solution.

To prepare a 20 mg/g solution, 20 mg of the compound was weighed accurately into a vial and 1 ml of vehicle was added directly onto the API and vortexed to give a solution.

Example 5: Therapeutic Activity of the Compounds

Example 5.1: Treatment and/or Prevention of Acute Pancreatis

Therapeutic efficacy of the compounds according to the present invention was assessed on an acute pancreatitis murine model. Tissue samples were obtained to allow post in-life analysis of pancreatitis parameters. Plasma samples were also obtained to assess animal exposure levels after administration of the compounds.

Animals: A total of 70 female Balb/c mice aged 8-10 weeks weighing approximately 20-25 g were used for the study (Charles River). After 7 days acclimatization, they were allocated into the different groups. Mice were housed in IVC cages (up to 5 mice per cage) with individual mice identified by tail mark. Cages, bedding, and water were sanitized before use. Animals were provided with Corn-o-cobs enrichment bedding to provide environment enrichment and nesting material. All animals had free access to a standard certified commercial diet and water. The animal holding room were maintained as follows—room temperature at 20-24 °C, humidity at 30-70% and a 12 h light/dark cycle used. Although animals used in this study were immuno-competent, preparation of dosing solutions and dosing/weighing of animals were carried out in a sterile biosafety cabinet.

Test Substance and Formulation: in a first experiment, compounds Ia-001a, Ia-001aTz, Ic-001aTz/004a, Ic-007a, Ib-010a, IIIc-061a, IVc-059a were weighed and solubilized in DMSO. Final formulation was in 5% DMSO, 10% Solutol, 10% PEG400, 75% 0.9% Saline and pH adjusted to 7 with 0.5M NaOH solution.

In a second experiment, compounds Ic-001aTz2, IIc-007a, IIIa-001aTz, IIIc-061a, IIIc-061a-E3, IVc-059a were weighed and solubilized in DMSO. Final formulation is in 5% DMSO, 10% Solutol, 10% PEG400, 75% 0.9% Saline and pH adjusted to 7 with 0.5M NaOH solution. For per os (PO) dosing IVc-059a is formulated in water. Drug solutions were formulated on the day of dosing.

The purposes of this study were to assess efficacy compounds in an acute pancreatitis model (14 days), generate tissue samples to allow post in-life analysis of pancreatitis parameters and generate four plasma samples to assess animal exposure levels after first and last injection obtained from blood samples taken 1 h and 24 h after first and last injection.

Study Design: On the first study day animals were randomly be assigned to treatment groups, ensuring an equal spread of bodyweight. Mice (except negative control group) were treated with test compounds were given 5 minutes prior to caerulein dosing, followed by injection with caerulein at 2 g/kg via intraperitoneal route (IP) daily during the study.

TABLE 33

First experiment.

| Group | No. Animals | Agent | Dose level; Route |
|---|---|---|---|
| 1 | 3 | Negative control (non-induced) | Vehicle (tbc); IV |
| 2 | 3 | Negative control (Induced) | Vehicle (tbc); IV |
| 3 | 8 | Pirfenidone | 40 mg/kg; IV |
| 4 | 8 | Ia-001a | 15 mg/kg; IV |
| 5 | 8 | Ia-001aTz | 15 mg/kg; IV |
| 6 | 8 | Ic-001aTz/004a | 15 mg/kg; IV |
| 7 | 8 | Ic-007a | 15 mg/kg; IV |
| 8 | 8 | Ib-010a | 150 mg/kg; PO |
| 9 | 8 | IIIc-061a | 15 mg/kg; IV |
| 10 | 8 | IVc-059a | 150 mg/kg; PO |

TABLE 34

Second experiment.

| Group | No. Animals | Compounds | Dose level; Route |
|---|---|---|---|
| 1 | 3 | Negative control (non-induced) | Vehicle (tbc); IV |
| 2 | 3 | Negative control (Induced) | Vehicle (tbc); IV |
| 3 | 8 | Pirfenidone | 40 mg/kg; IV |
| 4 | 8 | Ic-001aTz2 | 15 mg/kg; IV |
| 5 | 8 | IIc-007a | 15 mg/kg; IV |
| 6 | 8 | IIIa-001aTz | 15 mg/kg; IV |
| 7 | 8 | IIIc-061a | 15 mg/kg; IV |
| 8 | 8 | IIIc-061a-E3 | 150 mg/kg; PO |
| 9 | 8 | IVc-059a | 15 mg/kg; IV |
| 10 | 8 | IVc-059a | 150 mg/kg; PO |

Treatment of test compounds were given 5 minutes prior to caerulein dosing.

Serial Observations

Bodyweight: the bodyweight of all mice on the study were measured and recorded daily; this information was used to calculate precise dosing for each animal.

General signs and symptoms: mice were observed daily and any signs of distress or changes to general condition e.g., starred fur, lack of movement, difficulty breathing were noted.

Sampling and post in-life analyses: at times indicated above a whole blood sample (60 μl) were taken from the lateral tail vein into tubes coated with K2-EDTA. Plasma samples were prepared and stored frozen at −20 °C. Plasma samples were sent to client bioanalysis provider Eurofins (FR) for quantification of compound.

Terminal Sampling: Prior to termination animals were weighed. Terminal study animals were culled via CO2 inhalation. A terminal blood sample was taken via cardiac puncture and plasma prepared. Lipase and Amylase activities were measured via ELISA using commercially available ELISA kits. Remaining plasma was stored for future cytokine analyses. Pancreas tissue was resected and weighed, and a section (50 g) snap frozen and analysed for quantification of compound in pancreas sample. A section (50 g) was processed for measurement of MPO activity, IL-33 and TGF-B levels via ELISA. The remainder was fixed in formalin and embedded in paraffin wax. H&E staining was carried out and section assessed using Schmidts standard scoring system, examining: edema, inflammatory infiltration, parenchymal necrosis, haemorrhage. Massons' Trichrome staining was carried out and area covered by fibrotic tissue quantified digitally using QuPath software. Terminal serum samples was used to assess blood chemistry using an IdeXX CHEM15 and LYTE4 clip (4 animals per treatment group).

Acute Pancreatitis Results after 15 Days IV Treatment

Histopathology assessment of pancreatic injury based on 4 criteria: Oedema, Inflammatory infiltration, Parenchymal necrosis, Haemorrhage and scored as described below.

TABLE 36

Score levels based on 4 criteria

| | Score Levels | | | |
|---|---|---|---|---|
| Item | 0 | 1 | 2 | 3 |
| Interstitial oedema | None | Interlobular | Lobule involved | Isolated island like acinar cells |
| Leukocyte infiltration | None | <20% | 20%-50% | >50% |
| Acinar cell necrosis | None | <5% | 5%-20% | >20% |
| Haemorrhage | None | 1-2 points | 3-5 points | >5 points |

TABLE 35 study schedule.

| Time (days) | T0 | T1 | T2 | T3 | T4 | T5 | T6 | T7 | T8 | T9 | T10 | T11 | T12 | T13 | T14 |
|---|---|---|---|---|---|---|---|---|---|---|---|---|---|---|---|
| Compound I.V. | Dose | Dose | Dose | Dose | Dose | Dose | Dose | Dose | Dose | Dose | Dose | Dose | Dose | Dose | Sacrifice |
| Caerulein I.P. | $1^{st}$ | $2^{nd}$ | $3^{rd}$ | $4^{th}$ | $5^{th}$ | $6^{th}$ | $7^{th}$ | $8^{th}$ | $9^{th}$ | $10^{th}$ | $11^{th}$ | $12^{th}$ | $13^{th}$ | $14^{th}$ | |
| Blood sampling | T0 + 1 h | | | | | | | | | | | | | T12 + 24 h | |
| for PK | T0 + 24 h | | | | | | | | | | | | | T13 + 1 h | |
| Organ analysis | | | | | | | | | | | | | | | Pancreas |

TABLE 37

| Results score levels for animal groups | | | | |
|---|---|---|---|---|
| | Scoring summary | | | |
| Score | Interstitial oedema 1 | Leukocyte infdtration 2 | Acinar cell necrosis 3 | Haemorrhage 4 |
| Negative control (non-induced) | 0-0-0 | 0-0-0 | 0-0-0 | 0-0-0 |
| Negative control (caerulein Induced) | 2-3-3 | 3-3-3 | 2-2-3 | 2-2-2 |
| Ia-001a (caerulein Induced) | 1-1-1-1-1-2-2 | 3-3-3-3-3-3-3 | 0-1-1-1-1-1-1 | 1-1-1-1-1-1-2 |
| Ia-001aTz (caerulein Induced) | 1-1-1-1-2-2-2-2 | 2-3-3-3-3-3-3-3 | 0-0-0-0-1-1-1-1 | 0-1-1-1-1-1-1-1 |
| Ic-001aTz/004a (caerulein Induced) | 1-1-1-1-2-2-2-3 | 1-3-3-3-3-3-3-3 | 1-1-1-1-2-2-2-2 | 1-1-1-1-1-1-1-1 |
| Ic-007a (caerulein Induced) | 1-1-1-1-1-1-1-1 | 3-3-3-3-3-3-3-3 | 1-1-1-1-1-1-1-1 | 1-1-1-1-1-1-1-1 |
| Ib-010a (caerulein Induced) | 1-1-1-1-2-2-2-2 | 3-3-3-3-3-3-3-3 | 1-1-1-1-1-1-1-1 | 0-0-1-1-1-1-1-1 |
| IIIc-061a (caerulein Induced) | 1-1-1-1-1-1-1-1 | 1-1-1-1-1-1-1-1 | 0-0-0-0-1-1-1-1 | 1-1-1-1-1-1-1-1 |
| IVc-059a (caerulein Induced) | 1-1-1-1-1-1-1-1 | 1-1-1-1-1-1-1-1 | 0-0-1-1-1-1-2-2 | 1-1-1-1-1-1-1-1 |
| Pirfenidone (caerulein Induced) | 1-1-1-1-1-1-1-1 | 2-2-2-2-2-2-2-2-2 | 0-0-1-1-1-1-1-1 | 0-0-0-0-1-1-1-1 |

Schmidt Score

Schmidt score is the evaluation of the efficacy of the compounds based on the four histopathology criteria as described in the table below. Order of compounds with increasing Schmidt score (highest score=10 is caerulein induced+vehicle treatment and lowest score=0 is non-induced animals). Graph of Schmidt score for the compounds in FIG. 2 were all products show improved Schmidts score compared to caerulein control animals.

TABLE 38

| Schmidt Score and four parameters table | | | | | | |
|---|---|---|---|---|---|---|
| Test compound | Interstitial oedema | Leukocyte infiltration | Acinar cell necrosis | Haemorrhage | Schmidt Score (H&E) | |
| Non-induced + vehicle | 0 | 0 | 0 | 0 | 0 | Intact apical boarder<br>Healthy acini with abundance of secretory granules<br>No signs of necrosis<br>No signs of oedema<br>No signs of haemorrhage |
| Induced + IIIc-061a | 1.0 | 1.0 | 0.5 | 1.0 | 3.5 | Mild oedema observed<br>Mild haemorrhage observed<br>Mild acinar cell necrosis observed<br>Mild leukocyte infiltration observed<br>Normal islet morphology observed<br>Unlike other treatment groups, areas had relatively normal overall pathology however mild oedema was observed |
| Induced + IVc-059a | 1.0 | 1.0 | 1.0 | 1.0 | 4.0 | Mild oedema less observed<br>Mild haemorrhage less observed<br>Mild acinar cell necrosis observed<br>Mild leukocyte infiltration observed<br>Some pancreatic islet hyperplasia observed<br>Disruption to the basophilic region |
| Induced + Pirfenidone | 1.0 | 2.0 | 0.8 | 0.4 | 4.1 | Mild oedema observed<br>Mild haemorrhage observed<br>Mild acinar cell necrosis observed<br>Leukocyte infiltration observed<br>Normal islet morphology observed in areas |
| Induced + Ib-001aTz | 1.5 | 2.9 | 0.6 | 0.9 | 5.9 | Oedema observed throughout pancreas<br>Mild haemorrhage observed<br>Mild acinar cell necrosis observed<br>Leukocyte infiltration throughout<br>Abnormal islet morphology observed (trace)<br>Disruption to the basophilic region |
| Induced + Ic-007a | 1.0 | 3.0 | 1.0 | 1.0 | 6.0 | Mild oedema observed<br>Mild haemorrhage observed<br>Mild acinar cell necrosis observed |

TABLE 38-continued

| Schmidt Score and four parameters table | | | | | | |
|---|---|---|---|---|---|---|
| Test compound | Interstitial oedema | Leukocyte infiltration | Acinar cell necrosis | Haemorrhage | Schmidt Score (H&E) | |
| Induced + Ib-010a | 1.5 | 3.0 | 1.0 | 0.8 | 6.3 | Leukocyte infiltration observed<br>Disruption to the basophilic region<br>Oedema observed throughout pancreas and within acini cells<br>Mild haemorrhage observed<br>Mild acinar cell necrosis observed |
| Induced + Ia-001a | 1.3 | 3.0 | 0.9 | 1.1 | 6.3 | Leukocyte infiltration observed<br>Disruption to the basophilic region<br>Oedema observed throughout pancreas<br>Haemorrhage observed<br>Mild acinar cell less necrosis observed |
| Induced + Ic-001aTz/004a | 1.6 | 2.8 | 1.5 | 1.0 | 6.9 | Leukocyte infiltration throughout<br>Abnormal islet morphology observed<br>Disruption to the basophilic region<br>Oedema observed throughout pancreas<br>Mild haemorrhage observed<br>Acinar cell necrosis observed |
| Induced + vehicle | 2.7 | 3.0 | 2.3 | 2.0 | 10.0 | Leukocyte infiltration throughout<br>Disruption to the basophilic region<br>Oedema observed throughout pancreas<br>Haemorrhage observed, particularly within the pancreas head<br>Acinar cell necrosis observed<br>Leukocyte infiltration throughout<br>Disruption to the basophilic region |

As showed in the Tables below, all compounds Ia-001a, Ia-001aTz, Ic-001aTz/004a, Ic-007a, Ib-010a, IIIc-061a, IVc-059a showed a significant decrease in pancreatic tissue levels of IL33 compared to the "induced" group. TGF-B levels were decreased significantly for Ic-007a, Ib-010a, IIIc-061a, IVc-059a. Global Schmidt scores especially improved for all compounds but especially for compounds IIIc-061a, IVc-059a.

Tables 39 and 40 below show terminal Pancreas concentrations of MPO in pancreatic tissue sample, IL33 tissue concentrations and TGF-B concentrations.

TABLE 39

| Test Compounds | Mean terminal BW (% of initial) | Mean terminal pancreas weight (g) | Pancreas MPO activity | Pancreas IL33 level | p-value versus induced | Pancreas TGF-B level | p-value versus induced |
|---|---|---|---|---|---|---|---|
| Vehicle | 93.8 | 0.148 | 2.81 | 76 ± 19 | — | 184 ± 107 | — |
| Ia-001a | 90.3 | 0.083 | 3.76 | 330 ± 162 | 0.017 | 592 ± 358 | 0.984 |
| Ia-001aTz | 89.1 | 0.084 | 2.68 | 154 ± 49 | 0.000 | 507 ± 289 | 0.663 |
| Ic-001aTz/004a | 93.5 | 0.104 | 2.15 | 180 ± 54 | 0.000 | 369 ± 195 | 0.113 |
| Ic-007a | 91.2 | 0.109 | 1.65 | 147 ± 47 | 0.000 | 188 ± 77 | 0.000 |
| Ib-010a | 91 | 0.091 | 1.83 | 157 ± 70 | 0.000 | 219 ± 140 | 0.00035 |
| IIIc-061a | 91.4 | 0.086 | 2.13 | 177 ± 80 | 0.000 | 295 ± 146 | 0.015 |
| IVc-059a | 93.3 | 0.09 | 2.88 | 86 ± 23 | 0.000 | 231 ± 199 | 0.020 |
| Pirfenidone | 97.6 | 0.136 | 1.26 | 78 ± 23 | 0.000 | 289 ± 170 | 0.024 |
| Induced | 93.8 | 0.148 | 2.81 | 628 ± 57 | 0.000 | 592 ± 358 | 0.015 |

TABLE 40

| Test Compounds | Serum amylase level | Serum lipase level | Serum IL33 level | Serum TGF-B level | Saline/PBS for formulation | Schmidt Score (H&E) |
|---|---|---|---|---|---|---|
| Vehicle | 43.69 | 11.66 | 37.22 | 10.88 | — | 1.0 |
| Ia-001a | 34.07 | 6.72 | 39.52 | 8.69 | Saline | 6.3 |
| Ia-001aTz | 35.35 | 8.57 | 37.02 | 8.69 | Saline | 5.9 |
| Ic-001aTz/004a | 36.51 | 8.21 | 35.43 | 8.99 | PBS | 6.9 |
| Ic-007a | 34.86 | 9.28 | 34.93 | 6.17 | PBS | 6.0 |
| Ib-010a | 37.46 | 9.06 | 35.36 | 6.87 | PBS | 6.3 |

TABLE 40-continued

| Test Compounds | Serum amylase level | Serum lipase level | Serum IL33 level | Serum TGF-B level | Saline/PBS for formulation | Schmidt Score (H&E) |
|---|---|---|---|---|---|---|
| IIIc-061a | 38.38 | 9.79 | 33.72 | 4.65 | Saline | 3.5 |
| IVc-059a | 38.56 | 10.21 | 46.54 | 5.69 | Saline | 4.0 |
| Pirfenidone | 37.71 | 7.65 | 39.16 | 5.5 | — | 4.1 |
| Induced | 43.69 | 11.66 | 37.22 | 10.88 | | 10.0 |

In a second experiment compounds Ic-001a-TZ(2), IIc-007a, Ia-015a, IIIc-061a, IVc-059a were assessed at 15 mg/k in the same model using pirfenidone 100 mg/kg as the positive control.

TABLE 41

| Results | | | | | | | |
|---|---|---|---|---|---|---|---|
| Groups (route and dose mg/kg) | Amylase mU/mL | Lipase mU/mL | MPO U/mg | IL-33 ng/mL | TGF-B ng/mL | Schmidt Score | Trichome staining (Fibrosis % area) |
| Non-induced | 25.887 ± 0.63 | 3.216 ± 0.212 | 1.37 ± 0.39 | 88 ± 37 | 355 ± 67 | 11.3 ± 0.6 | 0.33 ± 0.168 |
| Induced | 60.858 ± 7.088 | 9.027 ± 1.33 | 2.66 ± 0.28 | 719 ± 97 | 1292 ± 263 | 5.9 ± 1.3 | 5.313 ± 2.089 |
| Pirfenidone (100 mg/kg) | 45.171 ± 6.008 | 4.541 ± 1.457 | 1.68 ± 0.44 | 226 ± 151 | 578 ± 230 | 8 ± 1 | 1.277 ± 0.888 |
| Ic-001a-Tz(2) (IV, 15 mg/kg) | 50.912 ± 5.074 | 8.305 ± 3.036 | 2.63 ± 0.63 | 493 ± 126 | 696 ± 448 | 3.9 ± 0.8 | 1.366 ± 0.562 |
| IIc-007a (IV, 15 mg/kg) | 45.325 ± 6.579 | 6.481 ± 2.908 | 2.74 ± 0.76 | 340 ± 211 | 500 ± 195 | 8.3 ± 1.6 | 1.821 ± 1.12 |
| Ia-015a (IV, 15 mg/kg) | 51.669 ± 12.029 | 5.31 ± 2.219 | 2.68 ± 0.6 | 398 ± 148 | 547 ± 373 | 4.6 ± 0.8 | 1.704 ± 1.621 |
| IIc-061a (IV, 15 mg/kg) | 40.889 ± 6.556 | 5.038 ± 0.874 | 1.72 ± 0.21 | 240 ± 119 | 514 ± 227 | 10.9 ± 1.6 | 0.714 ± 0.452 |
| IVc-059a (IV, 15 mg/kg) | 41.149 ± 5.42 | 4.324 ± 1.121 | 1.813 ± 0.405 | 215 ± 84 | 403 ± 84 | 10.63 ± 2.33 | 1.048 ± 0.449 |

Amylase: All tested compounds, except for Ia-015a, resulted in significantly lower amylase activity levels than in induced vehicle treated controls, however levels did not reach that of non-induced animals.

Lipase: Lipase activity in serum was higher in animals induced and treated with vehicle than in non-induced animals. Treatment with the positive control pirfenidone, Ia-015a, IIIc-061a and IVc 059a resulted in lipase activity significantly lower than that in vehicle treated animals.

Myeloperoxidase (MPO): MPO activity in pancreatic tissue from animals induced and treated with vehicle was significantly higher than that from non-induced animals, indicative of pancreatitis. Treatment with the positive control pirfenidone, IIIc-061a and IVc-059a resulted in MPO activity levels that were significantly lower than induced vehicle treated controls.

IL-33 and TGF-B: All treatments, except for IIIc-061a and IVc-059a dosed PO, resulted in pancreas IL-33 levels that were lower than induced vehicle treated controls. As with serum TGF-B levels resulted in significantly lower TGF-B levels than induced vehicle treated controls.

The clinically used Schmidt scoring criteria based on interstitial oedema, leukocyte infiltration, acinar cell necrosis and haemorrhage was used to assess sections of pancreatic tissue stained with H&E. All tested compounds resulted in significantly lower Schmidt scores than induced vehicle treated controls, with IIIc-061a (IV) and IVc-059a (IV) having lower scores than the positive control pirfenidone.

Fibrosis staining: A commercially available staining kit (Abcam; ab150686, Trichrome Stain) was used to stain pancreas tissue sections for collagen. QuPath digital imaging software was used to quantify the percentage area covered by collagen (blue) staining. All tested compounds resulted in significantly lower areas of trichrome staining than induced vehicle treated controls.

Example 5.2: Treatment and/or Prevention of Pancreatic and Kidney Cancer

The objective of this study was to evaluate preclinically the in vivo therapeutic efficacy study of compounds according to the present invention for the treatment of subcutaneously murine pancreatic cancer syngenic model (Pan02) in female C57BL/6 mice and kidney cancer syngenic model (Renca) in female BALB/c mice.

Animals: C57BL/6 mouse females (For Pan02 model); BALB/c mouse females (For Renca model), 6-8 weeks, >17 g, up to 5 mice per cage Pan02 model treatment and groups: compounds Ia-001a-Tz, Ic-007a, Ib-010a, IVc-059a, IIc-007a as daily for 5 days/week for two weeks via IV bollus injection at a dose of 15 mg/kg.

Renca model treatment and groups: compounds Ia-001a-Tz, Ic-007a, Ib-010a, IVc-059a, IIc-007a as daily for 7 days/week for three weeks via IV bollus injection at a dose of 15 mg/kg Cell Culture: the Renca tumor cells were maintained in vitro with DMEM medium supplemented with 10% fetal bovine serum at 37 °C in an atmosphere of 5% $CO_2$ in air. The cells in exponential growth phase were harvested and quantitated by cell counter before tumor inoculation.

Cell Culture: the Pan02 tumor cells were maintained in vitro with RPMI 1640 medium supplemented with 10% fetal bovine serum at 37 °C in an atmosphere of 5% $CO2$ in air. The cells in exponential growth phase were harvested and quantitated by cell counter before tumor inoculation.

Tumor Inoculation for Renca model: each mouse was inoculated subcutaneously in the right rear flank region with Renca tumor cells ($1\times10^6$) in 0.1 mL of PBS for tumor development.

Tumor Inoculation for Pan02 model: each mouse was inoculated subcutaneously in the right front flank region with Pan02 tumor cells ($3\times10^6$) in 0.1 mL of PBS for tumor development.

Randomization: The randomization was started when the mean tumor size reaches approximately 100 (80-110) $mm^3$. For both models, 48 mice were enrolled in the study. All animals were randomly allocated to 6 study groups. Randomization were performed based on "Matched distribution" method using the multi-task method (StudyDirector™ software, version 3.1.399.19). The date of randomization was denoted as day 0.

Observation and Data Collection: After tumor cells inoculation, the animals were checked daily for morbidity and mortality. During routine monitoring, the animals were checked for any effects of tumor growth and treatments on behavior such as mobility, food and water consumption, body weight gain/loss (body weights were measured twice per week after randomization), eye/hair matting and any other abnormalities. Mortality and observed clinical signs were recorded for individual animals in detail.

Tumor volumes were measured twice per week after randomization in two dimensions using a caliper, and the volume were expressed in mm3 using the formula: "$V=(L\times W\times W)/2$, where V is tumor volume, L is tumor length (the longest tumor dimension) and W is tumor width (the longest tumor dimension perpendicular to L). Tumor weight were measured at the end of study. Dosing as well as tumor and body weight measurements were conducted in a Laminar Flow Cabinet.

Study Endpoints: Tumor growth inhibition (TGI): TGI % was used as an indication of antitumor activity, and expressed as: TGI (%)=100*(1-T/C) T and C were the mean tumor volume (or weight) of the treated and control groups, respectively, on a given day.

Statistical analysis of the difference in mean tumor volume among the groups were conducted using one of the methods below: Use the data collected on the last dosing/observation day for every single group in despite of diverse individual termination date.

Use the data collected on the day when mean Tumor Volume of vehicle group reaches the humane endpoints so that TGI can be derived for all/most mice enrolled in the study.

Use the data collected on the day when any of the treated or control groups was terminated even if the remaining groups are treated as scheduled.

Difference in AUC (AAUC)=Statistical analysis performed with a linear mixed effect regression model.

Study Termination: The efficacy study was performed for 3 weeks.

Statistical Analysis: To compare tumor volumes of different groups at a pre-specified day, Bartlett's test was firstly used to check the assumption of homogeneity of variance across all groups. When the p-value of Bartlett's test is >0.05, One-way ANOVA were used to test overall equality of means across all groups.

If the p-value of the One-way ANOVA is <0.05, post hoc testing by running Tukey's HSD (honest significant difference) tests for all pairwise comparisons, and Dunnett's tests for comparing each treatment group with the vehicle group were performed. When the p-value of Bartlett's test is <0.05, Kruskal-Wallis test were used to test overall equality of medians among all groups. If the p-value the Kruskal-Wallis test is <0.05, post hoc testing by running Conover's non-parametric test for all pairwise comparisons or for comparing each treatment group with the vehicle group were performed, both with single-step p-value adjustment. All statistical analyses were done in R-a language and environment for statistical computing and graphics (version 3.3.1). All tests are two-sided unless otherwise specified, and p-values of <0.05 are regarded as statistically significant.

Results

TABLE 42

Antitumor activity of test articles with data collected on day 13

| Group | Treatment | Tumor volume ± SEM ($mm^3$) | TGI (%) |
|---|---|---|---|
| Control | Vehicle, 5 μL/g, I.V., QD*5 for 2 weeks | 187.91 ± 11.19 (8) | — |
| Compound IVc-059a | IVc-059a, 15 mg/kg, 5 μL/g, I.V., QD*5 for 2 weeks | 148.49 ± 7.05 (8) | 20.98% |

TABLE 43

Statistical analysis of tumor volume with data collected on day 13

| Test | p-values | Significance level |
|---|---|---|
| Test of homogenity of variance and normality | | |
| Bartlett's test | 2.76E−05 | *** |
| Test of overall equality among groups | | |
| Kruskal-Wallis test | 0.00965 | ** |
| Test of equality between individual groups (Conover's non-parametric many-to-one comparison test) | | |
| Group Control versus Compound IVc-059a | 0.0226 | * |

Result Summary

In this study, the in vivo therapeutic efficacies of test compound IVc-059a for the treatment of subcutaneous murine pancreatic cancer syngenic model (Pan02) in female C57BL/6 mice was evaluated. Compound IVc-059a, administrated at 15 mg/kg I.V. significantly suppressed tumor growth, with TGI value of 20.98% (P<0.05).

TABLE 44

Mean % inhibition of tumor volume Pan02 model

| Day | 0 | 3 | 6 | 9 | 13 |
|---|---|---|---|---|---|
| IVc-059a | −0.11% | 19.86% | 18.64% | 18.49% | 20.98% |

Mean % Inhibition = (mean(Control NaCl)-mean(Cpd Treated))/mean(CControl NaQ) * 100%

TABLE 45

Mean % inhibition of tumor volume Renca model

| Day | 0 | 3 | 6 | 9 | 13 | 16 |
|---|---|---|---|---|---|---|
| IVc-059a | 0.05% | −0.90% | 5.02% | 14.83% | 23.07% | 19.42% |

Example 5.3: Treatment and/or prevention of Diabetic Retinopathy (DR)

Animal model: The db/db mouse model was used and compared with db/+mice as a non-diabetic control. The db/db mouse carried a mutation in the leptin receptor gene and was a model for obesity-induced type 2 diabetes. Bogdanov et al. PLoS One, 2014, 9, e97302 reported that db/db mice reproduce the features of the neurodegenerative process that occurred in the human diabetic eye. In addition, this model developed early microvascular abnormalities (vascular leakage) induced by diabetes (Hernindez et al.

Diabetes 2016, 65, 172-187; Hernandez et al. Diabetologia 2017, 60, 2285-2298). Therefore, this model was considered as an appropriate model for testing efficacy of the compounds of the present invention for the treatment of early stages of diabetic retinopathy (DR).

The effect of eye-drops containing Ia-007a on vascular leakage induced by diabetes was tested in the db/db mouse model. The mice, db/db (BKS.Cg-Dock7m+/+Leprdb/J) mice and non-diabetic (db/+) mice aged 8 weeks were purchased from Charles River Laboratories (Calco, Italy).

Animals had free access to ad libitum food (ENVIGO Global Diet Complete Feed for Rodents, Mucedola, Milan, Italy) and filtered water. Mice were maintained under tight environmental conditions of temperature (20 °C) and humidity (60%). Moreover, they had cycles of 12 h/12 h light/darkness.

Interventional Study: When the db/db mice were aged 10 weeks, Ia-007a eye-drops or vehicle eye drops were randomly administered directly onto the superior corneal surface of each eye using a syringe. One drop (5 μL) of Ia-007a (5 mg/mL) to each eye or vehicle (5 μL of 0.9% sodium chloride) to each eye were administered twice daily for 14 days. On day 15, the animals' eyes were instilled with a drop of Ia-007a or vehicle approximately one hour prior to necropsy. All the experiments were performed in accordance with the tenets of the European Community (86/609/CEE).

The permeability of retinal vasculature was examined ex vivo by assessing albumin leakage from the blood vessels into the retina using Evans Blue albumin method. For this purpose, four animals per group were intraperitoneally injected with a solution of Evans Blue (E2129 SIGMA, Sant Louis, Missouri, USA) (5 mg/mL dissolved in PBS pH 7.4). After injection, the animals turned blue, confirming dye uptake and distribution. After 2 h, the mice were euthanized by cervical dislocation and the eyes were enucleated. The retinas of each animal were isolated, weighed and rapidly protected from light. Flat-mounted slides were obtained, and cover slipped with a drop of the mounting medium Prolong Gold antifade reagent (Invitrogen, Thermo Fisher Scientific, Oregon, USA). Digital images from different random fields of all retinas were acquired using a confocal laser scanning microscope (FV1000; Olympus, Hamburg, Germany) at ×60 using the 561-nm laser line, and each image was recorded with identical beam intensity at a size of 1024 pixels×1024 pixels. For quantitative analysis of the albumin-bound Evans Blue, the number of extravasations per field of 0.44 $mm^2$ was counted. This analysis was performed by investigators unaware of treatment received by the mice.

Results

Figure 1:
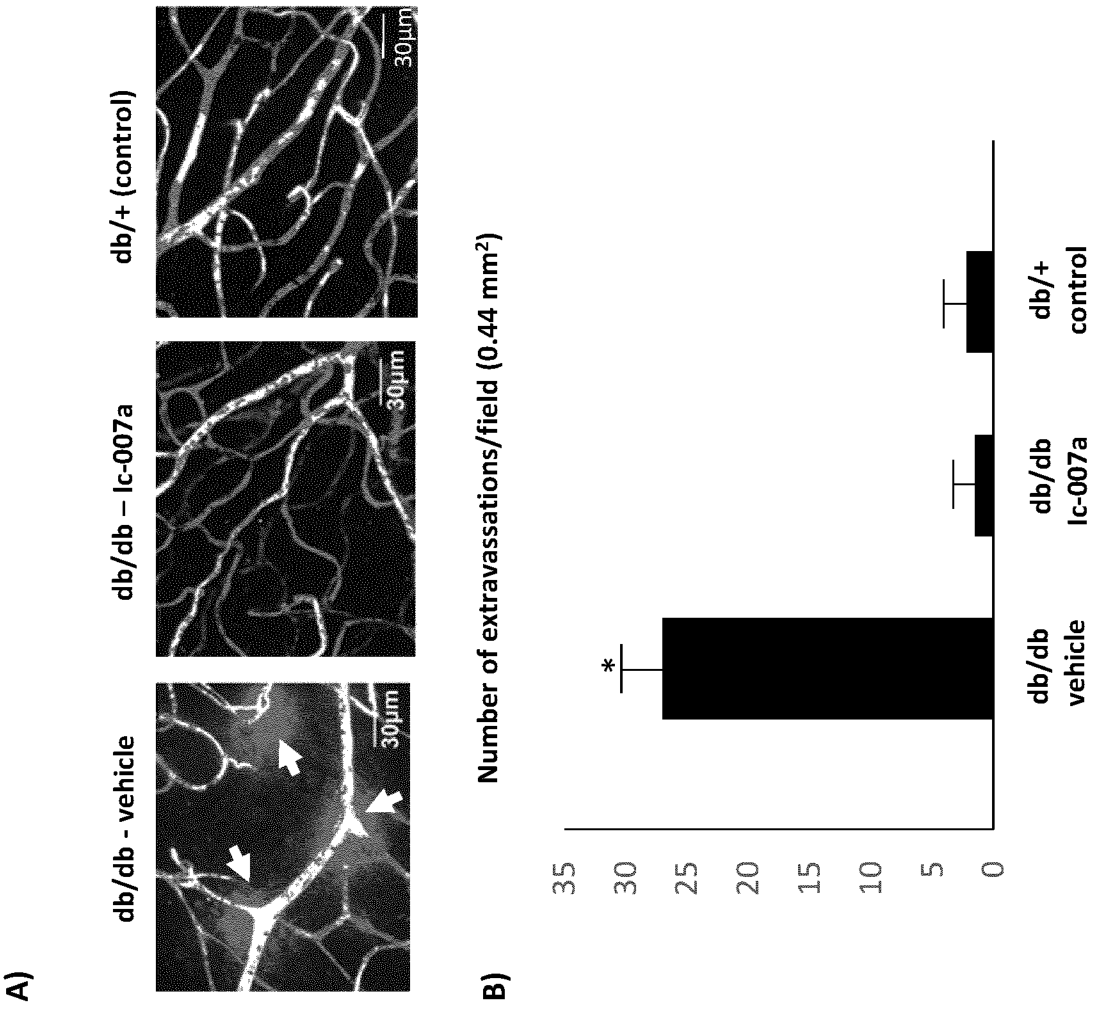
FIG. 1: (A) Confocal immunofluorescence images of vascular permeability assessed by Evans blue dye leakage in retinal whole mounts in a representative mouse from each experimental group.

Blood glucose concentration and body weight at the end of treatment were similar in db/db mice treated with Ia-007a eye drops than in db/db mice treated with vehicle. Extravascular locations of Evans Blue were identified in the diabetic mice retina (FIG. 1, white arrows). Topical treatment with Ia-007a was able to significantly reduce the number of extravasations per field, thus preventing the vascular leakage due to the disruption of the blood retinal barrier.

Example 5.4: Treatment and/or Prevention of Peritonitis

Therapeutic efficacy of the compounds of the present invention was assessed using thioglycolate-induced peritonitis murine models as described by Cook A D et al. (J Immunol. 2003; 171(9):4816-4823) and Tsai J M et al. (Blood Adv. 2019; 3(18):2713-2721. doi: 10.1182/bloodadvances.2018024026).

C57BL/6J mice were injected intraperitoneally (i.p.) with 1 mL of compounds at 50 mg/kg 1 h prior to the induction of peritonitis. Peritonitis was then induced with 1 ml of sterile thioglycolate broth 4% (wt/vol) or PBS as control. After 3 h, mice were anesthetized by i.p. injection with a solution of PBS containing 5 mg/ml ketamine and 1 mg/ml xylazine and peritoneal cavities were washed with 5 ml ice-cold sterile Ca2+/Mg2+-free HBSS 1×containing EDTA 2 mM. Peritoneal exudate cells (PECs) were centrifuged at 1200 rpm for 5 min at 4 °C and red cells lysed. PECs were washed, resuspended in PBS 10% FBS, incubated with anti-CD16/CD32 and mIgG FcR blockers and then stained with fluorescently conjugated antibodies to characterize migrated leukocytes (anti-CD45, anti-CD11b, anti-Ly6G, anti-CD8a, anti-CD4, anti-CD3). Cell viability was measured by 7-AAD exclusion. Specimens were acquired by flow cytometry using MACSQuant Analyzer (Miltenyi Biotec) and analysed using FlowJo software.

Animals: four C57BL/6J mice per group for each compound versus four vehicle treated mice.

Treatment with cpds: 50 mg/kg by i.p. injection of the compounds

Ic-007a: Injected volume: Ic-007a 68.5 μl of compound in DMSO (1,375 mg)+431.5 μl of PBS (500 μl total volume, 5.87 mM) mouse approx. 28 g IIc-007a: Injected volume: 67.25 μl of compound in DMSO (1,345 mg)+431.5 μl of PBS (500 μl total volume, 5.74 mM) mouse approx. 27 g IIIc-061a: Injected volume: 58.75 μl of compound in DMSO (1,175 mg)+441.25 μl of PBS (500 μl total volume, 4.56 mM) mouse approx. 23.5 g IVc-059a: Injected volume: 52.25 μl of compound in DMSO (1,045 mg)+447.75 μl of PBS (500 μl total volume, 5.25 mM) mouse approx. 20.9 g Treatment with products Ic-007a, IIc-007a, IIIc-061a, IVc-059a was done 60 mi before thioglycolate-induced peritonitis. Read out was done 1 h after thioglycolate injection.

Readout method: flow cytometry to characterise migrated leukocytes using anti-CD45, anti-CD11b, anti-Ly6G, anti-CD8a, anti-CD4, anti-CD3.

Results and statistical analysis: Results were analysed using FlowJo software. Data were shown as mean±SEM. Two-tailed Student's t test using a significance level of 0.05 is used for the statistical analysis.

Results

TABLE 46

Example of data for compound Ic-007a

| Cell counts | Vehicle treated mice | C76/24 treated mice | % of reduction |
|---|---|---|---|
| Leukocytes (CD45+ cells) | $60.8 \times 10^4$ ($\pm 10.8 \times 10^4$) | $31.3 \times 10^4$ ($\pm 6.66 \times 10^4$) | 48% |
| PMNs | $10.4 \times 10^4$ | $2.03 \times 10^4$ | 80% |

TABLE 46-continued

Example of data for compound Ic-007a

| Cell counts | Vehicle treated mice | C76/24 treated mice | % of reduction |
|---|---|---|---|
| (CD11b-Ly6G double + cells) | (±7.75 × $10^4$) | (±0.36 × $10^4$) | |
| CD4+ lymphocytes | 1.58 × $10^4$ (±0.54 × $10^4$) | 1.03 × $10^4$ (±0.15 × $10^4$) | 35% |
| CD8+ lymphocytes | 1.86 × $10^4$ (±0.59 × $10^4$) | 0.54 × $10^4$ (±0.15 × $10^4$) | 71% |

TABLE 47 summary of results for the four compounds

| Read Out | C20 treated mice over vehicle treated mice % of reduction | | | |
|---|---|---|---|---|
| Cell counts | Ic-007a | IIc-007a | IIIc-061a | IVc-059a |
| Leukocytes (CD45+ cells) | 48.0% | 11.8% | −2.4% | 4.0% |
| PMNs (CD11b-Ly6G double + cells) | 80.0% | 27.3% | −8.3% | −13.0% |
| CD4+ lymphocytes | 35.0% | 40.0% | 42.9% | 6.0% |
| CD8+ lymphocytes | 71.0% | 20.0% | 33.3% | 23.0% |

Compound Ic-007a had te strongest anti-inflammatory effect and decreasec the recruitment of leukocytes (48%), with a very strong effect on PMNs (80%), CD8+ lymphocytes (71%) and CD4+ lymphocytes (35%)

Example 5.5: Treatment and/or Prevention of Diabetic Cardiomyopathy

Therapeutic efficacy of the compounds of the present invention is tested using diabetic cardiomyopathy murine models described by Li C et al. (Cardiovasc Diabetol. 2019; 18(1):15. Published 2019 Feb. 2. doi:10.1186/s12933-019-0816-2).

Animal procedure and drug treatment: Thirty 8-week-old KK-Ay mice (genetic type 2 diabetes model) and C57BL/6J mice are housed in cages (4-6 per cage) with free access to the drink/feed boxes. Mice are housed in a room kept at 24 °C with 12:12 h light/dark cycle.

The type 2 diabetes model mice are fed a high-fat diet. Blood glucose is measured daily. The mice with a blood glucose concentration greater than 15 mM (200 mg/dL) for 2 consecutive weeks are used for the following experiments. Subsequently, animals are randomized into groups (15 per group) and raised for 8 weeks. The groups include the control groups: (1) healthy C57BL/6J mice with no treatment; (2) type 2 diabetic KK-Ay mice with no treatment; and (3) type 2 diabetic KK-Ay mice treated with the compounds of the present invention.

Echocardiographic evaluation: Echocardiographic measurement is performed before the experimental intervention and at the end of the study period. A M-mode echocardiography equipped with 17.5 MHz liner array transducer system (Vevo 2100™ High Resolution Imaging System; Visual Sonics) is used. Heart rate (HR) and the following structural variables are evaluated: left ventricular internal dimension in diastole (LVIDD), left ventricular internal dimension in systole (LVIDS), interventricular septal thickness in systole (IVSs) and in diastole (IVSd), and LV posterior wall thickness in systole (LVPWs) and diastole (LVPWd). LV mass is calculated using the formula $[(LVIDd+LVPWd+IVSd)^3-(LVIDd)^3\times1.04\times0.8+0.6]$. LV function is assessed by the following parameters including fractional shortening (FS), ejection fraction (EF), and E/A ratio. All measurements are conducted by a single investigator who is blinded to the experimental groups.

Myocardial hydroxyproline concentration: The myocardial hydroxyproline concentration of the left ventricle is measured to estimate the myocardial collagen content. The measurements are performed by a spectrophotometer using commercial kit (BioVision, Mountain View, CA, USA) according to the manufacturer's protocols.

Detection of serum lipids, glucose, insulin, and HbA1c levels: At the end of the study, mice are anaesthetized by inhalation of 3% isopentane in air. The fasting blood specimens are collected into commercial tubes containing lithium heparin as an anticoagulant via the sublingual vein from each animal and centrifuged for 6 min at 3000 rpm/min. The plasma is kept in a plain tube and stored at −20 °C until analysis. Total cholesterol (TC), triglyceride (TG), low-density lipoprotein cholesterol (LDL-C), and high-density lipoprotein cholesterol (HDL-C) plasma concentrations are determined by spectrophotometric methods. Blood glucose levels are measured using a glucometer (ACCU-CHEK, Roche, USA). After an overnight fast, fasting insulin and proinsulin levels are determined using mouse insulin and proinsulin enzyme-linked immunosorbent assay (ELISA) kits, respectively (Nanjing Jiancheng Biotech, China). Blood is also retained for measurement of HbA1c by a chromatographic-spectrophotometric-ion exchange kit (Biosystems, Spain).

Assessment of oxidative stress in heart tissue: Animals are euthanized, and hearts are removed and rinsed retrogradely with a Krebs-Ringer solution (115 mM NaCl, 5 mM KCl, 1.2 mM $KH_2PO_4$, 25 mM $NaHCO_3$, 1.2 mM $MgSO_4$, 1.25 mM $CaCl_2$ and 11 mM glucose) at the end of the study. The temperature of the perfusing solution is maintained at 37 °C. The hearts are then weighed, and cardiac tissues are homogenized on ice in chilled phosphate-buffered saline (PBS) at pH 7.4, containing 1 mM EDTA. The homogenates are centrifuged in cold saline for 10 min at 7000 rpm/min. The protein concentration of the supernatant is determined by the bovine serum albumin kit as a standard. The supernatants are used for analysis of the lipid hydroperoxide level and glutathione peroxidase (GSH-Px), superoxide dismutase (SOD), and malondialdehyde (MDA) levels. The measurements are performed by a spectrophotometer using commercial kits (Solarbio, China) according to the manufacturer's protocols. The lipid hydroperoxide level is expressed as nmol/mg protein. The GSH-Px, SOD, and MDA levels are expressed as mol/mg protein, nmol/mg protein, and mmol/mg protein, respectively. The expression level of NOX4 is measured by Western blotting. Mouse monoclonal anti-Nox4 (1:1000, Abcam) and horseradish peroxidase-conjugated secondary antibody (CWBIO) are used. p-Actin (1:1000, Abcam) is used as a reference.

Histological and immunohistochemical analysis: The heart tissues are fixed in 4% paraformaldehyde in 0.1 M phosphate buffer for 48 h, dehydrated and embedded in paraffin, sectioned at 4-µm thickness, and mounted on glass slides. Masson's trichrome staining is used to assess the extent of fibrosis in cardiac muscle.

For antigen retrieval, the deparaffinized slides are kept in a solution of 10 mM sodium citrate (pH 6.0) for 10 min at 100 °C. The sections are then incubated in 3% hydrogen peroxide for blocking endogenous peroxidase activity and incubated with primary antibody (mouse monoclonal antibody to TGF-β1, collagen I and collagen III; Abcam) for 1.5 h, followed by corresponding secondary antibody for 2.5 h at room temperature. Subsequently, the sections are washed in PBS three times and incubated in 0.02% diamino benzidine solution for 2-8 min. After counterstaining with haematoxylin, the slides are washed briefly, mounted with resinene, and observed in the light microscope.

Analysis of the Nrf2/ARE and TGF-β/SMAD pathway by western blotting: The Western blotting protocol is described in our previous study. Briefly, myocardial tissue is lysed in ice-cold RIPA buffer (150 of mM sodium chloride, 0.1% sodium dodecyl sulphate (SDS), 0.5% sodium deoxycholate, 1.0% NP-40, PMSF 1 mM, and 50 mM of Tris, pH 8.0) for total protein extraction. The total protein concentration is quantified by a BCA Protein Assay Kit (Medchem Express, USA). Equal amounts of protein are separated by 12% SDS-polyacrylamide gel electrophoresis (PAGE). Then, the protein is transferred from the gel to a polyvinylidene fluoride membrane. After blocking with 5% skim milk, the membrane is incubated overnight in primary antibody (Nrf2, HO-1, TGF-β1, p-Smad2, Smad2, p-Smad3, Smad3, Smad7, α-SMA 1:1000, Abcam). Bands are detected with specific horseradish peroxidase-conjugated secondary antibody (CWBIO). β-actin (1:1000, Abcam) is used as a reference of total cell protein.

Example 5.6: Treatment and/or Prevention of Diabetes and Diabetic Wound Healing Diabetes murine models using streptozotocin (STZ-induced diabetes) were used to assess efficacy of compounds of the present invention for a diabetic wound healing and generate tissue samples to allow post in-life analysis of skin tissue.

Animals: a total 104 Female CD-1 mice aged 5-7 weeks weighing approximately 25-30 g were implanted for the study. These were purchased from Charles River and acclimated for 7 days upon arrival.

Animal Housing: Mice were housed in IVC cages (up to 5 mice per cage) with individual mice identified by tail mark. Cages, bedding and water were sanitized before use. Animals were provided with Com-o-cobs enrichment bedding to provide environment enrichment and nesting material. Each cage was clearly labeled with a card indicating the number of animals, sex, strain, DOB, study number and start date and treatment. Cages were changed once a week with food and water replaced when necessary.

The animal holding room was maintained as follows—room temperature at 20-24 °C, humidity at 30-70% and a 12 h light/dark cycle used.

Aseptic technique and dosing: Although animals to be used in this study are immuno-competent, preparation of dosing solutions and dosing/weighing of animals were carried out in a sterile biosafety cabinet. IV dosing: Compounds were formulated in 5% DMSO: 10% Solutol: 10% PEG400: 75% PBS and pH adjusted to 7 with 0.5M NaOH solution. PO dosing: formulation is in water.

Drug solutions were formulated on the day of dosing, any remaining at the end of dosing are stored at −20 °C.

Study Design: Mice (except negative control group) were injected with STZ (55 mg/kg; IP) daily for 5 consecutive days. Mice were starved for 6 hours prior to injection. One week after completion of induction glucose levels were monitored and mice with levels less than 15 mml/L (280 mg/gL) were removed from the study as they had not developed the ideal severity of diabetes. Animals were anaethetised and a full thickness 6 mm wound created using a sterilized biopsy punch. Wounds were imaged (Days 0). Animals were treated and imaged every 2 days out to day 14 (when control, non-diabetic mouse wounds were healed). Wound images were digitally assessed for area of wound and percentage closure versus time plotted graphically.

TABLE 48

| Group | No. Animals | Tested compounds | Dose level; Route |
|---|---|---|---|
| 1 | 3 (3) | Negative control (non-induced) | Vehicle; IV |
| 2 | 3 (3) | Negative control (Induced) | Vehicle; IV |
| 3 | 8 (3) | Pirfenidone | 250 mg/kg; PO |
| 4 | 8 (3) | Ia-001a | 15 mg/kg; IV |
| 5 | 8 (3) | Ia-001aTZ | 15 mg/kg; IV |
| 7 | 8 (3) | Ib-010a | 15 mg/kg; IV |
| 8 | 8 (3) | IIIc-061a | 15 mg/kg; IV |
| 9 | 8 (3) | IVc-059a | 15 mg/kg; IV |
| 10 | 8 (3) | IVc-059a | 150 mg/kg; PO |

Treatment will continue for 2 weeks (14 days). Animal numbers in brackets are dosed for 7 days, then sampled for mid-study PD analysis.

TABLE 49 study schedule:

| Time (Weeks) | W1 | W2 | W3 | W4 | W5 |
|---|---|---|---|---|---|
| STZ | Dose (5 days) | — | — | — | — |
| Testing | | Blood Glucose | Blood Glucose | Blood Glucose Wound image immediately after image every 2 days | Blood Glucose Wound Image every 2 days |
| Compound | — | — | — | IV Dose, daily PO Dose, daily | IV Dose, daily PO Dose, daily |
| Organ | | | | 3 animals per group sampled after 7 days dosing. Skin tissue sampled. | |

Serial Observations

Bodyweight: the bodyweight of all mice on the study were measured and recorded daily; this information is used to calculate precise dosing for each animal.

General signs and symptoms: mice were observed daily and any signs of distress or changes to general condition, e.g., starred fur, lack of movement, difficulty breathing are noted.

Mid Study sampling: Following 7 days dosing 3 animals per group were killed and wound tissue removed and divided into 2 sections (A) and (B):

(A) First section is FFPE and stained with the following: H&E, Masson's Trichrome, CD31, TGF-β.

(B) Second section are homogenised and used for the following ELISAs: SOD, GTPx, Catalase, TNF-α, IL-6, TGF-β levels.

Termination: Terminal study animals are culled via $CO_2$ inhalation. Prior to termination animals are weighed. Early Termination: Early termination of an animal is performed if a weight loss of >20% is measured and for any compromised animal showing critical signs and symptoms or inability to eat/drink.

Results:

Blood Glucose: Induction with STZ resulted in a significant increase in blood glucose in comparison to non-induced vehicle controls. Treatment with Ia-001a, IIIc-061a and IVc-059a IV resulted in a significant reduction in blood glucose levels in comparison to induced vehicle controls. After 7 days already all compounds exhibited some degree of accelerating wound healing in the STZ-induced diabetes model (FIG. 10, 3 animals per group sampled after 7 days dosing). Skin tissue was sampled.

Example 5.7: Treatment and/or Prevention of Diabetic Foot Ulcers

Compounds of the present inventions are tested using a rat model of diabetic ulcers as described by Zhang Y et al. (J Diabetes Res. 2016, 2016, 5782904. doi:10.1155/2016/5782904).

Wound-healing in skin and other mucosal tissues involves a complex sequence of events including the clotting case, acute and chronic inflammation, reepithelialization, granulation tissue formation, wound contraction, and connective-tissue remodelling. However, several genetic and acquired conditions, such as aging, malnutrition (e.g., vitamin C and protein deficiency), infection, hypoxia, and genetic diseases such as Ehlers-Danlos syndrome, can impair this reparative process. Among these conditions, diabetes mellitus is a most common cause of impaired or nonhealing wounds. As an example, the clinical significance of long-term hyperglycemia is highlighted by alarming data showing that 85% of nonhealing diabetic foot ulcers ultimately require amputation. The "pathway to a chronic wound," as outlined by authors of a recent study, focused on prolonged or chronic inflammation characterized by activation of macrophages (as well as accumulation of neutrophils) that resulted in elevated levels of proinflammatory cytokines, reactive oxygen species, matrix metalloproteinases (MMPs), and other neutral proteinases (e.g., elastase). This, coupled with a deficiency of endogenous proteinase inhibitors, all leads to "excessive matrix degradation, degradation of growth factors, and impaired epithelialization."

In the first experiment, fifteen adult male Sprague-Dawley rats (body weight 300-325 g, Charles River Laboratories International, Inc., Wilmington, MA) are injected through the tail vein with either 10 mM citrated saline buffer pH 4.5 (nondiabetic controls, NDCs) or the same solution containing streptozotocin (STZ; ENZO Life Sciences, Inc., Plymouth Meeting, PA; 70 mg/kg body weight) to induce type I diabetes. The rats are then distributed into the five experimental groups described below (n=3 rats/group). All rats are given unlimited access to food and water. Within 48 hours, the STZ-injected rats exhibited severely elevated glucose levels in their urine. Three weeks after inducing diabetes, the back skins of all the rats are shaved and a series of six standard wounds per rat, each 6 mm in diameter, are made using a surgical trephine. The following five experimental groups are established (in this initial experiment, treatment in all groups was for seven days; a longer-term study is described below in experiment 3): nondiabetic control (NDC) rats treated by daily topical application of white petrolatum jelly ("vehicle"); diabetic rats (D group) topically treated daily with vehicle alone; diabetic rats treated with the tested compounds.

At the end of this time period, the six circular wounds per rat are clinically assessed by measuring with a caliper the diameter of the wounds in millimeters, blood samples are collected, the rats are sacrificed, and skin samples are dissected for histological/histochemical and biochemical assessment as described below.

On day seven after creating the standardized wounds, all animals are anesthetized, blood samples are collected for blood glucose (One Touch Ultra Glucometer; Johnson & Johnson, New Brunswick, NJ) and HbA1c (Bayer A1CNow Selfcheck, Sunnyvale, CA) measurements, and, after the procedures below are completed, the rats are sacrificed by CO2 inhalation.

Photographs are taken for clinical measurements to assess wound closure (18 wounds per experimental group). The percent reduction of the wound surface is calculated by measuring the diameter (in millimeters) of each wound before and after the treatment protocol.

Wound tissues on day 7 are excised from two sites per rat and pooled for biochemical analysis. Each pool of tissue is homogenized, extracted at 4 °C with 5 M urea in 50 mM Tris-HCl buffer (pH 7.8) containing 0.2 M NaCl and 5 mM $CaCl_2$) overnight, and then centrifuged for 1 hour at 11,000× g, as described by us previously. The supernatants are dialyzed against the Tris-HCl, NaCl, and CaCl2 buffer, and the proteinases are partially purified by ammonium sulfate added to 60% saturation. The precipitated proteinases are analyzed by ELISA for collagenases MMP-8 (Sigma-Aldrich Life Sciences Inc., St. Louis, MO) and MMP-13 (TSZ Scientific LLC, Framingham, MA).

Biopsies of each of two wound sites, including surrounding nonwounded tissue, are taken and fixed in 10% neutral buffered formalin for 24 hours and then transferred to 50% ethanol prior to grossing, alcohol dehydration, xylene clearing, paraffin embedding, and sectioning. Five-micron sections are stained with H&E and Masson's Trichrome and the distance between wound margins is measured histomorphometrically using a calibrated ocular micrometer and confirmed image analysis. The last two wounds per rat are dissected, hydrolyzed, and analyzed for hydroxyproline as described below.

At the end of the 14-day and 30-day treatment protocols, the physical measurements and histologic and histochemical assessments are the same as those described above for the 7-day experiment. In addition, for all three time periods, tissue samples from the 6 mm punch biopsies are hydrolyzed twice in 2N NaOH at 120 °C for 1 hour each time. 50 μL aliquots of the skin tissue hydrolysates are then analyzed for hydroxyproline, an amino acid essentially found only in collagen.

Example 5.8: Treatment and/or Prevention of Diabetic Retinopathy and Diabetic Nephropathy Therapeutic efficacy of the compounds according to the present invention was assessed using diabetic mouse model using the DBA/2 mouse strain with STZ induction of diabetes and follow diabetic retinopathy including kidney damage. Five weeks after induction of diabetes via low dose STZ injection for 5 consecutive days, the urinary albumin: Cr ratio is 424-fold compared to 36.9 for age-matched controls.

For treatment of diabetic nephropathy, DBA/2 mice were induced with STZ (low dose for 5 consecutive days). One week after completion of induction, glucose levels were monitored and mice with levels less than 15 mml/L (280 mg/0.1 L) were removed from the study as they had not developed diabetes of sufficient severity to result in renal injury. Glucose levels were monitored weekly and 5 weeks after STZ induction biochemical assessment of renal injury was carried out by measuring urine albumin and creatinine levels and confirming they were within the desired range. After successful completion of this stage animals were assigned to treatment groups.

Treatment was performed for four weeks (IV dosing) with weekly assessment of blood glucose and urine albumin/creatinine levels. At the end of the treatment period animals, the following samples were taken:

- Blood for measurement of glucose and Blood Urea Nitrogen (BUN)
- Blood for measurement of serum creatinine
- Urine for final albumin/creatinine ratio.
- Kidney was resected and FFPE: Picro-Sirius Red, Masson's Trichrome and H&E staining was carried out to identify areas of fibrosis, along with evidence of Mesangial sclerosis, Arteriolar hyalinosis, Glomerular Basal Membrane (GBM) thickening To assess compound effect on diabetic retinopathy, animals had weekly images taken via Fundus Camera. Immediately prior to sacrifice, animals were injected with FITC-dextran via tail vein. During sampling, the eyes were sampled and fixed in formalin. Retinal Flatmounts were prepared and examined fluorescently looking at compound effects on vascularity and leakiness of vessels (indicted by high background staining). Animal groups (n=8 mice per group):

TABLE 50

| Group | No. Animals | Compounds |
|---|---|---|
| 1 | 3 | Negative control (non-induced) |
| 2 | 3 | Positive control (Induced) |
| 3 | 8 | Captopril 50 mg/kg |
| 4 | 8 | Ia-001a 15 mg/kgI.V. |
| 5 | 8 | Ia-001aTZ 15 mg/kg TV. |
| 6 | 8 | Ic-007a 15 mg/kg LV. |
| 7 | 8 | Ib-010a 15 mg/kgLV. |
| 8 | 8 | IIIc-061a 15 mg/kg I.V. |
| 9 | 8 | IVc-059a 15 mg/kg I.V. |
| 10 | 8 | IVc-059a 150 mg/kg P.O. |

Treatment continued for 4 weeks (28 days) with weekly measurement of blood glucose and urine albumin/creatinine.

Sacrifice after last compound (agent) dosing, organ, and blood sampling.

Serial Observations

Bodyweight: The bodyweight of all mice on the study was measured and recorded daily; this information was used to calculate precise dosing for each animal.

General signs and symptoms: Mice were observed daily and any signs of distress or changes to general condition, e.g., starred fur, lack of movement, difficulty breathing were noted.

Sampling and Post In-Life Analyses

- Immediately prior to terminal sampling 4 animals per group were injected with FITC-dextran for retinal flatmount assessment.
- Terminal Sampling:
  - Terminal blood samples were taken via cardiac puncture and plasma/serum prepared from each animal.
    - Blood glucose measured
    - Serum creatinine measured
    - BUN measured
    - Urine ALB/CREATININE
    - ELISAs for CRP, TNF-α, IL-6 and TGF-β
    - Remaining plasma were stored for cytokine analyses
  - Kidney tissue were resected and weighed
    - One kidney was snap frozen for possible bioanalysis or other analysis.
    - One kidney was fixed in formalin and embedded in paraffin wax.
      - H&E and Masson's Trichrome staining Screening for
        - Mesangial and glomerulo-sclerosis,
        - Arteriolar hyalinosis
        - GBM thickening
  - Eye tissue to be FFPE
    - Other eye (4 per treatment group) was used for Retinal flatmount analysis to measure vascular patterning
    - Area covered by vessels
    - Assessment of vascular leakage Termination: Terminal study animals were culled via $CO_2$ inhalation. Prior to termination animals were weighed.

Results: compounds Ia-001a, IIIc-061 and IVc-059a significantly reduced the blood glucose level in DBA/2 mouse strain with STZ induction of diabetes as shown in FIG. 9 (one and two weeks shown).

TABLE 51 study schedule

| Time (Weeks) | W1 | W2 | W3 | W4 | W5 | W6 | W7 | W8 | W9 | End W9 Sacrifice |
|---|---|---|---|---|---|---|---|---|---|---|
| STZ | Dose (5 days) | — | — | — | — | — | — | — | — | — |
| Testing | | Blood Glucose | Blood Glucose | | Blood Glucose Urine ALB/CREA | Blood Glucose Urine ALB/CREA | Blood Glucose Urine ALB/CREA | Blood Glucose Urine ALB/CREA | Blood Glucose Urine ALB/CREA | Blood Glucose Urine ALB/CREA |
| Compound | — | — | — | — | — | IV Dose, daily | IV Dose, daily | IV Dose, daily | IV Dose, daily | — |
| Organ | | | | | | | | | | Blood (Plasma) Kidneys Eyes |

Example 5.9: Treatment and/or Prevention of BehçEt's Disease (BD)

Therapeutic efficacy of the compounds according to the present invention is tested using Behçet's disease munne model as described by ZHENG et al. (Acta Derm Venereol 2015; 95: 952-958).

Behçet's disease is a chronic, recurrent, multisystemic, inflammatory disorder affecting mainly the oral and urogenital mucosa and the uveal tract. Although the etiology and pathogenesis of Behçet's disease are unknown, numerous etiologies have been proposed, including environmental, infectious, and immunological factors; an autoimmune basis, characterized by circulating immune complexes and complement activation, gained increasing acceptance. To test and understand immunopathogenesis of Behçet's disease, animal models are developed based on environmental pollutants, bacterial and human heat shock protein derived peptides, and virus injections. Using these animal models separately and/or concurrently allows for a more effective investigation into Behçet's disease.

Animal models have been recently developed to find efficient and safe treatment options. Neutrophil activation is one of the immunopathogenesis aspects of BD. Neutrophils have a pivotal role in innate immune responses. As typical BD lesions such as pustular folliculitis, pathergy reactions, and hypopyon have significant neutrophil infiltrations, neutrophil functions and activation status have been investigated. There are conflicting reports of increased, normal, or decreased basal and fMLP stimulated superoxide productions, phagocytosis, chemotaxis, and neutrophil-endothelial adhesion in BD. In HLA-transgenic mic presumed model for BD, the only abnormality seen is increased superoxide release in response to fMLP. High superoxide responses are also present in HLA-B51+ patients and healthy controls in the same study.

Behcet Disease-like mouse model is developed by inoculating HSV type 1 grown in Vero cells in 4-5-week-old male Institute of Cancer Research (ICR) mice. Briefly, the earlobes of experimental mice are scratched with a needle and they are inoculated twice with the virus, with a 10-day interval. The infected mice are observed for 16 weeks after the final inoculation. HSV-inoculated mice presenting at least 2 Behcet-like symptoms are used as a BD-like mouse model (n=5). Both uninfected ICR mice (n=2) and HSV-inoculated, but asymptomatic, mice.

Example 5.10: Treatment and/or Prevention of Uveitis (UVE)

Therapeutic efficacy of the compounds of the present invention are tested using animal models of autoimmune uveitis including Endotoxin-Induced Uveitis (EIU) in the rat as described by Fruchon S et al. (Molecules. 2013; 18(8): 9305-9316. Published 2013 Aug. 5. doi:10.3390/molecules18089305). This model is considered as a clinically relevant model for human anterior uveitis. It consists in the systemic administration of lipopolysaccharide (LPS) which results in an acute inflammatory response in the anterior and posterior segments of the eye with a breakdown of blood-ocular barrier and inflammatory cell infiltration. Clinical signs of EIU reflect the changes observed in human disease. The therapeutic effect of compounds of the present invention are thus tested in the model of EIU in rats, in comparison with the "gold standard" dexamethasone.

Animals: Only animals with no visible signs of ocular defects are enrolled. Animals are examined during the pre-test period and particular attention is given to the eyes. They are held in observation for one week before experimentation. Animals are housed individually in standard cages and had free access to food and tap water.

Ocular Tolerability Study: The study consisted of three groups of three male Sprague-Dawley rats. On day 0, animals are weighed, anesthetized and administered by a single 5 μL intra-vitreal injection in both eyes. The first group receives the saline vehicle (NaCl 0.9%), and the other groups receives different doses of the compounds of the present invention. Each animal is then assessed by clinical observation and eye examinations. Ocular examinations include funduscopy, slit-lamp examination (SLE) of the cornea using fluorescein dye enabling McDonald-Shadduck scoring. The McDonald-Shadduck Scoring System addresses: conjunctival parameters (congestion, swelling and discharge), aqueous flare (intensity of the Tyndall phenomenon) as presumptive evidence of breakdown of the blood-aqueous barrier; injection of secondary and tertiary vessels in the iris; cloudiness, relative area thereof, neovascularization and epithelial integrity (fluorescein labelling) of the cornea; integrity of the lens. After final ocular examination, all animals are sacrificed. Eyes are collected at necropsy, fixed in modified Davidson's solution for 12 h, followed by 10% neutral buffered formalin and processed for histology. Hematoxylin-Eosin-stained tissue sections are evaluated via light microscopy by a board-certified veterinary pathologist.

Endotoxin-Induced Uveitis (EIU) Rat Model: Thirty-six female albino Lewis rats are randomly divided into six groups of six animals each. EIU is induced by a 100 μL footpad injection of sterile pyrogen-free saline solution containing 200 μg of LPS (lipopolysaccharide from *Salmonella typhimurium*, Sigma-Aldrich, Saint-Quentin, France). Animals are treated immediately before EIU induction by a 5 μL intra-vitreal injection in both eyes of a saline solution (NaCl 0.9%) containing no active ingredient, or with tested compounds, or 20 μg of dexamethasone. Animals are examined by slit-lamp (SLE) at 24 h, i.e., the clinical peak of the disease in this model. The intensity of clinical ocular inflammation is scored on a scale from 0 to 5 for each eye. Grade 0 indicates no inflammation. Grade 1 indicates the presence of a minimal iris and conjunctival vasodilatation but without the observation of flare or cells in the anterior chamber (AC). Grade 2 indicates the presence of moderate iris and conjunctival vessel dilation but without evident flare or cells in the AC. Grade 3 indicates the presence of intense iris vessel dilation, flare and less than ten cells per slit-lamp field in the AC. Grade 4 indicates the presence of more severe clinical signs than Grade 3, with more than ten cells per slit-lamp field in the AC, with or without the formation of a hypopyon. Grade 5 indicates the presence of intense inflammatory reaction, fibrin formation in the AC and total seclusion of the pupil. At the end of experiment, i.e., 24 h after LPS challenge, rats are anesthetized by intra-peritoneal injection of pentobarbital (30 mg/kg) then killed with a lethal dose of pentobarbital.

Measurement of Cytokine Concentrations in Ocular Fluids: Aqueous humour and vitreous from both eyes of each animal are taken after sacrifice. Pro-inflammatory T helper cytokines TNFα, IL-1β, IL-2, IL-6, IL-17 and IFNγ as well as anti-inflammatory cytokines IL-4 and IL-10 quantities are determined by Multiplex analysis.

Measurement of Cytokine Concentrations in Serum: Sera from the three groups of rats (saline vehicle, compound 10 μg and dexamethasone) are collected at the end of the experiment and stored at −80 °C. They are used for the simultaneous determination of five cytokine (IFNγ, TNFα, IL-2, IL-4 and IL-10) levels with Cytometric Bead Array (rat CBA Flex set, BD Biosciences, San Jose, CA, USA) on a FACS Calibur flow cytometer (BD Biosciences) according to the manufacturer's instructions. The amounts of each of the cytokines are analyzed in relation to standard curves using the FCAP Array software (BD Biosciences).

Example 5.11: Treatment and/or Prevention of Diabetic Sensorimotor Polyneuropathy and Diabetic Neuropathy Therapeutic efficacy of the compounds of the present invention are tested using rat models of diabetic peripheral neuropathy (Kambiz S. et al. (PLoS One. 2015; 10(6): e0131144]; PLoS One. 2015; 10(5):e0126892. Published 2015 May 18. doi:10.1371/journal.pone.0126892).

Animals: WAG/RijHsd female rats (n=27, 10 weeks old, weighing 130-150 gram) are purchased from Charles River (l'Arbresle, France). The animals are pair-housed in hooded cages at room temperature on a 12-hour light/dark schedule and are given water and food ad libitum.

Induction of diabetes: Diabetes is induced in 21 rats by a single intra-peritoneal injection of STZ (Sigma-Aldrich, St. Louis, MO, USA) at a dose of 65 mg/kg body weight in 0.05 mol/L sodium citrate buffer, pH 4.5, as described previously. The rats are randomly assigned into 3 groups: A, B and C (n=7 in each group). Following diabetes induction, group A is killed after 4 weeks, group B after 6 weeks and group C after 8 weeks. The control group consists of 6 rats who receive a single intra-peritoneal injection with an equal volume of vehicle without STZ. Control rats are followed for 8 weeks. Blood glucose is measured from tail vein blood by a glucometer (OneTouch, LifeScan, Milpitas, CA, USA). Diabetes is diagnosed in rats, when blood glucose levels are higher than 20 mmol/L during the entire 4 weeks after the induction of diabetes.

The blood flow and oxygenation of the plantar hind paws' skin: A combined laser doppler flowmetry and spectrophotometry system (O2C, LEA Medizintechnik, Giessen, Germany), is used to non-invasively measure blood flow and oxygen saturation of the glabrous plantar hind paws. In both diabetic and control rats the percentage oxygen saturation and amount of skin blood flow are assessed at 4, 6, and 8 weeks.

Rewarming rate after cold exposure: The temperature of the skin is assessed using the built-in infrared digital video camera (320×240 pixels) by 1 Hz data acquisition system (ThermaCAM Researcher 2001 HS; FLIR Systems, Berchem, Belgium), and all data are continuously collected by a laptop. The distance between the camera and the hind paw is 13 cm±2 cm. The pixel size of the temperature recordings is 0.8×0.8 mm. The skin temperature of the entire plantar hind paw is recorded while the animal was fixed after placing the animal on a 14 °C plate for 5 seconds. The minimum temperature of the plantar hind paws is exported to text files using ThermaCAM Researcher Pro (version 2001-HS; FLIR Systems, Wilsonville, Oregon, USA). The area of interest is selected by drawing a line surrounding the entire plantar hind paws. The average rewarming rate is demonstrated as the increase in skin temperature per 120 seconds.

Thermal sensitivity: In order to determine the occurrence of thermal hypersensitivity, cold and hot plate tests are performed as described previously. In short, rats are placed in an open-ended chamber with clear walls with a surface temperature of either 5 °C. (cold plate) or 50 °C. (hot plate). These experiments are performed on separate days to prevent interference. The time until hind paw withdrawal or licking is observed.

Von Frey test: In the von Frey test, used to determine the mechanical sensitivity threshold for nociception, each rat is placed in a chamber with a mesh metal floor. Then, von Frey hairs, ranging from 2 to 300 grams, are applied 5 times, and was scored positive when a minimum of 3 paw flicks (the animal's reflex withdrawal response) are observed, as described previously. The control group served as the reference group.

Electromyography (EMG): Innervation of motor axons in muscles is evaluated by recording the evoked CMAP peak-peak amplitudes and latencies of the gastrocnemius muscles in the diabetic groups and control animals. CMAP peak-peak amplitudes and latencies are recorded and averaged over a batch of 20 responses. The average amplitudes in each diabetes group are compared to the control group. The MNCV is calculated as the distance of stimulating electrode to recording electrode (mm)/latency (ms).

Tissue preparation: After 4, 6, or 8 weeks, the animals are killed by an overdose of pentobarbital (100 mg/kg ip). For each rat, the plantar skin of the hind paw is dissected and directly immersion-fixed in 2% paraformaldehyde-lysin-periodate (PLP) for 24 hours at 4 °C. The skin is further processed and embedded in gelatin as described previously. Finally, the embedded skin is sectioned at 40 m with a freezing microtome and collected in glycerol for long-term storage at −20 °C.

The pancreas tissue of the rats is harvested, fixed in 10% neutral buffered formalin solution, and embedded in paraffin. Subsequently, these specimens are stained with hematoxylin and eosin (H&E). Each specimen is evaluated by a bright-field microscope and scanned into digital slides (Nanozoomer 2.0 series, Hamamatzu, Japan).

Immunohistochemistry: Immunohistochemistry of the skin sections is performed as previously described to semi quantify the density of sensory nerve fibers innervating the skin, and to evaluate the presence of CD-31 positive endothelial cells. The skin sections are incubated for 48 hours in a cocktail of 2% BSA containing the diluted primary antibody Protein Gene Product 9.5 (PGP9.5, 1/10.000, anti-rabbit, Enzo Life Sciences, New York, USA), or anti-CD31+(1/5000, anti-rabbit, Spring Bioscience, California, USA) at 4 °C. Subsequently, skin sections are incubated with the appropriate secondary biotinylated antibody labelled with horseradish peroxidase (HRP) (1/200, Biotine, Sigma-Aldrich, St. Louis, MO, USA) for 90 min at RT. The 3, -3' diaminobenzidine (DAB) reaction is then used to reveal the antigenic binding sites of the primary antibodies. Thereafter, the sections are mounted on slides and the CD31+ stained sections stained with 0.05% thionin for 4 minutes, which coloured the keratinocytes blue. Finally, all skin sections are dehydrated using absolute ethanol (<0.01% methanol), transferred to xylene, and cover slipped with Permount (Fisher Scientific, Hampton, NH).

Each skin section is scanned in 3 layers of 8 μm each by Nanozoomer 2.0 series (Nanozoomer 2.0 series, Hamamatzu, Japan). Four proximal and 4 distal skin sections of the plantar hind paw are quantified for epidermal nerve fibers in the center part of the plantar hind paw (80.000 m2) using a 40×objective in ImageScope software (Aperio ImageScope v11.1.2.760). The average labeled nerve fibers per mm2 and the average epidermal thickness are calculated for each rat. Percentage CD31-positive cells is calculated by Leica Cell-D (Olympus, Imaging software for life science microscopy, USA) in 4 proximal and 4 distal skin sections over the entire upper dermis of the plantar hind paw.

Example 5.12: Treatment and/or Prevention of Intestinal Fibrosis

Therapeutic efficacy of the compounds of the present invention is tested using rat or murine models as described by Pham B T et al. (Physiol Rep. 2015; 3(4):ei2323. doi: 10.14814/phy2.12323).

Preparation of rat and mouse intestinal cores: Adult nonfasted male Wistar rats and C57BL/6 mice are used (Harlan PBC, Zeist, The Netherlands). The rats and mice are housed on a 12 h light/dark cycle in a temperature and humidity-controlled room with food (Harlan chow no 2018, Horst, The Netherlands) and water ad libitum. The animals are allowed to acclimatize for at least seven days before the start of the experiment.

Rats and mice are anesthetized with isoflurane/02 (Nicholas Piramal, London, UK). Rat jejunum (about 25 cm distal from the stomach and 15 cm in length) and mouse jejunum (about 15 cm distal from the stomach and 10 cm in length) are excised and preserved in ice-cold Krebs-Henseleit buffer (KHB) supplemented with 25 mm d-glucose (Merck, Darmstadt, Germany), 25 mm $NaHCO_3$(Merck), 10 mm HEPES (MP Biomedicals, Aurora, OH), saturated with carbogen (95% 02/5% CO2) and adjusted to pH 7.4. The jejunum is cleaned by flushing KHB through the lumen and subsequently divided into 2 cm segments. These segments are filled with 3% (w/v) agarose solution in 0.9% NaCl at 37 °C and embedded in an agarose core-embedding unit.

Preparation of human intestinal cores: Healthy human jejunum tissue is obtained for research from intestine that was resected from patients who underwent a pancreaticoduodenectomy.

The healthy jejunum is preserved in ice-cold KHB until the embedding procedure. The submucosa, muscularis, and serosa are carefully removed from the mucosa within an hour after collection of the tissue. The mucosa is divided into 0.4 cm×1 cm sheets. These sheets are embedded in 3% agarose (w/v) solution in 0.9% NaCl at 37 °C and inserted in embedding unit.

Preparation of PCIS: PCIS is prepared in ice-cold KHB by the Krumdieck tissue slicer (Alabama Research and Development). The slices with a wet weight of 3-4 mg had an estimated thickness of 300-400 μm. Slices are stored in ice-cold KHB until the start of the experiments.

Incubation of intestinal slices: Slices are incubated in 12-well plates for human PCIS (hPCIS) and rat PCIS (rPCIS) or in 24-well plates for mouse PCIS (mPCIS). hPCIS and rPCIS are incubated individually in 1.3 mL and mPCIS in 0.5 mL of Williams Medium E with L-glutamine (Invitrogen, Paisly, UK) supplemented with 25 mm glucose, 50 μg/mL gentamycin (Invitrogen), and 2.5 μg/mL amphotericin-B (Invitrogen). During incubation (at 37 °C and 80% 02/5% CO2) in an incubator (MCO-18M, Sanyo), the plates are horizontally shaken at 90 rpm (amplitude 2 cm). rPCIS are incubated up to 24 h, mPCIS and hPCIS were incubated up to 72 h, with and without human TGF-β1 (Roche Diagnostics, Mannheim, Germany) in the concentration range from 1 to 10 ng/mL. All incubations are performed manifold (using 3-6 slices incubated individually in separate wells) and are repeated with intestine from 3 to 16 different humans, rats, or mice.

Viability and morphology: The viability is assessed by measuring the adenosine triphosphate (ATP) content of the PCIS. Briefly, after incubation, slices are transferred to 1 mL sonication solution (containing 70% ethanol and 2 mm EDTA), snap-frozen in liquid nitrogen and stored at −80 °C. To determine the viability, ATP levels are measured in the supernatant of samples sonicated for 45 see and centrifuged for 2 min at 4 °C at 16.000×g, using the ATP bioluminescence kit (Roche Diagnostics, Mannheim, Germany). ATP values (μmol) are normalized to the total protein content (g) of the PCIS estimated by Lowry method (BIO-rad RC DC Protein Assay, Bio Rad, Veenendaal, The Netherlands). To assess the morphology, incubated slices are fixed in 4% formalin and embedded in paraffin. Sections of 4 m are cut and stained with hematoxylin and eosin (HE). HE sections are scored according to a modified Park score, describing the sequence of development of tissue injury in the intestine after ischemia and reperfusion. The integrity of seven segments of the PCIS are scored on a scale from 0 to 3. Viability of the epithelium, stroma, crypts, and muscle layer are scored separately rating 0 if there is no necrosis, and 3 if massive necrosis is present. The other parts of the intestinal slice are rated as follows: Shape of the epithelium: 0=cubic epithelium, 3=more than 2/3 of the cells are flat, flattening of the villi: 0=normal, 3=more than 2/3 of the villi are flattened, and the amount of edema: 0=no edema, 3=severe edema. A maximum score of 21 indicates severe damage. In human samples, the morphological score of muscularis mucosae is determined in the "muscle layer" section. B.T.P., W.T.v.H. and J.N. performed the blind scoring; the mean of three total scores is calculated.

Gene expression: The expression of the fibrosis genes, namely COL1A1, αSMA, HSP47, CTGF, FN2, TGF-β1, PAI-1, and SYN were determined by either the Tagman or SYBRgreen method. In hPCIS, ELA gene expression was also measured by SYBRgreen method.

Intestinal fibrosis is a serious, yet common, outcome in patients with inflammatory bowel disease (IBD). Despite advances in developing novel treatment modalities to control chronic gut inflammation characteristic of IBD, no effective anti-fibrotic therapies exist to date. As such, a deeper understanding of the molecular mechanisms underlying intestinal fibrosis and the availability of relevant animal models are critical to move this area of investigation forward.

IL-17 and associated mediators: Th17 cells define a subset of T helper cells that mainly produce IL-17A, but also IL-17F, IL-21, and IL-22, and are increasingly recognized as paramount in several chronic inflammatory disorders, including IBD (7). IL-17A is implicated in fibrosis in multiple organs, including lung (8), liver (9), and heart (10); recent studies also support its role in the intestine, linking IL-17/Th17 immune responses and other associated mediators in the pathogenesis of gut fibrosis.

Other animal models of gut fibrosis are described herein below:

TABLE 52

| CATEGORY | MODEL | MODE OF ADMINISTRATION/OUTCOME |
|---|---|---|
| Chemically-Induced | DSS | Administered in drinking water, causing epithelial damage and permeabilization of the colonic mucosa with subsequent acute |

TABLE 52-continued

| CATEGORY | MODEL | MODE OF ADMINISTRATION/OUTCOME |
|---|---|---|
| | | inflammation; cycling of DSS causes chronic inflammation and ensuing fibrosis |
| | TNBS | Colonic enema administration of TNBS/ethanol damages epithelial barrier and causes a T cell-dependent transmural inflammation; long-term administration results in colonic fibrosis |
| Microbial | PG-PS | Injection directly into the cecal or small bowel wall induces granulomatous enterocolitis with significant fibrosis |
| | Fecal injection | Injection of fecal suspension directly into the bowel wall of colon causes aggressive colitis and transmural fibrosis |
| | Chronic *Salmonella* infection | Oral administration after pre-treatment with streptomycin causes colonic mucosal and transmural inflammation with significant fibrosis |
| | AIEC infection | Gavage of the human CD isolate of AIEC, NRG857, after pre-treatment with streptomycin causes ileo-colonic inflammation and Th1- and Th17-mediated and fibrosis |
| Genetically-Manipulated Mice | TGFβ1-Tg TβRIIΔk-fib-Tg | Enema administration of these adenoviral vectors overexpressing TGFβ into the colon leads to acute and chronic inflammation, ECM deposition and thickening of muscularis layers |
| | MCP-1-Tg | Intramural injection of adenoviral vector carrying MCP-1 in the rectum leads to transmural inflammation, collagen deposition, and fibrosis |
| | IL-10 deficient | Genetic deletion of IL-10 results in transmural inflammatory lesions of the colon, crypt abscesses, and thickening of the bowel wall; evidence of increased susceptibility to developing post-surgical fibrosis in small intestines after ileo-cecal resection |
| Immune-Mediated | T cell transfer | Transfer of donor $CD4^+/CD45RB^{high}$ T cells into immunodeficient recipient mice results in wasting disease, colitis and mild fibrosis |
| Spontaneous | SAMP1/YitFc mouse strain | Develops spontaneous terminal ileitis and subsequent fibrosis |

Example 5.13: Treatment and/or Prevention of Ovarian Fibrosis

Therapeutic efficacy of the compounds of the present invention is tested using ovarian hyperstimulation syndrome (OHSS) murine model described by Pala $ et al. (Drug Des Devel Ther. 2015; 9:1761-1766. Published 2015 Mar. 24. doi:10.2147/DDDT.S75266) in order to examine the effects of the tested compounds on ovarian histopathology, serum VEGF, and endothelin 1 levels in ovarian hyperstimulation syndrome (OHSS) in an experimental setting.

Animals: Female Wistar albino rats, 22 days of age are used and randomly divided into groups. Follicle-stimulating hormone 10 IU is administered subcutaneously in 15 rats on 4 consecutive days, with OHSS induction on day 5 by 30 IU of human chorionic gonadotropin. Group 1 comprises 35-day-old control rats, group 2 comprises 35-day-old OHSS rats, group 3 comprises 27-day-old OHSS rats receiving the tested compounds for 7 days. All rats are then decapitated on day 35. Serum VEGF, endothelin 1, and ovarian follicular reserve are assessed in all rats.

Hematocrit and weight measurements are performed on day 13 and decapitation performed on day 35 under general anesthesia by intraperitoneal administration of ketamine (75 mg/kg) and xylazine (10 mg/kg).

Enzyme-linked immunosorbent assay: Approximately 3 mL of blood sample obtained from each rat decapitated. Sera are separated by centrifugation of blood samples at 2,500 rpm for 4 minutes and kept at −20 °C until VEGF and endothelin 1 assays. VEGF are assayed using a mouse VEGF enzyme-linked immunosorbent assay kit (ELM-VEGF-001; RayBio, USA) and endothelin are measured using an endothelin 1 E/Kit (EK-023-01; Phoenix Pharmaceuticals, USA).

Ovarian morphology: After laparotomy, ovaries are removed and cleaned of adhering tissue in culture medium and weighed. Ovarian tissue is fixed with 10% formaldehyde, and then paraffin-embedded tissue samples are cut into 4 μm cross sections for estimation of mean ovarian follicle count. The sections are stained with Masson's trichrome to determine OFR under light microscopy (Olympus BX-50). The 4 m-thick cross sections are mounted at 50 μm intervals onto microscope slides to prevent counting of the same structure twice, according to a previously described method. 12 Follicles are classified as primordial, primary, secondary, and tertiary. An atretic follicle (AF) is defined as a follicle presenting more than ten pyknotic nuclei; for the smallest follicles, the criteria for atresia are a degenerate oocyte, precocious antrum formation, or both.

Main outcome measures: The main outcome measures are age (days), weight (g), hematocrit (%), weight of ovaries (mg), serum levels of VEGF (μg/mL) and endothelin 1 (ng/mL), and total follicle count with determination of primordial, primary, secondary, and tertiary follicle numbers.

Example 5.14: Treatment and/or Prevention of Polycystic Ovary Syndrome (PCOS)

Therapeutic efficacy of the compounds of the present invention is tested using DHEA-induced ovarian hyperfibrosis animal model as described by Wang D et al. (J Ovarian Res. 2018; 11(1):6. Published 2018 Jan. 10. doi: 10.1186/s13048-017-0375-7).

The polycystic ovary syndrome (PCOS) is a common metabolic and endocrine disorder with pathological mechanisms remain unclear. The following study investigates the ovarian hyperfibrosis forming via transforming growth factor-β (TGF-β) signaling pathway in Dehydroepiandrosterone (DHEA)-induced polycystic ovary syndrome (PCOS) rat model.

Animals: Thirty female Sprague-Dawley (SD) rats, 21 days old, weighing ~50 g, are used for this assay. The animals are housed in specific-pathogen-free (SPF) environment with temperature of 22±1 °C, relative humidity of 50±1%, and a light/dark cycle of 12/12 h. Free access to food and water are provided.

Methods: Thirty female Sprague-Dawley rats are randomly divided into Blank group (n=6), Oil group (n=6), and Oil+DHEA-induced model group (n=6+12). The model groups are established by subcutaneous injection of DHEA for 35 consecutive days. Rats are additionally divided in vehicle group (n=6) and treated group (n=6). The treatment is given once a day and treatment will last for 35 days. Eighteen days post-treatment, vaginal smears are collected from all the rats on daily basis by judging cell types for 14 days, in order to determine their estrous cycles daily. On day 36, all the rats in Blank and Oil-treated groups and six rats of DHEA-induced model groups are euthanized (using intraperitoneal injection of excess 5% chloral hydrate), blood is collected (from the superior vena cava), bilateral ovaries and uteri is dissected.

Ovaries are fixed in 4% paraformaldehyde for 24 h at 4 °C, and then embedded in paraffin. The rest of the tissues are frozen in −80 °C for further western blotting and real time-polymerase chain reaction (RT-PCR) analysis.

The remaining 12 rats from the DHEA-induced model groups are randomized in additional two groups: treated group and vehicle treatment group (control group), six rats per group. During this treatment, DHEA is no longer given to rats. The treatment lasts for 2 weeks, after which all the animals are euthanized, and blood is collected, and bilateral ovaries and uteri are dissected following the instructions mentioned above.

Ovarian morphology, fibrin and collagen localization and expression in ovaries are detected using H&E staining, immunohistochemistry and Sirius red staining. The ovarian protein and RNA are examined using Western blot and RT-PCR.

Estrous cycle: On day 18 after DHEA treatment, vaginal smears are collected form all rats. Samples are then treated with toluidine blue for 30 min, and consequently cell morphology and estrous cycles are examined under the optical microscope (Leica Microsystems, Germany).

Serum hormones levels: Blood samples are collected from the superior vena cava. The serum is separated immediately and stored at −20 °C for further hormones determination by enzyme-linked immunosorbent assay (ELISA) (testosterone (T), estradiol (E2), luteinizing hormone (LH), follicle stimulating hormone (FSH)) (rat T, E2, LH and FSH ELISA Kits, USCN, Wuhan, China).

Example 5.15: Treatment and/or Prevention of Primary Biliary Cholangitis (PBC)

Therapeutic efficacy of the compounds of the present invention is assessed using PBC murine model as described by Hohenester S et al. (Cells. 2020, 9(2), 281. doi: 10.3390/cells9020281).

Cholestatic liver diseases such as primary biliary cholangitis (PBC) or primary sclerosing cholangitis (PSC) are chronic progressive disorders that frequently result in liver cirrhosis, with its subsequent complications. Hydrophobic bile salts are considered to promote liver fibrosis in cholestasis. However, evidence for this widely accepted hypothesis remains scarce.

In established animal models of cholestasis, e.g., by Mdr2 knockout, cholestasis and fibrosis are both secondary to biliary damage.

Therefore, to test the specific contribution of accumulating bile salts to liver fibrosis in cholestatic disease, the unique model of inducible hepatocellular cholestasis in cholate-fed Atp8blG308V/G308V mice is used. Glycochenodeoxycholate (GCDCA) is supplemented to humanize the murine bile salt pool, as confirmed by HPLC. Biomarkers of cholestasis and liver fibrosis are quantified. Hepatic stellate cells (HSC) isolated from wild-type mice are stimulated with bile salts. Proliferation, cell accumulation, and collagen deposition of HSC are determined. In cholestatic Atp8blG308V/G308V mice, increased hepatic expression of αSMA and collagen 1a mRNA and excess hepatic collagen deposition indicates development of liver fibrosis only upon GCDCA supplementation. In vitro, numbers of myofibroblasts and deposition of collagen are increased after incubation with hydrophobic but not hydrophilic bile salts and associated with EGFR and MEK1/2 activation. Bile salts may have direct pro-fibrotic effects on HSC, putatively involving EGFR and MEK1/2 signalling.

Animal Experiments: Male animals are used for in vivo studies at 8 weeks of age. Animals are kept in a 12 h light-dark cycle and housed in an enriched environment with ad libitum access to diet and water.

Serum Biochemistry and Serum Bile Salt Measurements Serum levels of alkaline phosphatase, bilirubin, and alanine aminotransferase are quantified from fresh serum in a Respons® 910 fully automated analyzer (DiaSys, Holzheim, Germany). Total serum bile salt levels are quantified enzymatically using a Diazyme total bile salts kit (Diazyme Laboratories, Poway, CA, USA) according to the manufacturer's instructions.

Liver Histology, Immunohistochemistry, and Hydroxyproline Quantification Paraffin blocks are cut into 4 μm thick slices and mounted on microscope slides (Superfrost plus, Thermo Scientific/Menzel, Braunschweig, Germany). After stepwise deparaffinization and rehydration, slides are stained with hematoxylin and eosin according to standard procedures. Immunohistochemistry is performed against alpha-SMA, using a monoclonal rabbit anti-alpha smooth muscle actin antibody (Abcam, Cambridge, UK). For collagen quantification, slides are stained for 1 h with Direct Red 80 (Sirius Red, Sigma-Aldrich, Darmstadt, Germany) and are destained twice in ethanol and once in xylol. To quantify total DNA as a surrogate of cell number, HSCs are incubated with PicoGreen® (Invitrogen, Carlsbad, CA, USA) and fluorescence signals are detected with a CytoFluor 4000 system (PerSeptive Biosystems, Framingham, MA, USA). Proliferation of HSC is quantified using a BrdU-assay kit (Roche, Penzberg, Germany) according to the manufacturer's instructions. To quantify total cell count, HSCs, seeded in Lab-Tek II Chamber Slides (Nunc, Rochester, NY, USA USA), are mounted on cover slides with Vectashield mounting medium including DAPI (Vector, Burlingame, CA, USA). Slides are scanned with a Pannoramic Midi Slide Scanner (3DHistech, Budapest, Hungary) and nucleus count is performed with ImageJ2 software on the complete slide (0.7 cm2).

Collagen Quantification In Vitro Cells are washed with PBS and stained for 1 h with 0.1% Sirius Red in saturated picric acid. Cells are then washed three times with 100% ethanol, the bound dye is dissolved in 50% methanol/sodium hydroxide (50 mmol/L), and absorption is measured at 540 nm.

Example 5.16: Treatment and/or Prevention of Hepatic Fibrosis or Cirrhosis (HF)

Therapeutic efficacy of the compounds according to the present invention for inhibiting spontaneous, chronic liver inflammation and fibrosis is assessed using established NOD-Inflammation Fibrosis (N-IF) murine models as described by Fransén Pettersson et al. (PLoS One. 2018; 13(9): e0203228. doi: 10.1371/journal.pone.0203228).

Animals: N-IF mice spontaneously develop chronic inflammation and liver fibrosis driven by T-cell receptor (TCR) transgenic natural killer T (NKT)-II cells generated in immunodeficient NOD.Rag2−/− mice. Several components of the liver pathology in the N-IF mouse overlap with those of human conditions in which a progressive chronic inflammation precedes the development of fibrosis. Moreover, the fibrosis developing in the N-IF mouse liver has been demonstrated to be associated with an accumulation of α-SMA expressing hepatic stellate cells. These phenotypic similarities make the N-IF mouse model unique compared to other available rodent models for liver fibrosis and provides a novel tool to test the efficacy of anti-fibrotic drug candidates.

Animals are observed daily for signs of bad health, urine is collected, and protein is measured in the urine. Liver and kidney weights are recorded at time of dissection. Liver and kidney are dissected from each animal fixed, sectioned and stained with Sirius Red and H&E. A piece of each liver is used for hydroxyproline measurements.

Hydroxyproline measurement: The hydroxyproline content of the liver and spleen is determined using the Hydroxyproline Colorimetric Assay Kit (BioVision, Milpitas, CA, USA).

Histology: Following treatment, mice are anesthetized and perfused with PBS via intra-cardiac puncture.

Livers and spleens are weighed, and organ biopsies are fixed in 4% neutral-buffered formalin, embedded in paraffin and sectioned.

Example 5.17: Treatment and/or Prevention of Non-Alcoholic Steatohepatitis (NASH)

Therapeutic efficacy of the compounds according to the present invention is assessed using NASH munne model as described by Barbara Ulmasov B. et al. (Hepatology Communications, 2018, 3(2) —https: doi.org 10.1002 hep4.1298).

Mice: C57BL/6J 5-week-old male mice are housed in standard facilities under controlled conditions of temperature, humidity, and a 12-hour/12-hour light/dark cycle with free access to water.

Choline Deficient, L-Amino-Acid Defined, High-Fat Mouse Model of NASH: The choline deficient, amino-acid defined, high-fat diet (CDAHFD)22 are obtained from Research Diets (A06071309; New Brunswick, NJ). This diet is formulated as a high-fat, choline-deficient diet that includes 0.1% methionine and 45% Kcal % fat (20% lard, 25% soybean oil). The control diet is a standard rodent chow containing 13.6% of calories from fat. Starting from the age of 6 weeks, 30 mice are placed on the CDAHFD and 30 mice are placed on the standard diet. At the end of 6 weeks, 10 mice from each dietary group are fasted for 5 hours and killed. Blood and liver samples are collected. Livers are divided into sections that are fixed in 10% phosphate-buffered formalin, frozen in liquid nitrogen, or placed in an RNA stabilization solution for future evaluation. The remaining mice are kept on the diets for 4 more weeks for a total of 10 weeks and then fasted, killed, and samples are collected.

Biochemical Analysis: Hepatic triglyceride content was measured using the Triglyceride Colorimetric Assay kit (Cayman Chemicals, Ann Arbor, MI) according to the manufacturer's instructions. Plasma levels of alanine aminotransferase (ALT), aspartate aminotransferase (AST), glucose, insulin, triglyceride, and cholesterol were measured commercially by Advanced Veterinary Laboratory (Saint Louis, MO).

RT-PCR: Real-Time Quantitative Reverse-Transcription Polymerase Chain Reaction are performed to calculate changes in mRNA abundance.

Histopathology: Formalin-fixed liver sections are embedded in paraffin, sectioned at 5 m, and stained by hematoxylin and eosin (H&E) using a standard protocol for microscopic evaluation. To evaluate liver collagen content, paraffin-embedded liver sections are stained with sirius red/fast green dyes. Sirius red binds to all types of collagens, whereas fast green stains noncollagenous proteins.

Liver sections are pretreated to remove paraffin, and nuclei are stained using Weigert's iron hematoxylin solution. After washing, tissues are stained with 0.1% sirius red (Direct Red 80; Sigma, Saint Louis, MO), 0.1% fast green FCF certified (Sigma) in saturated picric acid for 2 hours. Slides are then washed in water, dehydrated with ethanol and xylene, and finally are mounted in Permaslip (Alban Scientific, Inc., Saint Louis, MO). The degree of collagen accumulation is assessed by morphometric analysis.

Determination of Hepatic Hydroxyproline Content: Hydroxyproline content is determined as a measure of the amount of total collagen present in the liver. Liver tissues are homogenized in distilled water, precipitated with trichloroacetic acid, and hydrolyzed for 48 hours in 12 N HCl at 105 °C. Samples are evaporated, and dry pellets are reconstituted in distilled water. Reconstituted samples are centrifuged for 10 minutes at 13,000 g, and supernatants are diluted with 12 N HCl to achieve 4 N HCl concentration in the final samples. Liver hydroxyproline content is determined using the Sensitive Tissue Hydroxyproline Assay.

Immunohistochemistry: Formalin-fixed liver tissues are pretreated to remove paraffin by standard methods. Endogenous peroxidase activity is blocked by incubation in 3.3% hydrogen peroxide in methanol for 1 hour at room temperature.

Apoptotic Cell Detection in Liver Tissues: Apoptotic cells in liver tissues are identified by labelling and detecting DNA strand breaks by the terminal deoxynucleotidyl transferase-mediated deoxyuridine triphosphate nick-end labeling method (TUNEL) using the ApopTag Peroxidase Detection kit (Millipore, Temecula, CA). Stained apoptotic cells with hepatocyte morphology are counted. To detect apoptotic cells with HSC morphology, TUNEL-stained liver tissues are subsequently stained with the antibody to desmin (a marker of HSC), except that secondary antibody peroxidase activity is detected with the ImmPACT VIP Peroxidase Substrate kit (Vector Laboratories).

Western Blot: Western blotting is performed as described using the following primary antibodies: anti-phosphorylated mothers against decapentaplegic homolog 3 (p-SMAD3), ab52903, 1:1,000 (Abcam); anti-glyceraldehyde 3-phosphate dehydrogenase (anti-GAPDH), sc-25778 (Santa Cruz Biotechnology, Inc., Dallas, TX).

Example 5.18: Treatment and/or Prevention of Diabetic Nephropathy or Diabetic Kidney Disease (DN or DKD)

Therapeutic efficacy of the compounds according to the present invention is investigated in vivo using type I diabetes mouse model (STZ-induced diabetes).

Animal model: Male 10 weeks old 129/SV mice (Charles River, Germany) are held in individually ventilated cages, receiving a standard diet with free access to tap water.

Weight-matched 129/SV mice receive either 125 mg/kg body weight STZ (Sigma-Aldrich) in 50 mM sodium citrate (pH 4.5) or sodium citrate buffer (nondiabetic control group) intraperitoneally on day 1 and 4 for induction of hyperglycemia (glucose >15 mmol/l). Mice receive no insulin during the study.

Diabetic mice are administered placebo (saline) for 12 weeks or the tested compounds. Body weight and glucose levels are measured every week. HbA1c (Olympus AU400) and Kidney function (serum creatinine) are measured at 6 and 12 weeks. Albuminuria is assessed using a mouse albumin ELISA kit. Sensory nerve conduction velocity (NCV) studies are performed in mice anesthetized with 2% isoflurane at week 6 and 12. Tail sensory NCV is determined by stimulating proximally along the tail at a recorded distance of 3 cm. For the measurement, a neuro-screen from Toennies Inc. is used. After 12 weeks of follow up the mice are euthanized, and bilateral thoracotomy and laparotomy are performed, and kidneys are perfused with ice cold saline solution via the left heart ventricle.

Immunohistochemistry: For immunofluorescence, paraformaldehyde-fixed and paraffin-embedded tissue sections (2 μm) are processed. After blocking with 10% rabbit serum, paraffin sections are stained with antibodies against pP38 and F4/80 and with a secondary antibody conjugated to Cy3.

Example 5.19: Treatment and/or Prevention of Diabetic Nephropathy, Diabetic Kidney Disease and Diabetic Retionpathy in the STZ-Induced Diabetic Model A total of 70 female CD-1 mice aged 5-7 weeks weighing approximately 25-30 g were used for the study. These were purchased from Charles River, UK and had 7 days acclimatization period. Animals were housed in IVC cages (up to 5 per cage) with individual mice identified by tail mark. All animals were allowed free access to a standard certified commercial diet and sanitised water during the study. The holding room was maintained under standard conditions: 18-24 °C, 55-70% humidity and a 12 h light/dark cycle.

All protocols used in this study have been approved by the Animal Welfare and Ethical Review Committee, and all procedures were carried out under the guidelines of the Animal (Scientific Procedures) Act 1986.

Mice (except negative control group) were injected with STZ (55 mg/kg; IP) daily for 5 consecutive days. Mice were starved for 6 hours prior to injection. One week after completion of induction glucose levels were monitored and mice with levels less than 15 mml/L (280 mg/gL) were removed from the study as they had not developed the ideal severity of diabetes. Glucose levels were be monitored weekly and 5 weeks after STZ induction biochemical assessment of renal injury was carried out by measuring urine albumin and creatinine levels and confirming they were within the desired range. After successful completion of this stage animals were assigned to treatment groups.

TABLE 53

| Group | No. Animals | Agent | Dose level; Route |
|---|---|---|---|
| 1 | 3 | Negative control (non-induced) | Vehicle; IV |
| 2 | 3 | Negative control (Induced) | Vehicle; IV |
| 33 | 8 | Ia-001a | 15 mg/kg; IV |
| 4 | 8 | Ia-001a-TZ | 15 mg/kg; IV |
| 5 | 8 | Ic-001a-Tz/1-004a | 15 mg/kg; IV |
| 6 | 8 | Ic-007a | 15 mg/kg; IV |
| 7 | 8 | Ib-010a | 15 mg/kg; IV |
| 8 | 8 | IIIc-061a | 15 mg/kg; IV |
| 9 | 8 | IVc-059a | 15 mg/kg; IV |
| 10 | 8 | Captopril | 50 mg/kg; PO |

Treatment continued for 4 weeks (28 days) with weekly measurement of blood glucose and urine albumin/creatinine. The study schedule is detailed below looking at weekly (week 5 to 9) blood glucose levels, urine albumin creatinie ratios, and terminal (week 9) blood chemistry and cytokines, kidney histology and eye-retinal leakage.

TABLE 54

| Time (Weeks) | Week 1 | Week 2 | Week 3 | Week 4 | Week 5 | Week 6 | Week 7 | Week 8 | Week 9 | End-Week 9 Sacrifice |
|---|---|---|---|---|---|---|---|---|---|---|
| STZ | Daily for 5 days | — | — | — | — | — | — | — | — | — |
| Testing | | Blood Glucose | Blood Glucose | | Blood Glucose Urine ALB/CREA | Blood Glucose Urine ALB/CREA | Blood Glucose Urine ALB/CREA | Blood Glucose Urine ALB/CREA | Blood Glucose Urine ALB/CREA | Blood Glucose Urine ALB/CREA |
| Compound | — | — | — | — | — | IV Dose, daily | IV Dose, daily | IV Dose, daily | IV Dose, daily | — |
| Organ | | | | | | | | | | Blood (Plasma) Kidneys Eyes |

Results

Clinical Signs: An initial drop in bodyweight was observed for many treatment groups, this can be expected and inmost cases, bodyweight gradually recovered towards the end of the dosing period. Some animal bodyweights dropped below 90% of initial bodyweight, however no animals had to be put on a dosing holiday.

Blood Glucose: Induction with STZ resulted in a significant increase in blood glucose in comparison to non-induced vehicle controls (Table 55). Treatment with IVc-059a IV resulted in a significant reduction* * in blood glucose levels in comparison to induced vehicle controls on day 28. Treatment with IIIc-061a IV also resulted in a reduction in blood glucose levels, however this did not reach statistical significance.

TABLE 55

Mean blood glucose concentration on day 0 and day 28 of female ICR-CD1 mice in an STZ-induced diabetes model. Values shown are mean ± SD; n = 3 for non-induced and induced vehicle groups; n = 8 for all other treatment groups.

| Treatment Group | Treatment | n | Mean day 0 Concentration (mmol/L) (SD) | Mean day 28 Concentration (mmol/L) (SD) | p-value compared to vehicle control |
|---|---|---|---|---|---|
| 1 | Negative control (non-induced) | 3 | 6.7 (0.2) | 8.9 (1.8) | n/a |
| 2 | Negative control (Induced) | 3 | 24.9 (1.8) | 33.0 (–) | n/a |
| 3 | Ia-001a | 8 | 25.7 (6.3) | 31.6 (3.8) | 0.7082 |
| 4 | Ia-001a-TZ | 8 | 24.9 (7.4) | 30.8 (6.2) | 0.5618 |
| 5 | Ic-001a-Tz/1-004a | 8 | 25.8 (5.7) | 29.6 (7.8) | 0.3745 |
| 6 | Ic-007a | 8 | 25.5 (5.7) | 31.1 (4.6) | 0.6241 |
| 7 | Ib-010a | 8 | 25.1 (6.1) | 31.1 (3.4) | 0.6110 |
| 8 | IIIc-061a | 8 | 24.8 (6.2) | 26.3 (7.8) | 0.0775 |
| 9 | IVc-059a | 8 | 24.3 (6.4) | 23.7 (6.6) | 0.0159 |
| 10 | Captopril | 8 | 23.7 (6.9) | 32.2 (2.3) | 0.8256 |

Kidney weight: There was no statistical difference in either wet kidney weight, or in kidney weight as a percentage of animal bodyweight.

Urine Albumin: Creatinine (ALB: CRE): Urine was collected weekly and pooled for each treatment group.

Treatment with Ib-010a, IIIc-061a and IVc-059a resulted in reduced ALB:CREA (Table 56) on last treatment day 28 before sacrifice (week 9 of the schedule).

Blood Urea Nitrogen (BUN): Treatment with Ic-007, Ib-010a, IIIc-061a and IVc-059a resulted in blood urea nitrogen levels that were significantly lower than induced vehicle controls.

ELISAs: At the end of the treatment period blood was collected and processed to serum. Serum levels of CRP, TGF-β, IL-6 and TNF-α were quantified using commercially available ELISA kits, results are shown in Table 56.

Serum CRP: Serum CRP levels in female ICR-CD 1 mice in an STZ-induced diabetes model following 28 days of treatment. Serum CRP levels were significantly increased in STZ-induced animals. Treatment with Ia-001a, Ia-001aTz and the control Captopril resulted in significantly reduced levels of serum CRP compared with vehicle induced controls (**p=0.0074, *p=0304 and **p=0.0026 respectively, One-way ANOVA, Table 56).

Serum TGF-β: Serum TGF-β levels were significantly elevated in STZ-induced controls. Treatment with all compounds apart from Ic-007a and IIIc-061a resulted in TGF-β levels that were significantly lower than vehicle induced controls ($p<0.05$; One-way ANOVA, Table 56).

Serum IL-6 levels were significantly elevated in STZ-induced controls. Treatment with all compounds apart from IVc-059a and the control compound Captopril resulted in IL-6 levels that were significantly lower than vehicle induced controls ($p<0.05$; One-way ANOVA, Table 56).

Serum TNF-α levels were significantly elevated in STZ-induced controls. Treatment with Ia-001a, Ia-001aTz, Ic-001aTz/1-004a and IIIc-061a resulted in TNF-α levels that were significantly lower than vehicle induced controls ($p<0.05$; One-way ANOVA, Table 56).

Kidney histology: Collagen Quantification was performed at the end of the dosing period animals were killed and kidney resected. Tissue was formalin fixed and paraffin wax embedded and then stained with Masson's Trichrome according to manufacturer's instructions. Collagen was quantified using a published method by Chen et al., 2017. Collagen coverage was significantly increased in STZ-induced vehicle controls in comparison to non-induced vehicle controls. Treatment with IIIc-061a and IVc-059a resulted in significantly decreased collagen levels compared to induced vehicle controls (p=0.0210 and p=0.0134 respectively; One-way ANOVA, Table 56).

Disease Score: Kidney disease score was quantified using H&E staining and assessment of mesangial and glomerulosclerosis, arteriolar hyalinosis and GBM thickening. Obviously, disease score was significantly increased in STZ-induced vehicle controls in comparison to non-induced vehicle controls.

Treatment with all compounds apart from Ic-001aTz/1-004a resulted in significantly decreased disease score compared to induced vehicle controls ($p<0.005$; One-way ANOVA, Table 56).

Eye retina histology: at the end of the dosing period, immediately prior to terminal sampling 4 animals per group to be injected with FITC-dextran for retinal flatmount assessment and animals were killed and eyes resected. Retinal flat mounts were prepared and imaged using a fluorescent microscope (EVOS, Thermo Fisher). Area covered by vasculature was significantly increased in STZ-induced vehicle controls in comparison to non-induced vehicle controls. Treatment with Ic-007a, IIIc-061a and IVc-059a resulted in significantly decreased vasculature coverage compared to induced vehicle controls (p=0.0432, p=0.0337 and p=0.0131 respectively; One-way ANOVA, Table 56).

TABLE 56

Urine albumine creatinine ratio (ALB:CRE), Blood-BUN, Blood-CRP, Blood-TGF-beta, Blood-IL-6, Blood-TNF-alpha, Trichrome staining (Kidney fibrosis), disease score and eye area at day 28 of treatment (week 9 of the schedule)

| Group | Treatment 28 days | n | ALB:CRE | BUN | CRP | TGF-beta |
|---|---|---|---|---|---|---|
| 1 | Negative control (non-induced) | 3 | 1.45 | 15.8 ± 0.4 | 3558 ± 106 | 11.64 ± 0.81 |

TABLE 56-continued

Urine albumine creatinine ratio (ALB:CRE), Blood-BUN, Blood-CRP, Blood-TGF-beta, Blood-IL-6, Blood-TNF-alpha, Trichrome staining (Kidney fibrosis), disease score and eye area at day 28 of treatment (week 9 of the schedule)

| | | | | | | |
|---|---|---|---|---|---|---|
| 2 | Negative control (Induced) | 3 | 37.04 | 28.6 ± 0.9 | 6759 ± 993 | 19.64 ± 1.97 |
| 3 | Ia-001a | 8 | 35.68 | 25.1 ± 3.1 | 4759 ± 1181 | 15.54 ± 2.8 |
| 4 | Ia-001a-TZ | 8 | 29.86 | 25.3 ± 3.1 | 5191 ± 993 | 14.76 ± 2.95 |
| 5 | Ic-001a-Tz/1-004a | 8 | 35.10 | 24.1 ± 4.1 | 6077 ± 863 | 15.48 ± 1.73 |
| 6 | Ic-007a | 8 | 38.10 | 21.7 ± 3.0 | 5707 ± 892 | 16.66 ± 2.11 |
| 7 | Ib-010a | 8 | 24.28 | 20.5 ± 3.4 | 5915 ± 1352 | 13.17 ± 3.11 |
| 8 | IIIc-061a | 8 | 24.12 | 22.5 ± 4.1 | 5963 ± 849 | 17.35 ± 2.09 |
| 9 | IVc-059a | 8 | 18.85 | 22.5 ± 2.8 | 5691 ± 1395 | 13.47 ± 3.33 |
| 10 | Captopril | 8 | 24.40 | 28.5 ± 7.6 | 4534 ± 821 | 14.55 ± 2.86 |

| Group | IL-6 | TNF-alpha | Trichrome staining | Disease Score | Eye area |
|---|---|---|---|---|---|
| 1 | 70.56 ± 1.25 | 261.7 ± 21 | 0.48 ± 0.4 | 1 ± 0 | 6.7 ± 1.2 |
| 2 | 151.4 ± 15.59 | 389 ± 24 | 2.63 ± 0.5 | 11 ± 2 | 11.2 ± 1 |
| 3 | 114.16 ± 29.96 | 342.3 ± 15.6 | 1.87 ± 0.65 | 7 ± 1 | 9.9 ± 1.9 |
| 4 | 112.35 ± 20.01 | 327 ± 40.7 | 2.6 ± 0.98 | 8 ± 3 | 11.8 ± 1 |
| 5 | 104.66 ± 22.89 | 322.8 ± 40.1 | 2.48 ± 0.46 | 9 ± 1 | 10.7 ± 2.1 |
| 6 | 109.27 ± 19.03 | 326.8 ± 63 | 2.23 ± 0.61 | 7 ± 1 | 9.1 ± 1.1 |
| 7 | 102.72 ± 25.4 | 395.6 ± 46.7 | 1.97 ± 0.8 | 6 ± 1 | 11.8 ± 1 |
| 8 | 117.59 ± 29.21 | 324.6 ± 43.6 | 1.54 ± 0.55 | 8 ± 1 | 9.1 ± 1.1 |
| 9 | 120.88 ± 23.05 | 350.2 ± 41.4 | 1.48 ± 0.73 | 7 ± 1 | 8.7 ± 1.2 |
| 10 | 125.56 ± 15.75 | 415 ± 51.7 | 1.98 ± 0.47 | 6 ± 1 | 11.8 ± 1.4 |

Example 5.20: Treatment and/or Prevention of Polycystic Kidney Disease (PKD or PCKD)

Therapeutic efficacy of the compounds according to the present invention is investigated in vivo using Pcy mouse model as described by Lee E C et al. (Nat Commun 10, 4148 (2019).

Preclinical model: the pcy mouse, a genetically relevant rodent PKD model has a close correlation to human disease for use in novel agent efficacy evaluation. This model develops PKD associated with the gene that causes human disease, providing a translatable rodent model, which closely mirrors human PKD development. It has been thoroughly characterized for disease progression and response to treatment, providing a high level of confidence for drug discovery studies.

Animal model: pcy mouse, CD-1-pcy$^{Iusm}$ strain (CrownBio) bearing a gene mutation associated with the same gene that causes human nephronophthisis type 3. Disease symptoms and progression are slowly progressive renal cystic disease with cysts that develop in the collecting tubules and other segments of the nephron become cystic as disease progresses. Male and female mice are similarly affected by the disease. Mice are 5 weeks old and receive either normal diet, normal diet with the vehicle (negative control), respectively the positive control and the test compounds all mixed with the normal diet.

Controls: vehicle used for the compounds is used as the negative control in one animal group and tolvaptan a vasopressin receptor-2 (V2) antagonist is used as a positive control in one animal group. Read out and endpoints: Cyst volume and fibrosis in kidney, including histological verification, kidney weight, serum BUN, concentration of test article in the blood, body weight and food intake are recorded weekly.

Example 5.21: Treatment and/or Prevention of Radiation-Induced Fibrosis (RIF)

Therapeutic efficacy of the compounds according to the present invention is investigated in vivo using RIF mouse model as described by Ryu S H et al. (Oncotarget. 2016, 7(13), 15554-15565, doi: 10.18632/oncotarget.6952).

Radiation-induced fibrosis (RIF) is one of the most common late complications of radiation therapy. In RIF a mouse model, leg contracture assay is used to test in vivo efficacy of compounds.

Radiation-induced fibrosis (RIF) is characterized by excessive accumulation of extracellular matrix in skin and soft tissue, and the proliferation of fibroblasts is one of the most common late complications of radiation therapy. Also, RIF is an irreversible process to dead fibrous tissue and a dynamic process related to the remodelling of scar tissue by reactivated myofibroblasts.

RIF mouse model: Male BALB/c mice are used for the RIF mouse model. Under anesthesia, the right hind limb of each mouse receives radiation doses of 44 Gy (22 Gy×2 times for 2 weeks) using a linear accelerator. Specially designed shielding is used to protect the rest of the body, and a 1 cm thick bolus are applied over the skin to ensure an adequate radiation dose on the surface of the hind leg. After irradiation, mice are randomly divided into two groups. Each group will be treated once daily with saline (control group) or compounds (treated group). Mice who received no irradiation or drug are used as a negative control group.

To demonstrate the anti-fibrotic effect of compounds in the skin and soft tissue of irradiated legs, epithelial thickness from the surface of the epidermis to the base of the dermis is measured using H & E staining.

Example 5.22: Treatment and/or Prevention of Stargards Disease (SD)

Therapeutic efficacy of the compounds according to the present invention is investigated in vivo using SD mouse model as described by Fang Y. et al. (Faseb Journal, 2020, DOI: 10.1096/fj.201901784RR).

Animals: Mice Pigmented Abca4−/− mice (12954/SvJae-Abca4tm1Ght) will be purchased from The Jackson Laboratory (Bar Harbor, Maine, USA). Pigmented wild-type (WT) mice (12952/SvPas) is obtained from Janvier Labs (Le Genest-Saint-Isle, France). In each group, the male-to-female ratio is 1:1. The mice are bred and housed in a 12:12-h light (approximately 50 lux in cages)-dark cycle with food and water ad libitum.

Blue-light illumination (BLI): Age-matched pigmented Abca4−/− and WT mice (9 month old) are intraperitoneally anesthetized with three-component narcosis comprising 0.05 mg/kg of fentanyl, 5 mg/kg of midazolam, and 0.5 mg/kg of medetomidine. The pupils are dilated with a mixture of 0.5% tropicamide and 2.5% phenylephrine hydrochloride. METHOCEL (Omni Vision, Puchheim, Germany) is applied to moisten the cornea. During light illumination, a glass slip is placed on the cornea of the exposed eye. The illuminated eye of each mouse is exposed to blue light (wavelength: 430-nm) at an intensity of 50 mW/cm2 for 15 minutes. The nonilluminated eye as a control is covered carefully to shield from stray light.

A series of tests is performed including Optical Coherence Tomography (OCT), Light Microscopy and Transmission Electron Microscopy (TEM), quantification of bisretinoids by HPLC, as well as full-field electroretinography ERG before and seven days after BLI.

Example 5.23: Treatment and/or Prevention of Proliferative Vitreoretinopathy (PVR)

Therapeutic efficacy of the compounds according to the present invention is investigated in vivo using PVR mouse model as described by Hou H et al. (Ophthalmic Res 2018; 60:195-204. doi: 10.1159/000488492) or by Mirkus B. et al. (FEBS Open Bio. 2017; 7(8):1166-1177. Published 2017 Jun. 29. doi:10.1002/2211-5463.12252).

Animal samples: A mouse model of PVR is used by applying an intravitreal injection of a proteolytic enzyme, dispase. This model is known to induce glial activation as well as both epi- and subretinal membrane formation.

Female 4- to 6-month-old wild-type are anesthetized with pentobarbital (90 mg kg-1, i.p.), and also receive one drop of 1% procaine hydrochloride (Novocaine, EGIS, Budapest, Hungary) for local anesthesia and one drop of tropicamide (Mydrum, Chauvin Aubeans, Montpellier, France) for iris dilation. Four microliters of dispase (Sigma-Aldrich; 0.4 U·μL−1, dissolved in sterile physiological saline solution) is injected intravitreally into the right eyes under stereomicroscopic control (Ctrl) using an automatic pipette. Ctrl animals receive 4 μL of sterile physiological saline solution. Stratus optical coherence tomography images (OCT; Carl Zeiss Meditec, Dublin, CA, USA) are taken following injections to confirm PVR induction and monitor disease progression. Ctrl and dispase-treated mice are sacrificed at the 14th day following injections when signs of PVR formation were evident: presence of epiretinal membrane and/or retinal detachment on OCT examination.

Sample preparation and purification: The vitreous bodies of mice are isolated after guillotine removal of the cornea together with a scleral galler using a scalpel blade, followed by removal of the lens. After solubilization of the vitreous body with lysis buffer (pH 8.5) containing 7 m urea, 30 mm Tris, 2 m thiourea and 4% CHAPS, the lysates are sonicated in an ice-cold water bath for 5 min and centrifuged at 16 900 g for 10 min at 4 °C. The supernatants are transferred to LoBind Eppendorf tubes and purified by Ready-Prep 2-D CleanUp Kit (Bio-Rad Laboratories, Hercules, CA, USA) according to the manufacturer's protocol. Briefly, following precipitation and centrifugation, the pellets are dried and resuspended in 240 μL rehydration buffer containing 7 m urea, 2 m thiourea, 4% w/v CHAPS, 1% dithiothreitol (DTT), 2% v/v Bio-Lyte (Bio-Rad) and 0.001% bromophenol blue, and used immediately for isoelectric focusing. 2D gel electrophoresis: Three vitreous samples originating from each group were subjected to 2-DE.

First immobilized pH gradient (IPG) strips with an IPG (24 cm, pH 4-7; Bio-Rad) were rehydrated with extracted vitreous proteins using passive rehydration at 20 °C overnight. This is followed by isoelectric focusing performed by applying 300 V for 3 h, which is gradually increased to 3500 V in 5 h and then held at 3500 V for 18 h. After isoelectric focusing, the IPG strips are immediately placed at −70 °C until equilibration. The IPG strips are equilibrated for 15 min in equilibration buffer (500 mm Tris/HCl, pH 8.5, 6 m urea, 2% SDS, 20% glycerol) containing 0.6% DTT and for 15 min in equilibration buffer containing 1.2% iodoacetamide. In the second dimension, the strips are laid on top of 12% polyacrylamide gels and covered with agarose. Using a Protean Plus Dodeca Cell (Bio-Rad) the electrophoresis is carried out at 100 mA per gel for 24 h until the bromophenol blue dye reached the bottom of the gel. All 12 gels are run together under the same conditions. Proteins are stained using in-house prepared ruthenium II tris(bathophenanthroline disulfonate) fluorescent dye 25 and gel images are recorded using Pharos FX Plus Molecular Imager (Bio-Rad). Three biological replicates are analyzed in all cases, the samples from the Ctrl and the dispase-treated groups are processed together on the same day.

Example 5.24: Treatment and/or Prevention of Wet and Dry Age-Related Macular Degeneration (ARMD or AMD)

Therapeutic fficacy of the compounds according to the present invention is investigated in vivo using AMD murine model as described by Matsuda Y et al. (Mol Ther Nucleic Acids. 2019; 17:819-828. doi:10.1016/j.omtn.2019.07.018).

Animals: Female C57BL/6J mice are obtained from Charles River Laboratories Japan. Male BN rats are obtained. Male New Zealand White (NZW) rabbits are obtained from Kitayama Labes, Japan. Mice, rats, and rabbits are maintained under special pathogen-free conditions.

EMT Assay of RPE Cells: RPE cells cultured at 37 °C are seeded at 1×105 cells/well into 96-well microtiter culture plates. After incubation for 24 h, cells are treated with FGF2 (2 ng/mL) and TGF-β2 (3 ng/mL) with and without compounds according to the present invention for 3 days. The mRNA expression levels of the EMT biomarkers α-SMA and collagen type I are evaluated with quantitative real-time PCR.

Matrigel Plug Assay: 0.5 mL Matrigel Matrix GFR (growth factor reduced)-PRF (phenol red free) (BD Biosciences) solution is mixed with 1 μg FGF2 and subcutaneously implanted into the right flank of female C57BL/6J mice (8 weeks, n=3). The compounds according to the present invention are administered intraperitoneally, and Matrigel plugs are removed and photographed on day 7 post-implantation. Grading of angiogenesis is determined by the hemoglobin concentration in the Matrigel plug, using the cyanmethemoglobin method according to the manufacturer's instructions. The optical density at 540 nm (OD540) values of the samples are measured in a microplate reader, and the hemoglobin concentrations are calculated in accordance with hemoglobin standards (Sigma-Aldrich).

Mouse Laser-Induced CNV Models: Mydrin-P ophthalmic solution is instilled into the eyes of the male C57BL/6J mice to dilate the pupils. Then laser irradiation (wavelength, 532 nm; spot size, 50 μm; irradiation time, 0.1 s; laser output, 120 mW) is conducted on 6 sites of the eye using a slit lamp (SL-130) and a multicolor laser photocoagulator (MC-300), avoiding large retinal capillaries. Immediately after CNV induction by laser irradiation, the tested compounds according to the invention and control are administered via intravitreal injection. Seven days after laser irradiation, a 4% FITC-dextran solution is administered into the tail vein at a volume of 0.5 ml/animal. One to five minutes after administration of FITC-dextran, the animals are euthanized by cervical dislocation. The eyeballs are removed and fixed in 4% paraformaldehyde-phosphate buffer for 12-24 h. Choroidal flat mounts are prepared under a stereoscopic microscope. Photographs of CNV sites are taken using a confocal microscope. Throughout the laser induced CNV animal experiments, successful irradiation is confirmed for each irradiation as air bubble formation in the eye of animal models.

Rat Laser-Induced CNV and Subretinal Fibrosis Models: The same technique will be employed in the rat model using male BN rats. For the CNV model, laser settings are spot size 80 m and irradiation time of 0.05 s at 120 mW at 8 sites in the retina-choroid. For the subretinal fibrosis CNV model, the laser power used is 240 mW. Immediately after laser irradiation, intravitreal injection is performed with the control and tested compounds according to the present invention. For the subretinal fibrosis CNV studies, (1) saline vehicle and (2) compounds of the present invention (15 gg/eye for a single injection or 2 or 3 injections at 2-week intervals) are used. After laser irradiation, for the CNV studies, the FITC-dextran protocol as above is used 14 days after laser irradiation, with preparation of enucleated eyes for confocal microscopy of flat mount choroid. For the subretinal fibrosis studies, after 6 weeks, animals are sacrificed, and the enucleated eyes are prepared for histopathologic studies to quantify subretinal fibrosis using light microscopy. The eyes are embedded in paraffin blocks and sectioned and stained with Masson trichrome according to routine methods. Fibrosis is graded in a blinded manner by two or three independent investigators according to the following scale: grade 0, none; grade 1, minimal; grade 2, mild; grade 3, moderate; grade 4, severe.

Example 5.25: Treatment and/or Prevention of Pterygium (PTE)

Therapeutic efficacy of the compounds according to the present invention is assessed on choroidal angiogenesis and pterygium growth by using a choroidal neovascular murine model (CNV), a direct in vivo angiogenesis assay (DIVAA) and a pterygium murine model.

Pterygium is a benign fibrovascular growth of the ocular surface commonly associated to discomfort and red eye, and as disease progresses is often related to decreased vision (topographic astigmatism) and ocular motility restriction in severe cases. A wide variety of pro-inflammatory cytokines induced by fibrogenic growth factors, oxidative stress and DNA methylation have been implicated in the pathogenesis of pterygium. Since some of these factors are affected by exposure to ultraviolet (UV) light, current evidence from multiple sources suggests that individuals with high exposure to sunlight are at increased risk of pterygium. Despite the extensive research, there is no clear understanding of the pathogenesis of pterygium, but one of the most important factors contributing to the pathogenesis are the neoplastic changes of limbal stem cells associated to UV light exposure and the possible role of oncogenic virus (Human papillomavirus).

To date, three animal models for pterygium are described, using injection of human epithelial pterygium cells, exogenous extracellular matrix or UV scattered radiation in rabbit and mice. The results of the rabbit model using UV scattered light are focused on the computational prediction of the size and shape of the tissue growth, with no histological analysis. The mouse model showed histological characteristics of human pterygium, however, manipulation of rabbits for ophthalmological procedures is easier given that the ocular structure and size resembles more to that of human.

Methods: Mice receive water with or without tested compounds. For the CNV, the neovascular lesion volume is determined in choroid-retinal pigment epithelial (RPE) flat mounts using confocal microscopy seven days after laser induction. For DIVAA, silicone capsules containing 10,000 human pterygium epithelial cells are implanted in the flanks of mice subcutaneously. After eleven days, neovascularization (NV) is quantified using spectrofluorimetry after murine tail-vein injection of fluorescein isothiocyanate (FITC)-labeled dextran. A pterygium epithelial cell model is developed by injecting 10,000 human pterygium epithelial cells in the nasal subconjunctival space in athymic nude mice.

Main outcome measures: Student's t-test is used to evaluate the data for the CNV and DIVAA models and histologic preparations are used to evaluate pterygia lesions.

Example 5.26: Treatment and/or Prevention of Central Serous Chorioretinopathy (CSC)

Therapeutic efficacy of the compounds according to the present invention is investigated in vivo using CSC animal model as described by Wei-Da Chio, et al., Life Sci J 2019; 16(12):115-126]. ISSN: 1097-8135).

The pathogenesis of central serous chorioretinopathy (CSC) is still not fully understood. The involvement of corticosteroids is undisputed, although their exact role has not been clarified; other parts of the underlying mechanism of CSC have been mainly elucidated by imaging techniques such as fluorescein and indocyanine green angiography. Even though most cases of CSC are self-limiting, severe as well as recurrent courses exist, and for these patients only a limited number of treatment options are available: laser photocoagulation, with a risk of scotoma and choroidal neovascularization, and photodynamic therapy.

Method: The treatment is performed with males SD rats with CSCR. Right eye of cases are randomly divided into 2 groups (with control and with tested compounds) which underwent a series of examinations including indirect ophthalmoscopy, and OCT scanning every week. All SD rats are inducted into the CSCR model first. If CSCR disappears under OCT imaging, the compound is considered as efficient.

Example 5.27: Treatment and/or Prevention of Cystic Fibrosis (CF) Affecting the Lungs, but Also the Pancreas, Liver, Kidneys, and Intestine Therapeutic efficacy of the compounds according to the present invention is investigated in vivo using CF murine model as described by McCarron A et al. (Respir Res. 2018; 19(1):54. Published 2018 Apr. 2. doi: 10.1186/s12931-018-0750-y)

In humans, cystic fibrosis (CF) lung disease is characterised by chronic infection, inflammation, airway remodelling, and mucus obstruction. A lack of pulmonary manifestations in CF mouse models has hindered investigations of airway disease pathogenesis, as well as the development and testing of potential therapeutics. However, recently generated CF animal models including rat, ferret and pig models demonstrate a range of well characterised lung disease phenotypes with varying degrees of severity. Different airway phenotypes of currently available CF animal models are available and presents potential applications of each model in airway-related CF research. In particular, mutant alleles with common human CF-causing mutations (e.g., Phe508del or Gly551Asp) introduced into the mouse CFTR sequence have been developed.

Example 5.28: Treatment and/or Prevention of Idiopathic Pulmonary Fibrosis (IPF)

Therapeutic efficacy of the compounds according to the present invention is investigated in vivo using IPF animal model as described by Chen S S et al. (J Thorac Dis. 2017; 9(1):96-105. doi:10.21037/jtd.2017.01.22).

IPF is a chronic progressive interstitial lung disease with severe pulmonary fibrosis. The etiology of IPF remains unclear. Patients usually only survive 2-3 years after being diagnosed with IPF. The incidence and development of IPF are associated with epithelial cell injury, fibrocyte proliferation, inflammatory reactions, and extracellular matrix deposition. The pathological manifestation of IPF is usual interstitial pneumonia (UIP). Currently, the mortality in patients with IPF is quite high. However, effective treatments for IPF are lacking. The main cause of IPF-associated death is acute exacerbation of IPF (AE-IPF), which accounts for more than 50% of IPF-related deaths. Most patients with AE-IPF are unable to tolerate bronchoscopy or lung biopsy because of their critical condition. Lack of the biopsy of AE-IPF substantially limits in-depth investigations of AE-IPF. Experimental animal models that could mimic AE-IPF would be useful tools to study AE-IPF.

Animal models of bleomycin (BLM)-induced IPF are used. The rat model of IPF is developed by an intratracheal perfusion with BLM. Theoretically, a second intratracheal perfusion with BLM should induce additional lung injury in the rats that already develop pulmonary fibrosis from the first perfusion. The additional lung injury may resemble the pathological characteristics of AE-IPF.

Sprague Dawley (SD) rats are randomized into different groups: a control group treated with compounds alone, an AE-IPF model group with compounds+BLM+BLM group, an AE-IPF model group (cpd+BLM+BLM group), an IPF model group treated with compounds (Cpd+BLM group), an IPF model group (BLM group), and a normal control group without BLM.

Rats in the BLM+BLM groups undergo a second perfusion with BLM on day 28 after the first perfusion with BLM. Rats in the other two groups receive saline as the second perfusion. Six rats in each group are sacrificed on day 31, day 35, and day 42 after the first perfusion, respectively.

The pathophysiological characteristics of rats in the BLM+BLM group resemble those of patients with AE-IPF and as described (Chen S S, J Thorac Dis 2017; 9(1):96-105), a second perfusion with BLM appears to induce acute exacerbation of pulmonary fibrosis and may be used to model AE-IPF in rats.

Effects of compounds formulations in this rat model using AE-IPF induced using single and respectively two intratracheal bleomycin perfusions should improve histopathology findings (H & E- and Masson stained sections analyzed and scored for acute lung injury) as well as survival.

Example 5.29: Bleomycin Induced Pulmonary Fibrosis in C57BL/6 Mice with 21 Days

A total of 40 male Balb/c mice aged 8-10 weeks were used for the study. These were purchased from Charles River, UK and had 7 days acclimatization period. Animals were housed in IVC cages (up to 5 per cage) with individual mice identified by tail mark. All animals were allowed free access to a standard certified commercial diet and sanitised water during the study. The holding room was maintained under standard conditions: 18-24 °C, 55-70% humidity and a 12 h light/dark cycle.

All protocols used in this study have been approved by the Animal Welfare and Ethical Review Committee, and all procedures were carried out under the guidelines of the Animal (Scientific Procedures) Act 1986.

Mice were anesthetized using an IP injection of xylazine and ketamine. Once an appropriate plane of anaesthesia was achieved, animals had 1.0 U/kg bleomycin sulphate instilled via intratracheal route. The total volume of liquid was 50 μL. Mice were randomly assigned to treatment groups as showed in the Table 57 below:

TABLE 57

| Group Number | IT Induction | Treatment | Number of Animals | Termination | Dosing Regimen |
|---|---|---|---|---|---|
| 1 | Saline | Vehicle from Day 1 | 6 | Day 21 | QD (IV) |
| 2 | Bleomycin-1U/kg on Day 0 | Vehicle from Day 1 | 12 | Day 21 | QD (IV) |
| 3 | Bleomycin-1U/kg on Day 0 | Pirfenidone 100 mg/kg from Day 1 | 12 | Day 21 | QD (PO) |
| 4 | Bleomycin-1U/kg on Day 0 | IVc-059a 15 mg/kg from Day 1 | 12 | Day 21 | QD (IV) |

Dosing of IV and positive control (pirfenidone) started 24 hours after bleomycin instillation.

Drug solution was formulated immediately prior to dosing. For a dose of 15 mg/kg (enough for 12, 30 g mice) 4.5 mg of compound was weighed out. 75 μl (5%) DMSO added and mixed until drug is in solution. 150 μl (10%) solutol added and vortexed gently, 150 μl (10%) PEG400 added and vortexed gently. 1000 μl PBS (pH7) was added and matrix was measured to ensure pH 7.0 was maintained. Remaining PBS (to a total of 1500 μl) was added. Compound remained in solution.

Sampling after termination (Final dosing day): On sampling day, 2 hours post final dose, mice were sacrificed via an overdose of anaesthesia. Animals were sampled for the following: Serum: Immediately after sacrifice, blood was taken via cardiac puncture and placed into Eppendorf tubes. Tubes were stored at room temperature for at least 20 minutes before centrifuging at 6,000 rpm for 5 minutes. Samples were stored at −80 °C.

Gross Necropsy: Following termination, internal organs were exposed and observed. Any abnormalities were noted.

Lung: Lungs were inflated with formalin prior to resecting. Briefly, the trachea of the mouse was exposed, and a small incision made using a blade. Suture material was gently placed around the back of the trachea below the incision and loosely tied. Formalin was gently inserted into the lungs and the suture tightly closed to ensure inflation. Lungs were placed into formalin and stained with Trichrome and H&E stain for analysis of collagen deposition and disease progression (Ashcroft score). A section of lung tissue was snap frozen.

Ashcroft Scoring:

0 Normal Lung

1 Minimal fibrosis thickening of alveolar or bronchiolar vessels

2 Between minimal and moderate

3 Moderate thickening of walls without obvious damage to lung architecture

4 Between moderate and increased fibrosis with damage to lung structure

5 Increased fibrosis with definite damage to lung structure and formation of fibrous bands or small fibrous masses 6 Between increased fibrosis and severe distortion of lung structure 7 Severe distortion of structure and large fibrous areas; "honeycomb lung"

8 Total fibrous obliteration of the field

Results

Clinical Signs: No changes in bodyweight were noted and no animals had to have a dosing holiday during the study.

Ashcroft score: Lungs from each animal were FFPE, sectioned and stained with H&E according to an in-house protocol. Slides were imaged on a Glissando slide scanner to give whole slide images. Each lung was scored using the Ashcroft grading system to measure degree of inflammation/fibrosis as per Hubner et al., 2008. Scoring was performed in a blinded fashion. Both pirfenidone at 100 mg/kg and IVc-059a at 15 mg/kg reduced the onset of fibrosis in mouse lung (p=0.0018 and 0.0130, respectively, ANOVA). Treatment with pirfenidone had the same effect on the onset of fibrosis as treatment with IVc-059a (p=0.4441, 2-tailed T-test). Representative images are showed in FIG. 11A.

FIG. 11A shows representative images of lung fibrosis at day 21 of treatment: Example images of trichrome staining of connective tissue (×20); (A1) non-induced (healthy); A2, Bleomycine induced with vehicle treatment; A3, Bleomycine induced with pirfenidone 100 mg/kg treatment; A4, Bleomycine induced with IVc-059a treatment. FIG. 11B shows the Ashcroft score of healthy, bleomycine induced non-treated versus pirfenidone versus IVc-059a.

An entire lung from each animal was formalin fixed and stored in 70% ethanol. These sections were dehydrated in increasing concentrations of ethanol before being embedded in paraffin wax. Sections were cut at 5 μM and baked onto Superfrost slides for 2 h. Sections were stained using a commercially available kit for connective tissue (Abcam ab150686). Percent area covered by trichrome staining was quantified using Qupath and ImageJ software.

Example 5.30: In Vitro Results and ADME-Toxicology

A comprehensive evaluation of ADME-toxicology was performed on compounds Ic-007a, IIc-007a, IIIc-061a and IVc-059a.

Cardiac Ion Channel Assays (CiPA) Core QPatch Panel was assessed on Ic-007a, IIc-007a, IIIc-061a and IVc-059a: The three following assays were used for CiPA: Nav1.5 Human Sodium Ion Channel Cell Based QPatch CiPA Assay, hERG Human Potassium Ion Channel Cell Based QPatch CiPA Assay, Cav1.2 (L type) Human Calcium Ion Channel Cell Based QPatch CiPA Assay.

Hepatocytes microsomes and human hepatocytes metabolism was assessed. A comprehensive set of binding assays, enzymes, and uptake assays as well as solution properties, in vitro absorption, metabolism and toxicity were assessed. Gebnetic toxicity was assessed using AMES* and micronucleus assays.

*Ames is a bacterial assay for the identification of compounds that can produce gene mutation and it shows a high predictive value with rodent carcinogenicity tests. In the in vitro

* * In the in vitro Micronucleus assays used for the identification of compounds that induce chromosome damage (clastogens and aneugens)

Results

The highly polar compounds show low metabolism in liver microsomes with half lifes larger than 60 min. No significant toxic effect was observed on hepatocytes cell looking at viability. Most of the negatively charged compounds are highly bound to plasma proteins. No genotoxicity effect was observed. Compounds show no significant effect on the Ames fluctuation tests* TA100-S9, TA100+S9, TA1535-S9, TA1535+S9, TA1537-S9, TA1537+S9, TA98-S9, TA98+S9 in the concentration 5 μM to 0.1 mM. No Bacterial toxicity was observed on TA100-S9, TA1535-S9, TA1537-S9, TA98-S9.

No effects were observed in the Micronucleus assay for the concentration range assessed 8 μM to 1 mM. In the CiPA panel, three cell-based assays were used Cav1.2 (L-type) Human Calcium Ion Channel Cell Based Automated Patch Clamp CiPA Assay, the hERG Human Potassium Ion Channel Cell Based Automated Patch Clamp CiPA Assay and the Nav1.5 Human Sodium Ion Channel Cell Based Automated Patch Clamp CiPA Assay: all were assessed at 3 concentration levels and no significant inhibition was observed between 0.1 μM and 10 μM.

In a Safety panel assay compounds had no or very low inhibition effects on the following enzymatic systems showing a good safety profile on 5-HT transporter human (h) (antagonist radioligand); 5-HT1A (h) (agonist radioligand); 5-HT1B (h) (antagonist radioligand); 5-HT2A (h) (agonist radioligand); 5-HT2B (h) (agonist radioligand); 5-HT3 (h) (antagonist radioligand); A2A (h) (agonist radioligand); acetylcholinesterase (h); alpha 1A (h) (antagonist radioligand); alpha 2A (h) (antagonist radioligand); AR(h) (agonist radioligand); beta 1 (h) (agonist radioligand); beta 2 (h) (antagonist radioligand); BZD (central) (agonist radioligand); Ca2+ channel (L, dihydropyridine site) (antagonist radioligand); CB1 (h) (agonist radioligand); CB2 (h) (agonist radioligand); CCK1 (CCKA) (h) (agonist radioligand); D1 (h) (antagonist radioligand); D2S (h) (agonist radioligand); delta (DOP) (h) (agonist radioligand); dopamine transporter (h) (antagonist radioligand); ETA (h) (agonist radioligand); GR (h) (agonist radioligand); H1 (h) (antagonist radioligand); H2 (h) (antagonist radioligand); kappa (h) (KOP)

(agonist radioligand); KV channel (antagonist radioligand); Lek kinase (h); M1 (h) (antagonist radioligand); M2 (h) (antagonist radioligand); M3 (h) (antagonist radioligand); MAO-A (antagonist radioligand); mu (MOP) (h) (agonist radioligand); N neuronal alpha 4beta 2 (h) (agonist radioligand); Na+ channel (site 2) (antagonist radioligand); NMDA (antagonist radioligand); norepinephrine transporter (h) (antagonist radioligand); PDE3A (h); PDE4D2 (h); Potassium Channel hERG (human)-[3H] Dofetilide; V1a (h) (agonist radioligand).

The anti-inflammatory effect of compounds was in-line with partial cyclooxygenase enzymes inhibition for example Ic-007a, IIc-007a, IIIc-061a and IVc-059a showed partially inhibition of COX2 (cycloxygenase-2).

Example 5.31: In Vitro Profiling Using BioMap Plus

A series of in vitro assays was performed using human primary cell-based assays modeling complex tissue and disease biology of organs (vasculature, immune system, skin, lung) and general tissue biology for phenotypic profiling of compounds in conditions that preserve crosstalk and feedback mechanisms relevant to in vivo outcomes.

Potency, selectivity, safety, mechanism of action, and disease indication of compounds Ic-007a, IIc-007a, IIIc-061a, IVc-059a were assessed at concentrations 30 μM, 10 μM, 3.3 μM, 1.1 μM on the following cellular systems using BioMaps Plus phenotypic cellular assay (Eurofins-DiscoverX, San Francisco, CA, USA):

- Venular endothelial cells to assess for Cardiovascular Disease, Chronic Inflammation, Asthma, Allergy, Autoimmune Disease, Atopic Disease
- PBMCs with venular endothelial cells to assess for Cardiovascular Disease, Chronic Inflammation, Autoimmune Disease, Chronic Inflammation;
- B cells with PBMCs to assess for Autoimmune Disease, Inflammation;
- Bronchial epithelial cells to assess for Lung Inflammation, COPD
- Coronary artery smooth muscle cells to assess for Cardiovascular Inflammation, Restenosis
- Dermal fibroblasts to assess for Fibrosis, Chronic Inflammation, Wound Healing, Tissue Remodeling, Matrix Modulation
- Keratinocytes/Dermal fibroblasts to assess for Psoriasis, Dermatitis, Skin Biology
- Lung fibroblasts to assess for Fibrosis, Chronic Inflammation, Matrix Remodeling
- Venular endothelial cells with Macrophages to assess for Cardiovascular Inflammation, Restenosis, Chronic Inflammation BioMpas Plus References: Book: Phenotypic Drug Discovery, Chapter 2—Development and Validation of Disease Assays for Phenotypic Screening. Ellen L. Berg, Sheryl P. Denker and Alison O'Mahony. https://doi.org/10.1039/9781839160721-00020 ISBN 978-1-83916-072-1

Assessing bioactivity-exposure profiles of fruit and vegetable extracts in the BioMAP profiling system. Wetmore B A, Clewell R A, Cholewa B, Parks B, Pendse S N, Black M B, Mansouri K, Haider S, Berg E L, Judson R S, Houck K A, Martin M, Clewell H J 3rd, Andersen M E, Thomas R S, McMullen P D. Toxicology in Vitro. 2019,54, 41-57.

Results

Ic-007a was not cytotoxic at the concentrations tested in this study. Ic-007a was antiproliferative to human primary T cells (30 μM) and fibroblasts (30 μM, 10 μM, 3.3 μM, 1.1 μM). Ic-007a was active with 20 annotated readouts and mediated changes in key biomarker activities are listed by biological and disease classifications. Mainly Ic-007a impacted inflammation-related activities (decreased VCAM-1, sTNFα, MIP-1α, I-TAC, MIG; increased IL-8; modulated IP-10), immunomodulatory activities (decreased CD40, M-CSF), and tissue remodeling activities (decreased Collagen I, Collagen IV, TIMP-1, tPA, Collagen III, PAI-1, uPAR, bFGF).

IIc-007a was not cytotoxic at the concentrations tested in this study. IIc-007a did not have any antiproliferative effects on these human primary cells at the concentrations tested.

IIc-007a was active with 12 annotated readouts and mediated changes in key biomarker activities were listed by biological and disease classifications. Mainly IIc-007a impacted inflammation-related activities (decreased sTNFα, MIP-1α; increased IL-8; modulated MCP-1), immunomodulatory activities (decreased sIL-10, sIL-2), and tissue remodeling activities (decreased Collagen I, Collagen IV, Collagen III, PAI-1).

IIIc-061a was not cytotoxic at the concentrations tested in this study. IIIc-061a did not have any antiproliferative effects on these human primary cells at the concentrations tested. IIIc-061a was active with six annotated readouts and mediated changes in key biomarker activities were listed by biological and disease classifications. IIIc-061a impacted inflammation-related activities (decreased I-TAC, MIG), immunomodulatory activities (decreased sIL-17A), and tissue remodeling activities (decreased Collagen I, Collagen III, PAI-1).

IVc-059a was not cytotoxic at the concentrations tested in this study. IVc-059a was antiproliferative to human primary endothelial cells (1.1 μM). IVc-059a was active with three annotated readouts and mediated changes in key biomarker activities were listed by biological and disease classifications. IVc-059a impacted inflammation-related activities (decreased sTNFα) and immunomodulatory activities (decreased sIL-10, sIL-2).

Example 5.32: In Vitro Results on Human Retinal Pigment Epithelial Cells (RPE) ARPE-19 and Human Retinal Endothelial Cells (HRECs)

Compounds Ic-007a, IIc-007a, IVc-059a, and bevacizumab (BEVA)) were assessed for their effect on the disruption of the inner and outer blood retinal barrier induced by diabetic conditions. Two different concentrations of the compounds were assessed 25 μM and 50 μM Ic-007a, IIc-007a, IVc-059a. The mechanisms of actions involved in the anti-permeability effect of the tested treatments were explored by assessing permeability to fluorescent dextran and proinflammatory cytokines production using their mRNA expression levels by RT-PCR.

Outer Blood Retinal Barrier conditions: human retinal pigment epithelial cells (RPE) cultures ARPE-19, a spontaneously immortalised human RPE cell line were obtained from American Type Culture Collection (Manassas, VA, USA). ARPE-19 cells and they were cultured in euglycaemic conditions (D-glucose (D-Glc), 5.5 mmol/L) and hyperglycaemic conditions (D-glucose, 25 mmol/L) for 18 days at 37 °C under 5% (vol./vol.) $CO_2$ in medium (DMEM/F12) supplemented with 10% (vol./vol.) FBS (Hyclone; Thermo Fisher Scientific, UT, USA) and 1% (vol./vol.) penicillin/streptomycin (Hyclone; Thermo Fisher Scientific). ARPE-19 cells from passage 20 were used and the medium changed every 3-4 days. For permeability studies, ARPE-19 cells were seeded at 400,000 cells/ml (80,000 RPE cells/well) in 0.33 $cm^2$ HTS-Transwells (Costar; Corning, NY, USA). For real-time PCR, western blot analysis and immunofluorescence cells are seeded at 20,000 cells/ml.

Experimental conditions and treatments: apart from the euglycemic condition, eighteen different conditions were tested in cells cultured under 25 mmol/L D-glucose:

Condition 1) Control cells did not receive any treatment 5 mM D-Glucose

Condition 2) Cells are treated with diabetic milieu 25 mM D-Glucose+vehicle (days 15, 16 and 17 at one application/day) in order to evaluate their effect in preventing the cell damage provoked by the diabetic milieu.

Condition 3, 4, 5, 6, 7, 8) Cells were treated with 25 mM D-Glucose and two different concentrations of each product: Ic-007a (3, 4) 25 μg/mL (=53 μM) and 50 μg/mL (=107 μM); IIc-007a (5, 6) 25 μg/mL (=53 μM) and 50 μg/mL (=107 μM); IVc-059a (7, 8) 20 μg/mL (=50 μM) and 40 μg/mL (=100 μM) for 72 h (days 15, 16 and 17 at one application/day) to evaluate their potential cytotoxic effects.

Condition 9) Cells were treated with 25 mM D-Glucose and bevacizumab (0.2 mg/ml) for 72 h (days 15, 16 and 17 at one application/day) to evaluate their potential cytotoxic effects.

Condition 10)=Diabetic milieu; cells were treated with 25 mM D-Glucose+IL-10 (10 ng/ml)+TNF-α (25 ng/ml)+VEGF (25 ng/ml), for 48 h (days 16 and 17 at one application/day) in order to provoke the disruption of the monolayer.

Condition 11, 12, 13, 14, 15, 16) Cells were treated with diabetic milieu (25 mM D-Glucose+IL-1β (10 ng/ml)+TNF-α (25 ng/ml)+VEGF (25 ng/ml))+two concentrations of the new compounds (Ic-007a, IIc-007a and IVc-059a (days 15, 16 and 17 at one application/day) in order to evaluate their effect in preventing the cell damage provoked by the diabetic milieu.

Condition 17) Cells are treated with diabetic milieu (25 mM D-Glucose+IL-1β (10 ng/ml)+TNF-α (25 ng/ml)+VEGF (25 ng/ml))+bevacizumab (0.2 mg/mL) (days 15, 16 and 17 at one application/day) in order to evaluate their effect in preventing the cell damage provoked by the diabetic milieu.

Measurement of ARPE-19 permeability: The permeability of RPE cells was determined at 18 days by measuring the apical-to basolateral movements of FITC-dextran (40 kDa) (Sigma, St Louis, MI, USA) following a procedure previously reported by Villarroel et al. Exp Eye Res, 2009, 89, 913-920.

Inner Blood Retinal Barrier conditions: primary human retinal endothelial cells (HRECs) were obtained from a vial of cryopreserved cells purchased from Innoprot (Vizcay, Spain). These cells were isolated from human retinal tissue of cadaveric eyes digested with 0.1 mg/mL collagenase type I at 37 °C for 1 hour. Then, endothelial cells were finally selected with CD31 antibody-coated magnetic beads (DynaBeads; Dynal, Oslo, Norway). HRECs were thawed in the laboratory and cultured in endothelial basal medium (EBM) containing, 5.5 mM D-glucose, 5% FBS (Fetal Bovine Serum), 100 U/mL penicillin, 100 μg/mL streptomycin, and ECG (Endothelial Cell Growth Supplement) supplement (Innoprot, Vizcay, Spain). Human fibronectin (MerckMillipore, Madrid, Spain) at 5 μg/mL was used for cell attachment. Cells at passages 2-3 will be used for the experiments. For experimentation, HRECs were grown to confluence and then cell culture media was changed to medium supplemented with 1% FBS for 24 h and then exposed to different treatments.

Conditions treatments: The same conditions specified for the experiment in ARPE-19 cells were used.

Measurement of HREC permeability: Permeability in HREC monolayers were obtained on permeable supports at $12\times10^5$ cells/well (24 wells, PCF filters, Merk Millipore). Inserts were incubated for 48 hours at 37 °C in 5% $CO_2$-air to form the monolayer. At the end, medium was serum depleted 24 h before to proceed with the treatments. The lower chamber was filled with 600 μL of complete EBM medium and the upper chamber with 100 μL of cell suspension in serum depleted (1%).

To detect changes in the permeability, 100 μg/ml of fluorescent FITC-DEXTRAN (Sigma, Madrid, Spain), was added to the upper side of the insert. Aliquots of 200 μL from the basal compartment was read in a SpectraMax Gemini (Molecular Devices, Sunnyvale, CA) at a wavelength of excitation/emission 485/528 nm every 30 min. Finally, the concentration of dextran was determined by extrapolation of the fluorescence reads in a standard curve. Each condition was tested in triplicate.

Cell viability and proliferation: Cell counting and MTT assay was performed in HRECs to assess the viability of cells under the tested conditions. Viability and proliferation of HRECs was measured. Briefly, cells were stained with DAPI and photographs was taken (20×) in a fluorescent inverted microscope (Olympus iX71 with V-RFL-T Olympus). Cell nuclei were counted with the help of Image J software in three different fields for each condition. The experiments were repeated three times. In addition, the MTT assay (Sigma, Madrid, Spain) was used to evaluate the viability of cells. Briefly, 10 μl of 5 mg/ml MTT in PBS was added to each well after the treatments and incubated an additional 1 h at 37 °C. The medium was removed, and the formazan granules obtained were dissolved in 100% dimethyl sulfoxide (DMSO) and absorbance was detected at 562 nm with an ELISA plate reader (ELx800. Bio-Tek Instruments, VT, USA). This assay ruled out a potential bias in the results due to changes in cell proliferation among the different conditions.

Mechanisms of Action:

- Proinflammatory cytokines were evaluated in ARPE-19 cells by RT-PCR and mRNA for IL-6, TNF-α, IL-1β, IL-18, VEGF, IL-10, FGF were measured using the double delta CT method 2-ΔΔCT with Cts values for the gene of interest and the endogenous human B-actin to obtain ΔCT; mRNA values were expressed as relative change with respect to the condition 25 mM D-Gluc. (ref: Livak K J, Analysis of Relative Gene Expression Data Using Real-Time Quantitative PCR and the 2-ΔΔCT Method, Methods, 2001, 25(4), 402-408, doi 10.1006/meth.2001.1262)
- ROS production was evaluated using Cell Biolabs' OxiSelect™ Intracellular ROS Assay (Green Fluorescence) (Bionova, Madrid, Spain). The assay employs the cell-permeable fluorogenic probe 2', 7'-Dichlorodihydrofluorescin diacetate (DCFH-DA), oxidized to highly fluorescent 2', 7'-Dichlorodihydrofluorescein (DCF) by cellular ROS.
- Endothelin-1, PDGF and VCAM-1 expression was analyzed in HREC monolayers by immunohistochemical analysis and by RT-PCR.
- TJ expression (ZO) is analyzed in ARPE-19 and HREC monolayers by immunohistochemical analysis.

Results:

Permeability results of outer blood retinal barrier (ARPE19 monolayer) and inner blood retinal barrier (HREC) are show in Table 58. The compounds Ic-007a, IIc-007a, IVc-059a decreased the permeability of the outer and inner monolayers.

Effect of the compounds Ic-007a, IIc-007a, IVc-059a on the production of ROS and TNF-α, IL-1β, IL-6, IL-18 and VEGF-mRNA in ARPE19 monolayer cells exposed to non-diabetic and diabetic milieu are showed in Table 59.

TABLE 58

Permeability of outer blood retinal barrier and inner blood retinal barrier using leakage of FITC-Dextran fluorescence (ng/mL/$cm^2$).

| No | Condition | ARPE19 % permeability | ARPE19 p < 0.05 | HREC % permeability | HREC p < 0.05 |
|---|---|---|---|---|---|
| 1 | DMEN HAM'S F-12 1% 5,5 mM D-Gluc | 105.1 ± 34.1 | | 88.3 ± 26.2 | |
| 2 | DMEN HAM'S F-12 1% 25 mM D-Gluc (#) | 94.9 ± 10.3 | | 100.0 ± 15.6 | |
| 3 | (#) + Ic-007a 25 µg/mL | 75.2 ± 11.1 | | 126.3 ± 8.3 | |
| 4 | (#) + IIc-007a 25 µg/mL | 66.1 ± 4.9 | | 136.3 ± 16.7 | |
| 5 | (#) + IVc-059a 25 µg/mL | 70.2 ± 8.8 | | 109.9 ± 24.7 | |
| 6 | (#) + Ic-007a 50 µg/mL + VEGF, TNF-α, IL-β | 107.3 ± 43.9 | | 127.4 ± 2.1 | |
| 7 | (#) + IIc-007a 50 µg/mL + VEGF, TNF-α, IL-β | 113.1 ± 11.4 | | 147.7 ± 17.6 | |
| 8 | (#) + IVc-059a 50 µg/mL + VEGF, TNF-α, IL-β | 112.6 ± 19.8 | | 135.4 ± 6.7 | |
| 9 | (#) + BEVA 0.2 mg/mL | 109.5 ± 22.9 | | 127.1 ± 26.2 | |
| 10 | (#) + VEGF, TNF-α, IL-1β = DIABETIC MILIEU | 159.9 ± 5.0 | | 170.0 ± 12.0 | |
| 11 | (#) + Ic-007a 25 µg/mL + VEGF, TNF-α, IL-β | 103.7 ± 15.7 | * | 111.6 ± 24.2 | * |
| 12 | (#) + IIc-007a 25 µg/mL + VEGF, TNF-α, IL-β | 114.7 ± 19.0 | * | 135.8 ± 16.6 | * |
| 13 | (#) + IVc-059a 25 µg/mL + VEGF, TNF-α, IL-β | 98.5 ± 36.5 | * | 124.0 ± 6.3 | * |
| 14 | (#) + Ic-007a 50 µg/mL + VEGF, TNF-α, IL-β | 127.1 ± 13.5 | * | 159.0 ± 23.9 | |
| 15 | (#) + IIc-007a 50 µg/mL + VEGF, TNF-α, IL-β | 136.8 ± 13.0 | * | 145.2 ± 8.8 | |
| 16 | (#) + IVc-059a 50 µg/mL + VEGF, TNF-α, IL-β | 130.4 ± 24.8 | | 115.3 ± 14.7 | * |
| 17 | (#) + BEVA 0.2 mg/mL + VEGF, TNF-α, IL-β | 120.7 ± 30.1 | | 129.0 ± 35.3 | |

* p < 0.05 for FITC dextran leakage measured after 90 min in [ng/mL/$cm^2$] in comparison with diabetic milieu (25 mM D-Gluose + VEGF, TNF-α, IL-β)

TABLE 59

ROS and TNF-a, IL-1b, IL-6, IL-18 and VEGF mRNA production by ARPE19 monolayer cells in non-diabetic and diabetic milieu.

| No | Condition | ROS % | IL-1β R.Q. mRNA | IL-6 R.Q. mRNA | TNFα R.Q. mRNA | IL-18 R.Q. mRNA | VEGF R.Q. mRNA |
|---|---|---|---|---|---|---|---|
| 1 | DMEN HAM'S F-12 1% 5.5 mM D-Gluc | 86 ± 12 | 0.11 ± 0.02 | 0.93 ± 0.01 | 0.18 ± 0.16 | 1.08 ± 0.44 | 1.60 ± 0.05 |
| 2 | DMEN HAM'S F-12 1% 25 mM D-Gluc (#) | 100 ± 9 | 1.02 ± 0.20 | 1.00 ± 0.03 | 1.36 ± 0.86 | 1.04 ± 0.35 | 1.54 ± 0.32 |
| 3 | (#) + Ic-007a 25 µg/mL | 32 ± 15 | 0.12 ± 0.01 | 0.52 ± 0.49 | 0.27 ± 0.07 | 0.45 ± 0.18 | 0.09 ± 0.02 |
| 4 | (#) + IIc-007a 25 µg/mL | 55 ± 6.4 | 0.74 ± 0.26 | 0.73 ± 0.00 | 0.57 ± 0.18 | 0.75 ± 0.09 | 0.06 ± 0.01 |
| 5 | (#) + IVc-059a 25 µg/mL | 62 ± 9 | 0.20 ± 0.05 | 0.28 ± 0.11 | 0.27 ± 0.08 | 0.07 ± 0.01 | 0.11 ± 0.01 |
| 6 | (#) + Ic-007a 50 µg/mL | 26 ± 4.6 | 0.15 ± 0.03 | 0.20 ± 0.07 | 0.59 ± 0.33 | 0.07 ± 0.01 | 0.12 ± 0.03 |
| 7 | (#) + IIc-007a 50 µg/mL | 72 ± 11 | 0.24 ± 0.11 | 0.34 ± 0.08 | 0.45 ± 0.30 | 0.04 ± 0.00 | 0.12 ± 0.03 |
| 8 | (#) + IVc-059a 50 µg/mL | 116 ± 12 | 0.21 ± 0.13 | 0.28 ± 0.11 | 0.27 ± 0.10 | 0.04 ± 0.01 | 0.06 ± 0.03 |
| 9 | (#) + BEVA 0.2 mg/mL | 110 ± 54 | 1.46 ± 0.72 | 0.64 ± 0.34 | 0.46 ± 0.63 | 0.09 ± 0.01 | 1.68 ± 0.83 |
| 10 | (#) + VEGF, TNF-α, IL-1β = DIABETIC MILIEU | 145 ± 9.3 | 96.07 ± 48.11 | 65.49 ± 21.16 | 9.13 ± 1.84 | 2.22 ± 0.19 | 2.01 ± 0.69 |
| 11 | (#) + Ic-007a 25 µg/mL + VEGF, TNF-a, IL-1b | 33 ± 4.8 * | 12.21 ± 1.46 * | 0.52 ± 0.49 * | 11.26 ± 0.96 | 0.02 ± 0.00 * | 0.06 ± 0.02 * |
| 12 | (#) + IIc-007a 25 µg/mL + VEGF, TNF-a, IL-1β | 47 ± 7.6 * | 41.03 ± 17.57 * | 10.83 ± 6.90 * | 6.31 ± 0.06 * | 0.07 ± 0.01 * | 0.11 ± 0.01 * |
| 13 | (#) + IVc-059a 25 µg/mL + VEGF, TNF-a, IL-1β | 61 ± 40 * | 20.81 ± 5.11 * | 5.84 ± 1.13 * | 5.39 ± 1.01 * | 0.03 ± 0.01 * | 0.04 ± 0.00 * |
| 14 | (#) + Ic-007a 50 µg/mL + VEGF, TNF-a, IL-1b | 27 ± 13 * | 10.66 ± 3.01 * | 3.28 ± 1.46 * | 5.22 ± 3.96 | 0.02 ± 0.00 * | 0.17 ± 0.05 * |
| 15 | (#) + IIc-007a 50 µg/mL + VEGF, TNF-a, IL-1β | 74 ± 38 * | 11.39 ± 6.52 * | 1.50 ± 1.19 * | 4.24 ± 0.77 * | 0.03 ± 0.00 * | 0.13 ± 0.02 * |
| 16 | (#) + IVc-059a 50 µg/mL + VEGF, TNF-a, IL-1β | 159 ± 32 | 27.76 ± 5.18 * | 9.78 ± 2.30 * | 3.61 ± 1.82 * | 0.01 ± 0.00 * | 0.20 ± 0.03 * |
| 17 | (#) + BEVA 0.2 mg/mL + VEGF, TNF-α, IL-1β | 111 ± 50 | 31.22 ± 12.65 * | 32.35 ± 13.48 * | 1.37 ± 0.27 * | 0.53 ± 0.04 * | 3.88 ± 0.68 * |

ROS % to 25 mM D-Glucose; R.Q. = Relative Quantification mRNA for cytokines and growth factor values expressed as relative change with respect to the condition 25 mM D-Gluc.
* p < 0.05 between 25 mM D-Glc + VEGF + TNF-α + IL-1β (diabetic milieu) and the compounds Ic-007a, IIc-007a, IVc-059

The invention claimed is:

1. A substituted hydroquinone of formula (I):

(I)

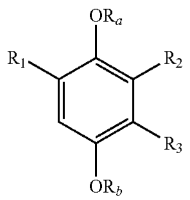

wherein:

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$;

$R_2$ and $R_3$ are H or $R_5$, with the proviso that when one of $R_2$ and $R_3$ is $R_5$, the other is H and when one of $R_2$ and $R_3$ is H, the other is $R_5$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_5$=$R_6$, $R_7$, or $R_8$;

$R_6$=CONH—$R_9$, $CONHCOR_9$, $CONH(CH_2)_n$-$R_9$, $CONHCH(COOR_4)(CH_2)_kR_9$;

wherein k=0-4;

$R_7$=benzoheteroaryl substituted with at least one or more groups selected from: $COOR_4$, $(CH_2)_nCOOR_4$, $SO_3H$, $(CH_2)_nSO_3H$, azoles [5-membered N-containing heterocycles], or fluorine;

$R_8$=$(CH_2)_mX(CH_2)_pR_9$;

X=O, S, $SO_2$, NH, NAc, or $N(CH_2)_qR_9$;

$R_9$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], fluorine, C═O, or NHCO—$R_{10}$;

$R_{10}$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], or fluorine;

wherein the aryl of $R_9$ and $R_{10}$ is an aromatic group containing from 6 to 14 carbon atoms, selected among phenyl, naphthyl, biphenyl group; and the heteroaryl of $R_9$ and $R_{10}$ is an aromatic group containing 1 to 14 carbon atoms and one or more nitrogen; and n, m, p and q are independently 1-4.

2. A compound of formula (I):

(I)

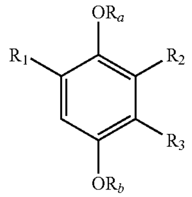

wherein:

$R_a$, $R_b$=H, $C_{1-4}$acyl, aryl$C_{1-4}$alkyl, $C_6$-$C_{10}$arylCO, HOOC$(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$;

$R_2$ and $R_3$ are H or $R_5$, with the proviso that when one of $R_2$ and $R_3$ is $R_5$, the other is H and when one of $R_2$ and $R_3$ is H, the other is $R_5$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_5$=$R_6$, or $R_7$;

$R_6$=CONH—$R_9$, $CONHCOR_9$, $CONH(CH_2)_n$-$R_9$, or $CONHCH(COOR_4)(CH_2)_kR_9$;

wherein k=0-4;

$R_7$=benzoheteroaryl substituted with at least one or more groups selected from: $COOR_4$, $(CH_2)_nCOOR_4$, $SO_3H$, $(CH_2)_nSO_3H$, azoles [5-membered N-containing heterocycles], or fluorine;

$R_9$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], fluorine, C═O, or NHCO—$R_{10}$;

$R_{10}$=aryl, heteroaryl, substituted with at least one or more groups selected from $COOR_4$, $(CH_2)_nCOOR_4$, $(CH_2)_n SO_3H$, $OR_4$, $SO_3H$, azoles [5-membered N-containing heterocycles], or fluorine; wherein the aryl of $R_9$ and $R_{10}$ is an aromatic group containing from 6 to 14 carbon atoms, selected among phenyl, naphthyl, biphenyl group; and the heteroaryl of $R_9$ and $R_{10}$ is an aromatic group containing 1 to 14 carbon atoms and one or more nitrogen; and n is independently 1-4.

3. The compound according to claim 2, wherein:

(a)

$R_a$, $R_b$=H, $C_{1-4}$acyl, aryl$C_{1-4}$alkyl, $C_6$-$C_{10}$arylCO, HOOC $(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_2$=H; $R_3$=$R_5$; and $R_5$=$R_6$=CONH—$R_9$;

or (b)

$R_a$, $R_b$=H, $C_{1-4}$acyl, aryl$C_{1-4}$alkyl, $C_6$-$C_{10}$arylCO, HOOC $(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$; $R_4$-H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl)methyl;

$R_3$=H; $R_2$=$R_5$; and $R_5$=$R_6$=CONH—$R_9$;

or wherein said compound is selected form the group consisting of:

4-(2-carboxyphenylaminocarbonyl)-2,5-dihydroxybenzoic acid;

4-(2-(1H-tetrazol-5-yl)phenylaminocarbonyl)-2,5-dihydroxybenzoic acid;

2,5-dihydroxy-4-(2-sulfophenylaminocarbonyl)benzoic acid;

4-(3-carboxyphenylaminocarbonyl)-2,5-dihydroxybenzoic acid;

4-(3-(1H-tetrazol-5-yl)phenylaminocarbonyl)-2,5-dihydroxybenzoic acid;

2,5-dihydroxy-4-(3-sulfophenylaminocarbonyl)benzoic acid;

4-(4-carboxyphenylaminocarbonyl)-2,5-dihydroxybenzoic acid;

4-(4-(1H-tetrazol-5-yl)phenylaminocarbonyl)-2,5-dihydroxybenzoic acid;

2,5-dihydroxy-4-(4-sulfophenylaminocarbonyl)benzoic acid;

4-(3-carboxy-4-hydroxyphenylaminocarbonyl)-2,5-dihydroxybenzoic acid;

4-(4-carboxy-3-hydroxyphenylaminocarbonyl)-2,5-dihydroxybenzoic acid;

4-(4-carboxy-2,5-dihydroxyphenylaminocarbonyl)-2,5-dihydroxybenzoic acid;

4-(2-carboxy-4-hydroxyphenylaminocarbonyl)-2,5-dihydroxybenzoic acid;

3,5-bis(2,5-dihydroxy-4-carboxybenzoylamino)benzoic acid;

3-(4-carboxy-2,5-dihydroxybenzamido)phthalic acid;

2-(4-carboxy-2,5-dihydroxybenzamido)terephthalic acid;

2-(4-carboxy-2,5-dihydroxybenzamido)isophthalic acid;

4-(4-carboxy-2,5-dihydroxybenzamido)phthalic acid;

5-(4-carboxy-2,5-dihydroxybenzamido)isophthalic acid;

2-(4-carboxy-2,5-dihydroxybenzamido)nicotinic acid;

2-(4-carboxy-2,5-dihydroxybenzamido)isonicotinic acid;

6-(4-carboxy-2,5-dihydroxybenzamido)nicotinic acid;

6-(4-carboxy-2,5-dihydroxybenzamido)picolinic acid;

2-(4-carboxy-2,5-dihydroxybenzamido)-5-fluoronicotinic acid;

6-(4-carboxy-2,5-dihydroxybenzamido)pyridine-2,5-dicarboxylic acid;

2-(4-carboxy-2,5-dihydroxybenzamido)pyridine-3,5-dicarboxylic acid;

3-(4-carboxy-2,5-dihydroxybenzamido)isonicotinic acid;

5-(4-carboxy-2,5-dihydroxybenzamido)nicotinic acid;

5-(4-carboxy-2,5-dihydroxybenzamido)picolinic acid;

3-(4-carboxy-2,5-dihydroxybenzamido)picolinic acid;

5-(4-carboxy-2,5-dihydroxybenzamido)-2-fluoroisonicotinic acid;

4-(4-carboxy-2,5-dihydroxybenzamido)nicotinic acid;

4-(4-carboxy-2,5-dihydroxybenzamido)picolinic acid;

4-(4-(carboxymethyl)phenylaminocarbonyl)-2,5-dihydroxybenzoic acid;

4-(3-(carboxymethyl)phenylaminocarbonyl)-2,5-dihydroxybenzoic acid;

2,5-dihydroxy-4-(3-(1-hydroxy-1H-pyrazol-4-yl)phenylaminocarbonyl)benzoic acid;

4-(2-(carboxymethyl)phenylaminocarbonyl)-2,5-dihydroxybenzoic acid;

ethyl 4-(2-(ethoxycarbonyl)phenylaminocarbonyl)-2,5-diacetoxybenzoate;

ethyl 4-(2-(ethoxycarbonyl)phenylaminocarbonyl)-2,5-dihydroxybenzoate;

ethyl 4-(2-(1H-tetrazol-5-yl)phenylaminocarbonyl)-2,5-diacetoxybenzoate;

ethyl 4-(2-(1H-tetrazol-5-yl)phenylaminocarbonyl)-2,5-dihydroxybenzoate;

ethyl 2,5-dihydroxy-4-(4-hydroxy-3-(methoxycarbonyl) phenylaminocarbonyl) benzoate;

ethyl 3,5-bis(2,5-diacetoxy-4-ethoxycarbonylbenzoylamino)benzoate;

ethyl 3,5-bis(2,5-dihydroxy-4-ethoxycarbonylbenzoylamino)benzoate;

ethyl 3-(4-(ethoxycarbonyl)-2,5-dihydroxybenzamido) isonicotinate;

Ethyl 4-(4-ethoxycarbonyl-2,5-dihydroxyphenylaminocarbonyl)-2,5-dihydroxybenzoate;

3-(2-carboxyphenylaminocarbonyl)-2,5-dihydroxybenzoic acid;

3-(2-(1H-tetrazol-5-yl)phenylaminocarbonyl)-2,5-dihydroxybenzoic acid;

2,5-dihydroxy-3-(2-sulfophenylaminocarbonyl)benzoic acid;

3-(3-carboxyphenylaminocarbonyl)-2,5-dihydroxybenzoic acid;

3-(3-(1H-tetrazol-5-yl)phenylaminocarbonyl)-2,5-dihydroxybenzoic acid;

2,5-dihydroxy-3-(3-sulfophenylaminocarbonyl)benzoic acid;

3-(4-carboxyphenylaminocarbonyl)-2,5-dihydroxybenzoic acid;

3-(4-(1H-tetrazol-5-yl)phenylaminocarbonyl)-2,5-dihydroxybenzoic acid;

2,5-dihydroxy-3-(4-sulfophenylaminocarbonyl)benzoic acid;

3-(3-carboxy-4-hydroxyphenylaminocarbonyl)-2,5-dihydroxybenzoic acid;

3-(4-carboxy-3-hydroxyphenylaminocarbonyl)-2,5-dihydroxybenzoic acid;

3-(2-carboxy-4-hydroxyphenylaminocarbonyl)-2,5-dihydroxybenzoic acid;

3,5-Bis(2,5-dihydroxy-3-carboxybenzoylamino)benzoic acid;

3-(3-carboxy-2,5-dihydroxybenzamido)phthalic acid;

2-(3-carboxy-2,5-dihydroxybenzamido)terephthalic acid;

2-(3-carboxy-2,5-dihydroxybenzamido)isophthalic acid;

4-(3-carboxy-2,5-dihydroxybenzamido)phthalic acid;

5-(3-carboxy-2,5-dihydroxybenzamido)isophthalic acid;

2-(3-carboxy-2,5-dihydroxybenzamido)nicotinic acid;
2-(3-carboxy-2,5-dihydroxybenzamido)isonicotinic acid;
6-(3-carboxy-2,5-dihydroxybenzamido)nicotinic acid;
6-(3-carboxy-2,5-dihydroxybenzamido)picolinic acid;
2-(3-carboxy-2,5-dihydroxybenzamido)-5-fluoronicotinic acid;
6-(3-carboxy-2,5-dihydroxybenzamido)pyridine-2,5-dicarboxylic acid;
2-(3-carboxy-2,5-dihydroxybenzamido)pyridine-3,5-dicarboxylic acid;
3-(3-carboxy-2,5-dihydroxybenzamido)isonicotinic acid;
5-(3-carboxy-2,5-dihydroxybenzamido)nicotinic acid;
5-(3-carboxy-2,5-dihydroxybenzamido)picolinic acid;
3-(3-carboxy-2,5-dihydroxybenzamido)picolinic acid
5-(3-carboxy-2,5-dihydroxybenzamido)-2-fluoroisonicotinic acid;
4-(3-carboxy-2,5-dihydroxybenzamido)nicotinic acid;
4-(3-carboxy-2,5-dihydroxybenzamido)picolinic acid;
3-(4-(carboxymethyl)phenylaminocarbonyl)-2,5-dihydroxybenzoic acid;
3-(3-(carboxymethyl)phenylaminocarbonyl)-2,5-dihydroxybenzoic acid;
2,5-dihydroxy-3-(3-(1-hydroxy-1H-pyrazol-4-yl)phenylaminocarbonyl)benzoic acid;
3-(2-(carboxymethyl)phenylaminocarbonyl)-2,5-dihydroxybenzoic acid;
ethyl 3-(2-(1H-tetrazol-5-yl)phenylaminocarbonyl)-2,5-dihydroxybenzoate; and
ethyl 3-(2-(ethoxycarbonylmethyl)phenylaminocarbonyl)-2,5-dihydroxybenzoate.

4. The compound according to claim 2, wherein:
(a)
$R_a$, $R_b$=H;
$R_1$=$SO_3H$;
$R_2$=H; $R_3$-$R_5$; and
$R_5$=$R_6$=CONH—$R_9$;
or
(b)
$R_a$, $R_b$=H;
$R_1$=$SO_3H$;
$R_3$=H; $R_2$=$R_5$; and
$R_5$=$R_6$=CONH—$R_9$;
or
wherein said compound is selected form the group consisting of:
2-(2,5-dihydroxy-4-sulfobenzamido)benzoic acid;
2,5-dihydroxy-4-(2-sulfophenylaminocarbonyl)benzenesulfonic acid;
3-(2,5-dihydroxy-4-sulfobenzamido)benzoic acid;
2,5-dihydroxy-4-(3-sulfophenylaminocarbonyl)benzenesulfonic acid;
4-(2,5-dihydroxy-4-sulfobenzamido)benzoic acid;
2,5-dihydroxy-4-(4-sulfophenylaminocarbonyl)benzenesulfonic acid;
5-(2,5-dihydroxy-4-sulfobenzamido)-2-hydroxybenzoic acid;
4-(2,5-dihydroxy-4-sulfobenzamido)-2-hydroxybenzoic acid;
2-(2,5-dihydroxy-4-sulfobenzamido)-5-hydroxybenzoic acid;
3,5-bis(2,5-dihydroxy-4-sulfobenzamido)benzoic acid;
3-(2,5-dihydroxy-4-sulfobenzamido)phthalic acid;
2-(2,5-dihydroxy-4-sulfobenzamido)terephthalic acid;
2-(2,5-dihydroxy-4-sulfobenzamido)isophthalic acid;
4-(2,5-dihydroxy-4-sulfobenzamido)phthalic acid;
5-(2,5-dihydroxy-4-sulfobenzamido)isophthalic acid;
2-(2,5-dihydroxy-4-sulfobenzamido)nicotinic acid;

2-(2,5-dihydroxy-4-sulfobenzamido)isonicotinic acid;
6-(2,5-dihydroxy-4-sulfobenzamido)nicotinic acid;
6-(2,5-dihydroxy-4-sulfobenzamido)picolinic acid;
2-(2,5-dihydroxy-4-sulfobenzamido)-5-fluoronicotinic acid;
6-(2,5-dihydroxy-4-sulfobenzamido)pyridine-2,5-dicarboxylic acid;
2-(2,5-dihydroxy-4-sulfobenzamido)pyridine-3,5-dicarboxylic acid;
3-(2,5-dihydroxy-4-sulfobenzamido)isonicotinic acid;
5-(2,5-dihydroxy-4-sulfobenzamido)nicotinic acid;
5-(2,5-dihydroxy-4-sulfobenzamido)picolinic acid;
3-(2,5-dihydroxy-4-sulfobenzamido)picolinic acid;
5-(2,5-dihydroxy-4-sulfobenzamido)-2-fluoroisonicotinic acid;
4-(2,5-dihydroxy-4-sulfobenzamido)nicotinic acid;
4-(2,5-dihydroxy-4-sulfobenzamido)picolinic acid;
(4-(2,5-dihydroxy-4-sulfobenzamido)phenyl)acetic acid;
(3-(2,5-dihydroxy-4-sulfobenzamido)phenyl)acetic acid;
(2-(2,5-dihydroxy-4-sulfobenzamido)phenyl)acetic acid;
2-(2,5-dihydroxy-3-sulfobenzamido)benzoic acid;
2,5-dihydroxy-3-(2-sulfophenylaminocarbonyl)benzenesulfonic acid;
3-(2,5-dihydroxy-3-sulfobenzamido)benzoic acid;
2,5-dihydroxy-3-(3-sulfophenylaminocarbonyl)benzenesulfonic acid;
4-(2,5-dihydroxy-3-sulfobenzamido)benzoic acid;
2,5-dihydroxy-3-(4-sulfophenylaminocarbonyl)benzenesulfonic acid;
5-(2,5-dihydroxy-3-sulfobenzamido)-2-hydroxybenzoic acid;
4-(2,5-dihydroxy-3-sulfobenzamido)-2-hydroxybenzoic acid;
2-(2,5-dihydroxy-3-sulfobenzamido)-5-hydroxybenzoic acid;
3-(2,5-dihydroxy-3-sulfobenzamido)-5-(2,5-dihydroxy-4-sulfobenzamido)benzoic acid
3-(2,5-dihydroxy-3-sulfobenzamido)phthalic acid;
2-(2,5-dihydroxy-3-sulfobenzamido)terephthalic acid;
2-(2,5-dihydroxy-3-sulfobenzamido)isophthalic acid;
4-(2,5-dihydroxy-3-sulfobenzamido)phthalic acid;
5-(2,5-dihydroxy-3-sulfobenzamido)isophthalic acid;
2-(2,5-dihydroxy-3-sulfobenzamido)nicotinic acid;
2-(2,5-dihydroxy-3-sulfobenzamido)isonicotinic acid;
6-(2,5-dihydroxy-3-sulfobenzamido)nicotinic acid;
6-(2,5-dihydroxy-3-sulfobenzamido)picolinic acid;
2-(2,5-dihydroxy-3-sulfobenzamido)-5-fluoronicotinic acid;
6-(2,5-dihydroxy-3-sulfobenzamido)pyridine-2,5-dicarboxylic acid;
2-(2,5-dihydroxy-3-sulfobenzamido)pyridine-3,5-dicarboxylic acid;
3-(2,5-dihydroxy-3-sulfobenzamido)isonicotinic acid;
5-(2,5-dihydroxy-3-sulfobenzamido)nicotinic acid;
5-(2,5-dihydroxy-3-sulfobenzamido)picolinic acid;
3-(2,5-dihydroxy-3-sulfobenzamido)picolinic acid;
5-(2,5-dihydroxy-3-sulfobenzamido)-2-fluoroisonicotinic acid;
4-(2,5-dihydroxy-3-sulfobenzamido)nicotinic acid;
4-(2,5-dihydroxy-3-sulfobenzamido)picolinic acid;
(4-(2,5-dihydroxy-3-sulfobenzamido)phenyl)acetic acid;
(3-(2,5-dihydroxy-3-sulfobenzamido)phenyl)acetic acid; and
(2-(2,5-dihydroxy-3-sulfobenzamido)phenyl)acetic acid.

5. The compound according to claim 2, wherein:
(a)
$R_a$, $R_b$=H;

$R_1{=}(CH_2)_nCOOR_4$;

$R_4$-H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2{=}H$ or $R_5$, $R_3{=}R_5$; and $R_5{=}R_6{=}CONH{-}R_9$;

or (b)

$R_a$, $R_b{=}H$;

$R_1{=}(CH_2)_nCOOR_4$;

$R_4$-H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3{=}H$; $R_2$-$R_5$; and $R_5{=}R_6{=}CONH{-}R_9$;

or wherein said compound is selected from the group consisting of:

2-(4-(carboxymethyl)-2,5-dihydroxybenzamido)benzoic acid;

(2-(1H-tetrazol-5-yl)phenylaminocarbonyl)-2,5-dihydroxyphenyl) acetic acid;

(2,5-dihydroxy-4-(2-sulfophenylaminocarbonyl)phenyl) acetic acid;

3-(4-(carboxymethyl)-2,5-dihydroxybenzamido)benzoic acid;

(2,5-dihydroxy-4-(3-sulfophenylaminocarbonyl)phenyl) acetic acid;

4-(4-(carboxymethyl)-2,5-dihydroxybenzamido)benzoic acid;

2-(2,5-dihydroxy-4-(4-sulfophenylaminocarbonyl)phenyl)acetic acid;

5-(4-(carboxymethyl)-2,5-dihydroxybenzamido)-2-hydroxybenzoic acid;

4-(4-(carboxymethyl)-2,5-dihydroxybenzamido)-2-hydroxybenzoic acid;

2-(4-(carboxymethyl)-2,5-dihydroxybenzamido)-5-hydroxybenzoic acid;

3,5-Bis(2,5-dihydroxy-4-carboxymethylbenzoylamino) benzoic acid 3-(4-(carboxymethyl)-2,5-dihydroxybenzamido)phthalic acid;

2-(4-(carboxymethyl)-2,5-dihydroxybenzamido)terephthalic acid;

2-(4-(carboxymethyl)-2,5-dihydroxybenzamido)isophthalic acid;

4-(4-(carboxymethyl)-2,5-dihydroxybenzamido)phthalic acid;

5-(4-(carboxymethyl)-2,5-dihydroxybenzamido)isophthalic acid;

2-(4-(carboxymethyl)-2,5-dihydroxybenzamido)nicotinic acid;

2-(4-(carboxymethyl)-2,5-dihydroxybenzamido)isonicotinic acid;

6-(4-(carboxymethyl)-2,5-dihydroxybenzamido)nicotinic acid;

6-(4-(carboxymethyl)-2,5-dihydroxybenzamido)picolinic acid;

2-(4-(carboxymethyl)-2,5-dihydroxybenzamido)-5-fluoronicotinic acid;

6-(4-(carboxymethyl)-2,5-dihydroxybenzamido)pyridine-2,5-dicarboxylic acid;

2-(4-(carboxymethyl)-2,5-dihydroxybenzamido)pyridine-3,5-dicarboxylic acid;

3-(4-(carboxymethyl)-2,5-dihydroxybenzamido)isonicotinic acid;

5-(4-(carboxymethyl)-2,5-dihydroxybenzamido)nicotinic acid;

5-(4-(carboxymethyl)-2,5-dihydroxybenzamido)picolinic acid;

3-(4-(carboxymethyl)-2,5-dihydroxybenzamido)picolinic acid;

5-(4-(carboxymethyl)-2,5-dihydroxybenzamido)-2-fluorisonicotinic acid;

4-(4-(carboxymethyl)-2,5-dihydroxybenzamido)nicotinic acid;

4-(4-(carboxymethyl)-2,5-dihydroxybenzamido)picolinic acid;

(4-(4-(carboxymethyl)-2,5-dihydroxybenzamido)phenyl) acetic acid;

(3-(4-(carboxymethyl)-2,5-dihydroxybenzamido)phenyl) acetic acid;

(2-(4-(carboxymethyl)-2,5-dihydroxybenzamido)phenyl) acetic acid;

methyl 2-(4-(ethoxycarbonylmethyl)-2,5-dihydroxybenzamido)benzoate;

ethyl (4-(2-(1H-tetrazol-5-yl)phenylaminocarbonyl)-2,5-dihydroxyphenyl) acetate;

diethyl 5-(4-(ethoxycarbonylmethyl)-2,5-dihydroxybenzamido) isophthalate;

methyl 3,5-bis(4-(ethoxycarbonylmethyl)-2,5-dihydroxybenzamido)benzoate;

2-(3-(carboxymethyl)-2,5-dihydroxybenzamido)benzoic acid;

(2,5-dihydroxy-3-(2-sulfophenylaminocarbonyl)phenyl) acetic acid;

3-(3-(carboxymethyl)-2,5-dihydroxybenzamido)benzoic acid;

(2,5-dihydroxy-3-(3-sulfophenylaminocarbonyl)phenyl) acetic acid;

4-(3-(carboxymethyl)-2,5-dihydroxybenzamido)benzoic acid;

(2,5-dihydroxy-3-(4-sulfophenylaminocarbonyl)phenyl) acetic acid;

5-(3-(carboxymethyl)-2,5-dihydroxybenzamido)-2-hydroxybenzoic acid;

4-(3-(carboxymethyl)-2,5-dihydroxybenzamido)-2-hydroxybenzoic acid;

2-(3-(carboxymethyl)-2,5-dihydroxybenzamido)-5-hydroxybenzoic acid;

3,5-Bis(2,5-dihydroxy-3-carboxymethylbenzoylamino) benzoic acid 3-(3-(carboxymethyl)-2,5-dihydroxybenzamido)phthalic acid;

2-(3-(carboxymethyl)-2,5-dihydroxybenzamido)terephthalic acid;

2-(3-(carboxymethyl)-2,5-dihydroxybenzamido)isophthalic acid;

4-(3-(carboxymethyl)-2,5-dihydroxybenzamido)phthalic acid;

5-(3-(carboxymethyl)-2,5-dihydroxybenzamido)isophthalic acid;

2-(3-(carboxymethyl)-2,5-dihydroxybenzamido)nicotinic acid;

2-(3-(carboxymethyl)-2,5-dihydroxybenzamido)isonicotinic acid;
6-(3-(carboxymethyl)-2,5-dihydroxybenzamido)nicotinic acid;
6-(3-(carboxymethyl)-2,5-dihydroxybenzamido)picolinic acid;
2-(3-(carboxymethyl)-2,5-dihydroxybenzamido)-5-fluoronicotinic acid;
6-(3-(carboxymethyl)-2,5-dihydroxybenzamido)pyridine-2,5-dicarboxylic acid;
2-(3-(carboxymethyl)-2,5-dihydroxybenzamido)pyridine-3,5-dicarboxylic acid;
3-(3-(carboxymethyl)-2,5-dihydroxybenzamido)isonicotinic acid;
5-(3-(carboxymethyl)-2,5-dihydroxybenzamido)nicotinic acid;
5-(3-(carboxymethyl)-2,5-dihydroxybenzamido)picolinic acid;
3-(3-(carboxymethyl)-2,5-dihydroxybenzamido)picolinic acid;
5-(3-(carboxymethyl)-2,5-dihydroxybenzamido)-2-fluoroisonicotinic acid;
4-(3-(carboxymethyl)-2,5-dihydroxybenzamido)nicotinic acid;
4-(3-(carboxymethyl)-2,5-dihydroxybenzamido)picolinic acid;
(4-(3-(carboxymethyl)-2,5-dihydroxybenzamido)phenyl) acetic acid;
(3-(3-(carboxymethyl)-2,5-dihydroxybenzamido)phenyl) acetic acid; and
(2-(3-(carboxymethyl)-2,5-dihydroxybenzamido)phenyl) acetic acid.

6. The compound according to claim 2 having the formula (I):

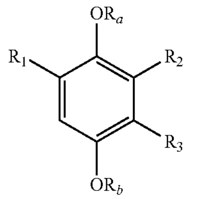

(I)

wherein:

(a)

$R_a$, $R_b$=H, $C_{1-4}$acyl, aryl$C_{1-4}$alkyl, $C_6$-$C_{10}$arylCO, HOOC $(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$=H; $R_3$=$R_5$; and $R_5$=$R_6$=CONH—$R_9$;

or (b)

$R_a$, $R_b$=H, $C_{1-4}$acyl, aryl$C_{1-4}$alkyl, $C_6$-$C_{10}$arylCO, HOOC $(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=CONH—$R_{10}$; $R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$=H; $R_2$=$R_5$; and $R_5$=$R_6$=CONH—$R_9$;

or wherein said compound is selected form the group consisting of:

5-(4-(2-(1H-tetrazol-5-yl)phenylaminocarbonyl)-2,5-dihydroxybenzamido)-2-hydroxybenzoic acid;
$N_1$,$N_4$-bis(2-(1H-tetrazol-5-yl) phenyl)-2,5-dihydroxyterephthalamide;
5-(4-(3-carboxy-4-hydroxyphenylaminocarbonyl)-2,5-dihydroxybenzamido)-2-hydroxybenzoic acid;
5-(2,5-dihydroxy-4-(4-hydroxy-3-sulfophenylaminocarbonyl)benzamido)-2-hydroxybenzenesulphonic acid;
4-(4-(4-carboxy-3-hydroxyphenylaminocarbonyl)-2,5-dihydroxybenzamido)-2-hydroxybenzoic acid;
4-(2,5-dihydroxy-4-(3-hydroxy-4-sulfophenylaminocarbonyl)benzamido)-2-hydroxybenzenesulphonic acid;
2-(2,5-dihydroxy-4-(4-hydroxy-2-carboxyphenylaminocarbonyl)benzamido)-5-hydroxybenzoic acid;
2-(2,5-dihydroxy-4-(4-hydroxy-2-sulfophenylaminocarbonyl)benzamido)-5-hydroxybenzene sulphonic acid;
methyl 5-(4-(2-(1H-tetrazol-5-yl)phenylaminocarbonyl)-2,5-dihydroxybenzamido)-2-hydroxybenzoate;
methyl 5-(2,5-diacetoxy-4-(4-acetoxy-3-(methoxycarbonyl)phenylaminocarbonyl)benzamido)-2-acetoxybenzoate;
methyl 5-(2,5-dihydroxy-4-(4-hydroxy-3-(methoxycarbonyl)phenylaminocarbonyl)benzamido)-2-hydroxybenzoate;
methyl 2-(2,5-dihydroxy-4-(4-hydroxy-2-(methoxycarbonyl)phenylaminocarbonyl)benzamido)-5-hydroxybenzoate;
1-(2,2-dimethylpropanoyloxy) ethyl 5-[[4-[3-[1-(2,2-dimethylpropanoyloxy) ethoxycarbonyl]-4-hydroxyphenyl]aminocarbonyl]-2,5-dihydroxy-benzoyl] amino]-2-hydroxybenzoate
5-(3-(3-carboxy-4-hydroxyphenylaminocarbonyl)-2,5-dihydroxybenzamido)-2-hydroxybenzoic acid;
5-(2,5-dihydroxy-3-(4-hydroxy-3-sulfophenylaminocarbonyl)benzamido)-2-hydroxybenzenesulphonic acid;
4-(3-(3-hydroxy-4-carboxyphenylaminocarbonyl)-2,5-dihydroxybenzamido)-2-hydroxybenzoic acid;
4-(2,5-dihydroxy-3-(3-hydroxy-4-sulfophenylaminocarbonyl)benzamido)-2-hydroxybenzenesulphonic acid;
2-(3-(2-carboxy-4-hydroxyphenylaminocarbonyl)-2,5-dihydroxybenzamido)-5-hydroxylbenzoic acid; and
2-(2,5-dihydroxy-3-(4-hydroxy-2-sulfophenylaminocarbonyl)benzamido)-5-hydroxybenzenesulphonic acid.

7. The compound according to claim 2 having the formula (I):

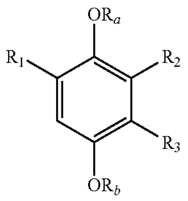

(I)

wherein:

$R_a$, $R_b$═H;

$R_1$═CONH—$R_{10}$;

$R_{10}$=phenyl substituted with $COOR_4$ and with $OR_4$;

$R_2$═H;

$R_3$═CONH—$R_9$;

$R_9$=phenyl substituted with $COOR_4$ and with $OR_4$; and $R_4$═H;

and wherein said compound is 5-(4-(3-carboxy-4-hydroxyphenylaminocarbonyl)-2,5-dihydroxybenzamido)-2-hydroxybenzoic acid.

8. The compound according to claim 2 having the formula (I):

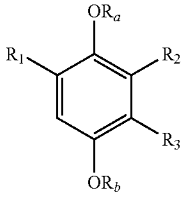

(I)

wherein:

$R_a$, $R_b$═H;

$R_1$═CONH—$R_{10}$;

$R_{10}$=phenyl substituted with $COOR_4$ and with $OR_4$;

$R_2$═CONH—$R_9$;

$R_3$═H;

$R_9$=phenyl substituted with $COOR_4$ and with $OR_4$; and $R_4$═H;

and wherein said compound is 5-(3-(3-carboxy-4-hydroxyphenylaminocarbonyl)-2,5-dihydroxybenzamido)-2-hydroxybenzoic acid.

9. The compound according to claim 2, wherein:

(a)

$R_a$, $R_b$═H;

$R_1$═$COOR_4$; $(CH_2)_nCOOR_4$; $R_4$-H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$═H; $R_3$═$R_5$; and $R_5$═$R_6$═$CONHCOR_9$;

or (b)

$R_a$, $R_b$═H;

$R^1$═$COOR_4$; $(CH_2)_nCOOR_4$; $R_4$-H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$═H; $R_2$-$R_5$; and $R_5$═$R_6$═$CONHCOR_9$;

or wherein said compound is selected form the group consisting of:

N-(1,3,4,5-tetrahydroxycyclohexylcarbonyl) 4-carboxy-2,5-dihydroxybenzamide;

N-(4-carboxy-2,5-dihydroxybenzoyl) 4-carboxy-2,5-dihydroxy-benzamide;

N-(3-carboxy-2,5-dihydroxybenzoyl) 4-carboxy-2,5-dihydroxy-benzamide;

N-(3,4-dihydroxybenzoyl) 4-carboxy-2,5-dihydroxybenzamide;

N-(3,5-dihydroxybenzoyl) 4-carboxy-2,5-dihydroxybenzamide;

N-(1,3,4,5-tetrahydroxycyclohexylcarbonyl) 3-carboxy-2,5-dihydroxybenzamide;

N-(4-carboxy-2,5-dihydroxybenzoyl) 3-carboxy-2,5-dihydroxy-benzamide;

N-(3-carboxy-2,5-dihydroxybenzoyl) 3-carboxy-2,5-dihydroxy-benzamide;

N-(3,4-dihydroxybenzoyl) 3-carboxy-2,5-dihydroxybenzamide;

N-(3,5-dihydroxybenzoyl) 3-carboxy-2,5-dihydroxybenzamide;

N-(1,3,4,5-tetrahydroxycyclohexylcarbonyl) 4-carboxymethyl-2,5-dihydroxybenzamide;

N-(4-carboxy-2,5-dihydroxybenzoyl) 4-carboxymethyl-2,5-dihydroxy-benzamide;

N-(3-carboxy-2,5-dihydroxybenzoyl) 4-carboxymethyl-2,5-dihydroxy-benzamide;

N-(3,4-dihydroxybenzoyl) 4-carboxymethyl-2,5-dihydroxybenzamide;

N-(3,5-dihydroxybenzoyl) 4-carboxymethyl-2,5-dihydroxybenzamide;

N-(1,3,4,5-tetrahydroxycyclohexylcarbonyl) 3-carboxymethyl-2,5-dihydroxybenzamide;

N-(4-carboxy-2,5-dihydroxybenzoyl) 3-carboxymethyl-2,5-dihydroxy-benzamide;

N-(3-carboxy-2,5-dihydroxybenzoyl) 3-carboxymethyl-2,5-dihydroxy-benzamide;

N-(3,4-dihydroxybenzoyl) 3-carboxymethyl-2,5-dihydroxybenzamide; and

N-(3,5-dihydroxybenzoyl) 3-carboxymethyl-2,5-dihydroxybenzamide.

10. A compound according to claim 2, wherein (a)

$R_a$, $R_b$═H;

$R_1$═$COOR_4$; $(CH_2)$ $COOR_4$; $R_4$═H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$-H; $R_3$-$R_5$; and $R_5$═$R_6$═$CONH(CH_2)_n$-$R_9$;

or (b)

$R_a$, $R_b$=H;

$R_1$=$COOR_4$; $(CH_2)_nCOOR_4$; $R_4$-H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$ aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$=H; $R_2$=$R_5$; and $R_5$=$R_6$-CONH$(CH_2)_n$-$R_9$;

or wherein said compound is selected from the group consisting of:

4-(3,4-dihydroxyphenylmethylaminocarbonyl)-2,5-dihydroxybenzoic acid;

4-(2-(3,4-dihydroxyphenyl)ethylaminocarbonyl)-2,5-dihydroxybenzoic acid;

4-(3,5-dihydroxyphenylmethylaminocarbonyl)-2,5-dihydroxybenzoic acid;

4-((4,5-dihydroxy-3-oxocyclohex-1-enyl) methylaminocarbonyl)-2,5-dihydroxybenzoic acid;

2,5-dihydroxy-4-((3,4,5-trihydroxycyclohexyl) methylaminocarbonyl)benzoic acid;

4-(2-carboxyphenylmethylaminocarbonyl)-2,5-dihydroxybenzoic acid;

4-(3-carboxyphenylmethylaminocarbonyl)-2,5-dihydroxybenzoic acid;

4-(4-carboxyphenylmethylaminocarbonyl) 2,5-dihydroxybenzoic acid;

3-(3,4-dihydroxyphenylmethylaminocarbonyl)-2,5-dihydroxybenzoic acid;

3-(2-(3,4-dihydroxyphenyl)ethylaminocarbonyl)-2,5-dihydroxybenzoic acid;

3-(3,5-dihydroxyphenylmethylaminocarbonyl)-2,5-dihydroxybenzoic acid;

3-((4,5-dihydroxy-3-oxocyclohex-1-enyl) methylaminocarbonyl)-2,5-dihydroxybenzoic acid;

2,5-dihydroxy-3-((3,4,5-trihydroxycyclohexyl) methylaminocarbonyl)benzoic acid;

3-(2-carboxyphenylmethylaminocarbonyl)-2,5-dihydroxybenzoic acid;

3-(3-carboxyphenylmethylaminocarbonyl)-2,5-dihydroxybenzoic acid;

3-(4-carboxyphenylmethylaminocarbonyl)-2,5-dihydroxybenzoic acid;

(4-(3,4-dihydroxyphenylmethylaminocarbonyl)-2,5-dihydroxyphenyl) acetic acid;

(4-(3,5-dihydroxyphenylmethylaminocarbonyl)-2,5-dihydroxyphenyl) acetic acid;

(4-((4,5-dihydroxy-3-oxocyclohex-1-enyl) methylaminocarbonyl)-2,5-dihydroxyphenyl) acetic acid;

(2,5-dihydroxy-4-((3,4,5-trihydroxycyclohexyl) methylaminocarbonyl)phenyl)acetic acid;

(4-(2-carboxyphenylmethylaminocarbonyl)-2,5-dihydroxyphenyl) acetic acid;

(4-(3-carboxyphenylmethylaminocarbonyl)-2,5-dihydroxyphenyl) acetic acid;

(4-(4-carboxyphenylmethylaminocarbonyl)-2,5-dihydroxyphenyl) acetic acid;

(3-(3,4-dihydroxyphenylmethylaminocarbonyl)-2,5-dihydroxyphenyl) acetic acid;

(3-(3,5-dihydroxyphenylmethylaminocarbonyl)-2,5-dihydroxyphenyl) acetic acid;

(3-((4,5-dihydroxy-3-oxocyclohex-1-enyl) methylaminocarbonyl)-2,5-dihydroxyphenyl) acetic acid;

(2,5-dihydroxy-3-((3,4,5-trihydroxycyclohexyl) methylcarbonylamino)phenyl)acetic acid;

(3-(2-carboxyphenylmethylaminocarbonyl)-2,5-dihydroxyphenyl) acetic acid;

(3-(3-carboxyphenylmethylaminocarbonyl)-2,5-dihydroxyphenyl) acetic acid; and (3-(4-carboxyphenylmethylaminocarbonyl)-2,5-dihydroxyphenyl) acetic acid.

11. A compound according to claim 2, wherein:

$R_a$, $R_b$=H;

$R_1$=$SO_3H$;

$R_2$=H; $R_3$=$R_5$; and $R_5$=$R_6$-CONH$(CH_2)_n$-$R_9$;

or wherein said compound is selected form the group consisting of:

2-((2,5-dihydroxy-4-sulfobenzamido)methyl)benzoic acid;

3-((2,5-dihydroxy-4-sulfobenzamido)methyl)benzoic acid; and 4-((2,5-dihydroxy-4-sulfobenzamido)methyl)benzoic acid.

12. The compound according to claim 2, wherein:

(a)

$R_a$, $R_b$=H;

$R_1$=$COOR_4$; $(CH_2)_nCOOR_4$; $R_4$-H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$=H; $R_3$-$R_5$; and $R_5$=$R_6$=CONHCH$(COOR_4)(CH_2)_kR_9$;

or (b)

$R_a$, $R_b$=H;

$R_1$=$COOR_4$; $(CH_2)_nCOOR_4$; $R_4$-H, $C_{1-4}$alkyl, aryl$C_{1-4}$ alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$=H; $R_2$-$R_5$; and $R_5$=$R_6$=CONHCH$(COOR_4)(CH_2)_kR_9$;

or wherein said compound is selected form the group consisting of:

4-(1-carboxy-2-(3,4-dihydroxyphenyl)ethylaminocarbonyl)-2,5-dihydroxybenzoic acid;

4-(carboxy (3,4-dihydroxyphenyl) methylaminocarbonyl)-2,5-dihydroxybenzoic acid;

3-(1-carboxy-2-(3,4-dihydroxyphenyl)ethylaminocarbonyl)-2,5-dihydroxybenzoic acid 3-(carboxy (3,4-dihydroxyphenyl) methylaminocarbonyl)-2,5-dihydroxybenzoic acid;

(4-(carboxy (3,4-dihydroxyphenyl) methylaminocarbonyl)-2,5-dihydroxyphenyl) acetic acid; and (3-(carboxy (3,4-dihydroxyphenyl) methylaminocarbonyl)-2,5-dihydroxyphenyl) acetic acid.

13. The compound according to claim 2, wherein:

(a)

$R_a$, $R_b$=H;

$R_1$=$COOR_4$, $(CH_2)_nCOOR_4$, $SO_3H$, $(CH_2)_nSO_3H$, CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$=H; $R_3$=$R_5$; and $R_5$=$R_7$=benzoheteroaryl substituted with at least one or more groups selected from:

$COOR_4$, $(CH_2)_nCOOR_4$, $SO_3H$, $(CH_2)_nSO_3H$, $OR_4$, azoles [5-membered N-containing heterocycles], or fluorine;

or (b)

$R_a$, $R_b$=H;

$R_1$=$COOR_4$, $(CH_2)_nCOOR_4$, $SO_3H$, $(CH_2)_nSO_3H$, CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$=H; $R_2$=$R_5$; and $R_5$=$R_7$=benzoheteroaryl substituted with at least one or more groups selected from:

COOR4, (CH2)nCOOR4, S3H, (CH2)nSO3H, OR4, azoles [5-membered N-containing heterocycles], or fluorine;

or wherein said compound is selected form the group consisting of:

2-(4-Carboxy-2,5-dihydroxyphenyl)-1H-benzo[d]imidazole-4-carboxylic acid;

Methyl 2-(4-ethoxycarbonyl-2,5-dihydroxyphenyl)-1H-benzo[d]imidazole-4-carboxylate;

2-(2,5-Dihydroxy-4-sulfophenyl)-1H-benzo[d]imidazole-4-carboxylic acid;

2-(4-Carboxy-2,5-dihydroxyphenyl)-1H-benzo[d]imidazole-5-carboxylic acid;

2-(2,5-Dihydroxy-4-sulfophenyl)-1H-benzo[d]imidazole-5-carboxylic acid;

2-(3-Carboxy-2,5-dihydroxyphenyl)-1H-benzo[d]imidazole-4-carboxylic acid;

2-(2,5-Dihydroxy-3-sulfophenyl)-1H-benzo[d]imidazole-4-carboxylic acid;

2-(3-Carboxy-2,5-dihydroxyphenyl)-1H-benzo[d]imidazole-5-carboxylic acid;

2-(2,5-Dihydroxy-3-sulfophenyl)-1H-benzo[d]imidazole-5-carboxylic acid;

2-(4-(Carboxymethyl)-2,5-dihydroxyphenyl)-1H-benzo[d]imidazole-4-carboxylic acid;

2-(4-(Carboxymethyl)-2,5-dihydroxyphenyl)-1H-benzo[d]imidazole-5-carboxylic acid;

2-(3-(Carboxymethyl)-2,5-dihydroxyphenyl)-1H-benzo[d]imidazole-4-carboxylic acid; and 2-(3-(Carboxymethyl)-2,5-dihydroxyphenyl)-1H-benzo[d]imidazole-5-carboxylic acid.

14. A compound of formula (I):

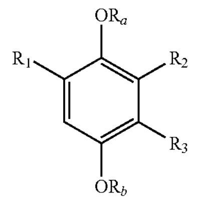

(I)

wherein:

$R_a$, $R_b$=H, $C_{1-4}$acyl, aryl$C_{1-4}$alkyl, $C_6$-$C_{10}$arylCO, $HOOC(CH_2)_nCO$, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, or CONH—$R_{10}$;

$R_2$ and $R_3$ are H or $R_5$, with the proviso that when one of $R_2$ and $R_3$ is $R_5$, the other is H and when one of $R_2$ and $R_3$ is H, the other is $R_5$;

$R_4$-H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_5$=$R_8$;

$R_8$=$(CH_2)_mX(CH_2)_pR_9$;

X=O, S, $SO_2$, NH, NAc, or $N(CH_2)_qR_9$;

$R_9$=aryl, heteroaryl, substituted with at least one or more groups selected from $COOR_4$, $(CH_2)_nCOOR_4$, $(CH_2)_nSO_3H$, $OR_4$, $SO_3H$, azoles [5-membered N-containing heterocycles], fluorine, C=O, or NHCO—$R_{10}$;

$R_{10}$=aryl, heteroaryl, substituted with at least one or more groups selected from $COOR_4$, $(CH_2)_nCOOR_4$, $(CH_2)_nSO_3H$, $OR_4$, $SO_3H$, azoles [5-membered N-containing heterocycles], or fluorine;

wherein the aryl of $R_9$ an $R_{10}$ is an aromatic group containing from 6 to 14 carbon atoms, selected among phenyl, naphthyl, or biphenyl group; and the heteroaryl $R_9$ an $R_{10}$ is an aromatic group containing 1 to 14 carbon atoms and one or more nitrogen; and n, m, p and q are an integer independently equal to 1-4.

15. The compound according to claim 14, wherein:

(a)

$R_a$, $R_b$=H, $C_{1-4}$acyl, aryl$C_{1-4}$alkyl, $C_6$-$C_{10}$arylCO, HOOC $(CH_2)_nCO$, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_2$=H; $R_3$=$R_5$; and $R_5$=$R_8$=$(CH_2)_mX(CH_2)_pR_9$;

wherein X=O, S, $SO_2$, NH, NAc, or $N(CH_2)_qR_9$;

or (b)

$R_a$, $R_b$=H, $C_{1-4}$acyl, aryl$C_{1-4}$alkyl, $C_6$-$C_{10}$arylCO, HOOC $(CH_2)_n$CO, $C_1$-$C_7$alkylNHCO, phosphono, phosphonooxymethyl, $C_1$-$C_6$acyloxymethyl, $C_1$-$C_6$acyloxy-1-ethyl, $C_1$-$C_6$alkoxycarbonyloxymethyl, or $C_1$-$C_6$alkoxycarbonyloxy-1-ethyl;

$R_1$=$COOR_4$, $(CH_2)_nCOOR_4$, $SO_3H$, $(CH_2)_nSO_3H$, CONH—$R_{10}$;

$R_4$=H, $C_{1-4}$alkyl, aryl$C_{1-4}$alkyl, functionalized $C_1$-$C_6$alkyl including morpholino-$C_1$-$C_6$alkyl, pyrrolidino-$C_1$-$C_6$alkyl, N-methylpiperazino-$C_1$-$C_6$alkyl, $C_6$-$C_{10}$aryl including o-methoxyphenyl (guaiacol ester), $C_1$-$C_6$acyloxymethyl, $C_1$-$C_6$acyloxy-1-ethyl, $C_1$-$C_6$alkoxycarbonyloxymethyl, $C_1$-$C_6$alkoxycarbonyloxy-1-ethyl, or (oxodioxolyl) methyl;

$R_3$=H; $R_2$=$R_5$; and $R_5$=$R_8$=$(CH_2)_mX(CH_2)_pR_9$;

wherein X=O, S, $SO_2$, NH, NAc, or $N(CH_2)_qR_9$;

or wherein said compound is selected form the group consisting of:

Bis(4-carboxy-2,5-dihydroxyphenylmethyl)amine;

4-((2,5-Dihydroxy-4-sulfophenylmethylamino)methyl)-2,5-dihydroxybenzoic acid;

4-((2,5-Dihydroxy-3-sulfophenylmethylamino)methyl)-2,5-dihydroxybenzoic acid;

Bis(2,5-dihydroxy-4-sulfophenylmethyl)amine;

N,N-Bis(4-carboxy-2,5-dihydroxyphenylmethyl)acetamide;

N-(2,5-dihydroxy-4-sulfophenylmethyl)N-(4-carboxy-2,5-dihydroxyphenylmethyl)acetamide;

N-(2,5-dihydroxy-3-sulfophenylmethyl)N-(4-carboxy-2,5-dihydroxyphenylmethyl)acetamide;

N,N-Bis(2,5-dihydroxy-4-sulfophenylmethyl)acetamide;

4-((2,5-Dihydroxy-4-carboxyphenyl)methylthiomethyl)-2,5-dihydroxybenzoic acid;

4-((2,5-Dihydroxy-4-sulfophenyl)methylthiomethyl)-2,5-dihydroxybenzoic acid;

4-((2,5-Dihydroxy-3-sulfophenyl)methylthiomethyl)-2,5-dihydroxybenzoic acid;

4-((2,5-Dihydroxy-4-sulfophenyl)methylthiomethyl)-2,5-dihydroxybenzenesulfonic acid;

4-((2,5-Dihydroxy-4-carboxyphenyl) methylsulfonylmethyl)-2,5-dihydroxybenzoic acid;

4-((2,5-Dihydroxy-4-sulfophenyl) methylsulfonylmethyl)-2,5-dihydroxybenzoic acid;

4-((2,5-Dihydroxy-3-sulfophenyl) methylsulfonylmethyl)-2,5-dihydroxybenzoic acid;

4-((2,5-Dihydroxy-4-sulfophenyl) methylsulfonylmethyl)-2,5-dihydroxybenzenesulfonic acid;

4-((2,5-Dihydroxy-4-carboxyphenyl) methoxymethyl)-2,5-dihydroxybenzoic acid;

4-((2,5-dihydroxy-4-sulfophenyl) methoxymethyl)-2,5-dihydroxybenzoic acid;

4-((2,5-dihydroxy-3-sulfophenyl) methoxymethyl)-2,5-dihydroxybenzoic acid;

4-((2,5-Dihydroxy-4-sulfophenyl) methoxymethyl)-2,5-dihydroxybenzenesulfonic acid;

Tris(4-carboxy-2,5-dihydroxyphenylmethyl)amine;

Tris(4-ethoxycarbonyl-2,5-dihydroxyphenylmethyl) amine;

Bis(3-carboxy-2,5-dihydroxyphenylmethyl)amine;

3-((2,5-Dihydroxy-3-sulfophenylmethylamino)methyl)-2,5-dihydroxybenzoic acid;

3-((2,5-Dihydroxy-4-sulfophenylmethylamino)methyl)-2,5-dihydroxybenzoic acid;

Bis(2,5-dihydroxy-3-sulfophenylmethyl)amine;

N,N-Bis(3-carboxy-2,5-dihydroxyphenylmethyl)acetamide;

N-(2,5-dihydroxy-3-sulfophenylmethyl)N-(3-carboxy-2,5-dihydroxyphenylmethyl)acetamide;

N-(2,5-dihydroxy-4-sulfophenylmethyl) N-(3-carboxy-2,5-dihydroxyphenylmethyl)acetamide;

N,N-Bis(2,5-dihydroxy-3-sulfophenylmethyl)acetamide;

3-((2,5-Dihydroxy-3-carboxyphenyl)methylthiomethyl)-2,5-dihydroxybenzoic acid;

3-((2,5-Dihydroxy-3-sulfophenyl)methylthiomethyl)-2,5-dihydroxybenzoic acid;

3-((2,5-Dihydroxy-4-sulfophenyl)methylthiomethyl)-2,5-dihydroxybenzoic acid;

3-((2,5-Dihydroxy-3-sulfophenyl)methylthiomethyl)-2,5-dihydroxybenzenesulfonic acid;

3-((2,5-Dihydroxy-3-carboxyphenyl) methylsulfonylmethyl)-2,5-dihydroxybenzoic acid;

3-((2,5-Dihydroxy-3-sulfophenyl) methylsulfonylmethyl)-2,5-dihydroxybenzoic acid;

3-((2,5-Dihydroxy-4-sulfophenyl) methylsulfonylmethyl)-2,5-dihydroxybenzoic acid;

3-((2,5-Dihydroxy-3-sulfophenyl) methylsulfonylmethyl)-2,5-dihydroxybenzenesulfonic acid;

3-((2,5-Dihydroxy-3-carboxyphenyl) methoxymethyl)-2,5-dihydroxybenzoic acid;

3-((2,5-dihydroxy-3-sulfophenyl) methoxymethyl)-2,5-dihydroxybenzoic acid;

3-((2,5-dihydroxy-4-sulfophenyl) methoxymethyl)-2,5-dihydroxybenzoic acid;

3-((2,5-Dihydroxy-3-sulfophenyl) methoxymethyl)-2,5-dihydroxybenzenesulfonic acid;

Methyl 3-((2,5-diacetoxy-3-methoxycarbonylphenyl) methylsulfonylmethyl)-2,5-diacetoxybenzoate;

Methyl 3-((2,5-dihydroxy-3-methoxycarbonylphenyl) methylsulfonylmethyl)-2,5-hydroxybenzoate;

2-Morpholinoethyl 3-((2,5-dihydroxy-3-(2-morpholinoethoxycarbonyl)phenyl)methylsulfonylmethyl)-2,5-hydroxybenzoate;

Tris(3-carboxy-2,5-dihydroxyphenylmethyl)amine; and

Tris(3-ethoxycarbonyl-2,5-dihydroxyphenylmethyl) amine.

16. The compound according to claim 2, having the formula (I):

(I)

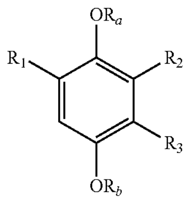

wherein:

$R_a$, $R_b$=H;

$R_1$=$COOR_4$;

$R_2$=H;

$R_3$=$R_8$;
$R_4$=H;
$R_8$=$(CH_2)_mX(CH_2)_pR_9$;
$R_9$=phenyl substituted with $COOR_4$ and with $OR_4$;
X=$N(CH_2)_qR_9$; and
m, p and q=1;
and wherein said compound is Tris(4-carboxy-2,5-dihydroxyphenylmethyl)amine.

17. The compound according to claim 2, having the formula (I):

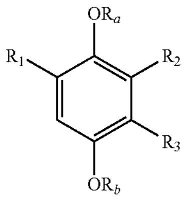

(I)

wherein:
$R_a$, $R_b$=H;
$R_1$=$COOR_4$;
$R_2$=$(CH_2)_mX(CH_2)_pR_9$;
$R_3$=H;
$R_9$=phenyl substituted with $COOR_4$ and with $OR_4$;
$R_4$=H;
X=$SO_2$; and
m and p=1;
and said compound is 3-((2,5-Dihydroxy-3-carboxyphenyl) methylsulfonylmethyl)-2,5-dihydroxybenzoic acid.

18. A pharmaceutical composition comprising a therapeutically effective amount of the compound according to claim 2 or a pharmaceutically acceptable salt or stereoisomer thereof, and a pharmaceutically acceptable excipient.

19. A method of treating autoimmune, immunological, rheumatology, vascular disorders, ophthalmologic disorders, fibrotic disorders, metabolic and gastro-intestinal disorders, neuroinflammatory and neurodegenerative diseases, neoplasms and cancer associated disorders, hormone related diseases, or immunological disorders resulting from viral and/or bacterial infectious diseases and/or complications thereof in a subject, comprising administering the pharmaceutical composition of claim 18 to said subject.

* * * * *